US007521240B2

(12) United States Patent
Perkins et al.

(10) Patent No.: US 7,521,240 B2
(45) Date of Patent: Apr. 21, 2009

(54) CHROMOSOME-BASED PLATFORMS

(75) Inventors: Edward Perkins, Duluth, MN (US); Carl Perez, Vancouver (CA); Michael Lindenbaum, Beaconsfield (CA); Amy Greene, Duluth, MN (US); Josephine Leung, Coquitlam (CA); Elena Fleming, North Vancouver (CA); Sandra Stewart, Vancouver (CA)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/006,076

(22) Filed: Dec. 6, 2004

(65) Prior Publication Data

US 2005/0181506 A1 Aug. 18, 2005

Related U.S. Application Data

(62) Division of application No. 10/161,403, filed on May 30, 2002.

(60) Provisional application No. 60/366,891, filed on Mar. 21, 2002, provisional application No. 60/294,758, filed on May 30, 2001.

(51) Int. Cl.
*C12N 15/87* (2006.01)
*C12N 15/90* (2006.01)

(52) U.S. Cl. ...................................... 435/462; 435/466

(58) Field of Classification Search ....................... None
See application file for complete search history.

(56) References Cited

U.S. PATENT DOCUMENTS

| | | | | |
|---|---|---|---|---|
| 4,673,640 | A | 6/1987 | Backman | |
| 4,775,630 | A | 10/1988 | Tibbetts et al. | |
| 4,801,540 | A | 1/1989 | Hiatt et al. | |
| 4,920,211 | A | 4/1990 | Tibbetts et al. | |
| 4,959,317 | A | 9/1990 | Sauer | |
| 5,190,871 | A | 3/1993 | Cox et al. | |
| 5,270,201 | A | 12/1993 | Richards et al. | |
| 5,272,071 | A | 12/1993 | Chappel | |
| 5,288,625 | A | 2/1994 | Hadlaczky | |
| 5,396,767 | A | 3/1995 | Suzuki | |
| 5,501,967 | A | 3/1996 | Offringa et al. | |
| 5,527,695 | A | 6/1996 | Hodges et al. | |
| 5,658,772 | A | 8/1997 | Odell et al. | |
| 5,691,140 | A | 11/1997 | Noren et al. | |
| 5,695,967 | A | 12/1997 | Van Bokkelen et al. | |
| 5,712,134 | A | 1/1998 | Hadlaczky | |
| 5,721,118 | A | 2/1998 | Scheffler | |
| 5,744,336 | A | 4/1998 | Hodges et al. | |
| 5,744,386 | A | 4/1998 | Kenney | |
| 5,804,177 | A | 9/1998 | Humphries | |
| 5,866,359 | A | 2/1999 | Cockett et al. | |
| 5,869,294 | A | 2/1999 | Harrington et al. | |
| 5,891,691 | A | 4/1999 | Hadlaczky | |
| 5,910,415 | A | 6/1999 | Hodges et al. | |
| 5,948,653 | A | 9/1999 | Pati et al. | |
| 6,025,155 | A | 2/2000 | Hadlaczky et al. | |
| 6,074,836 | A | 6/2000 | Bordignon et al. | |
| 6,077,697 | A | 6/2000 | Hadlaczky et al. | |
| 6,100,092 | A | 8/2000 | Borysyuk et al. | |
| 6,110,736 | A | 8/2000 | Hodges et al. | |
| 6,114,600 | A | 9/2000 | Ow et al. | |
| 6,126,320 | A | 10/2000 | Ichiyama | |
| 6,133,503 | A | 10/2000 | Scheffler | |
| 6,143,530 | A | 11/2000 | Crouzet et al. | |
| 6,143,949 | A | 11/2000 | Ozawa et al. | |
| 6,171,821 | B1 | 1/2001 | Korneluk et al. | |
| 6,171,861 | B1 | 1/2001 | Hartley et al. | |
| 6,262,341 | B1 | 7/2001 | Baszczynski et al. | |
| 6,355,860 | B1 | 3/2002 | Borysyuk et al. | |
| 6,365,373 | B2 | 4/2002 | Presta et al. | |
| 6,743,967 | B2 | 6/2004 | Hadlaczky et al. | |
| 6,746,870 | B1 | 6/2004 | Ow et al. | |
| 6,936,469 | B2 | 8/2005 | De Jong et al. | |
| 2002/0123145 | A1 | 9/2002 | Ow | |
| 2002/0160410 | A1 | 10/2002 | Hadlaczky et al. | |
| 2002/0160970 | A1 | 10/2002 | Hadlaczky et al. | |
| 2003/0003435 | A1 | 1/2003 | De Jong et al. | |
| 2003/0027337 | A1* | 2/2003 | Droge et al. | 435/456 |
| 2003/0033617 | A1 | 2/2003 | Hadlaczky et al. | |
| 2003/0059940 | A1 | 3/2003 | De Jong et al. | |
| 2003/0083293 | A1 | 5/2003 | Hadlaczky et al. | |
| 2003/0101480 | A1 | 5/2003 | Hadlaczky et al. | |
| 2003/0108914 | A1 | 6/2003 | Hadlaczky et al. | |

(Continued)

FOREIGN PATENT DOCUMENTS

GB 2331752 6/1999

(Continued)

OTHER PUBLICATIONS

Kim et al. (1998) Genome Res. 8:404-412.*
Abremski et al., "Studies on the Properties of P1 Site-Specific Recombination: Evidence for Topologically Unlinked Products following Recombination", *Cell*, 32:1301-1311, (1983).
Albert et al., "Site-specific integration of DNA into wild-type and mutant lox sites placed in the plant genome," *Plant J.* Apr. 7(4):649-59 (1995).
Albrecht et al., "Cationic lipide mediated transfer of c-abl and bcr antisense oligonucleotides to immature normal myeloid cells: Uptake, biological effects and modulation of gene expression", *Ann. Hematol.*, 72:73-79 (1996).

(Continued)

*Primary Examiner*—Nancy Vogel
(74) *Attorney, Agent, or Firm*—Jonathan M. Dermott; Edward R. Gimmi

(57) ABSTRACT

Artificial chromosomes, including ACes, that have been engineered to contain available sites for site-specific, recombination-directed integration of DNA of interest are provided. These artificial chromosomes permit tractable, efficient, rational engineering of the chromosome for a variety of applications.

24 Claims, 15 Drawing Sheets

U.S. PATENT DOCUMENTS

| | | | |
|---|---|---|---|
| 2003/0113917 A1 | 6/2003 | De Jong et al. |
| 2003/0119104 A1 | 6/2003 | Perkins et al. |
| 2003/0186390 A1 | 10/2003 | De Jong et al. |
| 2003/0224522 A1 | 12/2003 | De Jong et al. |
| 2003/0226164 A1 | 12/2003 | Suttie et al. |
| 2004/0143861 A1 | 7/2004 | Hadlaczky et al. |
| 2004/0163147 A1 | 8/2004 | Hadlaczky et al. |
| 2004/0214290 A1 | 10/2004 | Perez et al. |
| 2005/0112661 A1 | 5/2005 | De Jong et al. |
| 2005/0153909 A1 | 7/2005 | Hadlaczky et al. |
| 2006/0024820 A1 | 2/2006 | Perkins et al. |
| 2006/0095984 A1 | 5/2006 | Hadlaczky et al. |
| 2006/0143732 A1 | 6/2006 | Perez et al. |
| 2006/0150271 A1 | 7/2006 | Hadlaczky et al. |
| 2007/0061920 A1 | 3/2007 | Hadlaczky et al. |

FOREIGN PATENT DOCUMENTS

| | | |
|---|---|---|
| WO | 9400569 | 1/1994 |
| WO | 9423049 | 10/1994 |
| WO | 9640724 | 12/1996 |
| WO | 97/37012 | 10/1997 |
| WO | 9740183 | 10/1997 |
| WO | 9808964 | 3/1998 |
| WO | 98/55637 | 12/1998 |
| WO | 99/25821 | 5/1999 |
| WO | 0005393 | 2/2000 |
| WO | 0011155 | 3/2000 |
| WO | 00/55325 | 9/2000 |
| WO | 00/60091 | 10/2000 |
| WO | 01/11020 | 2/2001 |
| WO | 0107572 | 2/2001 |
| WO | 0109351 | 2/2001 |
| WO | 0187936 | 11/2001 |
| WO | 0224930 | 3/2002 |
| WO | WO 02/076508 | 10/2002 |
| WO | WO 02/096923 | 12/2002 |
| WO | WO 02/097059 | 12/2002 |
| WO | WO 03/093469 | 11/2003 |

OTHER PUBLICATIONS

Alton et al., "Nucleotide sequence analysis of the chloramphenicol resistance transposon Tn9", *Nature*, 282:864-869 (1979).
Altschul et al., "Basic Local Alignment Search Tool", *J. Mol. Biol.*, 213:403-414 (1990).
Araki et al., "Site-specific Recombinase, R, Encoded by Yeast Plasmid pSR1", *J. Mol. Biol.*, 225:25-37 (1992).
Araki et al., "Targeted integration of DNA using mutant lox sites in embryonic stem cells," *Nucleic Acids Res.* Feb. 15:25(4):868-72 (1997).
Argos et al., "The integrase family of site-specific recombinases: regional similarities and global diversity," *EMBO J.* Feb;5(2):433-40 (1986).
Auten et al., "Effects of Scaffold Attachment Region on Transgene Expression in Retrovirus Vector-Transduced Primary T Cells and Macrophages", *Hum. Gene Ther.*, 10:1389-1399 (1999).
Baldwin et al., "Cloning of the Luciferase Structural Genes from *Vibrio harveyi* and Expression of Bioluminescense in *Escherichia coli", Biochemistry,* 23:3663-3667 (1984).
Baubonis and Sauer, "Genomic targeting with purified Cre recombinase," *Nucleic Acids Res.* May 11; 21(9):2025-9 (1993).
Bell et al., "Stopped at the border: boundaries and insulators", *Curr. Opin. Gen. Devel.*, 9:191-198 (1999).
Bethke et al., "Segmental genomic replacement by Cre-mediated recombination: genotoxic stress activation of the p53 promoter in single-copy transformants", *Nuc. Acids Res.*, 25(14):2828-2834 (1997).
Borisjuk et al., "Tobacco ribosomal DNA spacer element stimulates amplification and expression of heterologous genes", *Nat. Biotech.*, 18:1303-1306 (2000).
Borisjuk et al., "Structural analysis of rDNA in the genus *Nicotiana", Plant Mol. Biol.*, 35:655-660 (1997).
Bouhassira et al., "Transcriptional Behavior of LCR Enhancer Elements Integrated at the Same Chromosomal Locus by Recombinase-Mediated Cassette Exchange", *Blood,* 90(9): 3332-3344 (1997).
Bouhassira et al., "Recombinase-Mediated-Cassette-Exchange (RMCE): A novel technique for integration of a single copy of transgenes at pre-determined chromosomal sites. Application to the study of the human β-globin LCR", *Blood,* 88(Supp. 1): 190a.
Bragonzi et al., "A new Chinese hamster ovary cell line expressing α2, 6-sialyltransferase used as universal host for the production of human-like sialylated recombinant glycoproteins", *Biochim. Biophys. Acta,* 1474:273-282 (2000).
Broach et al., "Recombinaton within the Yeast Plasmid 2μ Circle is Site-Specific ", *Cell,* 29:227-234 (1982).
Brummelkamp et al., "A System for Stable Expression of Short Interfering RNAs in Mammalian Cells", *Science,* 296:550-553 (2002).
Burke et al., "A mouse genomic library of yeast artificial chromosome clones", *Mammalian Genome,* 1 :65 (1991).
Call et al., "A Cre-*lox* recombination system for the targeted integration of circular yeast artificial chromosomes into embryonic stem cells", *Human Molecular Genetics,* 9(12):1745-1751 (2000).
Campbell et al., "Generation of a nested series of interstitial deletions in yeast artificial chromosomes carrying human DNA", *Proc. Natl. Acad. Sci. USA,* 88:5744-5748 (1991).
Carillo et al., "The Multiple Sequence Alignment Problem in Biology", *SIAM J. Appl. Math.*, 48(5):1073-1082 (1988).
Carswell et al., "Efficiency of Utilization of the Simian Virus 40 Late Polyadenylation Site: Effects of Upstream Sequences", *Mol. Cell. Biol.*, 9(10):4248-4258 (1989).
Cellini et al., "Detection of homologous recombination between yeast artificial chromosomes with overlapping inserts", *Nucl. Acids Res.*, 19(5):997-1000 (1991).
Chapman et al., "Effect of intron A from human cytomegalovirus (Towne) immediately-early gene on heterologous expression in mammalian cells", *Nuc. Acids Res.*, 19(14):3979-3986 (1991).
Chen et al., "Sequence organization of the circular plasmid pKD1 from the yeast *Kluyveromyces drosophilarum", Nuc. Acids Res.*, 14(11):4471-4481 (1986).
Chen et al., Characterization of a circular plasmid from the yeast *Kluyveromyces waltii, J. Gen. Microbiol.*, 138:337-345 (1992).
Choi et al., "A new approach for the identification and cloning of genes: the pBACwich system using Cre/*lox* site-specific recombination", *Nuc. Acids Res.*, 28(7):e19(i-vii) (2000).
Co et al., "Generation of transgenic mice and germline transmission of a mammalian artificial chromosome introduced into embryos by pronuclear microinjection", *Chromosome Research* , 8:183-191 (2000).
Corneille et al., "Efficient elimination of selectable marker genes from the plastid genome by the CRE-lox site -specific recombination system," *Plant J.* Jul;27(2):171-8 (2001).
Crisona et al., "Processive recombination by wild-type Gin and an Enhancer-independent mutant, "*J. Mol. Biol.* 243(3):437-57 (1994).
Cox, Michael M., "The FLP protein of the yeast 2-μm plasmid: Expression of a eukaryotic genetic recombination system in *Escherichia coli", Proc. Natl. Acad. Sci. USA*, 80:4223-4227 (1983).
Csonka et al., "Novel generation of human satellite DNA-based artificial chromosomes in mammalian cells", *J. Cell Sci.*, 113:3207-3216 (2000).
Czerwinski et al., "Human CD34 cells do not express glutathione S-transferase alpha", *Gene Ther.*, 4:268-270 (1997).
Dale et al., "Gene transfer with subsequent removal of the selection gene from the host genome", *Proc. Natl. Acad. Sci. USA*, 88:10558-10562 (1991).
Davies et al., "Somatic and germinal inheritance of FLP-mediated deletion in transgenic tobacco," *J. Exper. Bot. 50*:1447-56 (1999).
Day et al., "Transgene integration into the same chromosome location can produce alleles that express at a predictable level, or alleles that are differently silenced," *Genes Dev.* Nov. 15;14(22):2869-80 (2000).

de Jong et al., "Mammalian Artificial Chromosome Pilot Production Facility: Large-Scale Isolation of Functional Satellite DNA-Based Artificial Chromosomes", *Cytometry,* 35:129-133 (1999).

de Jong et al., "Efficient in-vitro transfer of a 60-Mb mammalian artificial chromosome into murine and hamster cells using cationic lipids and dendrimers", *Chrom. Res.,* 9:475-485 (2001).

Devereux et al., "A comprehensive set of sequence analysis programs for teh VAX", *Nuc. Acids Research,* 12(1):387-295 (1984).

De Wet et al., "Firefly Luciferase Gene: Structure and Expressionin Mammalian Cells", *Molecular and Cellular Biology,* 7(2):725-737 (1987).

Dhar et al., "Transfer of C hinese Hamster Chromosome 1 to Mouse Cells and Regional Assignment of 7 Genes: A Combination of Gene Transfer and Mircocell Fusion", *Somatic Cell and Molecular Genetics,* 10(6):547-559 (1984).

Emery et al., "A chromatin insulator protects retrovirus vectors from chromosomal position effects", *PNAS,* 97:(16):9150-9155 (2000).

Engebrecht, J. and Michael Silverman, "Identification of genes and gene products necessary for bacterial bioluminescence", *Proc. Natl. Acad. Sci. USA*, 81:4154-4158 (1984).

Enomoto et al., "Mapping of the *pin* Locus Coding for a Site-Specific Recombinase That Causes Flagellar-Phrase Variation in *Escherichia coli* K-12", *J. Bacteriol.,* 156(2):663-668 (1983).

Enosawa et al., "An attempt to add biological functions by genetic engineering in order to procuce high-perfomance bioreactor cells for hybrid artificial liver: Transfection of glutamine synthetase into Chinese hamster ovary (CHO) cell", *Cell Transpla.,* 6(5):537-540 (1997).

Enriquez-Harris et al., "A pause site for RNA polymerase II is associated with termination of transcription", *EMBO Journal,* 10(7):1833-1842 (1991).

Falco et al., "Genetic Properties of Chromosomally Integrated 2μ Plasmid DNA in Yeast", *Cell,* 29:573-584 (1982).

Feng et al., "Site-specific chromosomal integration in mammalian cells: highly efficient CRE recombinase-mediated cassette exchange," *J Mol Biol.* Oct. 1;292(4):779-85 (1999).

Ferrari et al., "Chinese Hamster Ovary Cells with Constitutively Expressed Sialidase Anitsense RNA Produce Recombinant DNase in Batch Culture with Increased Sialic Acid", *Biotech. Bioengin.,* 60(5):589-595 (1998).

Finkel and Johnson, "The Fis protein: it's not just for DNA inversion anymore," *Mol Microbiol. Nov*;6(22): 3257-65 (1992).

Frame et al., "Production of fertile transgenic maize plants by silicon carbide whisker-mediated transformation", *Plant J.,* 6(6):941-948 (1994).

Friedman, "Integration host factor: A protein for all reasons," *Cell* 55:545-554 (1988).

Fukushige et al., "Genomic targeting with a positive-selection *lox* integration vector allows highly reproducible gene expression in mammalian cells", *Proc. Natl. Acad. Sci. USA,* 89:7905-7909 (1992).

Gan et al., "Functional Characterization of the Internal Ribosome Entry Site of eIF4G mRNA", *Biol. Chem.,* 273(9):5006-5012 (1998).

Garcia-Ortiz et al., "ΔhGHR, a Novel Biosafe Cell Surface-Labeling Molecule for Analysis and Selection of Genetically Transduced Human Cells", *Hum. Gene Ther.,* 11:333-346 (2000).

Garrick et al., "Repeat-induced gene silencing in mammals", *Nature Genetics,* 18:56-59 (1998).

Gleave et al., "Selectable marker-free transgenic plants without sexual crossing: transient expression of cre recombinase and use of a conditional lethal dominant gene", *Plant Mol Biol. May*;40(2):223-35 (1999).

Golic et al., "The FLP Recombinase of Yeast Catalyzes Site-Specific Recombination in the Drosophila Genome", *Cell,* 59:499-509 (1989).

Goodwin et al., "The 3'-Flanking Sequence of the Bovine Growth Hormone Gene Contains Novel Elements Required for Efficient and Accurate Polyadenylation", *J. Biol. Chem.,* 267(23):16330-16334 (1992).

Gribskov et al., "Sigma factors from *E. coli, B. subtilis,* phage SP01, and phage T4 are homologous proteins", *Nuc. Acids Res.,* 14(16):6745-6763 (1986).

Groth et al., "A phage integrase directs efficient site-specific integration in human cells," *Proc Natl Acad Sci U S A.* May 23;97(11):5995-6000 (2000).

Hadlaczky, Gyula, "Satellite DNA-based artificial chromosomes for use in gene therapy", *Current Opinion in Molecular Therapeutics,* 3(2):125-132 (2001).

Hajdukiewicz et al., "Multiple pathways for Cre/lox-mediated recombination in plastids," *Plant Jul*;27(2):161-70 (2001).

Haldiman, A. and Barry L. Wanner, "Conditional-Replication, Integration, Excision, and retrieval Plasmid-Host Systems for Gene Structure-Function Studies of Bacteria", *Journal of Bacteriology,* 183(21):6384-6393 (2001).

Hall et al., "Expression and Regulation of *Escherichia coli lacZ* Gene Fusions in Mammalian Cells", *J. Mol. Appl. Gen.,* 2:101-109 (1983).

Harborth et al., "Identification of essential genes in cultured mammalian cells using small interfering RNAs", *J. Cell Sci.,* 114:4557-4565 (2001).

Hartman et al., "Two dominant-acting selectable markers for gene transfer studies in mammalian cells", *Proc. Natl. Acad. Sci. USA,* 85:8047-8051 (1988).

Hartmann et al., "Identification of UV/blue light-response elements in the *Arabidopsis thaliana* chalcone synthase promoter using a homologous protoplast transient expression system", *Plant Mol. Biol.,* 36:741-754 (1998).

Hatfull and Grindley, "Resolvases and DNA-Invertases: a family of enzymes active in site-specific recombination," Genetic Recombination, Chap. 11, pp. 357-396 (1998).

Hoess et al., "The role of the *loxP* spacer region in P1 site-specific recombination", *Nuc. Acid. Res.,* 14(5):2287-2300 (1986).

Hoess et al., "P1 site-specific recombination: Nucleotide sequence of the recombining sites", *Proc. Natl. Acad. Sci. USA,* 79:3398-3402 (1982).

Hohn et al., "Elimination of selection markers from transgenic plants," Curr Opin Biotechnol. Apr;12(2):139-43 (2001).

Hollo et al., "Evidence for a megareplicon covering megabases of centronmeric chromosome segments", *Chromosome Research,* 4:240-247 (1996).

Holmen et al., "Efficient Lipid-Mediated Transfection of DNA into Primary Rat Hepatocytes", In Vitro *Cell. Dev. Biol.,* 30:347-351 (1995).

Iglesias et al., "Molecular and cytogenetic analyses of stably and unstably expressed transgene loci in tobacco," *Plant Cell. Aug*;9(8):1251-64 (1997).

Ioannou et al., "A new bacteriophage P1-derived vector for the propagation of large human DNA fragments", *Nat. Genet.,* 6:84-89 (1994).

Ito et al., "Solid phase synthesis of polynucleotides. VI. Further studies on polystyrene copolymers for the solid support", *Nucleic Acids Research* 10(5):1755-1769 (1982).

Jackson et al., "The novel mechanism of initiation of picornavirus RNA translation", *TIBS,* 15:477-483 (1990).

Johnson et al., "Genetic mapping of variable length rDNA segments to centromeric regions of mouse Chromosomes 11, 12, 15, 16, and 18", *Mamm. Genome,* 4:49-52 (1993).

Kereso et al., "De novo chromosome formations by large-scale amplification of the centromeric region of mouse chromosomes", *Chromo. Res.,* 4:226-239 (1996).

Kilby et al., "Site-specific recombinases: tools for genome engineering", *TIG,* 9(12):413-421 (1993).

Kilby et al., "FLP recombinase in transgenic plants: constitutive activity in stably transformed tobacco and generation of marked cell clones in *Arabidopsis", Plant J.,* 8(5):637-642 (1995).

Kilby et al., "Controlled induction of GUS marked clonal sectors in Arabidopsis," *J Exp Bot. May*;51(346):853-63 (2000).

Kim et al., "Development of a serum-free medium for dihydrofolate reductase-deficient Chinese hamster ovary cells (DG44) using a statistical design: beneficial effect of weaning of cells", In Vitro *Cell. Dev. Biol.,* 35:178-182 (1999).

Kim et al., "Use of the human elongation factor 1*x* promoter as a versatile and efficient expression system", *Gene,* 91:217-223 (1990).

Klein et al., "High-velocity microprojectiles for delivering nucleic acids into living cells", *Nature,* 327:70-73 (1987).

Klippel et al., "Analysis of strand exchange and DNA binding of enhancer-independent Gin recombinase mutants", *EMBO J.*, 12(3):1047-1057 (1993).
Kohli et al., "Transgene organization in rice engineered through direct DNA transfer supports a two-phase integration mechanism mediated by the establishment of integration hot spots," *Proc Natl Acad Sci U S A*.Jun. 9;95(12):7203-8 (1998).
Kolb and Siddell, "Genomic targeting of a bicistronic DNA fragment by Cre-mediated site-specific recombination," *Gene*. Dec. 12;203(2):209-16 (1997).
Kolot et al., "Site-specific recombination in mammalian cells expressing the Int recombinase of bacteriophage HK022," *Mol Biol Rep. Aug;*26(3):207-13 (1999).
Kononov et al., "Integration of T-DNA binary vector 'backbone' sequences into the tobacco genome: evidence for multiple complex patterns of integration," *Plant J. May;*11(5):945-57 (1997).
Kooter and Mol, "Trans-inactivation of gene expression in plants," *Curr. Opin. Biotech. 4*:166-171 (1993).
Kozak, Marilyn, "Structural Features in Eukaryotic mRNAs that Modulate the Initiation of Translation", *J. Biol. Chem.*, 266(30):19867-19870 (1991).
Kuroiwa et al., "Manipulation of human minichromosomes to carry greater than megabase-sized chromosome inserts", *Nature Biotech.*, 18:1086-1090 (2000).
Kutsukake et al., "A gene for DNA invertase and an invertible DNA in *Escherichia coli* K-12," *Gene* 34(2-3):343-50 (1985).
Lahm et al., "Identification of transgenic mice by direct PCR analysis of lysates of epithelial cells obtained from the inner surface of the rectum", *Transg. Res.*, 7:131-134, (1998).
Lakso et al., "Targeted oncogene activation by site-specific recombination in transgenic mice", *Proc. Natl. Acad. Sci. USA,* 89:6232-6236 (1992).
Lambert et al., "Functional complementation of ataxia-telangiectasia group D (AT-D) cells by microcell-mediated chromosome transfer and mapping of the AT-D locus to the region 11q22-23", *Proc. Natl. Acad. Sci. USA,* 88:5907-5911 (1991).
Landy, Arthur, "Mechanistic and structural complexity in the site-specific recombination pathways of Int and FLP", *Curr. Opin. Genet. Dev.,* 3:699-707 (1993).
Landy, Arthur, "Dynamic, Structural, and Regulatory Aspects of λ Site-specific Recombination", *Annu. Rev. Biochem.*, 58:913-949 (1989).
Lange-Gustafson et al., "Purification and Properties of Int-h, a Variant Protein Involved in Site-specific Recombination of Bacteriophage λ", *J. Biol. Chem.*, 259(20):12727-12732 (1984).
Le Bolc'h et al., "Cationic Phosphonolipids as non Viral Vectors for DNA Transfection", *Tetra. Letters,* 36(37):6681-6684 (1995).
Levitt et al., "Definition of an efficient synthetic poly(A) site", *Genes and Dev.,* 3:1019-1025 (1989).
Loeffler et al., "Gene Transfer into Primary and Established Mammalian Cell Lines with Lipopolyamine-Coated DNA", *Meth. Enzymol.,* 217:599-629 (1993).
Loonstra et al., "Growth inhibition and DNA damage induced by Cre recombinase in mammalian cells, " *Proc Natl Acad Sci U S A*.Jul. 31;98(16):9209-14 (2001).
Lorbach et al., "Site-specific Recombination in Human Cell Catalyzed by Phage λ Integrase Mutants", *J. Mol. Biol.*, 296:1175-1181 (2000).
Lyznik et al., "Activity of yeast FLP recombinase in maize and rice protoplasts," *Nucleic Acid Res.* Feb. 25:21(4)969-75 (1993).
Lyznik, et al., "FLP-mediated recombination of FRT sites in the maize genome," *Nucleic Acid Res.* Oct. 1;24(19):3784-9 (1996).
Macejak et al., "Internal initiation of translation mediated by the 5' leader of a cellular mRNA", *Nature,* 353:90-94 (1991).
Maeser et al., "The Gin recombinase of phage Mu can catalyse site-specific recombination in plant protoplasts", *Mol. Gen. Genet.*, 230:170-176 (1991).
Matzke et al., "Transgene silencing by the host genome defense: implications for the evolution of epigenetic control mechanisms in plants and vertebrates," *Plant Mol Biol. Jun;*43(2-3):401-15 (2000).
Matsuzaki et al., "Chromosome Engineering in *Saccharomyces cerevisiae* by Using a Site-Specific Recombination System of a Yeast Plasmid", *J. Bacteriol.*, 172:610-618 (1990).
McFarland, Douglas C., "Preparation of pure cell cultures by cloning", *Meth. Cell Sci.*, 22:63-66 (2000).
McNeill et al., "Microcell Fusion", *Meth. Enzymol.,* 254:133-152 (1995).
Medberry et al., "Intra-chromosomal rearrangements generated by Cre-lox site-specific recombination," *Nucleic Acid Res.*Feb. 11;23(3):485-90 (1995).
Meinkoth et al., "Hybridization of Nucleic Acids Immobilized on Solid Supports", *Anal. Biochem.*, 138:267-284 (1984).
Meyer, "Transcriptional transgene silencing and chromatin components," Plant Mol Biol. Jun;43(2-3):221-34 (2000).
Miller et al., "*int*-j: an *int* Mutation of Phage λ That Enhances Site-Specific Recombinaton", *Cell,* 20:721-729 (1980).
Miyagishi et al., "U6 promoter-driven siRNAS with four uridine 3'overhangs efficiently suppress targeted gene expression in mammalian cells", *Nature Biotech.,* 19:497-500 (2002).
Monteith DP, Leung JD, Borowski AH, Co DO, Praznovszky T, Jirik FR, Hadlaczky G, Perez CF, "Pronuclear microinjection of purified artificial chromosomes for generation of transgenic mice: pick-and-inject technique," Method Mol. Biol. 240:227-42 (2004).
Moralli et al., "Insertion of a *lox*P site in a size-reduced human accessory chromosome", *Cytogenet. Cell Genet.,* 94:113-120 (2001).
Moreira et al., "Upstream sequence elements enhance poly(A) site efficiency of the C2 complement gene and are phylogenetically conserved", *EMBO J.,* 14(15):3809-3819 (1995).
Morgan et al., "Characteristics of an Infinite Life Span Diploid Human Fibroblast Cell Strain and a Near-Diploid Strain Arising from a Clone of Cells Expressing a Transfected v-*myc* Oncogene", *Experimental Cell Res.,* 197:125-136 (1991).
Morris, A.E. and James Schmid,"Effects of Insulin and LongR$^3$ on Serum-Free Chinese Hamster Ovary Cell Cultures Expressing Two Recombinant Proteins", *Biotechnol. Prog.,* 16:693-697 (2000).
Muskens et al., "Role of inverted DNA repeats in transcriptional and post-transcriptional gene silencing," *Plant Mol Biol. Jun;*43(2-3):243-60 (2000).
Nanbru et al., "Alternative Translation of the Proto-oncogene c-*myc* by an Internal Ribosome Entry Site", *J. Biol. Chem.*, 272(51):32061-32066 (1997).
NCBI Nucleotide X65279.
NCBI Nucleotide U75992.
NCBI Nucleotide U07648.
NCBI Nucleotide AF272711.
NCBI Nucleotide S69414.
NCBI Nucleotide U09365.
NCBI Nucleotide U13369.
NCBI Nucleotide V00846.
NCBI Nucleotide X82564.
NCBI Nucleotide Y08422.
Needleman et al., "A General Method Applicable to the Search for Similarities in the Amino Acid Sequence of Two Proteins", *J. Mol. Biol.*, 48:443-453 (1970).
Odell et al., "Site-directed recombination in the genome of transgenic tobacco", *Mol. Gen. Genet.*, 223:369-378 (1990).
Ogilvie et al., "Automated Synthesis of Gene Fragments", *Science,* 214:270-274 (1981).
O'Gorman et al., "Recombinase-mediated gene activation and site-specific integration in mammalian cells," *Science*.Mar. 15:251(4999):1351-5 (1991).
Oh et al., "Homeotic gene *Antennapedia* mRNA contains 5'-noncoding sequences that confer translational initiation by internal ribosome binding", *Genes and Dev.,* 6:1643-1653 (1992).
Okabe et al., ""Green mice" as a source of ubiquitous green cells", *FEBS Lett.*, 407:313-319 (1997).
Onouchi et al., "Operation of an efficient site-specific recombination system *Zygosaccharomyces rouxii* in tobacco cells", *Nuc. Acids Res.*, 19(23):6373-6378 (1991).
Onouchi et al., "Visualization of site-specific recombination catalyzed by a recombinase from *Zygosaccharomyces rouxii* in *Arabidopsis thaliana," Mol Gen Genet.* Jun. 25:247(6):653-60 (1995).

Oumard et al., "Translation of NRF mRNA in Mediated by Highly Efficient Internal Ribosome Entry", *Mol. Cell. Biol.*, 20(8):2755-2759 (2000).

Ow, David W., "Recombinase-directed chromosome engineering in plants", *Curr. Opin. Biotechnol.*, 7:181-186 (1996).

Ow, "The right chemistry for marker gene removal?, " *Nat Biotechnol. Feb*;19(2):115-6. No abstract available (2000).

Ow, "Recombinase-directed plant transformation for the post-genomic era," *Plant Molecular Biology*, 48:183-200 (1996).

Park et al., "Expression of carbamoyl phosphate synthetase I and ornithine transcarbamoylase genes in Chinese hamster ovary *dhfr*-cells decreases accumulation of ammonium ion in culture media", *J. Biotechnol.*, 81:129-140 (2000).

Paszkowski et al., "Plant Gene Vectors and Genetic Transformation: DNA-Mediated Direct Gene Transfer to Plants", *Cell Culture and Somatic Cell Genetics of Plants*, 6:51-65 (1989).

Paszkowski et al., "Direct gene transfer to plants", *EMBO J.*, 3(12):2717-2722 (1984).

Pavan et al., "Generation of deletion derivatives by targeted transformaion of human-derived yeast artificial chromosomes", *Proc. Natl. Acad. Sci. USA*, 87:1300-1304 (1990).

Pawliuk et al., "Selection of Retrovirally Transduced Hematopoietic Cells Using CD24 as a Marker of Gene Transfer", *Blood*, 84(9):2968-2877 (1994).

Pawlowski and Somers, "Transgene inheritance in plants genetically engineered by microprojectile bombardment," *Mol Biotechnol. Aug*;6(1):17-30 (1996).

Person et al., "Improved tools for biological sequence comparison", *Proc. Natl. Acad. Sci. USA*, 85:2444-2448 (1988).

Perez et al., "Satellite DNA-based artificial chromosomes-chromosomal vectors", *Trends in Biotechnology*, 18(10):402-403 (2000).

Perez, CF, Vanderbyl SL, Mills KA, Ledebur HC, "The ACE System: A versatile chromosome engineering technology with applications for gene-based cell therapy", BioProcessing 2004; 3:61-68.

Perkins et al., "Yeast and human genes that affect the *Escherichia coli* SOS response", *Proc. Natl. Acad. Sci. USA*, 96:2204-2209 (1999).

Potrykus et al., "Molecular and general genetics of a hybrid foreign gene introduced into tobacco by direct gene transfer", *Mol. Gen. Genet.*, 199:169-177 (1985).

Prati et al., "Antisense Strategies for Glycosylation Engineering of Chinese Hamster Ovary (CHO) Cells", *Biotechnol. Bioeng.*, 59(4):445-450 (1998).

Presentation: Ed Perkins, "An Efficient, Tractable Chromosome-Based Platform For Gene Therapy", BioFuture Conference and Exhibition, Sept. 5, 2001.

Presentation: Ed Perkins, "Development of Chromosome-based Expression Platforms for Therapeutic Protein Production and Human Gene Therapy", UCSF Seminars, Oct. 18, 2001.

Press Release: "Chromos Reports Data on Delivery of Artificial Chromosomes Carrying Genes to Target Cells", Sep. 17, 2001.

Press Release: "Chromos Presents New Chromosome-Based Platform Technology for Gene Therapy", Jun. 4, 2001.

Press Release: "Chromos Initiates Research Into Plant Artificia Chromosomes", Jan. 23, 2001.

Press Release: "Chromos Announces Expression of Therapeutic Protein in Transgenic Animal Carrying an Artificial Chromsome", Nov. 8, 2000.

Press Release: "Chromos and Biological Research Center Announce Publication of Human Artificial Chromosome Methodolgy in the Journal of Cell Science", Sep. 12, 2000.

Press Release: "Chromos Reports Data on Transgenic Animals Carrying Artificial Chromosomes", Mar. 28, 2000.

Press Release: "Chromos Announces US Patents Covering Artificial Chromosome Technology", Mar. 6, 2000.

Press Release: "Chromos Molecular Systems Reports In Vitro and In Vivo Stability of Functional Mammalian Artificial Chromosome", Mar. 18, 1999.

Press Release: "Chromos Molecular Systems Demonstrates Large-Scale Isolation of Mammalian Artificial Chromosomes", Feb. 3, 1999.

Prioleau et al., "An insulator element and condensed chromatin region separate the chicken β-globin locus from an independently regulated erythroid-specific folate receptor gene", *EMBO J.*, 18(14):4035-4048 (1999).

Qin et al., "Cre recombinase-mediated site-specific recombination between plant chromosomes", *Proc. Natl. Acad. Sci. USA*, 91:1706-1710 (1994).

Qin et al., "Site-specific cleavage of chromosmes in vitro through Cre-lox recombination, " *Nucleic Acids Res.* Jun. 11;23(11):1923-7 (1995).

Ramakrishnan et al., "Modulated Binding of SATB1, a Matrix Attachment Region Protein, to the AT-Rich Sequence Flanking the Major Breakpoint Region of *BCL2", Mol. Cell. Biol.*, 20(2):868-877 (2000).

Reich et al., "Efficient Transformation of Alfalfa Protoplasts by the Intranuclear Mircoinjection of Ti Plasmids", *Biotechnology*, 4:1001-1004 (1986).

Remy et al., "Gene Transfer with a Series of Lipophilie DNA-Binding Molecules", *Bioconjugate Chem.*, 5:647-654 (1994).

Rossi et al., "Genomic analysis using a yeast artificial chromosome library with mouse DNA inserts", *Proc. Natl. Acad. Sci. USA*, 89:2456-2460 (1992).

Rowe et al., "Gene mapping 18S ribosomal RNA-related RNA-related loci to mouse Chromosomes 5, 6, 9, 12, 17, 18, 19, and X", *Mammalian Genome*, 7:886-889 (1996).

Russell et al., "Directed excision of a transgene from the plant genome", *Mol. Genet. Genet.*, 234:49-59 (1992).

Sadowski, "Site-specific genetic recombination: hops, flips, and flops," FASEB J. Jun. 1993;7(9):760-7 (1993).

Sadowski, "Stie-specific recombinases: changing partners and doing the twist, " *J. Bacteriol.* Feb.;165(2):341-7 (1986).

Sambrook et al. (Eds.) *Molecular Cloning: A Laboratory Manual*, 2nd Edition, Cold Spring Harbor Laboratory Press, Chapter 8 and p. B6-B14 (1989).

Sanford, J.A. and Elton Stubblefield, "General Protocol for Microcell-Mediated Chromosome Transfer", *Somatic Cell and Molecular Genetics*, 13(3):279-284 (1987).

Sauer, Brian, "Manipulation of Transgenes by Site-Specific Recombination: Use of Cre Recombinase", *Method in Enzymology*, 225:890-900 (1993).

Sauer et al., "Targeted Insertion of Exogenous DNA into the Eukaryotic Genosome by the Cre Recombinase", *New Biologist*, 2(5):441-449 (1990).

Sauer, Brian, "Site-specific recombination: developments and applications", *Curr. Opin. Biotechnol.*, 5:521-527 (1994).

Sburlati et al., "Snythesis of Bisected Glycoforms of Recombinant IFN-β by Overexpression of β- 1,4-*N*-Acetylglucosaminyltransferase III in Chinese Hamster Ovary Cells", *Biotechol. Prog.*, 14:189-192 (1998).

Schmidt et al., "Illegitimate Cre-dependent chromosome rearrangements in transgenic mouse spermatids," *Proc Natl Acad Sci USA*. Dec. 5;97(25):13702-7 (2000).

Schminke, Robert T., "Gene Amplication in Cultured Animals Cells", *Cell*, 37:705-713 (1984).

Schwartz, R.M. and M.O. Dayhoff, "Matrices for Detecting Distant Relationships", *Atlas of Protein Sequence and Structure*, pp. 353-358 (1978).

Seibler et al., "Double-Reciprocal Crossover Mediated by FLP-Recombinase: A Concept and an Assay", *Biochemistry*, 36:1740-1747 (1997).

Seibler et al., "DNA Cassette Exchange in Es Cells Mediated by FLP Recombinase: An Efficient Strategy for Repeated Modification Tagged Loci by Marker-Free Constructs", *Biochemistry*, 37:6229-6234 (1998).

Smith, T.F. and Michael S. Waterman, "Comparison of Biosequences", *Adv. Appl. Math.*, 2:482-489 (1981).

Smith et al., "Multiple mechanisms on *N*-phosphonaceltyl-L-aspartate resistance in human cells lines: Carbamyl-*P* synthetase/aspartate transcarbamylase/dihydro-orotase gene amplification is frequent only when chromosome 2 is rearranged", *Proc. Natl. Acad. Sci. USA*, 94:1816-1821 (1997).

Srivastava et al., "Single-copy transgenic wheat generated through the resolution of complex integration patterns, " *Proc Natl Acad Sci U S A.* Sep. 28;96(20)11117-21. (1999).

Srivastava et al., A general strategy for introducing a single copy transgene into plant genome: deomonstration of single copy transgenic lines of wheat (Triticum aestivum), published on the Internet (1997).

Srivastava et al., "Molecular characterization of the fate of transgenes in transformed wheat (Triticum aestivum L.)," *Theor. Appl. Genet.* 92:1031-1037 (1996).

Srivastava and Ow, "Single-copy primary transformants of maize obtained through the co-introduction of a recombinase-expressing contruct," *Plant Mol Biol. Jul.*; 46(5):561-6 (2001).

Stack et al., "A ubiquitin-based tagging system for controlled modulation of protein stability", *Nature Biotechnol.*, 18:1298-1302 (2000).

Stark et al., "Catalysis by site-specific recombinases", *TIG,* 8(12):432-439 (1992).

Stein et al., "Translation of Vascular Endothelial Growth Factor mRNA by Internal Ribosome Entry: Implications for Translation under Hypoxia", *Mol. Cell. Biol.,* 18(6):3112-3119 (1998).

Stewart et al., "Retrofitting of satellite repeat DNA-based murine artificial chromosome (ACes) to contain IoxP recombination sites", *Gene Therapy,* 9:719-723 (2002).

Stoneley et al., "C-Myc 5' untranslated region contains an internal ribosome entry segment", *Oncogene,* 16:423-428 (1997).

Straus, William M., "Transfection of Mammalian Cells via Lipofection", from *Meth. Mol. Biol.,* (D. Markie, Ed.), *Humana Press, Inc.,* Totowa, NJ. vol. 54, pp. 307-327.

Svenson et al., "Adenovirus 2 early region 1A stimulates expression of both viral and cellular genes", *EMBO J.*, 3(4):789-794 (1984).

Takebe et al., "SRα Promoter: an Efficient and Versatile Mammalian cDNA Expression System Composed of the Simian Virus 40 Early Promoter and the R-US Segment of Human T-Cell Leukemia Virus Type 1 Long Terminal Repeat", *Mol. Cell. Biol.,* 8:466-472 (1988).

Takebe et al., "Generation of Dual Resistance to 4-Hydroperycyclophosphamide and Methotrexate by Retroviral Transfer of the Human Aldehyde Dehydrogenase Class 1 Gene and a Mutated Dihydrofolate Reductase Gene", *Mol. Ther.,* 3:88-96 (2001).

Teifel et al., "New Lipid Mixture for Efficient Lipid-Mediated Trasfection of BHK Cells", *Biotechniques,* 19(1):79-80,82 (1995).

Telenius et al., "Stability of a functional murine satellite DNA-based artificial chromosome across mammalian species", *Chrom. Res.,* 7:3-7 (1999).

*The Arabidopsis Genome Initiative,* "Analysis of the genome sequence of the flowering plant *Arabidopsis thaliana", Nature,* 408:796-815 (2000).

Thorpe and Smith, "In vitro site-specific integration of bacteriophage DNA catalyzed by a recombinase of the resolvase/invertase family," *Proc Natl Acad Sci U S A.* May 12;95(10):5505-10 (1998).

Thyagarajan et al., "Mammalian genomes contain active recombinase recognition sites," *Gene* Feb. 22:244(1-2):47-54 (2000).

Toh et al., "Isolation and characterization of a rat liver alkaline phosphatase gene. A single gene with two promoters", *FEBS,* pp. 331-337 (1989).

Tornow, J. and George M. Santangelo, "Efficient expression of the *Saccharomyces cerevisiae* glycolytic gene *ADH1* is dependent upon a *cis* acting regulatory element ($UAS_{RPG}$) found initially in genes enoding ribosomal proteins", *Gene,* 90:79-85 (1990).

Utatsa et al., "Yeast Plasmids Resembling 2μm DNA: Regional Similarities and Diversities at the Molecular Level", *J. Bacter.,* 169(12):5537-5545 (1987).

Vagner et al., "Alternative Translation of Human Fibroblast Growth Factor 2 mRNA Occurs by Internal Entry of Ribosomes", *Mol. Cell. Biol.,* 15:35-44 (1995).

van Haaren et al., "Prospects of applying a combination of DNA transposition and site-specific recombination in plants: a strategy for gene identification and cloning", *Plant Mol. Biol.,* 23:525-533 (1993).

Vanderbyl et al., "A Flow Cytometry Technique for Measuring Chromosome-Mediated Gene Transfer", *Cytometry,* 44:100-105 (2001).

Vanderbyl S, MacDonald GN, Sidhu S, Gung L, Telenius A, Perez C, Perkins E, "Transfer and stable transgene expression of a mammalian artificial chromosome into bone marrow-derived human mesenchymal stem cells", *Stem Cells* 22(3):324-33 (2004).

Vergunst and Hooykaas, "Cre/lox-mediated site-specific integration of Agrobacterium T-DNA in Arabidopsis thaliana by transient expression of cre," *Plant Mol Biol. Oct.*;38(3):393-406 (1998).

Vergunst et al., "VirB/D4-dependent protein translation from Agrobacterium into plant cells," *Science.* Nov. 3;290(5493):979-82 (2000).

Vergunst et al., "Cre/lox-mediated recombination in Arabidopsis: evidence for transmission of a translocation and a deletion event," *Chromosoma Jul.*; 109(4):287-97 (2000).

Vergunst et al., "Site-specific integration of Agrobacterium T-DNA in Arabidopsis thaliana mediated by Cre recombinase," *Nucleic Acids Res.,* Jun. 1;26(11):2729-34 (1998).

Vollrath et al., "Physical mapping of large DNA by chromosome fragmentation", *Proc. Natl. Acad. Sci. USA,* 85:6027-6031 (1988).

Voziyanov et al., "A general model for site-specific recombination by the integrase family recombinase," Nulceic Acids Res. Feb. 15;27(4):930-41 (1999).

Wang et al., "Expression of a Reporter Gene After Microinjection of Mammalian Artificial Chromosomes Into Pronuclei of Bovine Zygotes", *Molecular Reproduction and Development,* 60:433-438 (2001).

Watson et al., Molecular Biology of the Gene, 4th Ed., The Benjamin/ Cummings Publishing Company, Inc., p. 224.

Weeks et al., "Rapid Production of Multiple Independent Lines of Fertile Transgenic Wheat (Triticum aestivum)," *Plant Physiol. Aug.* ;102(4):1077-1084 (1993).

Wegner et al., "Cis-acting sequencs from mouse rDNA promote plasmid DNA amplification and persistence in mouse cells: implication of HMG-I in their function", *Nuc. Acids Res.,* 17(23):9909-9932 (1989).

Weikert et al., "Engineering Chinese hamster ovary cells to maximize sialic acid content of recombinant glycoproteins", *Nature Biotechn.,* 17:1116:1120 (1999).

Wigler et al., "DNA-mediated transfer of the adenine phosphoribosyltransferase locus into mammalian cells", *Proc. Natl. Acad. Sci. USA,* 76(3)1373-1376 (1979).

Yang et al., "Effects of Ammonia on CHO Cell Growth, Erythropoietin Production, and Glycosylation", *Biotechnol. Bioengin.,* 68:370-830 (2000).

Yang et al., "Visualizing gene expression by whole-body fluorescence imaging", *PNAS,* 97(22):12278-12282 (2000).

Ye et al., "*Ultrabithorax* and *Antennapedia* 5' Untranslated Regions Promote Developmentally Regulated Internal Translation Initiation", *Mol. Cell. Biol.,* 17(3):1714-1721 (1997).

Yu et al., "RNA interference by expression of short-interfering RNAs and hairpin RNAs in mammalian cells", *PNAS,* 99(9):6047-6052 (2002).

Zaworski et al., "Serum-Free Transfection and Selection in Chinese Hamster Ovary (CHO) Cells", *Biotechniques,* 15(5):863-866 (1993).

Zuo et al., "Chemical-regulated, site-specific DNA excision in transgenic plants," Nat Biotechnol. Feb.;19(2):157-61 (2001).

Lindenbaum M, Perkins E, Csonka E, Fleming E, Garcia L, Greene A, Gung L, Hadlaczky G, Lee E, Leung J, MacDonald N, Maxwell A, Mills K, Monteith D, Perez CF, Shellard J, Stewart S, Stodola T, Vandenborre D, Vanderbyl S, Ledebur HC Jr., "A mammalian artificial chromosome engineering system (ACE System) applicable to biopharmaceutical protein production, transgenesis and gene-based cell therapy", *Nucleic Acids Res.,* Dec. 7;32(21):e172 (2004).

Sauer B., "Multiplex Cre/Lox recombination permits selective-site specific DNA targeting to both a natural and an engineered site in the yeast genome", *Nucl. Acids. Res. 24*(23):4608-4613 (1996).

Vasquez et al., "Manipulating the mammalian genome by homologous recombination", *Proc. Natl. Acad. Sci. USA 98*(15):8403-8410 (2001).

Bankhead, et al., "Characterization of mutation of bacteriophage lambda integrase: Putative role in core binding and strand exchange for a converved residue", Jour. Biol. Chem. 275(47):36949-36956 (2000).

Csonka, et al., "Novel generation of human satellite DNA-based artificial chromosomes in mammalian cells", Jour. Cell Science, 113(18):3207-3216 (2000).

Guiducci, et al., "Use of a human minichromosome as a cloning and expression vector for mammalian cells", Human Molec. Genetics, 8(8):1417-1424 (1999).

Kilburn et al., "Insertion of a telomere repeat sequence into a mammlian gene causes chromosome instability", Molec. Cell. Biol. 21(1):126-135 (2001).

Wu et al., "Genetic analysis of second-site revertants of bacteriophage lambda integrase mutants", Jour. Bacteriology 179(12):4030-4038 (1997).

Brown et al., "Artificial chromosomes: ideal_vectors.?" Trends in Biotechnology (_TIBTECH) 18:218-223 (May 2000).

de Jong et al., "Chromosome and DNA-Mediated Gene Transfer in Cultured Mammalian Cells", International Review of Cytology, 92:133-158 (1984).

Hadlaczky and Szalay, Mammalian artificial chromosomes: Introduction of novel genes into mammalian artificial chromosomes, Abstract from International Symposium on Gene Therapy of Cancer, AIDS and Genetic Disorders, Trieste (Italy) (Apr. 10-13, 1996) (available at http://www.chromos.com/contents.html).

Hadlaczky et al., "Centromere proteins", Chromosoma 97:282-288 (1989).

Hadlaczky et al., "Direct evidence for the non-random localization of mammalian chromosomes in the interphase nucleus", Exp. Cell Res. 167:1-15 (1986).

Hadlaczky et al., "DNA Synthesis And Division In Interkingdom Heterokaryons", In Vitro, 16(8):647-650 (1980).

Hadlaczky et al., "Centromere formation in mouse cells cotransformed with human DNA and a dominant marker gene", Proc. Natl. Acad. Sci.USA 88:8106-8110 (1991).

Hadlaczky et al., Protein depleted chromosomes, Chromosoma 81:557-567 (1981).

Hadlaczky et al., Structure of isolated protein-depleted chromosomes of plants, Chromosoma 86:643-659 (1982).

Hadlaczky, Structure of metaphase chromosomes of plants, Internatl. Rev. Cytol. 94:57-76 (1985).

Oberle V, de Jong, G, Drayer, J, Hoekstra, D, "Efficient transfer of chromosome-based DNA contructs into mammalian cells," Biochimica et Biophysica Acta 1676: 223-30 (2004).

Szakal B, Cserpan I, Csonka E, Monostori E, Udvardy A, Hadlaczky G, "Cloning, characterization and localization of Chinese hamster HP1 isoforms", Chromosome Res. 12(5):483-93 (2004).

Assaad, F. and E. Singer, "Somatic and germinal recombination of a direct repeat in Arabidopsis," Genetics, 132:553-556, (1992).

Avramova, Z., "Heterochromatin in animals and plants," Plant Physiology, 129:40-49, (2000).

Brown, W., "Mammalian artificial chromosomes, " Current Opinions in Genetics & Development, 6(3):281-288, (1996).

Brown, W., letter to the Editor in response to "Satellite DNA-based artificial chromosomes-chromosomal vectors," Trends in Biotechnology, 18:403, (2000).

Bryant, J., "Origins and complexes: the initiation of DNA replication, " Journal of Experimental Biology, 52:(355):193-202, (2001).

Burns et al., "Formation of megachromosomes from heterochromatic blocks of Nicotiana Tomentosiformis", Genetics 75:497-502 (1973).

Choi et al., "A new approach for the identification and cloning of gene: the pBACwich system using Cre/*lox* site-specific recombination", Nucleic Acids Research, 28:(7):i-vii (2000).

Co, D.O., et al., "Generation of transgenic mice and germline transmission of a mammalian artificial chromosome introduced into embryos by pronuclear microinjection, " Chromosome Research, 8:183-191, (2000).

Copenhaver, G.P., et al., "Genetic definition and sequence analysis of arabidopsis centromeres," Science, 286:2468-2474, (1999).

de Jong, G., et al., "Efficent in-vitro transfer of 60-Mb mammalian artificial chromosome into murine and hamster cells using cationic lipids and dendrimers, " Chromosome Research, 9(6):475-485, (2001).

Donald, T., et al., "Ribosomal RNA genes specific to the B chromosomes in brachycome dichromosomatica are not transcribed in leaf tissue," Genome, 40:674-681, (1997).

Ferl, et al., in Buchanan et al., Biochemistry & Molecular Biology of Plants, American Society of Plant Physiologists, Rockville, MD 20855, p. 324, (2000).

Gage, F.H., "Cell therapy, " Nature, 392:18-24, (1998).

Gerstel, D.U., "Phenotypic and chromosomal abnormalities associated with the introduction of heterochromation from nicotiana otophora into N. Tabacum, " Genetics, 56:483-502, (1967).

Ohgawara, T., et al., "Uptake of liposome-encapsulated plasmid DNA by plant protoplasts and molecular fate of foreign DNA," Protoplasma, 116:145-148, (1983).

Perez, C., et al., "Satellite DNA-based artificial chromosomes-chromosomal vectors," Trends in Biotechnology, 18:402-403, (2000).

Potrykus, I., "Gene transfer to cereals: an assessment," Bio/Technology, 8(6):535-542, (1990).

Praznovszky, T., al., "De novo chromosome formation in rodent cells," Proceedings of the National Academy or Sciences of the United States of America, 88:11042-11046, (1991).

Saffery, R. and K.H. Choo, "Strategies for engineering human chromosomes with therapeutic protential," Journal of Gene Medicine, 4:5-13, (2002).

Vos, J., "Mammalian artificial chromosomes as tools for gene therapy, " Current Opinions in Genetics & Development, 8:351-359, (1998).

Wada, M., et al., "HPRT yeast artificial chromosome transfer into human cells by four methods and an involvement of homologous recombination," Biochemical and Biophysical Research Communications, 200(3):1693-1700 (1994).

Willard, H., "Artificial chromosomes coming to life," Science, 290:1308-1309, (2000).

* cited by examiner

λ integrase recombination attP × attB ⟶ attL × attR

| | Core Region |
|---|---|
| attP | CAGCTTTTTTATACTAAGTTG |
| attB | CTGCTTTTTTATACTAACTTG |
| attL | CTGCTTTTTTATACTAAGTTG |
| attR | CAGCTTTTTTATACTAACTTG |

pCXLamIntR integrase expression vector

CHROMOSOME-BASED PLATFORMS

RELATED APPLICATIONS

This application is a divisional of and claims priority under 35 U.S.C. §120 to copending U.S. application Ser. No. 10/161,403, filed May 30, 2002, to EDWARD PERKINS, CARL PEREZ, MICHAEL LINDENBAUM, AMY GREENE, JOSEPHINE LEUNG, ELENA FLEMING, SANDRA STEWART and JOAN SHELLARD, entitled "CHROMOSOME-BASED PLATFORMS," which claims benefit of priority under 35 U.S.C. §119(e) to U.S. provisional application Ser. No. 60/294,758, filed May 30, 2001, to EDWARD PERKINS, CARL PEREZ, MICHAEL LINDENBAUM, AMY GREENE and JOSEPHINE LEUNG, entitled "CHROMOSOME-BASED PLATFORMS" and to U.S. provisional application Ser. No. 60/366,891, filed Mar. 21, 2002, to EDWARD PERKINS, CARL PEREZ, MICHAEL LINDENBAUM, AMY GREENE, JOSEPHINE LEUNG, ELENA FLEMING and SANDRA STEWART, entitled "CHROMOSOME-BASED PLATFORMS." The subject matter of each of these applications and provisional applications are herein incorporated by reference in their entirety.

This application is related to Provisional Application No. 60/294,687, filed May 30, 2001, by CARL PEREZ AND STEVEN FABIJANSKI entitled PLANT ARTIFICIAL CHROMOSOMES, USES THEREOF AND METHODS FOR PREPARING PLANT ARTIFICIAL CHROMOSOMES and to U.S. Provisional Application No. 60/296,329, filed Jun. 4, 2001, by CARL PEREZ AND STEVEN FABIJANSKI entitled PLANT ARTIFICIAL CHROMOSOMES, USES THEREOF AND METHODS FOR PREPARING PLANT ARTIFICIAL CHROMOSOMES. This application also is related to the above U.S. Provisional Application No. 60/294,758, filed May 30, 2001, by EDWARD PERKINS et al. entitled CHROMOSOME-BASED PLATFORMS and to the above U.S. Provisional Application No. 60/366,891, filed Mar. 21, 2002, by EDWARD PERKINS et al. entitled CHROMOSOME-BASED PLATFORMS. This application also is related to U.S. application Ser. No. 10/161,408 and to International PCT application No. PCT/US02/17451, published as WO 2002/096923, each filed on the same day herewith, entitled PLANT ARTIFICIAL CHROMOSOMES, USES THEREOF AND METHODS OF PREPARING PLANT ARTIFICIAL CHROMOSOMES to Perez et al.

This application is related to U.S. application Ser. No. 08/695,191, filed Aug. 7, 1996 by GYULA HADLACZKY and ALADAR SZALAY, entitled ARTIFICIAL CHROMOSOMES, USES THEREOF AND METHODS FOR PREPARING ARTIFICIAL CHROMOSOMES, now U.S. Pat. No. 6,025,155. This application also is related to U.S. application Ser. No. 08/682,080, filed Jul. 15, 1996 by GYULA HADLACZKY and ALADAR SZALAY, entitled ARTIFICIAL CHROMOSOMES, USES THEREOF AND METHODS FOR PREPARING ARTIFICIAL CHROMOSOMES, now U.S. Pat. No. 6,077,697. This application also is related to U.S. application Ser. No. 08/629,822, filed Apr. 10, 1996 by GYULA HADLACZKY and ALADAR SZALAY, entitled ARTIFICIAL CHROMOSOMES, USES THEREOF AND METHODS FOR PREPARING ARTIFICIAL CHROMOSOMES (now abandoned), and also is related to U.S. Pat. No. 6,743,967, which is based on U.S. application Ser. No. 09/096,648, filed Jun. 12, 1998, by GYULA HADLACZKY and ALADAR SZALAY, entitled ARTIFICIAL CHROMOSOMES, USES THEREOF AND METHODS FOR PREPARING ARTIFICIAL CHROMOSOMES and to U.S. application Ser. No. 08/835,682, filed Apr. 10, 1997 by GYULA HADLACZKY and ALADAR SZALAY, entitled ARTIFICIAL CHROMOSOMES, USES THEREOF AND METHODS FOR PREPARING ARTIFICIAL CHROMOSOMES (now abandoned). This application also is related to copending U.S. application Ser. No. 09/724,726, filed Nov. 28, 2000, U.S. application Ser. No. 09/724,872, filed Nov. 28, 2000, U.S. application Ser. No. 09/724,693, filed Nov. 28, 2000, U.S. application Ser. No. 09/799,462, filed Mar. 5, 2001, U.S. application Ser. No. 09/836,911, filed Apr. 17, 2001, and U.S. application Ser. No. 10/125,767, filed Apr. 17, 2002, each of which is by GYULA HADLACZKY and ALADAR SZALAY, and is entitled ARTIFICIAL CHROMOSOMES, USES THEREOF AND METHODS FOR PREPARING ARTIFICIAL CHROMOSOMES. This application also is related to International PCT application No. WO 97/40183. The subject matter of each of these provisional applications, international applications, and applications is incorporated by reference in its entirety.

FIELD OF INVENTION

Artificial chromosomes, including ACes, that have been engineered to contain available sites for site-specific, recombination-directed integration of DNA of interest are provided. These artificial chromosomes permit tractable, efficient, rational engineering of the chromosome.

BACKGROUND

Artificial Chromosomes

A variety of artificial chromosomes for use in plants and animals, particularly higher plants and animals are available. In particular, U.S. Pat. Nos. 6,025,155 and 6,077,697 provide heterochromatic artificial chromosomes designated therein as satellite artificial chromosomes (SATACs) and now designated artificial chromosome expression systems (ACes). These chromosomes are prepared by introducing heterologous DNA into a selected plant or animal cell under conditions that result in integration into a region of the chromosome that leads to an amplification event resulting in production of a dicentric chromosome. Subsequent treatment and growth of cells with dicentric chromosomes, including further amplifications, ultimately results in the artificial chromosomes provided therein. In order to introduce a desired heterologous gene (or a plurality of heterologous genes) into the artificial chromosome, the process is repeated introducing the desired heterologous genes and nucleic acids in the initial targeting step. This process is time consuming and tedious. Hence, more tractable and efficient methods for introducing heterologous nucleic acid molecules into artificial chromosomes, particularly ACes, are needed.

Therefore, it is an object herein to provide engineered artificial chromosomes that permit tractable, efficient and rational engineering of artificial chromosomes.

SUMMARY OF THE INVENTION

Provided herein are artificial chromosomes that permit tractable, efficient and rational engineering thereof. In particular, the artificial chromosomes provided herein contain one or a plurality of loci (sites) for site-specific, recombination-directed integration of DNA. Thus, provided herein are platform artificial chromosome expression systems ("platform ACes") containing single or multiple site-specific, recombination sites. The artificial chromosomes and ACes artificial chromosomes include plant and animal chromosomes. Any recombinase system that effects site-specific recombination is contemplated for use herein.

In one embodiment, chromosomes, including platform ACes, are provided that contain one or more lambda att sites designed for recombination-directed integration in the presence of lambda integrase, and that are mutated so that they do not require additional factors. Methods for preparing such chromosomes, vectors for use in the methods, and uses of the resulting chromosomes also are provided.

Platform ACes containing the recombination site(s) and methods for introducing heterologous nucleic acid into such sites and vectors therefor, are provided.

Also provided herein is a bacteriophage lambda (λ) integrase site-specific recombination system.

Methods using recombinase mediated recombination target gene expression vectors and/or genes for insertion thereof into platform chromosomes and the resulting chromosomes are provided.

Combinations and kits containing the combinations of vectors encoding a recombinase and integrase and primers for introduction of the site recognized thereby also are provided. The kits optionally include instructions for performing site-directed integration or preparation of ACes containing such sites.

Also provided herein are mammalian and plant cells comprising the artificial chromosomes and ACes described herein. The cells can be nuclear donor cells, stem cells, such as a mesenchymal stem cell, a hematopoietic stem cell, an adult stem cell or an embryonic stem cell.

Also provided is a lamba-intR mutein comprising a glutamic acid to arginine change at position 174 of wild-type lambda-integrase3. Also provided are transgenic animals and methods for producing a transgenic animal, comprising introducing a ACes into an embryonic cell, such as a stem cell or embryo. The ACes can comprise heterologous nucleic acid that encodes a therapeutic product. The transgenic animal can be a fish, insect, reptile, amphibians, arachnid or mammal. In certain embodiments, the ACes is introduced by cell fusion, lipid-mediated transfection by a carrier system, microinjection, microcell fusion, electroporation, microprojectile bombardment or direct DNA transfer.

The platform ACes, including plant and animal ACes, such as MACs, provided herein can be introduced into cells, such as, but not limited to, animal cells, including mammalian cells, and into plant cells. Hence plant cells that contain platform MACs, animal cells that contain platform PACs and other combinations of cells and platform ACes are provided.

DETAILED DESCRIPTION OF THE INVENTION

A. Definitions

Figure 1:
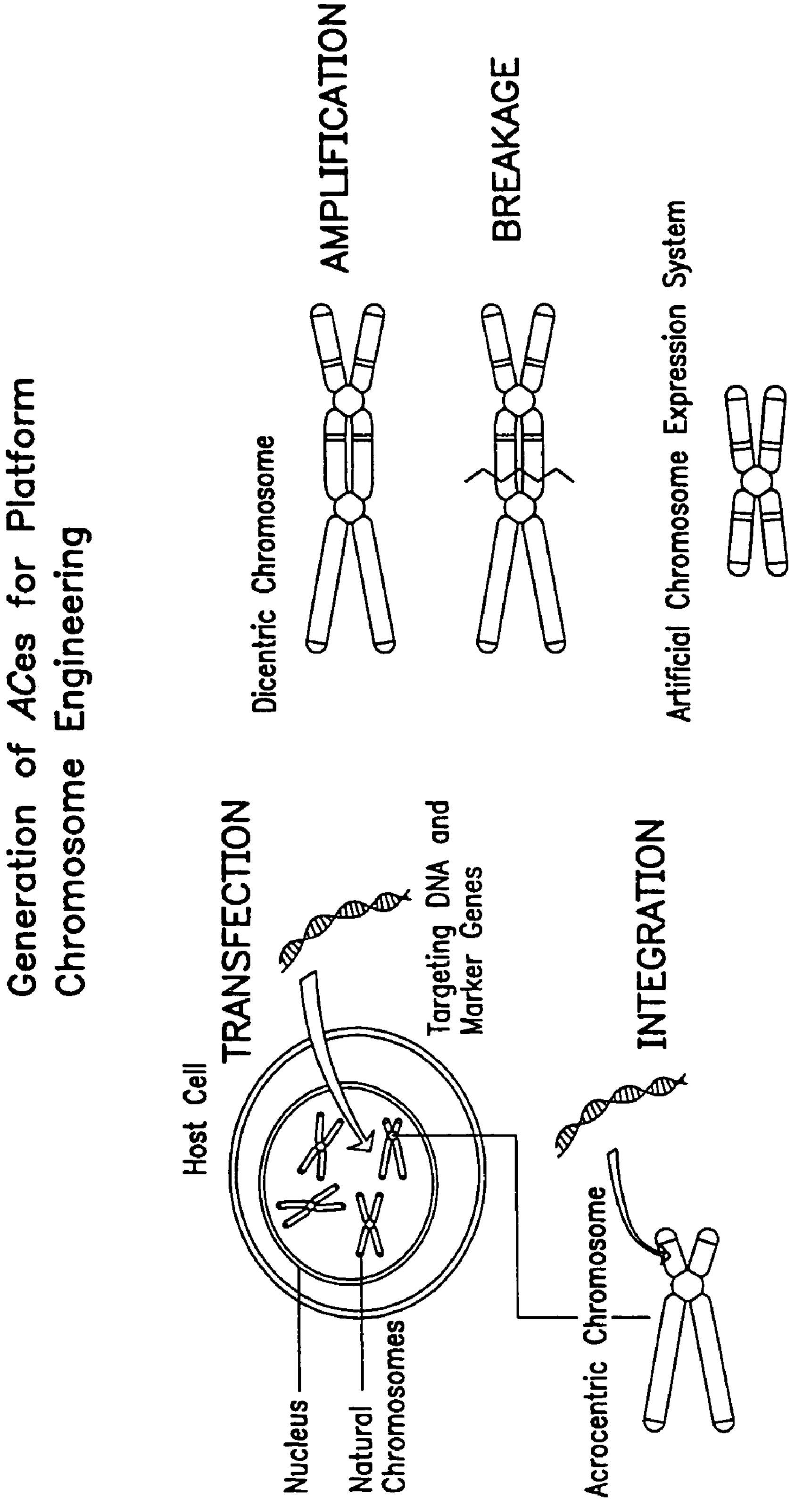
FIG. 1 provides a diagram depicting creation of an exemplary ACes artificial chromosome prepared using methods detailed in U.S. Pat. Nos. 6,025,155 and 6,077,697 and International PCT application No. WO 97/40183 . In this exemplified embodiment, the nucleic acid is targeted to an acrocentric chromosome in an animal or plant, and the heterologous nucleic acid includes a sequence-specific recombination site and marker genes.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. Where reference is made to a URL or other such indentifier or address, it understood that such identifiers can change and particular information on the internet can come and go, but equivalent information can be found by searching the internet. Reference thereto evidences the availability and public dissemination of such information.

As used herein, nucleic acid refers to single-stranded and/or double-stranded polynucleotides, such as deoxyribonucleic acid (DNA) and ribonucleic acid (RNA), as well as analogs or derivatives of either RNA or DNA. Also included in the term "nucleic acid" are analogs of nucleic acids such as peptide nucleic acid (PNA), phosphorothioate DNA, and other such analogs and derivatives. When referring to probes or primers, optionally labeled, with a detectable label, such as a fluorescent or radiolabel, single-stranded molecules are contemplated. Such molecules are typically of a length such that they are statistically unique and of low copy number (typically less than 5, preferably less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleotides long.

As used herein, DNA is meant to include all types and sizes of DNA molecules including cDNA, plasmids and DNA including modified nucleotides and nucleotide analogs.

As used herein, nucleotides include nucleoside mono-, di-, and triphosphates. Nucleotides also include modified-nucleotides, such as, but are not limited to, phosphorothioate nucleotides and deazapurine nucleotides and other nucleotide analogs.

As used herein, heterologous or foreign DNA and RNA are used interchangeably and refer to DNA or RNA that does not occur naturally as part of the genome in which it is present or which is found in a location or locations and/or in amounts in a genome or cell that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Heterologous DNA and RNA may also encode RNA or proteins that mediate or alter expression of endogenous DNA by affecting transcription, translation, or other regulatable biochemical processes.

Examples of heterologous DNA include, but are not limited to, DNA that encodes a gene product or gene product(s) of interest, introduced for purposes of modification of the endogenous genes or for production of an encoded protein. For example, a heterologous or foreign gene may be isolated from a different species than that of the host genome, or alternatively, may be isolated from the host genome but operably linked to one or more regulatory regions which differ from those found in the unaltered, native gene. Other examples of heterologous DNA include, but are not limited to, DNA that encodes traceable marker proteins, such as a protein that confers traits including, but not limited to, herbicide, insect, or disease resistance; traits, including, but not limited to, oil quality or carbohydrate composition. Antibodies that are encoded by heterologous DNA may be secreted or expressed on the surface of the cell in which the heterologous DNA has been introduced.

As used herein, operative linkage or operative association, or grammatical variations thereof, of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA.

In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation.

Alternatively, consensus ribosome binding sites (see, e.g., Kozak (1991) *J. Biol. Chem.* 266:19867-19870) can be inserted immediately 5' of the start codon and may enhance expression.

As used herein, a sequence complementary to at least a portion of an RNA, with reference to antisense oligonucleotides, means a sequence having sufficient complementarity to be able to hybridize with the RNA, preferably under moderate or high stringency conditions, forming a stable duplex. The ability to hybridize depends on the degree of complementarity and the length of the antisense nucleic acid. The longer the hybridizing nucleic acid, the more base mismatches it can contain and still form a stable duplex (or triplex, as the case may be). One skilled in the art can ascertain a tolerable degree of mismatch by use of standard procedures to determine the melting point of the hybridized complex.

As used herein, regulatory molecule refers to a polymer of deoxyribonucleic acid (DNA) or ribonucleic acid (RNA) or a polypeptide that is capable of enhancing or inhibiting expression of a gene.

As used herein, recognition sequences are particular sequences of nucleotides that a protein, DNA, or RNA molecule, or combinations thereof, (such as, but not limited to, a restriction endonuclease, a modification methylase and a recombinase) recognizes and binds. For example, a recognition sequence for Cre recombinase (see, e.g., SEQ ID NO:58) is a 34 base pair sequence containing two 13 base pair inverted repeats (serving as the recombinase binding sites) flanking an 8 base pair core and designated loxP (see, e.g., Sauer (1994) *Current Opinion in Biotechnology* 5:521-527). Other examples of recognition sequences, include, but are not limited to, attB and attP, attR and attL and others (see, e.g., SEQ ID Nos. 8, 41-56 and 72), that are recognized by the recombinase enzyme Integrase (see, SEQ ID Nos. 37 and 38 for the nucleotide and encoded amino acid sequences of an exemplary lambda phage integrase).

The recombination site designated attB is an approximately 33 base pair sequence containing two 9 base pair core-type Int binding sites and a 7 base pair overlap region; attP (SEQ ID No. 72) is an approximately 240 base pair sequence containing core-type Int binding sites and arm-type Int binding sites as well as sites for auxiliary proteins IHF, FIS, and Xis (see, e.g., Landy (1993) *Current Opinion in Biotechnology* 3:699-7071 see, e.g., SEQ ID Nos. 8 and 72).

As used herein, a recombinase is an enzyme that catalyzes the exchange of DNA segments at specific recombination sites. An integrase herein refers to a recombinase that is a member of the lambda (λ) integrase family.

As used herein, recombination proteins include excisive proteins, integrative proteins, enzymes, co-factors and associated proteins that are involved in recombination reactions using one or more recombination sites (see, Landy (1993) *Current Opinion in Biotechnology* 3:699-707). The recombination proteins used herein can be delivered to a cell via an expression cassette on an appropriate vector, such as a plasmid, and the like. In other embodiments, the recombination proteins can be delivered to a cell in protein form in the same reaction mixture used to deliver the desired nucleic acid, such as a platform ACes, donor target vectors, and the like.

As used herein the expression "lox site" means a sequence of nucleotides at which the gene product of the cre gene, referred to herein as Cre, can catalyze a site-specific recombination event. A LoxP site is a 34 base pair nucleotide sequence from bacteriophage P1 (see, e.g., Hoess et al. (1982) *Proc. Natl. Acad. Sci. U.S.A.* 79:3398-3402). The LoxP site contains two 13 base pair inverted repeats separated by an 8 base pair spacer region as follows: (SEQ ID NO. 57):

ATAACTTCGTATA ATGTATGC TATACGAAGTTAT *E. coli*DH5Δlac and yeast strain BSY23 transformed with plasmid pBS44 carrying two loxP sites connected with a LEU2 gene are available from the American Type Culture Collection (ATCC) under accession numbers ATCC 53254 and ATCC 20773, respectively. The lox sites can be isolated from plasmid pBS44 with restriction enzymes EcoRI and SalI, or XhoI and BamHI. In addition, a preselected DNA segment can be inserted into pBS44 at either the SalI or BamHI restriction enzyme sites. Other lox sites include, but are not limited to, LoxB, LoxL, LoxC2 and LoxR sites, which are nucleotide sequences isolated from *E. coli* (see, e.g., Hoess et al. (1982) *Proc. Natl. Acad. Sci. U.S.A.* 79:3398). Lox sites can also be produced by a variety of synthetic techniques (see, e.g., Ito et al. (1982) *Nuc. Acid Res.* 10:1755 and Ogilvie et al. (1981) *Science* 270:270).

As used herein, the expression "cre gene" means a sequence of nucleotides that encodes a gene product that effects site-specific recombination of DNA in eukaryotic cells at lox sites. One cre gene can be isolated from bacteriophage P1 (see, e.g., Abremski et al. (1983) *Cell* 32:1301-1311). *E. coli* DH1 and yeast strain BSY90 transformed with plasmid pBS39 carrying a cre gene isolated from bacteriophage P1 and a GALL regulatory nucleotide sequence are available from the American Type Culture Collection (ATCC) under accession numbers ATCC 53255 and ATCC 20772, respectively. The cre gene can be isolated from plasmid pBS39 with restriction enzymes XhoI and SalI.

As used herein, site-specific recombination refers to site-specific recombination that is effected between two specific sites on a single nucleic acid molecule or between two different molecules that requires the presence of an exogenous protein, such as an integrase or recombinase.

For example, Cre-lox site-specific recombination can include the following three events:

a. deletion of a pre-selected DNA segment flanked by lox sites;
b. inversion of the nucleotide sequence of a pre-selected DNA segment flanked by lox sites; and
c. reciprocal exchange of DNA segments proximate to lox sites located on different DNA molecules.

This reciprocal exchange of DNA segments can result in an integration event if one or both of the DNA molecules are circular. DNA segment refers to a linear fragment of single- or double-stranded deoxyribonucleic acid (DNA), which can be derived from any source. Since the lox site is an asymmetrical nucleotide sequence, two lox sites on the same DNA molecule can have the same or opposite orientations with respect to each other. Recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the gene product of the cre gene. Thus, the Cre-lox system can be used to specifically delete, invert, or insert DNA. The precise event is controlled by the orientation of lox DNA sequences, in cis the lox sequences direct the Cre recombinase to either delete (lox sequences in direct orientation) or invert (lox sequences in inverted orientation) DNA flanked by the sequences, while in trans the lox sequences can direct a homologous recombination event resulting in the insertion of a recombinant DNA.

As used herein, a chromosome is a nucleic acid molecule, and associated proteins, that is capable of replication and segregation within a cell upon cell division. Typically, a chromosome contains a centromeric region, replication origins, telomeric regions and a region of nucleic acid between the centromeric and telomeric regions.

As used herein, a centromere is any nucleic acid sequence that confers an ability to segregate to daughter cells through cell division. A centromere may confer stable segregation of a nucleic acid sequence, including an artificial chromosome containing the centromere, through mitotic or meiotic divisions, including through both mitotic and meiotic divisions. A particular centromere is not necessarily derived from the same species in which it is introduced, but has the ability to promote DNA segregation in cells of that species.

As used herein, euchromatin and heterochromatin have their recognized meanings. Euchromatin refers to chromatin that stains diffusely and that typically contains genes, and heterochromatin refers to chromatin that remains unusually condensed and that has been thought to be transcriptionally inactive. Highly repetitive DNA sequences (satellite DNA) are usually located in regions of the heterochromatin surrounding the centromere (pericentric or pericentromeric heterochromatin). Constitutive heterochromatin refers to heterochromatin that contains the highly repetitive DNA which is constitutively condensed and genetically inactive.

As used herein, an acrocentric chromosome refers to a chromosome with arms of unequal length.

As used herein, endogenous chromosomes refer to genomic chromosomes as found in a cell prior to generation or introduction of an artificial chromosome.

As used herein, artificial chromosomes are nucleic acid molecules, typically DNA, that stably replicate and segregate alongside endogenous chromosomes in cells and have the capacity to accommodate and express heterologous genes contained therein. It has the capacity to act as a gene delivery vehicle by accommodating and expressing foreign genes contained therein. A mammalian artificial chromosome (MAC) refers to chromosomes that have an active mammalian centromere(s). Plant artificial chromosomes, insect artificial chromosomes and avian artificial chromosomes refer to chromosomes that include centromeres that function in plant, insect and avian cells, respectively. A human artificial chromosome (HAC) refers to chromosomes that include centromeres that function in human cells. For exemplary artificial chromosomes, see, e.g., U.S. Pat. Nos. 6,025,155; 6,077,697; 5,288,625; 5,712,134; 5,695,967; 5,869,294; 5,891,691 and 5,721,118 and published International PCT application Nos, WO 97/40183 and WO 98/08964. Artificial chromosomes include those that are predominantly heterochromatic (formerly referred to as satellite artificial chromosomes (SATACs); see, e.g., U.S. Pat. Nos. 6,077,697 and 6,025,155 and published International PCT application No. WO 97/40183), minichromosomes that contain a de novo centromere (see, U.S. Pat. Nos. 5,712,134, 5,891,691 and 5,288,625), artificial chromosomes predominantly made up of repeating nucleic acid units and that contain substantially equivalent amounts of euchromatic and heterochromatic DNA and in vitro assembled artificial chromosomes (see, copending U.S. provisional application Ser. No. 60/294,687, filed on May 30, 2001).

As used herein, the term "satellite DNA-based artificial chromosome (SATAC)" is interchangable with the term "artificial chromosome expression system (ACes)". These artificial chromosomes (ACes) include those that are substantially all neutral non-coding sequences (heterochromatin) except for foreign heterologous, typically gene-encoding nucleic acid, that is interspersed within the heterochromatin for the expression therein (see U.S. Pat. Nos. 6,025,155 and 6,077,697 and International PCT application No. WO 97/40183), or that is in a single locus as provided herein. Also included are ACes that may include euchromatin and that result from the process described in U.S. Pat. Nos. 6,025,155 and 6,077,697 and International PCT application No. WO 97/40183 and outlined herein. The delineating structural feature is the presence of repeating units, that are generally predominantly heterochromatin. The precise structure of the ACes will depend upon the structure of the chromosome in which the initial amplification event occurs; all share the common feature of including a defined pattern of repeating units. Generally ACes have more heterochromatin than euchromatin. Foreign nucleic acid molecules (heterologous genes) contained in these artificial chromosome expression systems can include any nucleic acid whose expression is of interest in a particular host cell. Such foreign nucleic acid molecules, include, but are not limited to, nucleic acid that encodes traceable marker proteins (reporter genes), such as fluorescent proteins, such as green, blue or red fluorescent proteins (GFP, BFP and RFP, respectively), other reporter genes, such as β-galactosidase and proteins that confer drug resistance, such as a gene encoding hygromycin-resistance. Other examples of heterologous nucleic acid molecules include, but are not limited to, DNA that encodes therapeutically effective substances, such as anti-cancer agents, enzymes and hormones, DNA that encodes other types of proteins, such as antibodies, and DNA that encodes RNA molecules (such as antisense or siRNA molecules) that are not translated into proteins.

As used herein, an artificial chromosome platform, also referred to herein as a "platform ACes" or "ACes platform", refers to an artificial chromosome that has been engineered to include one or more sites for site-specific, recombination-directed integration. In particular, ACes that are so-engineered are provided. Any sites, including but not limited to any described herein, that are suitable for such integration are contemplated. Plant and animal platform ACes are provided. Among the ACes contemplated herein are those that are predominantly heterochromatic (formerly referred to as satellite artificial chromosomes (SATACs); see, e.g., U.S. Pat. Nos. 6,077,697 and 6,025,155 and published International PCT application No. WO 97/40183), artificial chromosomes predominantly made up of repeating nucleic acid units and that contain substantially equivalent amounts of euchromatic and heterochromatic DNA resulting from an amplification event depicted in the referenced patent and herein. Included among the ACes for use in generating platforms, are artificial chromosomes that introduce and express heterologous nucleic acids in plants (see, copending U.S. provisional application Ser. No. 60/294,687, filed on May 30, 2001). These include artificial chromosomes that have a centromere derived from a plant, and, also, artificial chromosomes that have centromeres that may be derived from other organisms but that function in plants.

As used herein a "reporter ACes" refers to an ACes that comprises one or a plurality of reporter constructs, where the reporter construct comprises a reporter gene in operative linkage with a regulatory region responsive to test or known compounds.

As used herein, amplification, with reference to DNA, is a process in which segments of DNA are duplicated to yield two or multiple copies of substantially similar or identical or nearly identical DNA segments that are typically joined as substantially tandem or successive repeats or inverted repeats.

As used herein, amplification-based artificial chromosomes are artificial chromosomes derived from natural or endogenous chromosomes by virtue of an amplification event, such as one initiated by introduction of heterologous nucleic acid into rDNA in a chromosome. As a result of such an event, chromosomes and fragments thereof exhibiting segmented or repeating patterns arise. Artificial chromosomes can be formed from these chromosomes and fragments. Hence, amplification-based artificial chromosomes refer to engineered chromosomes that exhibit an ordered segmentation that is not observed in naturally occurring chromosomes and that distinguishes them from naturally occurring chromosomes. The segmentation, which can be visualized using a variety of chromosome analysis techniques known to those of skill in the art, correlates with the structure of these artificial chromosomes. In addition to containing one or more centromeres, the amplification-based artificial chromosomes, throughout the region or regions of segmentation are predominantly made up of nucleic acid units also referred to as "amplicons", that is (are) repeated in the region and that have a similar gross structure. Repeats of an amplicon tend to be of similar size and share some common nucleic acid sequences. For example, each repeat of an amplicon may contain a replication site involved in amplification of chromosome segments and/or some heterologous nucleic acid that was utilized in the initial production of the artificial chromosome. Typically, the repeating units are substantially similar in nucleic acid composition and may be nearly identical.

The amplification-based artificial chromosomes differ depending on the chromosomal region that has undergone amplification in the process of artificial chromosome formation. The structures of the resulting chromosomes can vary depending upon the initiating event and/or the conditions under which the heterologous nucleic acid is introduced, including modification to the endogenous chromosomes. For example, in some of the artificial chromosomes provided herein, the region or regions of segmentation may be made up predominantly of heterochromatic DNA. In other artificial chromosomes provided herein, the region or regions of segmentation may be made up predominantly of euchromatic DNA or may be made up of similar amounts of heterochromatic and euchromatic DNA.

As used herein an amplicon is a repeated nucleic acid unit. In some of the artificial chromosomes described herein, an amplicon may contain a set of inverted repeats of a megareplicon. A megareplicon represents a higher order replication unit. For example, with reference to some of the predominantly heterochromatic artificial chromosomes, the megareplicon can contain a set of tandem DNA blocks (e.g., ~7.5 Mb DNA blocks) each containing satellite DNA flanked by non-satellite DNA or may be made up of substantially rDNA. Contained within the megareplicon is a primary replication site, referred to as the megareplicator, which may be involved in organizing and facilitating replication of the pericentric heterochromatin and possibly the centromeres. Within the megareplicon there may be smaller (e.g., 50-300 kb) secondary replicons.

In artificial chromosomes, such as those provided U.S. Pat. Nos. 6,025,155 and 6,077,697 and International PCT application No. WO 97/40183, the megareplicon is defined by two tandem blocks (~7.5 Mb DNA blocks in the chromosomes provided therein). Within each artificial chromosome or among a population thereof, each amplicon has the same gross structure but may contain sequence variations. Such variations will arise as a result of movement of mobile genetic elements, deletions or insertions or mutations that arise, particularly in culture. Such variation does not affect the use of the artificial chromosomes or their overall structure as described herein.

As used herein, amplifiable, when used in reference to a chromosome, particularly the method of generating artificial chromosomes provided herein, refers to a region of a chromosome that is prone to amplification. Amplification typically occurs during replication and other cellular events involving recombination (e.g., DNA repair). Such regions include regions of the chromosome that contain tandem repeats, such as satellite DNA, rDNA, and other such sequences.

As used herein, a dicentric chromosome is a chromosome that contains two centromeres. A multicentric chromosome contains more than two centromeres.

As used herein, a formerly dicentric chromosome is a chromosome that is produced when a dicentric chromosome fragments and acquires new telomeres so that two chromosomes, each having one of the centromeres, are produced. Each of the fragments is a replicable chromosome. If one of the chromosomes undergoes amplification of primarily euchromatic DNA to produce a fully functional chromosome that is predominantly (at least more than 50%) euchromatin, it is a minichromosome. The remaining chromosome is a formerly dicentric chromosome. If one of the chromosomes undergoes amplification, whereby heterochromatin (such as, for example, satellite DNA) is amplified and a euchromatic portion (such as, for example, an arm) remains, it is referred to as a sausage chromosome. A chromosome that is substantially all heterochromatin, except for portions of heterologous DNA, is called a predominantly heterochromatic artificial chromosome. Predominantly heterochromatic artificial chromosomes can be produced from other partially heterochromatic artificial chromosomes by culturing the cell containing such chromosomes under conditions such as BrdU treatment that destabilize the chromosome and/or growth under selective conditions so that a predominantly heterochromatic artificial chromosome is produced. For purposes herein, it is understood that the artificial chromosomes may not necessarily be produced in multiple steps, but may appear after the initial introduction of the heterologous DNA. Typically, artificial chromosomes appear after about 5 to about 60, or about 5 to about 55, or about 10 to about 55 or about 25 to about 55 or about 35 to about 55 cell doublings after initiation of artificial chromosome generation, or they may appear after several cycles of growth under selective conditions and BrdU treatment.

As used herein, an artificial chromosome that is predominantly heterochromatic (i.e., containing more heterochromatin than euchromatin, typically more than about 50%, more than about 70%, or more than about 90% heterochromatin) may be produced by introducing nucleic acid molecules into cells, such as, for example, animal or plant cells, and selecting cells that contain a predominantly heterochromatic artificial chromosome. Any nucleic acid may be introduced into cells in such methods of producing the artificial chromosomes. For example, the nucleic acid may contain a selectable marker and/or optionally a sequence that targets nucleic acid to the pericentric, heterochromatic region of a chromosome, such as in the short arm of acrocentric chromosomes and nucleolar organizing regions. Targeting sequences include, but are not limited to, lambda phage DNA and rDNA for production of predominantly heterochromatic artificial chromosomes in eukaryotic cells.

After introducing the nucleic acid into cells, a cell containing a predominantly heterochromatic artificial chromosome is selected. Such cells may be identified using a variety of procedures. For example, repeating units of heterochromatic DNA of these chromosomes may be discerned by G-banding and/or fluorescence in situ hybridization (FISH) techniques. Prior to such analyses, the cells to be analyzed may be enriched with artificial chromosome-containing cells by sorting the cells on the basis of the presence of a selectable marker, such as a reporter protein, or by growing (culturing) the cells under selective conditions. It also is possible, after introduction of nucleic acids into cells, to select cells that have a multicentric, typically dicentric, chromosome, a formerly multicentric (typically dicentric) chromosome and/or various heterochromatic structures, such as a megachromosome and a sausage chromosome, that contain a centromere and are predominantly heterochromatic and to treat them such that desired artificial chromosomes are produced. Cells containing a new chromosome are selected. Conditions for generation of a desired structure include, but are not limited to, further growth under selective conditions, introduction of additional nucleic acid molecules and/or growth under selective conditions and treatment with destabilizing agents, and other such methods (see International PCT application No. WO 97/40183 and U.S. Pat. Nos. 6,025,155 and 6,077,697).

As used herein, a "selectable marker" is a nucleic acid segment, generally DNA, that allows one to select for or against a molecule or a cell that contains it, often under particular conditions. These markers can encode an activity, such as, but not limited to, production of RNA, peptide, or protein, or can provide a binding site for RNA, peptides, proteins, inorganic and organic compounds and compositions. Examples of selectable markers include but are not limited to: (1) nucleic acid segments that encode products that provide resistance against otherwise toxic compounds (e.g., antibiotics); (2) nucleic acid segments that encode products that are otherwise lacking in the recipient cell (e.g., tRNA genes, auxotrophic markers); (3) nucleic acid segments that encode products that suppress the activity of a gene product; (4) nucleic acid segments that encode products that can be identified, such as phenotypic markers, including β-galactosidase, red, blue and/or green fluorescent proteins (FPs), and cell surface proteins; (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides or siRNA molecules for use in RNA interference); (7) nucleic acid segments that bind products that modify a substrate (e.g. restriction endonucleases); (8) nucleic acid segments that can be used to isolate a desired molecule (e.g. specific protein binding sites); (9) nucleic acid segments that encode a specific nucleotide sequence that can be otherwise non-functional, such as for PCR amplification of subpopulations of molecules; and/or (10) nucleic acid segments, which when absent, directly or indirectly confer sensitivity to particular compounds. Thus, for example, selectable markers include nucleic acids encoding fluorescent proteins, such as green fluorescent proteins, β-galactosidase and other readily detectable proteins, such as chromogenic proteins or proteins capable of being bound by an antibody and FACs sorted. Selectable markers such as these, which are not required for cell survival and/or proliferation in the presence of a selection agent, also are referred to herein as reporter molecules. Other selectable markers, e.g., the neomycin phosphotransferase gene, provide for isolation and identification of cells containing them by conferring properties on the cells that make them resistant to an agent, e.g., a drug such as an antibiotic, that inhibits proliferation of cells that do not contain the marker.

As another example, interference of gene expression by double stranded RNA has been shown in *Caenorhabditis elegans,* plants, *Drosophila*, protozoans and mammals. This method is known as RNA interference (RNAi) and utilizes short, double-stranded RNA molecules (siRNAs). The siRNAs are generally composed of a 19-22 bp double-stranded RNA stem, a loop region and a 1-4 bp overhang on the 3' end. The reduction of gene expression has been accomplished by direct introduction of the siRNAs into the cell (Harborth J et al., 2001, J Cell Sci 114(pt 24):4557-65) as well as the introduction of DNA encoding and expressing the siRNA molecule. The encoded siRNA molecules are under the regulation of an RNA polymerase III promoter (see, e.g., Yu et al., 2002, Proc Natl Acad Sci USA 99(9);6047-52; Brummelkamp et al., 2002, Science 296(5567):550-3; Miyagishi et al., 2002, Nat Biotechnol 20(5):497-500; and the like). In certain embodiments, RNAi in mammalian cells may have advantages over other therapeutic methods. For example, producing siRNA molecules that block viral genetic activities in infected cells may reduce the effects of the virus. Platform ACes provided herein encoding siRNA molecule(s) are an additional utilization of the platform ACes technology. The platform ACes could be engineered to encode one or more siRNA molecules to create gene "knockdowns". In one embodiment, a platform ACes can be engineered to encode both the siRNA molecule and a replacement gene. For example, a mouse model or cell culture system could be generated using a platform ACes that has a knockdown of the endogenous mouse gene, by siRNA, and the human gene homolog expressing in place of the mouse gene. The placement of siRNA encoding sequences under the regulation of a regulatable or inducible promoter would allow one to temporally and/or spatially control the knockdown effect of the corresponding gene.

As used herein, a reporter gene includes any gene that expresses a detectable gene product, which may be RNA or protein. Generally reporter genes are readily detectable. Examples of reporter genes include, but are not limited to nucleic acid encoding a fluorescent protein, CAT (chloramphenicol acetyl transferase) (Alton et al. (1979) *Nature* 282: 864-869) luciferase, and other enzyme detection systems, such as beta-galactosidase; firefly luciferase (deWet et al. (1987) *Mol. Cell. Biol.* 7:725-737); bacterial luciferase (Engebrecht and Silverman (1984) *Proc. Natl. Acad. Sci. U.S.A.* 81:4154-4158; Baldwin et al. (1984) *Biochemistry* 23:3663-3667); and alkaline phosphatase (Toh et al. (1989) *Eur. J. Biochem.* 182:231-238, Hall et al. (1983)*J. Mol. Appl. Gen.* 2:101).

As used herein, growth under selective conditions means growth of a cell under conditions that require expression of a selectable marker for survival.

As used herein, an agent that destabilizes a chromosome is any agent known by those skilled in the art to enhance amplification events, and/or mutations. Such agents, which include BrdU, are well known to those skilled in the art.

In order to generate an artificial chromosome containing a particular heterologous nucleic acid of interest, it is possible to include the nucleic acid in the nucleic acid that is being introduced into cells to initiate production of the artificial chromosome. Thus, for example, a nucleic acid can be introduced into a cell along with nucleic acid encoding a selectable marker and/or a nucleic acid that targets to a heterochromatic region of a chromosome. For introducing a heterologous nucleic acid into the cell, it can be included in a fragment that includes a selectable marker or as part of a separate nucleic acid fragment and introduced into the cell with a selectable marker during the process of generating the artificial chromosomes. Alternatively, heterologous nucleic acid can be introduced into an artificial chromosome at a later time after the initial generation of the artificial chromosome.

As used herein, the minichromosome refers to a chromosome derived from a multicentric, typically dicentric, chromosome that contains more euchromatic than heterochromatic DNA. For purposes herein, the minichromosome contains a de novo centromere (e.g., a neocentromere). In some embodiments, for example, the minichromosome contains a centromere that replicates in animals, e.g., a mammalian centromere or in plants, e.g., a plant centromere.

As used herein, in vitro assembled artificial chromosomes or synthetic chromosomes can be either more euchromatic than heterochromatic or more heterochromatic than euchromatic and are produced by joining essential components of a chromosome in vitro. These components include at least a centromere, a megareplicator, a telomere and optionally secondary origins of replication.

As used herein, in vitro assembled plant or animal artificial chromosomes are produced by joining essential components (at least the centromere, telomere(s), megareplicator and optional secondary origins of replication) that function in plants or animals. In particular embodiments, the megareplicator contains sequences of rDNA, particularly plant or animal rDNA.

As used herein, a plant is a eukaryotic organism that contains, in addition to a nucleus and mitochondria, chloroplasts capable of carrying out photosynthesis. A plant can be unicellular or multicellular and can contain multiple tissues and/or organs. Plants can reproduce sexually or asexually and can be perennial or annual in growth. Plants can also be terrestrial or aquatic. The term "plant" includes a whole plant, plant cell, plant protoplast, plant calli, plant seed, plant organ, plant tissue, and other parts of a whole plant.

As used herein, stable maintenance of chromosomes occurs when at least about 85%, preferably 90%, more preferably 95%, of the cells retain the chromosome. Stability is measured in the presence of a selective agent. Preferably these chromosomes also are maintained in the absence of a selective agent. Stable chromosomes also retain their structure during cell culturing, suffering no unintended intrachromosomal or interchromosomal rearrangements.

As used herein, de novo with reference to a centromere, refers to generation of an excess centromere in a chromosome as a result of incorporation of a heterologous nucleic acid fragment using the methods herein.

As used herein, BrdU refers to 5-bromodeoxyuridine, which during replication is inserted in place of thymidine. BrdU is used as a mutagen; it also inhibits condensation of metaphase chromosomes during cell division.

As used herein, ribosomal RNA (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In mouse cells, the presence of ribosomal DNA (rDNA, which is DNA containing sequences that encode rRNA) has been verified on at least 11 pairs out of 20 mouse chromosomes (chromosomes 5, 6, 7, 9, 11, 12, 15, 16, 17, 18, and 19) (see e.g., Rowe et al. (1996) *Mamm. Genome* 7:886-889 and Johnson et al. (1993) *Mamm. Genome* 4:49-52). In *Arabidopsis thaliana* the presence of rDNA has been verified on chromosomes 2 and 4 (18S, 5.8S, and 25S rDNA) and on chromosomes 3,4, and 5 (5S rDNA)(see The *Arabidopsis* Genome Initiative (2000) Nature 408:796-815). In eukaryotic cells, the multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence. In the human and mouse, these tandem arrays of rDNA units are located adjacent to the pericentric satellite DNA sequences (heterochromatin). The regions of these chromosomes in which the rDNA is located are referred to as nucleolar organizing regions (NOR) which loop into the nucleolus, the site of ribosome production within the cell nucleus.

As used herein, a megachromosome refers to a chromosome that, except for introduced heterologous DNA, is substantially composed of heterochromatin. Megachromosomes are made up of an array of repeated amplicons that contain two inverted megareplicons bordered by introduced heterologous DNA (see, e.g., FIG. 3 of U.S. Pat. No. 6,077,697 for a schematic drawing of a megachromosome). For purposes herein, a megachromosome is about 50 to 400 Mb, generally about 250-400 Mb. Shorter variants also are referred to as truncated megachromosomes (about 90 to 120 or 150 Mb), dwarf megachromosomes (~150-200 Mb), and a micro-megachromosome (~50-90 Mb, typically 50-60 Mb). For purposes herein, the term megachromosome refers to the overall repeated structure based on an array of repeated chromosomal segments (amplicons) that contain two inverted megareplicons bordered by any inserted heterologous DNA. The size will be specified.

As used herein, gene therapy involves the transfer or insertion of nucleic acid molecules into certain cells, which also are referred to as target cells, to produce specific products that are involved in preventing, curing, correcting, controlling or modulating diseases, disorders and deleterious conditions. The nucleic acid is introduced into the selected target cells in a manner such that the nucleic acid is expressed and a product encoded thereby is produced. Alternatively, the nucleic acid may in some manner mediate expression of DNA that encodes a therapeutic product. This product may be a therapeutic compound, which is produced in therapeutically effective amounts or at a therapeutically useful time. It may also encode a product, such as a peptide or RNA, that in some manner mediates, directly or indirectly, expression of a therapeutic product. Expression of the nucleic acid by the target cells within an organism afflicted with a disease or disorder thereby provides for modulation of the disease or disorder. The nucleic acid encoding the therapeutic product may be modified prior to introduction into the cells of the afflicted host in order to enhance or otherwise alter the product or expression thereof.

For use in gene therapy, cells can be transfected in vitro, followed by introduction of the transfected cells into an organism. This is often referred to as ex vivo gene therapy. Alternatively, the cells can be transfected directly in vivo within an organism.

As used herein, therapeutic agents include, but are not limited to, growth factors, antibodies, cytokines, such as tumor necrosis factors and interleukins, and cytotoxic agents and other agents disclosed herein and known to those of skill in the art. Such agents include, but are not limited to, tumor necrosis factor, α-interferon, β-interferon, nerve growth factor, platelet derived growth factor, tissue plasminogen activator; or, biological response modifiers such as, for example, lymphokines, interleukin-1 (IL-1), interleukin-2 (IL-2), interleukin-6 (IL-6), granulocyte macrophage colony stimulating factor (GMCSF), granulocyte colony stimulating factor (G-CSF), erythropoietin (EPO), pro-coagulants such as tissue factor and tissue factor variants, pro-apoptotic agents such FAS-ligand, fibroblast growth factors (FGF), nerve growth factor and other growth factors.

As used herein, a therapeutically effective product is a product that is encoded by heterologous DNA that, upon introduction of the DNA into a host, a product is expressed that effectively ameliorates or eliminates the symptoms, manifestations of an inherited or acquired disease or that cures the disease.

As used herein, transgenic plants and animals refer to plants and animals in which heterologous or foreign nucleic acid is expressed or in which the expression of a gene naturally present in the plant or animal has been altered by virtue of introduction of heterologous or foreign nucleic acid.

As used herein, IRES (internal ribosome entry site; see, e.g., SEQ ID No. 27 and nucleotides 2736-3308 SEQ ID No. 28) refers to a region of a nucleic acid molecule, such as an mRNA molecule, that allows internal ribosome entry sufficient to initiate translation, which initiation can be detected in an assay for cap-independent translation (see, e.g., U.S. Pat. No. 6,171,821). The presence of an IRES within an mRNA molecule allows cap-independent translation of a linked protein-encoding sequence that otherwise would not be translated.

Internal ribosome entry site (IRES) elements were first identified in picornaviruses, which elements are considered the paradigm for cap-independent translation. The 5' UTRs of all picornaviruses are long and mediate translational initiation by directly recruiting and binding ribosomes, thereby circumventing the initial cap-binding step. IRES elements are frequently found in viral mRNA, they are rare in non-viral mRNA. Among non-viral mRNA molecules that contain functional IRES elements in their respective 5' UTRs are those encoding immunoglobulin heavy chain binding protein (BiP) (Macejak et al. (1991) *Nature* 353:90-94); *Drosophila Antennapedia* (Oh et al. (1992) *Genes Dev,* 6:1643-1653); *D. Ultrabithorax* (Ye et al. (1997) *Mol. Cell Biol.* 17:1714-21); fibroblast growth factor 2 (Vagner et al. (1995) *Mol. Cell Biol.* 15:35-44); initiation factor eIF4G (Gan et al. (1998) *J. Biol. Chem.* 273:5006-5012); proto-oncogene c-myc (Nanbru et al. (1995) *J. Biol. Chem.* 272:32061-32066; Stoneley (1998) *Oncogene* 16:423-428); $IRES_H$; from the 5'UTR of NRF1 gene (Oumard et al. (2000) *Mol. and Cell Biol.,* 20(8):2755-2759); and vascular endothelial growth factor (VEGF) (Stein et al. (1998) *Mol. Cell Biol.* 18:3112-9).

As used herein, a promoter, with respect to a region of DNA, refers to a sequence of DNA that contains a sequence of bases that signals RNA polymerase to associate with the DNA and initiate transcription of RNA (such as pol II for mRNA) from a template strand of the DNA. A promoter thus generally regulates transcription of DNA into mRNA. A particular promoter provided herein is the Ferritin heavy chain promoter (excluding the Iron Response Element, located in the 5'UTR), which was joined to the 37 bp Fer-1 enhancer element. This promoter is set forth as SEQ ID NO:128. The endogenous Fer-1 enhancer element is located upstream of the Fer-1 promoter (e.g., a Fer-1 oligo was cloned proximal to the core promoter).

As used herein, isolated, substantially pure nucleic acid, such as, for example, DNA, refers to nucleic acid fragments purified according to standard techniques employed by those skilled in the art, such as that found in Sambrook et al. ((2001) Molecular Cloning: A Laboratory Manual, Cold Spring Harbor Laboratory Press, Cold Spring Harbor, N.Y., 3rd edition).

As used herein, expression refers to the transcription and/or translation of nucleic acid. For example, expression can be the transcription of a gene that may be transcribed into an RNA molecule, such as a messenger RNA (mRNA) molecule. Expression may further include translation of an RNA molecule and translated into peptides, polypeptides, or proteins. If the nucleic acid is derived from genomic DNA, expression may, if an appropriate eukaryotic host cell or organism is selected, include splicing of the mRNA. With respect to an antisense construct, expression may refer to the transcription of the antisense DNA.

As used herein, vector or plasmid refers to discrete elements that are used to introduce heterologous nucleic acids into cells for either expression of the heterologous nucleic acid or for replication of the heterologous nucleic acid. Selection and use of such vectors and plasmids are well within the level of skill of the art.

As used herein, transformation/transfection refers to the process by which nucleic acid is introduced into cells. The terms transfection and transformation refer to the taking up of exogenous nucleic acid, e.g., an expression vector, by a host cell whether or not any coding sequences are in fact expressed. Numerous methods of transfection are known to the ordinarily skilled artisan, for example, by *Agrobacterium*-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski et al. (1984) *EMBO J.* 3:2717-2722; Potrykus et al. (1985) *Mol. Gen. Genet.* 199:169-177; Reich et al. (1986) *Biotechnology* 4:1001-1004; Klein et al. (1987) *Nature* 327:70-73; U.S. Pat. No. 6,143,949; Paszkowski et al. (1989) in *Cell Culture and Somatic Cell Genetics of Plants, Vol.* 6, Molecular Biology of Plant Nuclear Genes, eds. Schell, J and Vasil, L. K. Academic Publishers, San Diego, Calif., p. 52-68; and Frame et al. (1994) *Plant J.* 6:941-948), direct uptake using calcium phosphate (CaPO4; see,e.g., Wigler et al. (1979) *Proc. Natl. Acad. Sci. U.S.A.* 76:1373-1376), polyethylene glycol (PEG)-mediated DNA uptake, lipofection (see, e.g., Strauss (1996) *Meth. Mol. Biol.* 54:307-327), microcell fusion (see, EXAMPLES, see, also Lambert (1991) *Proc. Natl. Acad. Sci. U.S.A.* 88:5907-5911; U.S. Pat. No. 5,396,767, Sawford et al. (1987) *Somatic Cell Mol. Genet.* 13:279-284; Dhar et al. (1984) *Somatic Cell Mol. Genet.* 10:547-559; and McNeill-Killary et al. (1995) *Meth. Enzymol.* 254:133-152), lipid-mediated carrier systems (see, e.g., Teifel et al. (1995) *Biotechniques* 19:79-80; Albrecht et al. (1996) *Ann. Hematol.* 72:73-79; Holmen et al. (1995) *In Vitro Cell Dev. Biol. Anim.* 31:347-351; Remy et al. (1994) *Bioconjug. Chem.* 5:647-654; Le Bolch et al. (1995) *Tetrahedron Lett.* 36:6681-6684; Loeffler et al. (1993) *Meth. Enzymol.* 217:599-618) or other suitable method. Methods for delivery of ACes are described in copending U.S. application Ser. No. 09/815,979. Successful transfection is generally recognized by detection of the presence of the heterologous nucleic acid within the transfected cell, such as, for example, any visualization of the heterologous nucleic acid or any indication of the operation of a vector within the host cell.

As used herein, "delivery," which is used interchangeably with "transfection," refers to the process by which exogenous nucleic acid molecules are transferred into a cell such that they are located inside the cell. Delivery of nucleic acids is a distinct process from expression of nucleic acids.

As used herein, injected refers to the microinjection, such as by use of a small syringe, needle, or pipette, for injection of nucleic acid into a cell.

As used herein, substantially homologous DNA refers to DNA that includes a sequence of nucleotides that is sufficiently similar to another such sequence to form stable hybrids, with each other or a reference sequence, under specified conditions.

It is well known to those of skill in this art that nucleic acid fragments with different sequences may, under the same conditions, hybridize detectably to the same "target" nucleic acid. Two nucleic acid fragments hybridize detectably, under stringent conditions over a sufficiently long hybridization period, because one fragment contains a segment of at least about 10, 14 or 16 or more nucleotides in a sequence that is complementary (or nearly complementary) to a substantially contiguous sequence of at least one segment in the other nucleic acid fragment. If the time during which hybridization is allowed to occur is held constant, at a value during which, under preselected stringency conditions, two nucleic acid fragments with complementary base-pairing segments hybridize detectably to each other, departures from exact complementarity can be introduced into the base-pairing segments, and base-pairing will nonetheless occur to an extent sufficient to make hybridization detectable. As the departure from complementarity between the base-pairing segments of two nucleic acids becomes larger, and as conditions of the hybridization become more stringent, the probability decreases that the two segments will hybridize detectably to each other.

Two single-stranded nucleic acid segments have "substantially the same sequence", if (a) both form a base-paired duplex with the same segment, and (b) the melting temperatures of the two duplexes in a solution of 0.5×SSPE differ by less than 10° C. If the segments being compared have the same number of bases, then to have "substantially the same sequence", they will typically differ in their sequences at fewer than 1 base in 10. Methods for determining melting temperatures of nucleic acid duplexes are well known (see, e.g., Meinkoth et al. (1984) *Anal. Biochem.* 138:267-284 and references cited therein).

As used herein, a nucleic acid probe is a DNA or RNA fragment that includes a sufficient number of nucleotides to specifically hybridize to DNA or RNA that includes complementary or substantially complementary sequences of nucleotides. A probe may contain any number of nucleotides, from as few as about 10 and as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

To be used as a hybridization probe, the nucleic acid is generally rendered detectable by labeling it with a detectable moiety or label, such as $^{32}P$, $^{3}H$ and $^{14}C$, or by other means, including chemical labeling, such as by nick-translation in the presence of deoxyuridylate biotinylated at the 5'-position of the uracil moiety. The resulting probe includes the biotinylated uridylate in place of thymidylate residues and can be detected (via the biotin moieties) by any of a number of commercially available detection systems based on binding of streptavidin to the biotin. Such commercially available detection systems can be obtained, for example, from Enzo Biochemicals, Inc. (New York, N.Y.). Any other label known to those of skill in the art, including non-radioactive labels, may be used as long as it renders the probes sufficiently detectable, which is a function of the sensitivity of the assay, the time available (for culturing cells, extracting DNA, and hybridization assays), the quantity of DNA or RNA available as a source of the probe, the particular label and the means used to detect the label.

Once sequences with a sufficiently high degree of homology to the probe are identified, they can readily be isolated by standard techniques (see, e.g., Sambrook et al. (2001) *Molecular Cloning: A Laboratory Manual,* 3rd Edition, Cold Spring Harbor Laboratory Press).

As used herein, conditions under which DNA molecules form stable hybrids are considered substantially homologous, and a DNA or nucleic acid homolog refers to a nucleic acid that includes a preselected conserved nucleotide sequence, such as a sequence encoding a polypeptide. By the term "substantially homologous" is meant having at least 75%, preferably 80%, preferably at least 90%, most preferably at least 95% homology therewith or a less percentage of homology or identity and conserved biological activity or function.

The terms "homology" and "identity" are often used interchangeably. In this regard, percent homology or identity may be determined, for example, by comparing sequence information using a GAP computer program. The GAP program utilizes the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unary comparison matrix (containing a value of 1 for identities and 0 for non-identities) and the weighted comparison matrix of Gribskov and Burgess, *Nuc. Acids Res.* 14:6745 (1986), as described by Schwartz and Dayhoff, eds., *ATLAS OF PROTEIN SEQUENCE AND STRUCTURE,* National Biomedical Research Foundation, pp. 353-358 (1979); (2) a penalty of 3.0 for each gap and an additional 0.10 penalty for each symbol in each gap; and (3) no penalty for end gaps.

By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid of interest. Preferably the two molecules will hybridize under conditions of high stringency. Also contemplated are nucleic acid molecules that contain degenerate codons in place of codons in the hybridizing nucleic acid molecule.

Whether any two nucleic acid molecules have nucleotide sequences that are at least 75%, 80%, 85%, 90%, 95%, 96%, 97%, 98% or 99% "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database may be used to determine relative sequence identity.

In general, sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(I):387 (1984)), BLASTP, BLASTN, FASTA (Atschul, S. F., et al., *J Molec Biol* 215:403 (1990)).

Therefore, as used herein, the term "identity" represents a comparison between a test and a reference polypeptide or polynucleotide.

For example, a test polypeptide may be defined as any polypeptide that is 90% or more identical to a reference polypeptide.

As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions.

As used herein: stringency of hybridization in determining percentage mismatch encompass the following conditions or equivalent conditions thereto:

1) high stringency: 0.1×SSPE or SSC, 0.1% SDS, 65° C.

2) medium stringency: 0.2×SSPE or SSC, 0.1% SDS, 50° C.

3) low stringency: 1.0×SSPE or SSC, 0.1% SDS, 50° C.

or any combination of salt and temperature and other reagents that result in selection of the same degree of mismatch or matching. Equivalent conditions refer to conditions that select for substantially the same percentage of mismatch in the resulting hybrids. Additions of ingredients, such as formamide, Ficoll, and Denhardt's solution affect parameters such as the temperature under which the hybridization should be conducted and the rate of the reaction. Thus, hybridization in 5×SSC, in 20% formamide at 42° C. is substantially the same as the conditions recited above hybridization under conditions of low stringency. The recipes for SSPE, SSC and Denhardt's and the preparation of deionized formamide are described, for example, in Sambrook et al. (1989) *Molecular Cloning, A Laboratory Manual*, Cold Spring Harbor Laboratory Press, Chapter 8; see, Sambrook et al., vol. 3, p. B.13, see, also, numerous catalogs that describe commonly used laboratory solutions. It is understood that equivalent stringencies may be achieved using alternative buffers, salts and temperatures. As used herein, all assays and procedures, such as hybridization reactions and antibody-antigen reactions, unless otherwise specified, are conducted under conditions recognized by those of skill in the art as standard conditions.

As used herein, conservative amino acid substitutions, such as those set forth in Table 1, are those that do not eliminate biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Bejacmin/Cummings Pub. co., p.224). Conservative amino acid substitutions are made, for example, in accordance with those set forth in TABLE 1 as follows:

TABLE 1

| Original residue | Conservative substitution |
|---|---|
| Ala (A) | Gly; Ser, Abu |
| Arg (R) | Lys, orn |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val; Met; Nle; Nva |
| Leu (L) | Ile; Val; Met; Nle; Nva |
| Lys (K) | Arg; Gln; Glu |
| Met (M) | Leu; Tyr; Ile; NLe Val |
| Ornithine | Lys; Arg |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met; Nle; Nva |

Other substitutions also are permissible and may be determined empirically or in accord with known conservative substitutions.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, a splice variant refers to a variant produced by differential processing of a primary transcript of genomic DNA that results in more than one type of mRNA.

As used herein, a probe or primer based on a nucleotide sequence includes at least 10, 14, 16, 30 or 100 contiguous nucleotides from the reference nucleic acid molecule.

As used herein, recombinant production by using recombinant DNA methods refers to the use of the well known methods of molecular biology for expressing proteins encoded by cloned DNA.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities may be observed in vitro systems designed to test or use such activities. Thus, for purposes herein the biological activity of a luciferase is its oxygenase activity whereby, upon oxidation of a substrate, light is produced.

The terms substantially identical or similar varies with the context as understood by those skilled in the relevant art and generally means at least 40, 60, 80, 90, 95 or 98%.

As used herein, substantially identical to a product means sufficiently similar so that the property is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, vector (or plasmid) refers to discrete elements that are used to introduce heterologous DNA into cells for either expression or replication thereof. The vectors typically remain episomal, but may be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. An expression vector includes vectors capable of expressing DNA that is operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, protein-binding-sequence refers to a protein or peptide sequence that is capable of specific binding to other protein or peptide sequences generally, to a set of protein or peptide sequences or to a particular protein or peptide sequence.

As used herein, a composition refers to any mixture of two or more ingredients. It may be a solution, a suspension, liquid, powder, a paste, aqueous, non-aqueous or any combination thereof.

As used herein, a combination refers to any association between two or more items.

As used herein, fluid refers to any composition that can flow. Fluids thus encompass compositions that are in the form of semi-solids, pastes, solutions, aqueous mixtures, gels, lotions, creams and other such compositions.

As used herein, a cellular extract refers to a preparation or fraction that is made from a lysed or disrupted cell.

As used herein, the term "subject" refers to animals, plants, insects, and birds and other phyla, genera and species into which nucleic acid molecules may be introduced. Included are higher organisms, such as mammals, fish, insects and birds, including humans, primates, cattle, pigs, rabbits, goats, sheep, mice, rats, guinea pigs, hamsters, cats, dogs, horses, chicken and others.

As used herein, flow cytometry refers to processes that use a laser based instrument capable of analyzing and sorting out cells and or chromosomes based on size and fluorescence.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Recombination Systems

Site-specific recombination systems typically contain three elements: a pair of DNA sequences (the site-specific recombination sequences) and a specific enzyme (the site-specific recombinase). The site-specific recombinase catalyzes a recombination reaction between two site-specific recombination sequences.

A number of different site-specific recombinase systems are available and/or known to those of skill in the art, including, but not limited to: the Cre/lox recombination system using CRE recombinase (see, e.g., SEQ ID Nos. 58 and 59) from the *Escherichia coli* phage P1 (see, e.g., Sauer (1993) *Methods in Enzymology* 225:890-900; Sauer et al. (1990) *The New Biologist* 2:441-449), Sauer (1994) *Current Opinion in Biotechnology* 5:521-527; Odell et al. (1990) *Mol Gen Genet.* 223:369-378; Lasko et al. (1992) *Proc. Natl. Acad. Sci. U.S.A.* 89:6232-6236; U.S. Pat. No. 5,658,772), the FLP/FRT system of yeast using the FLP recombinase (see, SEQ ID Nos. 60 and 61) from the 2μ episome of *Saccharomyces cerevisiae* (Cox (1983) *Proc. Natl. Acad. Sci. U.S.A.* 80:4223; Falco et al. (1982) *Cell* 29:573-584; Golic et al. (1989) *Cell* 59:499-509; U.S. Pat. No. 5,744,336), the resolvases, including Gin recombinase of phage Mu (Maeser et al. (1991) *Mol Gen Genet.* 230:170-176; Klippel, A. et al (1993) *EMBO J.* 12:1047-1057; see, e.g., SEQ ID Nos. 64-67), Cin, Hin, αδ Tn3; the Pin recombinase of *E. coli* (see, e.g., SEQ ID Nos. 68 and 69; Enomoto et al. (1983) *J Bacteriol.* 6:663-668), the R/RS system of the pSR1 plasmid of *Zygosaccharomyces rouxii* (Araki et al. (1992) *J. Mol. Biol.* 225:25-37; Matsuzaki et al. (1990) *J. Bacteriol.* 172: 610-618) and site-specific recombinases from *Kluyveromyces drosophilarium* (Chen et al. (1986) *Nucleic Acids Res.* 314:4471-4481) and *Kluyveromyces waltii* (Chen et al. (1992) *J. Gen. Microbiol.* 138:337-345). Other systems are known to those of skill in the art (Stark et al. *Trends Genet.* 8:432-439; Utatsu et al. (1987) *J. Bacteriol.* 169:5537-5545; see, also, U.S. Pat. No. 6,171,861).

Members of the highly related family of site-specific recombinases, the resolvase family, such as γδ, Tn3 resolvase, Hin, Gin, and Cin also are available. Members of this family of recombinases are typically constrained to intramolecular reactions (e.g., inversions and excisions) and can require host-encoded factors. Mutants have been isolated that relieve some of the requirements for host factors (Maeser et al. (1991) *Mol. Gen. Genet.* 230:170-176), as well as some of the constraints of intramolecular recombination (see, U.S. Pat. No. 6,171,861).

The bacteriophage P1 Cre/lox and the yeast FLP/FRT systems are particularly useful systems for site-specific integration, inversion or excision of heterologous nucleic acid into, and out of, chromosomes, particularly ACes as provided herein. In these systems a recombinase (Cre or FLP) interacts specifically with its respective site-specific recombination sequence (lox or FRT, respectively) to invert or excise the intervening sequences. The sequence for each of these two systems is relatively short (34 bp for lox and 47 bp for FRT).

The FLP/FRT recombinase system has been demonstrated to function efficiently in plant cells (U.S. Pat. No. 5,744,386), and, thus, can be used for producing plant artificial chromosome platforms. In general, short incomplete FRT sites leads to higher accumulation of excision products than the complete full-length FRT sites. The system catalyzes intra- and intermolecular reactions, and, thus, can be used for DNA excision and integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the integration or excision event.

In the Cre-lox system, discovered in bacteriophage P1, recombination between loxP sites occurs in the presence of the Cre recombinase (see, e.g., U.S. Pat. No. 5,658,772). This system can be used to insert, invert or excise nucleic acid located between two lox sites. Cre can be expressed from a vector. Since the lox site is an asymmetrical nucleotide sequence, lox sites on the same DNA molecule can have the same or opposite orientation with respect to each other. Recombination between lox sites in the same orientation results in a deletion of the DNA segment located between the two lox sites and a connection between the resulting ends of the original DNA molecule. The deleted DNA segment forms a circular molecule of DNA. The original DNA molecule and the resulting circular molecule each contain a single lox site. Recombination between lox sites in opposite orientations on the same DNA molecule result in an inversion of the nucleotide sequence of the DNA segment located between the two lox sites. In addition, reciprocal exchange of DNA segments proximate to lox sites located on two different DNA molecules can occur. All of these recombination events are catalyzed by the product of the Cre coding region.

Any site-specific recombinase system known to those of skill in the art is contemplated for use herein. It is contemplated that one or a plurality of sites that direct the recombination by the recombinase are introduced into an artificial chromosome to produce platform ACes. The resulting platform ACes are introduced into cells with nucleic acid encoding the cognate recombinase, typically on a vector, and nucleic acid encoding heterologous nucleic acid of interest linked to the appropriate recombination site for insertion into the platform ACes. The recombinase-encoding-nucleic acid may be introduced into the cells on the same vector, or a different vector, encoding the heterologous nucleic acid.

An *E. coli* phage lambda integrase system for ACes platform engineering and for artificial chromosome engineering is provided (Lorbach et al. (2000) *J. Mol. Biol* 296:1175-1181). The phage lambda integrase (Landy, A. (1989) *Annu. Rev. Biochem.* 58:913-94) is adapted herein and the cognate att sites are provided. Chromosomes, including ACes, engineered to contain one or a plurality of att sites are provided, as are vectors encoding a mutant integrase that functions in the absence other factors. Methods using the modified chromosomes and vectors for introduction of heterologous nucleic acid also are provided.

For purposes herein, one or more of the sites (e.g., a single site or a pair of sites) required for recombination are introduced into an artificial chromosome, such as an ACes chromosome. The enzyme for catalyzing site-directed recombination is introduced with the DNA of interest, or separately, or is engineered onto the artificial chromosome under the control of a regulatable promoter.

As described herein, artificial chromosome platforms containing one or multiple recombination sites are provided. The methods and resulting products are exemplified with the lambda phage Att/Int system, but similar methods may be used for production of ACes platforms with other recombination systems.

The Att/Int system and vectors provided herein are not only intended for engineering ACes platforms, but may be used to engineer an Att/Int system into any chromosome. Introduction of att sites into a chromosome will permit engineering of natural chromosomes, such as by permitting targeted integration genes or regulatory regions, and by controlled excision of selected regions. For example, genes encoding a particular trait may be added to a chromosome, such as plant chromosome engineered to contain one or plurality of att sites. Such chromosomes may be used for screening DNA to identify genes. Large pieces of DNA can be introduced into cells and the cells screened phenotypically to select those having the desired trait.

C. Platforms

Provided herein are platform artificial chromosomes (platform ACes) containing single or multiple site-specific recombination sites.

Chromosome-based platform technology permits efficient and tractable engineering and subsequent expression of multiple gene targets. Methods are provided that use DNA vectors and fragments to create platform artificial chromosomes, including animal, particularly mammalian, artificial chromosomes, and plant artificial chromosomes. The artificial chromosomes contain either single or multiple sequence-specific recombination sites suitable for the placement of target gene expression vectors onto the platform chromosome. The engineered chromosome-based platform ACes technology is applicable for methods, including cellular and transgenic protein production, transgenic plant and animal production and gene therapy. The platform ACes also are useful for producing a library of ACes comprising random portions of a given genome (e.g., a mammalian, plant or prokaryotic genome) for genomic screening; as well as a library of cells comprising different and/or mutually exclusive ACes therein.

Exemplary of artificial chromosome platforms are those based on ACes. ACes artificial chromosomes are non-viral, self-replicating nucleic acid molecules that function as a natural chromosome, having all the elements required for normal chromosomal replication and maintenance within the cell nucleus. ACes artificial chromosomes do not rely on integration into the genome of the cell to be effective, and they are not limited by DNA carrying capacity and as such the therapeutic gene(s) of interest, including regulatory sequences, can be engineered into the ACes. In addition, ACes are stable in vitro and in vivo and can provide predictable long-term gene expression. Once engineered and delivered to the appropriate cell or embryo, ACes work independently alongside host chromosomes, for ACes that are predominantly heterochromatin producing only the products (proteins) from the genes it carries. As provided herein ACes are modified by introduction of recombination site(s) to provide a platform for ready introduction of heterologous nucleic acid. The ACes platforms can be used for production of transgenic animals and plants; as vectors for genetic therapy; for use as protein production systems; for animal models to identify and target new therapeutics; in cell culture for the development and production of therapeutic proteins; and for a variety of other applications.

1. Generation of Artificial Chromosomes

Artificial chromosomes may be generated by any method known to those of skill in the art. Of particular interest herein are the ACes artificial chromosomes, which contain a repeated unit. Methods for production of ACes are described in detail in U.S. Pat. Nos. 6,025,155 and 6,077,697, which, as with all patents, applications, publications and other disclosure, are incorporated herein in their entirety.

Generation of de novo ACes.

ACes can be generated by cotransfecting exogenous DNA—such as a mammary tissue specific DNA cassette including the gene sequences for a therapeutic protein, with a rDNA fragment and a drug resistance marker gene into the desired eukaryotic cell, such as plant or animal cells, such as murine cells in vitro. DNA with a selectable or detectable marker is introduced, and can be allowed to integrate randomly into pericentric heterochromatin or can be targeted to pericentric heterochromatin, such as that in rDNA gene arrays that reside on acrocentric chromosomes, such as the short arms of acrocentric chromosomes. This integration event activates the "megareplicator" sequence and amplifies the pericentric heterochromatin and the exogenous DNA, and duplicates a centromere. Ensuing breakage of this "dicentric" chromosome can result in the production of daughter cells that contain the substantially-original chromosome and the new artificial chromosome. The resulting ACes contain all the essential elements needed for stability and replication in dividing cells—centromere, origins of replications, and telomeres. ACes have been produced that express marker genes (lacZ, green fluorescent protein, neomycin-resistance, puromycin-resistance, hygromycin-resistance) and genes of interest. Isolated ACes, for example, have been successfully transferred intact to rodent, human, and bovine cells by electroporation, sonoporation, microinjection, and transfection with lipids and dendrimers.

To render the creation of ACes with desired genes more tractable and efficient, "platform" ACes (platform-ACes) can be produced that contain defined DNA sequences for enzyme-mediated homologous DNA recombination, such as by Cre or FLP recombinases (Bouhassira et al. (1996) *Blood* 88(*supplement* 1):190a; Bouhassira et al. (1997) *Blood,* 90:3332-3344; Siebler et al. (1997) *Biochemistry:* 36:1740-1747;

Siebler et al. (1998) *Biochemistry* 37: 6229-6234; and Bethke et al. (1997) *Nucl. Acids Res.* 25:2828-2834), and as exemplified herein the lambda phage integrase. A lox site contains two 13 bp inverted repeats to which Cre-recombinase binds and an intervening 8 bp core region. Only pairs of sites having identity in the central 6 bp of the core region are proficient for recombination; sites having non-identical core sequences (heterospecific lox sites) do not efficiently recombine with each other (Hoess et al. (1986) *Nucleic Acids Res.* 14:2287-2300).

Generating Acrocentric Chromosomes for Plant Artificial Chromosome Formation.

In human and mouse cells de novo formation of a satellite DNA based artificial chromosome (SATAC, also referred to as ACes) can occur in an acrocentric chromosome where the short arm contains only pericentric heterochromatin, the rDNA array, and telomere sequences. Plant species may not have any acrocentric chromosomes with the same physical structure described, but "megareplicator" DNA sequences reside in the plant rDNA arrays, also known as the nucleolar organizing regions (NOR). A structure like those seen in acrocentric mammalian chromosomes can be generated using site-specific recombination between appropriate arms of plant chromosomes.

Approach

Qin et al. ((1994) *Proc. Natl. Acad. Sci. U.S.A.* 91:1706-1710, 1994) describes crossing two *Nicotiana tabacum* transgenic plants. One plant contains a construct encoding a promoterless hygromycin-resistance gene preceded by a lox site (lox-hpt), the other plant carries a construct containing a cauliflower mosaic virus 35S promoter linked to a lox sequence and the cre DNA recombinase coding region (35S-lox-cre). The constructs were introduced separately by infecting leaf explants with *agrobacterium tumefaciens* which carries the kanamycin-resistance gene ($Kan^R$). The resultant $Kan^R$ transgenic plants were crossed. Plants that carried the appropriate DNA recombination event were identified by hygromycin-resistance.

Modification of the Above for Generation of ACes

The $Kan^R$ cultivars are initially screened, such as by FISH, to identify two sets of candidate transgenic plants. One set has one construct integrated in regions adjacent to the pericentric heterochromatin on the short arm of any chromosome. The second set of candidate plants has the other construct integrated in the NOR region of appropriate chromosomes. To obtain reciprocal translocation both sites must be in the same orientation. Therefore a series of crosses are required, $Kan^R$ plants generated, and FISH analyses performed to identify the appropriate "acrocentric" plant chromosome for de novo plant ACes formation.

2. Bacteriophage lambda Integrase-Based Site-Specific Recombination System

An integral part of the platform technology includes a site-specific recombination system that allows the placement of selected gene targets or genomic fragments onto the platform chromosomes. Any such system may be used. In particular, a method is provided for insertion of additional DNA fragments into the platform chromosome residing in the cell via sequence-specific recombination using the recombinase activity of the bacteriophage lambda integrase. The lambda integrase system is exemplary of the recombination systems contemplated for ACes. Any known recombination system, including any described herein, particularly any that operates without the need for additional factors or that, by virtue of mutation, does not require additional factors, is contemplated.

As noted the lambda integrase system provided herein can be used with natural chromosomes and artificial chromosomes in addition to ACes. Single or a plurality of recombination sites, which may be the same or different, are introduced into artificial chromosomes to produce artificial chromosome platforms.

3. Creation of Bacteriophage lambda Integrase Site-Specific Recombination System The lambda phage-encoded integrase (designated Int) is a prototypical member of the integrase family. Int effects integration and excision of the phage in and out of the *E. coli* genome via recombination between pairs of attachment sites designated attB/attP and attL/attR. Each att site contains two inverted 9 base pair core Int binding sites and a 7 base pair overlap region that is identical in wild-type att sites. Each site, except for attB contains additional Int binding sites. In flanking regions, there are recognition sequences for accessory DNA binding proteins, such as integration host factor (IHF), factor for inversion stimulation (FIS) and the phage encoded excision protein (XIS). Except for attB, Int is a heterobivalent DNA-binding protein and, with assistance from the accessory proteins and negative DNA supercoiling, binds simultaneously to core and arm sites within the same att site.

Int, like Cre and FLP, executes an ordered sequential pair of strand exchanges during integrative and excisive recombination. The natural pairs of target sequences for Int, attB and attP or attL and attR are located on the same or different DNA molecules resulting in intra or intermolecular recombination, respectively. For example, intramolecular recombination occurs between inversely oriented attB and attP, or between attL and attR sequences, respectively, leading to inversion of the intervening DNA segment.

Like the recombinase systems, such as Cre and FLP, Int directs site-specific recombination. Unlike the other systems, such Cre and FLP, Int generally requires additional protein factors for integrative and excisive recombination and negative supercoiling for integrative recombination. Hence, the Int system had not been used in eukaryotic targeting systems.

Mutant Int proteins, designated Int-h (E174K) and a derivative thereof Int-h/218(E174K/E218K) do not require accessory proteins to perform intramolecular integrative and excisive recombination in co-transfection assays in human cells (Lorbach et al. (2000) *J Mol. Biol.* 25 296:1175-1181); wild-type Int does not catalyze intramolecular recombination in human cells harboring target sites attB and attP. Hence it had been demonstrated that mutant Int can catalyze factor-independent recombination events in human cells.

There has been no demonstration by others that this system can be used for engineering of eukaryotic genomes or chromosomes. Provided herein are chromosomes, including artificial chromosomes, such as but not limited to ACes that contain att sites (e.g., platform ACes), and the use of such chromosomes for targeted integration of heterologous DNA into such chromosomes in eukaryotic cells, including animal, such as rodent and human, and plant cells. Mutant Int provided herein is shown to effect site-directed recombination between sites in artificial chromosomes and vectors containing cognate sites.

An additional component of the chromosome-based platform technology is the site-specific integration of target DNA sequences onto the platform. For this the native bacteriophage lambda integrase has been modified to carry out this sequence specific DNA recombination event in eukaryotic cells. The bacteriophage lambda integrase and its cognate DNA substrate att is a member of the site-specific recombinase family that also includes the bacteriophage P1 Cre/lox system as well as the *Saccharomyces cerevisiae* 2 micron based FLP/FRT system (see, e.g., Landy (1989) *Ann. Rev. Biochem* 58:913-949; Hoess et al. (1982) *Proc. Natl. Acad. Sci. U.S.A.* 79:3398-3402; Broach et al. (1982) *Cell* 29:227-234).

Figure 6:
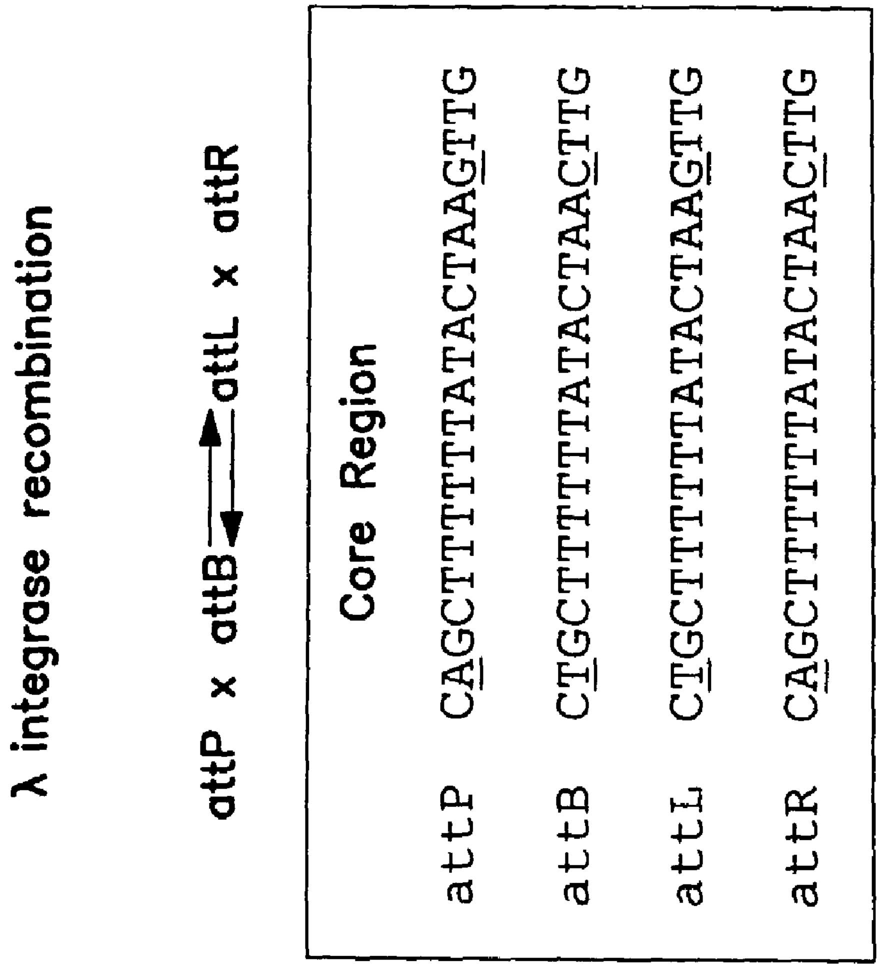
FIG. 6 sets forth the sequences of the core region of attP, attB, attL and attR (SEQ ID Nos. 33-36).

By combining DNA endonuclease and DNA ligase activity these recombinases recognize and catalyze DNA exchanges between sequences flanking the recognition site. During the integration of lambda genome into the *E. coli* (lambda recombination) genome, the phage integrase (INT) in association with accessory proteins catalyzes the DNA exchange between the attP site of the phage genome and the attB site of the bacterial genome resulting in the formation of attL and attR sites (FIG. 6). The engineered bacteriophage lambda integrase has been produced herein to carry out an intermolecular DNA recombination event between an incoming DNA molecule (primarily on a vector containing the bacterial attB site) and the chromosome-based platform carrying the lambda attP sequence independent of lambda bacteriophage or bacterial accessory proteins.

In contrast to the bi-directional Cre/lox and FLP/FRT system, the engineered lambda recombination system derived for chromosome-based platform technology is advantageously unidirectional because accessory proteins, which are absent, are required for excision of integrated nucleic acid upon further exposure to the lambda Int recombinase.

Figure 5:
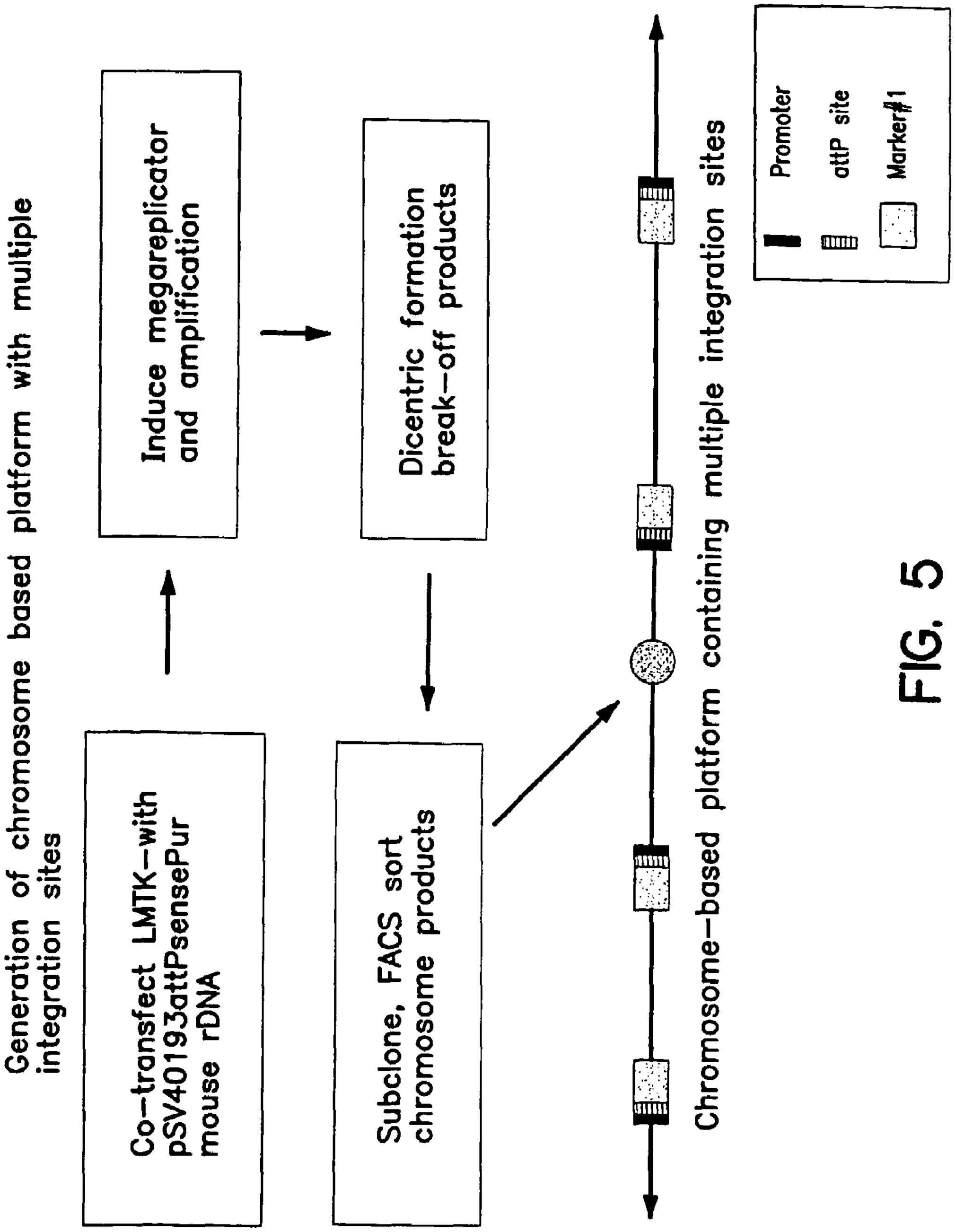
FIG. 5 depicts a method for formation of a chromosome platform with multiple recombination integration sites, such as attP sites.

4. Creation of Platform Chromosome Containing Single or Multiple Sequence-Specific Recombination Sites a. Multiple Sites For the creation of a platform chromosome containing multiple, sequence-specific recombination sites, artificial chromosomes are produced as depicted in FIG. 5 and Example 3. As discussed above, artificial chromosomes can be produced using any suitable methodology, including those described in U.S. Pat. Nos. 5,288,625; 5,712,134; 5,891,691; 6,025,155. Briefly, to prepare artificial chromosomes containing multiple recombination (e.g., integration) sites, nucleic acid (either in the form a one or more plasmids, such as the plasmid pSV40193attPsensePUR set forth in Example 3) is targeted into an amplifiable region of a chromosome, such as the pericentric region of a chromosome. Among such regions are the rDNA gene loci in acrocentric mammalian chromosomes. Hence, targeting nucleic acid for integration into the rDNA region of mammalian acrocentric chromosomes can include the mouse rDNA fragments (for targeting into rodent cell lines) or large human rDNA regions on BAC/PAC vectors (or subclones thereof in standard vectors) for targeting into human acrocentric chromosomes, such as for human gene therapy applications. The targeting nucleic acid generally includes a detectable or selectable marker, such as antibiotic resistance, such as puromycin and hygromycin, a recombination site (such as attP, attB, attL, attR or the like), and/or human selectable markers as required for gene therapy applications. Cells are grown under conditions that result in amplification and ultimately production of ACes artificial chromosomes having multiple recombination (e.g.,integration) sites therein. ACes having the desired size are selected for further engineering.

b. Creation of Platform Chromosome Containing a Single Sequence-Specific Recombination Site In this method a mammalian platform artificial chromosome is generated containing a single sequence-specific recombination site. In the Example below, this approach is demonstrated using a puromycin resistance marker for selection and a mouse rDNA fragment for targeting into the rDNA locus on mouse acrocentric chromosomes. Other selection markers and targeting DNA sequences as desired and known to those of skill in the art can be used. Additional resistance markers include genes conferring resistance to the antibiotics neomycin, blasticidin, hygromycin and zeocin. For applications, such as gene therapy in which potentially immunogenic responses are to be avoided, host, such as human, derived selectable markers or markers detectable with monoclonal antibodies (MAb) followed by fluorescent activated cell sorting (FACS) can be used. Examples in this class include, but are not limited to: human nerve growth factor receptor (detection with MAb); truncated human growth factor receptor (detection with MAb); mutant human dihydrofolate reductase (DHFR; detectable using a fluorescent methotrexate substrate); secreted alkaline phosphatase (SEAP; detectable with fluorescent substrate); thymidylate synthase (TS; confers resistance to fluorodeoxyuridine); human CAD gene (confers resistance to N-phosphonacetyl-L-aspartate (PALA)).

Figure 3:
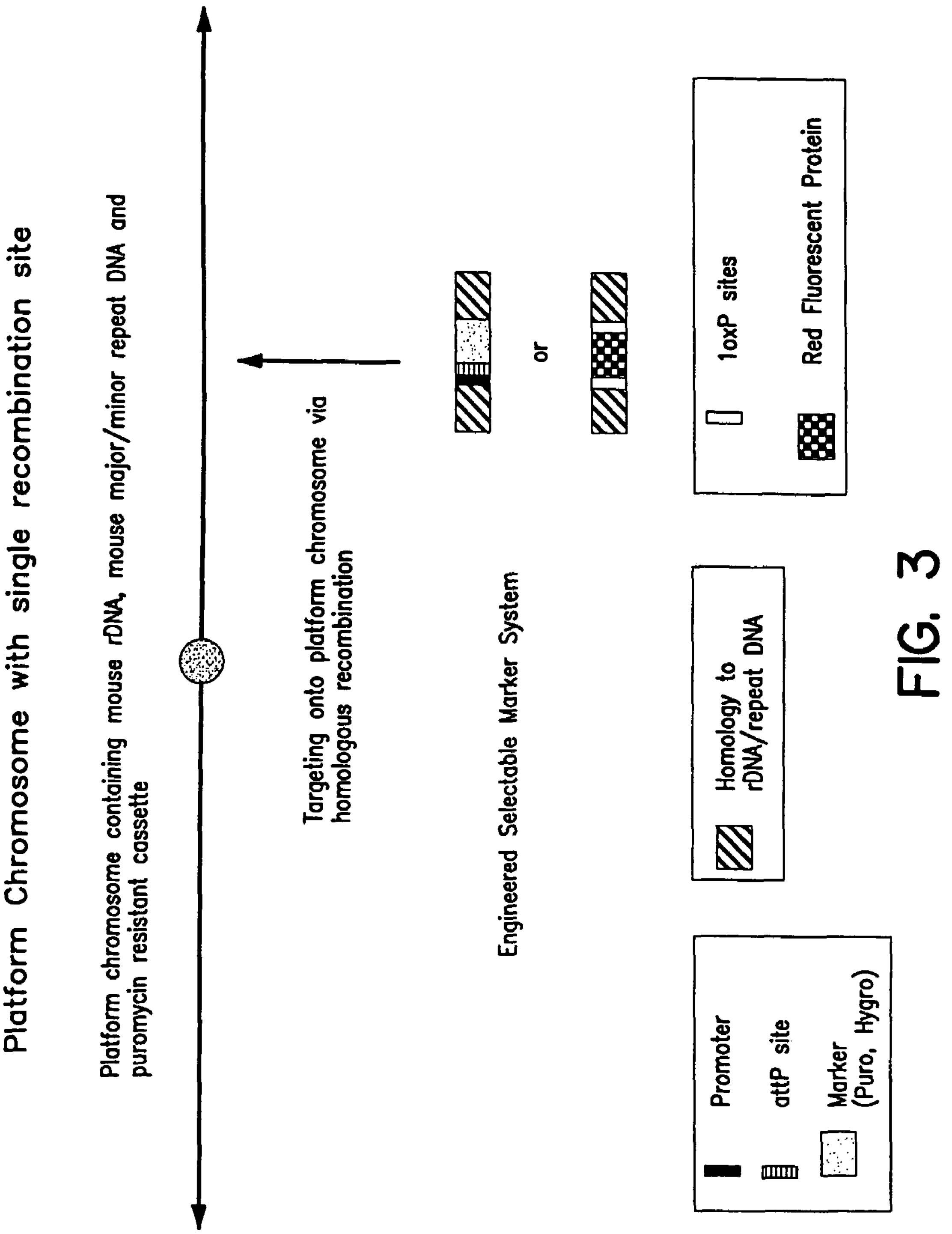
FIG. 3 depicts construction of an ACes platform chromosome with a single recombination site, such as loxP sites or an attP or attB site. This platform ACes chromosome is an exemplary artificial chromosome with a single recombination site.

To construct a platform artificial chromosome with a single site, an ACes artificial chromosome (or other artificial chromosome of interest) can be produced containing a selectable marker. A single sequence specific recombination site is targeted onto ACes via homologous recombination. For this, DNA sequences containing the site-specific recombination sequence are flanked with DNA sequences homologous to a selected sequence in the chromosome. For example, when using a chromosome containing rDNA or satellite DNA, such DNA can be used as homologous sequences to target the site-specific recombination sequence onto the chromosome. A vector is designed to have these homologous sequences flanking the site-specific recombination site and, after the appropriate restriction enzyme digest to generate free ends of homology to the chromosome, the DNA is transfected into cells harboring the chromosome. After transfection and integration of the site-specific cassette, homologous recombination events onto the platform chromosome are subcloned and identified, for example by screening single cell subclones via expression of resistance or a fluorescent marker and PCR analysis. In one embodiment, a platform artificial chromosome, such as a platform ACes, that contains a single copy of the recombination site is selected. Examples 2B and 2D exemplify the process, and FIG. 3 provides a diagram depicting one method for the creation of a platform mammalian chromosome containing a single sequence-specific recombination site.

Figure 9:
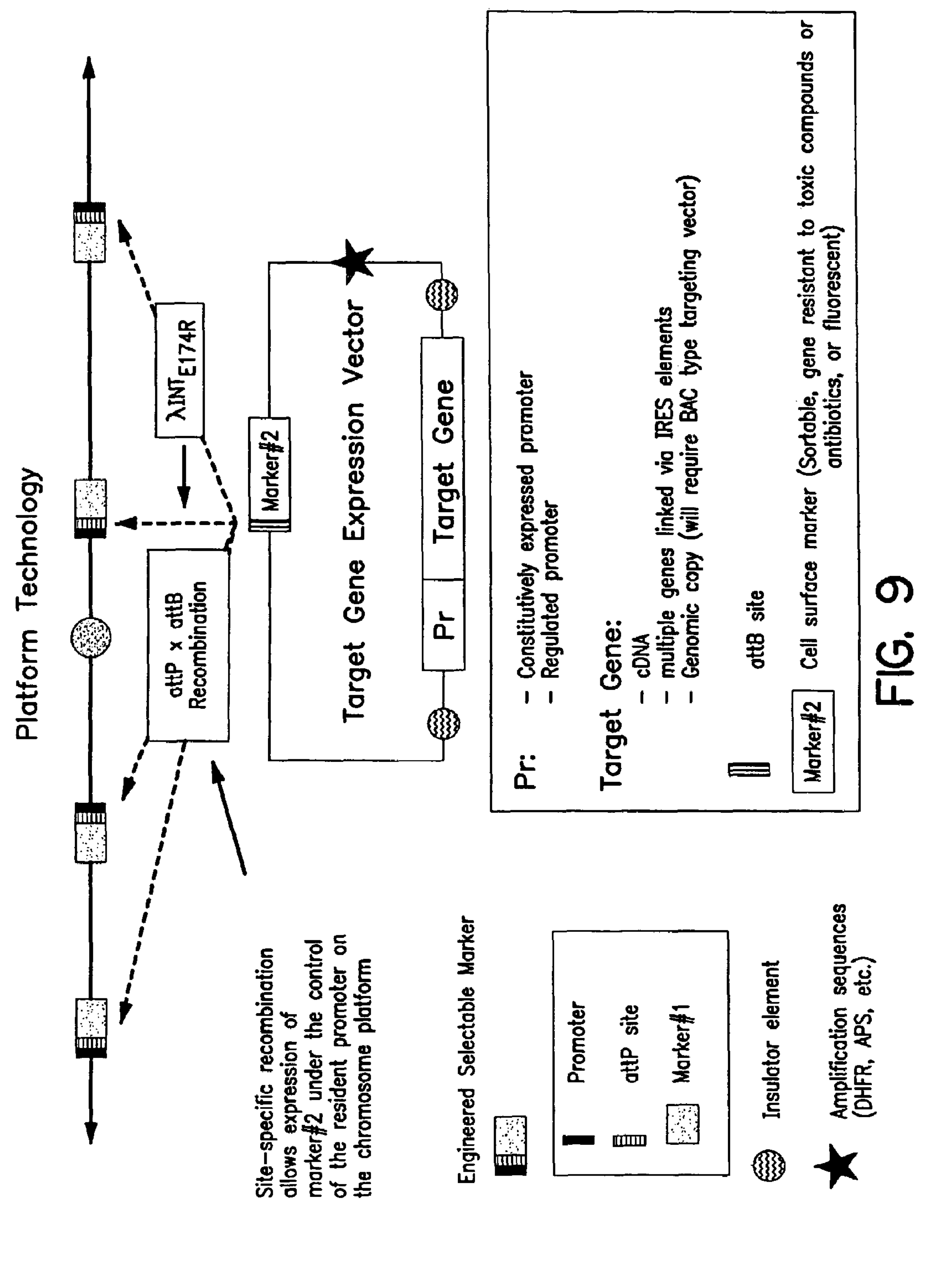
FIG. 9 diagrammatically summarizes the platform technology; marker 1 permits selection of the artificial chromosomes containing the integration site; marker 2, which is promoterless in the target gene expression vector, permits selection of recombinants. Upon recombination with the platform marker 2 is expressed under the control of a promoter resident on the platform.

5. Lambda integrase Mediated Recombination of Target Gene Expression Vector onto Platform Chromosome The third component of the chromosome-based platform technology involves the use of target gene expression vectors carrying, for example, genes for gene therapy, genes for transgenic animal or plant production, and those required for cellular protein production of interest. Using lambda integrase mediated site-specific recombination, or any other recombinase-mediated site-specific recombination, the target gene expression vectors are introduced onto the selected chromosome platform. The use of target gene expression vector permits use of the de novo generated chromosome-based platforms for a wide range of gene targets. Furthermore, chromosome platforms containing multiple attP sites provides the opportunity to incorporate multiple gene targets onto a single platform, thereby providing for expression of multiple gene targets, including the expression of cellular and genetic regulatory genes and the expression of all or parts of metabolic pathways. In addition to expressing small target genes, such as cDNA and hybrid cDNA/artificial intron constructs, the chromosome-based platform can be used for engineering and expressing large genomic fragments carrying target genes along with its endogenous genomic promoter sequences. This is of importance, for example, where the therapy requires precise cell specific expression and in instances where expression is best achieved from genomic clones rather than cDNA clones. FIG. 9 provides a diagram summarizing one embodiment of the chromosome-based technology.

Figure 8:
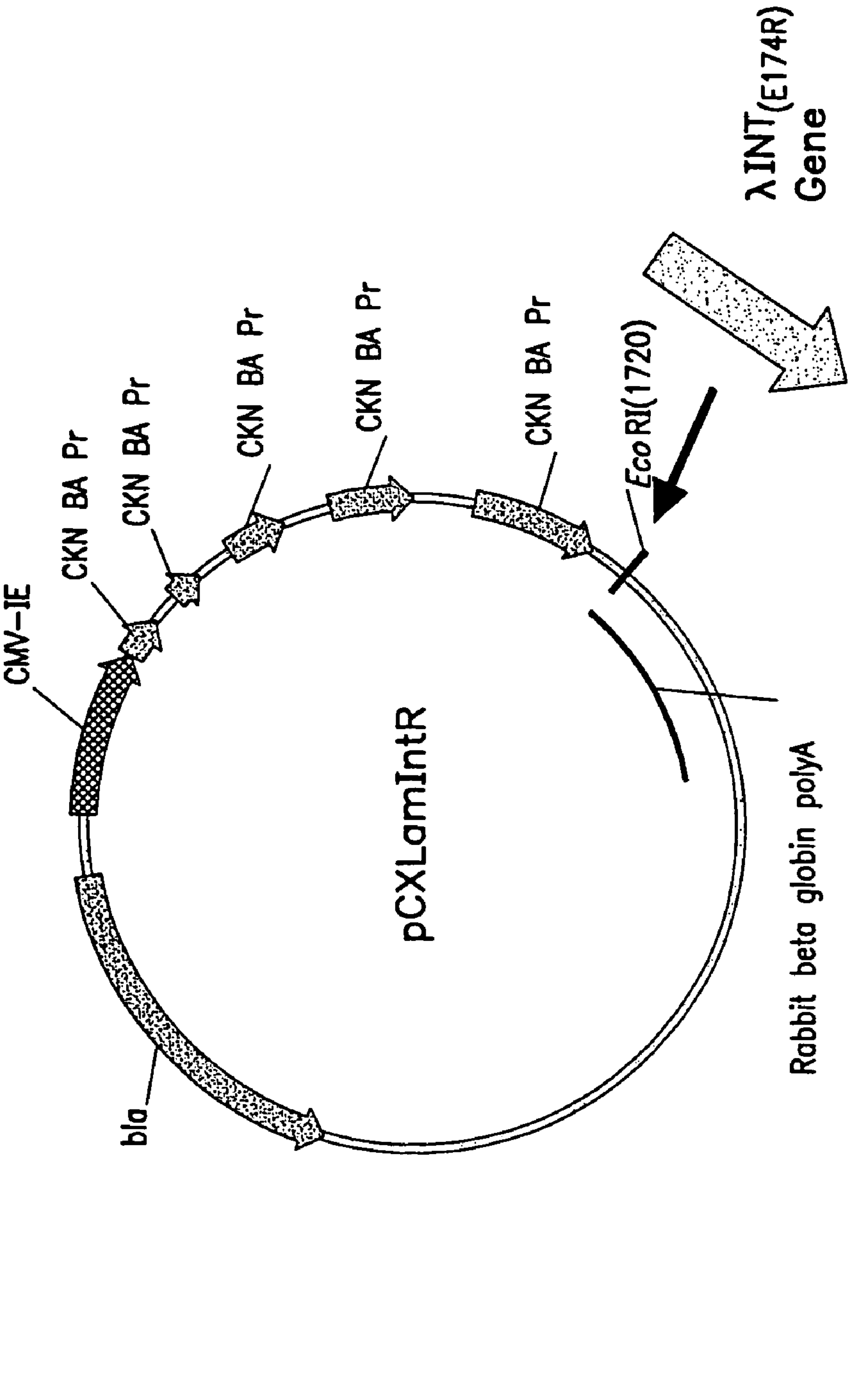
FIG. 8 provides a map of plasmid pCXLamIntR (SEQ ID NO: 112), which includes the Lambda integrase (E174R)-encoding nucleic acid.

A feature of the target gene expression vector that is of interest to include is a promoterless marker gene, which as exemplified (see, FIG. 9) contains an upstream attB site (marker 2 on FIG. 9). The nucleic acid encoding the marker is not expressed unless it is placed downstream from a promoter sequence. Using the recombinase technology provided herein, such as the lambda integrase technology ($\lambda INT_{E174R}$ on FIG. 8) provided herein, site-specific recombination between the attB site on the vector and the promoter-attP site (in the “sense” orientation) on the chromosome-based platform results in the expression of marker 2 on the target gene expression vector, thereby providing a positive selection for the lambda INT mediated site-specific recombination event. Site-specific recombination events on the chromosome-based platform versus random integrations next to a promoter in the genome (false positive) can be quickly screened by designing primers to detect the correct event by PCR. Examples of suitable marker 2 genes, include, but are not limited to, genes that confer resistance to toxic compounds or antibiotics, fluorescence activated cell sorting (FACS) sortable cell surface markers and various fluorescent markers. Examples of these genes include, but are not limited to, human L26a$^R$ (human homolog of *Saccharomyces cerevisiae* CYH$^8$ gene), neomycin, puromycin, blasticidin, CD24 (see, e.g., U.S. Pat. Nos. 5,804,177 and 6,074,836), truncated CD4, truncated low affinity nerve growth factor receptor (LNGFR), truncated LDL receptor, truncated human growth hormone receptor, GFP, RFP, BFP.

The target gene expression vectors contain a gene (target gene) for expression from the chromosome platform. The target gene can be expressed using various constitutive or regulated promoter systems across various mammalian species. For the expression of multiple target genes within the same target gene expression vector, the expression of the multiple targets can be coordinately regulated via viral-based or human internal ribosome entry site (IRES) elements (see, e.g., Jackson et al. (1990) *Trends Biochem Sci.* 15: 477-83; Oumard et al. (2000) *Mol. Cell. Biol.* 20: 2755-2759). Furthermore, using IRES type elements linked to a downstream fluorescent marker, e.g., green, red or blue fluorescent proteins (GFP, RFP, BFP) allows for the identification of high expressing clones from the integrated target gene expression vector.

In certain embodiments described herein, the promoterless marker can be transcriptionally downstream of the heterologous nucleic acid, wherein the heterologous nucleic acid encodes a heterologous protein, and wherein the expression level of the selectable marker is transcriptionally linked to the expression level of the heterologous protein. In addition, the selectable marker and the heterologous nucleic acid can be transcriptionally linked by the presence of a IRES between them. As set forth herein the selectable marker is selected from the group consisting of an antibiotic resistance gene, and a detectable protein, wherein the detectable protein is chromogenic or fluorescent. Expression from the target gene expression vector integrated onto the chromosome-based platform can be further enhanced using genomic insulator/boundary elements. The incorporation of insulator sequences into the target gene expression vector helps define boundaries in chromatin structure and thus minimizes influence of chromatin position effects/gene silencing on the expression of the target gene (Bell et al. (1999) *Current Opinion in Genetics and Development* 9:191-198; Emery et al. (2000) *Proc. Natl. Acad. Sci. U.S.A.* 97:9150-9155). Examples of insulator elements that can be included onto target gene expression vector in order to optimize expression include, but are not limited to:

1) chicken β-globin HS4 element (Prioleau et al. (1999) *EMBO J* 18: 4035-4048);
2) matrix attachment regions (MAR; see, e.g., Ramakrishnan et al. (2000) *Mol Cell. Biol.* 20:868-877);
3) scaffold attachment regions (SAR; see, e.g., Auten et al. (1999) *Human Gene Therapy* 10:1389-1399); and
4) universal chromatin opening elements (UCOE; W0/0005393 and W0/0224930)

The copy number of the target gene can be controlled by sequentially adding multiple target gene expression vectors containing the target gene onto multiple integration sites on the chromosome platform. Likewise, the copy number of the target gene can be controlled within an individual target gene expression vector by the addition of DNA sequences that promote gene amplification. For example, gene amplification can be induced utilizing the dihydrofolate reductase (DHFR) minigene with subsequent selection with methotrexate (see, e.g., Schimke (1984) *Cell* 37:705-713) or amplification promoting sequences from the rDNA locus (see, e.g., Wegner et al. (1989) *Nucl. Acids Res.* 17: 9909-9932).

6. Platforms with Other Recombinase System Sites

A "double lox" targeting strategy mediated by Cre-recombinase (Bethke et al. (1997) *Nucl. Acids Res.* 25:2828-2834) can be used. This strategy employs a pair of heterospecific lox sites—loxA and loxB, which differ by one nucleotide in the 8 bp spacer region. Both sites are engineered into the artificial chromosome and also onto the targeting DNA vector. This allows for a direct site-specific insertion of a commercially relevant gene or genes by a Cre-catalyzed double crossover event. In essence a platform ACes is engineered with a hygromycin-resistance gene flanked by the double lox sites generating lox-ACes, which is maintained in the thymidine kinase deficient cell, LMtk(−). The gene of interest, for example, for testing purposes, the green fluorescence protein gene, GFP and a HSV thymidine kinase gene (tk) marker, are engineered between the appropriate lox sites of the targeting vector. The vector DNA is cotransfected with plasmid pBS185 (Life Technologies) encoding the Cre recombinase gene into mammalian cells maintaining the dual/lox artificial chromosome. Transient expression of the Cre recombinase catalyzes the site-specific insertion of the gene and the tk-gene onto the artificial chromosome. The transfected cells are grown in HAT medium that selects for only those cells that have integrated and expressed the thymidine kinase gene. The HATR colonies are screened by PCR analyses to identify artificial chromosomes with the desired insertion.

To generate the lox-ACes, Lambda-Hyg$^R$-lox DNA is transfected into the LMtk(−) cell line harboring the precursor ACes. Hygromycin-resistant colonies are analyzed by FISH and Southern blotting for the presence of a single copy insert on the ACes.

To demonstrate the gene replacement technology, cell lines containing candidate lox-ACes are cotransfected with pTK-GFP-lox and pBS185 (encoding the Cre recombinase gene) DNA. After transfection, transient expression of plasmid pBS185 will provide sufficient burst of Cre recombinase activity to catalyze DNA recombination at the lox sites. Thus, a double crossover event between the ACes target and the exogenous targeting plasmid carrying the loxA and loxB permits the simple replacement of the hygromycin-resistance gene on the lox-ACes for the tk-GFP cassette from the targeting plasmid, with no integration of vector DNA. Transfected cells are grown in HAT-media to select for tk-expression. Correct targeting will result in the generation of HAT$^R$, hygromycin sensitive, and green fluorescent cells. The desired integration event is verified by Southern and PCR analyses. Specific PCR primer sets are used to amplify DNA sequences flanking the individual loxA and loxB sites on the lox-ACes before and after homologous recombination.

D. Exemplary Applications of the Platform ACes

Platform ACes are applicable and tractable for different/optimized cell lines. Those that include a fluorescent marker, for example, can be purified and isolated using fluorescent activated cell sorting (FACS), and subsequently delivered to a target cell. Those with selectable markers provide for efficient selection and provide a growth advantage. Platform ACes allow multiple payload delivery of donor target vectors via a positive-selection site-specific, recombination system, and they allow for the inclusion of additional genetic factors that improve protein production and protein quality.

The construction and use of the platform ACes as provided for each application may be similarly applied to other applications. Particular descriptions are for exemplification.

1. Cellular Protein Production Platform ACes (CPP ACes)

As described herein, ACes can be produced from acrocentric chromosomes in rodent (mouse, hamster) cell lines via megareplicator induced amplification of heterochromatin/rDNA sequences. Such ACes are ideal for cellular protein production as well as other applications described herein and known to those of skill in the art. ACes platforms that contain a plurality of recombination sites are particularly suitable for engineering as cellular protein production systems.

In one embodiment, CPP ACes involve a two-component system: the platform chromosome containing multiple engineering sites and the donor target vector containing a platform-specific recombination site with designed expression cassettes (see FIG. 9).

The platform ACes can be produced from any artificial chromosome, particularly the amplification-based artificial chromosomes. For exemplification, they are produced from rodent artificial chromosomes produced from acrocentric chromosomes using the technology of U.S. Pat. Nos. 6,077,697 and 6,025,155 and published International PCT application No. WO 97/40183, in which nucleic acid is targeted to the pericentric heterochromatic, and, particularly into rDNA to initiate the replication event(s). The ACes can be produced directly in the chosen cellular protein production cell lines, such as, but not limited to, CHO cells, hybridomas, plant cells, plant tissues, plant protoplasts, stem cells and plant calli.

a. Platform Construction

In the exemplary embodiment, the initial de novo platform construction requires co-transfecting with excess targeting DNA, such as, rDNA or lambda DNA without an attP region, and an engineered selectable marker. The engineered selectable marker should contain promoter, generally a constitutive promoter, such as human, viral, i.e., adenovirus or SV40 promoter, including the human ferritin heavy chain promoter (SEQ ID NO:128), SV40 and EF1α promoters, to control expression of a marker gene that provides a selective growth advantage to the cell. An example of such a marker gene is the *E. coli* hisD gene (encoding histidinol dehydrogenase) which is homologous and analogous to the *S. typhimurium* hisD a dominant marker selection system for mammalian cells previously described (see, Hartman et al. (1988) *Proc. Natl. Acad. Sci. U.S.A.* 85:8047-8051). Since histidine is an essential amino acid in mammals and a nutritional requirement in cell culture, the *E. coli* hisD gene can be used to select for histidine prototrophy in defined media. Furthermore more stringent selection can be placed on the cells by including histinol in the medium. Histidinol is itself permeable and toxic to cells. The hisD provides a means of detoxification.

Placed between the promoter and the marker gene is the bacteriophage lambda attP site to use the bacteriophage lambda integrase dependent site-specific recombination system (described herein). The insertion of an attP site downstream of a promoter element provide forward selection of site-specific recombination events onto the platform ACes.

b. Donor Target Vector Construction

A second component of the CPP platform ACes system involves the construction of donor target vectors containing a gene product(s) of interest for the CPP platform ACes. Individual donor target vectors can be designed for each gene product to be expressed thus enabling maximum usage of a de novo constructed platform ACes, so that one or a few CPP platform ACes will be required for many gene targets.

A key feature of the donor vector target is the promoterless marker gene containing an upstream attB site (marker 2 on FIG. 9). Normally the marker would not be expressed unless it is placed downstream of a promoter sequence. As discussed above, using the lambda integrase technology ($\lambda INT_{E174R}$ on FIG. 8 and FIG. 9), site-specific recombination between the attB site on the vector and the promoter-attP site on the CPP platform ACes result in the expression of the donor target vector marker providing positive selection for the site-specific event. Site-specific recombination events on the CPP ACes versus random integrations next to a promoter in the genome (false positive) can be quickly screened by designing primers to detect the correct event by PCR. In addition, since the lambda integrase reaction is unidirectional, i.e. excision reaction is not possible, a number of unique targets can be loaded onto the CPP platform ACes limited only by the number of markers available.

Additional features of the donor target vector include gene target expression cassettes flanked by either chromatin insulator regions, matrix attachment regions (MAR) or scaffold attachment regions (SAR). The use of these regions will provide a more "open" chromatin environment for gene expression and help alleviate silencing. An example of such a cassette for expressing a monoclonal antibody is described. For this purpose, a strong constitutive promoter, e.g. chicken β-actin or RNA PolI, is used to drive the expression of the heavy and light chain open reading frames. The heavy and light chain sequences flank a nonattenuated human IRES ($IRES_H$; from the 5'UTR of NRF1 gene; see Oumard et al., 2000, *Mol. and Cell Biol.,* 20(8):2755-2759) element thereby coordinating transcription of both heavy and light chain sequence. Distal to the light chain open reading frame resides an additional viral encoded IRES ($IRES_V$ modified ECMV internal ribosomal entry site (IRES)) element attenuating the expression of the fluorescent marker gene hrGFP from Renilla (Stratagene). By linking the hrGFP with an attenuated IRES, the heavy and light chains along with the hrGFP are monocistronic. Thus, the identification of hrGFP fluorescing cells will provide a means to detect protein producing cells. In addition, high producing cell lines can be identified and isolated by FACS thereby decreasing the time frame in finding high expressers. Functional monoclonal antibody will be confirmed by ELISA.

c. Additional Components in Cellular Protein Production Platform ACes (CPP Aces)

In addition to the aforementioned CPP ACes system, other genetic factors can be included to enhance the yield and quality of the expressed protein. Again to provide maximum flexibility, these additional factors can be inserted onto the CPP platform ACes by λINTE174R dependent site-specific recombination. Other factors that could be used with a CPP Platform ACes include for example, adenovirus E1 a trans-activation system which upregulates both cellular and viral promoters (see, e.g., Svensson and Akusjarvi (1984) EMBO 3:789-794; and U.S. Pat. Nos. 5,866,359; 4,775,630 and 4,920,211).

d. Targets for CHO-ACes Engineering to Enhance Cell Growth, such as CHO Cell Growth and Protein Production/Quality If adding these additional factors onto the CPP ACes is not prudent or desired, the host cell, CHO cells, can be engineered to express these factors (see, below, targets for CHO-ACes engineering to enhance CHO cell growth and protein production/quality). Additional factors to consider including are addition of insulin or IGF-1 to sustain viabililty; human sialyltransferases or related factors to produce more human-like glycoproteins; expression of factors to decrease ammonium accumulation during cell growth; expression of factors to inhibit apoptosis; expression of factors to improve protein secretion and protein folding; and expression of factors to permit serum-free transfection and selection.

1) Addition of Insulin or IGF-1 to Sustain Viabililty

Stimulatory factors and/or their receptors are expressed to set up an autocrine loop, to improve cell growth, such as CHO cell growth. Two exemplary candidates are insulin and IGF-1 (see, Biotechnol Prog 2000 September ;16(5):693-7). Insulin is the most commonly used growth factor for sustaining cell growth and viability in serum-free Chinese hamster ovary (CHO) cell cultures. Insulin and IGF-1 analog (LongR(3) serve as growth and viability factors for CHO cells.

CHO cells were modified to produce higher levels of essential nutrients and factors. A serum-free (SF) medium for dihydrofolate reductase-deficient Chinese hamster ovary cells (DG44 cells) was prepared. Chinese hamster ovary cells (DG44 cells), which are normally maintained in 10% serum medium, were gradually weaned to 0.5% serum medium to increase the probability of successful growth in SF medium (see, Kim et al. (199) *In Vitro Cell Dev Biol Anim* 35(4):178-82). A SF medium (SF-DG44) was formulated by supplementing the basal medium with these components; basal medium was prepared by supplementing Dulbecco's modified Eagle's medium and Ham's nutrient mixture F12 with hypoxanthine (10 mg/l) and thymidine (10 mg/l). Development of a SF medium for DG44 cells was facilitated using a Plackett-Burman design technique and weaning of cells.

2) Human Sialyltransferases or Related Factors to Produce more Human-Like Glycoproteins CHO cells have been modified by increasing their ability to process protein via addition of complex carbohydrates. This has been achieved by overexpression of relevant processing enzymes, or in some cases, reducing expression of relevant enzymes (see, Bragonzi et al. (2000) *Biochim Biophys Acta* 1474(3):273-282; see, also Weikert et al. (1999) *Nature biotech.* 17:1116-11121; Ferrari J et al. (1998) *Biotechnol Bioeng* 60(5):589-95). A CHO cell line expressing alpha2,6-sialyltransferase was developed for the production of human-like sialylated recombinant glycoproteins. The sialylation defect of CHO cells can be corrected by transfecting the alpha2,6-sialyltransferase (alpha2,6-ST) cDNA into the cells. Glycoproteins produced by such CHO cells display alpha2,6- and alpha2,3-linked terminal sialic acid residues, similar to human glycoproteins.

As another example for improving the production of human-like sialylated recombinant glycoproteins, a CHO cell line has been developed that constitutively expresses sialidase antisense RNA (see, Ferrari J et al. (1998) *Biotechnol Bioeng* 60(5):589-95). Several antisense expression vectors were prepared using different regions of the sialidase gene. Co-transfection of the antisense constructs with a vector conferring puromycin resistance gave rise to over 40 puromycin resistant clones that were screened for sialidase activity. A 5' 474 bp coding segment of the sialidase cDNA, in the inverted orientation in an SV 40-based expression vector, gave maximal reduction of the sialidase activity to about 40% wild-type values.

Oligosaccharide biosynthesis pathways in mammalian cells have been engineered for generation of recombinant glycoproteins (see, e.g., Sburlati (1998) *Biotechnol Prog* 14(2):189-92), which describes a Chinese hamster ovary (CHO) cell line capable of producing bisected oligosaccharides on glycoproteins. This cell line was created by overexpression of a recombinant N-acetylglucosaminyltransferase III (GnT-III) (see, also, Prati et al. (1998) *Biotechnol Bioeng* 59(4):445-50, which describes antisense strategies for glycosylation engineering of CHO cells).

3) Expression of Factors to Decrease Ammonium Accumulation During Cell Growth

Excess ammonium, which is a by-product of CHO cell metabolism can have detrimental effects on cell growth and protein quality (see, Yang et al. (2000) *Biotechnol Bioeng* 68(4):370-80). To solve this problem ammonium levels were modified by overexpressing carbamoyl phosphate synthetase I and ornithine transcarbamoylase or glutamine synthetase in CHO cells. Such modification resulted in reduced ammonium levels observed and an increase in the growth rate (see Kim et al. (2000) *J Biotechnol* 81(2-3):129-40; and Enosawa et al. (1997) *Cell Transplant* 6(5):537-40).

4) Expression of Factors to Improve Protein Secretion and Protein Folding

Overexpression of relevant enzymes can be engineered into the ACes to improve protein secretion and folding.

5) Expression of Factors to Permit Serum-Free Transfection and Selection

It is advantageous to have the ability to convert CHO cells in suspension growing in serum free medium to adherence with out having to resort to serum addition. Laminin or fibronectin addition is sufficient to make cells adherent (see, e.g., Zaworski et al. (1993) *Biotechniques* 15(5):863-6) so that expressing either of these genes in CHO cells under an inducible promoter should allow for reversible shift to adherence without requiring serum addition.

2. Platform ACes and Gene Therapy

The platform ACes provided herein are contemplated for use in mammalian gene therapy, particularly human gene therapy. Human ACes can be derived from human acrocentric chromosomes from human host cells, in which the amplified sequences are heterochromatic and/or human rDNA. Different platform ACes applicable for different tissue cell types are provided. The ACes for gene therapy can contain a single copy of a therapeutic gene inserted into a defined location on platform ACes. Therapeutic genes include genomic clones, cDNA, hybrid genes and other combinations of sequences. Preferred selectable markers are those from the mammalian host, such as human derived factors so that they are non-immunogenic, non-toxic and allow for efficient selection, such as by FACS and/or drug resistance.

Platform ACes, useful for gene therapy and other applications, as noted herein, can be generated by megareplicator dependent amplification, such as by the methods in U.S. Pat. Nos. 6,077,697 and 6,025,155 and published International PCT application No. WO 97/40183. In one embodiment, human ACes are produced using human rDNA constructs that target rDNA arrays on human acrocentric chromosomes and induce the megareplicator in human cells, particularly in primary cell lines (with sufficient number of doublings to form the ACes) or stem cells (such as hematopoietic stem cells, mesenchymal stem cells, adult stem cells or embryonic stem cells) to avoid the introduction of potentially harmful rearranged DNA sequences present in many transformed cell lines. Megareplicator induced ACes formation can result in multiple copies of targeting DNA/selectable markers in each amplification block on both chromosomal arms of the platform ACes.

In view of the considerations regarding immunogenicity and toxicity, the production of human platform ACes for gene therapy applications employs a two component system analogous to the platform ACes designed for cellular protein production (CPP platform ACes). The system includes a platform chromosome of entirely human DNA origin containing multiple engineering sites and a gene target vector carrying the therapeutic gene of interest.

a. Platform Construction

The initial de novo construction of the platform chromosome employs the co-transfection of excess targeting DNA and a selectable marker. In one embodiment, the DNA is targeted to the rDNA arrays on the human acrocentric chromosomes (chromosomes 13, 14, 15, 21 and 22). For example, two large human rDNA containing PAC clones 18714 and 18720 and the human PAC clone 558F8 are used for targeting (Genome Research (ML) now Incyte, BACPAC Resources, 747 52nd Street, Oakland Calif.). The mouse rDNA clone pFK161 (SEQ ID NO: 118), which was used to make the human SATAC from the 94-3 hamster/human hybrid cell line (see, e.g., published International PCT application No. WO 97/40183 and Csonka, et al, *Journal of Cell Science* 113: 3207-32161 and Example 1 for a description of pFK161) can also be used.

For animal applications, selectable markers should be non-immunogenic in the animal, such as a human, and include, but are not limited to: human nerve growth factor receptor (detected with a MAb, such as described in U.S. Pat. No. 6,365,373); truncated human growth factor receptor (detected with MAb), mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C).

Since megareplicator induced amplification generates multiple copies of the selectable marker, a second consideration for the selection of the human marker is the resulting dose of the expressed marker after ACes formation. High level of expression of certain markers may be detrimental to the cell and/or result in autoimmunity. One method to decrease the dose of the marker protein is by shortening its half-life, such as via the fusion of the well-conserved human ubiquitin tag (a 76 amino acid sequence) thus leading to increased turnover of the selectable marker. This has been used successfully for a number of reporter systems including DHFR (see, e.g., Stack et al. (2000) *Nature Biotechnology* 18:1298-1302 and references cited therein).

Using the ubiquitin tagged protein, a human selectable marker system analogous to the CPP ACes described herein is constructed. Briefly, a tagged selectable marker, such as for example one of those described herein, is cloned downstream of an attP site and expressed from a human promoter. Exemplary promoters contemplated for use herein include, but are not limited to, the human ferritin heavy chain promoter (SEQ ID NO:128); RNA PolI; EF1α; TR; glyceraldehyde-3-phosphate dehydrogenase core promoter (GAP); a GAP core promoter including a proximal insulin inducible element and the intervening GAP sequence; phosphofructokinase promoter; and phosphoglycerate kinase promoter. Also contemplated herein is an aldolase A promoter H1 & H2 (representing closely spaced transcriptional start sites) along with the proximal H enhancer. There are 4 promoters (e.g., transcriptional start sites) for this gene, each having different regulatory and tissue activity. The H (most proximal 2) promoters are ubiquitously expressed off the H enhancer. This resulting marker can then be co-transfected along with excess human rDNA targeting sequence into the host cells. An important criteria for the selection of the recipient cells is sufficient number of cell doublings for the formation and detection of ACes. Accordingly, the co-transfections should be attempted in human primary cells that can be cultured for long periods of time, such as for example, stem cells (e.g., hematopoietic, mesenchymal, adult or embryonic stem cells), or the like. Additional cell types, include, but are not limited to: single gene transfected cells exhibiting increased life-span; over-expressing c-myc cells, e.g. MSU1.1 (Morgan et al., 1991, Exp. Cell Res., November;197(1):125-136); over-expressing telomerase lines, such as TERT cells; SV40 large T-antigen transfected lines; tumor cell lines, such as HT1080; and hybrid human cell lines, such as the 94-3 hamster/human hybrid cell line.

b. Gene Target Vector

The second component of the GT platform ACes (GT ACes) system involves the use of engineered target vectors carrying the therapeutic gene of interest. These are introduced onto the GT platform ACes via site-specific recombination. As with the CPP ACes, the use of engineered target vectors maximizes the use of the de novo generated GT platform ACes for most gene targets. Furthermore, using lambda integrase technology, GT platform ACes containing multiple attP sites permits the opportunity to incorporate multiple therapeutic targets onto a single platform. This could be of value in cases where a defined therapy requires multiple gene targets, a single therapeutic target requires an additional gene regulatory factor or a GT ACes requires a "kill" switch.

Similar to the CPP ACes, a feature of the gene target vector is the promoterless marker gene containing an upstream attB site (marker 2 on FIG. 9). Normally, the marker (in this case, a cell surface antigen that can be sorted by FACS would be ideal) would not be expressed unless it is placed downstream of a promoter sequence. Using the lambda integrase technology ($\lambda INT_{E174R}$ on FIG. 9), site-specific recombination between the attB site on the vector and the promoter—attP site on the GT platform ACes results in the expression of marker#2 on the gene target vector, i.e. positive selection for the site-specific event. Site-specific recombination events on the GT ACes versus random integrations next to a promoter in the genome (false positive) can be quickly screened by designing primers to detect the correct event by PCR.

For expression of the therapeutic gene, human specific promoters, such as a ferritin heavy chain promoter (SEQ ID NO:128); EF1α or RNA PolI, are used. These promoters are for high level expression of a cDNA encoded therapeutic protein. In addition to expressing cDNA (or even hybrid cDNA/artificial intron constructs), the GT platform ACes are used for engineering and expressing large genomic fragments carrying therapeutic genes of interest expressed from native promoter sequences. This is of importance in situations where the therapy requires precise cell specific expression or in instances where expression is best achieved from genomic clones versus cDNA.

3. Selectable Markers for use, for Example, in Gene Therapy (GT)

The following are selectable markers that can be incorporated into human ACes and used for selection.

Dual Resistance to 4-Hydroperoxycyclophosphamide and Methotrexate by Retroviral Transfer of the Human Aldehyde Dehydrogenase Class 1 Gene and a Mutated Dihydrofolate Reductase Gene The genetic transfer of drug resistance to hematopoietic cells is one approach to overcoming myelosuppression caused by high-dose chemotherapy. Because cyclophosphamide (CTX) and methotrexate (MTX) are commonly used non-cross-resistant drugs, generation of dual drug resistance in hematopoietic cells that allows dose intensification may increase anti-tumor effects and circumvent the emergence of drug-resistant tumors, a retroviral vector containing a human cytosolic ALDH-1-encoding DNA clone and a human doubly mutated DHFR-encoding clone (Phe22/Ser31; termed F/S in the description of constructs) to generate increased resistance to CTX and MTX were constructed (Takebe et al. (2001) *Mol Ther* 3(1):88-96). This construct may be useful for protecting patients from high-dose CTX- and MTX-induced myelosuppression. ACes can be similarly constructed.

Multiple Mechanisms of N-phosphonacetyl-L-aspartate Resistance in Human Cell Lines: carbamyl-P synthetase/aspartate transcarbamylase/dihydro-orotase gene Amplification is Frequent only when Chromosome 2 is Rearranged Rodent cells resistant to N-phosphonacetyl-L-aspartate (PALA) invariably contain amplified carbamyl-P synthetase/aspartate transcarbamylase/dihydro-orotase (CAD) genes, usually in widely spaced tandem arrays present as extensions of the same chromosome arm that carries a single copy of CAD in normal cells (Smith et al. (1997) *Proc. Natl. Acad. Sci. U.S.A.* 94:1816-21). In contrast, amplification of CAD is very infrequent in several human tumor cell lines. Cell lines with minimal chromosomal rearrangement and with unrearranged copies of chromosome 2 rarely develop intrachromosomal amplifications of CAD. These cells frequently become resistant to PALA through a mechanism that increases the aspartate transcarbamylase activity with no increase in CAD copy number, or they obtain one extra copy of CAD by forming an isochromosome 2p or by retaining an extra copy of chromosome 2. In cells with multiple chromosomal aberrations and rearranged copies of chromosome 2, amplification of CAD as tandem arrays from rearranged chromosomes is the most frequent mechanism of PALA resistance. All of these different mechanisms of PALA resistance are blocked in normal human fibroblasts. Thus, ACes with multiple copies of the CAD gene would provide PALA resistance.

Retroviral Coexpression of Thymidylate Synthase and Dihydrofolate Reductase Confers Fluoropyrimidine and Antifolate Resistance Retroviral gene transfer of dominant selectable markers into hematopoietic cells can be used to select genetically modified cells in vivo or to attenuate the toxic effects of chemotherapeutic agents. Fantz et al. ((1998) *Biochem Biophys Res Comm* 243(1):6-12) have shown that retroviral gene transfer of thymidylate synthase (TS) confers resistance to TS directed anticancer agents and that co-expression of TS and dihydrofolate reductase (DHFR) confers resistance to TS and DHFR cytotoxic agents. Retroviral vectors encoding *Escherichia coli* TS, human TS, and the Tyr-to-His at residue 33 variant of human TS (Y33HhTS) were constructed and fibroblasts transfected with these vectors conferred comparable resistance to the TS-directed agent fluorodeoxyuridine (FdUrd, approximately 4-fold). Retroviral vectors that encode dual expression of Y33HhTS and the human L22Y DHFR (L22YhDHFR) variants conferred resistance to FdUrd (3- to 5-fold) and trimetrexate (30- to 140-fold). A L22YhDHFR-Y33HhTS chimeric retroviral vector was also constructed and transduced cells were resistant to FdUrd (3-fold), AG337 (3-fold), trimetrexate (100-fold) and methotrexate (5-fold). These results show that recombinant retroviruses can be used to transfer the cDNA that encodes TS and DHFR and dual expression in transduced cells is sufficiently high to confer resistance to TS and DHFR directed anticancer agents. ACes can be similarly constructed.

Human CD34+Cells do not Express Glutathione S-transferases alpha

The expression of glutathione S-transferases alpha (GST alpha) in human hematopoietic CD34+cells and bone marrow was studied using RT-PCR and immunoblotting (Czerwinski M, Kiem et al. (1997) *Gene Ther* 4(3):268-70). The GSTA1 protein conjugates glutathione to the stem cell selective alkylator busulfan. This reaction is the major pathway of elimination of the compound from the human body. Human hematopoietic CD34+ cells and bone marrow do not express GSTA1 message, which was present at a high level in liver, an organ relatively resistant to busulfan toxicity in comparison to bone marrow. Similarly, baboon CD34+ cells and dog bone marrow do not express GSTA1. Thus, human GSTA1 is a chemoprotective selectable marker in human stem cell gene therapy and could be employed in ACes construction.

Selection of Retrovirally Transduced Hematopoietic Cells using CD24 as a Marker of Gene Transfer Pawliuk et al. ((l1994) *Blood* 84(9):2868-2877) have investigated the use of a cell surface antigen as a dominant selectable marker to facilitate the detection and selection of retrovirally infected target cells. The small coding region of the human cell surface antigen CD24 (approximately 240 bp) was introduced into a myeloproliferative sarcoma virus (MPSV)-based retroviral vector, which was then used to infect day 4 5-fluorouracil (5-FU)-treated murine bone marrow cells. Within 48 hours of termination of the infection procedure CD24-expressing cells were selected by fluorescent-activated cell sorting (FACS) with an antibody directed against the CD24 antigen. Functional analysis of these cells showed that they included not only in vitro clonogenic progenitors and day 12 colony-forming unit-spleen but also cells capable of competitive long-term hematopoietic repopulation. Double-antibody labeling studies performed on recipients of retrovirally transduced marrow cells showed that some granulocytes, macrophages, erythrocytes, and, to a lesser extent, B and T lymphocytes still expressed the transduced CD24 gene at high levels 4 months later. No gross abnormalities in hematopoiesis were detected in mice repopulated with CD24-expressing cells. These results show that the use of the CD24 cell surface antigen as a retrovirally encoded marker permits rapid, efficient, and nontoxic selection in vitro of infected primary cells, facilitates tracking and phenotyping of their progeny, and provides a tool to identify elements that regulate the expression of transduced genes in the most primitive hematopoietic cells. ACes could be similarly constructed.

DeltahGHR, a Biosafe Cell Surface-Labeling Molecule for Analysis and Selection of Genetically Transduced Human Cells A selectable marker for retroviral transduction and selection of human and murine cells is known (see, Garcia-Ortiz et al. (2000) *Hum Gene Ther* 11(2):333-46). The molecule expressed on the cell surface of the transduced population is a truncated version of human growth hormone receptor (deltahGHR), capable of ligand (hGH) binding, but devoid of the domains involved in signal triggering. The engineered molecule is stably expressed in the target cells as an inert protein unable to trigger proliferation or to rescue the cells from apoptosis after ligand binding. This new marker, has a wide application spectrum, since hGHR in the human adult is highly expressed only in liver cells, and lower levels have been reported in certain lymphocyte cell populations. The deltahGHR label has high biosafety potential, as it belongs to a well-characterized hormonal system that is nonessential in adults, and there is extensive clinical experience with hGH administration in humans. The differential binding properties of several monoclonal antibodies (MAbs) are used in a cell rescue method in which the antibody used to select deltahGHR-transduced cells is eluted by competition with hGH or, alternatively biotinylated hGH is used to capture tagged cells. In the latter system, the final purified population is recovered free of attached antibodies in hGH (a substance approved for human use)-containing medium. Such a system could be used to identify ACes containing cells.

4. Transgenic Models for Evaluation of Genes and Discovery of New Traits in Plants Of interest is the use of plants and plant cells containing artificial chromosomes for the evaluation of new genetic combinations and discovery of new traits. Artificial chromosomes, by virtue of the fact that they can contain significant amounts of DNA can also therefore encode numerous genes and accordingly a multiplicity of traits. It is contemplated here that artificial chromosomes, when formed from one plant species, can be evaluated in a second plant species. The resultant phenotypic changes observed, for example, can indicate the nature of the genes contained within the DNA contained within the artificial chromosome, and hence permit the identification of novel genetic activities. Artificial chromosomes containing euchromatic DNA or partially containing euchromatic DNA can serve as a valuable source of new traits when transferred to an alien plant cell environment. For example, it is contemplated that artificial chromosomes derived from dicot plant species can be introduced into monocot plant species by transferring a dicot artificial chromosome. The dicot artificial chromosome possessing a region of euchromatic DNA containing expressed genes.

The artificial chromosomes can be designed to allow the artificial chromosome to recombine with the naturally occurring plant DNA in such a fashion that a large region of naturally occurring plant DNA becomes incorporated into the artificial chromosome. This allows the artificial chromosome to contain new genetic activities and hence carry novel traits. For example, an artificial chromosome can be introduced into a wild relative of a crop plant under conditions whereby a portion of the DNA present in the chromosomes of the wild relative is transferred to the artificial chromosome. After isolation of the artificial chromosome, this naturally occurring region of DNA from the wild relative, now located on the artificial chromosome can be introduced into the domesticated crop species and the genes encoded within the transferred DNA expressed and evaluated for utility. New traits and gene systems can be discovered in this fashion. The artificial chromosome can be modified to contain sequences that promote homologous recombination within plant cells, or be modified to contain a genetic system that functions as a site-specific recombination system.

Artificial chromosomes modified to recombine with plant DNA offer many advantages for the discovery and evaluation of traits in different plant species. When the artificial chromosome containing DNA from one plant species is introduced into a new plant species, new traits and genes can be introduced. This use of an artificial chromosome allows for the ability to overcome the sexual barrier that prevents transfer of genes from one plant species to another species. Using artificial chromosomes in this fashion allows for many potentially valuable traits to be identified including traits that are typically found in wild species. Other valuable applications for artificial chromosomes include the ability to transfer large regions of DNA from one plant species to another, such as DNA encoding potentially valuable traits such as altered oil, carbohydrate or protein composition, multiple genes encoding enzymes capable of producing valuable plant secondary metabolites, genetic systems encoding valuable agronomic traits such as disease and insect resistance, genes encoding functions that allow association with soil bacterium such as growth promoting bacteria or nitrogen fixing bacteria, or genes encoding traits that confer freezing, drought or other stress tolerances. In this fashion, artificial chromosomes can be used to discover regions of plant DNA that encode valuable traits.

The artificial chromosome can also be designed to allow the transfer and subsequent incorporation of these valuable traits now located on the artificial chromosome into the natural chromosomes of a plant species. In this fashion the artificial chromosomes can be used to transfer large regions of DNA encoding traits normally found in one plant species into another plant species. In this fashion, it is possible to derive a plant cell that no longer needs to carry an artificial chromosome to posses the novel trait. Thus, the artificial chromosome would serve as the transfer mechanism to permit the formation of plants with greater degree of genetic diversity.

The design of an artificial chromosome to accomplish the afore-mentioned purposes can include within the artificial chromosome the presence of specific DNA sequences capable of acting as sites for homologous recombination to take place. For example, the DNA sequence of *Arabidopsis* is now known. To construct an artificial chromosome capable of recombining with a specific region of *Arabidopsis* DNA, a sequence of *Arabidopsis* DNA, normally located near a chromosomal location encoding genes of potential interest can be introduced into an artificial chromosome by methods provided herein. It may be desirable to include a second region of DNA within the artificial chromosome that provides a second flanking sequence to the region encoding genes of potential interest, to promote a double recombination event which would ensure transfer of the entire chromosomal region, encoding genes of potential interest, to the artificial chromosome. The modified artificial chromosome, containing the DNA sequences capable of homologous recombination region, can then be introduced into *Arabidopsis* cells and the homologous recombination event selected.

It is convenient to include a marker gene to allow for the selection of a homologous recombination event. The marker gene is preferably inactive unless activated by an appropriate homologous recombination event. For example, U.S. Pat. No. 5,272,071, describes a method where an inactive plant gene is activated by a recombination event such that desired homologous recombination events can be easily scored. Similarly, U.S. Pat. No. 5,501,967 describes a method for the selection of homologous recombination events by activation of a silent selection gene first introduced into the plant DNA, the gene being activated by an appropriate homologous recombination event. Both of these methods can be applied to enable a selective process to be included to select for recombination between an artificial chromosome and a plant chromosome. Once the homologous recombination event is detected, the artificial chromosome, once selected, is isolated and introduced into a recipient cell, for example, tobacco, corn, wheat or rice, and the expression of the newly introduced DNA sequences evaluated.

Phenotypic changes in the recipient plant cells containing the artificial chromosome, or in regenerated plants containing the artificial chromosome, allows for the evaluation of the nature of the traits encoded by the *Arabidopsis* DNA, under conditions naturally found in plant cells, including the naturally occurring arrangement of DNA sequences responsible for the developmental control of the traits in the normal chromosomal environment.

Traits such as durable fungal or bacterial disease resistance, new oil and carbohydrate compositions, valuable secondary metabolites such as phytosterols, flavonoids, efficient nitrogen fixation or mineral utilization, resistance to extremes of drought, heat or cold are all found within different populations of plant species and are often governed by multiple genes. The use of single gene transformation technologies does not permit the evaluation of the multiplicity of genes controlling many valuable traits. Thus, incorporation of these genes into artificial chromosomes allows the rapid evaluation of the utility of these genetic combinations in heterologous plant species.

The large scale order and structure of the artificial chromosome provides a number of unique advantages in screening for new utilities or novel phenotypes within heterologous plant species. The size of new DNA that can be carried by an artificial chromosome can be millions of base pairs of DNA, representing potentially numerous genes that may have novel utility in a heterologous plant cell. The artificial chromosome is a "natural" environment for gene expression, the problems of variable gene expression and silencing seen for genes transferred by random insertion into a genome should not be observed. Similarly, there is no need to engineer the genes for expression, and the genes inserted would not need to be recombinant genes. Thus, one expects the expression from the transferred genes to be temporal and spatial, as observed in the species from where the genes were initially isolated. A valuable feature for these utilities is the ability to isolate the artificial chromosomes and to further isolate, manipulate and introduce into other cells artificial chromosomes carrying unique genetic compositions.

Thus, the use of artificial chromosomes and homologous recombination in plant cells can be used to isolate and identify many valuable crop traits.

In addition to the use of artificial chromosomes for the isolation and testing of large regions of naturally occurring DNA, methods for the use of artificial chromosomes and cloned DNA also are contemplated. Similar to that described above, artificial chromosomes can be used to carry large regions of cloned DNA, including that derived from other plant species.

The ability to incorporate novel DNA elements into an artificial chromosome as it is being formed allows for the development of artificial chromosomes specifically engineered as a platform for testing of new genetic combinations, or "genomic" discoveries for model species such as *Arabidopsis*. It is known that specific "recombinase" systems can be used in plant cells to excise or re-arrange genes. These same systems can be used to derive new gene combinations contained on an artificial chromosome.

The artificial chromosomes can be engineered as platforms to accept large regions of cloned DNA, such as that contained in Bacterial Artificial Chromosomes (BACs) or Yeast Artificial Chromosomes (YACs). It is further contemplated, that as a result of the typical structure of artificial chromosomes containing tandemly repeated DNA blocks, that sequences other than cloned DNA sequence can be introduced by recombination processes. In particular recombination within a predefined region of the tandemly repeated DNA within the artificial chromosome provides a mechanism to "stack" numerous regions of cloned DNA, including large regions of DNA contained within BACs or YACs clones. Thus, multiple combinations of genes can be introduced onto artificial chromosomes and these combinations tested for functionality. In particular, it is contemplated that multiple YACs or BACs can be stacked onto an artificial chromosomes, the BACs or YACs containing multiple genes of complex pathways or multiple genetic pathways. The BACs or YACs are typically selected based on genetic information available within the public domain, for example from the *Arabidopsis* Information Management System (aims.cps.msu.edu/aims/index.html) or the information related to the plant DNA sequences available from the Institute for Genomic Research (www.tigr.org) and other sites known to those skilled in the art. Alternatively, clones can be chosen at random and evaluated for functionality. It is contemplated that combinations providing a desired phenotype can be identified by isolation of the artificial chromosome containing the combination and analyzing the nature of the inserted cloned DNA.

In this regard, it is contemplated that the use of site-specific recombination sequences can have considerable utility in developing artificial chromosomes containing DNA sequences recognized by recombinase enzymes and capable of accepting DNA sequences containing same. The use of site-specific recombination as a means to target an introduced DNA to a specific locus has been demonstrated in the art and such methods can be employed. The recombinase systems can also be used to transfer the cloned DNA regions contained within the artificial chromosome to the naturally occurring plant or mammalian chromosomes.

As noted herein, many site-specific recombinases are known and can be identified (Kilby et al. (1993) *Trends in Genetics* 9:413-418). The three recombinase systems that have been extensively employed include: an activity identified as R encoded by the pSR1 plasmid of *Zygosaccharomyes rouxii*, FLP encoded for the 2 um circular plasmid from *Saccharomyces cerevisiae* and Cre-lox from the phage P1.

The integration function of site-specific recombinases is contemplated as a means to assist in the derivation of genetic combinations on artificial chromosomes. In order to accomplish this, it is contemplated that a first step of introducing site-specific recombinase sites into the genome of a plant cell in an essentially random manner is conducted, such that the plant cell has one or more site-specific recombinase recognition sequences on one or more of the plant chromosomes. An artificial chromosome is then introduced into the plant cell, the artificial chromosome engineered to contain a recombinase recognition site (e.g., integration site) capable of being recognized by a site-specific recombinase. Optionally, a gene encoding a recombinase enzyme also is included, preferably under the control of an inducible promoter. Expression of the site-specific recombinase enzyme in the plant cell, either by induction of a inducible recombinase gene, or transient expression of a recombinase sequence, causes a site-specific recombination event to take place, leading to the insertion of a region of the plant chromosomal DNA (containing the recombinase recognition site) into the recombinase recognition site of the artificial chromosome, and forming an artificial chromosome containing plant chromosomal DNA. The artificial chromosome can be isolated and introduced into a heterologous host, preferably a plant host, and expression of the newly introduced plant chromosomal DNA can be monitored and evaluated for desirable phenotypic changes. Accordingly, carrying out this recombination with a population of plant cells wherein the chromosomally located recombinase recognition site is randomly scattered throughout the chromosomes of the plant, can lead to the formation of a population of artificial chromosomes, each with a different region of plant chromosomal DNA, and each potentially representing a novel genetic combination.

This method requires the precise site-specific insertion of chromosomal DNA into the artificial chromosome. This precision has been demonstrated in the art. For example, Fukushige and Sauer ((1992) Proc. Natl. Acad. Sci. USA, 89:7905-7909) demonstrated that the Cre-lox homologous recombination system could be successfully employed to introduce DNA into a predefined locus in a chromosome of mammalian cells. In this demonstration a promoter-less antibiotic resistance gene modified to include a lox sequence at the 5' end of the coding region was introduced into CHO cells. Cells were re-transformed by electroporation with a plasmid that contained a promoter with a lox sequence and a transiently expressed Cre recombinase gene. Under the conditions employed, the expression of the Cre enzyme catalyzed the homologous recombination between the lox site in the chromosomally located promoter-less antibiotic resistance gene, and the lox site in the introduced promoter sequence, leading to the formation of a functional antibiotic resistance gene. The authors demonstrated efficient and correct targeting of the introduced sequence, 54 of 56 lines analyzed corresponded to the predicted single copy insertion of the DNA due to Cre catalyzed site-specific homologous recombination between the lox sequences.

Accordingly a lox sequence may be first added to a genome of a plant species capable of being transformed and regenerated to a whole plant to serve as a recombinase target DNA sequence for recombination with an artificial chromosome. The lox sequence may be optimally modified to further contain a selectable marker which is inactive but can be activated by insertion of the lox recombinase recognition sequence into the artificial chromosome.

A promoterless marker gene or selectable marker gene linked to the recombinase recognition sequence, which is first inserted into the chromosomes of a plant cell can be used to engineer a platform chromosome. A promoter is linked to a recombinase recognition site, in an orientation that allows the promoter to control the expression of the marker or selectable marker gene upon recombination within the artificial chromosome. Upon a site-specific recombination event between a recombinase recognition site in a plant chromosome and the recombinase recognition site within the introduced artificial chromosome, a cell is derived with a recombined artificial chromosome, the artificial chromosome containing an active marker or selectable marker activity that permits the identification and or selection of the cell.

The artificial chromosomes can be transferred to other plant or animal species and the functionality of the new combinations tested. The ability to conduct such an inter-chromosomal transfer of sequences has been demonstrated in the art. For example, the use of the Cre-lox recombinase system to cause a chromosome recombination event between two chromatids of different chromosomes has been shown.

Any number of recombination systems may be employed as described herein, such as, but not limited to, bacterially derived systems such as the att/int system of phage lambda, and the Gin/gix system.

More than one recombination system may be employed, including, for example, one recombinase system for the introduction of DNA into an artificial chromosome, and a second recombinase system for the subsequent transfer of the newly introduced DNA contained within an artificial chromosome into the naturally occurring chromosome of a second plant species. The choice of the specific recombination system used will be dependent on the nature of the modification contemplated.

By having the ability to isolate an artificial chromosome, in particular, artificial chromosomes containing plant chromosomal DNA introduced via site-specific recombination, and re-introduce the chromosome into other mammalian or plant cells, particularly plant cells, these new combinations can be evaluated in different crop species without the need to first isolate and modify the genes, or carry out multiple transformations or gene transfers to achieve the same combination isolation and testing combinations of the genes in plants. The use of a site-specific recombinase also allows the convenient recovery of the plant chromosomal region into other recombinant DNA vectors and systems, such as mammalian or insect systems, for manipulation and study.

Also contemplated herein are ACes, cell lines and methods for use in screening a new chromosomal combinations, deletions, truncations with eucaryotic genome that take advantage of the site-specific recombination systems incorporated onto platform ACes provided herein. For example, provided herein is a cell line useful for making a library of ACes, comprising a multiplicity of heterologous recombination sites randomly integrated throughout the endogenous chromosomes. Also provided herein is a method of making a library of ACes comprising random portions of a genome, comprising introducing one or more ACes into a cell line comprising a multiplicity of heterologous recombination sites randomly integrated throughout the endogenous chromosomes, under conditions that promote the site-specific chromosomal arm exchange of the ACes into, and out of, a multiplicity of the heterologous recombination sites within the cell's chromosomal DNA; and isolating said multiplicity of ACes, thereby producing a library of ACes whereby multiple ACes have different portions of the genome within. Also provided herein is a library of cells useful for genomic screening, said library comprising a multiplicity of cells, wherein each cell comprises an ACes having a mutually exclusive portion of a chromosomal nucleic acid therein. The library of cells can be from a different species and/or cell type than the chromosomal nucleic acid within the ACes. Also provided is a method of making one or more cell lines, comprising a) integrating into endogenous chromosomal DNA of a selected cell species, a multiplicity of heterologous recombination sites, b) introducing a multiplicity of ACes under conditions that promote the site-specific chromosomal arm exchange of the ACes into, and out of, a multiplicity of the heterologous recombination sites integrated within the cell's endogenous chromosomal DNA;

c) isolating said multiplicity of ACes, thereby producing a library of ACes whereby a multiplicity of ACes have mutually exclusive portions of the endogenous chromosomal DNA therein;

d) introducing the isolated multiplicity of ACes of step c) into a multiplicity of cells, thereby creating a library of cells;

e) selecting different cells having mutually exclusive ACes therein and clonally expanding or differentiating said different cells into clonal cell cultures, thereby creating one or more cell lines.

These ACes, cell lines and methods utilize the site-specific recombination sites on platform ACes analogous YAC manipulation related to: the methods of generating terminal deletions in normal and artificial chromosomes (e.g., ACes; as described in Vollrath et al., 1988, *PNAS, USA,* 85:6027-66031; and Pavan et al., *PNAS, USA,* 87:1300-1304); the methods of generating interstitial deletions in normal and artificial chromosomes (as described in Campbell et al., 1991, *PNAS, USA,* 888:5744-5748); and the methods of detecting homologous recombination between two ACes (as described in Cellini et al., 1991, *Nuc. Acid Res.,* 19(5):997-1000).

5. Use of Plateform ACes in Pharmacogenomic/toxicology Applications (Development of "Reporter ACes")

In addition to the placement of genes onto ACes chromosomes for therapeutic protein production or gene therapy, the platform can be engineered via the IntR lambda integrase to carry reporter-linked constructs (reporter genes) that monitor changes in cellular physiology as measured by the particular reporter gene (or a series of different reporter genes) readout. The reporter linked constructs are designed to include a gene that can be detected (by for example fluorescence, drug resistance, immunohistochemistry, or transcript production, and the like) with well-known regulatory sequences that would control the expression of the detectable gene. Exemplary regulatory promoter sequences are well-known in the art.

A) Reporter ACes for Drug Pathway Screening

The ACes can be engineered to carry reporter-linked constructs that indicate a signal is being transduced through one or a number of pathways. For example, transcriptionally regulated promoters from genes at the end (or any other chosen point) of particular signal transduction pathways could be engineered on the ACes to express the appropriate readout (either by fluorescent protein production or drug resistance) when the pathway is activated (or down-regulated as well). In one embodiment, a number of reporters from different pathways can be placed on an ACes chromosome. Cells (and/or whole animals) containing such a Reporter ACes could be exposed to a variety of drugs or compounds and monitored for the effects of the drugs or compounds upon the selected pathway(s) by the reporter gene(s). Thus, drugs or compounds can be classified or identified by particular pathways they excite or down-regulate. Similarly, transcriptional profiles obtained from genomic array experiments can be biologically validated using the reporter ACes provided herein.

B) Reporter ACes for Toxic Compound Testing

Environmental or man-made genotoxicants can be tested in cell lines carrying a number of reporter-genes platform ACes linked to promoters that are transcriptionally regulated in response to DNA damage, induced apoptosis or necrosis, and cell-cycle perturbations. Furthermore, new drugs and/or compounds could be tested in a similar manner with the genotoxicant ACes reporter for their cellular/genetic toxicity by such a screen. Likewise, toxic compound testing could be carried out in whole transgenic animals carrying the ACes chromosome that measures genotoxicant exposure ("canary in a coal mine"). Thus, the same or similar type ACes could be used for toxicity testing in either a cell-based or whole animal setting. An example would include ACes that carry reporter-linked genes controlled by various cytochrome P450 profiled promoters and the like.

C) Reporter ACes for Individualized Pharmacogenomics/Drug Profiling

A common disease may arise via various mechanisms. In many instances there are multiple treatments available for a given disease. However, the success of a given treatment may depend upon the mechanism by which the disease originated and/or by the genetic background of the patient. In order to establish the most effective treatment for a given patient one could utilize the ACes reporters provided herein. ACes reporters can be used in patient cell samples to determine an individualized drug regimen for the patient. In addition, potential polymorphisms affecting the transcriptional regulation of an individual's particular gene can be assessed by this approach.

D) Reporter ACes for Classification of Similar Patient Tumors

As with other diseases as described in 5.C) above, cancer cells arise via different mechanisms. Furthermore, as a cancerous cell propagates it may undergo genomic alterations. An ACes reporter transferred to cells of different patients having the same disease, i.e. similar cancers, could be used to categorize the particular cancer of each patient, thereby facilitating the identification of the most effective therapeutic regimen. Examples would include the validation of array profiling of certain classes of breast cancers. Subsequently, appropriate drug profiling could be carried out as described above.

E) Reporter ACes as a "Differentiation" Sensor

Using the ACes reporter as a "differentiation" sensor in stem cells or other progenitor cells in order to enrich by selection (either FACS based screening, drug selection and/or use of suicide gene) for a particular class of differentiated or undifferentiated cells. For example, in one embodiment, this assay could also be used for compound screening for small molecule modifiers of cell differentiation.

F) Whole Animal Studies with Reporter ACes

Finally, with whole-body fluorescence imaging technology (Yang et al. (2000) PNAS 97:12278) any of the above Reporter ACes methods could be used in conjunction with whole-body imaging to monitor reporter genes within whole animals without sacrificing the animal. This would allow temporal and spatial analysis of expression patterns under a given set of conditions. The conditions tested may include for example, normal differentiation of a stem cell, response to drug or compound treatment whether targeted to the diseased tissue or presented systemically, response to genotoxicants, and the like.

The following examples are included for illustrative purposes only and are not intended to limit the scope of the invention.

EXAMPLE 1 pFK161

Cosmid pFK161 (SEQ ID NO: 118) was obtained from Dr. Gyula Hadlaczky and contains a 9 kb NotI insert derived from a murine rDNA repeat (see clone 161 described in PCT Application Publication No. WO97/40183 by Hadlaczky et al. for a description of this cosmid). This cosmid, referred to as clone 161 contains sequence corresponding to nucleotides 10,232-15,000 in SEQ ID NO. 26. It was produced by inserting fragments of the megachromosome (see, U.S. Pat. No. 6,077,697 and International PCT application No. WO 97/40183). For example, H1D3, which was deposited at the European Collection of Animal Cell Culture (ECACC) under Accession No. 96040929, is a mouse-hamster hybrid cell line carrying this megachromosome into plasmid pWE15 (Stratagene, La Jolla, Calif.; SEQ ID No. 31) as follows. Half of a 100 μl low melting point agarose block (mega-plug) containing isolated SATACs was digested with NotI overnight at 37° C. Plasmid pWE15 was similarly digested with NotI overnight. The mega-plug was then melted and mixed with the digested plasmid, ligation buffer and T4 DNA ligase. Ligation was conducted at 16° C. overnight. Bacterial DH5α cells were transformed with the ligation product and transformed cells were plated onto LB/Amp plates. Fifteen to twenty colonies were grown on each plate for a total of 189 colonies. Plasmid DNA was isolated from colonies that survived growth on LB/Amp medium and analyzed by Southern blot hybridization for the presence of DNA that hybridized to a pUC19 probe. This screening methodology assured that all clones, even clones lacking an insert but yet containing the pWE15 plasmid, would be detected.

Liquid cultures of all 189 transformants were used to generate cosmid minipreps for analysis of restriction sites within the insert DNA. Six of the original 189 cosmid clones contained an insert. These clones were designated as follows: 28 (~9-kb insert), 30 (~9-kb insert), 60 (~4-kb insert), 113 (~9-kb insert), 157 (~9-kb insert) and 161 (~9-kb insert). Restriction enzyme analysis indicated that three of the clones (113, 157 and 161) contained the same insert. 100 For sequence analysis the insert of cosmid clone no. 1e61 was subcloned as follows. To obtain the end fragments of the insert of clone no. 161, the clone was digested with NotI and BamHI and ligated with NotI/BamHI-digested pBluescript KS (Stratagene, La Jolla, Calif.). Two fragments of the insert of clone no. 161 were obtained: a 0.2-kb and a 0.7-kb insert fragment. To subclone the internal fragment of the insert of clone no. 161, the same digest was ligated with BamHI-digested pUC19. Three fragments of the insert of clone no. 161 were obtained: a 0.6-kb, a 1.8-kb and a 4.8-kb insert fragment.

The insert corresponds to an internal section of the mouse ribosomal RNA gene (rDNA) repeat unit between positions 7551-15670 as set forth in GENBANK accession no. X82564, which is provided as SEQ ID NO. 18. The sequence data obtained for the insert of clone no. 161 is set forth in SEQ ID NOS. 19-25. Specifically, the individual subclones corresponded to the following positions in GENBANK accession no. X82564 (SEQ ID NO: 18) and in SEQ ID NOs. 19-25:

| Subclone | Start in X82564 | End | Site | SEQ ID No. |
|---|---|---|---|---|
| 161k1 | 7579 | 7755 | Notl, BamHI | 19 |
| 161m5 | 7756 | 8494 | BamHI | 20 |
| 161m7 | 8495 | 10231 | BamHI | 21 (shows only sequence corresponding to nt. 8495-8950), 22 (shows only sequence corresponding to nt. 9851-10231) |
| 161m12 | 10232 | 15000 | BamHI | 23 (shows only sequence corresponding to nt. 10232-10600), 24 (shows only sequence corresponding to nt. 14267-15000) |
| 161k2 | 15001 | 15676 | Notl, BamHI | 25 |

The sequence set forth in SEQ ID NOs. 19-25 diverges in some positions from the sequence presented in positions 7551-15670 of GENBANK accession no. X82564. Such divergence may be attributable to random mutations between repeat units of rDNA.

For use herein, the rDNA insert from the clone was prepared by digesting the cosmid with Notl and Bg/II and was purified as described above. Growth and maintenance of bacterial stocks and purification of plasmids were performed using standard well known methods (see, e.g., Sambrook et al. (1989) *Molecular Cloning: A Laboratory Manual,* 2nd Edition, Cold Spring Harbor Laboratory Press), and plasmids were purified from bacterial cultures using Midi- and Maxi-preps Kits (Qiagen, Mississauga, Ontario).

pDsRed1N1

This vector is available from Clontech (see SEQ ID No. 29) and encodes the red fluorescent protein (DsRed; Genbank accession no. AF272711; SEQ ID Nos. 39 and 40). DsRed, which has a vivid red fluorescence, was isolated from the IndoPacific sea anemone relative *Discosoma* species. The plasmid pDsRed1N1 (Clontech; SEQ ID No. 29) constitutively expresses a human codon-optimized variant of the fluorescent protein under control of the CMV promoter. Unmodified, this vector expresses high levels of DsRed1 and includes sites for creating N-terminal fusions by cloning proteins of interest into the multiple cloning site (MCS). It is Kan and Neo resistant for selection in bacterial or eukaryotic cells.

Plasmid pMG

Plasmid pMG (InvivoGen, San Diego, Calif.; see SEQ. ID. NO. 27 for the nucleotide sequence of pMG) contains the hygromycin phosphotransferase gene under the control of the immediate-early human cytomegalovirus (hCMV) enhancer/promoter with intron A. Vector pMG also contains two transcriptional units allowing for the coexpression of two heterologous genes from a single vector sequence.

The first transcriptional unit of pMG contains a multiple cloning site for insertion of a gene of interest, the hygromycin phosphotransferase gene (hph) and the immediate-early human cytomegalovirus (hCMV) enhancer/promoter with intron A (see, e.g., Chapman et al. (1991) *Nuc. Acids Res.* 19:3979-3986) located upstream of hph and the multiple cloning site, which drives the expression of hph and any gene of interest inserted into the multiple cloning site as a polycistronic mRNA. The first transcriptional unit also contains a modified EMCV internal ribosomal entry site (IRES) upstream of the hph gene but downstream of the hCMV promoter and MCS for ribosomal entry in translation of the hph gene (see SEQ ID NO. 27, nucleotides 2736-3308). The IRES is modified by insertion of the constitutive *E. coli* promoter (EM7) within an intron (IM7) into the end of the IRES. In mammalian cells, the *E. coli* promoter is treated as an intron and is spliced out of the transcript. A polyadenylation signal from the bovine growth hormone (bGh) gene (see, e.g., Goodwin and Rottman (1992) *J. Biol. Chem.* 267:16330-16334) and a pause site derived from the 3' flanking region of the human α2 globin gene (see, e.g., Enriquez-Harris et al. (1991) *EMBO J.* 10:1833-1842) are located at the end of the first transcription unit. Efficient polyadenylation is facilitated by inserting the flanking sequence of the bGh gene 3' to the standard AAUAAA hexanucleotide sequence.

The second transcriptional unit of pMG contains another multiple cloning site for insertion of a gene of interest and an EF-1α/HTLV hybrid promoter located upstream of this multiple cloning site, which drives the expression of any gene of interest inserted into the multiple cloning site. The hybrid promoter is a modified human elongation factor-1 alpha (EF-1 alpha) gene promoter (see, e.g., Kim et al. (1990) *Gene* 91:217-223) that includes the R segment and part of the U5 sequence (R-U5') of the human T-cell leukemia virus (HTLV) type I long terminal repeat (see, e.g., Takebe et al. (1988) *Mol. Cell. Biol* 8:466-472). The Simian Virus 40 (SV40) late polyadenylation signal (see Carswell and Alwine (1989) *Mol. Cell. Biol.* 9:4248-4258) is located downstream of the multiple cloning site. Vector pMG contains a synthetic polyadenylation site for the first and second transcriptional units at the end of the transcriptional unit based on the rabbit β-globin gene and containing the AATAAA hexanucleotide sequence and a GT/T-rich sequence with 22-23 nucleotides between them (see, e.g., Levitt et al. (1989) *Genes Dev.* 3:1019-1025). A pause site derived from the C2 complement gene (see, Moreira et al. (1995) *EMBO J.* 14:3809-3819) also is located at the 3' end of the second transcriptional unit.

Vector pMG also contains an ori sequence (ori pMB1) located between the SV40 polyadenylation signal and the synthetic polyadenylation site.

EXAMPLE 2

Figure 2:
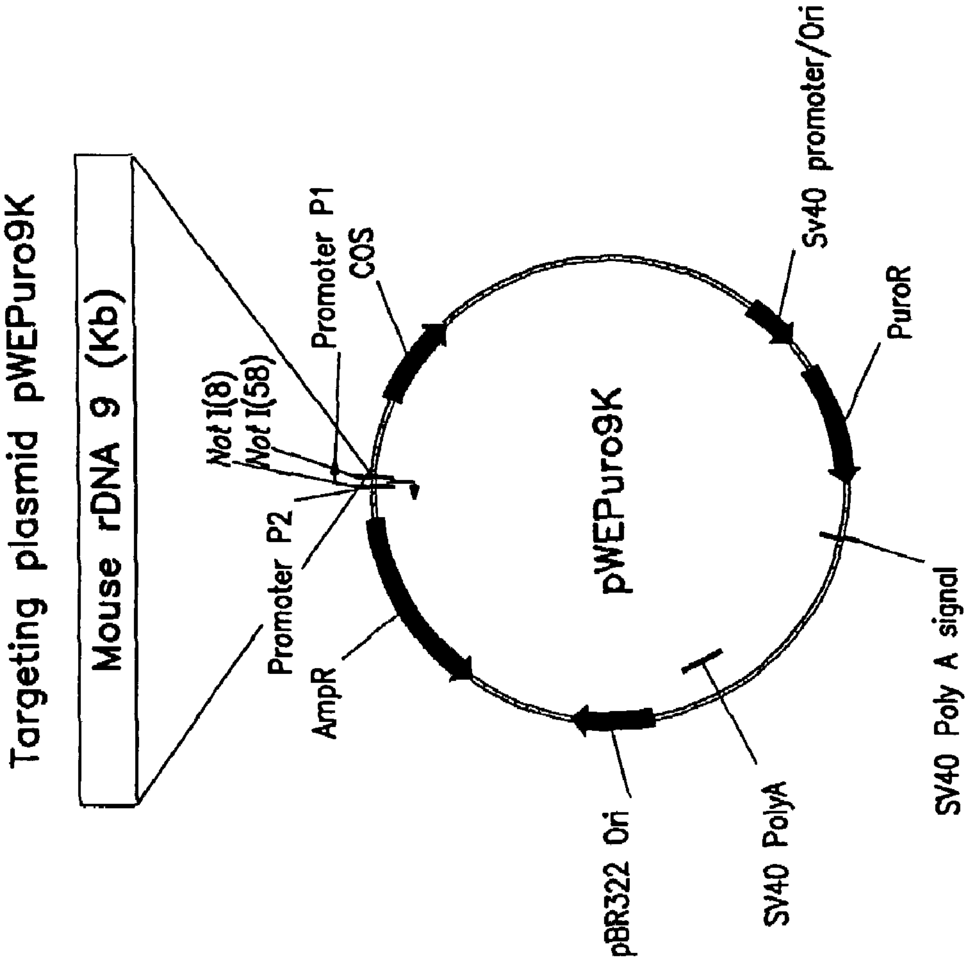
FIG. 2 provides a map of pWEPuro9K, which is a targeting vector derived from the vector pWE15 (GenBank Accession #X65279; SEQ ID No. 31). Plasmid pWE15 was modified by replacing the SalI (Klenow filled)/SmaI neomycin resistance encoding fragment with the PvuII/BamHI (Klenow filled) puromycin resistance-encoding fragment (isolated from plasmid pPUR, Clontech Laboratories, Inc., Palo Alto, Calif.; GenBank Accession no. U07648; SEQ ID No. 30) resulting in plasmid pWEPuro. Subsequently a 9 Kb NotI fragment from the plasmid pFK161 (see Example 1, see, also Csonka et al. (2000) *Journal of Cell Science* 113:3207-32161; and SEQ ID NO: 118), containing a portion of the mouse rDNA region, was cloned into the NotI site of pWEPuro resulting in plasmid pWEPuro9K.

A. Construction of Targeting Vector and Transfection into LMtk− cells for the Generation of Platform Chromosomes A targeting vector derived from the vector pWE15 (GeneBank Accession #X65279) was modified by replacing the Sa/I (Klenow filled)/SmaI neomycin resistance containing fragment with the PvuII/BamHI (Klenow filled) puromycin resistance containing fragment (isolated from plasmid pPUR, Clontech Laboratories, Inc. Palo Alto, Calif.; SEQ ID No. 30) resulting in plasmid pWEPuro. Subsequently a 9 Kb NotI fragment from the plasmid pFK161 (SEQ ID NO: 118) containing a portion of the mouse rDNA region was cloned into the NotI site of pWEPuro resulting in plasmid pWEPuro9K (FIG. 2). The vector pWEPuro9K was digested with SpeI to linearize and transfected into LMtk– mouse cells. Puromycin resistant colonies were isolated and subsequently tested for artificial chromosome formation via fluorescent in situ hybridization (FISH) (using mouse major and minor DNA repeat sequences, the puromycin gene and telomeres sequences as probes), and fluorescent activated cell sorting (FACS). From this sort, a subclone was isolated containing an artificial chromosome, designated 5B11.12, which carries 4-8 copies of the puromycin resistance gene contained on the pWEPuro9K vector. FISH analysis of the 5B11.12 subclone demonstrated the presence of telomeres and mouse minor on the ACes. DOT PCR has been done on the 5B11.12 ACes revealing the absence of uncharacterized euchromatic regions on the ACes. A recombination site, such as an att or loxP engineering site or a plurality thereof, was introduced onto this ACes thereby providing a platform for site-specific introduction of heterologous nucleic acid.

B. Targeting a Single Sequence Specific Recombination Site onto Platform Chromosomes After the generation of the 5B11.12 platform, a single sequence-specific recombination site is placed onto the platform chromosome via homologous recombination. For this, DNA sequences containing the site-specific recombination sequence can be flanked with DNA sequences of homology to the platform chromosome. For example, using the platform chromosome made from the pWEPuro9K vector, mouse rDNA sequences or mouse major satellite DNA can be used as homologous sequences to target onto the platform chromosome. A vector is designed to have these homologous sequences flanking the site-specific recombination site and, after the appropriate restriction enzyme digest to generate free ends of homology to the platform chromosome, the DNA is transfected into cells harboring the platform chromosome (FIG. 3). Examples of site-specific cassettes that are targeted to the platform chromosome using either mouse rDNA or mouse major repeat DNA include the SV40-attP-hygro cassette and a red fluorescent protein (RFP) gene flanked by loxP sites (Cre/lox, see, e.g., U.S. Pat. No. 4,959,317 and description herein). After transfection and integration of the site-specific cassette, homologous recombination events onto the platform chromosome are subcloned and identified by FACS (e.g. screen and single cell subclone via expression of resistance or fluorescent marker) and PCR analysis.

For example, a vector can be constructed containing regions of the mouse rDNA locus flanking a gene cassette containing the SV40 early reporter-bacteriophage lambda attP site-hygromycin selectable marker (see FIG. 4 and described below). The use of the bacteriophage lambda attP site for lambda integrase-mediated site-specific recombination is described below. Homologous recombination event of the SV40-attP-hygro cassette onto the platform chromosome was identified using PCR primers that detect the homologous recombination and further confirmed by FISH analysis. After identifying subcloned colonies containing the platform chromosome with a single site-specific recombination site, cells carrying the platform chromosome with a single site-specific recombination site can now be engineered with site-specific recombinases (e.g. lambda INT, Cre) for integrating a target gene expression vector.

C. Targeting a Red Fluorescent Protein (RFP) Gene Flanked by loxP Sites onto 5B11.12 Platform As another example, while loxP recombination sites could have been introduced onto the ACes during de novo biosynthesis, it was thought that this might result in multiple segments of the ACes containing a high number of loxP sites, potentially leading to instability upon Cre-mediated recombination. A gene targeting approach was therefore devised to introduce a more limited number of loxP recombination sites into a locus of the 5B11-12 ACes containing introduced and possibly co-amplified endogenous rDNA sequences. Although there are more than 200 copies of rDNA genes in the haploid mouse genome distributed amongst 5-11 chromosomes (depending on strain), rDNA sequences were chosen as the target on the ACes since they represent a less frequent target than that of the satellite repeat sequences. Moreover, having observed much stronger pWEPuro9K hybridization to the 5B11-12 ACes than to other $LMTK^-$ chromosomes and in light of the observation that the transcribed spacer sequences within the rDNA may be less conserved than the rRNA coding regions, it was contemplated that a targeting vector based on the rDNA gene segment in pWEPuro9K would have a higher probability of targeting to the ACes rather than to other $LMTK^-$ chromosomes. Accordingly, a targeting vector, pBSFKLoxDsRedLox, was designed and constructed based on the rDNA sequences contained in pWEPuro9K.

The plasmid pBSFKLoxDsRedLox was generated in 4 steps. First, the NotI rDNA insert of pWEPuro9K (FIG. 2) was inserted into pBS SK-(Stratagene) giving rise to pBSFK. Second, a loxP polylinker cassette was generated by PCR amplification of pNEB193 (SEQ ID NO:32; New England Biolabs) using primers complementary to the M13 forward and reverse priming sites at their 3'end and a 34 bp 5' extension comprising a LoxP site. This cassette was reinserted into pNEB193 generating p193LoxMCSLox. Third, the DsRed gene from pDsRed1-N1 (SEQ ID NO:29; Clontech) was then cloned into the polylinker between the loxP sites generating p193LoxDsRedLox. Fourth, a fragment consisting of the DsRed gene flanked by loxP sites was cloned into a unique NdeI within the rDNA insert of pBSFK generating pBSFKLoxDsRedLox.

A gel purified 11 Kb PmlI/EcoRV fragment of pBSFKLoxDsRedLox was used for transfection. To detect targeted integration, PCR primers were designed from rDNA sequences within the 5' NotI-PmlI fragment of pWEPuro9K that is not present on the targeting fragment (5'primer) and sequence within the LoxDsRedLox cassette (3' primer). If the targeting DNA integrated correctly within the rDNA sequences, PCR amplification using these primers would give rise to a 2.3 Kb band. PCR reactions containing 1-4 μl of genomic DNA were carried out according to the MasterTaq protocol (Eppendorf), using murine rDNA 5' primer (5'-CGGACAATGCGGTTGTGCGT-3'; SEQ ID NO:72) and DsRed 3'primer (5'GGCCCCGTAATGCAGAAGAA-3'; SEQ ID NO:73) and PCR products were analyzed by agarose gel electrophoresis.

$1.5\times10^6$ 5B11-12 $LMTK^-$ cells were transfected with 2 μg of the pBSFKLoxDsRedLox targeting DNA described above using Lipofectamine Plus (Invitrogen). For flow sorting, harvested cells were suspended in medium and applied to the Becton Dickinson Vantage SE cell sorter, equipped with 488 nm lasers for excitation and 585/42 bandpass filter for optimum detection of RFP fluorescence. Cells were sorted using dPBS as sheath buffer. Negative control parental 5B11-12 cells and a positive control LMTK⁻ cell line stably transfected with DsRed were used to establish the selection gates. The RFP positive gated populations were recovered, diluted in medium supplemented with 1× penicillin-streptomycin (Invitrogen), then plated and cultured as previously described. After 4 rounds of enrichment, the percentage of RFP positive cells reached levels of 50% or higher. DNA from populations was analyzed by PCR for evidence of targeted integration. Ultimately, single cell subclones were established from positive pools and were analyzed by PCR and PCR-positive clones confirmed by FISH as described below.

DNA was purified from pools or single cell clones using previously described methods set forth in Lahm et al., *Transgenic Res.,* 1998;

7:131-134, or in some cases using a Wizard Genomic DNA purification kit (Promega). For FISH analysis, a biotinylated DsRed gene probe was generated by PCR using DsRed specific primers and biotin-labeled dUTP (5' RFP primer: 5'-GGTTTAAAGTGCGCTCCTCCAAGAACGTCATC-3', SEQ ID NO:74; and 3' RFP primer: 5'AGATCTAGAGCCGCCGCTACAGGAACAGGTGGTGGCGGCC-3'; SEQ ID NO:75). To maximize the signal intensity of the DsRed probe, Tyramide amplification was carried out according to the manufacturers protocols (NEN).

The process of testing the feasibility of a more general targeting strategy that would not rely on enrichment via drug selection of stably transfected clones can be summarized as follows. A red fluorescent protein gene (RFP; encoded by the DsRed gene) was inserted between the loxP sites of the targeting vector to form pBSFKLoxDsRedLox. After transfection with PBSFKLoxDsRedLox, sequential rounds of high speed flow sorting and expansion of sorted cells in culture could then be used to enrich for stable transformants expressing RFP. In the event of targeted integration, PCR screening with primers that amplify from a spacer region within the segment of the 45s pre-rRNA gene in pWEPuro9K to a specific anchor sequence within the DsRed gene in the targeting cassette would give rise to a diagnostic 2.3 Kb band. However, as rDNA clusters are found on several chromosomes, confirmation of targeting to an ACes would require fluorescence in situ hybridization (FISH) analysis. Finally, the flanking of the DsRed gene by loxP sites would allow for its removal and subsequent replacement with other genes of interest.

After transfection of the targeting sequence into 5B11-12 cells, enrichment for targeted clones was carried out using a combination of flow cytometry to detect red-fluorescing cells and PCR screening. Ultimately 17 single cell subclones were identified as potential targeted clones by PCR and of these 16 were found by FISH to contain the DsRed integration event into the ACes. These subclones are referred to herein as D11-C4, D11-C12, D11-H3, C9-C9, C9-B9, C9-F4, C9-H8, C9-F2, C9-G8, C9-B6, C9-G3, C9-E12, C9-A11, C11-E3, C11-A9 and C11-H4. PCR analysis of genomic DNA isolated from the D11 -C4 subclone gave rise to a 2.3 Kb band, indicative of a targeted integration into an rDNA locus. Further analysis of the subclone by FISH analysis with a DsRed gene probe demonstrated integration of the LoxDsRedLox targeting cassette on the ACes co-localizing with one of the regions of rDNA staining seen on the 5B11-12 ACes, consistent with a targeted integration into an rDNA locus of the ACes, while integrations on other chromosomes were not observed. Since transfected cells were maintained as heterogeneous populations through several cycles of sorting and replating it was not possible to estimate the frequency of targeted events. In most mammalian cell lines the frequency of gene targeting via homologous recombination is roughly $10^{-5}$-$10^{-7}$ treated cells. Despite the low frequency of these events in mammalian cells, it is clear that an RFP expression based screening paradigm, coupled with PCR analysis, can effectively detect and enrich for such infrequent events in a large population. In instances where drug selection is not possible or not desirable, such a system may provide a useful alternative. It was also verified that the modified ACes in subclone D11-C4 could be purified by flow cytometry. The results indicate that the flow karyogram of the D11-C4 subclone was unaltered from that of the 5B11-12 cell line. Thus, the D11-C4 ACes can be purified in high yield from native chromosomes of the host cell line.

D. Reduction of LoxP on ACes to a Single Site.

The strong hybridization signal detected by FISH on the ACes using the DsRed gene probe suggests that several copies of the targeting cassette may be present on the ACes in the D11-C4 line. This also suggests that multiple rDNA genes have been correctly targeted.

Accordingly, in certain embodiments where necessary, the number of loxP sites on the ACes can be reduced to a single site by in situ treatment with Cre recombinase, provided that the sites are co-linear. Such a process is described for multiple loxP-flanked integrations on a native mouse chromosome (Garrick et al., *Nature Genet.,* 1998, Jan;18(1):56-59). Reduction to a single loxP site on the D11-C4 ACes would result in the loss of the DsRed gene, forming the basis of a useful screen for this event.

For this purpose, a Cre expression plasmid pCX-Cre/GFP III has been generated by first deleting the EcoRi fragment of pCX-eGFP (SEQ ID NO:71) containing the eGFP coding sequence and replacing it with that of a PCR amplified Cre recombinase coding sequence (SEQ ID NO:58), generating pCX-Cre. Next, the AseI/SspI fragment of pD2eGFP-N1 (containing the CMV promoter driving the D2EGFP gene with SV40 polyA signal; Clontech; SEQ ID NO:87) was inserted into the filled HindIII site of pCX-Cre, generating pCX-CreGFP II. Control plasmid pCX-CreRev\GFP III was generated in similar fashion except that the Cre recombinase coding sequence was inserted in the antisense orientation. LMTK⁻ cell line D11-C4 (containing first generation platform ACes with multiple loxP-DsRED sites) and 5B11-12 cell line (containing ACes with no loxP-DsRED sites) are maintained in culture as described above. D11C4 cells are transfected with 2 μg of plasmid pCX-CreGFP III or 2 μg pCX-CreRev\GFP III using Lipofectamine (Invitrogen) as previously described.

Forty-eight to seventy-two hours after transfection, transfected D11-C4 cells are harvested and GFP positive cells are sorted by cell cytometry using a FACSta Vantage cell sorter (Beckton-Dickinson) as follows: All D11-C4 cells transfected with pCX-Cre\GFP III or control plasmid pCX-CreRev\GFP III that exhibit GFP fluorescent higher than the gate level established by untransfected cells are collected and placed in culture a further 7-14 days. After 7-14 days the initial D11-C4 cells are harvested and analyzed by cell cytometry as follows: Untransfected D11-C4 cells are used to establish the gate that defines the RFP positive population, while 5B11-12 cells are used to set the RFP negative gate.

The GFP positive population of D11-C4 transfected with pCX-Cre\GFP III should show decreased red fluorescence compared to pCX-CreRev\GFP III transfected or untransfected control D11-C4 cells. The cells exhibiting greatly decreased or no RFP expression are collected and single cell clones subsequently established. These clones will be expanded and analyzed by fluorescence in-situ hybridization and Southern blotting to confirm the removal of loxP-DsRed gene copies.

EXAMPLE 3

Figure 4:
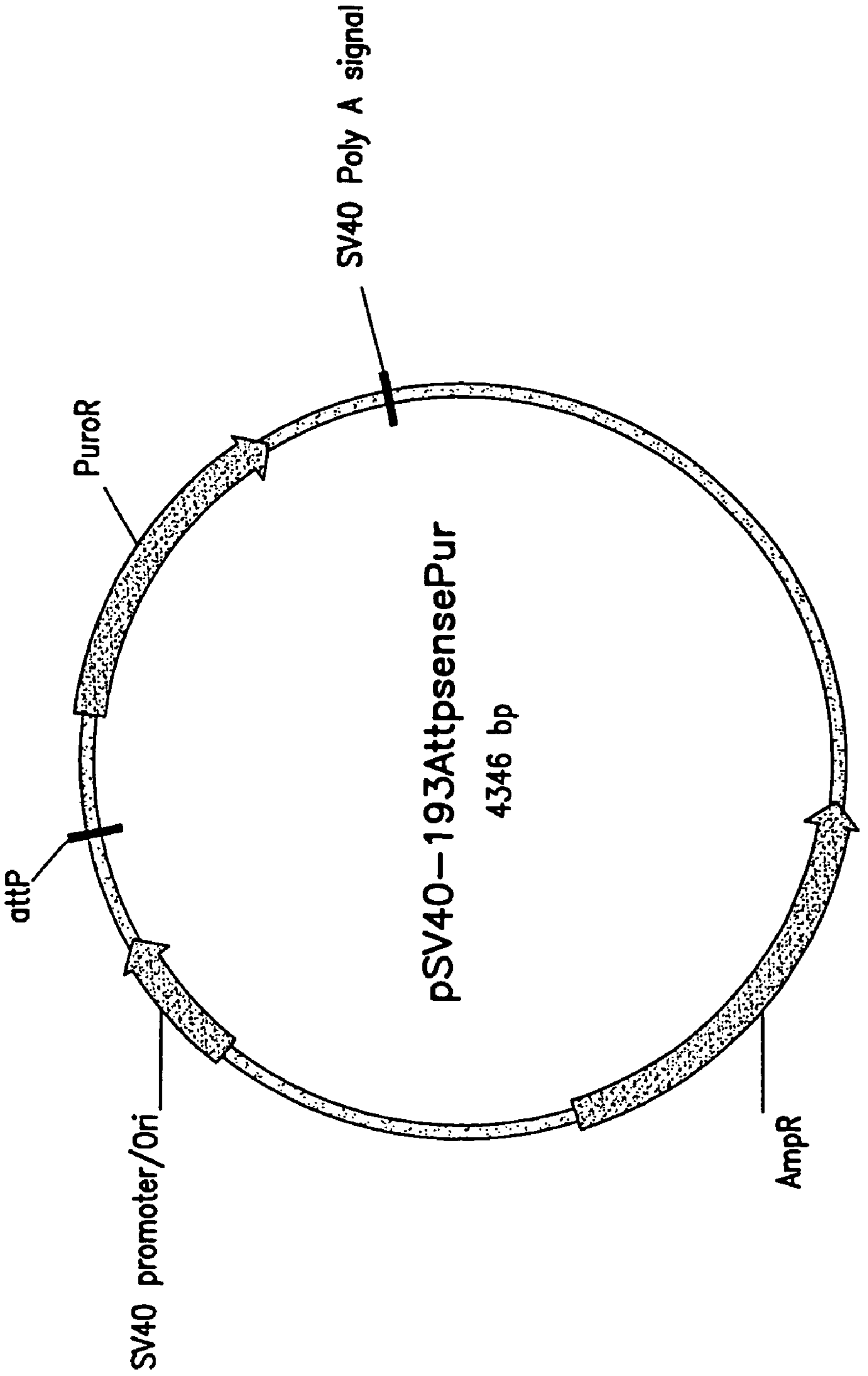
FIG. 4 provides a map of plasmid pSV40-193attPsensePur.

Construction of Targeting Vector and Transfection into LMtk– Cells for the Generation of Platform Chromosomes Containing Multiple Site-Specific Recombination Sites An example of a selectable marker system for the creation of a chromosome-based platform is shown in FIG. 4. This system includes a vector containing the SV40 early promoter immediately followed by (1) a 282 base pair (bp) sequence containing the bacteriophage lambda attP site and (2) the puromycin resistance marker. Initially a PvuII/StuI fragment containing the SV40 early promoter from plasmid pPUR (Clontech Laboratories, Inc., Palo Alto, Calif.; Seq ID No. 30) was subcloned into the EcoRI/CRI site of pNEB193 (a PUC19 derivative obtained from New England Biolabs, Beverly, Mass.; SEQ ID No. 32) generating the plasmid pSV40193. The only differences between pUC19 and pNEB193 are in the polylinker region. A unique AscI site (GGCGCGCC) is located between the BamHI site and the SmaI site, a unique PacI site (TTAATTAA) is located between the BamHI site and the XbaI site and a unique PmeI site (GTTTAAAC) is located between the PstI site and the SalI site.

The attP site was PCR amplified from lambda genome (GenBank Accession #NC 001416) using the following primers:

```
                                      SEQ ID No. 1
attPUP: CCTTGCGCTAATGCTCTGTTACAGG

                                      SEQ ID No. 2
attPDWN: CAGAGGCAGGGAGTGGGACAAAATTG
```

After amplification and purification of the resulting fragment, the attP site was cloned into the SmaI site of pSV40193 and the orientation of the attP site was determined by DNA sequence analysis (plasmid pSV40193attP). The gene encoding puromycin resistance (Puro) was isolated by digesting the plasmid pPUR (Clontech Laboratories, Inc. Palo Alto, Calif.) with AgeI/BamHI followed by filling in the overhangs with Klenow and subsequently cloned into the AscI site downstream of the attP site of pSV40193attP generating the plasmid pSV40193attPsensePUR (FIG. 4; SEQ ID NO:113)).

The plasmid pSV40193attPsensePUR was digested with ScaI and co-transfected with the plasmid pFK161 (SEQ ID NO: 118) into mouse LMtk– cells and platform artificial chromosomes were identified and isolated as described above. The process for generating this exemplary platform ACes containing multiple site-specific recombination sites is summarized in FIG. 5. One platform ACes resulting from this experiment is designated B19-18. This platform ACes chromosome may subsequently be engineered to contain target gene expression nucleic acids using the lambda integrase mediated site-specific recombination system as described herein in Example 7 and 8.

EXAMPLE 4

Figure 7:
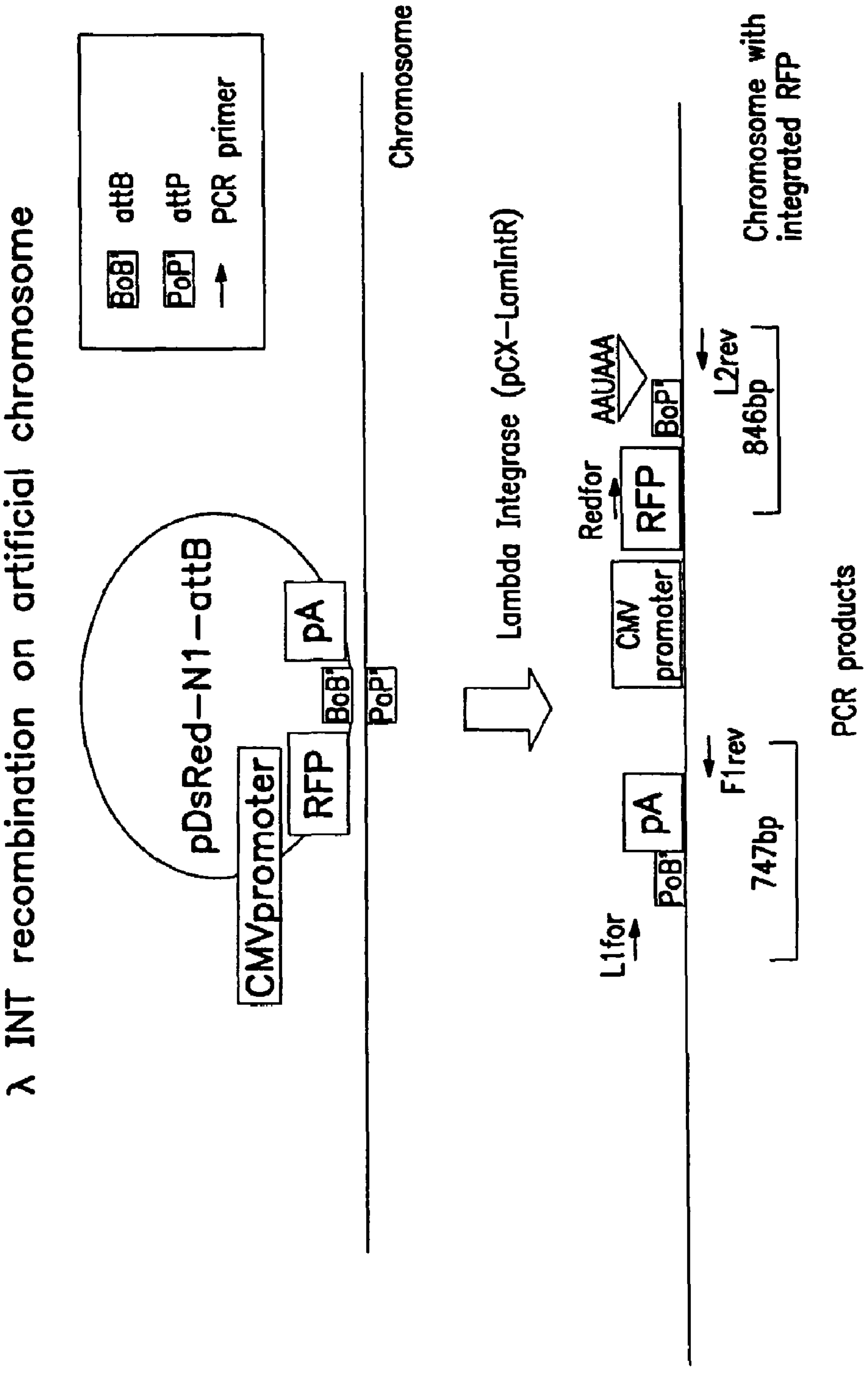
FIG. 7 depicts insertional recombination of a vector encoding a marker gene, DsRed and an attB site with an artificial chromosome containing an attP site.

Lambda Integrase Mediated Site-Specific Recombination of a RFP Expressing Vector onto Artificial Chromosomes In this example, a vector expressing the red fluorescent protein (RFP) was produced and recombined into the attP site residing on an artificial chromosome within LMTK$^-$ cells. This recombination is depicted in FIG. 7.

A. Construction of Expression Vectors Containing Wild-type and Mutant Lambda Integrase Mutations at the glutamic acid at position 174 in the lambda integrase protein relaxes the requirement for the accessory protein IHF during recombination and DNA supercoiling in vitro (see, Miller et al. (1980) *Cell* 20:721-729; Lange-Gustafson et al. (1984) *J. Biol. Chem.* 259:12724-12732). Mutations at this site promote attP, attB intramolecular recombination in mammalian cells (Lorbach et al. (2000) *J. Mol. Biol* 296:1175-1181).

To construct nucleic acid encoding the mutant, lambda integrase was PCR amplified from bacteriophage lambda DNA (cl857 ind Sam 7; New England Biolabs) using the following primers:

```
Lamint1                              (SEQ ID No. 3)
TTCGAATTCATGGGAAGAAGGCGAAGTCATGAGCG)

Lamint2                              (SEQ ID No. 4)
(TTCGAATTCTTATTTGATTTCAATTTTGTCCCAC).
```

The resulting PCR product was digested with EcoR I and cloned into the EcoR I site of pUC19. Lambda integrase was mutated at amino acid position 174 using QuikChange Site-Directed Mutagenesis Kit (Stratagene) and the following oligos (generating a glutamic acid to arginine change at position 174):

```
LambdaINTE174R                       (SEQ ID No. 6)
(CGCGCAGCAAAATCTAGAGTAAGGAGATCAAGACTTACGGCTGACG),

LamintR174rev                        (SEQ ID No. 7)
(CGTCAGCCGTAAGTCTTGATCTCCTTACTCTAGATTTTGCTGCGCG).
```

The resulting site directed mutant was confirmed by sequence analysis. The wildtype and mutant lambda genes were cloned into the EcoR I site of pCX creating pCX-LamInt (SEQ ID NO: 127) and pCXLamIntR (FIG. 8; SEQ ID NO: 112).

The plasmid pCX (SEQ ID No. 70) was derived from plasmid pCXeGFP (SEQ ID No. 71). Excision of the EcoRI fragment containing the eGFP marker generated pCX. To generate plasmid pCXLamINTR (SEQ ID NO: 112) an EcoRI fragment containing the lambda integrase E174R (SEQ ID No. 37) mutation was cloned into the EcoRI site of pCX, and to generate plasmid pCX-LamINT, an EcoRI fragment containing the wild-type lambda integrase was cloned into the EcoRI site of pCX.

B. Construction of Integration Vector Containing attB and DsRed

The plasmid pDsRedN1 (Clontech Laboratories, Palo Alto, Calif.; SEQ ID No. 29) was digested with Hpa I and ligated to the following annealed oligos:

```
attB1                                (SEQ ID No. 8)
(TGAAGCCTGCTTTTTTATACTAACTTGAGCGAA)

attB2                                (SEQ ID No. 9)
(TTCGCTCAAGTTAGTATAAAAAAGCAGGCTTCA)
```

The resulting vector (pDsRedN1-attB) was confirmed by PCR and sequence analysis.

C. Transfection into LMtk– Cells

LM(tk–) cells containing the Prototype A ACes (L1-18; Chromos Molecular Systems Inc., Burnaby, BC Canada)

were co-transfected with pDsRedN1 or pDsRedN1-attB and either pCXLamInt (SEQ ID NO: 127) or pCXLamIntR (SEQ ID NO: 112) using Lipofectamine Plus Reagent (LifeTechnologies, Gaithersburg, Md.). The transfected cells were grown in DMEM (LifeTechnologies, Gaithersburg, Md.) with 10% FBS (CanSera) and G418 (CalBiochem) at a concentration of 1 mg/ml.

D. Enrichment by Cell Sorting

The transfected cells were sorted using a FACs Vantage SE cell sorter (Becton Dickenson) to enrich for cells expressing DsRed. The cells were excited with a 488 nm Argon laser at 200 watts and cells fluorescing in the 585/42 detection channel were collected. The sorted cells were returned to growth medium for recovery and expansion. After three successive enrichments for cells expressing DsRed, single cell sorting into 96 well plates was performed using the same parameters. Duplicate plates of the single cell clones were made for PCR analysis.

E. PCR Analysis of Single Cell Clones

Pools of cells from each row and column of the 96 well plate were used for DNA isolation. DNA was prepared using a Wizard Genomic DNA purification kit (Promega Inc, Madison, Wis.). Nested PCR analysis on the DNA pools was performed to confirm the site-specific recombination event using the following primer sets:

```
attPdwn2                              (SEQ ID No. 10)
(TCTTCTCGGGCATAAGTCGGACACC)

CMVen                                 (SEQ ID No. 11)
(CTCACGGGGATTTCCAAGTCTCCAC)

followed by:
attPdwn                               (SEQ ID No. 12)
(CAGAGGCAGGGAGTGGGACAAAATTG)

CMVen2                                (SEQ ID No. 13)
(CAACTCCGCCCCATTGACGCAAATG).
```

The resulting PCR reactions were analyzed by gel electrophoresis and the potential individual clones containing the site-specific recombination event were identified by combining the PCR results of all of the pooled rows and columns for each 96 well plate. The individual clones were then further analyzed by PCR using the following primers that flank the recombination junction. L1for and F1rev flank the attR junction whereas REDfor and L2rev flank the attL junction (see FIG. 7):

```
L1for                                 (SEQ ID No. 14)
AGTATCGCCGAACGATTAGCTCTTCA

F1rev                                 (SEQ ID No. 15)
GCCGATTTCGGCCTATTGGTTAAA

REDfor                                (SEQ ID No. 16)
CCGCCGACATCCCCGACTACAAGAA

L2rev                                 (SEQ ID No. 17)
TTCCTTCGAAGGGGATCCGCCTACC.
```

F. Sequence Analysis of Recombination Junctions

PCR products spanning the recombination junction were Topo-cloned into pcDNA3.1D/V5H is (Invitrogen Inc., San Diego, Calif.) and then sequenced by cycle-sequencing. The clones were confirmed to have the correct attR and attL junctions by cycle sequencing.

G. Fluorescent In Situ Hybridization (FISH)

The cell lines containing the correct recombination junction sequence were further analyzed by fluorescent in situ hybridization (FISH) by probing with the DsRed coding region labeled with biotin and visualizing with the Tyramide Signal Amplification system (TSA; NEN Life Science Products). The results indicate that the RFP sequence is present on the ACes.

H. Southern Analysis

Genomic DNA was harvested from the cell lines containing an ACes with the correct recombinant event and digested with EcoR I. The digested DNAs were separated on a 0.7% agarose gel, transferred and fixed to a nylon membrane and probed with RFP coding sequences. The result showed that there is an integrated copy of RFP coding sequence in each clone.

EXAMPLE 5

Delivery of a Second Gene Encoding GFP onto the RFP Platform ACes

A. Construction of Integration Vector Containing attB and GFP (pD2eGFPIresPuroattB).

The plasmid pIRESpuro2 (Clontech, Palo Alto, Calif.; SEQ ID NO: 88) was digested with EcoRI and NotI then ligated to the D2eGFP EcoRI-NotI fragment from pD2eGFP-N1 (Clontech, Palo Alto, Calif.) to create pD2eGFPIresPuro2. Subsequently, oligos encoding the attB site were annealed and ligated into the NruI site of pD2eGFPIresPuro2 to create pD2eGFPIresPuroattB. The orientation of attB in the NruI site was determined by PCR.

B. Transfection of LMtk− Cells

The LMtk− cells containing the RFP platform ACes produced in Example 4, which has multiple attP sites, were co-transfected with pCXLamIntR and pD2eGFPIresPuroattB using LipofectAMINE PLUS reagent. Five μg of each vector was placed into a tube containing 750 μl of DMEM (Dulbecco's modified Eagles Medium). Twenty μl of the Plus reagent was added to the DNA and incubated at room temperature for 15 minutes. A mixture of 30 μl of lipofectamine and 750 μl DMEM was added to the DNA mixture and incubated an additional 15 minutes at room temperature. The DNA mixture was then added dropwise to approximately 3 million cells attached to a 10 cm dish in 5 mls of DMEM. The cells were incubated 4 hours (37° C., 5% $CO_2$) with the DNA-lipid mixture, after which DMEM with 20% fetal bovine serum was added to the dishes to bring the culture medium to 10% fetal bovine serum. The dishes were incubated at 37° C. with 5% $CO_2$.

Plasmid pD2eGFPIresPuroattB has a puromycin gene transcriptionally linked to the GFP gene via an IRES element. Two days after the transfection the cells were placed in medium containing puromycin at 4 μg/ml to select for cells containing the pD2eGFPIresPuroattB plasmid integrated into the genome. Twenty-three clones were isolated after 17 days of selection with puromycin. These clones were expanded and then analyzed for the presence of the GFP gene on the ACes by 2-color (RFP/biotin & GFP/digoxigenin) TSA-FISH (NEN) according to the manufacturers protocol. Sixteen of the 23 clones produced a positive FISH signal on the ACes with a GFP probe.

EXAMPLE 6

Delivery Of ACes Into human Mesenchymal Stem Cells (hMSC)

A. Transfection

Transfection conditions for the most efficient delivery of the ACes into hMSCs (Cambrex BioWhittaker Product Code PT-2501, lot#F0658, East Rutherford, N.J.) were assayed using LipofectAMINE PLUS and Superfect. One million prototype B ACes, which is a murine derived 60 Mb ACes having primarily murine pericentric heterochromatin, and carrying a "payload" containing a hygromycin B selectable marker gene and a lacZ reporter gene (see , Telenius et al., 1999, *Chrom. Res.,* 7:3-7; and Kereso et al., 1996, *Chrom. Res.,* 4:226-239; each of which is incorporated herein by reference in its entirety), were combined with 1-12 μl of the transfection agent. In the case of LipofectAMINE PLUS, the PLUS reagent was combined with the ACes for 15 minutes followed by LipofectAMINE for a further 15 minutes. Superfect was complexed for minutes at a ratio of 2 μl Superfect per 1 million ACes. The ACes/transfection agent complex was then applied to 0.5 million recipient cells and the transfection was allowed to proceed according to the manufacturer's protocol. Percent transfected cells was determined on a FACS Vantage flow cytometer with argon laser tuned to 488 nm at 200 mW and FITC fluorescence collected through a standard FITC 530/30 nm band pass filter. After 24 hours, IdUrd labeled ACes were delivered to human MSCs in the range of 30-50%, varying with transfection agent and dose. ACes delivery curves were generated from data collected in experiments that varyied the dose of the transfection reagents. Dose response curves of Superfect and LipofectAMINE PLUS, showing delivery of ACes into recipient hMSCs cells, were prepared, measured by transfer of IdUrd labeled ACes and detected by flow cytometry. Superfect shows maximum delivery in the range of 30-50% at doses greater than 2 μl per million ACes. LipofectAMINE PLUS has a 42-48% delivery peak around 5-8 μl per million ACes. These dose curves were then correlated with toxicity data to determine the transfection conditions that will allow for highest potential transfection efficiency. Toxicity was determined by a modified plating efficiency assay (de Jong et al., 2001, *Chrom. Research,* 9:475-485). The population's normalized plating efficiency (at maximum % delivery doses) was in the range of 0.2-0.4 for Superfect and 0.5-0.6 with LipofectAMINE PLUS.

Due to the transfected population consisting of mixed cell types, flow cytometry allowed for the assessment of ACes delivery into each sub-population and the purification of the target population. Flow profiles showing forward scatter (cell size) and side scatter (internal cell granularity) revealed three distinct hMSC populations that were gated into three regions: R3 (small cell region), R4 (medium cell region), R5 (large cell region). Transfection conditions were further optimized by re-analyzing delivery curves and assessing the differences in delivery to each sub-population. Dose response curves of Superfect and LipofectAMINE were prepared showing % delivery to each sub-population represented by the gating on basis of cell size and granularity properties of the mixed population. Three distinct hMSC populations were gated and % delivery dose curves generated. Using Superfect and LipofectAMINE PLUS the overall % delivery increased with cell size (80-90% delivery in large cells). LipofectAMINE PLUS at high doses (8-12 μl per 1 million ACes) shows an increase in the overall proportion of chromosome transfer to the small population (10-20%). This suggests an advantage to using this transfection agent if the small-undifferentiated cell population is the desired target host cell.

B. Expression from Genes on ACes IN hMSCs

Following the delivery screening process conducted in section (A) above, the most promising results were subjected to further analyses to monitor expression and verify the presence of structurally intact ACes. The transfection conditions employed for these experiments were exactly the same as those that had been used during the screening process. Short-term expression was monitored by transfecting hMSCs with ACes containing a RFP gene (red fluorescent protein) set forth in Example 2C as "D11C4". The unselected population was harvested at 72-96 hours post transfection and % positive fluorescent cells measured by flow cytometry. RFP expression was in the range of 1-20%.

Long term-gene expression was assayed by selecting for hygromycin B resistant cells over a period of 7-10 days. Cytogenetic analysis was done to detect presence of intact ACes by Fluorescent In Situ hybridization (FISH), where metaphase chromosomes were hybridized to a mouse major satellite-DNA probe (targeting murine pericentric heterochromatin) and a lambda probe (hybridizing to the lacZ gene). The human mesenchymal transfected culture could not undergo standard sub-cloning as diffuse colonies form with limited doublings available for expansion. Cytogenetic analysis was performed on the entire population, sampling over a period of 3-10 days post-transfection. The hygromycin resistant population was then blocked in mitosis with colchicine and analyzed for presence of intact ACes by FISH. Preliminary FISH results show approximately 2-8% of the hMSC-transfected population had an intact ACes. This compared to rat skeletal muscle myoblast clones, which were in the range of 60-95%. To increase the % of intact ACes in the hMSC-transfected population an enrichment step can be utilized as described in Example 2C.

C. Differentiation of The hMSCs

In initial experiments where transfected hMSCs cells have been induced to differentiate into adipose or osteocytes, the results indicate that the transfected cells appear to be differentiating at a rate comparable to the untransfected controls and the cultures are lineage specific as tested by microscopic examination, FISH, Oil Red O staining (adipocyte assay), and calcium secretion (osteocyte assay).

Accordingly, these results indicate that the artificial chromosomes (ACes) provided herein can be successfully transferred into hMSC target cells. Targeting MSCs (such as hMSCs) permits gene transfer into cells in an undifferentiated state where the cells are easier to expand and purify. The genetically modified cells can then be differentiated in vitro or injected into a site in vivo where the microenvironment will induce transformation into specific cell lineages.

EXAMPLE 7

Delivery of a Promoterless Marker Gene to a Platform ACes

Platform ACes containing pSV40attPsensePURO (FIG. 4) were constructed as set forth in Examples 3 and 4.

A. Construction of Targeting Vectors.

The base vector p18attBZeo (3166 bp; SEQ ID NO: 114) was constructed by ligating the 1067 bp HindIII-SspI fragment containing attBZeo, obtained from pLITattBZeo (SEQ ID NO:91), into pUC18 (SEQ ID NO: 122) digested with HindIII and SspI.

1. p18attBZEO-eGFP (6119 bp; SEQ ID NO: 126) was constructed by inserting the 2977 bp SpeI-HindIII fragment from pCXeGFP (SEQ ID NO:71; Okabe, et al. (1997) *FEBS Lett* 407:313-319) containing the eGFP gene into p18attBZeo (SEQ ID NO: 114) digested with HindIII and XbaI.

Figure 10:
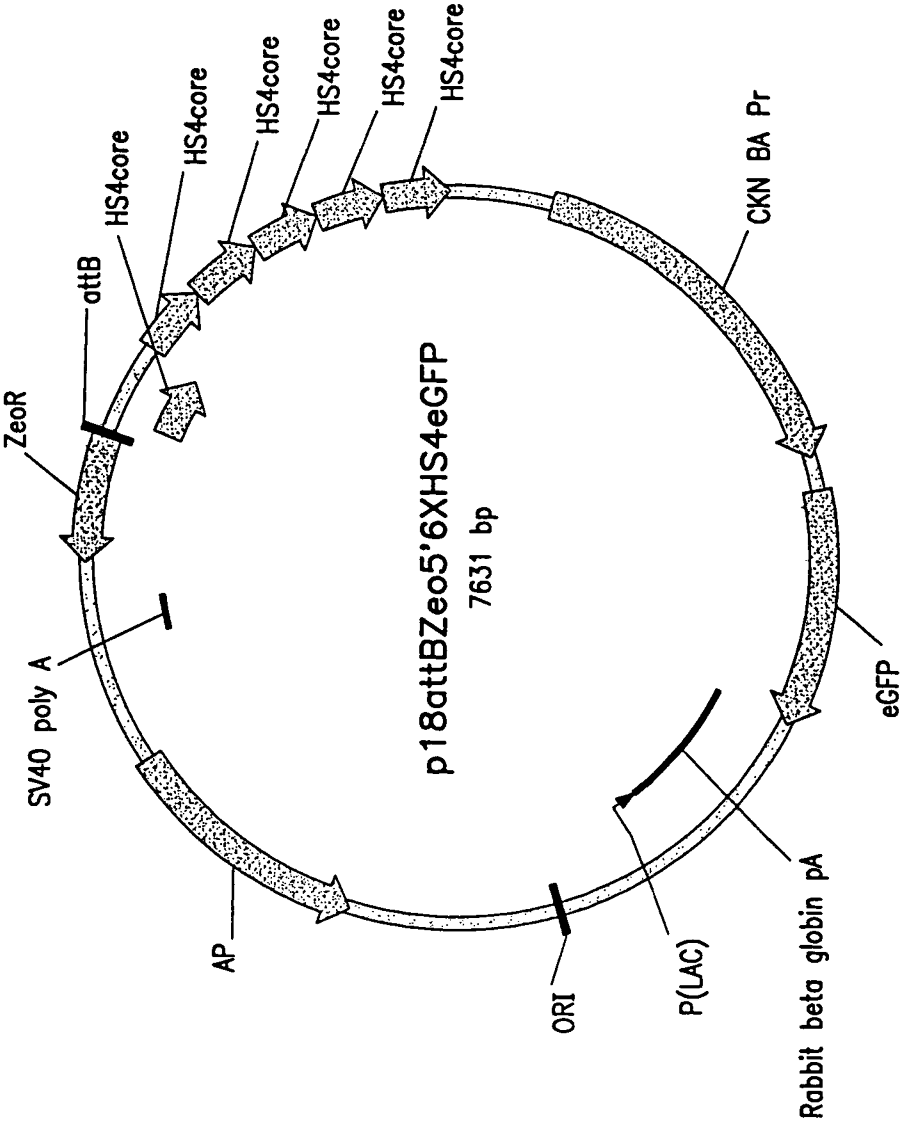
FIG. 10 provides the vector map for the plasmid p18attBZEO-5'6XHS4eGFP (SEQ ID NO: 116).

2. p18attBZEO-5'6XHS4eGFP (FIG. 10; 7631 bp; SEQ ID NO: 116) was constructed by ligating the 4465 bp HindIII fragment from 17084-022002/420B pCXeGFPattB (6XHS4)2 (SEQ ID NO: 123), which contains the eGFP gene under the regulation of the chicken beta actin promoter, 6 copies of the HS4 core element located 5' of the chicken beta actin promoter and the polyadenylation signal, into the HindIII site of p18attBZeo (SEQ ID NO: 114).

Figure 11:
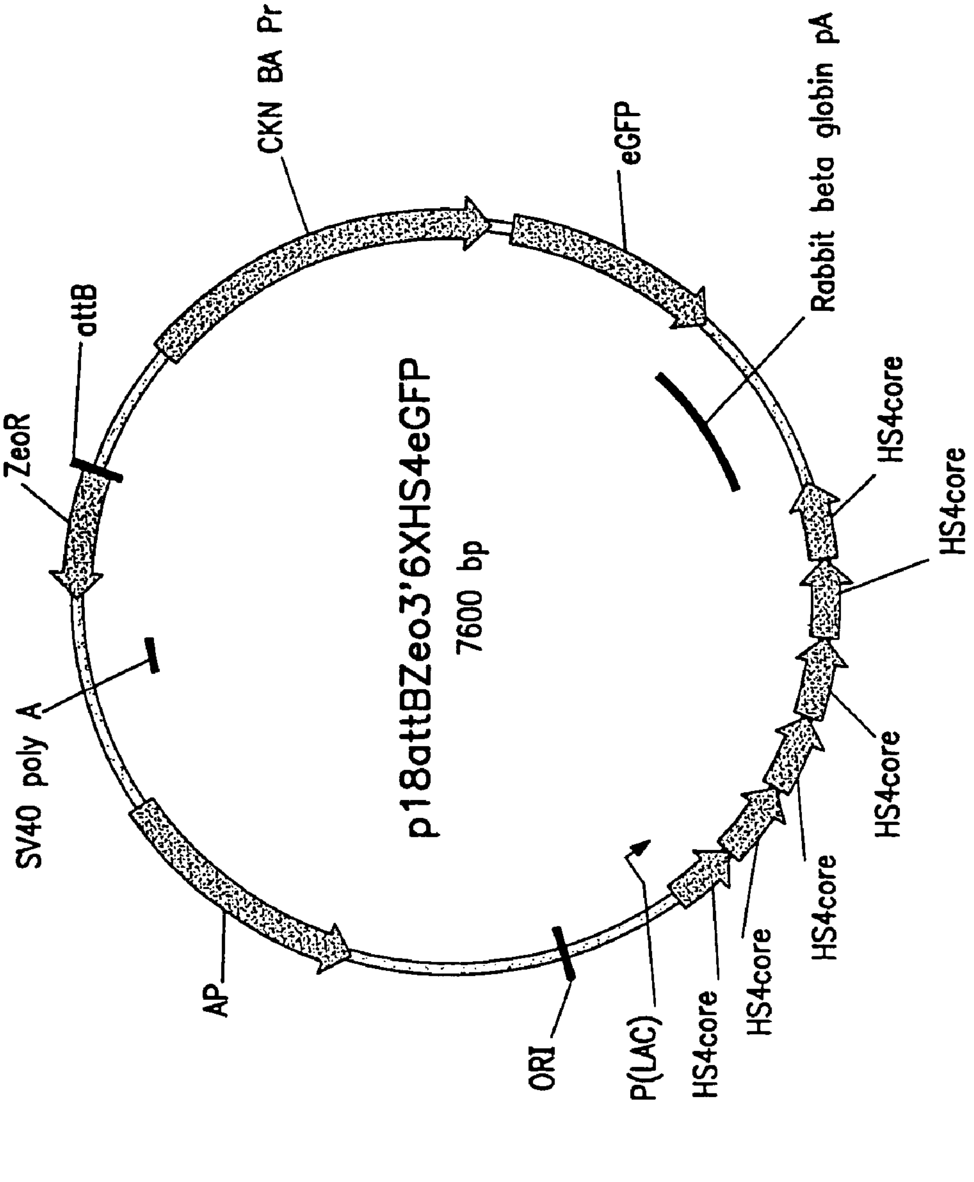
FIG. 11 provides the vector map for the plasmid p18attBZEO-3'6XHS4eGFP (SEQ ID NO: 115).

3. p18attBZEO-3'6XHS4eGFP (FIG. 11; 7600 bp; SEQ ID NO: 115) was created by removing the 5'6XHS4 element from p18attBZeo-(6XHS4)2eGFP (SEQ ID NO: 110). p18attBZeo-(6XHS4)2eGFP was digested with EcoRV and SpeI, treated with Klenow and religated to form p18attBZeo3'6XHS4eGFP (SEQ ID NO: 115).

Figure 12:
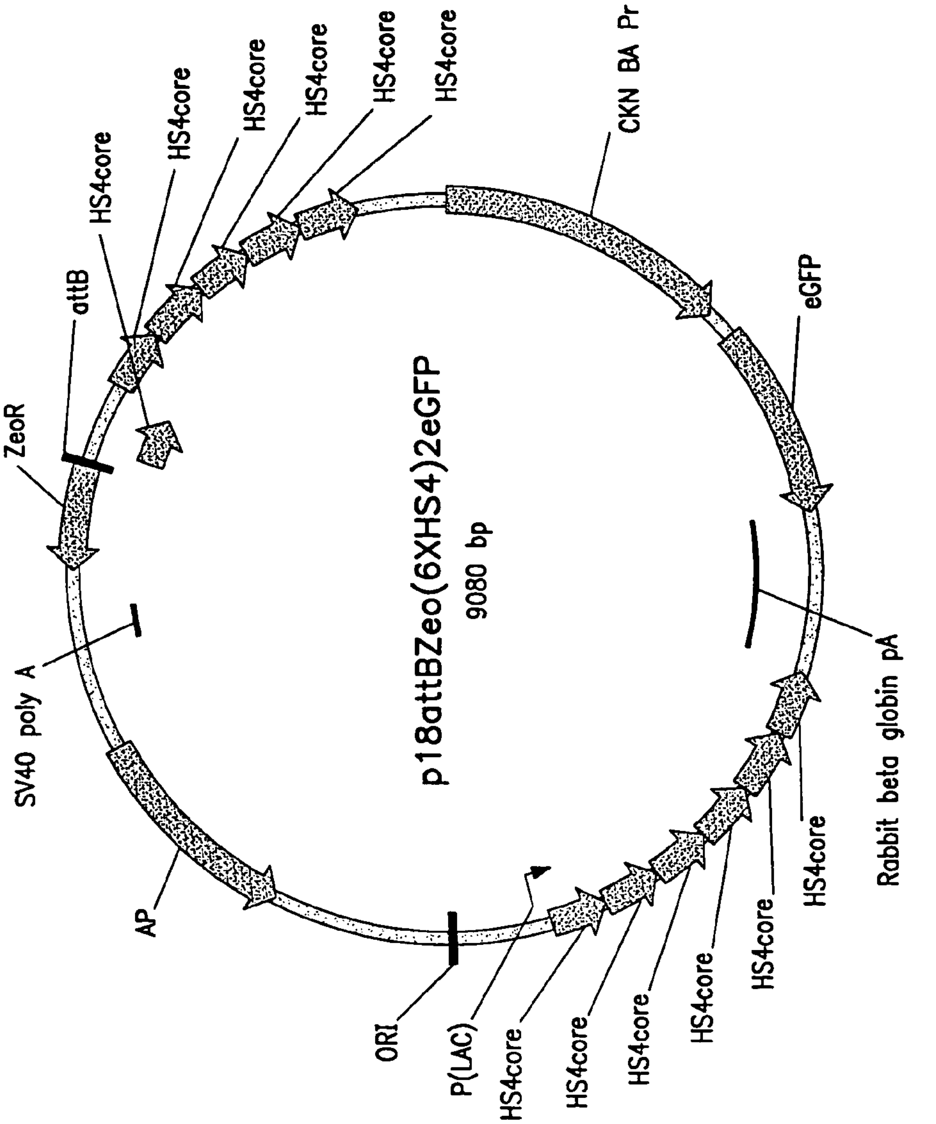
FIG. 12 provides the vector map for the plasmid p18attBZEO-(6XHS4)2eGFP (SEQ ID NO: 110).

4. p18attBZEO-(6XHS4)2eGFP (FIG. 12; 9080 bp; SEQ ID NO: 110) was created in two steps. First, the EcoRI-SpeI fragment from pCXeGFPattB(6XHS4)2 (SEQ ID NO: 123), which contains 6 copies of the HS4 core element, was ligated into p18attBZeo (SEQ ID NO: 114) digested with EcoRI and XbaI to create p18attBZeo6XHS4 (4615 bp; SEQ ID NO: 117). Next, p18attBZeo6XHS4 was digested with HindIII and ligated to the 4465 bp HindIII fragment from pCXeGFPattB(6XHS4)2, which contains the eGFP gene under the regulation of the chicken beta actin promoter, 6 copies of the HS4 core element located 5' of the chicken beta actin promoter and the polyadenylation signal.

TABLE 2

| Targeting plasmid | No. zeocin resistant clones | No. clones with expected PCR product size | No. clones with correct sequence at recombination junction |
|---|---|---|---|
| p18attBZEO-eGFP | 12 | 12 | NT* |
| p18attBZEO-5'6XHS4eGFP | 11 | 11 | NT |
| p18attBZEO-3'6XHS4eGFP | 11 | 11 | NT |
| p18attBZEO-(6XHS4)2eGFP | 9 | 9 | 4/4 |

*NT = not tested

B. Transfection and Selection with Drug.

The mouse cell line containing the 2$^{nd}$ generation platform ACE, B19-38 (constructed as set forth in Example 3), was plated onto four 10 cm dishes at approximately 5 million cells per dish. The cells were incubated overnight in DMEM with 10% fetal calf serum at 37° C. and 5% $CO_2$. The following day the cells were transfected with 5 μg of each of the 4 vectors listed in Example 7.A. above and 5 μg of pCXLamIntR (SEQ ID NO: 112), for a total of 10 μg per 10 cm dish. Lipofectamine Plus reagent was used to transfect the cells according to the manufacturers protocol. Two days post-transfection zeocin was added to the medium at 500 μg/ml. The cells were maintained in selective medium until colonies formed. The colonies were then ring-cloned (see, e.g., McFarland, 2000, Methods Cell Sci, March;22(1):63-66).

C. Analysis of Clones (PCR, SEQUENCING).

Genomic DNA was isolated from each of the candidate clones with the Wizard kit (Promega) and following the manufacturers protocol. The following primer set was used to analyze the genomic DNA isolated from the zeocin resistant clones: 5PacSV40-CTGTTAATTAACTGTGGAATGTGTG TCAGTTAGGGTG (SEQ ID NO:76); Antisense Zeo-TGAACAGGGTCACGTCGTCC (SEQ ID NO:77). PCR amplification with the above primers and genomic DNA from the site-specific integration of any of the 4 zeocin vectors would result in a 673 bp PCR product.

As set forth in Table 2, of the 4 zeocin resistant candidate clones thusfar analyzed by PCR, all 4 exhibit the correct sequence for a site-specific integration event.

EXAMPLE 8

Integration of a PCR Product by Site-Specific Recombination In this example a gene is integrated onto the platform ACes by site-specific recombination without cloning said gene into a vector.

A. PCR Primer Design.

PCR primers are designed to contain an attB site at the 5' end of one of the primers in the primer set. The remaining primers, which could be one or more than one primer, do not contain an attB site, but are complementary to sequences flanking the gene or genes of interest and any associated regulatory sequences. In first example, 2 primers (one containing an attB site) are used to amplify a selective gene such as puromycin.

Figure 13:
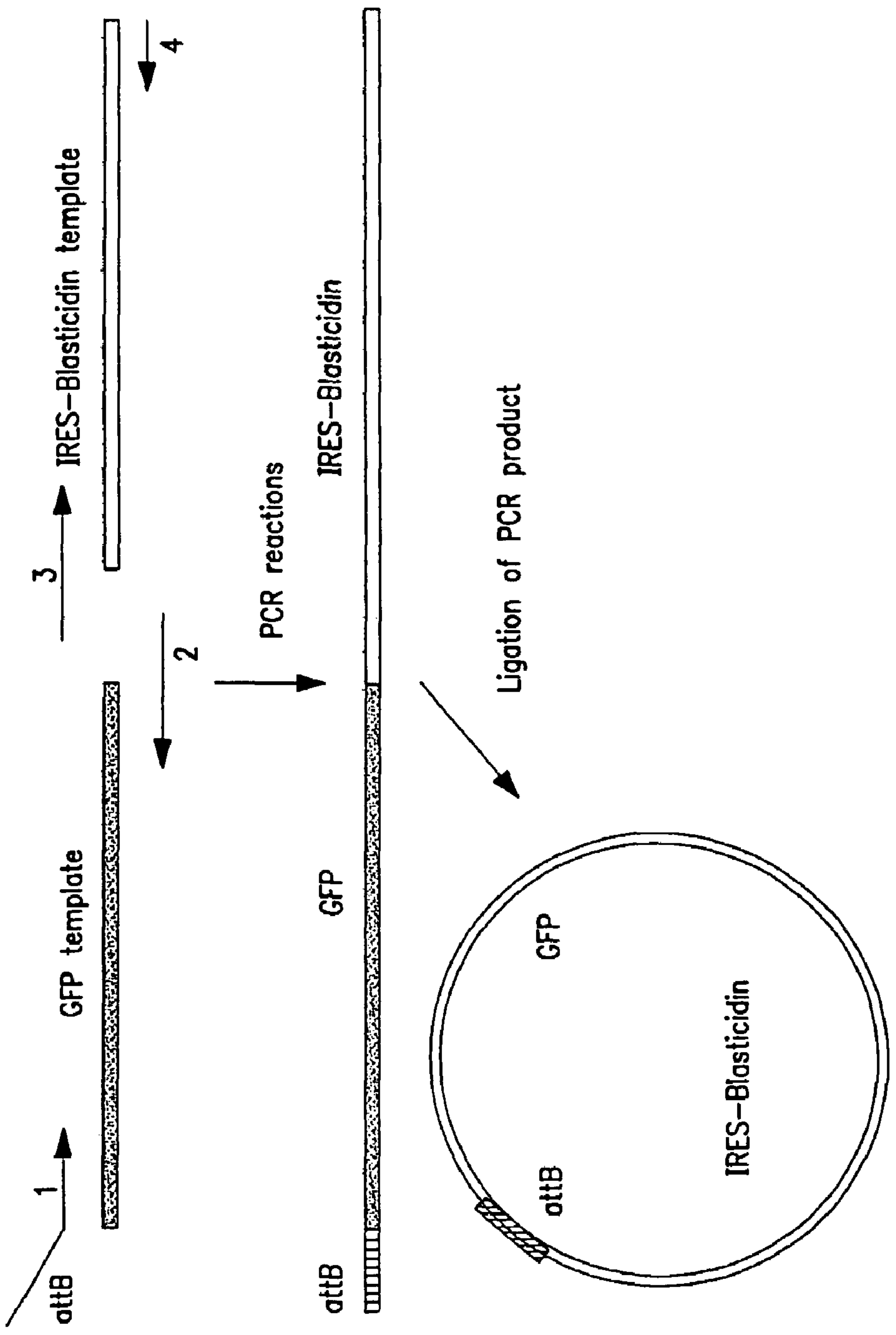
FIGS. 13 AND 14 depict the integration of a PCR product by site-specific recombination as set forth in Example 8.

In a second example as shown in FIG. 13, the primer set includes primers 1 & 2 that amplify the GFP gene without amplification of an upstream promoter. Primer 1 contains the attB site at the 5' end of the oligo. Primers 3 & 4 are designed to amplify the IRES-blasticidin DNA sequences from the vector pIRESblasticidin. The 5'end of primer 3 contains sequences complementary to the 5' end of primer 2 such that annealing can occur between 5' ends of the two primers.

B. PCR Reaction and Subsequent Ligation to Create Circulat Molecules from the PCR Product In the first example set forth above in Section A, the two PCR primers are combined with a puromycin DNA template such as pPUR (Clontech), a heat stable DNA polymerase and appropriate conditions for DNA amplification. The resulting PCR product (attB-Puromycin) is then then purified and self-ligated to form a circular molecule.

In the second example set forth above in Section A, amplification of the GFP gene and IRES-blasticidin sequences is accomplished by combining primers 1 & 2 with DNA template pD2eGFP and primers 3 & 4 with template pIRESblasticidin under appropriate conditions to amplify the desired template. After initial amplification of the two products (attB-GFP & IRES-blasticidin) in separate reactions, a second round of amplification using both of the PCR products from the first round of amplification together with primers 1 and 4 amplifies the fusion product attB-GFP-IRES-blasticidin (FIG. 13). This technique of using complementary sequences in primer design to create a fusion product is employed in *Saccharomyces cerevisiae* for allele replacement (Erdeniz et al (1997) *Gen Res* 7:1174-1183). The amplified product is then purified from the PCR reaction mixture by standard methods and ligated to form a circular molecule.

C. Introduction of PCR Product onto the ACes using a Recombinase

The circular PCR product is then be introduced to the platform ACes using the bacteriophage lambda integrase E174R. The introduction can be performed in vivo by transfecting the pCXLamIntR (SEQ ID NO: 112) vector encoding the lambda integrase mutant E174R together with the circularized PCR product into a cell line containing the platform ACE.

D. Selection for Marker Gene

Figure 14:
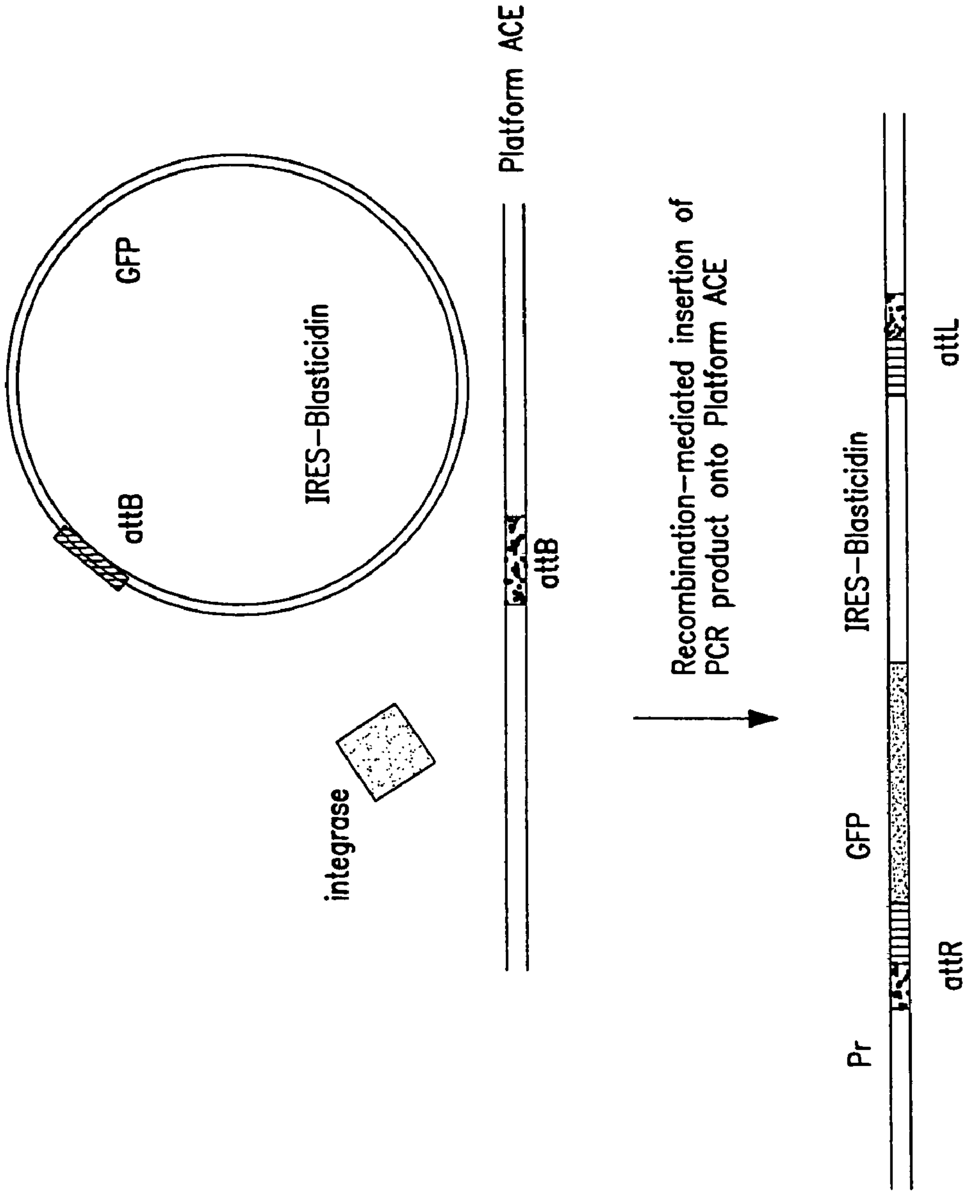

The marker gene (in this case either puromycin, blasticidin or GFP) is used to enrich the population for cells containing the proper integration event. A proper integration event in the second example (FIG. 14) juxtaposes a promoter residing on the platform ACes 5' to the attB-GFP-IRES-Blasticidin PCR product, allowing for transcription of both GFP and blasticidin. If enrichment is done by drug selection, blasticidin is added to the medium on the transfected cells 24-48 hours post-transfection. Selection is maintained until colonies are formed on the plates. If enrichment is done by cell sorting, cells are sorted 2-4 days post-transfection to enrich for cells expressing the fluorescent marker (GFP in this case).

E. Analysis of Clones

Clonal isolates are analyzed by PCR, FISH and sequence analysis to confirm proper integration events.

EXAMPLE 9

Construction of a Human Platform ACes "ACE 0.1"

A. Construction of the Targeting Vector pPACrDNA

Figure 15:
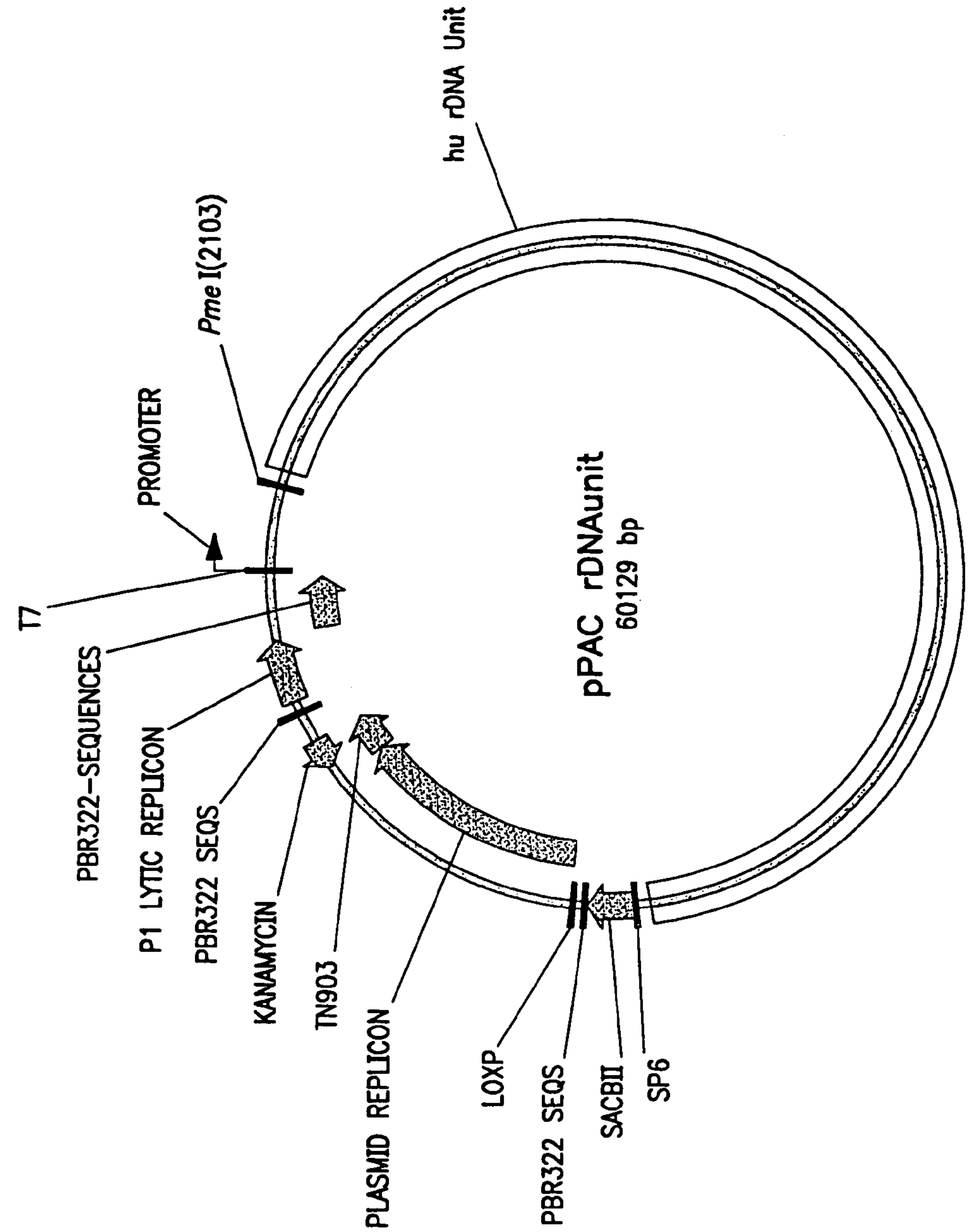
FIG. 15 provides the vector map for the plasmid pPACrDNA as set forth in Example 9.A.

Genome Systems (IncyteGenomics) was supplied with the primers 5'HETS (GGGCCGAAACGATCTCAACCTATT; SEQ ID NO:78), and 3'HETS (CGCAGCGGCCCTCCTACTC; SEQ ID NO:79), which were used to amplify a 538bp PCR product homologous to nt 9680-10218 of the human rDNA sequences (GenBank Accession No. U13369) and used as a probe to screen a human genomic P1AC (P1 Artificial Chromosome) library constructed in the vector pCYPAC2 (Ioannou et al. (1994) *Nat. Genet.* 6(1): 84-89). Genome Systems clone #18720 was isolated in this screen and contains three repeats of human rDNA as assessed by restriction analysis. GS clone #18720, was digested with PmeI, a restriction enzyme unique to a single repeat of the human rDNA (45Kbp), and then religated to form pPACrDNA (FIG. 15). The insert in pPACrDNA was analyzed by restriction digests and sequence analysis of the 5' and 3' termini. The pPACrDNA, rDNA sequences are homologous to Genbank Accession #U13369, containing an insert of about 45 kB comprising a single repeat beginning from the end of one repeat at ~33980 (relative to the Genbank sequence) through the beginning of the next repeat up to approximately 35120 (the repeat offset from that listed in the GenBank file). Thus, the rDNA sequence is just over 1 copy of the repeat extending from 33980 (+/−10 bp) to the end of the first repeat (43 Kbp) and continuing into the second repeat to bp 35120 (+/−10 bp).

B. Transfection and ACes Formation.

Five hundred thousand MSU1.1 cells (Morgan et al., 1991, Exp. Cell Res., November;197(1):125-136; provided by Dr. Justin McCormick at Michigan State University) were plated per 6 cm plate (3 plates total) and allowed to grow overnight. The cells were 70-80% confluent the following day. One plate was transfected with 15 μg pPACrDNA (linearized with Pme I) and 2 μg pSV40attPsensePuro (linearized with Sca I; see Example 3). The remaining plates were controls and were transfected with either 20 μg pBS (Stratagene) or 20 μg pSV40attBsensePuro (linearized with Sca I). All three plates were transfected using a $CaPO_4$ protocol.

C. Selection of Puromycin Resistant Colonies

One day post-transfection the cells were "glycerol shocked" by the addition of PBS medium containing 10% glycerol for 30 seconds. Subsequently, the glycerol was removed and replaced with fresh DMEM. Four days post-transfection selective medium was added. Selective medium contains 1 μg/ml puromycin. The transfection plates were maintained at 37° C. with 5% $CO_2$ in selective medium for 2 weeks at which point colonies could be seen on the plate transfected with pPACrDNA and pSV40attPsensePuro. The colonies were ring-cloned from the plate on day 17 post-selection and expanded in selective medium for analysis. Only two colonies (M2-2d & M2-2b) were able to proliferate in the selective medium after cloning. No colonies were seen on the control plates after 37 days in selective medium.

D. Analysis of Clones

FISH analysis was performed on the candidate clones to detect ACes formation. Metaphase spreads from the candidate clones were probed in multiple probe combinations. In one experiment, the probes used were biotin-labeled human alphoid DNA (pPACrDNA) and digoxigenin-labeled mouse major DNA (pFK161) as a negative control. Candidate M2-2d was single cell subcloned by flow sorting and the candidate subclones were reanalyzed by FISH. Subclone 1B1 of M2-2d was determined to be a platform ACes and also is designated human Platform ACE 0.1.

EXAMPLE 10

Site-Specific Integration of a Marker Gene onto a Human Platform ACE 0.1

The promoterless delivery method was used to deliver a promoterless blasticidin marker gene onto the human platform ACes with excellent results. The human ACes platform with a promoterless blasticidin marker gene resulted in 21 of 38 blasticidin resistant clones displaying a PCR product of the expected size from the population co-transfected with pLIT38attBBSRpolyA10 and pCXLamIntR (FIG. 8; SEQ ID NOs. 111 and 112). Whereas, the population transfected with pBlueScript resulted in 0 blasticidin resistant colonies.

A. Construction of pLIT38attB-BSRpolyA10 & pLIT38attB-BSRpolyA2.

The vector pLITMUS 38 (New England Biolabs; U.S. Pat. No. 5,691,140; SEQ ID NO: 119) was digested with EcoRV and ligated to two annealed oligomers, which form an attB site (attB1 5'-TGAAGCCTGCTTTTTTATACTAACTTGAGCGAA-3' (SEQ ID NO:8); attB2 5'-TTCGCTCAAGTTAGTATAAAAAAGCAGGCTTCA-3'; SEQ ID NO:9). This ligation reaction resulted in the vector pLIT38attB (SEQ ID NO: 120). The blasticidin resistance gene and SV40 polyA site were PCR amplified with primers: 5BSD (ACCATGAAAACATTTAACATTTCTCAACA; SEQ ID NO:80) and SV40polyA (TTTATTTGTGAAATTTGTGATGCTATTGC; SEQ ID NO:81) using pPAC4 (Frengen, E., et al. (2000) Genomics 68 (2), 118-126; GenBank Accession No. U75992) as template. The blasticidin-SV40polyA PCR product was then ligated into pLIT38attB at the BamHI site, which was Klenow treated following digestion with BamHI. pLIT38attB-BSDpolyA10 (SEQ ID NO: 111) and pLIT38attB-BSDpolyA2 (SEQ ID NO: 121) are the two resulting orientations of the PCR product ligated into the vector.

B. Transfection of MSU1.1 Cells Containing Human Platform ACE 0.1.

MSU1.1 cells containing human platform ACE 0.1 (see Example 9) were expanded and plated to five 10 cm dishes with $1.3\times10^6$ cells per dish. The cells were incubated overnight in DMEM with 10% fetal bovine serum, at 37° C. and 5% $CO_2$. The following day the cells were transfected with 5 μg of each plasmid as set forth in Table 3, for a total of 10 μg of DNA per plate of cells transfected (see Table 3) using ExGen 500 in vitro transfection reagent (MBI fermentas, cat. no. R0511). The transfection was performed according to the manufacturers protocol. Cells were incubated at 37° C. with 5% $CO_2$ in DMEM with 10% fetal bovine serum following the transfection.

TABLE 3

| Plate # | Plasmid 1 | Plasmid 2 | No. $Bsd^R$ Colonies |
|---|---|---|---|
| 1 | pBS | None | 0 |
| 2 | pCXLamInt | pLIT38attB-BSRpolyA10 | 16 |
| 3 | pCXLamIntR | pLIT38attB-BSRpolyA10 | 40 |
| 4 | pCXLamInt | pLIT38attB-BSRpolyA2 | 28 |
| 5 | pCXLamIntR | pLIT38attB-BSRpolyA2 | 36 |

C. Selection of Blasticidin Resistant Clones.

Three days following the transfection the cells were split from a 10 cm dish to two 15 cm dishes. The cells were maintained in DMEM with 10% fetal bovine serum for 4 days in the 15 cm dishes. Seven days post-transfection blasticidin was introduced into the medium. Stably transfected cells were selected with 1 μg/ml blasticidin. The number of colonies formed on each plate is listed in Table 3. These colonies were ring-cloned and expanded for PCR analysis. Upon expansion in blasticidin containing medium some clones failed to live and therefore do not have corresponding PCR data.

D. PCR Analysis

Thirty-eight of the 40 clones from plate 3 grew after ring-cloning.

Genomic DNA was isolated from these clones with the Promega Wizard Genomic cDNA purification kit, digested with EcoRI and used as template in a PCR reaction with the following primers: 3BSP-TTAATTTCGGG TATATTTGAGTGGA (SEQ ID NO:82); 5PacSV40-CTGT-TAATTAACTGTGGAA TGTGTGTCAGTTAGGGTG (SEQ ID NO:76). The PCR conditions were as follows. 100 ng of genomic DNA was amplified with 0.5 μl Herculase polymerase (Stratagene) in a 50 μl reaction that contained 12.5 pmole of each primer, 2.5 mM of each dNTP, and 1× Herculase buffer (Stratagene). The reactions were placed in a PerkinEimer thermocycler programmed as follows: Initial denaturation at 95° C. for 10 minutes; 35 cycles of 94° C. for 1 minute, 53° C. for 1 minute, 72° C. for 1 minute, and 72° C. for 1 minute; Final extension for 10 minutes at 72° C.; and 4° C. hold. If pLIT38attB-BSRpolyA10 integrates onto the human platform ACE 0.1 correctly, PCR amplification with the above primers should yield an 804bp product. Twenty-one of the 38 clones from plate 3 produced a PCR product of the expected 804bp size.

EXAMPLE 11

Delivery of a Vector Comprising a Promoterless Marker Gene and a Gene Encoding a Therapeutic Product to a Platform ACes Platform ACes containing pSV40attPsensePURO (FIG. 4) were constructed as set forth in Examples 3 and 4.

A. Construction of Delivery Vectors

1. Erythropoietin cDNA vector, p18EPOcDNA.

The erythropoietin cDNA was PCR amplified from a human cDNA library (E. Perkins et al., 1999, *Proc. Natl. Acad. Sci. USA* 96(5): 2204-2209) using the following primers: EP05XBA-TATCTAGAATGGGGGTGC ACGAAT-GTCCTGCC (SEQ ID NO: 83); EPO3BSI-TACGTACGT-CATC TGTCCCCTGTCCTGCAGGC (SEQ ID NO: 84). The cDNA was amplified through two successive rounds of PCR using the following conditions: heat denaturation at 95° C. for 3 minutes; cycles of a 30 second denaturation (95° C.), 30 seconds of annealing (60° C.), and 1 minute extension (72° C.); the last cycle is followed by a 7 minute extension at 72° C. BIO—X-ACT (BIOLINE) was used to amplify the erythropoietin cDNA from 2.5 ng of the human cDNA library in the first round of amplification. Five μl of the first amplification product was used as template for the second round of amplification. Two PCR products were produced from the second amplification with Taq polymerase (Eppendorf), each product was cloned into pCR2.1-Topo (Invitrogen) and sequenced. The larger PCR product contained the expected cDNA sequence for erythropoietin. The erythropoietin cDNA was moved from pTopoEPO into p18attBZeo(6XHS4)2eGFP (SEQ ID NO: 110). pTopoEPO was digested with BsiWI and XbaI to release a 588 bp EPO cDNA. BsrGI and BsiWI create compatable ends. The eGFP gene was removed from p18attBZeo(6XHS4)2eGFP by digestion with BsiWI and XbaI, the 8.3 Kbp vector backbone was gel purified and ligated to the 588 bp EPO cDNA to create p18EPOcDNA (SEQ ID NO: 124).

2. Genomic erythropoietin vector, p18genEPO.

The erythropoietin genomic clone was PCR amplified from a human genomic library (Clontech) using the following primers: GENEPO3BSI-CGTACGTCATCTGTCCCCT GTCCTGCA (SEQ ID NO: 85); GENEPO 5XBA -TCTA-GAATGGGGGT GCACGGTGAGTACT (SEQ ID NO: 86). The reaction conditions for the amplification were as follows: heat denaturation for 3 minutes (95° C.); 30 cycles of a 30 second denaturation (95° C.), 30 seconds annealing (from 65° C. decreasing 0.5° C. per cycle to 50° C.), and 3 minutes extension (72° C.); 15 cycles of a 30 second denaturation (95° C.), 30 seconds annealing (50° C.), and 3 minute extension (72° C.); the last cycle is followed by a 7 minute extension at 72° C. The erythropoietin genomic PCR product (2147 bp) was gel purified and cloned into pCR2.1Topo to create pTopogenEPO. Sequence analysis revealed 2bp substitutions and insertions in the intronic sequences of the genomic clone of erythropoietin. A partial digest with XbaI and complete digest with BsiWI excised the erythropoietin genomic insert from pTopogenEPO. The resulting 2158 bp genomic erythropoietin fragment was ligated into the 8.3 Kbp fragment resulting from the digestion of p18attBZeo(6XHS4)2eGFP (SEQ ID NO: 110) with XbaI and BsrGI to create p18genEPO (SEQ ID NO: 125).

B. Transfection and Selection with Drug

The erythropoietin genomic and cDNA genes were each moved onto the platform ACes B19-38 (constructed as set forth in Example 3) by co-transfecting with pCXLamIntR. Control transfections were also performed using pCXLamInt (SEQ ID NO: 127) together with either p18EPOcDNA (SEQ ID NO: 124) or p18genEPO (SEQ ID NO: 125). Lipofectamine Plus was used to transfect the DNA's into B19-38 cells according to the manufacturer's protocol. The cells were placed in selective medium (DMEM with 10% FBS and Zeocin @ 500 μg/ml) 48 hours post-transfection and maintained in selective medium for 13 days.

Clones were isolated 15 days post-transfection.

C. Analysis of Clones (ELISA, PCR)

1. ELISA Assays

Thirty clones were tested for erythropoietin production by an ELISA assay using a monoclonal anti-human erythropoietin antibody (R&D Systems, Catalogue #MAB287), a polyclonal anti-human erythropoietin antibody (R & D Systems, Catalogue #AB-286-NA) and alkaline phosphotase conjugated goat-anti-rabbit IgG (heavy and light chains) (Jackson ImmunoResearch Laboratories, Inc., Catalogue #111-055-144).

The negative control was a Zeocin resistant clone isolated from B19-38 cells transfected with p18attBZeo(6XHS4) (SEQ ID NO: 117; no insert control vector) and pCXLamIntR (SEQ ID NO: 112). The preliminary ELISA assay was executed as follows: 1) Nunc-Immuno Plates (MaxiSorb 96-well, Catalogue #439454) were coated with 75 µl of a 1/200 dilution (in Phosphate buffered Saline, pH 7.4 (PBS), Sigma Catalogue #P-3813) of monoclonal anti-human erythropoietin antibody overnight at 4° C. 2) The following day the plates were washed 3 times with 300 µl PBS containing 0.15% Tween 20 (Sigma, Catalogue #P-9416). 3) The plates were then blocked with 300 µl of 1% Bovine Serum Albumin (BSA; Sigma Catalogue #A-7030) in PBS for 1 hour at 37° C. 4) Repeat the washes as in step 2. 5) The clonal supernatants (75 µl per clone per well of 96-well plate) were then added to the plate and incubated for 1 hour at 37° C. The clonal supernatant analyzed in the ELISA assay had been maintained on the cells 7 days prior to analysis. 6) Repeat the washes of step 2. 7) Add 75 µl of polyclonal anti-human erythropoietin antibody (1/250 dilution in dilution buffer (0.5% BSA, 0.01% Tween 20, 1X PBS, pH 7.4) and incubate 1 hour at 37° C. 8) Repeat washes of step 2. 9) Add 75 µl of goat anti-rabbit conjugated alkaline phosphatase diluted 1/4000 in dilution buffer and incubate 1 hour at 37° C. 10) Repeat washes of step 2. 11) Add 75 µl substrate, p-nitrophenyl phosphate (Sigma N2640), diluted to 1 mg/ml in substrate buffer (0.1 Ethanolamine-HCl (Sigma, Catalogue #E-6133), 5 mM $MgCl_2$ (Sigma, Catalogue #M-2393), pH 9.8). Incubate the plates in the dark for 1 hour at room temperature (22° C.). 12) Read the absorption at 405 nm (reference wavelength 495 nm) on an Universal Microplate Reader (Bio-Tek Instruments, Inc., model #ELX800 UV). The erythropoietin standard curve was derived from readings of diluted human recombinant Erythropoietin (Roche, catalogue #1-120-166; dilution range 125-7.8 mUnits/ml). From this preliminary assay the 21 clones displaying the highest expression of erythropoietin were analyzed a second time in the same manner using medium supernatants that had been on the clones for 24 hours and a 1:3 dilution therof.

2. PCR Analysis

Genomic DNA was isolated from the 21 clones with the best expression (as assessed by the initial ELISA assay above) as well as the B19-38 cell line and used for PCR analysis. Genomic DNA was isolated using the Wizard genomic DNA purification kit (Promega) according to the manufacturers protocol. Amplification was performed on 100 ng of genomic DNA as template with MasterTaq DNA Polymerase (Eppendorf) and the primer set 5PacSV40-CTGTTAATTAACTGTGGAATGTGTG TCAGTTAGGGTG (SEQ ID NO: 76) and Antisense Zeo-TGAACAGGGTCACGTCGTCC (SEQ ID NO: 77). The amplification conditions were as follows: heat denaturation for 3 minutes (95° C.); 30 cycles of a 30 second denaturation (95° C.), 30 seconds annealing (from 65° C. decreasing 0.5° C. per cycle to 50° C.), and 1 minutes extension (72° C.); 15 cycles of a 30 second denaturation (95° C.), 30 seconds annealing (50° C.), and 1 minute extension (72° C.); the last cycle is followed by a 10 minute extension at 72° C. PCR products were size separated by gel electrophoresis. Of the 21 clones analyzed 19 produced a PCR product of 650 bp as expected for a site-specific integration event. All nineteen clones were the result of transformations with p19EPOcDNA (5) or p18genEPO (14) and pCXLamIntR (i.e. mutant integrase). The remaining two clones, both of which were the result of transformation with p18genEPO (SEQ ID NO: 125) and pCXLamInt (i.e. wildtype integrase; SEQ ID NO: 127), produced a 400 bp PCR product.

EXAMPLE 12

Preparation of a Transformation Vector Useful for the Induction of Plant Artificial Chromosome Formation Plant artificial chromosomes (PACs) can be generated by introducing nucleic acid, such as DNA, which can include a targeting DNA, for example rDNA or lambda DNA, into a plant cell, allowing the cell to grow, and then identifying from among the resulting cells those that include a chromosome with a structure that is distinct from that of any chromosome that existed in the cell prior to introduction of the nucleic acid. The structure of a PAC reflects amplification of chromosomal DNA, for example, segmented, repeat region-containing and heterochromatic structures. It also is possible to select cells that contain structures that are precursors to PACs, for example, chromosomes containing more than one centromere and/or fragments thereof, and culture and/or manipulate them to ultimately generate a PAC within the cell.

In the method of generating PACs, the nucleic acid can be introduced into a variety of plant cells. The nucleic acid can include targeting DNA and/or a plant expressable DNA encoding one or multiple selectable markers (e.g., DNA encoding bialophos (bar) resistance) or scorable markers (e.g., DNA encoding GFP). Examples of targeting DNA include, but are not limited to, *N. tabacum* rDNA intergenic spacer sequence (IGS) and *Arabidopsis* rDNA such as the 18S, 5.8S, 26S rDNA and/or the intergenic spacer sequence. The DNA can be introduced using a variety of methods, including, but not limited to *Agrobacterium*-mediated methods, PEG-mediated DNA uptake and electroporation using, for example, standard procedures according to Hartmann et al [(1998) *Plant Molecular Biology* 36:741]. The cell into which such DNA is introduced can be grown under selective conditions and can initially be grown under non-selective conditions and then transferred to selective media. The cells or protoplasts can be placed on plates containing a selection agent to grow, for example, individual calli. Resistant calli can be scored for scorable marker expression. Metaphase spreads of resistant cultures can be prepared, and the metaphase chromosomes examined by FISH analysis using specific probes in order to detect amplification of regions of the chromosomes. Cells that have artificial chromosomes with functioning centromeres or artificial chromosomal intermediate structures, including, but not limited to, dicentric chromosomes, formerly dicentric chromosomes, minichromosomes, heterochromatin structures (e.g. sausage chromosomes), and stable self-replicating artificial chromosomal intermediates as described herein, are identified and cultured. In particular, the cells containing self-replicating artificial chromosomes are identified.

The DNA introduced into a plant cell for the generation of PACs can be in any form, including in the form of a vector. An exemplary vector for use in methods of generating PACs can be prepared as follows.

For the production of artificial chromosomes, plant transformation vectors, as exemplified by pAgIIa and pAgIIb, containing a selectable marker, a targeting sequence, and a scorable marker were constructed using procedures well known in the art to combine the various fragments.

The vectors can be prepared using vector pAg1 as a base vector and inserting the following DNA fragments into pAg1: DNA encoding β-glucoronidase under the control of the nopaline synthase (NOS) promoter fragment and flanked at the 3' end by the NOS terminator fragment, a fragment of mouse satellite DNA and an *N. tabacum* rDNA intergenic spacer sequence (IGS). In constructing plant transformation vectors, vector pAg2 can also be used as the base vector.

1. Construction of pAG1

Vector pAg1 (SEQ. ID. NO: 89) is a derivative of the CAMBIA vector named pCambia 3300 (Center for the Application of Molecular Biology to International Agriculture, i.e., CAMBIA, Canberra, Australia;

www.cambia.org), which is a modified version of vector pCambia 1300 to which has been added DNA from the bar gene confering resistance to phosphinothricin. The nucleotide sequence of pCambia 3300 is provided in SEQ. ID. NO: 90. pCambia 3300 also contains a lacZ alpha sequence containing a polylinker region.

pAg1 was constructed by inserting two new functional DNA fragments into the polylinker of pCambia 3300: one sequence containing an attB site and a promoterless zeomycin resistance-encoding DNA flanked at the 3' end by a SV40 polyA signal sequence, and a second sequence containing DNA from the hygromycin resistance gene (hygromycin phosphotransferase) confering resistance to hygromycin for selection in plants. Although the zeomycin-SV40 polyA signal fusion is not expected to function in plant cells, it can be activated in mammalian cells by insertion of a functional promoter element into the attB site by site-specific recombination catalyzed by the Lambda att integrase. Thus, the inclusion of the attB-zeomycin sequences allows for evaluation of functionality of plant artificial chromosomes in mammalian cells by activation of the zeomycin resistance-encoding DNA, and provides an att site for further insertion of new DNA sequences into plant artificial chromosomes formed as a result of using pAg1 for plant transformation. The second functional DNA fragment allows for selection of plant cells with hygromycin. Thus, pAg1 contains DNA from the bar gene confering resisance to phosphinothricin, DNA from the hygromycin resistance gene, both resistance-encoding DNAs under the control of a separate cauliflower mosaic virus (CaMV) 35S promoter, and the attB-promoterless zeomycin resistance-encoding DNA.

pAg1 is a binary vector containing *Agrobacterium* right and left T-DNA border sequences for use in *Agrobacterium*-mediated transformation of plant cells or protoplasts with the DNA located between the border sequences. pAg1 also contains the pBR322 Ori for replication in *E. coli*. pAg1 was constructed by ligating HindIII/PstI-digested p3300attBZeo with HindIII/PstI-digested pBSCaMV35SHyg as follows.

a. Generation of p3300attBZeo

Plasmid pCambia 3300 was digested with PstI/Ec/136 II and ligated with PstI/StuI-digested pLITattBZeo (the nucleotide sequence of pLITattBZeo is provided in SEQ. ID. NO: 91, which contains DNA encoding the zeocin resistance gene and an attB Integrase recognition sequence, to generate p3300attBZeo, which contains an attB site, a promoterless zeomycin resistance-encoding DNA flanked at the 3' end by a SV40 polyA signal, and a reconstructed PstI site.

b. Generation of pBSCaMV35SHyg

A DNA fragment containing DNA encoding hygromycin phosphotransferase flanked by the CaMV 35S promoter and the CaMV 35S polyA signal sequence was obtained by PCR amplification of plasmid pCambia 1302 (GenBank Accession No. AF234298 and SEQ. ID. NO: 92). The primers used in the amplification reaction were as follows:

```
CaMV35SpolyA:                         SEQ. ID. NO: 93
5'-CTGAATTAACGCCGAATTAATTCGGGGGATCTG-3'

CaMV35Spr:                            SEQ. ID. NO: 94
5'-CTAGAGCAGCTTGCCAACATGGTGGAGCA-3'
```

The 2100-bp PCR fragment was ligated with EcoRV-digested pBluescript II SK+ (Stratagene, La Jolla, Calif., U.S.A.) to generate pBSCaMV35SHyg.

c. Generation of pAg1

To generate pAg1, pBSCaMV35SHyg was digested with HindIII/PstI and ligated with HindIII/PstI-digested p3300attBZeo. Thus, pAg1 contains the pCambia 3300 backbone with DNA conferring resistance to phophinothricin and hygromycin under the control of separate CaMV 35S promoters, an attB-promoterless zeomycin resistance-encoding DNA recombination cassette and unique sites for adding additional markers, e.g., DNA encoding GFP. The attB site can be used as described herein for the addition of new DNA sequences to plant artificial chromosomes, including PACs formed as a result of using the pAg1 vector, or derivatives thereof, in the production of PACs. The attB site provides a convenient site for recombinase-mediated insertion of DNAs containing a homologous att site.

2. pAG2

The vector pAg2 (SEQ. ID. NO: 95) is a derivative of vector pAg1 formed by adding DNA encoding a green fluorescent protein (GFP), under the control of a NOS promoter and flanked at the 3' end by a NOS polyA signal, to pAg1. pAg2 was constructed as follows. A DNA fragment containing the NOS promoter was obtained by digestion of pGEM-T-NOS, or pGEMEasyNOS (SEQ. ID. NO: 96), containing the NOS promoter in the cloning vector pGEM-T-Easy (Promega Biotech, Madison, Wis., U.S.A.), with XbaI/NcoI and was ligated to an XbaI/NcoI fragment of pCambia 1302 containing DNA encoding GFP (without the CaMV 35S promoter) to generate p1302NOS (SEQ. ID. NO: 97) containing GFP-encoding DNA in operable association with the NOS promoter. Plasmid p1302NOS was digested with SmaI/BsiWI to yield a fragment containing the NOS promoter and GFP-encoding DNA. The fragment was ligated with PmeI/Bs/WI-digested pAg1 to generate pAg2. Thus, pAg2 contains DNA from the bar gene confering resistance to phosphinothricin, DNA conferring resistance to hygromycin, both resistance-encoding DNAs under the control of a cauliflower mosaic virus 35S promoter, DNA encoding kanamycin resistance, a GFP gene under the control of a NOS promoter and the attB-zeomycin resistance-encoding DNA. One of skill in the art will appreciate that other fragments can be used to generate the pAg1 and pAg2 derivatives and that other herterlogous DNA can be incorporated into pAg1 and pAg2 derivatives using methods well known in the art.

3. pAgIIa and pAgIIb Transformation Vectors

Vectors pAgIIa and pAgIIb were constructed by inserting the following DNA fragments into pAg1: DNA encoding β-glucoronidase, the nopaline synthase terminator fragment, the nopaline synthase (NOS) promoter fragment, a fragment of mouse satellite DNA and an *N. tabacum* rDNA intergenic spacer sequence (IGS). The construction of pAgIIa and pAgIIb was as follows.

An *N. tabacum* rDNA intergenic spacer (IGS) sequence (SEQ. ID.

NO: 98; see also GenBank Accession No. Y08422; see also Borysyuk et al. (2000) *Nature Biotechnology* 18:1303-1306; Borysyuk et al. (1997) *Plant Mol. Biol.* 35:655-660; U.S. Pat.

Nos. 6,100,092 and 6,355,860) was obtained by PCR amplification of tobacco genomic DNA. The IGS can be used as a targeting sequence by virtue of its homology to tobacco rDNA genes; the sequence also is an amplification promoter sequence in plants. This fragment was amplified using standard PCR conditions (e.g., as described by Promega Biotech, Madison, Wis., U.S.A.) from tobacco genomic DNA using the primers shown below:

```
NTIGS-FI                               (SEQ ID No. 99)
5'-GTG CTA GCC AAT GTT TAA CAA GAT G-3'
and

NTIGS-RI                               (SEQ ID No. 100)
5'-ATG TCT TAA AAA AAA AAA CCC AAG TGA C-3'
```

Following amplification, the fragment was cloned into pGEM-T Easy to give pIGS-I A fragment of mouse satellite DNA (Msat1 fragment;

GenBank Accession No. V00846; and SEQ ID No. 101) was amplified via PCR from pSAT-1 using the following primers:

```
MSAT-F1                                (SEQ ID No. 102)
5'-AAT ACC GCG GAA GCT TGA CCT GGA ATA TCG C-3'
and

MSAT-Ri                                (SEQ ID No. 103)
5'-ATA ACC GCG GAG TCC TTC AGT GTG CA T-3'
```

This amplification added a SacII and a HindIII site at the 5'end and a SacII site at the 3' end of the PCR fragment. This fragment was then cloned into the SacII site in pIGS-1 to give pMIGS-1, providing a eukaryotic centromere-specific DNA and a convenient DNA sequence for detection via FISH.

A functional marker gene containing a NOS-promoter: GUS:NOS terminator fusion was then constructed containing the NOS promoter (GenBank Accession No. U09365; SEQ ID No. 104), *E. coli* β-glucuronidase coding sequence (from the GUS gene; GenBank Accession No. S69414; and SEQ ID No. 105), and the nopaline synthase terminator sequence (GenBank Accession No. U09365; SEQ ID No. 107). The NOS promoter in pGEM-T-NOS was added to a promoterless GUS gene in pBlueScript (Stratagene, La Jolla, Calif., U.S.A.) using NotI/SpeI to form pNGN-1, which has the NOS promoter in the opposite orientation relative to the GUS gene.

pMIGS-1 was digested with NotI/SpeI to yield a fragment containing the mouse major satellite DNA and the tobacco IGS which was then added to NotI-digested pNGN-1 to yield pNGN-2. The NOS promoter was then re-oriented to provide a functional GUS gene, yielding pNGN-3, by digestion and religation with SpeI. Plasmid pNGN-3 was then digested with HindIII, and the HindIII fragment containing the β-glucuronidase coding sequence and the rDNA intergenic spacer, along with the Msat sequence, was added to pAG-1 to form pAgIIa (SEQ ID NO: 108), using the unique HindIII site in pAg1 located near the right T-DNA border of pAg1, within the T-DNA region.

Another plasmid vector, referred to as pAgIIb, was also recovered, which contained the inserted HindIII fragment (SEQ ID NO: 108) in the opposite orientation relative to that observed in pAgIIa. Thus, pAgIIa and pAgIIb differ only in the orientation of the HindIII fragment containing the mouse major satellite sequence, the GUS DNA sequence and the IGS sequence. The nucleotide sequence of pAgIIa is provided in SEQ. ID. NO: 109.

Since modifications will be apparent to those of skill in this art, it is intended that this invention be limited only by the scope of the appended claims.

What is claimed is:

1. A method of introducing heterologous nucleic acid into an artificial chromosome, comprising:

contacting an animal or plant artificial chromosome comprising one or a plurality of att site(s) with a nucleic acid molecule comprising an insect artificial chromosome (IAC) and comprising both the heterologous nucleic acid and an att recombination site, in the presence of a recombinase that promotes recombination between the sites in the chromosome and in the nucleic acid molecule, wherein:

the one or a plurality of att site(s) are heterologous to the chromosome;

the recombinase is lambda integrase and the att site is a substrate for lambda integrase; and the one or a plurality of att site(s) directs site-directed integration in the presence of lambda integrase.

2. The method of claim 1, wherein the nucleic acid molecule encodes a therapeutic protein, antisense nucleic acid, or comprises an artificial chromosome.

3. The method of claim 1, wherein the nucleic acid molecule with a recombination site is a PCR product.

4. The method of claim 1, wherein the recombinase is a protein and the recombination event occurs in vitro.

5. A method for introducing heterologous nucleic acid into a human mesenchymal cell, comprising:

(a) introducing into the human mesenchymal cell a platform-ACes, wherein the platform-ACes has a first recombination site;

(b) introducing into the resulting cell a vector comprising at least a second recombination site and the heterologous nucleic acid; and (c) incubating the resulting mixture in the presence of at least one recombination protein under conditions whereby recombination between the first and second recombination sites is effected, thereby introducing the heterologous nucleic acid into the platform-ACes within the mesenchymal cells.

6. The method of claim 5, wherein the at least one recombination protein is encoded by a bacteriophage selected from the group consisting of bacteriophage lambda integrase (Int), phi 80, P22, P2, 186, P4 and P1.

7. The method of claim 6, wherein the at least one recombination protein is encoded by bacteriophage lambda integrase (Int), or a mutant of bacteriophage lambda integrase (Int).

8. The method of claim 5, wherein the at least one recombination protein is selected from the group consisting of Int, IHF, Xis, Fis, Cre, γδ, Tn3 resolvase, Hin, Gin, Cin and Flp.

9. The method of claim 5, wherein the recombination sites are selected from the group consisting of att and lox P sites.

10. The method of claim 5, wherein the first and/or second recombination site contains at least one mutation in the sequence of nucleic acids encoding the recombination site that removes one or more stop codons introduced by virtue of the recombination site.

11. The method of claim 5, wherein the first and/or second recombination site contains at least one mutation in the sequence of nucleic acids encoding the recombination site that avoids hairpin formation introduced by virtue of the recombination site.

12. The method of claim 5, wherein the first and/or second recombination sites comprises at least a first nucleic acid sequence selected from among:

| | | | |
|---|---|---|---|
| a) | RKYCWGCTTTYKTRTACNAASTSGB | (m-att); | (SEQ ID NO: 41) |
| b) | AGCCWGCTTTYKTRTACNAACTSGB | (m-attB); | (SEQ ID NO: 42) |
| c) | GTTCAGCTTTCKTRTACNAACTSGB | (m-attR); | (SEQ ID NO: 43) |
| d) | AGCCWGCTTTCKTRTACNAAGTSGB | (m-attL); | (SEQ ID NO: 44) |
| e) | GTTCAGCTTTYKTRTACNAAGTSGB | (m-attP1); | (SEQ ID NO: 45) |
| f) | AGCCTGCTTTTTTGTACAAACTTGT | (attB1); | (SEQ ID NO: 46) |
| g) | AGCCTGCTTTCTTGTACAAACTTGT | (attB2); | (SEQ ID NO: 47) |
| h) | ACCCAGCTTTCTTGTACAAACTTGT | (attB3); | (SEQ ID NO: 48) |
| i) | GTTCAGCTTTTTTGTACAAACTTGT | (attR1); | (SEQ ID NO: 49) |

-continued

```
j) GTTCAGCTTTCTTGTACAAACTTGT  (attR2);      (SEQ ID NO: 50)

k) GTTCAGCTTTCTTGTACAAAGTTGG  (attR3);      (SEQ ID NO: 51)

l) AGCCTGCTTTTTTGTACAAAGTTGG  (attL1);      (SEQ ID NO: 52)

m) AGCCTGCTTTCTTGTACAAAGTTGG  (attL2);      (SEQ ID NO: 53)

n) ACCCAGCTTTCTTGTACAAAGTTGG  (attL3);      (SEQ ID NO: 54)

o) GTTCAGCTTTTTTGTACAAAGTTGG  (attP1);      (SEQ ID NO: 55)
   or

p) GTTCAGCTTTCTTGTACAAAGTTGG  (attP2);      (SEQ ID NO: 56)
   and
```

q) a corresponding or complementary DNA or RNA sequence to any of a)-p), wherein:

R=A or G, K=G or T/U, Y=C or T/U, W=A or T/U, N=A or C or G or T/U, S=C or G, and B=C or G or T/U; and a corresponding DNA or RNA sequence effects recombination with a site comprising a sequence of nucleotides set forth in any of a)-p); and the core region does not contain a stop codon in one or more reading frames.

13. The method of claim 5, wherein the first and/or second recombination site comprises at least a first nucleic acid sequence selected from the group consisting of:

a mutated att recombination site containing at least one mutation that enhances recombinational specificity relative to the absence of the mutation; and a nucleic acid molecule whose sequence is complementary to the mutated att recombination site sequence.

14. The method of claim 5, wherein the vector comprising the second recombination site further encodes at least one selectable marker.

15. The method of claim 14, wherein the marker is a promoterless marker, which, upon recombination is under the control of a prometer and is thereby expressed.

16. The method of claim 15, where the first recombination site is attP and is in the sense orientation relative to a promoter on the platform ACes prior to recombination.

17. The method of claim 15, wherein the selectable marker is selected from the group consisting of a gene that provides a selective growth advantage, an antibiotic resistance gene, and a gene encoding a detectable protein, wherein the detectable protein is chromogenic, fluorescent, or capable of being bound by an antibody and FACs sorted.

18. The method of claim 17, wherein the selectable marker is selected from the group consisting of green fluorescent protein (GFP), red fluorescent protein (RFP), blue fluorescent protein (BFP), and *E. coli* histidinol dehydrogenase (hisD).

19. The method of claim 15. wherein the promoterless marker is transcriptionally downstream of the heterologous nucleic acid, wherein the heterologous nucleic acid encodes a heterologous protein, and wherein the expression level of the selectable marker is transcriptionally linked to the expression level of the heterologous protein.

20. The method of claim 19, wherein the selectable marker and the heterologous nucleic acid are transcriptionally linked by the presence of an IRES between them.

21. The method of claim 20, wherein the selectable marker is selected from the group consisting of a gene that provides a selective growth advantage, an antibiotic resistance gene, and a gene encoding a detectable protein, wherein the detectable protein is chromogenic or fluorescent.

22. The method of claim 21, wherein the selectable marker is selected from the group consisting of green fluorescent protein (GFP), red fluorescent protein (RFP), blue fluorescent protein (BFP), and *E. coli* histidinol dehydrogenase.

23. The method of claim 19, further comprising expressing the heterologous protein and isolating the heterologous protein.

24. The method of claim 5, wherein the vector is a PCR product comprising a second recombination site.

* * * * *

SEQUENCE LISTING

```
<160> NUMBER OF SEQ ID NOS: 129

<210> SEQ ID NO 1
<211> LENGTH: 25
<212> TYPE: DNA
<213> ORGANISM: Artificial Sequence
<220> FEATURE:
<223> OTHER INFORMATION: Primer: attPUP

<400> SEQUENCE: 1

ccttgcgcta atgctctgtt acagg                                        25


<210> SEQ ID NO 2
<211> LENGTH: 26
<212> TYPE: DNA
<213> ORGANISM: Artificial Sequence
<220> FEATURE:
<223> OTHER INFORMATION: Primer: attPDWN

<400> SEQUENCE: 2

cagaggcagg gagtgggaca aaattg                                       26


<210> SEQ ID NO 3
<211> LENGTH: 35
<212> TYPE: DNA
<213> ORGANISM: Artificial Sequence
<220> FEATURE:
```

-continued

<223> OTHER INFORMATION: Primer: Lamint 1

<400> SEQUENCE: 3
ttcgaattca tgggaagaag gcgaagtcat gagcg 35

<210> SEQ ID NO 4
<211> LENGTH: 34
<212> TYPE: DNA
<213> ORGANISM: Artificial Sequence
<220> FEATURE:
<223> OTHER INFORMATION: Primer: Lamint 2

<400> SEQUENCE: 4
ttcgaattct tatttgattt caattttgtc ccac 34

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cggacaatgc ggttgtgcgt 20

<210> SEQ ID NO 6
<211> LENGTH: 46
<212> TYPE: DNA
<213> ORGANISM: Artificial Sequence
<220> FEATURE:
<223> OTHER INFORMATION: primer

<400> SEQUENCE: 6
cgcgcagcaa aatctagagt aaggagatca agacttacgg ctgacg 46

<210> SEQ ID NO 7
<211> LENGTH: 46
<212> TYPE: DNA
<213> ORGANISM: Artificial Sequence
<220> FEATURE:
<223> OTHER INFORMATION: LambdaINTER174rev

<400> SEQUENCE: 7
cgtcagccgt aagtcttgat ctccttactc tagattttgc tgcgcg 46

<210> SEQ ID NO 8
<211> LENGTH: 33
<212> TYPE: DNA
<213> ORGANISM: Artificial Sequence
<220> FEATURE:
<223> OTHER INFORMATION: attB1

<400> SEQUENCE: 8
tgaagcctgc ttttttatac taacttgagc gaa 33

<210> SEQ ID NO 9
<211> LENGTH: 33
<212> TYPE: DNA
<213> ORGANISM: Artificial Sequence
<220> FEATURE:
<223> OTHER INFORMATION: attB2

<400> SEQUENCE: 9
ttcgctcaag ttagtataaa aaagcaggct tca 33

-continued

<210> SEQ ID NO 10
<211> LENGTH: 25
<212> TYPE: DNA
<213> ORGANISM: Artificial Sequence
<220> FEATURE:
<223> OTHER INFORMATION: Primer: attPdwn2

<400> SEQUENCE: 10
tcttctcggg cataagtcgg acacc 25

<210> SEQ ID NO 11
<211> LENGTH: 25
<212> TYPE: DNA
<213> ORGANISM: Artificial Sequence
<220> FEATURE:
<223> OTHER INFORMATION: Primer:CMVen

<400> SEQUENCE: 11
ctcacgggga tttccaagtc tccac 25

<210> SEQ ID NO 12
<211> LENGTH: 26
<212> TYPE: DNA
<213> ORGANISM: Artificial Sequence
<220> FEATURE:
<223> OTHER INFORMATION: Primer:attPdwn

<400> SEQUENCE: 12
cagaggcagg gagtgggaca aaattg 26

<210> SEQ ID NO 13
<211> LENGTH: 25
<212> TYPE: DNA
<213> ORGANISM: Artificial Sequence
<220> FEATURE:
<223> OTHER INFORMATION: Primer:CMVEN2

<400> SEQUENCE: 13
caactccgcc ccattgacgc aaatg 25

<210> SEQ ID NO 14
<211> LENGTH: 26
<212> TYPE: DNA
<213> ORGANISM: Artificial Sequence
<220> FEATURE:
<223> OTHER INFORMATION: Primer:L1

<400> SEQUENCE: 14
agtatcgccg aacgattagc tcttca 26

<210> SEQ ID NO 15
<211> LENGTH: 24
<212> TYPE: DNA
<213> ORGANISM: Artificial Sequence
<220> FEATURE:
<223> OTHER INFORMATION: Primer:F1 rev

<400> SEQUENCE: 15
gccgatttcg gcctattggt taaa 24

<210> SEQ ID NO 16
<211> LENGTH: 25
<212> TYPE: DNA
<213> ORGANISM: Artificial Sequence
<220> FEATURE:
<223> OTHER INFORMATION: Primer:RED -continued

<400> SEQUENCE: 16
ccgccgacat ccccgactac aagaa 25

<210> SEQ ID NO 17
<211> LENGTH: 25
<212> TYPE: DNA
<213> ORGANISM: Artificial Sequence
<220> FEATURE:
<223> OTHER INFORMATION: Primer:L2rev

<400> SEQUENCE: 17
ttccttcgaa ggggatccgc ctacc 25

<210> SEQ ID NO 18
<211> LENGTH: 22118
<212> TYPE: DNA
<213> ORGANISM: Mus musculus
<300> PUBLICATION INFORMATION:
<308> DATABASE ACCESSION NUMBER: GenBank X82564
<309> DATABASE ENTRY DATE: 1996-04-09

<400> SEQUENCE: 18
gaattcccct atccctaatc cagattggtg gaataacttg gtatagatgt ttgtgcatta 60
aaaaccctgt aggatcttca ctctaggtca ctgttcagca ctggaacctg aattgtggcc 120
ctgagtgata ggtcctggga catatgcagt tctgcacaga cagacagaca gacagacaga 180
cagacagaca gacagacgtt acaaacaaac acgttgagcc gtgtgccaac acacacacaa 240
acaccactct ggccataatt attgaggacg ttgatttatt attctgtgtt tgtgagtctg 300
tctgtctgtc tgtctgtctg tctgtctgtc tatcaaacca aaagaaacca aacaattatg 360
cctgcctgcc tgcctgcctg cctacacaga gaaatgattt cttcaatcaa tctaaaacga 420
cctcctaagt ttgccttttt tctctttctt tatctttttc ttttttcttt tcttcttcct 480
tccttccttc cttccttcct tccttccttt ctttctttct ttctttcttt cttactttct 540
ttctttcctt cttacattta ttcttttcat acatagtttc ttagtgtaag catccctgac 600
tgtcttgaag acactttgta ggcctcaatc ctgtaagagc cttcctctgc ttttcaaatg 660
ctggcatgaa tgttgtacct cactatgacc agcttagtct tcaagtctga gttactggaa 720
aggagttcca agaagactgg ttatattttt catttattat tgcattttaa ttaaaattta 780
atttcaccaa aagaatttag actgaccaat tcagagtctg ccgtttaaaa gcataaggaa 840
aaagtaggag aaaaacgtga ggctgtctgt ggatggtcga ggctgcttta gggagcctcg 900
tcaccattct gcacttgcaa accgggccac tagaacccgg tgaagggaga aaccaaagcg 960
acctggaaac aataggtcac atgaaggcca gccacctcca tcttgttgtg cgggagttca 1020
gttagcagac aagatggctg ccatgcacat gttgtctttc agcttggtga ggtcaaagta 1080
caaccgagtc acagaacaag gaagtataca cagtgagttc caggtcagcc agagtttaca 1140
cagagaaacc acatcttgaa aaaaacaaaa aaataaatta aataaatata atttaaaaat 1200
ttaaaaatag ccgggagtga tggcgcatgt ctttaatccc agctctcttc aggcagagat 1260
gggaggattt ctgagtttga ggccagcctg gtctgcaaag tgagttccag gacagtcagg 1320
gctatacaga gaaaccctgt cttgaaaact aaactaaatt aaactaaact aaactaaaaa 1380
aatataaaat aaaaatttta aagaatttta aaaaactaca gaaatcaaac ataagcccac 1440
gagatggcaa gtaactgcaa tcatagcaga aatattatac acacacacac acacagactc 1500
tgtcataaaa tccaatgtgc cttcatgatg atcaaatttc gatagtcagt aatactagaa 1560

-continued

```
gaatcatatg tctgaaaata aaagccagaa ccttttctgc ttttgttttc ttttgcccca   1620
agatagggtt tctctcagtg tatccctggc atccctgcct ggaacttcct ttgtaggttt   1680
ggtagcctca aactcagaga ggtcctctct gcctgcctgc ctgcctgcct gcctgcctgc   1740
ctgcctgcct gcctgcctca cttcttctgc cacccacaca accgagtcga acctaggatc   1800
tttatttctt tctctttctc tcttctttct ttctttcttt ctttctttct ttctttcttt   1860
ctttctttct ttcttattca attagttttc aatgtaagtg tgtgtttgtg ctctatctgc   1920
tgcctatagg cctgcttgcc aggagagggc aacagaacct aggagaaacc accatgcagc   1980
tcctgagaat aagtgaaaaa acaacaaaaa aaggaaattc taatcacata gaatgtagat   2040
atatgccgag gctgtcagag tgctttttaa ggcttagtgt aagtaatgaa aattgttgtg   2100
tgtcttttat ccaaacacag aagagaggtg gctcggcctg catgtctgtt gtctgcatgt   2160
agaccaggct ggccttgaac acattaatct gtctgcctct gcttccctaa tgctgcgatt   2220
aaaggcatgt gccaccactg cccggactga tttcttcttt tttttttttt tggaaaatac   2280
ctttctttct ttttctctct ctctttcttc cttccttcct ttctttctat tctttttttc   2340
tttctttttt cttttttttt tttttttaa aatttgccta aggttaaagg tgtgctccac   2400
aattgcctca gctctgctct aattctcttt aaaaaaaaac aaacaaaaaa aaaaccaaaa   2460
cagtatgtat gtatgtatat ttagaagaaa tactaatcca ttaataactc tttttcccta   2520
aaattcatgt cattcttgtt ccacaaagtg agttccagga cttaccagag aaaccctgtg   2580
ttcaaatttc tgtgttcaag gtcaccctgg cttacaaagt gagttccaag tccgataggg   2640
ctacacagaa aaaccatatc tcagaaaaaa aaaaagttcc aaacacacac acacacacac   2700
acacacacac acacacacac acacacacac acacacacag cgcgccgcgg cgatgagggg   2760
aagtcgtgcc taaaataaat atttttctgg ccaaagtgaa agcaaatcac tatgaagagg   2820
tactcctaga aaaaataaat acaaacgggc tttttaatca ttccagcact gttttaattt   2880
aactctgaat ttagtcttgg aaaagggggc gggtgtgggt gagtgagggc gagcgagcag   2940
acgggcgggc gggcgggtga gtggccggcg gcggtggcag cgagcaccag aaaacaacaa   3000
accccaagcg gtagagtgtt ttaaaaatga gacctaaatg tggtggaacg gaggtcgccg   3060
ccaccctcct cttccactgc ttagatgctc ccttcccctt actgtgctcc cttcccctaa   3120
ctgtgcctaa ctgtgcctgt tccctcaccc cgctgattcg ccagcgacgt actttgactt   3180
caagaacgat tttgcctgtt ttcaccgctc cctgtcatac tttcgttttt gggtgcccga   3240
gtctagcccg ttcgctatgt tcgggcggga cgatggggac cgtttgtgcc actcgggaga   3300
agtggtgggt gggtacgctg ctccgtcgtg cgtgcgtgag tgccggaacc tgagctcggg   3360
agaccctccg gagagacaga atgagtgagt gaatgtggcg gcgcgtgacg gatctgtatt   3420
ggtttgtatg gttgatcgag accattgtcg ggcgacacct agtggtgaca agtttcggga   3480
acgctccagg cctctcaggt tggtgacaca ggagagggaa gtgcctgtgg tgaggcgacc   3540
agggtgacag gaggccgggc aagcaggcgg gagcgtctcg gagatggtgt cgtgtttaag   3600
gacggtctct aacaaggagg tcgtacaggg agatggccaa agcagaccga gttgctgtac   3660
gccctttggg gaaaaatgct agggttggtg gcaacgttac taggtcgacc agaaggctta   3720
agtcctaccc cccccccct ttttttttt tttcctccag aagccctctc ttgtccccgt   3780
caccgggggc accgtacatc tgaggccgag aggacgcgat gggcccggct tccaagccgg   3840
tgtggctcgg ccagctggcg cttcgggtct tttttttttt tttttttttt ttttcctcca   3900
gaagccttgt ctgtcgctgt caccgggggc gctgtacttc tgaggccgag aggacgcgat   3960
```

-continued gggccccggc ttccaagccg gtgtggctcg gccagctgga gcttcgggtc tttttttttt 4020
tttttttttt tttttttctc cagaagcctt gtctgtcgct gtcaccgggg gcgctgtact 4080
tctgaggccg agaggacgcg atgggtcggc ttccaagccg atgtggcggg gccagctgga 4140
gcttcgggtt tttttttttc ctccagaagc cctctcttgt ccccgtcacc gggggcgctg 4200
tacttctgag gccgagagga cgtgatgggc ccgggttcca ggcggatgtc gcccggtcag 4260
ctggagcttt ggatcttttt tttttttttt cctccagaag ccctctcttg tccccgtcac 4320
cgggggcacc ttacatctga gggcgagagg acgtgatggg tccggcttcc aagccgatgt 4380
ggcggggcca gctggagctt cgggtttttt ttttttcctc cagaagccct ctcttgtccc 4440
cgtcaccggg ggcgctgtac ttctgaggcc gagaggacgt gatgggcccg ggttccaggc 4500
ggatgtcgcc cggtcagctg gagctttgga tcattttttt ttttccctcc agaagccctc 4560
tcttgtcccc gtcaccgggg gcaccgtaca tctgaggccg agaggacacg atgggcctgt 4620
cttccaagcc gatgtggccc ggccagctgg agcttcgggt cttttttttt ttttttcctc 4680
cagaagcctt gtctgtcgct gtcacccggg gcgctgtact tctgaggccg agaggacgcg 4740
atgggcccgg cttccaagcc ggtgtggctc ggccagctgg agcttcgggt cttttttttt 4800
tttttttttt ttcctccaga aaccttgtct gtcgctgtca cccggggcgc ttgtacttct 4860
gatgccgaga ggacgcgatg ggcccgtctt ccaggccgat gtggcccggt cagctggagc 4920
tttggatctt tttttttttt ttttcctcca gaagccctct cttgtccccg tcaccggggg 4980
caccttacat ctgaggccta gaggacacga tgggcccggg ttccaggccg atgtggcccg 5040
gtcagctgga gctttggatc tttttttttt ttttcttcca gaagccctct tgtccccgtc 5100
accggtggca ctgtacatct gaggcggaga ggacattatg ggcccggctt ccaatccgat 5160
gtggcccggt cagctggagc tttggatctt attttttttt taattttttc ttccagaagc 5220
cctcttgtcc ctgtcaccgg tggcacggta catctgaggc cgagaggaca ttatgggccc 5280
ggcttccagg ccgatgtggc ccggtcagct ggagctttgg atcttttttt tttttttttct 5340 tttttcctcc agaagccctc tctgtccctg tcaccggggg ccctgtacgt ctgaggccga 5400
gggaaagcta tgggcgcggt tttctttcat tgacctgtcg gtcttatcag ttctccgggt 5460
tgtcagggtc gaccagttgt tcctttgagg tccggttctt ttcgttatgg ggtcattttt 5520
gggccacctc cccaggtatg acttccaggc gtcgttgctc gcctgtcact ttcctccctg 5580
tctcttttat gcttgtgatc ttttctatct gttcctattg gacctggaga taggtactga 5640
cacgctgtcc tttccctatt aacactaaag gacactataa agagaccctt tcgatttaag 5700
gctgttttgc ttgtccagcc tattcttttt actggcttgg gtctgtcgcg gtgcctgaag 5760
ctgtccccga gccacgcttc ctgctttccc gggcttgctg cttgcgtgtg cttgctgtgg 5820
gcagcttgtg acaactgggc gctgtgactt tgctgcgtgt cagacgtttt tcccgatttc 5880
cccgaggtgt cgttgtcaca cctgtcccgg ttggaatggt ggagccagct gtggttgagg 5940
gccaccttat ttcggctcac tttttttttt tttttttctc ttggagtccc gaacctccgc 6000
tcttttctct tcccggtctt tcttccacat gcctcccgag tgcatttctt tttgtttttt 6060
ttcttttttt tttttttttt ttggggaggt ggagagtccc gagtacttca ctcctgtctg 6120
tggtgtccaa gtgttcatgc cacgtgcctc ccgagtgcac ttttttttgt ggcagtcgct 6180
cgttgtgttc tcttgttctg tgtctgcccg tatcagtaac tgtcttgccc cgcgtgtaag 6240
acattcctat ctcgcttgtt tctcccgatt gcgcgtcgtt gctcactctt agatcgatgt 6300

-continued

```
ggtgctccgg agttctcttc gggccagggc caagccgcgc caggcgaggg acggacattc   6360
atggcgaatg gcggccgctc ttctcgttct gccagcgggc cctcgtctct ccaccccatc   6420
cgtctgccgg tggtgtgtgg aaggcagggg tgcggctctc cggcccgacg ctgccccgcg   6480
cgcacttttc tcagtggttc gcgtggtcct tgtggatgtg tgaggcgccc ggttgtgccc   6540
tcacgtgttt cactttggtc gtgtctcgct tgaccatgtt cccagagtcg gtggatgtgg   6600
ccggtggcgt tgcataccct tcccgtctgg tgtgtgcacg cgctgtttct tgtaagcgtc   6660
gaggtgctcc tggagcgttc caggtttgtc tcctaggtgc ctgcttctga gctggtggtg   6720
gcgctcccca ttccctggtg tgcctccggt gctccgtctg gctgtgtgcc ttcccgtttg   6780
tgtctgagaa gcccgtgaga ggggggtcga ggagagaagg aggggcaaga ccccccttct   6840
tcgtcgggtg aggcgcccac cccgcgacta gtacgcctgt gcgtagggct ggtgctgagc   6900
ggtcgcggct ggggttggaa agtttctcga gagactcatt gctttcccgt ggggagcttt   6960
gagaggcctg gctttcgggg gggaccggtt gcagggtctc ccctgtccgc ggatgctcag   7020
aatgcccttg gaagagaacc ttcctgttgc cgcagacccc cccgcgcggt cgcccgcgtg   7080
ttggtcttct ggtttccctg tgtgctcgtc gcatgcatcc tctctcggtg gccggggctc   7140
gtcggggttt tgggtccgtc ccgccctcag tgagaaagtt tccttctcta gctatcttcc   7200
ggaaagggtg cgggcttctt acggtctcga ggggtctctc ccgaatggtc ccctggaggg   7260
ctcgccccct gaccgcctcc cgcgcgcgca gcgtttgctc tctcgtctac cgcggcccgc   7320
ggcctccccg ctccgagttc ggggagggat cacgcggggc agagcctgtc tgtcgtcctg   7380
ccgttgctgc ggagcatgtg gctcggcttg tgtggttggt ggctggggag agggctccgt   7440
gcacaccccc gcgtgcgcgt actttcctcc cctcctgagg gccgccgtgc ggacggggtg   7500
tgggtaggcg acggtgggct cccgggtccc cacccgtctt cccgtgcctc acccgtgcct   7560
tccgtcgcgt gcgtccctct cgctcgcgtc cacgactttg gccgctcccg cgacggcggc   7620
ctgcgccgcg cgtggtgcgt gctgtgtgct tctcgggctg tgtggttgtg tcgcctcgcc   7680
ccccccttcc cgcggcagcg ttcccacggc tggcgaaatc gcgggagtcc tccttcccct   7740
cctcggggtc gagagggtcc gtgtctggcg ttgattgatc tcgctctcgg ggacgggacc   7800
gttctgtggg agaacggctg ttggccgcgt ccggcgcgac gtcggacgtg gggacccact   7860
gccgctcggg ggtcttcgtc ggtaggcatc ggtgtgtcgg catcggtctc tctctcgtgt   7920
cggtgtcgcc tcctcgggct cccggggggc cgtcgtgttt cgggtcggct cggcgctgca   7980
ggtgtggtgg gactgctcag gggagtggtg cagtgtgatt cccgccggtt ttgcctcgcg   8040
tgccctgacc ggtccgacgc ccgagcggtc tctcggtccc ttgtgaggac cccettccgg   8100
gaggggcccg tttcggccgc ccttgccgtc gtcgccggcc ctcgttctgc tgtgtcgttc   8160
ccccctcccc gctcgccgca gccggtcttt tttcctctct cccccccctct cctctgactg   8220
acccgtggcc gtgctgtcgg accccccgca tgggggcggc cgggcacgta cgcgtccggg   8280
cggtcaccgg ggtcttgggg gggggccgag gggtaagaaa gtcggctcgg cgggcgggag   8340
gagctgtggt ttggagggcg tcccggcccc gcggccgtgg cggtgtcttg cgcggtcttg   8400
gagagggctg cgtgcgaggg gaaaaggttg ccccgcgagg gcaaagggaa agaggctagc   8460
agtggtcatt gtcccgacgg tgtggtggtc tgttggccga ggtgcgtctg gggggctcgt   8520
ccggccctgt cgtccgtcgg gaaggcgcgt gttggggcct gccggagtgc cgaggtgggt   8580
accctggcgg tgggattaac cccgcgcgcg tgtcccggtg tggcggtggg ggctccggtc   8640
gatgtctacc tccctctccc cgaggtctca ggccttctcc gcgcgggctc tcggccctcc   8700
```

-continued

```
cctcgttcct ccctctcgcg gggttcaagt cgctcgtcga cctcccctcc tccgtccttc   8760
catctctcgc gcaatggcgc cgcccgagtt cacggtgggt tcgtcctccg cctccgcttc   8820
tcgccggggg ctggccgctg tccggtctct cctgcccgac ccccgttggc gtggtcttct   8880
ctcgccggct tcgcggactc ctggcttcgc ccggagggtc agggggcttc ccggttcccc   8940
gacgttgcgc ctcgctgctg tgtgcttggg gggggcccgc tgcggcctcc gcccgcccgt   9000
gagcccctgc cgcacccgcc ggtgtgcggt ttcgcgccgc ggtcagttgg gccctggcgt   9060
tgtgtcgcgt cgggagcgtg tccgcctcgc ggcggctaga cgcgggtgtc gccgggctcc   9120
gacgggtggc ctatccaggg ctcgcccccg ccgacccccg cctgcccgtc ccggtggtgg   9180
tcgttggtgt ggggagtgaa tggtgctacc ggtcattccc tcccgcgtgg tttgactgtc   9240
tcgccggtgt cgcgcttctc tttccgccaa cccccacgcc aacccaccac cctgctctcc   9300
cggcccggtg cggtcgacgt tccggctctc ccgatgccga ggggttcggg atttgtgccg   9360
gggacggagg ggagagcggg taagagaggt gtcggagagc tgtcccgggg cgacgctcgg   9420
gttggctttg ccgcgtgcgt gtgctcgcgg acgggttttg tcggaccccg acggggtcgg   9480
tccggccgca tgcactctcc cgttccgcgc gagcgcccgc ccggctcacc cccggtttgt   9540
cctcccgcga ggctctccgc cgccgccgcc tcctcctcct ctctcgcgct ctctgtcccg   9600
cctggtcctg tcccaccccc gacgctccgc tcgcgcttcc ttacctggtt gatcctgcca   9660
ggtagcatat gcttgtctca aagattaagc catgcatgtc taagtacgca cggccggtac   9720
agtgaaactg cgaatggctc attaaatcag ttatggttcc tttggtcgct cgctcctctc   9780
ctacttggat aactgtggta attctagagc taatacatgc cgacgggcgc tgaccccct   9840
tcccgggggg ggatgcgtgc atttatcaga tcaaaaccaa cccggtgagc tccctcccgg   9900
ctccggccgg gggtcgggcg ccggcggctt ggtgactcta gataacctcg ggccgatcgc   9960
acgcccccg tggcggcgac gacccattcg aacgtctgcc ctatcaactt tcgatggtag  10020
tcgccgtgcc taccatggtg accacgggtg acggggaatc agggttcgat tccggagagg  10080
gagcctgaga aacggctacc acatccaagg aaggcagcag gcgcgcaaat tacccactcc  10140
cgacccgggg aggtagtgac gaaaaataac aatacaggac tctttcgagg ccctgtaatt  10200
ggaatgagtc cactttaaat cctttaacga ggatccattg gagggcaagt ctggtgccag  10260
cagccgcggt aattccagct ccaatagcgt atattaaagt tgctgcagtt aaaaagctcg  10320
tagttggatc ttgggagcgg gcgggcggtc cgccgcgagg cgagtcaccg cccgtccccg  10380
ccccttgcct ctcggcgccc cctcgatgct cttagctgag tgtcccgcgg ggcccgaagc  10440
gtttactttg aaaaaattag agtgttcaaa gcaggcccga gccgcctgga taccgcagct  10500
aggaataatg gaataggacc gcggttctat tttgttggtt ttcggaactg aggccatgat  10560
taagagggac ggccgggggc attcgtattg cgccgctaga ggtgaaattc ttggaccggc  10620
gcaagacgga ccagagcgaa agcatttgcc aagaatgttt tcattaatca agaacgaaag  10680
tcggaggttc gaagacgatc agataccgtc gtagttccga ccataaacga tgccgactgg  10740
cgatgcggcg gcgttattcc catgacccgc cgggcagctt ccgggaaacc aaagtctttg  10800
ggttccgggg ggagtatggt tgcaaagctg aaacttaaag gaattgacgg aagggcacca  10860
ccaggagtgg gcctgcggct taatttgact caacacggga aacctcaccc ggcccggaca  10920
cggacaggat tgacagattg atagctcttt ctcgattccg tgggtggtgg tgcatggccg  10980
ttcttagttg gtggagcgat ttgtctggtt aattccgata acgaacgaga ctctggcatg  11040
```

-continued

```
ctaactagtt acgcgacccc cgagcggtcg gcgtccccca acttcttaga gggacaagtg  11100
gcgttcagcc acccgagatt gagcaataac aggtctgtga tgcccttaga tgtccggggc  11160
tgcacgcgcg ctacactgac tggctcagcg tgtgcctacc ctgcgccggc aggcgcgggt  11220
aacccgttga accccattcg tgatggggat cggggattgc aattattccc catgaacgag  11280
gaattcccag taagtgcggg tcataagctt gcgttgatta agtccctgcc ctttgtacac  11340
accgcccgtc gctactaccg attggatggt ttagtgaggc cctcggatcg gccccgccgg  11400
ggtcggccca cggccctggc ggagcgctga gaagacggtc gaacttgact atctagagga  11460
agtaaaagtc gtaacaaggt ttccgtaggt gaacctgcgg aaggatcatt aaacgggaga  11520
ctgtggagga gcggcggcgt ggcccgctct ccccgtcttg tgtgtgtcct cgccgggagg  11580
cgcgtgcgtc ccgggtcccg tcgcccgcgt gtggagcgag gtgtctggag tgaggtgaga  11640
gaaggggtgg gtggggtcgg tctgggtccg tctgggaccg cctccgattt cccctccccc  11700
tcccctctcc ctcgtccggc tctgacctcg ccaccctacc gcggcggcgg ctgctcgcgg  11760
gcgtcttgcc tctttcccgt ccggctcttc cgtgtctacg aggggcggta cgtcgttacg  11820
ggtttttgac ccgtcccggg ggcgttcggt cgtcggggcg cgcgctttgc tctcccggca  11880
cccatccccg ccgcggctct ggcttttcta cgttggctgg ggcggttgtc gcgtgtgggg  11940
ggatgtgagt gtcgcgtgtg ggctcgcccg tcccgatgcc acgcttttct ggcctcgcgt  12000
gtcctccccg ctcctgtccc gggtacctag ctgtcgcgtt ccggcgcgga ggtttaagga  12060
ccccgggggg gtcgccctgc cgcccccagg gtcgggggc ggtggggccc gtagggaagt  12120
cggtcgttcg ggcggctctc cctcagactc catgaccctc ctccccccgc tgccgccgtt  12180
cccgaggcgg cggtcgtgtg ggggggtgga tgtctggagc cccctcgggc gccgtggggg  12240
cccgacccgc gccgccggct tgcccgattt ccgcgggtcg gtcctgtcgg tgccggtcgt  12300
gggttcccgt gtcgttcccg tgtttttccg ctcccgaccc ttttttttttc ctccccccca  12360
cacgtgtctc gtttcgttcc tgctggccgg cctgaggcta cccctcggtc catctgttct  12420
cctctctctc cggggagagg agggcggtgg tcgttggggg actgtgccgt cgtcagcacc  12480
cgtgagttcg ctcacacccg aaataccgat acgactctta gcggtggatc actcggctcg  12540
tgcgtcgatg aagaacgcag ctagctgcga gaattaatgt gaattgcagg acacattgat  12600
catcgacact tcgaacgcac ttgcggcccc gggttcctcc cggggctacg cctgtctgag  12660
cgtcggttga cgatcaatcg cgtcacccgc tgcggtgggt gctgcgcggc tgggagtttg  12720
ctcgcagggc caaccccca acccgggtcg ggccctccgt ctcccgaagt tcagacgtgt  12780
gggcggttgt cggtgtggcg cgcgcgcccg cgtcgcggag cctggtctcc cccgcgcatc  12840
cgcgctcgcg gcttcttccc gctccgccgt tcccgccctc gcccgtgcac cccggtcctg  12900
gcctcgcgtc ggcgcctccc ggaccgctgc ctcaccagtc tttctcggtc ccgtgccccg  12960
tgggaaccca ccgcgccccc gtggcgcccg ggggtgggcg cgtccgcatc tgctctggtc  13020
gaggttggcg gttgagggtg tgcgtgcgcc gaggtggtgg tcggtcccct gcggccgcgg  13080
ggttgtcggg gtggcggtcg acgagggccg gtcggtcgcc tgcggtggtt gtctgtgtgt  13140
gtttgggtct tgcgctgggg gaggcggggt cgaccgctcg cggggttggc gcggtcgccc  13200
ggcgccgcgc accctccggc ttgtgtggag ggagagcgag ggcgagaacg gagagaggtg  13260
gtatccccgg tggcgttgcg agggagggtt tggcgtcccg cgtccgtccg tccctccctc  13320
cctcggtggg cgccttcgcg ccgcacgcgg ccgctagggg cggtcggggc ccgtggcccc  13380
cgtggctctt cttcgtctcc gcttctcctt cacccgggcg gtacccgctc cggcgccggc  13440
```

-continued

```
ccgcgggacg ccgcggcgtc cgtgcgccga tgcgagtcac ccccgggtgt tgcgagttcg  13500
gggagggaga gggcctcgct gacccgttgc gtcccggctt ccctgggggg gacccggcgt  13560
ctgtgggctg tgcgtcccgg gggttgcgtg tgagtaagat cctccacccc cgccgccctc  13620
ccctcccgcc ggcctctcgg ggacccccctg agacggttcg ccggctcgtc ctcccgtgcc  13680
gccgggtgcc gtctctttcc cgcccgcctc ctcgctctct tcttcccgcg gctgggcgcg  13740
tgtcccccct ttctgaccgc gacctcagat cagacgtggc gacccgctga atttaagcat  13800
attagtcagc ggaggaaaag aaactaacca ggattccctc agtaacggcg agtgaacagg  13860
gaagagccca gcgccgaatc cccgccgcgc gtcgcggcgt gggaaatgtg gcgtacggaa  13920
gacccactcc ccggcgccgc tcgtgggggg cccaagtcct tctgatcgag gcccagcccg  13980
tggacggtgt gaggccggta gcggccccgg cgcgccgggc tcgggtcttc ccggagtcgg  14040
gttgcttggg aatgcagccc aaagcgggtg gtaaactcca tctaaggcta aataccggca  14100
cgagaccgat agtcaacaag taccgtaagg gaaagttgaa aagaactttg aagagagagt  14160
tcaagagggc gtgaaaccgt taagaggtaa acgggtgggg tccgcgcagt ccgcccggag  14220
gattcaaccc ggcggcgcgc gtccggccgt gcccggtggt cccggcggat ctttcccgct  14280
ccccgttcct cccgacccct ccacccgcgc gtcgttcccc tcttcctccc cgcgtccggc  14340
gcctccggcg gcgggcgcgg ggggtggtgt ggtggtggcg cgcgggcggg gccgggggtg  14400
gggtcggcgg gggaccgccc ccggccggcg accggccgcc gccgggcgca cttccaccgt  14460
ggcggtgcgc cgcgaccggc tccgggacgg ccgggaaggc ccggtgggga aggtggctcg  14520
gggggggcgg cgcgtctcag ggcgcgccga accacctcac cccgagtgtt acagccctcc  14580
ggccgcgctt tcgccgaatc ccggggccga ggaagccaga tacccgtcgc cgcgctctcc  14640
ctctcccccc gtccgcctcc cgggcgggcg tgggggtggg ggccgggccg cccctcccac  14700
ggcgcgaccg ctctcccacc cccctccgtc gcctctctcg gggcccggtg gggggcgggg  14760
cggactgtcc ccagtgcgcc ccgggcgtcg tcgcgccgtc gggtcccggg gggaccgtcg  14820
gtcacgcgtc tcccgacgaa gccgagcgca cggggtcggc ggcgatgtcg gctacccacc  14880
cgacccgtct tgaaacacgg accaaggagt ctaacgcgtg cgcgagtcag gggctcgtcc  14940
gaaagccgcc gtggcgcaat gaaggtgaag ggccccgccc gggggcccga ggtgggatcc  15000
cgaggcctct ccagtccgcc gagggcgcac caccggcccg tctcgcccgc cgcgccgggg  15060
aggtggagca cgagcgtacg cgttaggacc cgaaagatgg tgaactatgc ttgggcaggg  15120
cgaagccaga ggaaactctg gtggaggtcc gtagcggtcc tgacgtgcaa atcggtcgtc  15180
cgacctgggt ataggggcga aagactaatc gaaccatcta gtagctggtt ccctccgaag  15240
tttccctcag gatagctggc gctctcgctc ccgacgtacg cagttttatc cggtaaagcg  15300
aatgattaga ggtcttgggg ccgaaacgat ctcaacctat tctcaaactt taaatgggta  15360
agaagcccgg ctcgctggcg tggagccggg cgtggaatgc gagtgcctag tgggccactt  15420
ttggtaagca gaactggcgc tgcgggatga accgaacgcc gggttaaggc gcccgatgcc  15480
gacgctcatc agaccccaga aaaggtgttg gttgatatag acagcaggac ggtggccatg  15540
gaagtcggaa tccgctaagg agtgtgtaac aactcacctg ccgaatcaac tagccctgaa  15600
aatggatggc gctggagcgt cgggcccata cccggccgtc gccgcagtcg gaacggaacg  15660
ggacgggagc ggccgcgggt gcgcgtctct cggggtcggg ggtgcgtggc gggggcccgt  15720
cccccgcctc ccctccgcgc gccgggttcg cccccgcggc gtcgggcccc gcggagccta  15780
```

-continued

```
cgccgcgacg agtaggaggg ccgctgcggt gagccttgaa gcctagggcg cgggcccggg 15840
tggagccgcc gcaggtgcag atcttggtgg tagtagcaaa tattcaaacg agaactttga 15900
aggccgaagt ggagaagggt tccatgtgaa cagcagttga acatgggtca gtcggtcctg 15960
agagatgggc gagtgccgtt ccgaagggac gggcgatggc ctccgttgcc ctcggccgat 16020
cgaaagggag tcgggttcag atccccgaat ccggagtggc ggagatgggc gccgcgaggc 16080
cagtgcggta acgcgaccga tcccggagaa gccggcggga ggcctcgggg agagttctct 16140
tttctttgtg aagggcaggg cgccctggaa tgggttcgcc ccgagagagg ggcccgtgcc 16200
ttggaaagcg tcgcggttcc ggcggcgtcc ggtgagctct cgctggccct tgaaaatccg 16260
ggggagaggg tgtaaatctc gcgccgggcc gtacccatat ccgcagcagg tctccaaggt 16320
gaacagcctc tggcatgttg gaacaatgta ggtaagggaa gtcggcaagc cggatccgta 16380
acttcgggat aaggattggc tctaagggct gggtcggtcg ggctggggcg cgaagcgggg 16440
ctgggcgcgc gccgcggctg gacgaggcgc cgccgccctc tcccacgtcc ggggagaccc 16500
cccgtccttt ccgcccgggc ccgccctccc ctcttccccg cggggccccg tcgtcccccg 16560
cgtcgtcgcc acctctcttc ccccctcctt cttcccgtcg gggggcgggt cgggggtcgg 16620
cgcgcggcgc gggctccggg gcggcgggtc caaccccgcg ggggttccgg agcgggagga 16680
accagcggtc cccggtgggg cggggggccc ggacactcgg ggggccggcg gcggcggcga 16740
ctctggacgc gagccgggcc cttcccgtgg atcgcctcag ctgcggcggg cgtcgcggcc 16800
gctcccgggg agcccggcgg gtgccggcgc gggtcccctc cccgcggggc ctcgctccac 16860
ccccccatcg cctctcccga ggtgcgtggc gggggcgggc gggcgtgtcc cgcgcgtgtg 16920
gggggaacct ccgcgtcggt gttcccccgc cgggtccgcc ccccgggccg cggttttccg 16980
cgcggcgccc ccgcctcggc cggcgcctag cagccgactt agaactggtg cggaccaggg 17040
gaatccgact gtttaattaa aacaaagcat cgcgaaggcc cgcggcgggt gttgacgcga 17100
tgtgatttct gcccagtgct ctgaatgtca aagtgaagaa attcaatgaa gcgcgggtaa 17160
acggcgggag taactatgac tctcttaagg tagccaaatg cctcgtcatc taattagtga 17220
cgcgcatgaa tggatgaacg agattcccac tgtccctacc tactatccag cgaaaccaca 17280
gccaagggaa cgggcttggc ggaatcagcg gggaaagaag accctgttga gcttgactct 17340
agtctggcac ggtgaagaga catgagaggt gtagaataag tgggaggccc ccggcgcccg 17400
gccccgtcct cgcgtcgggg tcggggcacg ccggcctcgc gggccgccgg tgaaatacca 17460
ctactctcat cgtttttttca ctgacccggt gaggcggggg ggcgagcccc gaggggctct 17520
cgcttctggc gccaagcgtc cgtcccgcgc gtgcgggcgg gcgcgacccg ctccggggac 17580
agtgccaggt ggggagtttg actggggcgg tacacctgtc aaacggtaac gcaggtgtcc 17640
taaggcgagc tcagggagga cagaaacctc ccgtggagca gaagggcaaa agctcgcttg 17700
atcttgattt tcagtacgaa tacagaccgt gaaagcgggg cctcacgatc cttctgacct 17760
tttgggtttt aagcaggagg tgtcagaaaa gttaccacag ggataactgg cttgtggcgg 17820
ccaagcgttc atagcgacgt cgctttttga tccttcgatg tcggctcttc ctatcattgt 17880
gaagcagaat tcaccaagcg ttggattgtt cacccactaa tagggaacgt gagctgggtt 17940
tagaccgtcg tgagacaggt tagttttacc ctactgatga tgtgttgttg ccatggtaat 18000
cctgctcagt acgagaggaa ccgcaggttc agacatttgg tgtatgtgct tggctgagga 18060
gccaatgggg cgaagctacc atctgtggga ttatgactga acgcctctaa gtcagaatcc 18120
gcccaagcgg aacgatacgg cagcgccgaa ggagcctcgg ttggccccgg atagccgggt 18180
```

-continued

```
ccccgtccgt cccgctcggc ggggtccccg cgtcgccccg cggcggcgcg gggtctcccc  18240
ccgccgggcg tcgggaccgg ggtccggtgc ggagagccgt tcgtcttggg aaacggggtg  18300
cggccggaaa gggggccgcc ctctcgcccg tcacgttgaa cgcacgttcg tgtggaacct  18360
ggcgctaaac cattcgtaga cgacctgctt ctgggtcggg gtttcgtacg tagcagagca  18420
gctccctcgc tgcgatctat tgaaagtcag ccctcgacac aagggtttgt ctctgcgggc  18480
tttcccgtcg cacgcccgct cgctcgcacg cgaccgtgtc gccgcccggg cgtcacgggg  18540
gcggtcgcct cggcccccgc gcggttgccc gaacgaccgt gtggtggttg ggggggggat  18600
cgtcttctcc tccgtctccc gaggacggtt cgtttctctt tccccttccg tcgctctcct  18660
tgggtgtggg agcctcgtgc cgtcgcgacc gcggcctgcc gtcgcctgcc gccgcagccc  18720
cttgccctcc ggccttggcc aagccggagg gcggaggagg gggatcggcg gcggcggcga  18780
ccgcggcgcg gtgacgcacg gtgggatccc catcctcggc gcgtccgtcg gggacggccg  18840
gttggagggg cgggaggggt ttttcccgtg aacgccgcgt tcggcgccag gcctctggcg  18900
gccggggggg cgctctctcc gcccgagcat ccccactccc gcccctcctc ttcgcgcgcc  18960
gcggcggcga cgtgcgtacg aggggaggat gtcgcggtgt ggaggcggag agggtccggc  19020
gcggcgcctc ttccattttt tcccccccaa cttcggaggt cgaccagtac tccgggcgac  19080
actttgtttt ttttttttcc cccgatgctg gaggtcgacc agatgtccga aagtgtcccc  19140
cccccccccc ccccccggcg cggagcggcg gggccactct ggactctttt tttttttttt  19200
tttttttttt ttaaattcct ggaaccttta ggtcgaccag ttgtccgtct tttactcctt  19260
catataggtc gaccagtact ccgggtggta ctttgtcttt ttctgaaaat cccagaggtc  19320
gaccagatat ccgaaagtcc tctctttccc tttactcttc cccacagcga ttctcttttt  19380
tttttttttt tttggtgtgc ctctttttga cttatataca tgtaaatagt gtgtacgttt  19440
atatacttat aggaggaggt cgaccagtac tccgggcgac actttgtttt tttttttttt  19500
tccaccgatg atggaggtcg accagatgtc cgaaagtgtc ccgtccccccc cctcccccccc  19560
ccgcgacgcg gcgggctcac tctggactct tttttttttt tttttttttt tttaaatttc  19620
tggaacctta aggtcgacca gttgtccgtc tttcactcat tcatataggt cgaccggtgg  19680
tactttgtct ttttctgaaa atcgcagagg tcgaccagat gtcagaaagt ctggtggtcg  19740
ataaattatc tgatctagat ttgtttttct gtttttcagt tttgtgttgt tttgtgttgt  19800
tttgtgttgt tttgttttgt tttgttttgt tttgttttgt tttgttttgt tttgttttgt  19860
tttgtgttgt gttgtgttgt gttgtgttgg gttgggttgg gttgggttgg gttgggttgg  19920
gttgggttgg gttgggttgt gttgtttggt tttgtgttgt ttggtgttgt tggttttgtt  19980
ttgtttgctg ttgttttgtg ttttgcgggt cgaacagttg tccctaaccg agtttttttg  20040
tacacaaaca tgcacttttt ttaaaataaa tttttaaaat aaatgcgaaa atcgaccaat  20100
tatccctttc cttctctctc ttttttaaaa attttctttg tgtgtgtgtg tgtgtgtgtg  20160
tgtgtgtgtg tgcgtgtgtg tgtgtgtgtg cgtgcagcgt gcgcgcgctc gttttataaa  20220
tacttataat aataggtcgc cgggtggtgg tagcttcccg gactccagag gcagaggcag  20280
gcagacttct gagttcgagg ccagcctggt ctacagagga accctgtctc gaaaaatgaa  20340
aataaataca tacatacata catacataca tacatacata catacataca tacatatgag  20400
gttgaccagt tgtcaatcct ttagaatttt gtttttaatt aatgtgatag agagatagat  20460
aatagataga tggatagagt gatacaaata taggtttttt tttcagtaaa tatgaggttg  20520
```

-continued

```
attaaccact tttccctttt taggtttttt tttttttccc ctgtccatgt ggttgctggg  20580

atttgaactc aggaccctgg caggtcaact ggaaaacgtg ttttctatat atataaatag  20640

tggtctgtct gctgtttgtt tgtttgcttg cttgcttgct tgcttgcttg cttgcttgct  20700

tgcttttttt tttcttctga gacagtattt ctctgtgtaa cctggtgccc tgaaactcac  20760

tctgtagacc agcctggcct caatcgaact cagaaatcct cctgcctctt gtctacctcc  20820

caattttgga gtaaaggtgt gctacaccac tgcctggcat tattatcatt atcattatta  20880

attttattat tagacagaac gaaatcaact agttggtcct gtttcgttaa ttcatttgaa  20940

attagttgga ccaattagtt ggctggtttg ggaggtttct tttgtttccg atttgggtgt  21000

ttgtggggct ggggatcagg tatctcaacg gaatgcatga aggttaaggt gagatggctc  21060

gatttttgta aagattactt ttcttagtct gaggaaaaaa taaaataata ttgggctacg  21120

tttcattgct tcatttctat ttctctttct ttctttcttt ctttcagata aggaggtcgg  21180

ccagttcctc ctgccttctg gaagatgtag gcattgcatt gggaaaagca ttgtttgaga  21240

gatgtgctag tgaaccagag agtttggatg tcaagccgta taatgtttat tacaatatag  21300

aaaagttcta acaaagtgat ctttaacttt tttttttttt tttctccttc tacttctact  21360

tgttctcact ctgccaccaa cgcgctttgt acattgaatg tgagctttgt tttgcttaac  21420

agacatatat tttttctttt ggttttgctt gacatggttt ccctttctat ccgtgcaggg  21480

ttcccagacg gccttttgag aataaaatgg gaggccagaa ccaaagtctt ttgaataaag  21540

caccacaact ctaacctgtt tggctgtttt ccttcccaag gcacagatct ttcccagcat  21600

ggaaaagcat gtagcagttg taggacacac tagacgagag caccagatct cattgtgggt  21660

ggttgtgaac cacccaccat gtggttgcct gggatttgaa ctcaggatct tcagaagacg  21720

agtcagggct ctaaaccgat gagccatctc tccagccctc ctacattcct tcttaaggca  21780

tgaatgatcc cagcatggga agacagtctg ccctctttgt ggtatatcac catatactca  21840

ataaaataat gaaatgaatg aagtctccac gtatttattt cttcgagcta tctaaattct  21900

ctcacagcac ctccccctcc cccacactgc ctttctccct atgtttgggt ggggctgggg  21960

gaggggtggg gtgggggcag ggatctgcat gtcttcttgc aggtctgtga actatttgcg  22020

atggcctggt tctctgaact gttgagcctt gtctatccag aggctgactg gctagttttc  22080

tacctgaagt ccctgagtga tgatttccct gtgaattc                          22118
```

<210> SEQ ID NO 19
<211> LENGTH: 175
<212> TYPE: DNA
<213> ORGANISM: Mus musculus

<400> SEQUENCE: 19

```
ctcccgcgcg gcccccgtgt tcgccgttcc cgtggcgcgg acaatgcggt tgtgcgtcca     60

cgtgtgcgtg tccgtgcagt gccgttgtgg agtgcctcgc tctcctcctc ctccccggca    120

gcgttcccac ggttggggac caccggtgac ctcgccctct tcgggcctgg atccg         175
```

<210> SEQ ID NO 20
<211> LENGTH: 755
<212> TYPE: DNA
<213> ORGANISM: Mus musculus

<400> SEQUENCE: 20

```
ggtctggtgg gaattgttga cctcgctctc gggtgcggcc tttggggaac ggcggggtcg     60

gtcgtgcccg gcgccggacg tgtgtcgggg cccacttccc gctcgagggt ggcggtggcg    120
```

-continued gcggcgttgg tagtctcccg tgttgcgtct tcccgggctc ttgggggggg tgccgtcgtt 180
ttcggggccg gcgttgcttg gcttacgcag gcttggtttg ggactgcctc aggagtcgtg 240
ggcggtgtga ttcccgccgg ttttgcctcg cgtctgcctg ctttgcctcg ggtttgcttg 300
gttcgtgtct cgggagcggt ggtttttttt tttttcgggt cccggggaga ggggtttttc 360
cgggggacgt tcccgtcgcc ccctgccgcc ggtgggtttt cgtttcgggc tgtgttcgtt 420
tccccttccc cgtttcgccg tcggttctcc ccggtcggtc ggccctctcc ccggtcggtc 480
gcccggccgt gctgccggac ccccccttct ggggggggatg cccgggcacg cacgcgtccg 540
ggcggccact gtggtccggg agctgctcgg caggcgggtg agccagttgg aggggcgtca 600
tgcccccgcg ggctcccgtg gccgacgcgg cgtgttcttt ggggggggcct gtgcgtgcgg 660 gaaggctgcg cacgttgtcg gtccttgcga gggaaagagg cttttttttt ttagggggtc 720
gtccttcgtc gtcccgtcgg cggtggatcc ggcct 755

<210> SEQ ID NO 21
<211> LENGTH: 463
<212> TYPE: DNA
<213> ORGANISM: Mus musculus

<400> SEQUENCE: 21
ggccgaggtg cgtctgcggg ttggggctcg tccggccccg tcgtcctccg ggaaggcgtt 60
tagcgggtac cgtcgccgcg ccgaggtggg cgcacgtcgg tgagataacc ccgagcgtgt 120
ttctggttgt tggcggcggg ggctccggtc gatgtcttcc cctccccctc tccccgaggc 180
caggtcagcc tccgcctgtg ggcttcgtcg gccgtctccc ccccctcac gtccctcgcg 240 agcgagcccg tccgttcgac cttccttccg ccttccccccc atctttccgc gctccgttgg 300
ccccggggtt ttcacggcgc cccccacgct cctccgcctc tccgcccgtg gtttggacgc 360
ctggttccgg tctccccgcc aaaccccggt tgggttggtc tccggccccg gcttgctctt 420
cgggtctccc aacccccggc cggaagggtt cgggggttcc ggg 463

<210> SEQ ID NO 22
<211> LENGTH: 378
<212> TYPE: DNA
<213> ORGANISM: Mus musculus

<400> SEQUENCE: 22
ggattcttca ggattgaaac ccaaaccggt tcagtttcct ttccggctcc ggccgggggg 60
ggcggccccg ggcggtttgg tgagttagat aacctcgggc cgatcgcacg cccccccgtgg 120 cggcgacgac ccattcgaac gtctgcccta tcaactttcg atggtagtcg atgtgcctac 180
catggtgacc acgggtgacg gggaatcagg gttcgattcc ggagagggag cctgagaaac 240
ggctaccaca tccaaggaag gcagcaggcg cgcaaattac ccactcccga cccggggagg 300
tagtgacgaa aaataacaat acaggactct ttcgaggccc tgtaattgga atgagtccac 360
tttaaatcct ttaagcag 378

<210> SEQ ID NO 23
<211> LENGTH: 378
<212> TYPE: DNA
<213> ORGANISM: Mus musculus

<400> SEQUENCE: 23
gatccattgg agggcaagtc tggtgccagc agccgcggta attccagctc caatagcgta 60

-continued

```
tattaaagtt gctgcagtta aaaagctcgt agttggatct tgggagcggg cgggcggtcc    120

gccgcgaggc gagtcaccgc ccgtccccgc cccttgcctc tcggcgcccc ctcgatgctc    180

ttagctgagt tgtcccgcgg ggcccgaagc gtttactttg aaaaaattag agttgtttca    240

aagcaggccc gagccgcctg gataccgcca gctaggaaat aatggaatag gaccgcggtt    300

cctattttgt ttggttttcg gaactgagcc catgattaag ggaaacggcc gggggcattc    360

ccttattgcg cccccccta                                                 378


<210> SEQ ID NO 24
<211> LENGTH: 719
<212> TYPE: DNA
<213> ORGANISM: Mus musculus

<400> SEQUENCE: 24

ggatctttcc cgctccccgt tcctcccggc ccctccaccc gcgcgtctcc ccccttcttt     60

tcccctctcc ggaggggggg gaggtggggg cgcgtgggcg gggtcggggg tggggtcggc    120

gggggaccgc ccccggccgg caaaaggccg ccgccgggcg cacttcaacc gtagcggtgc    180

gccgcgaccg gctacgagac ggctgggaag gcccgacggg gaatgtggct cggggggggc    240

ggcgcgtctc agggcgcgcc gaaccacctc accccgagtg ttacagccct ccggccgcgc    300

tttcgcggaa tcccggggcc gaggggaagc ccgataccog tcgccgcgct tttcccctcc    360

ccccgtccgc ctcccgggcg ggcgtggggg tgggggccgg gccgcccctc ccacgcccgt    420

ggtttctctc tctcccggtc tcggccggtt tggggggggg agcccggttg ggggcggggc    480

ggactgtcct cagtgcgccc cgggcgtcgt cgcgccgtcg ggcccggggg gttctctcgg    540

tcacgccgcc cccgacgaag ccgagcgcac ggggtcggcg gcgatgtcgg ctacccaccc    600

gacccgtctt gaaacacgga ccaaggagtc taacgcgtgc gcgagtcagg ggctcgcacg    660

aaagccgccg tggcgcaatg aaggtgaagg gccccgtccg gggcccgag gtgggatcc      719


<210> SEQ ID NO 25
<211> LENGTH: 685
<212> TYPE: DNA
<213> ORGANISM: Mus musculus

<400> SEQUENCE: 25

cgaggcctct ccagtccgcc gagggcgcac caccggcccg tctcgcccgc cgcgtcgggg     60

aggtggagca cgagcgtacg cgttaggacc cgaaagatgg tgaactatgc ctgggcaggg    120

cgaagccaga ggaaactctg gtggaggtcc gtagcggtcc tgacgtgcaa atcggtcgtc    180

cgacctgggt ataggggcga aagactaatc gaaccatcta gtagctggtt ccctccgaag    240

tttccctcag gatagctggc gctctcgcaa ccttcggaag cagttttatc cgggtaaagg    300

cggaatggat taggaggtct tggggccgga aacgatctca aactatttct caaactttaa    360

atgggtaagg aagcccggct cgctggcgtg gagccgggcg tggaatgcga gtgcctagtg    420

ggccactttt ggtaagcaga actggcgctg cgggatgaac cgaacgccgg gttaaggcgc    480

ccgatgccga cgctcatcag accccagaaa aggtgttggt tgatatagac agcaggacgg    540

tggccatgga agtcggaatc cgctaaggag tgtgtaacaa ctcacctgcc gaatcaacta    600

gccctgaaaa tggatggcgc tggagcgtcg ggcccatacc cggccgtcgc cggcagtcgg    660

aacgggacgg gacgggagcg gccgc                                          685


<210> SEQ ID NO 26
<211> LENGTH: 5162
```

-continued

<212> TYPE: DNA
<213> ORGANISM: Artificial Sequence
<220> FEATURE:
<223> OTHER INFORMATION: Chimeric bacterial plasmid

<400> SEQUENCE: 26

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gcttggtacc     900
gagctcggat cgatatctgc ggccgcgtcg acggaattca gtggatccac tagtaacggc     960
cgccagtgtg ctggaattaa ttcgctgtct gcgagggcca gctgttgggg tgagtactcc    1020
ctctcaaaag cgggcatgac ttctgcgcta agattgtcag tttccaaaaa cgaggaggat    1080
ttgatattca cctggcccgc ggtgatgcct ttgagggtgg ccgcgtccat ctggtcagaa    1140
aagacaatct ttttgttgtc aagcttgagg tgtggcaggc ttgagatctg gccatacact    1200
tgagtgacaa tgacatccac tttgcctttc tctccacagg tgtccactcc caggtccaac    1260
tgcaggtcga gcatgcatct agggcggcca attccgcccc tctccctccc ccccccctaa    1320
cgttactggc cgaagccgct tggaataagg ccggtgtgcg tttgtctata tgtgattttc    1380
caccatattg ccgtcttttg gcaatgtgag ggcccggaaa cctggccctg tcttcttgac    1440
gagcattcct aggggtcttt cccctctcgc caaaggaatg caaggtctgt tgaatgtcgt    1500
gaaggaagca gttcctctgg aagcttcttg aagacaaaca acgtctgtag cgaccctttg    1560
caggcagcgg aaccccccac ctggcgacag gtgcctctgc ggccaaaagc cacgtgtata    1620
agatacacct gcaaaggcgg cacaacccca gtgccacgtt gtgagttgga tagttgtgga    1680
aagagtcaaa tggctctcct caagcgtatt caacaagggg ctgaaggatg cccagaaggt    1740
accccattgt atgggatctg atctggggcc tcggtgcaca tgctttacat gtgtttagtc    1800
gaggttaaaa aaacgtctag gccccccgaa ccacggggac gtggttttcc tttgaaaaac    1860
acgatgataa gcttgccaca acccgggatc caccggtcgc caccatggtg agcaagggcg    1920
aggagctgtt caccggggtg gtgcccatcc tggtcgagct ggacggcgac gtaaacggcc    1980
acaagttcag cgtgtccggc gagggcgagg gcgatgccac ctacggcaag ctgaccctga    2040
agttcatctg caccaccggc aagctgcccg tgccctggcc caccctcgtg accaccctga    2100
cctacggcgt gcagtgcttc agccgctacc ccgaccacat gaagcagcac gacttcttca    2160
```

-continued

```
agtccgccat gcccgaaggc tacgtccagg agcgcaccat cttcttcaag gacgacggca   2220

actacaagac ccgcgccgag gtgaagttcg agggcgacac cctggtgaac cgcatcgagc   2280

tgaagggcat cgacttcaag gaggacggca acatcctggg gcacaagctg gagtacaact   2340

acaacagcca caacgtctat atcatggccg acaagcagaa gaacggcatc aaggtgaact   2400

tcaagatccg ccacaacatc gaggacggca gcgtgcagct cgccgaccac taccagcaga   2460

acacccccat cggcgacggc cccgtgctgc tgcccgacaa ccactacctg agcacccagt   2520

ccgccctgag caaagacccc aacgagaagc gcgatcacat ggtcctgctg gagttcgtga   2580

ccgccgccgg gatcactctc ggcatggacg agctgtacaa gtaaagcggc cctagagctc   2640

gctgatcagc ctcgactgtg cctctagttg ccagccatct gttgtttgcc cctcccccgt   2700

gccttccttg accctggaag gtgccactcc cactgtcctt tcctaataaa atgaggaaat   2760

tgcatcgcat tgtctgagta ggtgtcattc tattctgggg ggtggggtgg ggcaggacag   2820

caagggggag gattgggaag acaatagcag gcatgctggg gatgcggtgg gctctatggc   2880

ttctgaggcg gaaagaacca gctggggctc gagtgcattc tagttgtggt ttgtccaaac   2940

tcatcaatgt atcttatcat gtctgtatac cgtcgacctc tagctagagc ttggcgtaat   3000

catggtcata gctgtttcct gtgtgaaatt gttatccgct cacaattcca cacaacatac   3060

gagccggaag cataaagtgt aaagcctggg gtgcctaatg agtgagctaa ctcacattaa   3120

ttgcgttgcg ctcactgccc gctttccagt cgggaaacct gtcgtgccag ctgcattaat   3180

gaatcggcca acgcgcgggg agaggcggtt tgcgtattgg gcgctcttcc gcttcctcgc   3240

tcactgactc gctgcgctcg gtcgttcggc tgcggcgagc ggtatcagct cactcaaagg   3300

cggtaatacg gttatccaca gaatcagggg ataacgcagg aaagaacatg tgagcaaaag   3360

gccagcaaaa ggccaggaac cgtaaaaagg ccgcgttgct ggcgtttttc cataggctcc   3420

gcccccctga cgagcatcac aaaaatcgac gctcaagtca gaggtggcga aacccgacag   3480

gactataaag ataccaggcg tttccccctg gaagctccct cgtgcgctct cctgttccga   3540

ccctgccgct taccggatac ctgtccgcct ttctcccttc gggaagcgtg gcgctttctc   3600

aatgctcacg ctgtaggtat ctcagttcgg tgtaggtcgt tcgctccaag ctgggctgtg   3660

tgcacgaacc ccccgttcag cccgaccgct gcgccttatc cggtaactat cgtcttgagt   3720

ccaacccggt aagacacgac ttatcgccac tggcagcagc cactggtaac aggattagca   3780

gagcgaggta tgtaggcggt gctacagagt tcttgaagtg gtggcctaac tacggctaca   3840

ctagaaggac agtatttggt atctgcgctc tgctgaagcc agttaccttc ggaaaaagag   3900

ttggtagctc ttgatccggc aaacaaacca ccgctggtag cggtggtttt tttgtttgca   3960

agcagcagat tacgcgcaga aaaaaaggat ctcaagaaga tcctttgatc ttttctacgg   4020

ggtctgacgc tcagtggaac gaaaactcac gttaagggat tttggtcatg agattatcaa   4080

aaaggatctt cacctagatc cttttaaatt aaaaatgaag ttttaaatca atctaaagta   4140

tatatgagta aacttggtct gacagttacc aatgcttaat cagtgaggca cctatctcag   4200

cgatctgtct atttcgttca tccatagttg cctgactccc cgtcgtgtag ataactacga   4260

tacgggaggg cttaccatct ggccccagtg ctgcaatgat accgcgagac ccacgctcac   4320

cggctccaga tttatcagca ataaaccagc cagccggaag ggccgagcgc agaagtggtc   4380

ctgcaacttt atccgcctcc atccagtcta ttaattgttg ccgggaagct agagtaagta   4440

gttcgccagt taatagtttg cgcaacgttg ttgccattgc tacaggcatc gtggtgtcac   4500

gctcgtcgtt tggtatggct tcattcagct ccggttccca acgatcaagg cgagttacat   4560
```

gatcccccat gttgtgcaaa aaagcggtta gctccttcgg tcctccgatc gttgtcagaa 4620
gtaagttggc cgcagtgtta tcactcatgg ttatggcagc actgcataat tctcttactg 4680
tcatgccatc cgtaagatgc ttttctgtga ctggtgagta ctcaaccaag tcattctgag 4740
aatagtgtat gcggcgaccg agttgctctt gcccggcgtc aatacgggat aataccgcgc 4800
cacatagcag aactttaaaa gtgctcatca ttggaaaacg ttcttcgggg cgaaaactct 4860
caaggatctt accgctgttg agatccagtt cgatgtaacc cactcgtgca cccaactgat 4920
cttcagcatc ttttactttc accagcgttt ctgggtgagc aaaaacagga aggcaaaatg 4980
ccgcaaaaaa gggaataagg gcgacacgga aatgttgaat actcatactc ttcctttttc 5040
aatattattg aagcatttat cagggttatt gtctcatgag cggatacata tttgaatgta 5100
tttagaaaaa taaacaaata ggggttccgc gcacatttcc ccgaaaagtg ccacctgacg 5160
tc 5162

<210> SEQ ID NO 27
<211> LENGTH: 5627
<212> TYPE: DNA
<213> ORGANISM: Artificial Sequence
<220> FEATURE:
<223> OTHER INFORMATION: pMG plasmid from InvivoGen; IRES sequence modified EMCV nucleotides 2736-3308

<400> SEQUENCE: 27
caccggcgaa ggaggcctag atctatcgat tgtacagcta gctcgacatg ataagataca 60
ttgatgagtt tggacaaacc acaactagaa tgcagtgaaa aaaatgcttt atttgtgaaa 120
tttgtgatgc tattgcttta tttgtgaaat ttgtgatgct attgctttat ttgtaaccat 180
tataagctgc aataaacaag ttaacaacaa caattgcatt cattttatgt ttcaggttca 240
gggggaggtg tgggaggttt tttaaagcaa gtaaaacctc tacaaatgtg gtagatccat 300
ttaaatgtta attaagaaca tgtgagcaaa aggccagcaa aaggccagga accgtaaaaa 360
ggccgcgttg ctggcgtttt tccataggct ccgcccccct gacgagcatc acaaaaatcg 420
acgctcaagt cagaggtggc gaaacccgac aggactataa agataccagg cgtttccccc 480
tggaagctcc ctcgtgcgct ctcctgttcc gaccctgccg cttaccggat acctgtccgc 540
ctttctccct tcgggaagcg tggcgctttc tcatagctca cgctgtaggt atctcagttc 600
ggtgtaggtc gttcgctcca agctgggctg tgtgcacgaa ccccccgttc agcccgaccg 660
ctgcgcctta tccggtaact atcgtcttga gtccaacccg gtaagacacg acttatcgcc 720
actggcagca gccactggta acaggattag cagagcgagg tatgtaggcg gtgctacaga 780
gttcttgaag tggtggccta actacggcta cactagaaga acagtatttg gtatctgcgc 840
tctgctgaag ccagttacct tcggaaaaag agttggtagc tcttgatccg gcaaacaaac 900
caccgctggt agcggtggtt tttttgtttg caagcagcag attacgcgca gaaaaaaagg 960
atctcaagaa gatcctttga tcttttctac ggggtctgac gctcagtgga acgaaaactc 1020
acgttaaggg attttggtca tggctagtta attaagctgc aataaacaat cattattttc 1080
attggatctg tgtgttggtt ttttgtgtgg gcttggggga gggggaggcc agaatgactc 1140
caagagctac aggaaggcag gtcagagacc ccactggaca aacagtggct ggactctgca 1200
ccataacaca caatcaacag gggagtgagc tggatcgagc tagagtccgt tacataactt 1260
acggtaaatg gcccgcctgg ctgaccgccc aacgaccccc gcccattgac gtcaataatg 1320
acgtatgttc ccatagtaac gccaataggg actttccatt gacgtcaatg ggtggagtat 1380

-continued

```
ttacggtaaa ctgcccactt ggcagtacat caagtgtatc atatgccaag tacgccccct   1440
attgacgtca atgacggtaa atggcccgcc tggcattatg cccagtacat gaccttatgg   1500
gactttccta cttggcagta catctacgta ttagtcatcg ctattaccat ggtgatgcgg   1560
ttttggcagt acatcaatgg gcgtggatag cggtttgact cacggggatt tccaagtctc   1620
caccccattg acgtcaatgg gagtttgttt tggcaccaaa atcaacggga ctttccaaaa   1680
tgtcgtaaca actccgcccc attgacgcaa atgggcggta ggcgtgtacg gtgggaggtc   1740
tatataagca gagctcgttt agtgaaccgt cagatcgcct ggagacgcca tccacgctgt   1800
tttgacctcc atagaagaca ccgggaccga tccagcctcc gcggccggga acggtgcatt   1860
ggaacgcgga ttccccgtgc caagagtgac gtaagtaccg cctatagagt ctataggccc   1920
acccccttgg cttcttatgc atgctatact gtttttggct tggggtctat acacccccgc   1980
ttcctcatgt tataggtgat ggtatagctt agcctatagg tgtgggttat tgaccattat   2040
tgaccactcc cctattggtg acgatacttt ccattactaa tccataacat ggctctttgc   2100
cacaactctc tttattggct atatgccaat acactgtcct tcagagactg acacggactc   2160
tgtattttta caggatgggg tctcatttat tatttacaaa ttcacatata caacaccacc   2220
gtccccagtg cccgcagttt ttattaaaca taacgtggga tctccacgcg aatctcgggt   2280
acgtgttccg gacatgggct cttctccggt agcggcggag cttctacatc cgagccctgc   2340
tcccatgcct ccagcgactc atggtcgctc ggcagctcct tgctcctaac agtggaggcc   2400
agacttaggc acagcacgat gcccaccacc accagtgtgc cgcacaaggc cgtggcggta   2460
gggtatgtgt ctgaaaatga gctcggggag cgggcttgca ccgctgacgc atttggaaga   2520
cttaaggcag cggcagaaga agatgcaggc agctgagttg ttgtgttctg ataagagtca   2580
gaggtaactc ccgttgcggt gctgttaacg gtggagggca gtgtagtctg agcagtactc   2640
gttgctgccg cgcgcgccac cagacataat agctgacaga ctaacagact gttcctttcc   2700
atgggtcttt tctgcagtca cccgggggat ccttcgaacg tagctctaga ttgagtcgac   2760
gttactggcc gaagccgctt ggaataaggc cggtgtgcgt ttgtctatat gttattttcc   2820
accatattgc cgtcttttgg caatgtgagg gcccggaaac ctggccctgt cttcttgacg   2880
agcattccta ggggtctttc ccctctcgcc aaaggaatgc aaggtctgtt gaatgtcgtg   2940
aaggaagcag ttcctctgga agcttcttga agacaaacaa cgtctgtagc gaccctttgc   3000
aggcagcgga accccccacc tggcgacagg tgcctctgcg gccaaaagcc acgtgtataa   3060
gatacacctg caaaggcggc acaaccccag tgccacgttg tgagttggat agttgtggaa   3120
agagtcaaat ggctctcctc aagcgtattc aacaaggggc tgaaggatgc ccagaaggta   3180
ccccattgta tgggatctga tctggggcct cggtgcacat gctttacatg tgtttagtcg   3240
aggttaaaaa aacgtctagg ccccccgaac cacggggacg tggttttcct ttgaaaaaca   3300
cgataatacc atgggtaagt gatatctact agttgtgacc ggcgcctagt gttgacaatt   3360
aatcatcggc atagtatatc ggcatagtat aatacgactc actataggag ggccaccatg   3420
tcgactacta accttcttct ctttcctaca gctgagatca ccggtaggag ggccatcatg   3480
aaaaagcctg aactcaccgc gacgtctgtc gcgaagtttc tgatcgaaaa gttcgacagc   3540
gtctccgacc tgatgcagct ctcggagggc gaagaatctc gtgctttcag cttcgatgta   3600
ggagggcgtg gatatgtcct gcgggtaaat agctgcgccg atggtttcta caaagatcgt   3660
tatgtttatc ggcactttgc atcggccgcg ctcccgattc cggaagtgct tgacattggg   3720
```

-continued gaattcagcg agagcctgac ctattgcatc tcccgccgtg cacagggtgt cacgttgcaa 3780
gacctgcctg aaaccgaact gcccgctgtt ctgcaacccg tcgcggagct catggatgcg 3840
atcgctgcgg ccgatcttag ccagacgagc gggttcggcc cattcggacc gcaaggaatc 3900
ggtcaataca ctacatggcg tgatttcata tgcgcgattg ctgatcccca tgtgtatcac 3960
tggcaaactg tgatggacga caccgtcagt gcgtccgtcg cgcaggctct cgatgagctg 4020
atgctttggg ccgaggactg ccccgaagtc cggcacctcg tgcacgcgga tttcggctcc 4080
aacaatgtcc tgacggacaa tggccgcata acagcggtca ttgactggag cgaggcgatg 4140
ttcggggatt cccaatacga ggtcgccaac atcttcttct ggaggccgtg gttggcttgt 4200
atggagcagc agacgcgcta cttcgagcgg aggcatccgg agcttgcagg atcgccgcgg 4260
ctccgggcgt atatgctccg cattggtctt gaccaactct atcagagctt ggttgacggc 4320
aatttcgatg atgcagcttg ggcgcagggt cgatgcgacg caatcgtccg atccggagcc 4380
gggactgtcg ggcgtacaca aatcgcccgc agaagcgcgg ccgtctggac cgatggctgt 4440
gtagaagtac tcgccgatag tggaaaccga cgccccagca ctcgtccgag ggcaaaggaa 4500
tgagtcgaga attcgctaga gggccctatt ctatagtgtc acctaaatgc tagagctcgc 4560
tgatcagcct cgactgtgcc ttctagttgc cagccatctg ttgtttgccc ctcccccgtg 4620
ccttccttga ccctggaagg tgccactccc actgtccttt cctaataaaa tgaggaaatt 4680
gcatcgcatt gtctgagtag gtgtcattct attctggggg gtggggtggg gcaggacagc 4740
aagggggagg attgggaaga caatagcagg catgcgcagg gcccaattgc tcgagcggcc 4800
gcaataaaat atctttattt tcattacatc tgtgtgttgg tttttgtgt gaatcgtaac 4860 taacatacgc tctccatcaa aacaaaacga aacaaaacaa actagcaaaa taggctgtcc 4920
ccagtgcaag tgcaggtgcc agaacatttc tctatcgaag gatctgcgat cgctccggtg 4980
cccgtcagtg ggcagagcgc acatcgccca cagtccccga gaagttgggg ggaggggtcg 5040
gcaattgaac cggtgcctag agaaggtggc gcggggtaaa ctgggaaagt gatgtcgtgt 5100
actggctccg cctttttccc gagggtgggg gagaaccgta tataagtgca gtagtcgccg 5160
tgaacgttct ttttcgcaac gggtttgccg ccagaacaca gctgaagctt cgaggggctc 5220
gcatctctcc ttcacgcgcc cgcccgccta cctgaggccg ccatccacgc cggttgagtc 5280
gcgttctgcc gcctcccgcc tgtggtgcct cctgaactgc gtccgccgtc taggtaagtt 5340
taaagctcag gtcgagaccg ggcctttgtc cggcgctccc ttggagccta cctagactca 5400
gccggctctc cacgctttgc ctgaccctgc ttgctcaact ctacgtcttt gtttcgtttt 5460
ctgttctgcg ccgttacaga tccaagctgt gaccggcgcc tacgtaagtg atatctacta 5520
gatttatcaa aaagagtgtt gacttgtgag cgctcacaat tgatacttag attcatcgag 5580
agggacacgt cgactactaa ccttcttctc tttcctacag ctgagat 5627

<210> SEQ ID NO 28
<211> LENGTH: 553
<212> TYPE: DNA
<213> ORGANISM: Artificial Sequence
<220> FEATURE:
<223> OTHER INFORMATION: pMG plasmid from InvivoGen: EMCV IRES sequence

<400> SEQUENCE: 28
aacgttactg gccgaagccg cttggaataa ggccggtgtg cgtttgtcta tatgttattt 60
tccaccatat tgccgtcttt tggcaatgtg agggcccgga aacctggccc tgtcttcttg 120
acgagcattc ctaggggtct ttcccctctc gccaaaggaa tgcaaggtct gttgaatgtc 180

-continued

```
gtgaaggaag cagttcctct ggaagcttct tgaagacaaa caacgtctgt agcgaccctt    240

tgcaggcagc ggaacccccc acctggcgac aggtgcctct gcggccaaaa gccacgtgta    300

taagatacac ctgcaaaggc ggcacaaccc cagtgccacg ttgtgagttg gatagttgtg    360

gaaagagtca aatggctctc ctcaagcgta ttcaacaagg ggctgaagga tgcccagaag    420

gtaccccatt gtatgggatc tgatctgggg cctcggtgca catgctttac gtgtgtttag    480

tcgaggttaa aaaacgtcta ggccccccga accacgggga cgtggttttc ctttgaaaaa    540

cacgatgata ata                                                       553
```

<210> SEQ ID NO 29
<211> LENGTH: 4692
<212> TYPE: DNA
<213> ORGANISM: Artificial Sequence
<220> FEATURE:
<223> OTHER INFORMATION: pDSred1-N1 plasmid from Clontech

<400> SEQUENCE: 29

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgtcagatcc gctagcgcta    600

ccggactcag atctcgagct caagcttcga attctgcagt cgacggtacc gcgggcccgg    660

gatccaccgg tcgccaccat ggtgcgctcc tccaagaacg tcatcaagga gttcatgcgc    720

ttcaaggtgc gcatggaggg caccgtgaac ggccacgagt tcgagatcga gggcgagggc    780

gagggccgcc cctacgaggg ccacaacacc gtgaagctga aggtgaccaa gggcggcccc    840

ctgcccttcg cctgggacat cctgtccccc cagttccagt acggctccaa ggtgtacgtg    900

aagcaccccg ccgacatccc cgactacaag aagctgtcct tccccgaggg cttcaagtgg    960

gagcgcgtga tgaacttcga ggacggcggc gtggtgaccg tgacccagga ctcctccctg   1020

caggacggct gcttcatcta caaggtgaag ttcatcggcg tgaacttccc ctccgacggc   1080

cccgtaatgc agaagaagac catgggctgg gaggcctcca ccgagcgcct gtacccccgc   1140

gacggcgtgc tgaagggcga gatccacaag gccctgaagc tgaaggacgg cggccactac   1200

ctggtggagt tcaagtccat ctacatggcc aagaagcccg tgcagctgcc cggctactac   1260

tacgtggact ccaagctgga catcacctcc cacaacgagg actacaccat cgtggagcag   1320

tacgagcgca ccgagggccg ccaccacctg ttcctgtagc ggccgcgact ctagatcata   1380

atcagccata ccacatttgt agaggtttta cttgctttaa aaaacctccc acacctcccc   1440

ctgaacctga aacataaaat gaatgcaatt gttgttgtta acttgtttat tgcagcttat   1500

aatggttaca aataaagcaa tagcatcaca aatttcacaa ataaagcatt tttttcactg   1560

cattctagtt gtggtttgtc caaactcatc aatgtatctt aaggcgtaaa ttgtaagcgt   1620
```

-continued taatattttg ttaaaattcg cgttaaattt ttgttaaatc agctcatttt ttaaccaata 1680
ggccgaaatc ggcaaaatcc cttataaatc aaaagaatag accgagatag ggttgagtgt 1740
tgttccagtt tggaacaaga gtccactatt aaagaacgtg gactccaacg tcaaagggcg 1800
aaaaaccgtc tatcagggcg atggcccact acgtgaacca tcaccctaat caagtttttt 1860
ggggtcgagg tgccgtaaag cactaaatcg gaaccctaaa gggagccccc gatttagagc 1920
ttgacgggga aagccggcga acgtggcgag aaaggaaggg aagaaagcga aaggagcggg 1980
cgctagggcg ctggcaagtg tagcggtcac gctgcgcgta accaccacac ccgccgcgct 2040
taatgcgccg ctacagggcg cgtcaggtgg cacttttcgg ggaaatgtgc gcggaacccc 2100
tatttgttta tttttctaaa tacattcaaa tatgtatccg ctcatgagac aataaccctg 2160
ataaatgctt caataatatt gaaaaaggaa gagtcctgag gcggaaagaa ccagctgtgg 2220
aatgtgtgtc agttagggtg tggaaagtcc ccaggctccc cagcaggcag aagtatgcaa 2280
agcatgcatc tcaattagtc agcaaccagg tgtggaaagt ccccaggctc cccagcaggc 2340
agaagtatgc aaagcatgca tctcaattag tcagcaacca tagtcccgcc cctaactccg 2400
cccatcccgc ccctaactcc gcccagttcc gcccattctc cgccccatgg ctgactaatt 2460
ttttttattt atgcagaggc cgaggccgcc tcggcctctg agctattcca gaagtagtga 2520
ggaggctttt ttggaggcct aggcttttgc aaagatcgat caagagacag gatgaggatc 2580
gtttcgcatg attgaacaag atggattgca cgcaggttct ccggccgctt gggtggagag 2640
gctattcggc tatgactggg cacaacagac aatcggctgc tctgatgccg ccgtgttccg 2700
gctgtcagcg caggggcgcc cggttctttt tgtcaagacc gacctgtccg gtgccctgaa 2760
tgaactgcaa gacgaggcag cgcggctatc gtggctggcc acgacgggcg ttccttgcgc 2820
agctgtgctc gacgttgtca ctgaagcggg aagggactgg ctgctattgg gcgaagtgcc 2880
ggggcaggat ctcctgtcat ctcaccttgc tcctgccgag aaagtatcca tcatggctga 2940
tgcaatgcgg cggctgcata cgcttgatcc ggctacctgc ccattcgacc accaagcgaa 3000
acatcgcatc gagcgagcac gtactcggat ggaagccggt cttgtcgatc aggatgatct 3060
ggacgaagag catcaggggc tcgcgccagc cgaactgttc gccaggctca aggcgagcat 3120
gcccgacggc gaggatctcg tcgtgaccca tggcgatgcc tgcttgccga atatcatggt 3180
ggaaaatggc cgcttttctg gattcatcga ctgtggccgg ctgggtgtgg cggaccgcta 3240
tcaggacata gcgttggcta cccgtgatat tgctgaagag cttggcggcg aatgggctga 3300
ccgcttcctc gtgctttacg gtatcgccgc tcccgattcg cagcgcatcg ccttctatcg 3360
ccttcttgac gagttcttct gagcgggact ctggggttcg aaatgaccga ccaagcgacg 3420
cccaacctgc catcacgaga tttcgattcc accgccgcct tctatgaaag gttgggcttc 3480
ggaatcgttt tccgggacgc cggctggatg atcctccagc gcggggatct catgctggag 3540
ttcttcgccc accctagggg gaggctaact gaaacacgga aggagacaat accggaagga 3600
acccgcgcta tgacggcaat aaaaagacag aataaaacgc acggtgttgg gtcgtttgtt 3660
cataaacgcg gggttcggtc ccagggctgg cactctgtcg ataccccacc gagaccccat 3720
tggggccaat acgcccgcgt ttcttccttt tccccacccc accccccaag ttcgggtgaa 3780
ggcccagggc tcgcagccaa cgtcggggcg gcaggccctg ccatagcctc aggttactca 3840
tatatacttt agattgattt aaaacttcat ttttaattta aaaggatcta ggtgaagatc 3900
ctttttgata atctcatgac caaaatccct taacgtgagt tttcgttcca ctgagcgtca 3960
gaccccgtag aaaagatcaa aggatcttct tgagatcctt tttttctgcg cgtaatctgc 4020

-continued

```
tgcttgcaaa caaaaaaacc accgctacca gcggtggttt gtttgccgga tcaagagcta   4080

ccaactcttt ttccgaaggt aactggcttc agcagagcgc agataccaaa tactgtcctt   4140

ctagtgtagc cgtagttagg ccaccacttc aagaactctg tagcaccgcc tacatacctc   4200

gctctgctaa tcctgttacc agtggctgct gccagtggcg ataagtcgtg tcttaccggg   4260

ttggactcaa gacgatagtt accggataag gcgcagcggt cgggctgaac ggggggttcg   4320

tgcacacagc ccagcttgga gcgaacgacc tacaccgaac tgagatacct acagcgtgag   4380

ctatgagaaa gcgccacgct tcccgaaggg agaaaggcgg acaggtatcc ggtaagcggc   4440

agggtcggaa caggagagcg cacgagggag cttccagggg gaaacgcctg gtatctttat   4500

agtcctgtcg ggtttcgcca cctctgactt gagcgtcgat ttttgtgatg ctcgtcaggg   4560

gggcggagcc tatggaaaaa cgccagcaac gcggcctttt tacggttcct ggccttttgc   4620

tggccttttg ctcacatgtt ctttcctgcg ttatcccctg attctgtgga taaccgtatt   4680

accgccatgc at                                                      4692
```

<210> SEQ ID NO 30
<211> LENGTH: 4257
<212> TYPE: DNA
<213> ORGANISM: Artificial Sequence
<220> FEATURE:
<223> OTHER INFORMATION: pPur plasmid from Clontech

<400> SEQUENCE: 30

```
ctgtggaatg tgtgtcagtt agggtgtgga aagtccccag gctccccagc aggcagaagt     60

atgcaaagca tgcatctcaa ttagtcagca accaggtgtg gaaagtcccc aggctcccca    120

gcaggcagaa gtatgcaaag catgcatctc aattagtcag caaccatagt cccgccccta    180

actccgccca tcccgcccct aactccgccc agttccgccc attctccgcc ccatggctga    240

ctaatttttt ttatttatgc agaggccgag gccgcctcgg cctctgagct attccagaag    300

tagtgaggag gcttttttgg aggcctaggc ttttgcaaaa agcttgcatg cctgcaggtc    360

ggccgccacg accggtgccg ccaccatccc ctgacccacg cccctgaccc ctcacaagga    420

gacgaccttc catgaccgag tacaagccca cggtgcgcct cgccacccgc gacgacgtcc    480

cccgggccgt acgcaccctc gccgccgcgt tcgccgacta ccccgccacg cgccacaccg    540

tcgacccgga ccgccacatc gagcgggtca ccgagctgca agaactcttc ctcacgcgcg    600

tcgggctcga catcggcaag gtgtgggtcg cggacgacgg cgccgcggtg gcggtctgga    660

ccacgccgga gagcgtcgaa gcgggggcgg tgttcgccga gatcggcccg cgcatggccg    720

agttgagcgg ttcccggctg gccgcgcagc aacagatgga aggcctcctg gcgccgcacc    780

ggcccaagga gcccgcgtgg ttcctggcca ccgtcggcgt ctcgcccgac caccagggca    840

agggtctggg cagcgccgtc gtgctccccg gagtggaggc ggccgagcgc gccggggtgc    900

ccgccttcct ggagacctcc gcgccccgca acctcccctt ctacgagcgg ctcggcttca    960

ccgtcaccgc cgacgtcgag gtgcccgaag gaccgcgcac ctggtgcatg acccgcaagc   1020

ccggtgcctg acgcccgccc cacgacccgc agcgcccgac cgaaaggagc gcacgacccc   1080

atggctccga ccgaagccga cccgggcggc cccgccgacc ccgcacccgc ccccgaggcc   1140

caccgactct agaggatcat aatcagccat accacatttg tagaggtttt acttgcttta   1200

aaaaacctcc cacacctccc cctgaacctg aaacataaaa tgaatgcaat tgttgttgtt   1260

aacttgttta ttgcagctta taatggttac aaataaagca atagcatcac aaatttcaca   1320
```

-continued aataaagcat tttttcact gcattctagt tgtggtttgt ccaaactcat caatgtatct 1380
tatcatgtct ggatccccag gaagctcctc tgtgtcctca taaaccctaa cctcctctac 1440
ttgagaggac attccaatca taggctgccc atccaccctc tgtgtcctcc tgttaattag 1500
gtcacttaac aaaaaggaaa ttgggtaggg gtttttcaca gaccgctttc taagggtaat 1560
tttaaaatat ctgggaagtc ccttccactg ctgtgttcca gaagtgttgg taaacagccc 1620
acaaatgtca acagcagaaa catacaagct gtcagctttg cacaagggcc caacaccctg 1680
ctcatcaaga agcactgtgg ttgctgtgtt agtaatgtgc aaaacaggag gcacattttc 1740
cccacctgtg taggttccaa aatatctagt gttttcattt ttacttggat caggaaccca 1800
gcactccact ggataagcat tatccttatc caaaacagcc ttgtggtcag tgttcatctg 1860
ctgactgtca actgtagcat tttttggggt tacagtttga gcaggatatt tggtcctgta 1920
gtttgctaac acaccctgca gctccaaagg ttccccacca acagcaaaaa aatgaaaatt 1980
tgacccttga atgggttttc cagcaccatt ttcatgagtt ttttgtgtcc ctgaatgcaa 2040
gtttaacata gcagttaccc caataacctc agttttaaca gtaacagctt cccacatcaa 2100
aatatttcca caggttaagt cctcatttaa attaggcaaa ggaattcttg aagacgaaag 2160
ggcctcgtga tacgcctatt tttataggtt aatgtcatga taataatggt ttcttagacg 2220
tcaggtggca cttttcgggg aaatgtgcgc ggaaccccta tttgtttatt tttctaaata 2280
cattcaaata tgtatccgct catgagacaa taaccctgat aaatgcttca ataatattga 2340
aaaaggaaga gtatgagtat tcaacatttc cgtgtcgccc ttattccctt ttttgcggca 2400
ttttgccttc ctgtttttgc tcacccagaa acgctggtga aagtaaaaga tgctgaagat 2460
cagttgggtg cacgagtggg ttacatcgaa ctggatctca acagcggtaa gatccttgag 2520
agttttcgcc ccgaagaacg ttttccaatg atgagcactt ttaaagttct gctatgtggc 2580
gcggtattat cccgtgttga cgccgggcaa gagcaactcg gtcgccgcat acactattct 2640
cagaatgact tggttgagta ctcaccagtc acagaaaagc atcttacgga tggcatgaca 2700
gtaagagaat tatgcagtgc tgccataacc atgagtgata acactgcggc caacttactt 2760
ctgacaacga tcggaggacc gaaggagcta accgcttttt tgcacaacat gggggatcat 2820
gtaactcgcc ttgatcgttg ggaaccggag ctgaatgaag ccataccaaa cgacgagcgt 2880
gacaccacga tgcctgcagc aatggcaaca acgttgcgca aactattaac tggcgaacta 2940
cttactctag cttcccggca acaattaata gactggatgg aggcggataa agttgcagga 3000
ccacttctgc gctcggccct tccggctggc tggtttattg ctgataaatc tggagccggt 3060
gagcgtgggt ctcgcggtat cattgcagca ctggggccag atggtaagcc ctcccgtatc 3120
gtagttatct acacgacggg gagtcaggca actatggatg aacgaaatag acagatcgct 3180
gagataggtg cctcactgat taagcattgg taactgtcag accaagttta ctcatatata 3240
ctttagattg atttaaaact tcatttttaa tttaaaagga tctaggtgaa gatccttttt 3300
gataatctca tgaccaaaat cccttaacgt gagttttcgt tccactgagc gtcagacccc 3360
gtagaaaaga tcaaaggatc ttcttgagat cctttttttc tgcgcgtaat ctgctgcttg 3420
caaacaaaaa aaccaccgct accagcggtg gtttgtttgc cggatcaaga gctaccaact 3480
ctttttccga aggtaactgg cttcagcaga gcgcagatac caaatactgt ccttctagtg 3540
tagccgtagt taggccacca cttcaagaac tctgtagcac cgcctacata cctcgctctg 3600
ctaatcctgt taccagtggc tgctgccagt ggcgataagt cgtgtcttac cgggttggac 3660
tcaagacgat agttaccgga taaggcgcag cggtcgggct gaacgggggg ttcgtgcaca 3720

-continued

```
cagcccagct tggagcgaac gacctacacc gaactgagat acctacagcg tgagctatga   3780

gaaagcgcca cgcttcccga agggagaaag gcggacaggt atccggtaag cggcagggtc   3840

ggaacaggag agcgcacgag ggagcttcca gggggaaacg cctggtatct ttatagtcct   3900

gtcgggtttc gccacctctg acttgagcgt cgatttttgt gatgctcgtc aggggggcgg   3960

agcctatgga aaaacgccag caacgcggcc tttttacggt tcctggcctt ttgctggcct   4020

tttgctcaca tgttctttcc tgcgttatcc cctgattctg tggataaccg tattaccgcc   4080

tttgagtgag ctgataccgc tcgccgcagc cgaacgaccg agcgcagcga gtcagtgagc   4140

gaggaagcgg aagagcgcct gatgcggtat tttctcctta cgcatctgtg cggtatttca   4200

caccgcatat ggtgcactct cagtacaatc tgctctgatg ccgcatagtt aagccag      4257
```

```
<210> SEQ ID NO 31
<211> LENGTH: 8136
<212> TYPE: DNA
<213> ORGANISM: Artificial Sequence
<220> FEATURE:
<223> OTHER INFORMATION: pWE15 cosmid vector
<300> PUBLICATION INFORMATION:
<308> DATABASE ACCESSION NUMBER: GenBank X65279
<309> DATABASE ENTRY DATE: 1995-04-14

<400> SEQUENCE: 31
```

```
ctatagtgag tcgtattatg cggccgcgaa ttcttgaaga cgaaagggcc tcgtgatacg     60

cctattttta taggttaatg tcatgataat aatggtttct tagacgtcag gtggcacttt    120

tcggggaaat gtgcgcggaa cccctatttg tttatttttc taaatacatt caaatatgta    180

tccgctcatg agacaataac cctgataaat gcttcaataa tattgaaaaa ggaagagtat    240

gagtattcaa catttccgtg tcgcccttat tccctttttt gcggcatttt gcttcctgtt    300

tttgctcacc cagaaacgct ggtgaaagta aaagatgctg aagatcagtt gggtgcacga    360

gtgggttaca tcgaactgga tctcaacagc ggtaagatcc ttgagagttt tcgccccgaa    420

gaacgttttc caatgatgag cacttttaaa gttctgctat gtggcgcggt attatcccgt    480

gttgacgccg ggcaagagca actcggtcgc cgcatacact attctcagaa tgacttggtt    540

gagtactcac cagtcacaga aaagcatctt acggatggca tgacagtaag agaattatgc    600

agtgctgcca taaccatgag tgataacact gcggccaact tacttctgac aacgatcgga    660

ggaccgaagg agctaaccgc ttttttgcac aacatggggg atcatgtaac tcgccttgat    720

cgttgggaac cggagctgaa tgaagccata ccaaacgacg agcgtgacac cacgatgcct    780

gcagcaatgg caacaacgtt gcgcaaacta ttaactggcg aactacttac tctagcttcc    840

cggcaacaat taatagactg gatggaggcg gataaagttg caggaccact tctgcgctcg    900

gcccttccgg ctggctggtt tattgctgat aaatctggag ccggtgagcg tgggtctcgc    960

ggtatcattg cagcactggg gccagatggt aagccctccc gtatcgtagt tatctacacg   1020

acggggagtc aggcaactat ggatgaacga aatagacaga tcgctgagat aggtgcctca   1080

ctgattaagc attggtaact gtcagaccaa gtttactcat atatacttta gattgattta   1140

aaacttcatt tttaatttaa aaggatctag gtgaagatcc tttttgataa tctcatgacc   1200

aaaatccctt aacgtgagtt ttcgttccac tgagcgtcag accccgtaga aaagatcaaa   1260

ggatcttctt gagatccttt ttttctgcgc gtaatctgct gcttgcaaac aaaaaaacca   1320

ccgctaccag cggtggtttg tttgccggat caagagctac caactctttt tccgaaggta   1380

actggcttca gcagagcgca gataccaaat actgtccttc tagtgtagcc gtagttaggc   1440
```

-continued

```
caccacttca agaactctgt agcaccgcct acatacctcg ctctgctaat cctgttacca   1500
gtggctgctg ccagtggcga taagtcgtgt cttaccgggt tggactcaag acgatagtta   1560
ccggataagg cgcagcggtc gggctgaacg gggggttcgt gcacacagcc cagcttggag   1620
cgaacgacct acaccgaact gagataccta cagcgtgagc tatgagaaag cgccacgctt   1680
ccgaagggag aaaggcggac aggtatccgg taagcggcag ggtcggaaca ggagagcgca   1740
cgagggagct tccaggggga aacgcctggt atctttatag tcctgtcggg tttcgccac    1800
ctctgacttg agcgtcgatt tttgtgatgc tcgtcagggg ggcggagcct atggaaaaac   1860
gccagcaacg cggccttttt acggttcctg gccttttgct ggccttttgc tcacatgttc   1920
tttcctgcgt tatcccctga ttctgtggat aaccgtatta ccgcctttga gtgagctgat   1980
accgctcgcc gcagccgaac gaccgagcgc agcgagtcag tgagcgagga agcggaagag   2040
cgctgacttc cgcgtttcca gactttacga aacacggaaa ccgaagacca ttcatgttgt   2100
tgctcaggtc gcagacgttt tgcagcagca gtcgcttcac gttcgctcgc gtatcggtga   2160
ttcattctgc taaccagtaa ggcaaccccg ccagcctagc cgggtcctca acgacaggag   2220
cacgatcatg cgcacccgtc agatccagac atgataagat acattgatga gtttggacaa   2280
accacaacta gaatgcagtg aaaaaaatgc tttatttgtg aaatttgtga tgctattgct   2340
ttatttgtaa ccattataag ctgcaataaa caagttaaca acaacaattg cattcatttt   2400
atgtttcagg ttcaggggga ggtgtgggag gtttttttaaa gcaagtaaaa cctctacaaa   2460
tgtggtatgg ctgattatga tctctagtca aggcactata catcaaatat tccttattaa   2520
cccctttaca aattaaaaag ctaaaggtac acaatttttg agcatagtta ttaatagcag   2580
acactctatg cctgtgtgga gtaagaaaaa acagtatgtt atgattataa ctgttatgcc   2640
tacttataaa ggttacagaa tatttttcca taattttctt gtatagcagt gcagcttttt   2700
cctttgtggt gtaaatagca aagcaagcaa gagttctatt actaaacaca gcatgactca   2760
aaaaacttag caattctgaa ggaaagtcct tggggtcttc tacctttctc ttcttttttg   2820
gaggagtaga atgttgagag tcagcagtag cctcatcatc actagatggc atttcttctg   2880
agcaaaacag gttttcctca ttaaaggcat tccaccactg ctcccattca tcagttccat   2940
aggttggaat ctaaaataca caaacaatta gaatcagtag tttaacacat tatacactta   3000
aaaattttat atttacctta gagctttaaa tctctgtagg tagtttgtcc aattatgtca   3060
caccacagaa gtaaggttcc ttcacaaaga tccggaccaa agcggccatc gtgcctcccc   3120
actcctgcag ttcgggggca tggatgcgcg gatagccgct gctggtttcc tggatgccga   3180
cggatttgca ctgccggtag aactcgcgag gtcgtccagc ctcaggcagc agctgaacca   3240
actcgcgagg ggatcgagcc cggggtgggc gaagaactcc agcatgagat ccccgcgctg   3300
gaggatcatc cagccggcgt cccggaaaac gattccgaag cccaaccttt catagaaggc   3360
ggcggtggaa tcgaaatctc gtgatggcag gttgggcgtc gcttggtcgg tcatttcgaa   3420
ccccagagtc ccgctcagaa gaactcgtca agaaggcgat agaaggcgat gcgctgcgaa   3480
tcgggagcgg cgataccgta aagcacgagg aagcggtcag cccattcgcc gccaagctct   3540
tcagcaatat cacgggtagc caacgctatg tcctgatagc ggtccgccac acccagccgg   3600
ccacagtcga tgaatccaga aaagcggcca ttttccacca tgatattcgg caagcaggca   3660
tcgccatggg tcacgacgag atcctcgccg tcgggatgcg cgccttgagc ctggcgaaca   3720
gttcggctgg cgcgagcccc tgatgctctt cgtccagatc atcctgatcg acaagaccgg   3780
```

-continued

```
cttccatccg agtacgtgct cgctcgatgc gatgtttcgc ttggtggtcg aatgggcagg   3840
tagccggatc aagcgtatgc agccgccgca ttgcatcagc catgatggat actttctcgg   3900
caggagcaag gtgagatgac aggagatcct gccccggcac ttcgcccaat agcagccagt   3960
cccttcccgc ttcagtgaca acgtcgagca cagctgcgca aggaacgccc gtcgtggcca   4020
gccacgatag ccgcgctgcc tcgtcctgca gttcattcag ggcaccggac aggtcggtct   4080
tgacaaaaag aaccgggcgc ccctgcgctg acagccggaa cacggcggca tcagagcagc   4140
cgattgtctg ttgtgcccag tcatagccga atagcctctc cacccaagcg gccggagaac   4200
ctgcgtgcaa tccatcttgt tcaatcatgc gaaacgatcc tcatcctgtc tcttgatcag   4260
atcttgatcc cctgcgccat cagatccttg gcggcaagaa agccatccag tttactttgc   4320
agggcttccc aaccttacca gagggcgccc cagctggcaa ttccggttcg cttgctgtcc   4380
ataaaaccgc ccagtctagc tatcgccatg taagcccact gcaagctacc tgctttctct   4440
ttgcgcttgc gttttccctt gtccagatag cccagtagct gacattcatc cggggtcagc   4500
accgtttctg cggactggct ttctacgtgt tccgcttcct ttagcagccc ttgcgccctg   4560
agtgcttgcg gcagcgtgaa agctttttgc aaaagcctag gcctccaaaa aagcctcctc   4620
actacttctg gaatagctca gaggccgagg cggcctaaat aaaaaaaatt agtcagccat   4680
ggggcggaga atgggcggaa ctgggcggag ttaggggcgg gatgggcgga gttaggggcg   4740
ggactatggt tgctgactaa ttgagatgca tgctttgcat acttctgcct gctggggagc   4800
ctggggactt tccacacctg gttgctgact aattgagatg catgctttgc atacttctgc   4860
ctgctgggga gcctggggac tttccacacc ctaactgaca cacattccac agccggatct   4920
gcaggaccca acgctgcccg agatgcgccg cgtgcggctg ctggagatgg cggacgcgat   4980
ggatatgttc tgccaagggt tggtttgcgc attcacagtt ctccgcaaga attgattggc   5040
tccaattctt ggagtggtga atccgttagc gaggtgccgc cggcttccat tcaggtcgag   5100
gtggcccggc tccatgcacc gcgacgcaac gcggggaggc agacaaggta tagggcggcg   5160
cctacaatcc atgccaaccc gttccatgtg ctcgccgagg cgcataaatc gccgtgacga   5220
tcagcggtcc aatgatcgaa gttaggctgg taagagccgc gagcgatcct tgaagctgtc   5280
cctgatggtc gtcatctacc tgcctggaca gcatggcctg caacgcggca tcccgatgcc   5340
gccggaagcg agaagaatca taatggggaa ggccatccag cctcgcgtcg cgaacgccag   5400
caagacgtag cccagcgcgt cggccgccca tgccggcgat aatggcctgc ttctcgccga   5460
aacgtttggt ggcgggacca gtgacgaagg cttgagcgag ggcgtgcaag attccgaata   5520
ccgcaagcga caggccgatc atcgtcgcgc tccagcgaaa gcggtcctcg ccgaaaatga   5580
cccagagcgc tgccggcacc tgtcctacga gttgcatgat aaagaagaca gtcataagtg   5640
cggcgacgat agtcatgccc cgcgcccacc ggaaggagct gactgggttg aaggctctca   5700
agggcatcgg tcgacgctct ccccttatgcg actcctgcat taggaagcag cccagtagta   5760
ggttgaggcc gttgagcacc gccgccgcaa ggaatggtgc atgcaaggag atggcgccca   5820
acagtccccc ggccacgggc ctgccaccat acccacgccg aaacaagcgc tcatgagccc   5880
gaagtggcga gcccgatctt ccccatcggt gatgtcggcg atataggcgc cagcaaccgc   5940
acctgtggcg ccggtgatgc cggccacgat gcgtccggcg tagaggatct tggcagtcac   6000
agcatgcgca tatccatgct tcgaccatgc gctcacaaag taggtgaatg cgcaatgtag   6060
tacccacatc gtcatcgctt tccactgctc tcgcgaataa agatggaaaa tcaatctcat   6120
ggtaatagtc catgaaaatc cttgtattca taaatcctcc aggtagctat atgcaaattg   6180
```

-continued aaacaaaaga gatggtgatc tttctaagag atgatggaat ctcccttcag tatcccgatg 6240
gtcaatgcgc tggatatggg atagatggga atatgctgat tttatggga cagagttgcg 6300 aactgttccc aactaaaatc attttgcacg atcagcgcac tacgaacttt acccacaaat 6360
agtcaggtaa tgaatcctga tataaagaca ggttgataaa tcagtcttct acgcgcatcg 6420
cacgcgcaca ccgtagaaag tctttcagtt gtgagcctgg gcaaaccgtt aactttcggc 6480
ggctttgctg tgcgacaggc tcacgtctaa aaggaaataa atcatgggtc ataaaattat 6540
cacgttgtcc ggcgcggcga cggatgttct gtatgcgctg tttttccgtg gcgcgttgct 6600
gtctggtgat ctgccttcta aatctggcac agccgaattg cgcgagcttg gttttgctga 6660
aaccagacac acagcaactg aataccagaa agaaaatcac tttacctttc tgacatcaga 6720
agggcagaaa tttgccgttg aacacctggt caatacgcgt tttggtgagc agcaatattg 6780
cgcttcgatg acgcttggcg ttgagattga tacctctgct gcacaaaagg caatcgacga 6840
gctggaccag cgcattcgtg acaccgtctc cttcgaactt attcgcaatg gagtgtcatt 6900
catcaaggac gccgctatcg caaatggtgc tatccacgca gcggcaatcg aaacacctca 6960
gccggtgacc aatatctaca acatcagcct tggtatccag cgtgatgagc cagcgcagaa 7020
caaggtaacc gtcagtgccg ataagttcaa agttaaacct ggtgttgata ccaacattga 7080
aacgttgatc gaaaacgcgc tgaaaaacgc tgctgaatgt gcggcgctgg atgtcacaaa 7140
gcaaatggca gcagacaaga aagcgatgga tgaactggct tcctatgtcc gcacggccat 7200
catgatggaa tgtttccccg gtggtgttat ctggcagcag tgccgtcgat agtatgcaat 7260
tgataattat tatcatttgc gggtcctttc cggcgatccg ccttgttacg gggcggcgac 7320
ctcgcgggtt ttcgctattt atgaaaattt tccggtttaa ggcgtttccg ttcttcttcg 7380
tcataactta atgtttttat ttaaaatacc ctctgaaaag aaaggaaacg acaggtgctg 7440
aaagcgagct ttttggcctc tgtcgtttcc tttctctgtt tttgtccgtg gaatgaacaa 7500
tggaagtcaa caaaaagcag ctggctgaca ttttcggtgc gagtatccgt accattcaga 7560
actggcagga acagggaatg cccgttctgc gaggcggtgg caagggtaat gaggtgcttt 7620
atgactctgc cgccgtcata aaatggtatg ccgaaaggga tgctgaaatt gagaacgaaa 7680
agctgcgccg ggaggttgaa gaactgcggc aggccagcga ggcagatcca caggacgggt 7740
gtggtcgcca tgatcgcgta gtcgatagtg gctccaagta gcgaagcgag caggactggg 7800
cggcggcaaa gcggtcggac agtgctccga gaacgggtgc gcatagaaat tgcatcaacg 7860
catatagcgc tagcagcacg ccatagtgac tggcgatgct gtcggaatgg acgatatccc 7920
gcaagaggcc cggcagtacc ggcataacca agcctatgcc tacagcatcc agggtgacgg 7980
tgccgaggat gacgatgagc gcattgttag atttcataca cggtgcctga ctgcgttagc 8040
aatttaactg tgataaacta ccgcattaaa gcttatcgat gataagcggt caaacatgag 8100
aattcgcggc cgcaattaac cctcactaaa ggatcc 8136

<210> SEQ ID NO 32
<211> LENGTH: 2713
<212> TYPE: DNA
<213> ORGANISM: Artificial Sequence
<220> FEATURE:
<223> OTHER INFORMATION: pNEB193 plasmid

<400> SEQUENCE: 32
tcgcgcgttt cggtgatgac ggtgaaaacc tctgacacat gcagctcccg gagacggtca 60

-continued

```
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccgggggc    420
gcgccggatc cttaattaag tctagagtcg actgtttaaa cctgcaggca tgcaagcttg    480
gcgtaatcat ggtcatagct gtttcctgtg tgaaattgtt atccgctcac aattccacac    540
aacatacgag ccggaagcat aaagtgtaaa gcctggggtg cctaatgagt gagctaactc    600
acattaattg cgttgcgctc actgcccgct ttccagtcgg gaaacctgtc gtgccagctg    660
cattaatgaa tcggccaacg cgcggggaga ggcggtttgc gtattgggcg ctcttccgct    720
tcctcgctca ctgactcgct gcgctcggtc gttcggctgc ggcgagcggt atcagctcac    780
tcaaaggcgg taatacggtt atccacagaa tcaggggata acgcaggaaa gaacatgtga    840
gcaaaaggcc agcaaaaggc caggaaccgt aaaaaggccg cgttgctggc gtttttccat    900
aggctccgcc cccctgacga gcatcacaaa aatcgacgct caagtcagag gtggcgaaac    960
ccgacaggac tataaagata ccaggcgttt ccccctggaa gctccctcgt gcgctctcct   1020
gttccgaccc tgccgcttac cggatacctg tccgcctttc tcccttcggg aagcgtggcg   1080
ctttctcata gctcacgctg taggtatctc agttcggtgt aggtcgttcg ctccaagctg   1140
ggctgtgtgc acgaaccccc cgttcagccc gaccgctgcg ccttatccgg taactatcgt   1200
cttgagtcca acccggtaag acacgactta tcgccactgg cagcagccac tggtaacagg   1260
attagcagag cgaggtatgt aggcggtgct acagagttct tgaagtggtg gcctaactac   1320
ggctacacta gaaggacagt atttggtatc tgcgctctgc tgaagccagt taccttcgga   1380
aaaagagttg gtagctcttg atccggcaaa caaaccaccg ctggtagcgg tggttttttt   1440
gtttgcaagc agcagattac gcgcagaaaa aaaggatctc aagaagatcc tttgatcttt   1500
tctacggggt ctgacgctca gtggaacgaa aactcacgtt aagggatttt ggtcatgaga   1560
ttatcaaaaa ggatcttcac ctagatcctt ttaaattaaa aatgaagttt taaatcaatc   1620
taaagtatat atgagtaaac ttggtctgac agttaccaat gcttaatcag tgaggcacct   1680
atctcagcga tctgtctatt tcgttcatcc atagttgcct gactccccgt cgtgtagata   1740
actacgatac gggagggctt accatctggc cccagtgctg caatgatacc gcgagaccca   1800
cgctcaccgg ctccagattt atcagcaata aaccagccag ccggaagggc cgagcgcaga   1860
agtggtcctg caactttatc cgcctccatc cagtctatta attgttgccg ggaagctaga   1920
gtaagtagtt cgccagttaa tagtttgcgc aacgttgttg ccattgctac aggcatcgtg   1980
gtgtcacgct cgtcgtttgg tatggcttca ttcagctccg gttcccaacg atcaaggcga   2040
gttacatgat cccccatgtt gtgcaaaaaa gcggttagct ccttcggtcc tccgatcgtt   2100
gtcagaagta agttggccgc agtgttatca ctcatggtta tggcagcact gcataattct   2160
cttactgtca tgccatccgt aagatgcttt tctgtgactg gtgagtactc aaccaagtca   2220
ttctgagaat agtgtatgcg gcgaccgagt tgctcttgcc cggcgtcaat acgggataat   2280
accgcgccac atagcagaac tttaaaagtg ctcatcattg gaaaacgttc ttcggggcga   2340
aaactctcaa ggatcttacc gctgttgaga tccagttcga tgtaacccac tcgtgcaccc   2400
aactgatctt cagcatcttt tactttcacc agcgtttctg ggtgagcaaa aacaggaagg   2460
```

-continued caaaatgccg caaaaaaggg aataagggcg acacggaaat gttgaatact catactcttc 2520
ccttttcaat attattgaag catttatcag ggttattgtc tcatgagcgg atacatattt 2580
gaatgtattt agaaaaataa acaaataggg gttccgcgca catttccccg aaaagtgcca 2640
cctgacgtct aagaaaccat tattatcatg acattaacct ataaaaatag gcgtatcacg 2700
aggccctttc gtc 2713

<210> SEQ ID NO 33
<211> LENGTH: 21
<212> TYPE: DNA
<213> ORGANISM: Artificial Sequence
<220> FEATURE:
<223> OTHER INFORMATION: attP

<400> SEQUENCE: 33
cagctttttt atactaagtt g 21

<210> SEQ ID NO 34
<211> LENGTH: 21
<212> TYPE: DNA
<213> ORGANISM: Artificial Sequence
<220> FEATURE:
<223> OTHER INFORMATION: attB

<400> SEQUENCE: 34
ctgctttttt atactaactt g 21

<210> SEQ ID NO 35
<211> LENGTH: 21
<212> TYPE: DNA
<213> ORGANISM: Artificial Sequence
<220> FEATURE:
<223> OTHER INFORMATION: attL

<400> SEQUENCE: 35
ctgctttttt atactaagtt g 21

<210> SEQ ID NO 36
<211> LENGTH: 21
<212> TYPE: DNA
<213> ORGANISM: Artificial Sequence
<220> FEATURE:
<223> OTHER INFORMATION: attR

<400> SEQUENCE: 36
cagctttttt atactaactt g 21

<210> SEQ ID NO 37
<211> LENGTH: 1071
<212> TYPE: DNA
<213> ORGANISM: Artificial Sequence
<220> FEATURE:
<223> OTHER INFORMATION: Integrase E174R
<220> FEATURE:
<221> NAME/KEY: CDS
<222> LOCATION: (1)...(1071)
<223> OTHER INFORMATION: Nucleotide sequence encoding Integrase E147R

<400> SEQUENCE: 37 atg gga aga agg cga agt cat gag cgc cgg gat tta ccc cct aac ctt 48
Met Gly Arg Arg Arg Ser His Glu Arg Arg Asp Leu Pro Pro Asn Leu
1 5 10 15 tat ata aga aac aat gga tat tac tgc tac agg gac cca agg acg ggt 96
Tyr Ile Arg Asn Asn Gly Tyr Tyr Cys Tyr Arg Asp Pro Arg Thr Gly -continued

```
                20                  25                  30

aaa gag ttt gga tta ggc aga gac agg cga atc gca atc act gaa gct      144
Lys Glu Phe Gly Leu Gly Arg Asp Arg Arg Ile Ala Ile Thr Glu Ala
            35                  40                  45

ata cag gcc aac att gag tta ttt tca gga cac aaa cac aag cct ctg      192
Ile Gln Ala Asn Ile Glu Leu Phe Ser Gly His Lys His Lys Pro Leu
        50                  55                  60

aca gcg aga atc aac agt gat aat tcc gtt acg tta cat tca tgg ctt      240
Thr Ala Arg Ile Asn Ser Asp Asn Ser Val Thr Leu His Ser Trp Leu
 65                  70                  75                  80

gat cgc tac gaa aaa atc ctg gcc agc aga gga atc aag cag aag aca      288
Asp Arg Tyr Glu Lys Ile Leu Ala Ser Arg Gly Ile Lys Gln Lys Thr
                85                  90                  95

ctc ata aat tac atg agc aaa att aaa gca ata agg agg ggt ctg cct      336
Leu Ile Asn Tyr Met Ser Lys Ile Lys Ala Ile Arg Arg Gly Leu Pro
            100                 105                 110

gat gct cca ctt gaa gac atc acc aca aaa gaa att gcg gca atg ctc      384
Asp Ala Pro Leu Glu Asp Ile Thr Thr Lys Glu Ile Ala Ala Met Leu
        115                 120                 125

aat gga tac ata gac gag ggc aag gcg gcg tca gcc aag tta atc aga      432
Asn Gly Tyr Ile Asp Glu Gly Lys Ala Ala Ser Ala Lys Leu Ile Arg
    130                 135                 140

tca aca ctg agc gat gca ttc cga gag gca ata gct gaa ggc cat ata      480
Ser Thr Leu Ser Asp Ala Phe Arg Glu Ala Ile Ala Glu Gly His Ile
145                 150                 155                 160

aca aca aac cat gtc gct gcc act cgc gca gca aaa tct aga gta agg      528
Thr Thr Asn His Val Ala Ala Thr Arg Ala Ala Lys Ser Arg Val Arg
                165                 170                 175

aga tca aga ctt acg gct gac gaa tac ctg aaa att tat caa gca gca      576
Arg Ser Arg Leu Thr Ala Asp Glu Tyr Leu Lys Ile Tyr Gln Ala Ala
            180                 185                 190

gaa tca tca cca tgt tgg ctc aga ctt gca atg gaa ctg gct gtt gtt      624
Glu Ser Ser Pro Cys Trp Leu Arg Leu Ala Met Glu Leu Ala Val Val
        195                 200                 205

acc ggg caa cga gtt ggt gat tta tgc gaa atg aag tgg tct gat atc      672
Thr Gly Gln Arg Val Gly Asp Leu Cys Glu Met Lys Trp Ser Asp Ile
    210                 215                 220

gta gat gga tat ctt tat gtc gag caa agc aaa aca ggc gta aaa att      720
Val Asp Gly Tyr Leu Tyr Val Glu Gln Ser Lys Thr Gly Val Lys Ile
225                 230                 235                 240

gcc atc cca aca gca ttg cat att gat gct ctc gga ata tca atg aag      768
Ala Ile Pro Thr Ala Leu His Ile Asp Ala Leu Gly Ile Ser Met Lys
                245                 250                 255

gaa aca ctt gat aaa tgc aaa gag att ctt ggc gga gaa acc ata att      816
Glu Thr Leu Asp Lys Cys Lys Glu Ile Leu Gly Gly Glu Thr Ile Ile
            260                 265                 270

gca tct act cgt cgc gaa ccg ctt tca tcc ggc aca gta tca agg tat      864
Ala Ser Thr Arg Arg Glu Pro Leu Ser Ser Gly Thr Val Ser Arg Tyr
        275                 280                 285

ttt atg cgc gca cga aaa gca tca ggt ctt tcc ttc gaa ggg gat ccg      912
Phe Met Arg Ala Arg Lys Ala Ser Gly Leu Ser Phe Glu Gly Asp Pro
    290                 295                 300

cct acc ttt cac gag ttg cgc agt ttg tct gca aga ctc tat gag aag      960
Pro Thr Phe His Glu Leu Arg Ser Leu Ser Ala Arg Leu Tyr Glu Lys
305                 310                 315                 320

cag ata agc gat aag ttt gct caa cat ctt ctc ggg cat aag tcg gac     1008
Gln Ile Ser Asp Lys Phe Ala Gln His Leu Leu Gly His Lys Ser Asp
                325                 330                 335

acc atg gca tca cag tat cgt gat gac aga ggc agg gag tgg gac aaa     1056
```

-continued

```
Thr Met Ala Ser Gln Tyr Arg Asp Asp Arg Gly Arg Glu Trp Asp Lys
            340                 345                 350

att gaa atc aaa taa                                             1071
Ile Glu Ile Lys  *
        355


<210> SEQ ID NO 38
<211> LENGTH: 356
<212> TYPE: PRT
<213> ORGANISM: Artificial Sequence
<220> FEATURE:
<223> OTHER INFORMATION: Integrase E147R

<400> SEQUENCE: 38

Met Gly Arg Arg Arg Ser His Glu Arg Arg Asp Leu Pro Pro Asn Leu
 1               5                  10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Arg Val Arg
                165                 170                 175

Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
        195                 200                 205

Thr Gly Gln Arg Val Gly Asp Leu Cys Glu Met Lys Trp Ser Asp Ile
    210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
    290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335
```

-continued

```
Thr Met Ala Ser Gln Tyr Arg Asp Asp Arg Gly Arg Glu Trp Asp Lys
            340                 345                 350

Ile Glu Ile Lys
        355


<210> SEQ ID NO 39
<211> LENGTH: 876
<212> TYPE: DNA
<213> ORGANISM: Discosoma species
<220> FEATURE:
<221> NAME/KEY: CDS
<222> LOCATION: (45)...(737)
<223> OTHER INFORMATION: Nucleotide sequence encoding red flourescent
      protein (FP593)
<300> PUBLICATION INFORMATION:
<308> DATABASE ACCESSION NUMBER: GenBank AF272711
<309> DATABASE ENTRY DATE: 2000-09-26

<400> SEQUENCE: 39

agtttcagcc agtgacaggg tgagctgcca ggtattctaa caag atg agt tgt tcc      56
                                                 Met Ser Cys Ser
                                                  1

aag aat gtg atc aag gag ttc atg agg ttc aag gtt cgt atg gaa gga      104
Lys Asn Val Ile Lys Glu Phe Met Arg Phe Lys Val Arg Met Glu Gly
 5                  10                  15                  20

acg gtc aat ggg cac gag ttt gaa ata aaa ggc gaa ggt gaa ggg agg      152
Thr Val Asn Gly His Glu Phe Glu Ile Lys Gly Glu Gly Glu Gly Arg
                25                  30                  35

cct tac gaa ggt cac tgt tcc gta aag ctt atg gta acc aag ggt gga      200
Pro Tyr Glu Gly His Cys Ser Val Lys Leu Met Val Thr Lys Gly Gly
            40                  45                  50

cct ttg cca ttt gct ttt gat att ttg tca cca caa ttt cag tat gga      248
Pro Leu Pro Phe Ala Phe Asp Ile Leu Ser Pro Gln Phe Gln Tyr Gly
        55                  60                  65

agc aag gta tat gtc aaa cac cct gcc gac ata cca gac tat aaa aag      296
Ser Lys Val Tyr Val Lys His Pro Ala Asp Ile Pro Asp Tyr Lys Lys
    70                  75                  80

ctg tca ttt cct gag gga ttt aaa tgg gaa agg gtc atg aac ttt gaa      344
Leu Ser Phe Pro Glu Gly Phe Lys Trp Glu Arg Val Met Asn Phe Glu
 85                 90                  95                 100

gac ggt ggc gtg gtt act gta tcc caa gat tcc agt ttg aaa gac ggc      392
Asp Gly Gly Val Val Thr Val Ser Gln Asp Ser Ser Leu Lys Asp Gly
                105                 110                 115

tgt ttc atc tac gag gtc aag ttc att ggg gtg aac ttt cct tct gat      440
Cys Phe Ile Tyr Glu Val Lys Phe Ile Gly Val Asn Phe Pro Ser Asp
            120                 125                 130

gga cct gtt atg cag agg agg aca cgg ggc tgg gaa gcc agc tct gag      488
Gly Pro Val Met Gln Arg Arg Thr Arg Gly Trp Glu Ala Ser Ser Glu
        135                 140                 145

cgt ttg tat cct cgt gat ggg gtg ctg aaa gga gac atc cat atg gct      536
Arg Leu Tyr Pro Arg Asp Gly Val Leu Lys Gly Asp Ile His Met Ala
    150                 155                 160

ctg agg ctg gaa gga ggc ggc cat tac ctc gtt gaa ttc aaa agt att      584
Leu Arg Leu Glu Gly Gly Gly His Tyr Leu Val Glu Phe Lys Ser Ile
165                 170                 175                 180

tac atg gta aag aag cct tca gtg cag ttg cca ggc tac tat tat gtt      632
Tyr Met Val Lys Lys Pro Ser Val Gln Leu Pro Gly Tyr Tyr Tyr Val
                185                 190                 195

gac tcc aaa ctg gat atg acg agc cac aac gaa gat tac aca gtc gtt      680
Asp Ser Lys Leu Asp Met Thr Ser His Asn Glu Asp Tyr Thr Val Val
            200                 205                 210
```

```
gag cag tat gaa aaa acc cag gga cgc cac cat ccg ttc att aag cct    728
Glu Gln Tyr Glu Lys Thr Gln Gly Arg His His Pro Phe Ile Lys Pro
        215                 220                 225

ctg cag tga actcggctca gtcatggatt agcggtaatg gccacaaaag            777
Leu Gln  *
    230

gcacgatgat cgttttttag gaatgcagcc aaaaattgaa ggttatgaca gtagaaatac  837

aagcaacagg ctttgcttat taaacatgta attgaaaac                         876
```

<210> SEQ ID NO 40
<211> LENGTH: 230
<212> TYPE: PRT
<213> ORGANISM: Discosoma species

<400> SEQUENCE: 40

```
Met Ser Cys Ser Lys Asn Val Ile Lys Glu Phe Met Arg Phe Lys Val
 1               5                  10                  15

Arg Met Glu Gly Thr Val Asn Gly His Glu Phe Glu Ile Lys Gly Glu
            20                  25                  30

Gly Glu Gly Arg Pro Tyr Glu Gly His Cys Ser Val Lys Leu Met Val
        35                  40                  45

Thr Lys Gly Gly Pro Leu Pro Phe Ala Phe Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Ser Gln Asp Ser Ser
            100                 105                 110

Leu Lys Asp Gly Cys Phe Ile Tyr Glu Val Lys Phe Ile Gly Val Asn
        115                 120                 125

Phe Pro Ser Asp Gly Pro Val Met Gln Arg Arg Thr Arg Gly Trp Glu
    130                 135                 140

Ala Ser Ser Glu Arg Leu Tyr Pro Arg Asp Gly Val Leu Lys Gly Asp
145                 150                 155                 160

Ile His Met Ala Leu Arg Leu Glu Gly Gly Gly His Tyr Leu Val Glu
                165                 170                 175

Phe Lys Ser Ile Tyr Met Val Lys Lys Pro Ser Val Gln Leu Pro Gly
            180                 185                 190

Tyr Tyr Tyr Val Asp Ser Lys Leu Asp Met Thr Ser His Asn Glu Asp
        195                 200                 205

Tyr Thr Val Val Glu Gln Tyr Glu Lys Thr Gln Gly Arg His His Pro
    210                 215                 220

Phe Ile Lys Pro Leu Gln
225                 230
```

<210> SEQ ID NO 41
<211> LENGTH: 25
<212> TYPE: DNA
<213> ORGANISM: Artificial Sequence
<220> FEATURE:
<223> OTHER INFORMATION: m-att;
<220> FEATURE:
<221> NAME/KEY: misc_difference
<222> LOCATION: 18
<223> OTHER INFORMATION: n is a or g or c or t/u

<400> SEQUENCE: 41

-continued rkycwgcttt yktrtacnaa stsgb 25

<210> SEQ ID NO 42
<211> LENGTH: 25
<212> TYPE: DNA
<213> ORGANISM: Artificial Sequence
<220> FEATURE:
<223> OTHER INFORMATION: m-attB;
<220> FEATURE:
<221> NAME/KEY: misc_difference
<222> LOCATION: 18
<223> OTHER INFORMATION: n is a or g or c or t/u

<400> SEQUENCE: 42
agccwgcttt yktrtacnaa ctsgb 25

<210> SEQ ID NO 43
<211> LENGTH: 25
<212> TYPE: DNA
<213> ORGANISM: Artificial Sequence
<220> FEATURE:
<223> OTHER INFORMATION: m-attR
<220> FEATURE:
<221> NAME/KEY: misc_difference
<222> LOCATION: 18
<223> OTHER INFORMATION: n is a or g or c or t/u

<400> SEQUENCE: 43
gttcagcttt cktrtacnaa ctsgb 25

<210> SEQ ID NO 44
<211> LENGTH: 25
<212> TYPE: DNA
<213> ORGANISM: Artificial Sequence
<220> FEATURE:
<223> OTHER INFORMATION: m-attL
<220> FEATURE:
<221> NAME/KEY: misc_difference
<222> LOCATION: 18
<223> OTHER INFORMATION: n is a or g or c or t/u

<400> SEQUENCE: 44
agccwgcttt cktrtacnaa gtsgb 25

<210> SEQ ID NO 45
<211> LENGTH: 25
<212> TYPE: DNA
<213> ORGANISM: Artificial Sequence
<220> FEATURE:
<223> OTHER INFORMATION: m-attP1
<220> FEATURE:
<221> NAME/KEY: misc_difference
<222> LOCATION: 18
<223> OTHER INFORMATION: n is a or g or c or t/u

<400> SEQUENCE: 45
gttcagcttt yktrtacnaa gtsgb 25

<210> SEQ ID NO 46
<211> LENGTH: 25
<212> TYPE: DNA
<213> ORGANISM: Artificial Sequence
<220> FEATURE:
<223> OTHER INFORMATION: attB1

<400> SEQUENCE: 46
agcctgcttt tttgtacaaa cttgt 25

-continued

<210> SEQ ID NO 47
<211> LENGTH: 25
<212> TYPE: DNA
<213> ORGANISM: Artificial Sequence
<220> FEATURE:
<223> OTHER INFORMATION: attB2

<400> SEQUENCE: 47
agcctgcttt cttgtacaaa cttgt 25

<210> SEQ ID NO 48
<211> LENGTH: 25
<212> TYPE: DNA
<213> ORGANISM: Artificial Sequence
<220> FEATURE:
<223> OTHER INFORMATION: attB3

<400> SEQUENCE: 48
acccagcttt cttgtacaaa cttgt 25

<210> SEQ ID NO 49
<211> LENGTH: 25
<212> TYPE: DNA
<213> ORGANISM: Artificial Sequence
<220> FEATURE:
<223> OTHER INFORMATION: attR1

<400> SEQUENCE: 49
gttcagcttt tttgtacaaa cttgt 25

<210> SEQ ID NO 50
<211> LENGTH: 25
<212> TYPE: DNA
<213> ORGANISM: Artificial Sequence
<220> FEATURE:
<223> OTHER INFORMATION: attR2

<400> SEQUENCE: 50
gttcagcttt cttgtacaaa cttgt 25

<210> SEQ ID NO 51
<211> LENGTH: 25
<212> TYPE: DNA
<213> ORGANISM: Artificial Sequence
<220> FEATURE:
<223> OTHER INFORMATION: attR3

<400> SEQUENCE: 51
gttcagcttt cttgtacaaa gttgg 25

<210> SEQ ID NO 52
<211> LENGTH: 25
<212> TYPE: DNA
<213> ORGANISM: Artificial Sequence
<220> FEATURE:
<223> OTHER INFORMATION: attL1

<400> SEQUENCE: 52
agcctgcttt tttgtacaaa gttgg 25

<210> SEQ ID NO 53
<211> LENGTH: 25
<212> TYPE: DNA
<213> ORGANISM: Artificial Sequence
<220> FEATURE:
<223> OTHER INFORMATION: attL2

-continued

<400> SEQUENCE: 53
agcctgcttt cttgtacaaa gttgg 25

<210> SEQ ID NO 54
<211> LENGTH: 25
<212> TYPE: DNA
<213> ORGANISM: Artificial Sequence
<220> FEATURE:
<223> OTHER INFORMATION: attL3

<400> SEQUENCE: 54
acccagcttt cttgtacaaa gttgg 25

<210> SEQ ID NO 55
<211> LENGTH: 25
<212> TYPE: DNA
<213> ORGANISM: Artificial Sequence
<220> FEATURE:
<223> OTHER INFORMATION: attP1

<400> SEQUENCE: 55
gttcagcttt tttgtacaaa gttgg 25

<210> SEQ ID NO 56
<211> LENGTH: 25
<212> TYPE: DNA
<213> ORGANISM: Artificial Sequence
<220> FEATURE:
<223> OTHER INFORMATION: attP2,P3

<400> SEQUENCE: 56
gttcagcttt cttgtacaaa gttgg 25

<210> SEQ ID NO 57
<211> LENGTH: 34
<212> TYPE: DNA
<213> ORGANISM: Artificial Sequence
<220> FEATURE:
<223> OTHER INFORMATION: Lox P site

<400> SEQUENCE: 57
ataacttcgt ataatgtatg ctatacgaag ttat 34

<210> SEQ ID NO 58
<211> LENGTH: 1032
<212> TYPE: DNA
<213> ORGANISM: Escherichia coli
<220> FEATURE:
<221> NAME/KEY: CDS
<222> LOCATION: (1)...(1032)
<223> OTHER INFORMATION: nucleotide sequence encoding Cre recombinase

<400> SEQUENCE: 58 atg tcc aat tta ctg acc gta cac caa aat ttg cct gca tta ccg gtc 48
Met Ser Asn Leu Leu Thr Val His Gln Asn Leu Pro Ala Leu Pro Val
1 5 10 15 gat gca acg agt gat gag gtt cgc aag aac ctg atg gac atg ttc agg 96
Asp Ala Thr Ser Asp Glu Val Arg Lys Asn Leu Met Asp Met Phe Arg
20 25 30 gat cgc cag gcg ttt tct gag cat acc tgg aaa atg ctt ctg tcc gtt 144
Asp Arg Gln Ala Phe Ser Glu His Thr Trp Lys Met Leu Leu Ser Val
35 40 45 tgc cgg tcg tgg gcg gca tgg tgc aag ttg aat aac cgg aaa tgg ttt 192
Cys Arg Ser Trp Ala Ala Trp Cys Lys Leu Asn Asn Arg Lys Trp Phe
50 55 60

-continued

```
ccc gca gaa cct gaa gat gtt cgc gat tat ctt cta tat ctt cag gcg      240
Pro Ala Glu Pro Glu Asp Val Arg Asp Tyr Leu Leu Tyr Leu Gln Ala
 65                  70                  75                  80

cgc ggt ctg gca gta aaa act atc cag caa cat ttg ggc cag cta aac      288
Arg Gly Leu Ala Val Lys Thr Ile Gln Gln His Leu Gly Gln Leu Asn
                 85                  90                  95

atg ctt cat cgt cgg tcc ggg ctg cca cga cca agt gac agc aat gct      336
Met Leu His Arg Arg Ser Gly Leu Pro Arg Pro Ser Asp Ser Asn Ala
            100                 105                 110

gtt tca ctg gtt atg cgg cgg atc cga aaa gaa aac gtt gat gcc ggt      384
Val Ser Leu Val Met Arg Arg Ile Arg Lys Glu Asn Val Asp Ala Gly
        115                 120                 125

gaa cgt gca aaa cag gct cta gcg ttc gaa cgc act gat ttc gac cag      432
Glu Arg Ala Lys Gln Ala Leu Ala Phe Glu Arg Thr Asp Phe Asp Gln
    130                 135                 140

gtt cgt tca ctc atg gaa aat agc gat cgc tgc cag gat ata cgt aat      480
Val Arg Ser Leu Met Glu Asn Ser Asp Arg Cys Gln Asp Ile Arg Asn
145                 150                 155                 160

ctg gca ttt ctg ggg att gct tat aac acc ctg tta cgt ata gcc gaa      528
Leu Ala Phe Leu Gly Ile Ala Tyr Asn Thr Leu Leu Arg Ile Ala Glu
                165                 170                 175

att gcc agg atc agg gtt aaa gat atc tca cgt act gac ggt ggg aga      576
Ile Ala Arg Ile Arg Val Lys Asp Ile Ser Arg Thr Asp Gly Gly Arg
            180                 185                 190

atg tta atc cat att ggc aga acg aaa acg ctg gtt agc acc gca ggt      624
Met Leu Ile His Ile Gly Arg Thr Lys Thr Leu Val Ser Thr Ala Gly
        195                 200                 205

gta gag aag gca ctt agc ctg ggg gta act aaa ctg gtc gag cga tgg      672
Val Glu Lys Ala Leu Ser Leu Gly Val Thr Lys Leu Val Glu Arg Trp
    210                 215                 220

att tcc gtc tct ggt gta gct gat gat ccg aat aac tac ctg ttt tgc      720
Ile Ser Val Ser Gly Val Ala Asp Asp Pro Asn Asn Tyr Leu Phe Cys
225                 230                 235                 240

cgg gtc aga aaa aat ggt gtt gcc gcg cca tct gcc acc agc cag cta      768
Arg Val Arg Lys Asn Gly Val Ala Ala Pro Ser Ala Thr Ser Gln Leu
                245                 250                 255

tca act cgc gcc ctg gaa ggg att ttt gaa gca act cat cga ttg att      816
Ser Thr Arg Ala Leu Glu Gly Ile Phe Glu Ala Thr His Arg Leu Ile
            260                 265                 270

tac ggc gct aag gat gac tct ggt cag aga tac ctg gcc tgg tct gga      864
Tyr Gly Ala Lys Asp Asp Ser Gly Gln Arg Tyr Leu Ala Trp Ser Gly
        275                 280                 285

cac agt gcc cgt gtc gga gcc gcg cga gat atg gcc cgc gct gga gtt      912
His Ser Ala Arg Val Gly Ala Ala Arg Asp Met Ala Arg Ala Gly Val
    290                 295                 300

tca ata ccg gag atc atg caa gct ggt ggc tgg acc aat gta aat att      960
Ser Ile Pro Glu Ile Met Gln Ala Gly Gly Trp Thr Asn Val Asn Ile
305                 310                 315                 320

gtc atg aac tat atc cgt aac ctg gat agt gaa aca ggg gca atg gtg     1008
Val Met Asn Tyr Ile Arg Asn Leu Asp Ser Glu Thr Gly Ala Met Val
                325                 330                 335

cgc ctg ctg gaa gat ggc gat tag                                     1032
Arg Leu Leu Glu Asp Gly Asp  *
            340
```

<210> SEQ ID NO 59
<211> LENGTH: 343
<212> TYPE: PRT
<213> ORGANISM: Escherichia coli -continued

<400> SEQUENCE: 59

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 60
<211> LENGTH: 1272
<212> TYPE: DNA
<213> ORGANISM: Saccharomyces cerevisiae
<220> FEATURE:
<221> NAME/KEY: CDS
<222> LOCATION: (1)...(1272)
<223> OTHER INFORMATION: nucleotide sequence encoding Flip recombinase

<400> SEQUENCE: 60

-continued

```
atg cca caa ttt ggt ata tta tgt aaa aca cca cct aag gtg ctt gtt       48
Met Pro Gln Phe Gly Ile Leu Cys Lys Thr Pro Pro Lys Val Leu Val
 1               5                  10                  15

cgt cag ttt gtg gaa agg ttt gaa aga cct tca ggt gag aaa ata gca       96
Arg Gln Phe Val Glu Arg Phe Glu Arg Pro Ser Gly Glu Lys Ile Ala
            20                  25                  30

tta tgt gct gct gaa cta acc tat tta tgt tgg atg att aca cat aac      144
Leu Cys Ala Ala Glu Leu Thr Tyr Leu Cys Trp Met Ile Thr His Asn
        35                  40                  45

gga aca gca atc aag aga gcc aca ttc atg agc tat aat act atc ata      192
Gly Thr Ala Ile Lys Arg Ala Thr Phe Met Ser Tyr Asn Thr Ile Ile
    50                  55                  60

agc aat tcg ctg agt ttc gat att gtc aat aaa tca ctc cag ttt aaa      240
Ser Asn Ser Leu Ser Phe Asp Ile Val Asn Lys Ser Leu Gln Phe Lys
 65                  70                  75                  80

tac aag acg caa aaa gca aca att ctg gaa gcc tca tta aag aaa ttg      288
Tyr Lys Thr Gln Lys Ala Thr Ile Leu Glu Ala Ser Leu Lys Lys Leu
                85                  90                  95

att cct gct tgg gaa ttt aca att att cct tac tat gga caa aaa cat      336
Ile Pro Ala Trp Glu Phe Thr Ile Ile Pro Tyr Tyr Gly Gln Lys His
            100                 105                 110

caa tct gat atc act gat att gta agt agt ttg caa tta cag ttc gaa      384
Gln Ser Asp Ile Thr Asp Ile Val Ser Ser Leu Gln Leu Gln Phe Glu
        115                 120                 125

tca tcg gaa gaa gca gat aag gga aat agc cac agt aaa aaa atg ctt      432
Ser Ser Glu Glu Ala Asp Lys Gly Asn Ser His Ser Lys Lys Met Leu
    130                 135                 140

aaa gca ctt cta agt gag ggt gaa agc atc tgg gag atc act gag aaa      480
Lys Ala Leu Leu Ser Glu Gly Glu Ser Ile Trp Glu Ile Thr Glu Lys
145                 150                 155                 160

ata cta aat tcg ttt gag tat act tcg aga ttt aca aaa aca aaa act      528
Ile Leu Asn Ser Phe Glu Tyr Thr Ser Arg Phe Thr Lys Thr Lys Thr
                165                 170                 175

tta tac caa ttc ctc ttc cta gct act ttc atc aat tgt gga aga ttc      576
Leu Tyr Gln Phe Leu Phe Leu Ala Thr Phe Ile Asn Cys Gly Arg Phe
            180                 185                 190

agc gat att aag aac gtt gat ccg aaa tca ttt aaa tta gtc caa aat      624
Ser Asp Ile Lys Asn Val Asp Pro Lys Ser Phe Lys Leu Val Gln Asn
        195                 200                 205

aag tat ctg gga gta ata atc cag tgt tta gtg aca gag aca aag aca      672
Lys Tyr Leu Gly Val Ile Ile Gln Cys Leu Val Thr Glu Thr Lys Thr
    210                 215                 220

agc gtt agt agg cac ata tac ttc ttt agc gca agg ggt agg atc gat      720
Ser Val Ser Arg His Ile Tyr Phe Phe Ser Ala Arg Gly Arg Ile Asp
225                 230                 235                 240

cca ctt gta tat ttg gat gaa ttt ttg agg aat tct gaa cca gtc cta      768
Pro Leu Val Tyr Leu Asp Glu Phe Leu Arg Asn Ser Glu Pro Val Leu
                245                 250                 255

aaa cga gta aat agg acc ggc aat tct tca agc aat aaa cag gaa tac      816
Lys Arg Val Asn Arg Thr Gly Asn Ser Ser Ser Asn Lys Gln Glu Tyr
            260                 265                 270

caa tta tta aaa gat aac tta gtc aga tcg tac aat aaa gct ttg aag      864
Gln Leu Leu Lys Asp Asn Leu Val Arg Ser Tyr Asn Lys Ala Leu Lys
        275                 280                 285

aaa aat gcg cct tat tca atc ttt gct ata aaa aat ggc cca aaa tct      912
Lys Asn Ala Pro Tyr Ser Ile Phe Ala Ile Lys Asn Gly Pro Lys Ser
    290                 295                 300

cac att gga aga cat ttg atg acc tca ttt ctt tca atg aag ggc cta      960
His Ile Gly Arg His Leu Met Thr Ser Phe Leu Ser Met Lys Gly Leu
```

-continued

```
305                 310                 315                 320

acg gag ttg act aat gtt gtg gga aat tgg agc gat aag cgt gct tct      1008
Thr Glu Leu Thr Asn Val Val Gly Asn Trp Ser Asp Lys Arg Ala Ser
            325                 330                 335

gcc gtg gcc agg aca acg tat act cat cag ata aca gca ata cct gat      1056
Ala Val Ala Arg Thr Thr Tyr Thr His Gln Ile Thr Ala Ile Pro Asp
            340                 345                 350

cac tac ttc gca cta gtt tct cgg tac tat gca tat gat cca ata tca      1104
His Tyr Phe Ala Leu Val Ser Arg Tyr Tyr Ala Tyr Asp Pro Ile Ser
        355                 360                 365

aag gaa atg ata gca ttg aag gat gag act aat cca att gag gag tgg      1152
Lys Glu Met Ile Ala Leu Lys Asp Glu Thr Asn Pro Ile Glu Glu Trp
    370                 375                 380

cag cat ata gaa cag cta aag ggt agt gct gaa gga agc ata cga tac      1200
Gln His Ile Glu Gln Leu Lys Gly Ser Ala Glu Gly Ser Ile Arg Tyr
385                 390                 395                 400

ccc gca tgg aat ggg ata ata tca cag gag gta cta gac tac ctt tca      1248
Pro Ala Trp Asn Gly Ile Ile Ser Gln Glu Val Leu Asp Tyr Leu Ser
            405                 410                 415

tcc tac ata aat aga cgc ata taa                                      1272
Ser Tyr Ile Asn Arg Arg Ile  *
            420


<210> SEQ ID NO 61
<211> LENGTH: 422
<212> TYPE: PRT
<213> ORGANISM: Saccharomyces cerevisiae

<400> SEQUENCE: 61

Pro Gln Phe Gly Ile Leu Cys Lys Thr Pro Pro Lys Val Leu Val Arg
 1               5                  10                  15

Gln Phe Val Glu Arg Phe Glu Arg Pro Ser Gly Glu Lys Ile Ala Leu
            20                  25                  30

Cys Ala Ala Glu Leu Thr Tyr Leu Cys Trp Met Ile Thr His Asn Gly
        35                  40                  45

Thr Ala Ile Lys Arg Ala Thr Phe Met Ser Tyr Asn Thr Ile Ile Ser
    50                  55                  60

Asn Ser Leu Ser Phe Asp Ile Val Asn Lys Ser Leu Gln Phe Lys Tyr
65                  70                  75                  80

Lys Thr Gln Lys Ala Thr Ile Leu Glu Ala Ser Leu Lys Lys Leu Ile
                85                  90                  95

Pro Ala Trp Glu Phe Thr Ile Ile Pro Tyr Tyr Gly Gln Lys His Gln
            100                 105                 110

Ser Asp Ile Thr Asp Ile Val Ser Ser Leu Gln Leu Gln Phe Glu Ser
        115                 120                 125

Ser Glu Glu Ala Asp Lys Gly Asn Ser His Ser Lys Lys Met Leu Lys
    130                 135                 140

Ala Leu Leu Ser Glu Gly Glu Ser Ile Trp Glu Ile Thr Glu Lys Ile
145                 150                 155                 160

Leu Asn Ser Phe Glu Tyr Thr Ser Arg Phe Thr Lys Thr Lys Thr Leu
                165                 170                 175

Tyr Gln Phe Leu Phe Leu Ala Thr Phe Ile Asn Cys Gly Arg Phe Ser
            180                 185                 190

Asp Ile Lys Asn Val Asp Pro Lys Ser Phe Lys Leu Val Gln Asn Lys
        195                 200                 205

Tyr Leu Gly Val Ile Ile Gln Cys Leu Val Thr Glu Thr Lys Thr Ser
    210                 215                 220
```

-continued

```
Val Ser Arg His Ile Tyr Phe Phe Ser Ala Arg Gly Arg Ile Asp Pro
225                 230                 235                 240

Leu Val Tyr Leu Asp Glu Phe Leu Arg Asn Ser Glu Pro Val Leu Lys
                245                 250                 255

Arg Val Asn Arg Thr Gly Asn Ser Ser Ser Asn Lys Gln Glu Tyr Gln
            260                 265                 270

Leu Leu Lys Asp Asn Leu Val Arg Ser Tyr Asn Lys Ala Leu Lys Lys
        275                 280                 285

Asn Ala Pro Tyr Ser Ile Phe Ala Ile Lys Asn Gly Pro Lys Ser His
    290                 295                 300

Ile Gly Arg His Leu Met Thr Ser Phe Leu Ser Met Lys Gly Leu Thr
305                 310                 315                 320

Glu Leu Thr Asn Val Val Gly Asn Trp Ser Asp Lys Arg Ala Ser Ala
                325                 330                 335

Val Ala Arg Thr Thr Tyr Thr His Gln Ile Thr Ala Ile Pro Asp His
            340                 345                 350

Tyr Phe Ala Leu Val Ser Arg Tyr Tyr Ala Tyr Asp Pro Ile Ser Lys
        355                 360                 365

Glu Met Ile Ala Leu Lys Asp Glu Thr Asn Pro Ile Glu Glu Trp Gln
    370                 375                 380

His Ile Glu Gln Leu Lys Gly Ser Ala Glu Gly Ser Ile Arg Tyr Pro
385                 390                 395                 400

Ala Trp Asn Gly Ile Ile Ser Gln Glu Val Leu Asp Tyr Leu Ser Ser
                405                 410                 415

Tyr Ile Asn Arg Arg Ile
            420


<210> SEQ ID NO 62
<211> LENGTH: 48
<212> TYPE: DNA
<213> ORGANISM: Artificial Sequence
<220> FEATURE:
<223> OTHER INFORMATION: IR2

<400> SEQUENCE: 62

gaagttccta ttccgaagtt cctattctct agaaagtata ggaacttc                  48


<210> SEQ ID NO 63
<211> LENGTH: 48
<212> TYPE: DNA
<213> ORGANISM: Artificial Sequence
<220> FEATURE:
<223> OTHER INFORMATION: IR1

<400> SEQUENCE: 63

gaagttccta tactttctag agaataggaa cttcggaata ggaacttc                  48


<210> SEQ ID NO 64
<211> LENGTH: 66
<212> TYPE: DNA
<213> ORGANISM: Bacteriophage mu
<220> FEATURE:
<221> NAME/KEY: CDS
<222> LOCATION: (1)...(66)
<223> OTHER INFORMATION: nucleotide sequence encoding GIN recombinase

<400> SEQUENCE: 64

tca act ctg tat aaa aaa cac ccc gcg aaa cga gcg cat ata gaa aac       48
Ser Thr Leu Tyr Lys Lys His Pro Ala Lys Arg Ala His Ile Glu Asn
 1               5                  10                  15
```

-continued

```
gac gat cga atc aat taa                                            66
Asp Asp Arg Ile Asn  *
             20


<210> SEQ ID NO 65
<211> LENGTH: 21
<212> TYPE: PRT
<213> ORGANISM: bacteriophage mu

<400> SEQUENCE: 65

Ser Thr Leu Tyr Lys Lys His Pro Ala Lys Arg Ala His Ile Glu Asn
 1               5                  10                  15

Asp Asp Arg Ile Asn
            20


<210> SEQ ID NO 66
<211> LENGTH: 69
<212> TYPE: DNA
<213> ORGANISM: Bacteriophage mu
<220> FEATURE:
<221> NAME/KEY: CDS
<222> LOCATION: (1)...(69)
<223> OTHER INFORMATION: nucleotide sequence encoding Gin recombinase

<400> SEQUENCE: 66

tat aaa aaa cat ccc gcg aaa cga acg cat ata gaa aac gac gat cga       48
Tyr Lys Lys His Pro Ala Lys Arg Thr His Ile Glu Asn Asp Asp Arg
 1               5                   10                  15

atc aat caa atc gat cgg taa                                            69
Ile Asn Gln Ile Asp Arg  *
             20


<210> SEQ ID NO 67
<211> LENGTH: 22
<212> TYPE: PRT
<213> ORGANISM: bacteriophage mu
<220> FEATURE:
<223> OTHER INFORMATION: Gin recombinase of bacteriophage mu

<400> SEQUENCE: 67

Tyr Lys Lys His Pro Ala Lys Arg Thr His Ile Glu Asn Asp Asp Arg
 1               5                  10                  15

Ile Asn Gln Ile Asp Arg
            20


<210> SEQ ID NO 68
<211> LENGTH: 555
<212> TYPE: DNA
<213> ORGANISM: Escherichia coli
<220> FEATURE:
<221> NAME/KEY: CDS
<222> LOCATION: (1)...(555)
<223> OTHER INFORMATION: nucleotide sequence encoding PIN recombinase

<400> SEQUENCE: 68

atg ctt att ggc tat gta cgc gta tca aca aat gac cag aac aca gat       48
Met Leu Ile Gly Tyr Val Arg Val Ser Thr Asn Asp Gln Asn Thr Asp
 1               5                   10                  15

cta caa cgt aat gcg ctg aac tgt gca gga tgc gag ctg att ttt gaa       96
Leu Gln Arg Asn Ala Leu Asn Cys Ala Gly Cys Glu Leu Ile Phe Glu
             20                  25                  30

gac aag ata agc ggc aca aag tcc gaa agg ccg gga ctg aaa aaa ctg      144
Asp Lys Ile Ser Gly Thr Lys Ser Glu Arg Pro Gly Leu Lys Lys Leu
         35                  40                  45
```

-continued

```
ctc agg aca tta tcg gca ggt gac act ctg gtt gtc tgg aag ctg gat      192
Leu Arg Thr Leu Ser Ala Gly Asp Thr Leu Val Val Trp Lys Leu Asp
     50                  55                  60

cgg ctg ggg cgt agt atg cgg cat ctt gtc gtg ctg gtg gag gag ttg      240
Arg Leu Gly Arg Ser Met Arg His Leu Val Val Leu Val Glu Glu Leu
 65                  70                  75                  80

cgc gaa cga ggc atc aac ttt cgt agt ctg acg gat tca att gat acc      288
Arg Glu Arg Gly Ile Asn Phe Arg Ser Leu Thr Asp Ser Ile Asp Thr
                 85                  90                  95

agc aca cca atg gga cgc ttt ttc ttt cat gtg atg ggt gcc ctg gct      336
Ser Thr Pro Met Gly Arg Phe Phe Phe His Val Met Gly Ala Leu Ala
            100                 105                 110

gaa atg gag cgt gaa ctg att gtt gaa cga aca aaa gct gga ctg gaa      384
Glu Met Glu Arg Glu Leu Ile Val Glu Arg Thr Lys Ala Gly Leu Glu
        115                 120                 125

act gct cgt gca cag gga cga att ggt gga cgt cgt ccc aaa ctt aca      432
Thr Ala Arg Ala Gln Gly Arg Ile Gly Gly Arg Arg Pro Lys Leu Thr
    130                 135                 140

cca gaa caa tgg gca caa gct gga cga tta att gca gca gga act cct      480
Pro Glu Gln Trp Ala Gln Ala Gly Arg Leu Ile Ala Ala Gly Thr Pro
145                 150                 155                 160

cgc cag aag gtg gcg att atc tat gat gtt ggt gtg tca act ttg tat      528
Arg Gln Lys Val Ala Ile Ile Tyr Asp Val Gly Val Ser Thr Leu Tyr
                165                 170                 175

aag agg ttt cct gca ggg gat aaa taa                                  555
Lys Arg Phe Pro Ala Gly Asp Lys  *
            180


<210> SEQ ID NO 69
<211> LENGTH: 184
<212> TYPE: PRT
<213> ORGANISM: Escherichia coli

<400> SEQUENCE: 69

Met Leu Ile Gly Tyr Val Arg Val Ser Thr Asn Asp Gln Asn Thr Asp
 1               5                  10                  15

Leu Gln Arg Asn Ala Leu Asn Cys Ala Gly Cys Glu Leu Ile Phe Glu
            20                  25                  30

Asp Lys Ile Ser Gly Thr Lys Ser Glu Arg Pro Gly Leu Lys Lys Leu
        35                  40                  45

Leu Arg Thr Leu Ser Ala Gly Asp Thr Leu Val Val Trp Lys Leu Asp
    50                  55                  60

Arg Leu Gly Arg Ser Met Arg His Leu Val Val Leu Val Glu Glu Leu
65                  70                  75                  80

Arg Glu Arg Gly Ile Asn Phe Arg Ser Leu Thr Asp Ser Ile Asp Thr
                85                  90                  95

Ser Thr Pro Met Gly Arg Phe Phe Phe His Val Met Gly Ala Leu Ala
            100                 105                 110

Glu Met Glu Arg Glu Leu Ile Val Glu Arg Thr Lys Ala Gly Leu Glu
        115                 120                 125

Thr Ala Arg Ala Gln Gly Arg Ile Gly Gly Arg Arg Pro Lys Leu Thr
    130                 135                 140

Pro Glu Gln Trp Ala Gln Ala Gly Arg Leu Ile Ala Ala Gly Thr Pro
145                 150                 155                 160

Arg Gln Lys Val Ala Ile Ile Tyr Asp Val Gly Val Ser Thr Leu Tyr
                165                 170                 175

Lys Arg Phe Pro Ala Gly Asp Lys
            180
```

-continued

<210> SEQ ID NO 70
<211> LENGTH: 4778
<212> TYPE: DNA
<213> ORGANISM: Artificial Sequence
<220> FEATURE:
<223> OTHER INFORMATION: pcx plasmid

<400> SEQUENCE: 70
gtcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggact atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atgggtcgag gtgagcccca cgttctgctt cactctcccc 420
atctcccccc cctccccacc cccaattttg tatttattta ttttttaatt attttgtgca 480
gcgatggggg cggggggggg gggggcgcgc gccaggcggg gcggggcggg gcgaggggcg 540
gggcggggcg aggcggagag gtgcggcggc agccaatcag agcggcgcgc tccgaaagtt 600
tccttttatg gcgaggcggc ggcggcggcg gccctataaa aagcgaagcg cgcggcgggc 660
gggagtcgct gcgttgcctt cgccccgtgc cccgctccgc gccgcctcgc gccgcccgcc 720
ccggctctga ctgaccgcgt tactcccaca ggtgagcggg cgggacggcc cttctcctcc 780
gggctgtaat tagcgcttgg tttaatgacg gctcgtttct tttctgtggc tgcgtgaaag 840
ccttaaaggg ctccgggagg gccctttgtg cggggggggag cggctcgggg ggtgcgtgcg 900
tgtgtgtgtg cgtggggagc gccgcgtgcg gcccgcgctg cccggcggct gtgagcgctg 960
cgggcgcggc gcggggcttt gtgcgctccg cgtgtgcgcg aggggagcgc ggccgggggc 1020
ggtgccccgc ggtgcggggg ggctgcgagg ggaacaaagg ctgcgtgcgg ggtgtgtgcg 1080
tgggggggtg agcagggggt gtgggcgcgg cggtcgggct gtaacccccc cctgcacccc 1140
cctccccgag ttgctgagca cggcccggct tcgggtgcgg ggctccgtgc ggggcgtggc 1200
gcggggctcg ccgtgccggg cgggggggtgg cggcaggtgg gggtgccggg cggggcgggg 1260
ccgcctcggg ccggggaggg ctcgggggag ggcgcggcg gccccggagc gccggcggct 1320
gtcgaggcgc ggcgagccgc agccattgcc ttttatggta atcgtgcgag agggcgcagg 1380
gacttccttt gtcccaaatc tggcggagcc gaaatctggg aggcgccgcc gcaccccctc 1440
tagcgggcgc gggcgaagcg gtgcggcgcc ggcaggaagg aaatgggcgg ggagggcctt 1500
cgtgcgtcgc cgcgccgccg tccccttctc catctccagc ctcggggctg ccgcaggggg 1560
acggctgcct tcggggggga cggggcaggg cggggttcgg cttctggcgt gtgaccggcg 1620
gctctagagc ctctgctaac catgttcatg ccttcttctt tttcctacag ctcctgggca 1680
acgtgctggt tgttgtgctg tctcatcatt ttggcaaaga attcactcct caggtgcagg 1740
ctgcctatca gaaggtggtg gctggtgtgg ccaatgccct ggctcacaaa taccactgag 1800
atctttttcc ctctgccaaa aattatgggg acatcatgaa gccccttgag catctgactt 1860
ctggctaata aaggaaattt attttcattg caatagtgtg ttggaatttt ttgtgtctct 1920
cactcggaag gacatatggg agggcaaatc atttaaaaca tcagaatgag tatttggttt 1980
agagtttggc aacatatgcc atatgctggc tgccatgaac aaaggtggct ataaagaggt 2040

-continued

```
catcagtata tgaaacagcc ccctgctgtc cattccttat tccatagaaa agccttgact   2100
tgaggttaga ttttttttat attttgtttt gtgttatttt tttctttaac atccctaaaa   2160
ttttccttac atgttttact agccagattt ttcctcctct cctgactact cccagtcata   2220
gctgtccctc ttctcttatg aagatccctc gacctgcagc ccaagcttgg cgtaatcatg   2280
gtcatagctg tttcctgtgt gaaattgtta tccgctcaca attccacaca acatacgagc   2340
cggaagcata aagtgtaaag cctggggtgc ctaatgagtg agctaactca cattaattgc   2400
gttgcgctca ctgcccgctt tccagtcggg aaacctgtcg tgccagcgga tccgcatctc   2460
aattagtcag caaccatagt cccgccccta actccgccca tcccgcccct aactccgccc   2520
agttccgccc attctccgcc ccatggctga ctaatttttt ttatttatgc agaggccgag   2580
gccgcctcgg cctctgagct attccagaag tagtgaggag gcttttttgg aggcctaggc   2640
ttttgcaaaa agctaacttg tttattgcag cttataatgg ttacaaataa agcaatagca   2700
tcacaaattt cacaaataaa gcattttttt cactgcattc tagttgtggt ttgtccaaac   2760
tcatcaatgt atcttatcat gtctggatcc gctgcattaa tgaatcggcc aacgcgcggg   2820
gagaggcggt ttgcgtattg ggcgctcttc cgcttcctcg ctcactgact cgctgcgctc   2880
ggtcgttcgg ctgcggcgag cggtatcagc tcactcaaag gcggtaatac ggttatccac   2940
agaatcaggg gataacgcag gaaagaacat gtgagcaaaa ggccagcaaa aggccaggaa   3000
ccgtaaaaag gccgcgttgc tggcgttttt ccataggctc cgcccccctg acgagcatca   3060
caaaaatcga cgctcaagtc agaggtggcg aaacccgaca ggactataaa gataccaggc   3120
gtttccccct ggaagctccc tcgtgcgctc tcctgttccg accctgccgc ttaccggata   3180
cctgtccgcc tttctccctt cgggaagcgt ggcgctttct caatgctcac gctgtaggta   3240
tctcagttcg gtgtaggtcg ttcgctccaa gctgggctgt gtgcacgaac cccccgttca   3300
gcccgaccgc tgcgccttat ccggtaacta tcgtcttgag tccaacccgg taagacacga   3360
cttatcgcca ctggcagcag ccactggtaa caggattagc agagcgaggt atgtaggcgg   3420
tgctacagag ttcttgaagt ggtggcctaa ctacggctac actagaagga cagtatttgg   3480
tatctgcgct ctgctgaagc cagttacctt cggaaaaaga gttggtagct cttgatccgg   3540
caaacaaacc accgctggta gcggtggttt ttttgtttgc aagcagcaga ttacgcgcag   3600
aaaaaaagga tctcaagaag atcctttgat cttttctacg gggtctgacg ctcagtggaa   3660
cgaaaactca cgttaaggga ttttggtcat gagattatca aaaaggatct tcacctagat   3720
ccttttaaat taaaaatgaa gttttaaatc aatctaaagt atatatgagt aaacttggtc   3780
tgacagttac caatgcttaa tcagtgaggc acctatctca gcgatctgtc tatttcgttc   3840
atccatagtt gcctgactcc ccgtcgtgta gataactacg atacgggagg gcttaccatc   3900
tggccccagt gctgcaatga taccgcgaga cccacgctca ccggctccag atttatcagc   3960
aataaaccag ccagccggaa gggccgagcg cagaagtggt cctgcaactt tatccgcctc   4020
catccagtct attaattgtt gccgggaagc tagagtaagt agttcgccag ttaatagttt   4080
gcgcaacgtt gttgccattg ctacaggcat cgtggtgtca cgctcgtcgt ttggtatggc   4140
ttcattcagc tccggttccc aacgatcaag gcgagttaca tgatccccca tgttgtgcaa   4200
aaaagcggtt agctccttcg gtcctccgat cgttgtcaga agtaagttgg ccgcagtgtt   4260
atcactcatg gttatggcag cactgcataa ttctcttact gtcatgccat ccgtaagatg   4320
cttttctgtg actggtgagt actcaaccaa gtcattctga gaatagtgta tgcggcgacc   4380
gagttgctct tgcccggcgt caatacggga taataccgcg ccacatagca gaactttaaa   4440
```

-continued

```
agtgctcatc attggaaaac gttcttcggg gcgaaaactc tcaaggatct taccgctgtt   4500

gagatccagt tcgatgtaac ccactcgtgc acccaactga tcttcagcat cttttacttt   4560

caccagcgtt tctgggtgag caaaaacagg aaggcaaaat gccgcaaaaa agggaataag   4620

ggcgacacgg aaatgttgaa tactcatact cttccttttt caatattatt gaagcattta   4680

tcagggttat tgtctcatga gcggatacat atttgaatgt atttagaaaa ataaacaaat   4740

aggggttccg cgcacatttc cccgaaaagt gccacctg                           4778
```

<210> SEQ ID NO 71
<211> LENGTH: 5510
<212> TYPE: DNA
<213> ORGANISM: Artificial Sequence
<220> FEATURE:
<223> OTHER INFORMATION: pCXeGFP plasmid

<400> SEQUENCE: 71

```
gtcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggact atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atgggtcgag gtgagcccca cgttctgctt cactctcccc    420

atctcccccc cctccccacc cccaattttg tatttattta tttttttaatt attttgtgca    480

gcgatggggg cggggggggg gggggcgcgc gccaggcggg gcggggcggg gcgaggggcg    540

gggcggggcg aggcggagag gtgcggcggc agccaatcag agcggcgcgc tccgaaagtt    600

tccttttatg gcgaggcggc ggcggcggcg gccctataaa aagcgaagcg cgcggcgggc    660

gggagtcgct gcgttgcctt cgccccgtgc cccgctccgc gccgcctcgc gccgcccgcc    720

ccggctctga ctgaccgcgt tactcccaca ggtgagcggg cgggacggcc cttctcctcc    780

gggctgtaat tagcgcttgg tttaatgacg gctcgtttct tttctgtggc tgcgtgaaag    840

ccttaaaggg ctccgggagg gccctttgtg cggggggggag cggctcgggg ggtgcgtgcg    900

tgtgtgtgtg cgtggggagc gccgcgtgcg gcccgcgctg cccggcggct gtgagcgctg    960

cgggcgcggc gcggggcttt gtgcgctccg cgtgtgcgcg aggggagcgc ggccgggggc   1020

ggtgccccgc ggtgcggggg ggctgcgagg ggaacaaagg ctgcgtgcgg ggtgtgtgcg   1080

tgggggggtg agcagggggt gtgggcgcgg cggtcgggct gtaacccccc cctgcacccc   1140

cctccccgag ttgctgagca cggcccggct tcgggtgcgg ggctccgtgc ggggcgtggc   1200

gcggggctcg ccgtgccggg cgggggggtgg cggcaggtgg gggtgccggg cggggcgggg   1260

ccgcctcggg ccggggaggg ctcgggggag ggcgcggcg gccccggagc gccggcggct    1320

gtcgaggcgc ggcgagccgc agccattgcc ttttatggta atcgtgcgag agggcgcagg   1380

gacttccttt gtcccaaatc tggcggagcc gaaatctggg aggcgccgcc gcaccccctc   1440

tagcgggcgc gggcgaagcg gtgcggcgcc ggcaggaagg aaatgggcgg ggagggcctt   1500

cgtgcgtcgc cgcgccgccg tccccttctc catctccagc ctcggggctg ccgcaggggg   1560

acggctgcct tcggggggga cggggcaggg cggggttcgg cttctggcgt gtgaccggcg   1620

gctctagagc ctctgctaac catgttcatg ccttcttctt tttcctacag ctcctgggca   1680
```

-continued

```
acgtgctggt tgttgtgctg tctcatcatt ttggcaaaga attcgccacc atggtgagca   1740
agggcgagga gctgttcacc ggggtggtgc ccatcctggt cgagctggac ggcgacgtaa   1800
acggccacaa gttcagcgtg tccggcgagg gcgagggcga tgccacctac ggcaagctga   1860
ccctgaagtt catctgcacc accggcaagc tgcccgtgcc ctggcccacc ctcgtgacca   1920
ccctgaccta cggcgtgcag tgcttcagcc gctaccccga ccacatgaag cagcacgact   1980
tcttcaagtc cgccatgccc gaaggctacg tccaggagcg caccatcttc ttcaaggacg   2040
acggcaacta caagacccgc gccgaggtga agttcgaggg cgacaccctg gtgaaccgca   2100
tcgagctgaa gggcatcgac ttcaaggagg acggcaacat cctggggcac aagctggagt   2160
acaactacaa cagccacaac gtctatatca tggccgacaa gcagaagaac ggcatcaagg   2220
tgaacttcaa gatccgccac aacatcgagg acggcagcgt gcagctcgcc gaccactacc   2280
agcagaacac ccccatcggc gacggccccg tgctgctgcc cgacaaccac tacctgagca   2340
cccagtccgc cctgagcaaa gaccccaacg agaagcgcga tcacatggtc ctgctggagt   2400
tcgtgaccgc cgccgggatc actctcggca tggacgagct gtacaagtaa gaattcactc   2460
ctcaggtgca ggctgcctat cagaaggtgg tggctggtgt ggccaatgcc ctggctcaca   2520
aataccactg agatcttttt ccctctgcca aaaattatgg ggacatcatg aagccccttg   2580
agcatctgac ttctggctaa taaaggaaat ttattttcat tgcaatagtg tgttggaatt   2640
ttttgtgtct ctcactcgga aggacatatg ggagggcaaa tcatttaaaa catcagaatg   2700
agtatttggt ttagagtttg gcaacatatg ccatatgctg gctgccatga acaaaggtgg   2760
ctataaagag gtcatcagta tatgaaacag ccccctgctg tccattcctt attccataga   2820
aaagccttga cttgaggtta gatttttttt atattttgtt ttgtgttatt tttttcttta   2880
acatccctaa aattttcctt acatgtttta ctagccagat ttttcctcct ctcctgacta   2940
ctcccagtca tagctgtccc tcttctctta tgaagatccc tcgacctgca gcccaagctt   3000
ggcgtaatca tggtcatagc tgtttcctgt gtgaaattgt tatccgctca caattccaca   3060
caacatacga gccggaagca taaagtgtaa agcctggggt gcctaatgag tgagctaact   3120
cacattaatt gcgttgcgct cactgcccgc tttccagtcg ggaaacctgt cgtgccagcg   3180
gatccgcatc tcaattagtc agcaaccata gtcccgcccc taactccgcc catcccgccc   3240
ctaactccgc ccagttccgc ccattctccg ccccatggct gactaatttt ttttatttat   3300
gcagaggccg aggccgcctc ggcctctgag ctattccaga agtagtgagg aggctttttt   3360
ggaggcctag gcttttgcaa aaagctaact tgtttattgc agcttataat ggttacaaat   3420
aaagcaatag catcacaaat ttcacaaata aagcattttt ttcactgcat tctagttgtg   3480
gtttgtccaa actcatcaat gtatcttatc atgtctggat ccgctgcatt aatgaatcgg   3540
ccaacgcgcg gggagaggcg gtttgcgtat tgggcgctct tccgcttcct cgctcactga   3600
ctcgctgcgc tcggtcgttc ggctgcggcg agcggtatca gctcactcaa aggcggtaat   3660
acggttatcc acagaatcag gggataacgc aggaaagaac atgtgagcaa aaggccagca   3720
aaaggccagg aaccgtaaaa aggccgcgtt gctggcgttt ttccataggc tccgcccccc   3780
tgacgagcat cacaaaaatc gacgctcaag tcagaggtgg cgaaacccga caggactata   3840
aagataccag gcgtttcccc ctggaagctc cctcgtgcgc tctcctgttc cgaccctgcc   3900
gcttaccgga tacctgtccg cctttctccc ttcgggaagc gtggcgcttt ctcaatgctc   3960
acgctgtagg tatctcagtt cggtgtaggt cgttcgctcc aagctgggct gtgtgcacga   4020
accccccgtt cagcccgacc gctgcgcctt atccggtaac tatcgtcttg agtccaaccc   4080
```

-continued

```
ggtaagacac gacttatcgc cactggcagc agccactggt aacaggatta gcagagcgag   4140

gtatgtaggc ggtgctacag agttcttgaa gtggtggcct aactacggct acactagaag   4200

gacagtattt ggtatctgcg ctctgctgaa gccagttacc ttcggaaaaa gagttggtag   4260

ctcttgatcc ggcaaacaaa ccaccgctgg tagcggtggt ttttttgttt gcaagcagca   4320

gattacgcgc agaaaaaaag gatctcaaga agatcctttg atcttttcta cggggtctga   4380

cgctcagtgg aacgaaaact cacgttaagg gattttggtc atgagattat caaaaaggat   4440

cttcacctag atccttttaa attaaaaatg aagttttaaa tcaatctaaa gtatatatga   4500

gtaaacttgg tctgacagtt accaatgctt aatcagtgag gcacctatct cagcgatctg   4560

tctatttcgt tcatccatag ttgcctgact ccccgtcgtg tagataacta cgatacggga   4620

gggcttacca tctggcccca gtgctgcaat gataccgcga gacccacgct caccggctcc   4680

agatttatca gcaataaacc agccagccgg aagggccgag cgcagaagtg gtcctgcaac   4740

tttatccgcc tccatccagt ctattaattg ttgccgggaa gctagagtaa gtagttcgcc   4800

agttaatagt ttgcgcaacg ttgttgccat tgctacaggc atcgtggtgt cacgctcgtc   4860

gtttggtatg gcttcattca gctccggttc ccaacgatca aggcgagtta catgatcccc   4920

catgttgtgc aaaaaagcgg ttagctcctt cggtcctccg atcgttgtca gaagtaagtt   4980

ggccgcagtg ttatcactca tggttatggc agcactgcat aattctctta ctgtcatgcc   5040

atccgtaaga tgcttttctg tgactggtga gtactcaacc aagtcattct gagaatagtg   5100

tatgcggcga ccgagttgct cttgcccggc gtcaatacgg gataataccg cgccacatag   5160

cagaacttta aaagtgctca tcattggaaa acgttcttcg gggcgaaaac tctcaaggat   5220

cttaccgctg ttgagatcca gttcgatgta acccactcgt gcacccaact gatcttcagc   5280

atcttttact ttcaccagcg tttctgggtg agcaaaaaca ggaaggcaaa atgccgcaaa   5340

aaagggaata agggcgacac ggaaatgttg aatactcata ctcttccttt ttcaatatta   5400

ttgaagcatt tatcagggtt attgtctcat gagcggatac atatttgaat gtatttagaa   5460

aaataaacaa ataggggttc cgcgcacatt tccccgaaaa gtgccacctg             5510
```

<210> SEQ ID NO 72
<211> LENGTH: 282
<212> TYPE: DNA
<213> ORGANISM: Artificial Sequence
<220> FEATURE:
<223> OTHER INFORMATION: attp

<400> SEQUENCE: 72

```
ccttgcgcta atgctctgtt acaggtcact aataccatct aagtagttga ttcatagtga     60

ctgcatatgt tgtgttttac agtattatgt agtctgtttt ttatgcaaaa tctaatttaa    120

tatattgata tttatatcat tttacgtttc tcgttcagct tttttatact aagttggcat    180

tataaaaaag cattgcttat caatttgttg caacgaacag gtcactatca gtcaaaataa    240

aatcattatt tgatttcaat tttgtcccac tccctgcctc tg                       282
```

<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73

-continued ggccccgtaa tgcagaagaa 20

<210> SEQ ID NO 74
<211> LENGTH: 32
<212> TYPE: DNA
<213> ORGANISM: Artificial Sequence
<220> FEATURE:
<223> OTHER INFORMATION: Primer

<400> SEQUENCE: 74
ggtttaaagt gcgctcctcc aagaacgtca tc 32

<210> SEQ ID NO 75
<211> LENGTH: 40
<212> TYPE: DNA
<213> ORGANISM: Artificial Sequence
<220> FEATURE:
<223> OTHER INFORMATION: Primer

<400> SEQUENCE: 75
agatctagag ccgccgctac aggaacaggt ggtggcggcc 40

<210> SEQ ID NO 76
<211> LENGTH: 37
<212> TYPE: DNA
<213> ORGANISM: Artificial Sequence
<220> FEATURE:
<223> OTHER INFORMATION: Primer 5PacSV40

<400> SEQUENCE: 76
ctgttaatta actgtggaat gtgtgtcagt tagggtg 37

<210> SEQ ID NO 77
<211> LENGTH: 20
<212> TYPE: DNA
<213> ORGANISM: Artificial Sequence
<220> FEATURE:
<223> OTHER INFORMATION: Primer Antisense Zeo

<400> SEQUENCE: 77
tgaacagggt cacgtcgtcc 20

<210> SEQ ID NO 78
<211> LENGTH: 24
<212> TYPE: DNA
<213> ORGANISM: Artificial Sequence
<220> FEATURE:
<223> OTHER INFORMATION: Primer 5' HETS

<400> SEQUENCE: 78
gggccgaaac gatctcaacc tatt 24

<210> SEQ ID NO 79
<211> LENGTH: 19
<212> TYPE: DNA
<213> ORGANISM: Artificial Sequence
<220> FEATURE:
<223> OTHER INFORMATION: Primer 3' HETS

<400> SEQUENCE: 79
cgcagcggcc ctcctactc 19

<210> SEQ ID NO 80
<211> LENGTH: 29
<212> TYPE: DNA
<213> ORGANISM: Artificial Sequence -continued
<220> FEATURE:
<223> OTHER INFORMATION: Primer 5BSD

<400> SEQUENCE: 80
accatgaaaa catttaacat ttctcaaca 29

<210> SEQ ID NO 81
<211> LENGTH: 29
<212> TYPE: DNA
<213> ORGANISM: Artificial Sequence
<220> FEATURE:
<223> OTHER INFORMATION: Primer SV40polyA

<400> SEQUENCE: 81
tttatttgtg aaatttgtga tgctattgc 29

<210> SEQ ID NO 82
<211> LENGTH: 25
<212> TYPE: DNA
<213> ORGANISM: Artificial Sequence
<220> FEATURE:
<223> OTHER INFORMATION: Primer 3BSP

<400> SEQUENCE: 82
ttaatttcgg gtatatttga gtgga 25

<210> SEQ ID NO 83
<211> LENGTH: 32
<212> TYPE: DNA
<213> ORGANISM: Artificial Sequence
<220> FEATURE:
<223> OTHER INFORMATION: Primer EPO5XBA

<400> SEQUENCE: 83
tatctagaat gggggtgcac gaatgtcctg cc 32

<210> SEQ ID NO 84
<211> LENGTH: 32
<212> TYPE: DNA
<213> ORGANISM: Artificial Sequence
<220> FEATURE:
<223> OTHER INFORMATION: Primer EPO3SBI

<400> SEQUENCE: 84
tacgtacgtc atctgtcccc tgtcctgcag gc 32

<210> SEQ ID NO 85
<211> LENGTH: 27
<212> TYPE: DNA
<213> ORGANISM: Artificial Sequence
<220> FEATURE:
<223> OTHER INFORMATION: Primer GENEPO3BSI

<400> SEQUENCE: 85
cgtacgtcat ctgtcccctg tcctgca 27

<210> SEQ ID NO 86
<211> LENGTH: 28
<212> TYPE: DNA
<213> ORGANISM: Artificial Sequence
<220> FEATURE:
<223> OTHER INFORMATION: Primer GENEPO5XBA

<400> SEQUENCE: 86
tctagaatgg gggtgcacgg tgagtact 28

-continued

<210> SEQ ID NO 87
<211> LENGTH: 4862
<212> TYPE: DNA
<213> ORGANISM: Artificial Sequence
<220> FEATURE:
<223> OTHER INFORMATION: pD2eGFP-1N plasmid from Clontech

<400> SEQUENCE: 87
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cgtcagatcc gctagcgcta 600
ccggactcag atctcgagct caagcttcga attctgcagt cgacggtacc gcgggcccgg 660
gatccaccgg tcgccaccat ggtgagcaag ggcgaggagc tgttcaccgg ggtggtgccc 720
atcctggtcg agctggacgg cgacgtaaac ggccacaagt tcagcgtgtc cggcgagggc 780
gagggcgatg ccacctacgg caagctgacc ctgaagttca tctgcaccac cggcaagctg 840
cccgtgccct ggcccaccct cgtgaccacc ctgacctacg gcgtgcagtg cttcagccgc 900
taccccgacc acatgaagca gcacgacttc ttcaagtccg ccatgcccga aggctacgtc 960
caggagcgca ccatcttctt caaggacgac ggcaactaca agacccgcgc cgaggtgaag 1020
ttcgagggcg acaccctggt gaaccgcatc gagctgaagg gcatcgactt caaggaggac 1080
ggcaacatcc tggggcacaa gctggagtac aactacaaca gccacaacgt ctatatcatg 1140
gccgacaagc agaagaacgg catcaaggtg aacttcaaga tccgccacaa catcgaggac 1200
ggcagcgtgc agctcgccga ccactaccag cagaacaccc ccatcggcga cggccccgtg 1260
ctgctgcccg acaaccacta cctgagcacc cagtccgccc tgagcaaaga ccccaacgag 1320
aagcgcgatc acatggtcct gctggagttc gtgaccgccg ccgggatcac tctcggcatg 1380
gacgagctgt acaagaagct tagccatggc ttcccgccgg aggtggagga gcaggatgat 1440
ggcacgctgc ccatgtcttg tgcccaggag agcgggatgg accgtcaccc tgcagcctgt 1500
gcttctgcta ggatcaatgt gtagatgcgc ggccgcgact ctagatcata atcagccata 1560
ccacatttgt agaggtttta cttgctttaa aaaacctccc acacctcccc ctgaacctga 1620
aacataaaat gaatgcaatt gttgttgtta acttgtttat tgcagcttat aatggttaca 1680
aataaagcaa tagcatcaca aatttcacaa ataaagcatt tttttcactg cattctagtt 1740
gtggtttgtc caaactcatc aatgtatctt aaggcgtaaa ttgtaagcgt taatattttg 1800
ttaaaattcg cgttaaattt ttgttaaatc agctcatttt ttaaccaata ggccgaaatc 1860
ggcaaaatcc cttataaatc aaaagaatag accgagatag ggttgagtgt tgttccagtt 1920
tggaacaaga gtccactatt aaagaacgtg gactccaacg tcaaagggcg aaaaaccgtc 1980
tatcagggcg atggcccact acgtgaacca tcaccctaat caagtttttt ggggtcgagg 2040
tgccgtaaag cactaaatcg gaaccctaaa gggagccccc gatttagagc ttgacgggga 2100

-continued

```
aagccggcga acgtggcgag aaaggaaggg aagaaagcga aaggagcggg cgctagggcg   2160
ctggcaagtg tagcggtcac gctgcgcgta accaccacac ccgccgcgct taatgcgccg   2220
ctacagggcg cgtcaggtgg cacttttcgg ggaaatgtgc gcggaacccc tatttgttta   2280
tttttctaaa tacattcaaa tatgtatccg ctcatgagac aataaccctg ataaatgctt   2340
caataatatt gaaaaaggaa gagtcctgag gcggaaagaa ccagctgtgg aatgtgtgtc   2400
agttagggtg tggaaagtcc ccaggctccc cagcaggcag aagtatgcaa agcatgcatc   2460
tcaattagtc agcaaccagg tgtggaaagt ccccaggctc cccagcaggc agaagtatgc   2520
aaagcatgca tctcaattag tcagcaacca tagtcccgcc cctaactccg cccatcccgc   2580
ccctaactcc gcccagttcc gcccattctc cgccccatgg ctgactaatt ttttttattt   2640
atgcagaggc cgaggccgcc tcggcctctg agctattcca gaagtagtga ggaggctttt   2700
ttggaggcct aggcttttgc aaagatcgat caagagacag gatgaggatc gtttcgcatg   2760
attgaacaag atggattgca cgcaggttct ccggccgctt gggtggagag gctattcggc   2820
tatgactggg cacaacagac aatcggctgc tctgatgccg ccgtgttccg gctgtcagcg   2880
caggggcgcc cggttctttt tgtcaagacc gacctgtccg gtgccctgaa tgaactgcaa   2940
gacgaggcag cgcggctatc gtggctggcc acgacgggcg ttccttgcgc agctgtgctc   3000
gacgttgtca ctgaagcggg aagggactgg ctgctattgg gcgaagtgcc ggggcaggat   3060
ctcctgtcat ctcaccttgc tcctgccgag aaagtatcca tcatggctga tgcaatgcgg   3120
cggctgcata cgcttgatcc ggctacctgc ccattcgacc accaagcgaa acatcgcatc   3180
gagcgagcac gtactcggat ggaagccggt cttgtcgatc aggatgatct ggacgaagag   3240
catcaggggc tcgcgccagc cgaactgttc gccaggctca aggcgagcat gcccgacggc   3300
gaggatctcg tcgtgaccca tggcgatgcc tgcttgccga atatcatggt ggaaaatggc   3360
cgcttttctg gattcatcga ctgtggccgg ctgggtgtgg cggaccgcta tcaggacata   3420
gcgttggcta cccgtgatat tgctgaagag cttggcggcg aatgggctga ccgcttcctc   3480
gtgctttacg gtatcgccgc tcccgattcg cagcgcatcg ccttctatcg ccttcttgac   3540
gagttcttct gagcgggact ctggggttcg aaatgaccga ccaagcgacg cccaacctgc   3600
catcacgaga tttcgattcc accgccgcct tctatgaaag gttgggcttc ggaatcgttt   3660
tccgggacgc cggctggatg atcctccagc gcggggatct catgctggag ttcttcgccc   3720
accctagggg gaggctaact gaaacacgga aggagacaat accggaagga acccgcgcta   3780
tgacggcaat aaaaagacag aataaaacgc acggtgttgg gtcgtttgtt cataaacgcg   3840
gggttcggtc ccagggctgg cactctgtcg ataccccacc gagaccccat tggggccaat   3900
acgcccgcgt ttcttccttt tccccacccc accccccaag ttcgggtgaa ggcccagggc   3960
tcgcagccaa cgtcggggcg gcaggccctg ccatagcctc aggttactca tatatacttt   4020
agattgattt aaaacttcat ttttaattta aaaggatcta ggtgaagatc ctttttgata   4080
atctcatgac caaaatccct taacgtgagt tttcgttcca ctgagcgtca gaccccgtag   4140
aaaagatcaa aggatcttct tgagatcctt tttttctgcg cgtaatctgc tgcttgcaaa   4200
caaaaaaacc accgctacca gcggtggttt gtttgccgga tcaagagcta ccaactcttt   4260
ttccgaaggt aactggcttc agcagagcgc agataccaaa tactgtcctt ctagtgtagc   4320
cgtagttagg ccaccacttc aagaactctg tagcaccgcc tacatacctc gctctgctaa   4380
tcctgttacc agtggctgct gccagtggcg ataagtcgtg tcttaccggg ttggactcaa   4440
```

-continued

```
gacgatagtt accggataag gcgcagcggt cgggctgaac ggggggttcg tgcacacagc   4500

ccagcttgga gcgaacgacc tacaccgaac tgagatacct acagcgtgag ctatgagaaa   4560

gcgccacgct tcccgaaggg agaaaggcgg acaggtatcc ggtaagcggc agggtcggaa   4620

caggagagcg cacgagggag cttccagggg gaaacgcctg gtatctttat agtcctgtcg   4680

ggtttcgcca cctctgactt gagcgtcgat ttttgtgatg ctcgtcaggg gggcggagcc   4740

tatggaaaaa cgccagcaac gcggcctttt tacggttcct ggccttttgc tggccttttg   4800

ctcacatgtt ctttcctgcg ttatcccctg attctgtgga taaccgtatt accgccatgc   4860

at                                                                  4862
```

<210> SEQ ID NO 88
<211> LENGTH: 5192
<212> TYPE: DNA
<213> ORGANISM: Artificial Sequence
<220> FEATURE:
<223> OTHER INFORMATION: pIRESpuro2 plasmid from Clontech

<400> SEQUENCE: 88

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttggtacc    900

gagctcggat cgatatctgc ggcctagcta gcgcttaagg cctgttaacc ggtcgtacgt    960

ctccggattc gaattcggat ccgcggccgc atagataact gatccagtgt gctggaatta   1020

attcgctgtc tgcgagggcc agctgttggg gtgagtactc cctctcaaaa gcgggcatga   1080

cttctgcgct aagattgtca gtttccaaaa acgaggagga tttgatattc acctggcccg   1140

cggtgatgcc tttgagggtg gccgcgtcca tctggtcaga aaagacaatc tttttgttgt   1200

caagcttgag gtgtggcagg cttgagatct ggccatacac ttgagtgaca atgacatcca   1260

ctttgccttt ctctccacag gtgtccactc ccaggtccaa ctgcaggtcg agcatgcatc   1320

tagggcggcc aattccgccc ctctccctcc cccccccta acgttactgg ccgaagccgc    1380

ttggaataag gccggtgtgc gtttgtctat atgtgatttt ccaccatatt gccgtctttt   1440

ggcaatgtga gggcccggaa acctggccct gtcttcttga cgagcattcc taggggtctt   1500

tcccctctcg ccaaaggaat gcaaggtctg ttgaatgtcg tgaaggaagc agttcctctg   1560

gaagcttctt gaagacaaac aacgtctgta gcgacccttt gcaggcagcg gaacccccca   1620
```

-continued

```
cctggcgaca ggtgcctctg cggccaaaag ccacgtgtat aagatacacc tgcaaaggcg   1680
gcacaacccc agtgccacgt tgtgagttgg atagttgtgg aaagagtcaa atggctctcc   1740
tcaagcgtat tcaacaaggg gctgaaggat gcccagaagg taccccattg tatgggatct   1800
gatctggggc ctcggtgcac atgctttaca tgtgtttagt cgaggttaaa aaaacgtcta   1860
ggccccccga accacgggga cgtggttttc ctttgaaaaa cacgatgata agcttgccac   1920
aacccacaag gagacgacct tccatgaccg agtacaagcc cacggtgcgc ctcgccaccc   1980
gcgacgacgt cccccgggcc gtacgcaccc tcgccgccgc gttcgccgac taccccgcca   2040
cgcgccacac cgtcgacccg gaccgccaca tcgagcgggt caccgagctg caagaactct   2100
tcctcacgcg cgtcgggctc gacatcggca aggtgtgggt cgcggacgac ggcgccgcgg   2160
tggcggtctg gaccacgccg gagagcgtcg aagcgggggc ggtgttcgcc gagatcggcc   2220
cgcgcatggc cgagttgagc ggttcccggc tggccgcgca gcaacagatg gaaggcctcc   2280
tggcgccgca ccggcccaag gagcccgcgt ggttcctggc caccgtcggc gtctcgcccg   2340
accaccaggg caagggtctg ggcagcgccg tcgtgctccc cggagtggag gcggccgagc   2400
gcgccggggt gcccgccttc ctggagacct ccgcgccccg caacctcccc ttctacgagc   2460
ggctcggctt caccgtcacc gccgacgtcg agtgcccgaa ggaccgcgcg acctggtgca   2520
tgacccgcaa gcccggtgcc tgacgcccgc cccacgaccc gcagcgcccg accgaaagga   2580
gcgcacgacc ccatggctcc gaccgaagcc gacccgggcg gccccgccga ccccgcaccc   2640
gcccccgagg cccaccgact ctagagctcg ctgatcagcc tcgactgtgc cttctagttg   2700
ccagccatct gttgtttgcc cctcccccgt gccttccttg accctggaag gtgccactcc   2760
cactgtcctt tcctaataaa atgaggaaat tgcatcgcat tgtctgagta ggtgtcattc   2820
tattctgggg ggtggggtgg ggcaggacag caagggggag gattgggaag acaatagcag   2880
gcatgctggg gatgcggtgg gctctatggc ttctgaggcg gaaagaacca gctggggctc   2940
gagtgcattc tagttgtggt ttgtccaaac tcatcaatgt atcttatcat gtctgtatac   3000
cgtcgacctc tagctagagc ttggcgtaat catggtcata gctgtttcct gtgtgaaatt   3060
gttatccgct cacaattcca cacaacatac gagccggaag cataaagtgt aaagcctggg   3120
gtgcctaatg agtgagctaa ctcacattaa ttgcgttgcg ctcactgccc gctttccagt   3180
cgggaaacct gtcgtgccag ctgcattaat gaatcggcca acgcgcgggg agaggcggtt   3240
tgcgtattgg gcgctcttcc gcttcctcgc tcactgactc gctgcgctcg gtcgttcggc   3300
tgcggcgagc ggtatcagct cactcaaagg cggtaatacg gttatccaca gaatcagggg   3360
ataacgcagg aaagaacatg tgagcaaaag gccagcaaaa ggccaggaac cgtaaaaagg   3420
ccgcgttgct ggcgtttttc cataggctcc gcccccctga cgagcatcac aaaaatcgac   3480
gctcaagtca gaggtggcga aacccgacag gactataaag ataccaggcg tttccccctg   3540
gaagctccct cgtgcgctct cctgttccga ccctgccgct taccggatac ctgtccgcct   3600
ttctcccttc gggaagcgtg gcgctttctc aatgctcacg ctgtaggtat ctcagttcgg   3660
tgtaggtcgt tcgctccaag ctgggctgtg tgcacgaacc ccccgttcag cccgaccgct   3720
gcgccttatc cggtaactat cgtcttgagt ccaacccggt aagacacgac ttatcgccac   3780
tggcagcagc cactggtaac aggattagca gagcgaggta tgtaggcggt gctacagagt   3840
tcttgaagtg gtggcctaac tacggctaca ctagaaggac agtatttggt atctgcgctc   3900
tgctgaagcc agttaccttc ggaaaaagag ttggtagctc ttgatccggc aaacaaacca   3960
```

-continued

```
ccgctggtag cggtggtttt tttgtttgca agcagcagat tacgcgcaga aaaaaaggat   4020

ctcaagaaga tcctttgatc ttttctacgg ggtctgacgc tcagtggaac gaaaactcac   4080

gttaagggat tttggtcatg agattatcaa aaaggatctt cacctagatc cttttaaatt   4140

aaaaatgaag ttttaaatca atctaaagta tatatgagta aacttggtct gacagttacc   4200

aatgcttaat cagtgaggca cctatctcag cgatctgtct atttcgttca tccatagttg   4260

cctgactccc cgtcgtgtag ataactacga tacgggaggg cttaccatct ggccccagtg   4320

ctgcaatgat accgcgagac ccacgctcac cggctccaga tttatcagca ataaaccagc   4380

cagccggaag ggccgagcgc agaagtggtc ctgcaacttt atccgcctcc atccagtcta   4440

ttaattgttg ccgggaagct agagtaagta gttcgccagt taatagtttg cgcaacgttg   4500

ttgccattgc tacaggcatc gtggtgtcac gctcgtcgtt tggtatggct tcattcagct   4560

ccggttccca acgatcaagg cgagttacat gatcccccat gttgtgcaaa aaagcggtta   4620

gctccttcgg tcctccgatc gttgtcagaa gtaagttggc cgcagtgtta tcactcatgg   4680

ttatggcagc actgcataat tctcttactg tcatgccatc cgtaagatgc ttttctgtga   4740

ctggtgagta ctcaaccaag tcattctgag aatagtgtat gcggcgaccg agttgctctt   4800

gcccggcgtc aatacgggat aataccgcgc cacatagcag aactttaaaa gtgctcatca   4860

ttggaaaacg ttcttcgggg cgaaaactct caaggatctt accgctgttg agatccagtt   4920

cgatgtaacc cactcgtgca cccaactgat cttcagcatc ttttactttc accagcgttt   4980

ctgggtgagc aaaaacagga aggcaaaatg ccgcaaaaaa gggaataagg gcgacacgga   5040

aatgttgaat actcatactc ttcctttttc aatattattg aagcatttat cagggttatt   5100

gtctcatgag cggatacata tttgaatgta tttagaaaaa taaacaaata ggggttccgc   5160

gcacatttcc ccgaaaagtg ccacctgacg tc                                  5192
```

<210> SEQ ID NO 89
<211> LENGTH: 11182
<212> TYPE: DNA
<213> ORGANISM: Artificial Sequence
<220> FEATURE:
<223> OTHER INFORMATION: pAg1 Plasmid

<400> SEQUENCE: 89

```
catgccaacc acagggttcc cctcgggatc aaagtacttt gatccaaccc ctccgctgct     60

atagtgcagt cggcttctga cgttcagtgc agccgtcttc tgaaaacgac atgtcgcaca    120

agtcctaagt tacgcgacag gctgccgccc tgcccttttc ctggcgtttt cttgtcgcgt    180

gttttagtcg cataaagtag aatacttgcg actagaaccg gagacattac gccatgaaca    240

agagcgccgc cgctggcctg ctgggctatg cccgcgtcag caccgacgac caggacttga    300

ccaaccaacg ggccgaactg cacgcggccg gctgcaccaa gctgttttcc gagaagatca    360

ccggcaccag gcgcgaccgc ccggagctgg ccaggatgct tgaccaccta cgccctggcg    420

acgttgtgac agtgaccagg ctagaccgcc tggcccgcag cacccgcgac ctactggaca    480

ttgccgagcg catccaggag gccggcgcgg gcctgcgtag cctggcagag ccgtgggccg    540

acaccaccac gccggccggc cgcatggtgt tgaccgtgtt cgccggcatt gccgagttcg    600

agcgttccct aatcatcgac cgcacccgga gcgggcgcga ggccgccaag gcccgaggcg    660

tgaagtttgg cccccgccct accctcaccc cggcacagat cgcgcacgcc cgcgagctga    720

tcgaccagga aggccgcacc gtgaaagagg cggctgcact gcttggcgtg catcgctcga    780

ccctgtaccg cgcacttgag cgcagcgagg aagtgacgcc caccgaggcc aggcggcgcg    840
```

-continued

```
gtgccttccg tgaggacgca ttgaccgagg ccgacgccct ggcggccgcc gagaatgaac    900
gccaagagga acaagcatga aaccgcacca ggacggccag gacgaaccgt ttttcattac    960
cgaagagatc gaggcggaga tgatcgcggc cgggtacgtg ttcgagccgc ccgcgcacgt   1020
ctcaaccgtg cggctgcatg aaatcctggc cggtttgtct gatgccaagc tggcggcctg   1080
gccggccagc ttggccgctg aagaaaccga gcgccgccgt ctaaaaaggt gatgtgtatt   1140
tgagtaaaac agcttgcgtc atgcggtcgc tgcgtatatg atgcgatgag taaataaaca   1200
aatacgcaag gggaacgcat gaaggttatc gctgtactta accagaaagg cgggtcaggc   1260
aagacgacca tcgcaaccca tctagcccgc gccctgcaac tcgccggggc cgatgttctg   1320
ttagtcgatt ccgatcccca gggcagtgcc cgcgattggg cggccgtgcg ggaagatcaa   1380
ccgctaaccg ttgtcggcat cgaccgcccg acgattgacc gcgacgtgaa ggccatcggc   1440
cggcgcgact tcgtagtgat cgacggagcg ccccaggcgg cggacttggc tgtgtccgcg   1500
atcaaggcag ccgacttcgt gctgattccg gtgcagccaa gcccttacga catatgggcc   1560
accgccgacc tggtggagct ggttaagcag cgcattgagg tcacggatgg aaggctacaa   1620
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tcccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact tttgatcga tcccggcatc ggccgttttc tctaccgcct   3120
ggcacgccgc gccgcaggca aggcagaagc cagatggttg ttcaagacga tctacgaacg   3180
```

-continued

```
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgcattctag gtactaaaac aattcatcca gtaaaatata   4980
atattttatt ttctcccaat caggcttgat ccccagtaag tcaaaaaata gctcgacata   5040
ctgttcttcc ccgatatcct ccctgatcga ccggacgcag aaggcaatgt cataccactt   5100
gtccgccctg ccgcttctcc caagatcaat aaagccactt actttgccat ctttcacaaa   5160
gatgttgctg tctcccaggt cgccgtggga aaagacaagt tcctcttcgg gcttttccgt   5220
ctttaaaaaa tcatacagct cgcgcggatc tttaaatgga gtgtcttctt cccagttttc   5280
gcaatccaca tcggccagat cgttattcag taagtaatcc aattcggcta agcggctgtc   5340
taagctattc gtatagggac aatccgatat gtcgatggag tgaaagagcc tgatgcactc   5400
cgcatacagc tcgataatct tttcagggct ttgttcatct tcatactctt ccgagcaaag   5460
gacgccatcg gcctcactca tgagcagatt gctccagcca tcatgccgtt caaagtgcag   5520
gacctttgga acaggcagct ttccttccag ccatagcatc atgtcctttt cccgttccac   5580
```

-continued

```
atcataggtg gtccctttat accggctgtc cgtcattttt aaatataggt tttcattttc   5640
tcccaccagc ttatatacct tagcaggaga cattccttcc gtatctttta cgcagcggta   5700
tttttcgatc agtttttttca attccggtga tattctcatt ttagccattt attatttcct   5760
tcctcttttc tacagtattt aaagataccc caagaagcta attataacaa gacgaactcc   5820
aattcactgt tccttgcatt ctaaaacctt aaataccaga aaacagcttt ttcaaagttg   5880
ttttcaaagt tggcgtataa catagtatcg acggagccga ttttgaaacc gcggtgatca   5940
caggcagcaa cgctctgtca tcgttacaat caacatgcta ccctccgcga gatcatccgt   6000
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc gggggatctg gattttagta ctggattttg   6300
gttttaggaa ttagaaattt tattgataga agtattttac aaatacaaat acatactaag   6360
ggtttcttat atgctcaaca catgagcgaa accctatagg aaccctaatt cccttatctg   6420
ggaactactc acacattatt atggagaaac tcgagtcaaa tctcggtgac gggcaggacc   6480
ggacggggcg gtaccggcag gctgaagtcc agctgccaga aacccacgtc atgccagttc   6540
ccgtgcttga agccggccgc ccgcagcatg ccgcgggggg catatccgag cgcctcgtgc   6600
atgcgcacgc tcgggtcgtt gggcagcccg atgacagcga ccacgctctt gaagccctgt   6660
gcctccaggg acttcagcag gtgggtgtag agcgtggagc ccagtcccgt ccgctggtgg   6720
cggggggaga cgtacacggt cgactcggcc gtccagtcgt aggcgttgcg tgccttccag   6780
gggcccgcgt aggcgatgcc ggcgacctcg ccgtccacct cggcgacgag ccagggatag   6840
cgctcccgca gacggacgag gtcgtccgtc cactcctgcg gttcctgcgg ctcggtacgg   6900
aagttgaccg tgcttgtctc gatgtagtgg ttgacgatgg tgcagaccgc cggcatgtcc   6960
gcctcggtgg cacggcggat gtcggccggg cgtcgttctg ggctcatggt agactcgaga   7020
gagatagatt tgtagagaga gactggtgat ttcagcgtgt cctctccaaa tgaaatgaac   7080
ttccttatat agaggaaggt cttgcgaagg atagtgggat tgtgcgtcat cccttacgtc   7140
agtggagata tcacatcaat ccacttgctt tgaagacgtg gttggaacgt cttctttttc   7200
cacgatgctc ctcgtgggtg ggggtccatc tttgggacca ctgtcggcag aggcatcttg   7260
aacgatagcc tttcctttat cgcaatgatg gcatttgtag gtgccacctt ccttttctac   7320
tgtccttttg atgaagtgac agatagctgg gcaatggaat ccgaggaggt ttcccgatat   7380
taccctttgt tgaaaagtct caatagccct ttggtcttct gagactgtat ctttgatatt   7440
cttggagtag acgagagtgt cgtgctccac catgttatca catcaatcca cttgctttga   7500
agacgtggtt ggaacgtctt ctttttccac gatgctcctc gtgggtgggg gtccatcttt   7560
gggaccactg tcggcagagg catcttgaac gatagccttt cctttatcgc aatgatggca   7620
tttgtaggtg ccaccttcct tttctactgt ccttttgatg aagtgacaga tagctgggca   7680
atggaatccg aggaggtttc ccgatattac cctttgttga aaagtctcaa tagccctttg   7740
gtcttctgag actgtatctt tgatattctt ggagtagacg agagtgtcgt gctccaccat   7800
gttggcaagc tgctctagcc aatacgcaaa ccgcctctcc ccgcgcgttg gccgattcat   7860
taatgcagct ggcacgacag gtttcccgac tggaaagcgg gcagtgagcg caacgcaatt   7920
```

-continued

```
aatgtgagtt agctcactca ttaggcaccc caggctttac actttatgct tccggctcgt   7980
atgttgtgtg gaattgtgag cggataacaa tttcacacag gaaacagcta tgaccatgat   8040
tacgaattcg agccttgact agagggtcga cggtatacag acatgataag atacattgat   8100
gagtttggac aaaccacaac tagaatgcag tgaaaaaaat gctttatttg tgaaatttgt   8160
gatgctattg ctttatttgt aaccattata agctgcaata aacaagttgg ggtgggcgaa   8220
gaactccagc atgagatccc cgcgctggag gatcatccag ccggcgtccc ggaaaacgat   8280
tccgaagccc aacctttcat agaaggcggc ggtggaatcg aaatctcgta gcacgtgtca   8340
gtcctgctcc tcggccacga agtgcacgca gttgccggcc gggtcgcgca gggcgaactc   8400
ccgcccccac ggctgctcgc cgatctcggt catggccggc ccggaggcgt cccggaagtt   8460
cgtggacacg acctccgacc actcggcgta cagctcgtcc aggccgcgca cccacaccca   8520
ggccagggtg ttgtccggca ccacctggtc ctggaccgcg ctgatgaaca gggtcacgtc   8580
gtcccggacc acaccggcga agtcgtcctc cacgaagtcc cgggagaacc cgagccggtc   8640
ggtccagaac tcgaccgctc cggcgacgtc gcgcgcggtg agcaccggaa cggcactggt   8700
caacttggcc atggatccag atttcgctca agttagtata aaaaagcagg cttcaatcct   8760
gcaggaattc gatcgacact ctcgtctact ccaagaatat caaagataca gtctcagaag   8820
accaaagggc tattgagact tttcaacaaa gggtaatatc gggaaacctc ctcggattcc   8880
attgcccagc tatctgtcac ttcatcaaaa ggacagtaga aaaggaaggt ggcacctaca   8940
aatgccatca ttgcgataaa ggaaaggcta tcgttcaaga tgcctctgcc gacagtggtc   9000
ccaaagatgg acccccaccc acgaggagca tcgtggaaaa agaagacgtt ccaaccacgt   9060
cttcaaagca agtggattga tgtgataaca tggtggagca cgacactctc gtctactcca   9120
agaatatcaa agatacagtc tcagaagacc aaagggctat tgagactttt caacaaaggg   9180
taatatcggg aaacctcctc ggattccatt gcccagctat ctgtcacttc atcaaaagga   9240
cagtagaaaa ggaaggtggc acctacaaat gccatcattg cgataaagga aaggctatcg   9300
ttcaagatgc ctctgccgac agtggtccca aagatggacc cccacccacg aggagcatcg   9360
tggaaaaaga agacgttcca accacgtctt caaagcaagt ggattgatgt gatatctcca   9420
ctgacgtaag ggatgacgca caatcccact atccttcgca agacccttcct ctatataagg   9480
aagttcattt catttggaga ggacacgctg aaatcaccag tctctctcta caaatctatc   9540
tctctcgagc tttcgcagat ccggggggc aatgagatat gaaaaagcct gaactcaccg   9600
cgacgtctgt cgagaagttt ctgatcgaaa agttcgacag cgtctccgac ctgatgcagc   9660
tctcggaggg cgaagaatct cgtgctttca gcttcgatgt aggagggcgt ggatatgtcc   9720
tgcgggtaaa tagctgcgcc gatggtttct acaaagatcg ttatgtttat cggcactttg   9780
catcggccgc gctcccgatt ccggaagtgc ttgacattgg ggagtttagc gagagcctga   9840
cctattgcat ctcccgccgt gcacagggtg tcacgttgca agacctgcct gaaaccgaac   9900
tgcccgctgt tctacaaccg gtcgcggagg ctatggatgc gatcgctgcg gccgatctta   9960
gccagacgag cgggttcggc ccattcggac cgcaaggaat cggtcaatac actacatggc  10020
gtgatttcat atgcgcgatt gctgatcccc atgtgtatca ctggcaaact gtgatggacg  10080
acaccgtcag tgcgtccgtc gcgcaggctc tcgatgagct gatgctttgg gccgaggact  10140
gccccgaagt ccggcacctc gtgcacgcgg atttcggctc caacaatgtc ctgacggaca  10200
atggccgcat aacagcggtc attgactgga gcgaggcgat gttcggggat tcccaatacg  10260
aggtcgccaa catcttcttc tggaggccgt ggttggcttg tatggagcag cagacgcgct  10320
```

-continued acttcgagcg gaggcatccg gagcttgcag gatcgccacg actccgggcg tatatgctcc 10380
gcattggtct tgaccaactc tatcagagct tggttgacgg caatttcgat gatgcagctt 10440
gggcgcaggg tcgatgcgac gcaatcgtcc gatccggagc cgggactgtc gggcgtacac 10500
aaatcgcccg cagaagcgcg gccgtctgga ccgatggctg tgtagaagta ctcgccgata 10560
gtggaaaccg acgccccagc actcgtccga gggcaaagaa atagagtaga tgccgaccgg 10620
atctgtcgat cgacaagctc gagtttctcc ataataatgt gtgagtagtt cccagataag 10680
ggaattaggg ttcctatagg gtttcgctca tgtgttgagc atataagaaa cccttagtat 10740
gtatttgtat ttgtaaaata cttctatcaa taaaatttct aattcctaaa accaaaatcc 10800
agtactaaaa tccagatccc ccgaattaat tcggcgttaa ttcagatcaa gcttggcact 10860
ggccgtcgtt ttacaacgtc gtgactggga aaaccctggc gttacccaac ttaatcgcct 10920
tgcagcacat ccccctttcg ccagctggcg taatagcgaa gaggcccgca ccgatcgccc 10980
ttcccaacag ttgcgcagcc tgaatggcga atgctagagc agcttgagct tggatcagat 11040
tgtcgtttcc cgccttcagt ttaaactatc agtgtttgac aggatatatt ggcgggtaaa 11100
cctaagagaa aagagcgttt attagaataa cggatattta aaagggcgtg aaaaggttta 11160
tccgttcgtc catttgtatg tg 11182

<210> SEQ ID NO 90
<211> LENGTH: 8428
<212> TYPE: DNA
<213> ORGANISM: Artificial Sequence
<220> FEATURE:
<223> OTHER INFORMATION: pCambia3300 Plasmid

<400> SEQUENCE: 90
catgccaacc acagggttcc cctcgggatc aaagtacttt gatccaaccc ctccgctgct 60
atagtgcagt cggcttctga cgttcagtgc agccgtcttc tgaaaacgac atgtcgcaca 120
agtcctaagt tacgcgacag gctgccgccc tgcccttttc ctggcgtttt cttgtcgcgt 180
gttttagtcg cataaagtag aatacttgcg actagaaccg gagacattac gccatgaaca 240
agagcgccgc cgctggcctg ctgggctatg cccgcgtcag caccgacgac caggacttga 300
ccaaccaacg ggccgaactg cacgcggccg gctgcaccaa gctgttttcc gagaagatca 360
ccggcaccag gcgcgaccgc ccggagctgg ccaggatgct tgaccaccta cgccctggcg 420
acgttgtgac agtgaccagg ctagaccgcc tggcccgcag cacccgcgac ctactggaca 480
ttgccgagcg catccaggag gccggcgcgg gcctgcgtag cctggcagag ccgtgggccg 540
acaccaccac gccggccggc cgcatggtgt tgaccgtgtt cgccggcatt gccgagttcg 600
agcgttccct aatcatcgac cgcacccgga gcgggcgcga ggccgccaag gcccgaggcg 660
tgaagtttgg cccccgccct accctcaccc cggcacagat cgcgcacgcc cgcgagctga 720
tcgaccagga aggccgcacc gtgaaagagg cggctgcact gcttggcgtg catcgctcga 780
ccctgtaccg cgcacttgag cgcagcgagg aagtgacgcc caccgaggcc aggcggcgcg 840
gtgccttccg tgaggacgca ttgaccgagg ccgacgccct ggcggccgcc gagaatgaac 900
gccaagagga acaagcatga aaccgcacca ggacggccag gacgaaccgt tttcattac 960 cgaagagatc gaggcggaga tgatcgcggc cgggtacgtg ttcgagccgc ccgcgcacgt 1020
ctcaaccgtg cggctgcatg aaatcctggc cggtttgtct gatgccaagc tggcggcctg 1080
gccggccagc ttggccgctg aagaaaccga gcgccgccgt ctaaaaaggt gatgtgtatt 1140

-continued tgagtaaaac agcttgcgtc atgcggtcgc tgcgtatatg atgcgatgag taaataaaca 1200
aatacgcaag gggaacgcat gaaggttatc gctgtactta accagaaagg cgggtcaggc 1260
aagacgacca tcgcaaccca tctagcccgc gccctgcaac tcgccggggc cgatgttctg 1320
ttagtcgatt ccgatcccca gggcagtgcc cgcgattggg cggccgtgcg ggaagatcaa 1380
ccgctaaccg ttgtcggcat cgaccgcccg acgattgacc gcgacgtgaa ggccatcggc 1440
cggcgcgact tcgtagtgat cgacggagcg ccccaggcgg cggacttggc tgtgtccgcg 1500
atcaaggcag ccgacttcgt gctgattccg gtgcagccaa gcccttacga catatgggcc 1560
accgccgacc tggtggagct ggttaagcag cgcattgagg tcacggatgg aaggctacaa 1620
gcggcctttg tcgtgtcgcg ggcgatcaaa ggcacgcgca tcggcggtga ggttgccgag 1680
gcgctggccg ggtacgagct gcccattctt gagtcccgta tcacgcagcg cgtgagctac 1740
ccaggcactg ccgccgccgg cacaaccgtt cttgaatcag aacccgaggg cgacgctgcc 1800
cgcgaggtcc aggcgctggc cgctgaaatt aaatcaaaac tcatttgagt taatgaggta 1860
aagagaaaat gagcaaaagc acaaacacgc taagtgccgg ccgtccgagc gcacgcagca 1920
gcaaggctgc aacgttggcc agcctggcag acacgccagc catgaagcgg gtcaactttc 1980
agttgccggc ggaggatcac accaagctga agatgtacgc ggtacgccaa ggcaagacca 2040
ttaccgagct gctatctgaa tacatcgcgc agctaccaga gtaaatgagc aaatgaataa 2100
atgagtagat gaattttagc ggctaaagga ggcggcatgg aaaatcaaga acaaccaggc 2160
accgacgccg tggaatgccc catgtgtgga ggaacgggcg gttggccagg cgtaagcggc 2220
tgggttgtct gccggccctg caatggcact ggaaccccca agcccgagga atcggcgtga 2280
cggtcgcaaa ccatccggcc cggtacaaat cggcgcggcg ctgggtgatg acctggtgga 2340
gaagttgaag gccgcgcagg ccgcccagcg gcaacgcatc gaggcagaag cacgccccgg 2400
tgaatcgtgg caagcggccg ctgatcgaat ccgcaaagaa tcccggcaac cgccggcagc 2460
cggtgcgccg tcgattagga agccgcccaa gggcgacgag caaccagatt ttttcgttcc 2520
gatgctctat gacgtgggca cccgcgatag tcgcagcatc atggacgtgg ccgttttccg 2580
tctgtcgaag cgtgaccgac gagctggcga ggtgatccgc tacgagcttc cagacgggca 2640
cgtagaggtt tccgcagggc cggccggcat ggccagtgtg tgggattacg acctggtact 2700
gatggcggtt tcccatctaa ccgaatccat gaaccgatac cgggaaggga agggagacaa 2760
gcccggccgc gtgttccgtc cacacgttgc ggacgtactc aagttctgcc ggcgagccga 2820
tggcggaaag cagaaagacg acctggtaga aacctgcatt cggttaaaca ccacgcacgt 2880
tgccatgcag cgtacgaaga aggccaagaa cggccgcctg gtgacggtat ccgagggtga 2940
agccttgatt agccgctaca agatcgtaaa gagcgaaacc gggcggccgg agtacatcga 3000
gatcgagcta gctgattgga tgtaccgcga gatcacagaa ggcaagaacc cggacgtgct 3060
gacggttcac cccgattact ttttgatcga tcccggcatc ggccgttttc tctaccgcct 3120
ggcacgccgc gccgcaggca aggcagaagc cagatggttg ttcaagacga tctacgaacg 3180
cagtggcagc gccggagagt tcaagaagtt ctgtttcacc gtgcgcaagc tgatcgggtc 3240
aaatgacctg ccggagtacg atttgaagga ggaggcgggg caggctggcc cgatcctagt 3300
catgcgctac cgcaacctga tcgagggcga agcatccgcc ggttcctaat gtacggagca 3360
gatgctaggg caaattgccc tagcagggga aaaaggtcga aaaggtctct ttcctgtgga 3420
tagcacgtac attgggaacc caaagccgta cattgggaac cggaacccgt acattgggaa 3480
cccaaagccg tacattggga accggtcaca catgtaagtg actgatataa aagagaaaaa 3540

-continued

```
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
gattgtactg agagtgcacc atatgcggtg tgaaataccg cacagatgcg taaggagaaa   4080
ataccgcatc aggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcatagctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgcattctag gtactaaaac aattcatcca gtaaaatata   4980
atattttatt ttctcccaat caggcttgat ccccagtaag tcaaaaaata gctcgacata   5040
ctgttcttcc ccgatatcct ccctgatcga ccggacgcag aaggcaatgt cataccactt   5100
gtccgccctg ccgcttctcc caagatcaat aaagccactt actttgccat ctttcacaaa   5160
gatgttgctg tctcccaggt cgccgtggga aaagacaagt tcctcttcgg gcttttccgt   5220
ctttaaaaaa tcatacagct cgcgcggatc tttaaatgga gtgtcttctt cccagttttc   5280
gcaatccaca tcggccagat cgttattcag taagtaatcc aattcggcta agcggctgtc   5340
taagctattc gtatagggac aatccgatat gtcgatggag tgaaagagcc tgatgcactc   5400
cgcatacagc tcgataatct tttcagggct ttgttcatct tcatactctt ccgagcaaag   5460
gacgccatcg gcctcactca tgagcagatt gctccagcca tcatgccgtt caaagtgcag   5520
gacctttgga acaggcagct ttccttccag ccatagcatc atgtcctttt cccgttccac   5580
atcataggtg gtccctttat accggctgtc cgtcattttt aaatataggt tttcattttc   5640
tcccaccagc ttatatacct tagcaggaga cattccttcc gtatctttta cgcagcggta   5700
tttttcgatc agtttttca attccggtga tattctcatt ttagccattt attatttcct   5760
tcctcttttc tacagtattt aaagataccc caagaagcta attataacaa gacgaactcc   5820
aattcactgt tccttgcatt ctaaaacctt aaataccaga aacagcttt ttcaaagttg   5880
```

-continued

```
ttttcaaagt tggcgtataa catagtatcg acggagccga ttttgaaacc gcggtgatca   5940
caggcagcaa cgctctgtca tcgttacaat caacatgcta ccctccgcga gatcatccgt   6000
gtttcaaacc cggcagctta gttgccgttc ttccgaatag catcggtaac atgagcaaag   6060
tctgccgcct tacaacggct ctcccgctga cgccgtcccg gactgatggg ctgcctgtat   6120
cgagtggtga ttttgtgccg agctgccggt cggggagctg ttggctggct ggtggcagga   6180
tatattgtgg tgtaaacaaa ttgacgctta gacaacttaa taacacattg cggacgtttt   6240
taatgtactg aattaacgcc gaattaattc gggggatctg gattttagta ctggattttg   6300
gttttaggaa ttagaaattt tattgataga agtattttac aaatacaaat acatactaag   6360
ggtttcttat atgctcaaca catgagcgaa accctatagg aaccctaatt cccttatctg   6420
ggaactactc acacattatt atggagaaac tcgagtcaaa tctcggtgac gggcaggacc   6480
ggacggggcg gtaccggcag gctgaagtcc agctgccaga aacccacgtc atgccagttc   6540
ccgtgcttga agccggccgc ccgcagcatg ccgcgggggg catatccgag cgcctcgtgc   6600
atgcgcacgc tcgggtcgtt gggcagcccg atgacagcga ccacgctctt gaagccctgt   6660
gcctccaggg acttcagcag gtgggtgtag agcgtggagc ccagtcccgt ccgctggtgg   6720
cggggggaga cgtacacggt cgactcggcc gtccagtcgt aggcgttgcg tgccttccag   6780
gggcccgcgt aggcgatgcc ggcgacctcg ccgtccacct cggcgacgag ccagggatag   6840
cgctcccgca gacggacgag gtcgtccgtc cactcctgcg gttcctgcgg ctcggtacgg   6900
aagttgaccg tgcttgtctc gatgtagtgg ttgacgatgg tgcagaccgc cggcatgtcc   6960
gcctcggtgg cacggcggat gtcggccggg cgtcgttctg ggctcatggt agactcgaga   7020
gagatagatt tgtagagaga gactggtgat ttcagcgtgt cctctccaaa tgaaatgaac   7080
ttccttatat agaggaaggt cttgcgaagg atagtgggat tgtgcgtcat cccttacgtc   7140
agtggagata tcacatcaat ccacttgctt tgaagacgtg gttggaacgt cttctttttc   7200
cacgatgctc ctcgtgggtg gggtccatc tttgggacca ctgtcggcag aggcatcttg    7260
aacgatagcc tttcctttat cgcaatgatg gcatttgtag gtgccacctt cctttctac    7320
tgtcctttg atgaagtgac agatagctgg gcaatggaat ccgaggaggt ttcccgatat    7380
taccctttgt tgaaaagtct caatagccct ttggtcttct gagactgtat ctttgatatt   7440
cttggagtag acgagagtgt cgtgctccac catgttatca catcaatcca cttgctttga   7500
agacgtggtt ggaacgtctt ctttttccac gatgctcctc gtgggtgggg gtccatcttt   7560
gggaccactg tcggcagagg catcttgaac gatagccttt cctttatcgc aatgatggca   7620
tttgtaggtg ccaccttcct tttctactgt cctttgatg aagtgacaga tagctgggca    7680
atggaatccg aggaggtttc ccgatattac cctttgttga aaagtctcaa tagccctttg   7740
gtcttctgag actgtatctt tgatattctt ggagtagacg agagtgtcgt gctccaccat   7800
gttggcaagc tgctctagcc aatacgcaaa ccgcctctcc ccgcgcgttg gccgattcat   7860
taatgcagct ggcacgacag gtttcccgac tggaaagcgg gcagtgagcg caacgcaatt   7920
aatgtgagtt agctcactca ttaggcaccc caggctttac actttatgct tccggctcgt   7980
atgttgtgtg gaattgtgag cggataacaa tttcacacag gaaacagcta tgaccatgat   8040
tacgaattcg agctcggtac ccggggatcc tctagagtcg acctgcaggc atgcaagctt   8100
ggcactggcc gtcgttttac aacgtcgtga ctgggaaaac cctggcgtta cccaacttaa   8160
tcgccttgca gcacatcccc ctttcgccag ctggcgtaat agcgaagagg cccgcaccga   8220
tcgcccttcc caacagttgc gcagcctgaa tggcgaatgc tagagcagct tgagcttgga   8280
```

-continued tcagattgtc gtttcccgcc ttcagtttaa actatcagtg tttgacagga tatattggcg 8340
ggtaaaccta agagaaaaga gcgtttatta gaataacgga tatttaaaag ggcgtgaaaa 8400
ggtttatccg ttcgtccatt tgtatgtg 8428

<210> SEQ ID NO 91
<211> LENGTH: 3438
<212> TYPE: DNA
<213> ORGANISM: Artificial Sequence
<220> FEATURE:
<223> OTHER INFORMATION: pLIT38attBZeo Plasmid

<400> SEQUENCE: 91
tcgaccctct agtcaaggcc ttaagtgagt cgtattacgg actggccgtc gttttacaac 60
gtcgtgactg ggaaaaccct ggcgttaccc aacttaatcg ccttgcagca catcccctt 120 tcgccagctg gcgtaatagc gaagaggccc gcaccgatcg cccttcccaa cagttgcgca 180
gcctgaatgg cgaatggcgc ttcgcttggt aataaagccc gcttcggcgg gctttttttt 240
gttaactacg tcaggtggca cttttcgggg aaatgtgcgc ggaaccccta tttgtttatt 300
tttctaaata cattcaaata tgtatccgct catgagacaa taaccctgat aaatgcttca 360
ataatattga aaaaggaaga gtatgagtat tcaacatttc cgtgtcgccc ttattccctt 420
ttttgcggca ttttgccttc ctgtttttgc tcacccagaa acgctggtga aagtaaaaga 480
tgctgaagat cagttgggtg cacgagtggg ttacatcgaa ctggatctca acagcggtaa 540
gatccttgag agttttcgcc ccgaagaacg ttctccaatg atgagcactt ttaaagttct 600
gctatgtggc gcggtattat cccgtgttga cgccgggcaa gagcaactcg gtcgccgcat 660
acactattct cagaatgact tggttgagta ctcaccagtc acagaaaagc atcttacgga 720
tggcatgaca gtaagagaat tatgcagtgc tgccataacc atgagtgata acactgcggc 780
caacttactt ctgacaacga tcggaggacc gaaggagcta accgcttttt tgcacaacat 840
gggggatcat gtaactcgcc ttgatcgttg ggaaccggag ctgaatgaag ccataccaaa 900
cgacgagcgt gacaccacga tgcctgtagc aatggcaaca acgttgcgca aactattaac 960
tggcgaacta cttactctag cttcccggca acaattaata gactggatgg aggcggataa 1020
agttgcagga ccacttctgc gctcggccct tccggctggc tggtttattg ctgataaatc 1080
tggagccggt gagcgtgggt ctcgcggtat cattgcagca ctggggccag atggtaagcc 1140
ctcccgtatc gtagttatct acacgacggg gagtcaggca actatggatg aacgaaatag 1200
acagatcgct gagataggtg cctcactgat taagcattgg taactgtcag accaagttta 1260
ctcatatata ctttagattg atttaccccg gttgataatc agaaaagccc caaaaacagg 1320
aagattgtat aagcaaatat ttaaattgta aacgttaata ttttgttaaa attcgcgtta 1380
aatttttgtt aaatcagctc attttttaac caataggccg aaatcggcaa aatcccttat 1440
aaatcaaaag aatagcccga gatagggttg agtgttgttc cagtttggaa caagagtcca 1500
ctattaaaga acgtggactc caacgtcaaa gggcgaaaaa ccgtctatca gggcgatggc 1560
ccactacgtg aaccatcacc caaatcaagt tttttggggt cgaggtgccg taaagcacta 1620
aatcggaacc ctaaagggag cccccgattt agagcttgac ggggaaagcg aacgtggcga 1680
gaaaggaagg gaagaaagcg aaaggagcgg gcgctagggc gctggcaagt gtagcggtca 1740
cgctgcgcgt aaccaccaca cccgccgcgc ttaatgcgcc gctacagggc gcgtaaaagg 1800
atctaggtga agatcctttt tgataatctc atgaccaaaa tcccttaacg tgagttttcg 1860

-continued

```
ttccactgag cgtcagaccc cgtagaaaag atcaaaggat cttcttgaga tcctttttt   1920

ctgcgcgtaa tctgctgctt gcaaacaaaa aaaccaccgc taccagcggt ggtttgtttg   1980

ccggatcaag agctaccaac tctttttccg aaggtaactg gcttcagcag agcgcagata   2040

ccaaatactg ttcttctagt gtagccgtag ttaggccacc acttcaagaa ctctgtagca   2100

ccgcctacat acctcgctct gctaatcctg ttaccagtgg ctgctgccag tggcgataag   2160

tcgtgtctta ccgggttgga ctcaagacga tagttaccgg ataaggcgca gcggtcgggc   2220

tgaacggggg gttcgtgcac acagcccagc ttggagcgaa cgacctacac cgaactgaga   2280

tacctacagc gtgagctatg agaaagcgcc acgcttcccg aagggagaaa ggcggacagg   2340

tatccggtaa gcggcagggt cggaacagga gagcgcacga gggagcttcc agggggaaac   2400

gcctggtatc tttatagtcc tgtcgggttt cgccacctct gacttgagcg tcgatttttg   2460

tgatgctcgt caggggggcg gagcctatgg aaaaacgcca gcaacgcggc ctttttacgg   2520

ttcctggcct tttgctggcc ttttgctcac atgtaatgtg agttagctca ctcattaggc   2580

accccaggct ttacacttta tgcttccggc tcgtatgttg tgtggaattg tgagcggata   2640

acaatttcac acaggaaaca gctatgacca tgattacgcc aagctacgta atacgactca   2700

ctagtggggc ccgtgcaatt gaagccggct ggcgccaagc ttctctgcag gattgaagcc   2760

tgctttttta tactaacttg agcgaaatct ggatccatgg ccaagttgac cagtgccgtt   2820

ccggtgctca ccgcgcgcga cgtcgccgga gcggtcgagt tctggaccga ccggctcggg   2880

ttctcccggg acttcgtgga ggacgacttc gccggtgtgg tccgggacga cgtgaccctg   2940

ttcatcagcg cggtccagga ccaggtggtg ccggacaaca ccctggcctg ggtgtgggtg   3000

cgcggcctgg acgagctgta cgccgagtgg tcggaggtcg tgtccacgaa cttccgggac   3060

gcctccgggc cggccatgac cgagatcggc gagcagccgt gggggcggga gttcgccctg   3120

cgcgacccgg ccggcaactg cgtgcacttc gtggccgagg agcaggactg acacgtgcta   3180

cgagatttcg attccaccgc cgccttctat gaaaggttgg gcttcggaat cgttttccgg   3240

gacgccggct ggatgatcct ccagcgcggg gatctcatgc tggagttctt cgcccacccc   3300

aacttgttta ttgcagctta taatggttac aaataaagca atagcatcac aaatttcaca   3360

aataaagcat ttttttcact gcattctagt tgtggtttgt ccaaactcat caatgtatct   3420

tatcatgtct gtataccg                                                 3438
```

<210> SEQ ID NO 92
<211> LENGTH: 10549
<212> TYPE: DNA
<213> ORGANISM: Artificial Sequence
<220> FEATURE:
<223> OTHER INFORMATION: pCambia1302 Plasmid
<300> PUBLICATION INFORMATION:
<308> DATABASE ACCESSION NUMBER: Genbank #AF234398
<309> DATABASE ENTRY DATE: 2000-04-24

<400> SEQUENCE: 92

```
catggtagat ctgactagta aaggagaaga acttttcact ggagttgtcc caattcttgt     60

tgaattagat ggtgatgtta atgggcacaa attttctgtc agtggagagg gtgaaggtga    120

tgcaacatac ggaaaactta cccttaaatt tatttgcact actggaaaac tacctgttcc    180

gtggccaaca cttgtcacta ctttctctta tggtgttcaa tgcttttcaa gatacccaga    240

tcatatgaag cggcacgact tcttcaagag cgccatgcct gagggatacg tgcaggagag    300

gaccatcttc ttcaaggacg acgggaacta caagacacgt gctgaagtca agtttgaggg    360
```

-continued

```
agacaccctc gtcaacagga tcgagcttaa gggaatcgat ttcaaggagg acggaaacat    420
cctcggccac aagttggaat acaactacaa ctcccacaac gtatacatca tggccgacaa    480
gcaaaagaac ggcatcaaag ccaacttcaa gacccgccac aacatcgaag acggcggcgt    540
gcaactcgct gatcattatc aacaaaatac tccaattggc gatggccctg tccttttacc    600
agacaaccat tacctgtcca cacaatctgc cctttcgaaa gatcccaacg aaaagagaga    660
ccacatggtc cttcttgagt ttgtaacagc tgctgggatt acacatggca tggatgaact    720
atacaaagct agccaccacc accaccacca cgtgtgaatt ggtgaccagc tcgaatttcc    780
ccgatcgttc aaacatttgg caataaagtt tcttaagatt gaatcctgtt gccggtcttg    840
cgatgattat catataattt ctgttgaatt acgttaagca tgtaataatt aacatgtaat    900
gcatgacgtt atttatgaga tgggttttta tgattagagt cccgcaatta tacatttaat    960
acgcgataga aaacaaaata tagcgcgcaa actaggataa attatcgcgc gcggtgtcat   1020
ctatgttact agatcgggaa ttaaactatc agtgtttgac aggatatatt ggcgggtaaa   1080
cctaagagaa aagagcgttt attagaataa cggatattta aaagggcgtg aaaaggttta   1140
tccgttcgtc catttgtatg tgcatgccaa ccacagggtt cccctcggga tcaaagtact   1200
ttgatccaac ccctccgctg ctatagtgca gtcggcttct gacgttcagt gcagccgtct   1260
tctgaaaacg acatgtcgca caagtcctaa gttacgcgac aggctgccgc cctgcccttt   1320
tcctggcgtt ttcttgtcgc gtgttttagt cgcataaagt agaatacttg cgactagaac   1380
cggagacatt acgccatgaa caagagcgcc gccgctggcc tgctgggcta tgcccgcgtc   1440
agcaccgacg accaggactt gaccaaccaa cgggccgaac tgcacgcggc cggctgcacc   1500
aagctgtttt ccgagaagat caccggcacc aggcgcgacc gcccggagct ggccaggatg   1560
cttgaccacc tacgccctgg cgacgttgtg acagtgacca ggctagaccg cctggcccgc   1620
agcacccgcg acctactgga cattgccgag cgcatccagg aggccggcgc gggcctgcgt   1680
agcctggcag agccgtgggc cgacaccacc acgccggccg gccgcatggt gttgaccgtg   1740
ttcgccggca ttgccgagtt cgagcgttcc ctaatcatcg accgcacccg gagcgggcgc   1800
gaggccgcca aggcccgagg cgtgaagttt ggcccccgcc ctaccctcac cccggcacag   1860
atcgcgcacg cccgcgagct gatcgaccag gaaggccgca ccgtgaaaga ggcggctgca   1920
ctgcttggcg tgcatcgctc gaccctgtac cgcgcacttg agcgcagcga ggaagtgacg   1980
cccaccgagg ccaggcggcg cggtgccttc cgtgaggacg cattgaccga ggccgacgcc   2040
ctggcggccg ccgagaatga acgccaagag gaacaagcat gaaaccgcac caggacggcc   2100
aggacgaacc gtttttcatt accgaagaga tcgaggcgga gatgatcgcg gccgggtacg   2160
tgttcgagcc gcccgcgcac gtctcaaccg tgcggctgca tgaaatcctg gccggtttgt   2220
ctgatgccaa gctggcggcc tggccggcca gcttggccgc tgaagaaacc gagcgccgcc   2280
gtctaaaaag gtgatgtgta tttgagtaaa acagcttgcg tcatgcggtc gctgcgtata   2340
tgatgcgatg agtaaataaa caaatacgca aggggaacgc atgaaggtta tcgctgtact   2400
taaccagaaa ggcgggtcag gcaagacgac catcgcaacc catctagccc gcgccctgca   2460
actcgccggg gccgatgttc tgttagtcga ttccgatccc cagggcagtg cccgcgattg   2520
ggcggccgtg cgggaagatc aaccgctaac cgttgtcggc atcgaccgcc cgacgattga   2580
ccgcgacgtg aaggccatcg gccggcgcga cttcgtagtg atcgacggag cgccccaggc   2640
ggcggacttg gctgtgtccg cgatcaaggc agccgacttc gtgctgattc cggtgcagcc   2700
aagcccttac gacatatggg ccaccgccga cctggtggag ctggttaagc agcgcattga   2760
```

-continued

```
ggtcacggat ggaaggctac aagcggcctt tgtcgtgtcg cgggcgatca aaggcacgcg   2820
catcggcggt gaggttgccg aggcgctggc cgggtacgag ctgcccattc ttgagtcccg   2880
tatcacgcag cgcgtgagct acccaggcac tgccgccgcc ggcacaaccg ttcttgaatc   2940
agaacccgag ggcgacgctg cccgcgaggt ccaggcgctg gccgctgaaa ttaaatcaaa   3000
actcatttga gttaatgagg taaagagaaa atgagcaaaa gcacaaacac gctaagtgcc   3060
ggccgtccga gcgcacgcag cagcaaggct gcaacgttgg ccagcctggc agacacgcca   3120
gccatgaagc gggtcaactt tcagttgccg gcggaggatc acaccaagct gaagatgtac   3180
gcggtacgcc aaggcaagac cattaccgag ctgctatctg aatacatcgc gcagctacca   3240
gagtaaatga gcaaatgaat aaatgagtag atgaatttta gcggctaaag gaggcggcat   3300
ggaaaatcaa gaacaaccag gcaccgacgc cgtggaatgc cccatgtgtg gaggaacggg   3360
cggttggcca ggcgtaagcg gctgggttgt ctgccggccc tgcaatggca ctggaacccc   3420
caagcccgag gaatcggcgt gacggtcgca aaccatccgg cccggtacaa atcggcgcgg   3480
cgctgggtga tgacctggtg gagaagttga aggccgcgca ggccgcccag cggcaacgca   3540
tcgaggcaga agcacgcccc ggtgaatcgt ggcaagcggc cgctgatcga atccgcaaag   3600
aatcccggca accgccggca gccggtgcgc cgtcgattag gaagccgccc aagggcgacg   3660
agcaaccaga tttttttcgtt ccgatgctct atgacgtggg cacccgcgat agtcgcagca   3720
tcatggacgt ggccgttttc cgtctgtcga agcgtgaccg acgagctggc gaggtgatcc   3780
gctacgagct tccagacggg cacgtagagg tttccgcagg gccggccggc atggccagtg   3840
tgtgggatta cgacctggta ctgatggcgg tttcccatct aaccgaatcc atgaaccgat   3900
accgggaagg gaagggagac aagcccggcc gcgtgttccg tccacacgtt gcggacgtac   3960
tcaagttctg ccggcgagcc gatggcggaa agcagaaaga cgacctggta gaaacctgca   4020
ttcggttaaa caccacgcac gttgccatgc agcgtacgaa gaaggccaag aacggccgcc   4080
tggtgacggt atccgagggt gaagccttga ttagccgcta caagatcgta aagagcgaaa   4140
ccgggcggcc ggagtacatc gagatcgagc tagctgattg gatgtaccgc gagatcacag   4200
aaggcaagaa cccggacgtg ctgacggttc accccgatta ctttttgatc gatcccggca   4260
tcggccgttt tctctaccgc ctggcacgcc gcgccgcagg caaggcagaa gccagatggt   4320
tgttcaagac gatctacgaa cgcagtggca gcgccggaga gttcaagaag ttctgtttca   4380
ccgtgcgcaa gctgatcggg tcaaatgacc tgccggagta cgatttgaag gaggaggcgg   4440
ggcaggctgg cccgatccta gtcatgcgct accgcaacct gatcgagggc gaagcatccg   4500
ccggttccta atgtacggag cagatgctag ggcaaattgc cctagcaggg gaaaaaggtc   4560
gaaaaggtct ctttcctgtg gatagcacgt acattgggaa cccaaagccg tacattggga   4620
accggaaccc gtacattggg aacccaaagc cgtacattgg gaaccggtca cacatgtaag   4680
tgactgatat aaaagagaaa aaaggcgatt tttccgccta aaactcttta aaacttatta   4740
aaactcttaa aacccgcctg gcctgtgcat aactgtctgg ccagcgcaca gccgaagagc   4800
tgcaaaaagc gcctaccctt cggtcgctgc gctccctacg ccccgccgct tcgcgtcggc   4860
ctatcgcggc cgctggccgc tcaaaaatgg ctggcctacg gccaggcaat ctaccagggc   4920
gcggacaagc cgcgccgtcg ccactcgacc gccggcgccc acatcaaggc accctgcctc   4980
gcgcgtttcg gtgatgacgg tgaaaacctc tgacacatgc agctcccgga gacggtcaca   5040
gcttgtctgt aagcggatgc cgggagcaga caagcccgtc agggcgcgtc agcgggtgtt   5100
```

-continued

```
ggcgggtgtc ggggcgcagc catgacccag tcacgtagcg atagcggagt gtatactggc   5160
ttaactatgc ggcatcagag cagattgtac tgagagtgca ccatatgcgg tgtgaaatac   5220
cgcacagatg cgtaaggaga aaataccgca tcaggcgctc ttccgcttcc tcgctcactg   5280
actcgctgcg ctcggtcgtt cggctgcggc gagcggtatc agctcactca aaggcggtaa   5340
tacggttatc cacagaatca ggggataacg caggaaagaa catgtgagca aaaggccagc   5400
aaaaggccag gaaccgtaaa aaggccgcgt tgctggcgtt tttccatagg ctccgccccc   5460
ctgacgagca tcacaaaaat cgacgctcaa gtcagaggtg gcgaaacccg acaggactat   5520
aaagatacca ggcgtttccc cctggaagct ccctcgtgcg ctctcctgtt ccgaccctgc   5580
cgcttaccgg atacctgtcc gcctttctcc cttcgggaag cgtggcgctt tctcatagct   5640
cacgctgtag gtatctcagt tcggtgtagg tcgttcgctc caagctgggc tgtgtgcacg   5700
aaccccccgt tcagcccgac cgctgcgcct tatccggtaa ctatcgtctt gagtccaacc   5760
cggtaagaca cgacttatcg ccactggcag cagccactgg taacaggatt agcagagcga   5820
ggtatgtagg cggtgctaca gagttcttga agtggtggcc taactacggc tacactagaa   5880
ggacagtatt tggtatctgc gctctgctga agccagttac cttcggaaaa agagttggta   5940
gctcttgatc cggcaaacaa accaccgctg gtagcggtgg tttttttgtt tgcaagcagc   6000
agattacgcg cagaaaaaaa ggatctcaag aagatccttt gatcttttct acggggtctg   6060
acgctcagtg gaacgaaaac tcacgttaag ggattttggt catgcattct aggtactaaa   6120
acaattcatc cagtaaaata taatatttta ttttctccca atcaggcttg atccccagta   6180
agtcaaaaaa tagctcgaca tactgttctt ccccgatatc ctccctgatc gaccggacgc   6240
agaaggcaat gtcataccac ttgtccgccc tgccgcttct cccaagatca ataaagccac   6300
ttactttgcc atctttcaca aagatgttgc tgtctcccag gtcgccgtgg gaaaagacaa   6360
gttcctcttc gggcttttcc gtctttaaaa aatcatacag ctcgcgcgga tctttaaatg   6420
gagtgtcttc ttcccagttt tcgcaatcca catcggccag atcgttattc agtaagtaat   6480
ccaattcggc taagcggctg tctaagctat tcgtataggg acaatccgat atgtcgatgg   6540
agtgaaagag cctgatgcac tccgcataca gctcgataat cttttcaggg ctttgttcat   6600
cttcatactc ttccgagcaa aggacgccat cggcctcact catgagcaga ttgctccagc   6660
catcatgccg ttcaaagtgc aggacctttg gaacaggcag ctttccttcc agccatagca   6720
tcatgtcctt ttcccgttcc acatcatagg tggtcccttt ataccggctg tccgtcattt   6780
ttaaatatag gttttcattt tctcccacca gcttatatac cttagcagga gacattcctt   6840
ccgtatcttt tacgcagcgg tatttttcga tcagtttttt caattccggt gatattctca   6900
ttttagccat ttattatttc cttcctcttt tctacagtat ttaaagatac cccaagaagc   6960
taattataac aagacgaact ccaattcact gttccttgca ttctaaaacc ttaaatacca   7020
gaaaacagct ttttcaaagt tgttttcaaa gttggcgtat aacatagtat cgacggagcc   7080
gattttgaaa ccgcggtgat cacaggcagc aacgctctgt catcgttaca atcaacatgc   7140
taccctccgc gagatcatcc gtgtttcaaa cccggcagct tagttgccgt tcttccgaat   7200
agcatcggta acatgagcaa agtctgccgc cttacaacgg ctctcccgct gacgccgtcc   7260
cggactgatg ggctgcctgt atcgagtggt gattttgtgc cgagctgccg gtcggggagc   7320
tgttggctgg ctggtggcag gatatattgt ggtgtaaaca aattgacgct tagacaactt   7380
aataacacat tgcggacgtt tttaatgtac tgaattaacg ccgaattaat tcgggggatc   7440
tggattttag tactggattt tggttttagg aattagaaat tttattgata gaagtatttt   7500
```

-continued acaaatacaa atacatacta agggtttctt atatgctcaa cacatgagcg aaaccctata 7560
ggaaccctaa ttcccttatc tgggaactac tcacacatta ttatggagaa actcgagctt 7620
gtcgatcgac agatccggtc ggcatctact ctatttcttt gccctcggac gagtgctggg 7680
gcgtcggttt ccactatcgg cgagtacttc tacacagcca tcggtccaga cggccgcgct 7740
tctgcgggcg atttgtgtac gcccgacagt cccggctccg gatcggacga ttgcgtcgca 7800
tcgaccctgc gcccaagctg catcatcgaa attgccgtca accaagctct gatagagttg 7860
gtcaagacca atgcggagca tatacgcccg gagtcgtggc gatcctgcaa gctccggatg 7920
cctccgctcg aagtagcgcg tctgctgctc catacaagcc aaccacggcc tccagaagaa 7980
gatgttggcg acctcgtatt gggaatcccc gaacatcgcc tcgctccagt caatgaccgc 8040
tgttatgcgg ccattgtccg tcaggacatt gttggagccg aaatccgcgt gcacgaggtg 8100
ccggacttcg gggcagtcct cggcccaaag catcagctca tcgagagcct gcgcgacgga 8160
cgcactgacg gtgtcgtcca tcacagtttg ccagtgatac acatggggat cagcaatcgc 8220
gcatatgaaa tcacgccatg tagtgtattg accgattcct tgcggtccga atgggccgaa 8280
cccgctcgtc tggctaagat cggccgcagc gatcgcatcc atagcctccg cgaccggttg 8340
tagaacagcg ggcagttcgg tttcaggcag gtcttgcaac gtgacaccct gtgcacggcg 8400
ggagatgcaa taggtcaggc tctcgctaaa ctccccaatg tcaagcactt ccggaatcgg 8460
gagcgcggcc gatgcaaagt gccgataaac ataacgatct ttgtagaaac catcggcgca 8520
gctatttacc cgcaggacat atccacgccc tcctacatcg aagctgaaag cacgagattc 8580
ttcgccctcc gagagctgca tcaggtcgga gacgctgtcg aacttttcga tcagaaactt 8640
ctcgacagac gtcgcggtga gttcaggctt tttcatatct cattgccccc cgggatctgc 8700
gaaagctcga gagagataga tttgtagaga gagactggtg atttcagcgt gtcctctcca 8760
aatgaaatga acttccttat atagaggaag gtcttgcgaa ggatagtggg attgtgcgtc 8820
atcccttacg tcagtggaga tatcacatca atccacttgc tttgaagacg tggttggaac 8880
gtcttctttt tccacgatgc tcctcgtggg tgggggtcca tctttgggac cactgtcggc 8940
agaggcatct tgaacgatag cctttccttt atcgcaatga tggcatttgt aggtgccacc 9000
ttccttttct actgtccttt tgatgaagtg acagatagct gggcaatgga atccgaggag 9060
gtttcccgat attacccttt gttgaaaagt ctcaatagcc ctttggtctt ctgagactgt 9120
atctttgata ttcttggagt agacgagagt gtcgtgctcc accatgttat cacatcaatc 9180
cacttgcttt gaagacgtgg ttggaacgtc ttcttttccc acgatgctcc tcgtgggtgg 9240
gggtccatct ttgggaccac tgtcggcaga ggcatcttga acgatagcct ttcctttatc 9300
gcaatgatgg catttgtagg tgccaccttc cttttctact gtccttttga tgaagtgaca 9360
gatagctggg caatggaatc cgaggaggtt tcccgatatt accctttgtt gaaaagtctc 9420
aatagccctt tggtcttctg agactgtatc tttgatattc ttggagtaga cgagagtgtc 9480
gtgctccacc atgttggcaa gctgctctag ccaatacgca aaccgcctct ccccgcgcgt 9540
tggccgattc attaatgcag ctggcacgac aggtttcccg actggaaagc gggcagtgag 9600
cgcaacgcaa ttaatgtgag ttagctcact cattaggcac cccaggcttt acactttatg 9660
cttccggctc gtatgttgtg tggaattgtg agcggataac aatttcacac aggaaacagc 9720
tatgaccatg attacgaatt cgagctcggt acccggggat cctctagagt cgacctgcag 9780
gcatgcaagc ttggcactgg ccgtcgtttt acaacgtcgt gactgggaaa accctggcgt 9840

-continued

```
tacccaactt aatcgccttg cagcacatcc ccctttcgcc agctggcgta atagcgaaga   9900

ggcccgcacc gatcgccctt cccaacagtt gcgcagcctg aatggcgaat gctagagcag   9960

cttgagcttg gatcagattg tcgtttcccg ccttcagttt agcttcatgg agtcaaagat  10020

tcaaatagag gacctaacag aactcgccgt aaagactggc gaacagttca tacagagtct  10080

cttacgactc aatgacaaga agaaaatctt cgtcaacatg gtggagcacg acacacttgt  10140

ctactccaaa aatatcaaag atacagtctc agaagaccaa agggcaattg agacttttca  10200

acaaagggta atatccggaa acctcctcgg attccattgc ccagctatct gtcactttat  10260

tgtgaagata gtggaaaagg aaggtggctc ctacaaatgc catcattgcg ataaaggaaa  10320

ggccatcgtt gaagatgcct ctgccgacag tggtcccaaa gatggacccc cacccacgag  10380

gagcatcgtg gaaaaagaag acgttccaac cacgtcttca aagcaagtgg attgatgtga  10440

tatctccact gacgtaaggg atgacgcaca atcccactat ccttcgcaag acccttcctc  10500

tatataagga agttcatttc atttggagag aacacggggg actcttgac              10549
```

<210> SEQ ID NO 93
<211> LENGTH: 33
<212> TYPE: DNA
<213> ORGANISM: Artificial Sequence
<220> FEATURE:
<223> OTHER INFORMATION: CaMV35SpolyA Primer

<400> SEQUENCE: 93

```
ctgaattaac gccgaattaa ttcgggggat ctg                                  33
```

<210> SEQ ID NO 94
<211> LENGTH: 29
<212> TYPE: DNA
<213> ORGANISM: Artificial Sequence
<220> FEATURE:
<223> OTHER INFORMATION: CaMV35Spr Primer

<400> SEQUENCE: 94

```
ctagagcagc ttgccaacat ggtggagca                                       29
```

<210> SEQ ID NO 95
<211> LENGTH: 12592
<212> TYPE: DNA
<213> ORGANISM: Artificial Sequence
<220> FEATURE:
<223> OTHER INFORMATION: pAg2 Plasmid

<400> SEQUENCE: 95

```
gtacgaagaa ggccaagaac ggccgcctgg tgacggtatc cgagggtgaa gccttgatta     60

gccgctacaa gatcgtaaag agcgaaaccg ggcggccgga gtacatcgag atcgagctag    120

ctgattggat gtaccgcgag atcacagaag gcaagaaccc ggacgtgctg acggttcacc    180

ccgattactt tttgatcgat cccggcatcg gccgttttct ctaccgcctg gcacgccgcg    240

ccgcaggcaa ggcagaagcc agatggttgt tcaagacgat ctacgaacgc agtggcagcg    300

ccggagagtt caagaagttc tgtttcaccg tgcgcaagct gatcgggtca aatgacctgc    360

cggagtacga tttgaaggag gaggcggggc aggctggccc gatcctagtc atgcgctacc    420

gcaacctgat cgagggcgaa gcatccgccg gttcctaatg tacggagcag atgctagggc    480

aaattgccct agcaggggaa aaaggtcgaa aaggtctctt tcctgtggat agcacgtaca    540

ttgggaaccc aaagccgtac attgggaacc ggaacccgta cattgggaac ccaaagccgt    600

acattgggaa ccggtcacac atgtaagtga ctgatataaa agagaaaaaa ggcgattttt    660
```

-continued

```
ccgcctaaaa ctctttaaaa cttattaaaa ctcttaaaac ccgcctggcc tgtgcataac    720
tgtctggcca gcgcacagcc gaagagctgc aaaaagcgcc taccettcgg tcgctgcgct    780
ccctacgccc cgccgcttcg cgtcggccta tcgcggccgc tggccgctca aaaatggctg    840
gcctacggcc aggcaatcta ccagggcgcg gacaagccgc gccgtcgcca ctcgaccgcc    900
ggcgcccaca tcaaggcacc ctgcctcgcg cgtttcggtg atgacggtga aaacctctga    960
cacatgcagc tcccggagac ggtcacagct tgtctgtaag cggatgccgg gagcagacaa   1020
gcccgtcagg gcgcgtcagc gggtgttggc gggtgtcggg gcgcagccat gacccagtca   1080
cgtagcgata gcggagtgta tactggctta actatgcggc atcagagcag attgtactga   1140
gagtgcacca tatgcggtgt gaaataccgc acagatgcgt aaggagaaaa taccgcatca   1200
ggcgctcttc cgcttcctcg ctcactgact cgctgcgctc ggtcgttcgg ctgcggcgag   1260
cggtatcagc tcactcaaag gcggtaatac ggttatccac agaatcaggg gataacgcag   1320
gaaagaacat gtgagcaaaa ggccagcaaa aggccaggaa ccgtaaaaag gccgcgttgc   1380
tggcgttttt ccataggctc cgcccccctg acgagcatca caaaaatcga cgctcaagtc   1440
agaggtggcg aaacccgaca ggactataaa gataccaggc gtttccccct ggaagctccc   1500
tcgtgcgctc tcctgttccg accctgccgc ttaccggata cctgtccgcc tttctccctt   1560
cgggaagcgt ggcgctttct catagctcac gctgtaggta tctcagttcg gtgtaggtcg   1620
ttcgctccaa gctgggctgt gtgcacgaac cccccgttca gcccgaccgc tgcgccttat   1680
ccggtaacta tcgtcttgag tccaacccgg taagacacga cttatcgcca ctggcagcag   1740
ccactggtaa caggattagc agagcgaggt atgtaggcgg tgctacagag ttcttgaagt   1800
ggtggcctaa ctacggctac actagaagga cagtatttgg tatctgcgct ctgctgaagc   1860
cagttacctt cggaaaaaga gttggtagct cttgatccgg caaacaaacc accgctggta   1920
gcggtggttt ttttgtttgc aagcagcaga ttacgcgcag aaaaaaagga tctcaagaag   1980
atcctttgat cttttctacg gggtctgacg ctcagtggaa cgaaaactca cgttaaggga   2040
ttttggtcat gcattctagg tactaaaaca attcatccag taaaatataa tattttattt   2100
tctcccaatc aggcttgatc cccagtaagt caaaaaatag ctcgacatac tgttcttccc   2160
cgatatcctc cctgatcgac cggacgcaga aggcaatgtc ataccacttg tccgccctgc   2220
cgcttctccc aagatcaata aagccactta ctttgccatc tttcacaaag atgttgctgt   2280
ctcccaggtc gccgtgggaa aagacaagtt cctcttcggg cttttccgtc tttaaaaaat   2340
catacagctc gcgcggatct ttaaatggag tgtcttcttc ccagttttcg caatccacat   2400
cggccagatc gttattcagt aagtaatcca attcggctaa gcggctgtct aagctattcg   2460
tatagggaca atccgatatg tcgatggagt gaaagagcct gatgcactcc gcatacagct   2520
cgataatctt ttcagggctt tgttcatctt catactcttc cgagcaaagg acgccatcgg   2580
cctcactcat gagcagattg ctccagccat catgccgttc aaagtgcagg acctttggaa   2640
caggcagctt tccttccagc catagcatca tgtccttttc ccgttccaca tcataggtgg   2700
tccctttata ccggctgtcc gtcattttta aatataggtt ttcattttct cccaccagct   2760
tatatacctt agcaggagac attccttccg tatcttttac gcagcggtat ttttcgatca   2820
gtttttttcaa ttccggtgat attctcattt tagccattta ttatttcctt cctcttttct   2880
acagtattta aagatacccc aagaagctaa ttataacaag acgaactcca attcactgtt   2940
ccttgcattc taaaacctta aataccagaa aacagctttt tcaaagttgt tttcaaagtt   3000
```

-continued

```
ggcgtataac atagtatcga cggagccgat tttgaaaccg cggtgatcac aggcagcaac   3060
gctctgtcat cgttacaatc aacatgctac cctccgcgag atcatccgtg tttcaaaccc   3120
ggcagcttag ttgccgttct tccgaatagc atcggtaaca tgagcaaagt ctgccgcctt   3180
acaacggctc tcccgctgac gccgtcccgg actgatgggc tgcctgtatc gagtggtgat   3240
tttgtgccga gctgccggtc ggggagctgt tggctggctg gtggcaggat atattgtggt   3300
gtaaacaaat tgacgcttag acaacttaat aacacattgc ggacgttttt aatgtactga   3360
attaacgccg aattaattcg gggatctgg attttagtac tggattttgg ttttaggaat   3420
tagaaatttt attgatagaa gtattttaca aatacaaata catactaagg gtttcttata   3480
tgctcaacac atgagcgaaa ccctatagga accctaattc ccttatctgg gaactactca   3540
cacattatta tggagaaact cgagtcaaat ctcggtgacg ggcaggaccg gacggggcgg   3600
taccggcagg ctgaagtcca gctgccagaa acccacgtca tgccagttcc cgtgcttgaa   3660
gccggccgcc cgcagcatgc cgcggggggc atatccgagc gcctcgtgca tgcgcacgct   3720
cgggtcgttg ggcagcccga tgacagcgac cacgctcttg aagccctgtg cctccaggga   3780
cttcagcagg tgggtgtaga gcgtggagcc cagtcccgtc cgctggtggc ggggggagac   3840
gtacacggtc gactcggccg tccagtcgta ggcgttgcgt gccttccagg ggcccgcgta   3900
ggcgatgccg gcgacctcgc cgtccacctc ggcgacgagc cagggatagc gctcccgcag   3960
acggacgagg tcgtccgtcc actcctgcgg ttcctgcggc tcggtacgga agttgaccgt   4020
gcttgtctcg atgtagtggt tgacgatggt gcagaccgcc ggcatgtccg cctcggtggc   4080
acggcggatg tcggccgggc gtcgttctgg gctcatggta gactcgagag agatagattt   4140
gtagagagag actggtgatt tcagcgtgtc ctctccaaat gaaatgaact tccttatata   4200
gaggaaggtc ttgcgaagga tagtgggatt gtgcgtcatc ccttacgtca gtggagatat   4260
cacatcaatc cacttgcttt gaagacgtgg ttggaacgtc ttcttttttcc acgatgctcc   4320
tcgtgggtgg gggtccatct ttgggaccac tgtcggcaga ggcatcttga acgatagcct   4380
ttcctttatc gcaatgatgg catttgtagg tgccaccttc cttttctact gtccttttga   4440
tgaagtgaca gatagctggg caatggaatc cgaggaggtt tcccgatatt accctttgtt   4500
gaaaagtctc aatagccctt tggtcttctg agactgtatc tttgatattc ttggagtaga   4560
cgagagtgtc gtgctccacc atgttatcac atcaatccac ttgctttgaa gacgtggttg   4620
gaacgtcttc tttttccacg atgctcctcg tgggtggggg tccatctttg ggaccactgt   4680
cggcagaggc atcttgaacg atagcctttc ctttatcgca atgatggcat ttgtaggtgc   4740
caccttcctt ttctactgtc cttttgatga agtgacagat agctgggcaa tggaatccga   4800
ggaggtttcc cgatattacc ctttgttgaa aagtctcaat agccctttgg tcttctgaga   4860
ctgtatcttt gatattcttg gagtagacga gagtgtcgtg ctccaccatg ttggcaagct   4920
gctctagcca atacgcaaac cgcctctccc cgcgcgttgg ccgattcatt aatgcagctg   4980
gcacgacagg tttcccgact ggaaagcggg cagtgagcgc aacgcaatta atgtgagtta   5040
gctcactcat taggcacccc aggctttaca ctttatgctt ccggctcgta tgttgtgtgg   5100
aattgtgagc ggataacaat ttcacacagg aaacagctat gaccatgatt acgaattcga   5160
gccttgacta gagggtcgac ggtatacaga catgataaga tacattgatg agtttggaca   5220
aaccacaact agaatgcagt gaaaaaaatg ctttatttgt gaaatttgtg atgctattgc   5280
tttatttgta accattataa gctgcaataa acaagttggg gtgggcgaag aactccagca   5340
tgagatcccc gcgctggagg atcatccagc cggcgtcccg gaaaacgatt ccgaagccca   5400
```

-continued

```
acctttcata gaaggcggcg gtggaatcga aatctcgtag cacgtgtcag tcctgctcct   5460
cggccacgaa gtgcacgcag ttgccggccg ggtcgcgcag ggcgaactcc cgccccccacg   5520
gctgctcgcc gatctcggtc atggccggcc cggaggcgtc ccggaagttc gtggacacga   5580
cctccgacca ctcggcgtac agctcgtcca ggccgcgcac ccacacccag gccagggtgt   5640
tgtccggcac cacctggtcc tggaccgcgc tgatgaacag ggtcacgtcg tcccggacca   5700
caccggcgaa gtcgtcctcc acgaagtccc gggagaaccc gagccggtcg gtccagaact   5760
cgaccgctcc ggcgacgtcg cgcgcggtga gcaccggaac ggcactggtc aacttggcca   5820
tggatccaga tttcgctcaa gttagtataa aaaagcaggc ttcaatcctg caggaattcg   5880
atcgacactc tcgtctactc caagaatatc aaagatacag tctcagaaga ccaaagggct   5940
attgagactt ttcaacaaag ggtaatatcg ggaaacctcc tcggattcca ttgcccagct   6000
atctgtcact tcatcaaaag gacagtagaa aaggaaggtg gcacctacaa atgccatcat   6060
tgcgataaag gaaaggctat cgttcaagat gcctctgccg acagtggtcc caaagatgga   6120
cccccaccca cgaggagcat cgtggaaaaa gaagacgttc caaccacgtc ttcaaagcaa   6180
gtggattgat gtgataacat ggtggagcac gacactctcg tctactccaa gaatatcaaa   6240
gatacagtct cagaagacca aagggctatt gagacttttc aacaaagggt aatatcggga   6300
aacctcctcg gattccattg cccagctatc tgtcacttca tcaaaaggac agtagaaaag   6360
gaaggtggca cctacaaatg ccatcattgc gataaaggaa aggctatcgt tcaagatgcc   6420
tctgccgaca gtggtcccaa agatggaccc ccacccacga ggagcatcgt ggaaaaagaa   6480
gacgttccaa ccacgtcttc aaagcaagtg gattgatgtg atatctccac tgacgtaagg   6540
gatgacgcac aatcccacta tccttcgcaa gaccttcctc tatataagga agttcatttc   6600
atttggagag gacacgctga aatcaccagt ctctctctac aaatctatct ctctcgagct   6660
ttcgcagatc cggggggggca atgagatatg aaaaagcctg aactcaccgc gacgtctgtc   6720
gagaagtttc tgatcgaaaa gttcgacagc gtctccgacc tgatgcagct ctcggagggc   6780
gaagaatctc gtgctttcag cttcgatgta ggagggcgtg gatatgtcct gcgggtaaat   6840
agctgcgccg atggtttcta caaagatcgt tatgtttatc ggcactttgc atcggccgcg   6900
ctcccgattc cggaagtgct tgacattggg gagtttagcg agagcctgac ctattgcatc   6960
tcccgccgtg cacagggtgt cacgttgcaa gacctgcctg aaaccgaact gcccgctgtt   7020
ctacaaccgg tcgcggaggc tatggatgcg atcgctgcgg ccgatcttag ccagacgagc   7080
gggttcggcc cattcggacc gcaaggaatc ggtcaataca ctacatggcg tgatttcata   7140
tgcgcgattg ctgatcccca tgtgtatcac tggcaaactg tgatggacga caccgtcagt   7200
gcgtccgtcg cgcaggctct cgatgagctg atgctttggg ccgaggactg ccccgaagtc   7260
cggcacctcg tgcacgcgga tttcggctcc aacaatgtcc tgacggacaa tggccgcata   7320
acagcggtca ttgactggag cgaggcgatg ttcggggatt cccaatacga ggtcgccaac   7380
atcttcttct ggaggccgtg gttggcttgt atggagcagc agacgcgcta cttcgagcgg   7440
aggcatccgg agcttgcagg atcgccacga ctccgggcgt atatgctccg cattggtctt   7500
gaccaactct atcagagctt ggttgacggc aatttcgatg atgcagcttg ggcgcagggt   7560
cgatgcgacg caatcgtccg atccggagcc gggactgtcg ggcgtacaca aatcgcccgc   7620
agaagcgcgg ccgtctggac cgatggctgt gtagaagtac tcgccgatag tggaaaccga   7680
cgccccagca ctcgtccgag ggcaaagaaa tagagtagat gccgaccgga tctgtcgatc   7740
```

-continued

```
gacaagctcg agtttctcca taataatgtg tgagtagttc ccagataagg gaattagggt   7800
tcctataggg tttcgctcat gtgttgagca tataagaaac ccttagtatg tatttgtatt   7860
tgtaaaatac ttctatcaat aaaatttcta attcctaaaa ccaaaatcca gtactaaaat   7920
ccagatcccc cgaattaatt cggcgttaat tcagatcaag cttggcactg gccgtcgttt   7980
tacaacgtcg tgactgggaa aaccctggcg ttacccaact taatcgcctt gcagcacatc   8040
ccccttttcgc cagctggcgt aatagcgaag aggcccgcac cgatcgccct tcccaacagt   8100
tgcgcagcct gaatggcgaa tgctagagca gcttgagctt ggatcagatt gtcgtttccc   8160
gccttcagtt tggggatcct ctagactgaa ggcgggaaac gacaatctga tcatgagcgg   8220
agaattaagg gagtcacgtt atgacccccg ccgatgacgc gggacaagcc gttttacgtt   8280
tggaactgac agaaccgcaa cgttgaagga gccactcagc cgcgggtttc tggagtttaa   8340
tgagctaagc acatacgtca gaaaccatta ttgcgcgttc aaaagtcgcc taaggtcact   8400
atcagctagc aaatatttct tgtcaaaaat gctccactga cgttccataa attcccctcg   8460
gtatccaatt agagtctcat attcactctc aatccaaata atctgcaccg gatctcgaga   8520
atcgaattcc cgcggccgcc atggtagatc tgactagtaa aggagaagaa cttttcactg   8580
gagttgtccc aattcttgtt gaattagatg gtgatgttaa tgggcacaaa ttttctgtca   8640
gtggagaggg tgaaggtgat gcaacatacg gaaaacttac ccttaaattt atttgcacta   8700
ctggaaaact acctgttccg tggccaacac ttgtcactac tttctcttat ggtgttcaat   8760
gcttttcaag atacccagat catatgaagc ggcacgactt cttcaagagc gccatgcctg   8820
agggatacgt gcaggagagg accatcttct tcaaggacga cgggaactac aagacacgtg   8880
ctgaagtcaa gtttgaggga gacaccctcg tcaacaggat cgagcttaag ggaatcgatt   8940
tcaaggagga cggaaacatc ctcggccaca agttggaata caactacaac tcccacaacg   9000
tatacatcat ggccgacaag caaaagaacg gcatcaaagc caacttcaag acccgccaca   9060
acatcgaaga cggcggcgtg caactcgctg atcattatca acaaaatact ccaattggcg   9120
atggccctgt ccttttacca gacaaccatt acctgtccac acaatctgcc ctttcgaaag   9180
atcccaacga aaagagagac cacatggtcc ttcttgagtt tgtaacagct gctgggatta   9240
cacatggcat ggatgaacta tacaaagcta gccaccacca ccaccaccac gtgtgaattg   9300
gtgaccagct cgaatttccc cgatcgttca aacatttggc aataaagttt cttaagattg   9360
aatcctgttg ccggtcttgc gatgattatc atataatttc tgttgaatta cgttaagcat   9420
gtaataatta acatgtaatg catgacgtta tttatgagat gggtttttat gattagagtc   9480
ccgcaattat acatttaata cgcgatagaa aacaaaatat agcgcgcaaa ctaggataaa   9540
ttatcgcgcg cggtgtcatc tatgttacta gatcgggaat taaactatca gtgtttgaca   9600
ggatatattg gcgggtaaac ctaagagaaa agagcgttta ttagaataac ggatatttaa   9660
aagggcgtga aaaggtttat ccgttcgtcc atttgtatgt gcatgccaac cacagggttc   9720
ccctcgggat caaagtactt tgatccaacc cctccgctgc tatagtgcag tcggcttctg   9780
acgttcagtg cagccgtctt ctgaaaacga catgtcgcac aagtcctaag ttacgcgaca   9840
ggctgccgcc ctgccctttt cctggcgttt tcttgtcgcg tgttttagtc gcataaagta   9900
gaatacttgc gactagaacc ggagacatta cgccatgaac aagagcgccg ccgctggcct   9960
gctgggctat gcccgcgtca gcaccgacga ccaggacttg accaaccaac gggccgaact  10020
gcacgcggcc ggctgcacca agctgttttc cgagaagatc accggcacca ggcgcgaccg  10080
cccggagctg gccaggatgc ttgaccacct acgccctggc gacgttgtga cagtgaccag  10140
```

-continued gctagaccgc ctggcccgca gcacccgcga cctactggac attgccgagc gcatccagga 10200
ggccggcgcg ggcctgcgta gcctggcaga gccgtgggcc gacaccacca cgccggccgg 10260
ccgcatggtg ttgaccgtgt tcgccggcat tgccgagttc gagcgttccc taatcatcga 10320
ccgcacccgg agcgggcgcg aggccgccaa ggcccgaggc gtgaagtttg gcccccgccc 10380
taccctcacc ccggcacaga tcgcgcacgc ccgcgagctg atcgaccagg aaggccgcac 10440
cgtgaaagag gcggctgcac tgcttggcgt gcatcgctcg accctgtacc gcgcacttga 10500
gcgcagcgag gaagtgacgc ccaccgaggc caggcggcgc ggtgccttcc gtgaggacgc 10560
attgaccgag gccgacgccc tggcggccgc cgagaatgaa cgccaagagg aacaagcatg 10620
aaaccgcacc aggacggcca ggacgaaccg tttttcatta ccgaagagat cgaggcggag 10680
atgatcgcgg ccgggtacgt gttcgagccg cccgcgcacg tctcaaccgt gcggctgcat 10740
gaaatcctgg ccggtttgtc tgatgccaag ctggcggcct ggccggccag cttggccgct 10800
gaagaaaccg agcgccgccg tctaaaaagg tgatgtgtat ttgagtaaaa cagcttgcgt 10860
catgcggtcg ctgcgtatat gatgcgatga gtaaataaac aaatacgcaa ggggaacgca 10920
tgaaggttat cgctgtactt aaccagaaag gcgggtcagg caagacgacc atcgcaaccc 10980
atctagcccg cgccctgcaa ctcgccgggg ccgatgttct gttagtcgat tccgatcccc 11040
agggcagtgc ccgcgattgg gcggccgtgc gggaagatca accgctaacc gttgtcggca 11100
tcgaccgccc gacgattgac cgcgacgtga aggccatcgg ccggcgcgac ttcgtagtga 11160
tcgacggagc gccccaggcg gcggacttgg ctgtgtccgc gatcaaggca gccgacttcg 11220
tgctgattcc ggtgcagcca agcccttacg acatatgggc caccgccgac ctggtggagc 11280
tggttaagca gcgcattgag gtcacggatg gaaggctaca agcggccttt gtcgtgtcgc 11340
gggcgatcaa aggcacgcgc atcggcggtg aggttgccga ggcgctggcc gggtacgagc 11400
tgcccattct tgagtcccgt atcacgcagc gcgtgagcta cccaggcact gccgccgccg 11460
gcacaaccgt tcttgaatca gaacccgagg gcgacgctgc ccgcgaggtc caggcgctgg 11520
ccgctgaaat taaatcaaaa ctcatttgag ttaatgaggt aaagagaaaa tgagcaaaag 11580
cacaaacacg ctaagtgccg gccgtccgag cgcacgcagc agcaaggctg caacgttggc 11640
cagcctggca gacacgccag ccatgaagcg ggtcaacttt cagttgccgg cggaggatca 11700
caccaagctg aagatgtacg cggtacgcca aggcaagacc attaccgagc tgctatctga 11760
atacatcgcg cagctaccag agtaaatgag caaatgaata aatgagtaga tgaattttag 11820
cggctaaagg aggcggcatg gaaaatcaag aacaaccagg caccgacgcc gtggaatgcc 11880
ccatgtgtgg aggaacgggc ggttggccag gcgtaagcgg ctgggttgtc tgccggccct 11940
gcaatggcac tggaaccccc aagcccgagg aatcggcgtg acggtcgcaa accatccggc 12000
ccggtacaaa tcggcgcggc gctgggtgat gacctggtgg agaagttgaa ggccgcgcag 12060
gccgcccagc ggcaacgcat cgaggcagaa gcacgccccg gtgaatcgtg gcaagcggcc 12120
gctgatcgaa tccgcaaaga atcccggcaa ccgccggcag ccggtgcgcc gtcgattagg 12180
aagccgccca agggcgacga gcaaccagat tttttcgttc cgatgctcta tgacgtgggc 12240
acccgcgata gtcgcagcat catggacgtg gccgttttcc gtctgtcgaa gcgtgaccga 12300
cgagctggcg aggtgatccg ctacgagctt ccagacgggc acgtagaggt ttccgcaggg 12360
ccggccggca tggccagtgt gtgggattac gacctggtac tgatggcggt ttcccatcta 12420
accgaatcca tgaaccgata ccgggaaggg aagggagaca agcccggccg cgtgttccgt 12480

-continued ccacacgttg cggacgtact caagttctgc cggcgagccg atggcggaaa gcagaaagac 12540
gacctggtag aaacctgcat tcggttaaac accacgcacg ttgccatgca gc 12592

<210> SEQ ID NO 96
<211> LENGTH: 3357
<212> TYPE: DNA
<213> ORGANISM: Artificial Sequence
<220> FEATURE:
<223> OTHER INFORMATION: pGEMEasyNOS Plasmid

<400> SEQUENCE: 96
tatcactagt gaattcgcgg ccgcctgcag gtcgaccata tgggagagct cccaacgcgt 60
tggatgcata gcttgagtat tctatagtgt cacctaaata gcttggcgta atcatggtca 120
tagctgtttc ctgtgtgaaa ttgttatccg ctcacaattc cacacaacat acgagccgga 180
agcataaagt gtaaagcctg gggtgcctaa tgagtgagct aactcacatt aattgcgttg 240
cgctcactgc ccgctttcca gtcgggaaac ctgtcgtgcc agctgcatta atgaatcggc 300
caacgcgcgg ggagaggcgg tttgcgtatt gggcgctctt ccgcttcctc gctcactgac 360
tcgctgcgct cggtcgttcg gctgcggcga gcggtatcag ctcactcaaa ggcggtaata 420
cggttatcca cagaatcagg ggataacgca ggaaagaaca tgtgagcaaa aggccagcaa 480
aaggccagga accgtaaaaa ggccgcgttg ctggcgtttt tccataggct ccgcccccct 540
gacgagcatc acaaaaatcg acgctcaagt cagaggtggc gaaacccgac aggactataa 600
agataccagg cgtttccccc tggaagctcc ctcgtgcgct ctcctgttcc gaccctgccg 660
cttaccggat acctgtccgc ctttctccct tcgggaagcg tggcgctttc tcatagctca 720
cgctgtaggt atctcagttc ggtgtaggtc gttcgctcca agctgggctg tgtgcacgaa 780
ccccccgttc agcccgaccg ctgcgcctta tccggtaact atcgtcttga gtccaacccg 840
gtaagacacg acttatcgcc actggcagca gccactggta acaggattag cagagcgagg 900
tatgtaggcg gtgctacaga gttcttgaag tggtggccta actacggcta cactagaaga 960
acagtatttg gtatctgcgc tctgctgaag ccagttacct tcggaaaaag agttggtagc 1020
tcttgatccg gcaaacaaac caccgctggt agcggtggtt tttttgtttg caagcagcag 1080
attacgcgca gaaaaaaagg atctcaagaa gatcctttga tcttttctac ggggtctgac 1140
gctcagtgga acgaaaactc acgttaaggg attttggtca tgagattatc aaaaaggatc 1200
ttcacctaga tccttttaaa ttaaaaatga agttttaaat caatctaaag tatatatgag 1260
taaacttggt ctgacagtta ccaatgctta atcagtgagg cacctatctc agcgatctgt 1320
ctatttcgtt catccatagt tgcctgactc cccgtcgtgt agataactac gatacgggag 1380
ggcttaccat ctggccccag tgctgcaatg ataccgcgag acccacgctc accggctcca 1440
gatttatcag caataaacca gccagccgga agggccgagc gcagaagtgg tcctgcaact 1500
ttatccgcct ccatccagtc tattaattgt tgccgggaag ctagagtaag tagttcgcca 1560
gttaatagtt tgcgcaacgt tgttgccatt gctacaggca tcgtggtgtc acgctcgtcg 1620
tttggtatgg cttcattcag ctccggttcc caacgatcaa ggcgagttac atgatccccc 1680
atgttgtgca aaaaagcggt tagctccttc ggtcctccga tcgttgtcag aagtaagttg 1740
gccgcagtgt tatcactcat ggttatggca gcactgcata attctcttac tgtcatgcca 1800
tccgtaagat gcttttctgt gactggtgag tactcaacca agtcattctg agaatagtgt 1860
atgcggcgac cgagttgctc ttgcccggcg tcaatacggg ataataccgc gccacatagc 1920
agaactttaa aagtgctcat cattggaaaa cgttcttcgg ggcgaaaact ctcaaggatc 1980

-continued

```
ttaccgctgt tgagatccag ttcgatgtaa cccactcgtg cacccaactg atcttcagca   2040

tcttttactt tcaccagcgt ttctgggtga gcaaaaacag gaaggcaaaa tgccgcaaaa   2100

aagggaataa gggcgacacg gaaatgttga atactcatac tcttcctttt tcaatattat   2160

tgaagcattt atcagggtta ttgtctcatg agcggataca tatttgaatg tatttagaaa   2220

aataaacaaa taggggttcc gcgcacattt ccccgaaaag tgccacctga tgcggtgtga   2280

aataccgcac agatgcgtaa ggagaaaata ccgcatcagg aaattgtaag cgttaatatt   2340

ttgttaaaat tcgcgttaaa tttttgttaa atcagctcat tttttaacca ataggccgaa   2400

atcggcaaaa tcccttataa atcaaaagaa tagaccgaga tagggttgag tgttgttcca   2460

gtttggaaca agagtccact attaaagaac gtggactcca acgtcaaagg gcgaaaaacc   2520

gtctatcagg gcgatggccc actacgtgaa ccatcaccct aatcaagttt tttggggtcg   2580

aggtgccgta aagcactaaa tcggaaccct aaagggagcc cccgatttag agcttgacgg   2640

ggaaagccgg cgaacgtggc gagaaaggaa gggaagaaag cgaaaggagc gggcgctagg   2700

gcgctggcaa gtgtagcggt cacgctgcgc gtaaccacca cacccgccgc gcttaatgcg   2760

ccgctacagg gcgcgtccat tcgccattca ggctgcgcaa ctgttgggaa gggcgatcgg   2820

tgcgggcctc ttcgctatta cgccagctgg cgaaaggggg atgtgctgca aggcgattaa   2880

gttgggtaac gccagggttt tcccagtcac gacgttgtaa aacgacggcc agtgaattgt   2940

aatacgactc actatagggc gaattgggcc cgacgtcgca tgctcccggc cgccatggcg   3000

gccgcgggaa ttcgattctc gagatccggt gcagattatt tggattgaga gtgaatatga   3060

gactctaatt ggataccgag gggaatttat ggaacgtcag tggagcattt ttgacaagaa   3120

atatttgcta gctgatagtg accttaggcg acttttgaac gcgcaataat ggtttctgac   3180

gtatgtgctt agctcattaa actccagaaa cccgcggctg agtggctcct tcaacgttgc   3240

ggttctgtca gttccaaacg taaaacggct tgtcccgcgt catcggcggg ggtcataacg   3300

tgactccctt aattctccgc tcatgatcag attgtcgttt cccgccttca gtctaga      3357
```

```
<210> SEQ ID NO 97
<211> LENGTH: 10122
<212> TYPE: DNA
<213> ORGANISM: Artificial Sequence
<220> FEATURE:
<223> OTHER INFORMATION: p1302NOS Plasmid

<400> SEQUENCE: 97

catggtagat ctgactagta aaggagaaga acttttcact ggagttgtcc caattcttgt     60

tgaattagat ggtgatgtta atgggcacaa attttctgtc agtggagagg gtgaaggtga    120

tgcaacatac ggaaaactta cccttaaatt tatttgcact actggaaaac tacctgttcc    180

gtggccaaca cttgtcacta ctttctctta tggtgttcaa tgcttttcaa gatacccaga    240

tcatatgaag cggcacgact tcttcaagag cgccatgcct gagggatacg tgcaggagag    300

gaccatcttc ttcaaggacg acgggaacta caagacacgt gctgaagtca agtttgaggg    360

agacaccctc gtcaacagga tcgagcttaa gggaatcgat ttcaaggagg acggaaacat    420

cctcggccac aagttggaat acaactacaa ctcccacaac gtatacatca tggccgacaa    480

gcaaaagaac ggcatcaaag ccaacttcaa gacccgccac aacatcgaag acggcggcgt    540

gcaactcgct gatcattatc aacaaaatac tccaattggc gatggccctg tccttttacc    600

agacaaccat tacctgtcca cacaatctgc cctttcgaaa gatcccaacg aaaagagaga    660
```

-continued

```
ccacatggtc cttcttgagt ttgtaacagc tgctgggatt acacatggca tggatgaact     720
atacaaagct agccaccacc accaccacca cgtgtgaatt ggtgaccagc tcgaatttcc     780
ccgatcgttc aaacatttgg caataaagtt tcttaagatt gaatcctgtt gccggtcttg     840
cgatgattat catataattt ctgttgaatt acgttaagca tgtaataatt aacatgtaat     900
gcatgacgtt atttatgaga tgggttttta tgattagagt cccgcaatta tacatttaat     960
acgcgataga aaacaaaata tagcgcgcaa actaggataa attatcgcgc gcggtgtcat    1020
ctatgttact agatcgggaa ttaaactatc agtgtttgac aggatatatt ggcgggtaaa    1080
cctaagagaa aagagcgttt attagaataa cggatattta aaagggcgtg aaaaggttta    1140
tccgttcgtc catttgtatg tgcatgccaa ccacagggtt cccctcggga tcaaagtact    1200
ttgatccaac ccctccgctg ctatagtgca gtcggcttct gacgttcagt gcagccgtct    1260
tctgaaaacg acatgtcgca caagtcctaa gttacgcgac aggctgccgc cctgcccttt    1320
tcctggcgtt ttcttgtcgc gtgttttagt cgcataaagt agaatacttg cgactagaac    1380
cggagacatt acgccatgaa caagagcgcc gccgctggcc tgctgggcta tgcccgcgtc    1440
agcaccgacg accaggactt gaccaaccaa cgggccgaac tgcacgcggc cggctgcacc    1500
aagctgtttt ccgagaagat caccggcacc aggcgcgacc gcccggagct ggccaggatg    1560
cttgaccacc tacgccctgg cgacgttgtg acagtgacca ggctagaccg cctggcccgc    1620
agcacccgcg acctactgga cattgccgag cgcatccagg aggccggcgc gggcctgcgt    1680
agcctggcag agccgtgggc cgacaccacc acgccggccg gccgcatggt gttgaccgtg    1740
ttcgccggca ttgccgagtt cgagcgttcc ctaatcatcg accgcacccg gagcgggcgc    1800
gaggccgcca aggcccgagg cgtgaagttt ggcccccgcc ctaccctcac cccggcacag    1860
atcgcgcacg cccgcgagct gatcgaccag gaaggccgca ccgtgaaaga ggcggctgca    1920
ctgcttggcg tgcatcgctc gaccctgtac cgcgcacttg agcgcagcga ggaagtgacg    1980
cccaccgagg ccaggcggcg cggtgccttc cgtgaggacg cattgaccga ggccgacgcc    2040
ctggcggccg ccgagaatga acgccaagag gaacaagcat gaaaccgcac caggacggcc    2100
aggacgaacc gtttttcatt accgaagaga tcgaggcgga gatgatcgcg gccgggtacg    2160
tgttcgagcc gcccgcgcac gtctcaaccg tgcggctgca tgaaatcctg gccggtttgt    2220
ctgatgccaa gctggcggcc tggccggcca gcttggccgc tgaagaaacc gagcgccgcc    2280
gtctaaaaag gtgatgtgta tttgagtaaa acagcttgcg tcatgcggtc gctgcgtata    2340
tgatgcgatg agtaaataaa caaatacgca aggggaacgc atgaaggtta tcgctgtact    2400
taaccagaaa ggcgggtcag gcaagacgac catcgcaacc catctagccc gcgccctgca    2460
actcgccggg gccgatgttc tgttagtcga ttccgatccc cagggcagtg cccgcgattg    2520
ggcggccgtg cgggaagatc aaccgctaac cgttgtcggc atcgaccgcc cgacgattga    2580
ccgcgacgtg aaggccatcg gccggcgcga cttcgtagtg atcgacggag cgccccaggc    2640
ggcggacttg gctgtgtccg cgatcaaggc agccgacttc gtgctgattc cggtgcagcc    2700
aagcccttac gacatatggg ccaccgccga cctggtggag ctggttaagc agcgcattga    2760
ggtcacggat ggaaggctac aagcggcctt tgtcgtgtcg cgggcgatca aaggcacgcg    2820
catcggcggt gaggttgccg aggcgctggc cgggtacgag ctgcccattc ttgagtcccg    2880
tatcacgcag cgcgtgagct acccaggcac tgccgccgcc ggcacaaccg ttcttgaatc    2940
agaacccgag ggcgacgctg cccgcgaggt ccaggcgctg gccgctgaaa ttaaatcaaa    3000
actcatttga gttaatgagg taaagagaaa atgagcaaaa gcacaaacac gctaagtgcc    3060
```

-continued

```
ggccgtccga gcgcacgcag cagcaaggct gcaacgttgg ccagcctggc agacacgcca   3120
gccatgaagc gggtcaactt tcagttgccg gcggaggatc acaccaagct gaagatgtac   3180
gcggtacgcc aaggcaagac cattaccgag ctgctatctg aatacatcgc gcagctacca   3240
gagtaaatga gcaaatgaat aaatgagtag atgaatttta gcggctaaag gaggcggcat   3300
ggaaaatcaa gaacaaccag gcaccgacgc cgtggaatgc cccatgtgtg gaggaacggg   3360
cggttggcca ggcgtaagcg gctgggttgt ctgccggccc tgcaatggca ctggaacccc   3420
caagcccgag gaatcggcgt gacggtcgca aaccatccgg cccggtacaa atcggcgcgg   3480
cgctgggtga tgacctggtg gagaagttga aggccgcgca ggccgcccag cggcaacgca   3540
tcgaggcaga agcacgcccc ggtgaatcgt ggcaagcggc cgctgatcga atccgcaaag   3600
aatcccggca accgccggca gccggtgcgc cgtcgattag gaagccgccc aagggcgacg   3660
agcaaccaga tttttcgtt ccgatgctct atgacgtggg cacccgcgat agtcgcagca    3720
tcatggacgt ggccgttttc cgtctgtcga agcgtgaccg acgagctggc gaggtgatcc   3780
gctacgagct tccagacggg cacgtagagg tttccgcagg gccggccggc atggccagtg   3840
tgtgggatta cgacctggta ctgatggcgg tttcccatct aaccgaatcc atgaaccgat   3900
accgggaagg gaagggagac aagcccggcc gcgtgttccg tccacacgtt gcggacgtac   3960
tcaagttctg ccggcgagcc gatggcggaa agcagaaaga cgacctggta gaaacctgca   4020
ttcggttaaa caccacgcac gttgccatgc agcgtacgaa gaaggccaag aacggccgcc   4080
tggtgacggt atccgagggt gaagccttga ttagccgcta caagatcgta aagagcgaaa   4140
ccgggcggcc ggagtacatc gagatcgagc tagctgattg gatgtaccgc gagatcacag   4200
aaggcaagaa cccggacgtg ctgacggttc accccgatta ctttttgatc gatcccggca   4260
tcggccgttt tctctaccgc ctggcacgcc gcgccgcagg caaggcagaa gccagatggt   4320
tgttcaagac gatctacgaa cgcagtggca gcgccggaga gttcaagaag ttctgtttca   4380
ccgtgcgcaa gctgatcggg tcaaatgacc tgccggagta cgatttgaag gaggaggcgg   4440
ggcaggctgg cccgatccta gtcatgcgct accgcaacct gatcgagggc gaagcatccg   4500
ccggttccta atgtacggag cagatgctag ggcaaattgc cctagcaggg gaaaaaggtc   4560
gaaaaggtct ctttcctgtg gatagcacgt acattgggaa cccaaagccg tacattggga   4620
accggaaccc gtacattggg aacccaaagc cgtacattgg gaaccggtca cacatgtaag   4680
tgactgatat aaaagagaaa aaaggcgatt tttccgccta aaactcttta aaacttatta   4740
aaactcttaa aacccgcctg gcctgtgcat aactgtctgg ccagcgcaca gccgaagagc   4800
tgcaaaaagc gcctaccctt cggtcgctgc gctccctacg ccccgccgct tcgcgtcggc   4860
ctatcgcggc cgctggccgc tcaaaaatgg ctggcctacg gccaggcaat ctaccagggc   4920
gcggacaagc cgcgccgtcg ccactcgacc gccggcgccc acatcaaggc accctgcctc   4980
gcgcgtttcg gtgatgacgg tgaaaacctc tgacacatgc agctcccgga gacggtcaca   5040
gcttgtctgt aagcggatgc cgggagcaga caagcccgtc agggcgcgtc agcgggtgtt   5100
ggcgggtgtc ggggcgcagc catgacccag tcacgtagcg atagcggagt gtatactggc   5160
ttaactatgc ggcatcagag cagattgtac tgagagtgca ccatatgcgg tgtgaaatac   5220
cgcacagatg cgtaaggaga aaataccgca tcaggcgctc ttccgcttcc tcgctcactg   5280
actcgctgcg ctcggtcgtt cggctgcggc gagcggtatc agctcactca aaggcggtaa   5340
tacggttatc cacagaatca ggggataacg caggaaagaa catgtgagca aaaggccagc   5400
```

-continued

```
aaaaggccag gaaccgtaaa aaggccgcgt tgctggcgtt tttccatagg ctccgccccc   5460
ctgacgagca tcacaaaaat cgacgctcaa gtcagaggtg gcgaaacccg acaggactat   5520
aaagatacca ggcgtttccc cctggaagct ccctcgtgcg ctctcctgtt ccgaccctgc   5580
cgcttaccgg atacctgtcc gcctttctcc cttcgggaag cgtggcgctt tctcatagct   5640
cacgctgtag gtatctcagt tcggtgtagg tcgttcgctc caagctgggc tgtgtgcacg   5700
aaccccccgt tcagcccgac cgctgcgcct tatccggtaa ctatcgtctt gagtccaacc   5760
cggtaagaca cgacttatcg ccactggcag cagccactgg taacaggatt agcagagcga   5820
ggtatgtagg cggtgctaca gagttcttga agtggtggcc taactacggc tacactagaa   5880
ggacagtatt tggtatctgc gctctgctga agccagttac cttcggaaaa agagttggta   5940
gctcttgatc cggcaaacaa accaccgctg gtagcggtgg tttttttgtt tgcaagcagc   6000
agattacgcg cagaaaaaaa ggatctcaag aagatccttt gatcttttct acggggtctg   6060
acgctcagtg gaacgaaaac tcacgttaag ggattttggt catgcattct aggtactaaa   6120
acaattcatc cagtaaaata taatatttta ttttctccca atcaggcttg atccccagta   6180
agtcaaaaaa tagctcgaca tactgttctt ccccgatatc ctccctgatc gaccggacgc   6240
agaaggcaat gtcataccac ttgtccgccc tgccgcttct cccaagatca ataaagccac   6300
ttactttgcc atctttcaca aagatgttgc tgtctcccag gtcgccgtgg gaaaagacaa   6360
gttcctcttc gggcttttcc gtctttaaaa aatcatacag ctcgcgcgga tctttaaatg   6420
gagtgtcttc ttcccagttt tcgcaatcca catcggccag atcgttattc agtaagtaat   6480
ccaattcggc taagcggctg tctaagctat tcgtataggg acaatccgat atgtcgatgg   6540
agtgaaagag cctgatgcac tccgcataca gctcgataat cttttcaggg ctttgttcat   6600
cttcatactc ttccgagcaa aggacgccat cggcctcact catgagcaga ttgctccagc   6660
catcatgccg ttcaaagtgc aggacctttg gaacaggcag ctttccttcc agccatagca   6720
tcatgtcctt ttcccgttcc acatcatagg tggtcccttt ataccggctg tccgtcattt   6780
ttaaatatag gttttcattt tctcccacca gcttatatac cttagcagga gacattcctt   6840
ccgtatcttt tacgcagcgg tatttttcga tcagtttttt caattccggt gatattctca   6900
ttttagccat ttattatttc cttcctcttt tctacagtat ttaaagatac cccaagaagc   6960
taattataac aagacgaact ccaattcact gttccttgca ttctaaaacc ttaaatacca   7020
gaaaacagct tttcaaagt tgttttcaaa gttggcgtat aacatagtat cgacggagcc    7080
gattttgaaa ccgcggtgat cacaggcagc aacgctctgt catcgttaca atcaacatgc   7140
taccctccgc gagatcatcc gtgtttcaaa cccggcagct tagttgccgt tcttccgaat   7200
agcatcggta acatgagcaa agtctgccgc cttacaacgg ctctcccgct gacgccgtcc   7260
cggactgatg ggctgcctgt atcgagtggt gattttgtgc cgagctgccg gtcggggagc   7320
tgttggctgg ctggtggcag gatatattgt ggtgtaaaca aattgacgct tagacaactt   7380
aataacacat tgcggacgtt tttaatgtac tgaattaacg ccgaattaat tcgggggatc   7440
tggattttag tactggattt tggttttagg aattagaaat tttattgata gaagtatttt   7500
acaaatacaa atacatacta agggtttctt atatgctcaa cacatgagcg aaaccctata   7560
ggaaccctaa ttcccttatc tgggaactac tcacacatta ttatggagaa actcgagctt   7620
gtcgatcgac agatccggtc ggcatctact ctatttcttt gccctcggac gagtgctggg   7680
gcgtcggttt ccactatcgg cgagtacttc tacacagcca tcggtccaga cggccgcgct   7740
tctgcgggcg atttgtgtac gcccgacagt cccggctccg gatcggacga ttgcgtcgca   7800
```

-continued

```
tcgaccctgc gcccaagctg catcatcgaa attgccgtca accaagctct gatagagttg   7860
gtcaagacca atgcggagca tatacgcccg gagtcgtggc gatcctgcaa gctccggatg   7920
cctccgctcg aagtagcgcg tctgctgctc catacaagcc aaccacggcc tccagaagaa   7980
gatgttggcg acctcgtatt gggaatcccc gaacatcgcc tcgctccagt caatgaccgc   8040
tgttatgcgg ccattgtccg tcaggacatt gttggagccg aaatccgcgt gcacgaggtg   8100
ccggacttcg ggcagtcct cggcccaaag catcagctca tcgagagcct gcgcgacgga   8160
cgcactgacg gtgtcgtcca tcacagtttg ccagtgatac acatggggat cagcaatcgc   8220
gcatatgaaa tcacgccatg tagtgtattg accgattcct tgcggtccga atgggccgaa   8280
cccgctcgtc tggctaagat cggccgcagc gatcgcatcc atagcctccg cgaccggttg   8340
tagaacagcg ggcagttcgg tttcaggcag gtcttgcaac gtgacaccct gtgcacggcg   8400
ggagatgcaa taggtcaggc tctcgctaaa ctccccaatg tcaagcactt ccggaatcgg   8460
gagcgcggcc gatgcaaagt gccgataaac ataacgatct ttgtagaaac catcggcgca   8520
gctatttacc cgcaggacat atccacgccc tcctacatcg aagctgaaag cacgagattc   8580
ttcgccctcc gagagctgca tcaggtcgga gacgctgtcg aacttttcga tcagaaactt   8640
ctcgacagac gtcgcggtga gttcaggctt tttcatatct cattgccccc ccggatctgc   8700
gaaagctcga gagagataga tttgtagaga gagactggtg atttcagcgt gtcctctcca   8760
aatgaaatga acttccttat atagaggaag gtcttgcgaa ggatagtggg attgtgcgtc   8820
atcccttacg tcagtggaga tatcacatca atccacttgc tttgaagacg tggttggaac   8880
gtcttctttt tccacgatgc tcctcgtggg tgggggtcca tctttgggac cactgtcggc   8940
agaggcatct tgaacgatag cctttccttt atcgcaatga tggcatttgt aggtgccacc   9000
ttccttttct actgtccttt tgatgaagtg acagatagct gggcaatgga atccgaggag   9060
gtttcccgat attacccttt gttgaaaagt ctcaatagcc ctttggtctt ctgagactgt   9120
atctttgata ttcttggagt agacgagagt gtcgtgctcc accatgttat cacatcaatc   9180
cacttgcttt gaagacgtgg ttggaacgtc ttcttttttcc acgatgctcc tcgtgggtgg   9240
gggtccatct ttgggaccac tgtcggcaga ggcatcttga acgatagcct ttcctttatc   9300
gcaatgatgg catttgtagg tgccaccttc cttttctact gtccttttga tgaagtgaca   9360
gatagctggg caatggaatc cgaggaggtt tcccgatatt accctttgtt gaaaagtctc   9420
aatagccctt tggtcttctg agactgtatc tttgatattc ttggagtaga cgagagtgtc   9480
gtgctccacc atgttggcaa gctgctctag ccaatacgca aaccgcctct ccccgcgcgt   9540
tggccgattc attaatgcag ctggcacgac aggtttcccg actggaaagc gggcagtgag   9600
cgcaacgcaa ttaatgtgag ttagctcact cattaggcac cccaggcttt acactttatg   9660
cttccggctc gtatgttgtg tggaattgtg agcggataac aatttcacac aggaaacagc   9720
tatgaccatg attacgaatt cgagctcggt acccggggat cctctagact gaaggcggga   9780
aacgacaatc tgatcatgag cggagaatta agggagtcac gttatgaccc ccgccgatga   9840
cgcgggacaa gccgttttac gtttggaact gacagaaccg caacgttgaa ggagccactc   9900
agccgcgggt ttctggagtt taatgagcta agcacatacg tcagaaacca ttattgcgcg   9960
ttcaaaagtc gcctaaggtc actatcagct agcaaatatt tcttgtcaaa aatgctccac  10020
tgacgttcca taaattcccc tcggtatcca attagagtct catattcact ctcaatccaa  10080
ataatctgca ccggatctcg agaatcgaat tcccgcggcc gc                     10122
```

-continued

<210> SEQ ID NO 98
<211> LENGTH: 621
<212> TYPE: DNA
<213> ORGANISM: Artificial Sequence
<220> FEATURE:
<223> OTHER INFORMATION: N. tabacum rDNA intergnic spacer (IGS) sequence
<300> PUBLICATION INFORMATION:
<308> DATABASE ACCESSION NUMBER: Genbank #Y08422
<309> DATABASE ENTRY DATE: 1997-10-31

<400> SEQUENCE: 98
gtgctagcca atgtttaaca agatgtcaag cacaatgaat gttggtggtt ggtggtcgtg 60
gctggcggtg gtggaaaatt gcggtggttc gagcggtagt gatcggcgat ggttggtgtt 120
tgcagcggtg tttgatatcg gaatcactta tggtggttgt cacaatggag gtgcgtcatg 180
gttattggtg gttggtcatc tatatatttt tataataata ttaagtattt tacctatttt 240
ttacatattt tttattaaat ttatgcattg tttgtatttt taaatagttt ttatcgtact 300
tgttttataa aatattttat tattttatgt gttatattat tacttgatgt attggaaatt 360
ttctccattg ttttttctat atttataata attttcttat ttttttttgt tttattatgt 420
attttttcgt tttataataa atatttatta aaaaaaatat tatttttgta aaatatatca 480
tttacaatgt ttaaaagtca tttgtgaata tattagctaa gttgtacttc tttttgtgca 540
tttggtgttg tacatgtcta ttatgattct ctggccaaaa catgtctact cctgtcactt 600
gggttttttt ttttaagaca t 621

<210> SEQ ID NO 99
<211> LENGTH: 25
<212> TYPE: DNA
<213> ORGANISM: Artificial Sequence
<220> FEATURE:
<223> OTHER INFORMATION: NTIGS-F1 Primer

<400> SEQUENCE: 99
gtgctagcca atgtttaaca agatg 25

<210> SEQ ID NO 100
<211> LENGTH: 28
<212> TYPE: DNA
<213> ORGANISM: Artificial Sequence
<220> FEATURE:
<223> OTHER INFORMATION: NTIGS-R1 Primer

<400> SEQUENCE: 100
atgtcttaaa aaaaaaaacc caagtgac 28

<210> SEQ ID NO 101
<211> LENGTH: 233
<212> TYPE: DNA
<213> ORGANISM: Mus Musculus
<300> PUBLICATION INFORMATION:
<308> DATABASE ACCESSION NUMBER: Genbank #V00846
<309> DATABASE ENTRY DATE: 1989-07-06

<400> SEQUENCE: 101
gacctggaat atggcgagaa aactgaaaat cacggaaaat gagaaataca cactttagga 60
cgtgaaatat ggcgaggaaa actgaaaaag gtggaaaatt tagaaatgtc cactgtagga 120
cgtggaatat ggcaagaaaa ctgaaaatca tggaaaatga gaaacatcca cttgacgact 180
tgaaaaatga cgaaatcact aaaaaacgtg aaaaatgaga aatgcacact gaa 233

-continued

<210> SEQ ID NO 102
<211> LENGTH: 31
<212> TYPE: DNA
<213> ORGANISM: Artificial Sequence
<220> FEATURE:
<223> OTHER INFORMATION: MSAT-F1 Primer

<400> SEQUENCE: 102
aataccgcgg aagcttgacc tggaatatcg c 31

<210> SEQ ID NO 103
<211> LENGTH: 27
<212> TYPE: DNA
<213> ORGANISM: Artificial Sequence
<220> FEATURE:
<223> OTHER INFORMATION: MSAT-Ri Primer

<400> SEQUENCE: 103
ataaccgcgg agtccttcag tgtgcat 27

<210> SEQ ID NO 104
<211> LENGTH: 277
<212> TYPE: DNA
<213> ORGANISM: Artificial Sequence
<220> FEATURE:
<223> OTHER INFORMATION: Nopaline Synthase Promoter Sequence
<300> PUBLICATION INFORMATION:
<308> DATABASE ACCESSION NUMBER: Genbank #U09365
<309> DATABASE ENTRY DATE: 1997-10-17

<400> SEQUENCE: 104
gagctcgaat ttccccgatc gttcaaacat ttggcaataa agtttcttaa gattgaatcc 60
tgttgccggt cttgcgatga ttatcatata atttctgttg aattacgtta agcatgtaat 120
aattaacatg taatgcatga cgttatttat gagatgggtt tttatgatta gagtcccgca 180
attatacatt taatacgcga tagaaaacaa aatatagcgc gcaaactagg ataaattatc 240
gcgcgcggtg tcatctatgt tactagatcg ggaattc 277

<210> SEQ ID NO 105
<211> LENGTH: 1812
<212> TYPE: DNA
<213> ORGANISM: Escherichia coli
<220> FEATURE:
<221> NAME/KEY: CDS
<222> LOCATION: (1)...(1812)
<223> OTHER INFORMATION: Beta-Glucuronidase
<300> PUBLICATION INFORMATION:
<308> DATABASE ACCESSION NUMBER: Genbank #S69414
<309> DATABASE ENTRY DATE: 1994-09-23

<400> SEQUENCE: 105

```
atg tta cgt cct gta gaa acc cca acc cgt gaa atc aaa aaa ctc gac       48
Met Leu Arg Pro Val Glu Thr Pro Thr Arg Glu Ile Lys Lys Leu Asp
 1               5                  10                  15

ggc ctg tgg gca ttc agt ctg gat cgc gaa aac tgt gga att gat cag       96
Gly Leu Trp Ala Phe Ser Leu Asp Arg Glu Asn Cys Gly Ile Asp Gln
            20                  25                  30

cgt tgg tgg gaa agc gcg tta caa gaa agc cgg gca att gct gtg cca      144
Arg Trp Trp Glu Ser Ala Leu Gln Glu Ser Arg Ala Ile Ala Val Pro
        35                  40                  45

ggc agt ttt aac gat cag ttc gcc gat gca gat att cgt aat tat gcg      192
Gly Ser Phe Asn Asp Gln Phe Ala Asp Ala Asp Ile Arg Asn Tyr Ala
    50                  55                  60

ggc aac gtc tgg tat cag cgc gaa gtc ttt ata ccg aaa ggt tgg gca      240
Gly Asn Val Trp Tyr Gln Arg Glu Val Phe Ile Pro Lys Gly Trp Ala
```

-continued

```
 65                  70                  75                  80

ggc cag cgt atc gtg ctg cgt ttc gat gcg gtc act cat tac ggc aaa      288
Gly Gln Arg Ile Val Leu Arg Phe Asp Ala Val Thr His Tyr Gly Lys
                 85                  90                  95

gtg tgg gtc aat aat cag gaa gtg atg gag cat cag ggc ggc tat acg      336
Val Trp Val Asn Asn Gln Glu Val Met Glu His Gln Gly Gly Tyr Thr
            100                 105                 110

cca ttt gaa gcc gat gtc acg ccg tat gtt att gcc ggg aaa agt gta      384
Pro Phe Glu Ala Asp Val Thr Pro Tyr Val Ile Ala Gly Lys Ser Val
        115                 120                 125

cgt atc acc gtt tgt gtg aac aac gaa ctg aac tgg cag act atc ccg      432
Arg Ile Thr Val Cys Val Asn Asn Glu Leu Asn Trp Gln Thr Ile Pro
    130                 135                 140

ccg gga atg gtg att acc gac gaa aac ggc aag aaa aag cag tct tac      480
Pro Gly Met Val Ile Thr Asp Glu Asn Gly Lys Lys Lys Gln Ser Tyr
145                 150                 155                 160

ttc cat gat ttc ttt aac tat gcc gga atc cat cgc agc gta atg ctc      528
Phe His Asp Phe Phe Asn Tyr Ala Gly Ile His Arg Ser Val Met Leu
                165                 170                 175

tac acc acg ccg aac acc tgg gtg gac gat atc acc gtg gtg acg cat      576
Tyr Thr Thr Pro Asn Thr Trp Val Asp Asp Ile Thr Val Val Thr His
            180                 185                 190

gtc gcg caa gac tgt aac cac gcg tct gtt gac tgg cag gtg gtg gcc      624
Val Ala Gln Asp Cys Asn His Ala Ser Val Asp Trp Gln Val Val Ala
        195                 200                 205

aat ggt gat gtc agc gtt gaa ctg cgt gat gcg gat caa cag gtg gtt      672
Asn Gly Asp Val Ser Val Glu Leu Arg Asp Ala Asp Gln Gln Val Val
    210                 215                 220

gca act gga caa ggc act agc ggg act ttg caa gtg gtg aat ccg cac      720
Ala Thr Gly Gln Gly Thr Ser Gly Thr Leu Gln Val Val Asn Pro His
225                 230                 235                 240

ctc tgg caa ccg ggt gaa ggt tat ctc tat gaa ctg tgc gtc aca gcc      768
Leu Trp Gln Pro Gly Glu Gly Tyr Leu Tyr Glu Leu Cys Val Thr Ala
                245                 250                 255

aaa agc cag aca gag tgt gat atc tac ccg ctt cgc gtc ggc atc cgg      816
Lys Ser Gln Thr Glu Cys Asp Ile Tyr Pro Leu Arg Val Gly Ile Arg
            260                 265                 270

tca gtg gca gtg aag ggc gaa cag ttc ctg att aac cac aaa ccg ttc      864
Ser Val Ala Val Lys Gly Glu Gln Phe Leu Ile Asn His Lys Pro Phe
        275                 280                 285

tac ttt act ggc ttt ggt cgt cat gaa gat gcg gac ttg cgt ggc aaa      912
Tyr Phe Thr Gly Phe Gly Arg His Glu Asp Ala Asp Leu Arg Gly Lys
    290                 295                 300

gga ttc gat aac gtg ctg atg gtg cac gac cac gca tta atg gac tgg      960
Gly Phe Asp Asn Val Leu Met Val His Asp His Ala Leu Met Asp Trp
305                 310                 315                 320

att ggg gcc aac tcc tac cgt acc tcg cat tac cct tac gct gaa gag     1008
Ile Gly Ala Asn Ser Tyr Arg Thr Ser His Tyr Pro Tyr Ala Glu Glu
                325                 330                 335

atg ctc gac tgg gca gat gaa cat ggc atc gtg gtg att gat gaa act     1056
Met Leu Asp Trp Ala Asp Glu His Gly Ile Val Val Ile Asp Glu Thr
            340                 345                 350

gct gct gtc ggc ttt aac ctc tct tta ggc att ggt ttc gaa gcg ggc     1104
Ala Ala Val Gly Phe Asn Leu Ser Leu Gly Ile Gly Phe Glu Ala Gly
        355                 360                 365

aac aag ccg aaa gaa ctg tac agc gaa gag gca gtc aac ggg gaa act     1152
Asn Lys Pro Lys Glu Leu Tyr Ser Glu Glu Ala Val Asn Gly Glu Thr
    370                 375                 380

cag caa gcg cac tta cag gcg att aaa gag ctg ata gcg cgt gac aaa     1200
```

-continued

```
Gln Gln Ala His Leu Gln Ala Ile Lys Glu Leu Ile Ala Arg Asp Lys
385                 390                 395                 400

aac cac cca agc gtg gtg atg tgg agt att gcc aac gaa ccg gat acc     1248
Asn His Pro Ser Val Val Met Trp Ser Ile Ala Asn Glu Pro Asp Thr
                405                 410                 415

cgt ccg caa ggt gca cgg gaa tat ttc gcg cca ctg gcg gaa gca acg     1296
Arg Pro Gln Gly Ala Arg Glu Tyr Phe Ala Pro Leu Ala Glu Ala Thr
            420                 425                 430

cgt aaa ctc gac ccg acg cgt ccg atc acc tgc gtc aat gta atg ttc     1344
Arg Lys Leu Asp Pro Thr Arg Pro Ile Thr Cys Val Asn Val Met Phe
        435                 440                 445

tgc gac gct cac acc gat acc atc agc gat ctc ttt gat gtg ctg tgc     1392
Cys Asp Ala His Thr Asp Thr Ile Ser Asp Leu Phe Asp Val Leu Cys
    450                 455                 460

ctg aac cgt tat tac gga tgg tat gtc caa agc ggc gat ttg gaa acg     1440
Leu Asn Arg Tyr Tyr Gly Trp Tyr Val Gln Ser Gly Asp Leu Glu Thr
465                 470                 475                 480

gca gag aag gta ctg gaa aaa gaa ctt ctg gcc tgg cag gag aaa ctg     1488
Ala Glu Lys Val Leu Glu Lys Glu Leu Leu Ala Trp Gln Glu Lys Leu
                485                 490                 495

cat cag ccg att atc atc acc gaa tac ggc gtg gat acg tta gcc ggg     1536
His Gln Pro Ile Ile Ile Thr Glu Tyr Gly Val Asp Thr Leu Ala Gly
            500                 505                 510

ctg cac tca atg tac acc gac atg tgg agt gaa gag tat cag tgt gca     1584
Leu His Ser Met Tyr Thr Asp Met Trp Ser Glu Glu Tyr Gln Cys Ala
        515                 520                 525

tgg ctg gat atg tat cac cgc gtc ttt gat cgc gtc agc gcc gtc gtc     1632
Trp Leu Asp Met Tyr His Arg Val Phe Asp Arg Val Ser Ala Val Val
    530                 535                 540

ggt gaa cag gta tgg aat ttc gcc gat ttt gcg acc tcg caa ggc ata     1680
Gly Glu Gln Val Trp Asn Phe Ala Asp Phe Ala Thr Ser Gln Gly Ile
545                 550                 555                 560

ttg cgc gtt ggc ggt aac aag aaa ggg atc ttc act cgc gac cgc aaa     1728
Leu Arg Val Gly Gly Asn Lys Lys Gly Ile Phe Thr Arg Asp Arg Lys
                565                 570                 575

ccg aag tcg gcg gct ttt ctg ctg caa aaa cgc tgg act ggc atg aac     1776
Pro Lys Ser Ala Ala Phe Leu Leu Gln Lys Arg Trp Thr Gly Met Asn
            580                 585                 590

ttc ggt gaa aaa ccg cag cag gga ggc aaa caa tga                     1812
Phe Gly Glu Lys Pro Gln Gln Gly Gly Lys Gln  *
        595                 600


<210> SEQ ID NO 106
<211> LENGTH: 603
<212> TYPE: PRT
<213> ORGANISM: Escherichia coli
<300> PUBLICATION INFORMATION:
<308> DATABASE ACCESSION NUMBER: Genbank #S69414
<309> DATABASE ENTRY DATE: 1994-09-23

<400> SEQUENCE: 106

Met Leu Arg Pro Val Glu Thr Pro Thr Arg Glu Ile Lys Lys Leu Asp
 1               5                  10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
```

-continued

```
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Trp Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
        435                 440                 445

Cys Asp Ala His Thr Asp Thr Ile Ser Asp Leu Phe Asp Val Leu Cys
    450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495
```

His Gln Pro Ile Ile Ile Thr Glu Tyr Gly Val Asp Thr Leu Ala Gly
500 505 510

Leu His Ser Met Tyr Thr Asp Met Trp Ser Glu Glu Tyr Gln Cys Ala
515 520 525

Trp Leu Asp Met Tyr His Arg Val Phe Asp Arg Val Ser Ala Val Val
530 535 540

Gly Glu Gln Val Trp Asn Phe Ala Asp Phe Ala Thr Ser Gln Gly Ile
545 550 555 560

Leu Arg Val Gly Gly Asn Lys Lys Gly Ile Phe Thr Arg Asp Arg Lys
565 570 575

Pro Lys Ser Ala Ala Phe Leu Leu Gln Lys Arg Trp Thr Gly Met Asn
580 585 590

Phe Gly Glu Lys Pro Gln Gln Gly Gly Lys Gln
595 600

<210> SEQ ID NO 107
<211> LENGTH: 277
<212> TYPE: DNA
<213> ORGANISM: Artificial Sequence
<220> FEATURE:
<223> OTHER INFORMATION: Nopaline Synthase Terminator Sequence
<300> PUBLICATION INFORMATION:
<308> DATABASE ACCESSION NUMBER: U09365
<309> DATABASE ENTRY DATE: 1995-10-17

<400> SEQUENCE: 107
gagctcgaat ttccccgatc gttcaaacat ttggcaataa agtttcttaa gattgaatcc 60
tgttgccggt cttgcgatga ttatcatata atttctgttg aattacgtta agcatgtaat 120
aattaacatg taatgcatga cgttatttat gagatgggtt tttatgatta gagtcccgca 180
attatacatt taatacgcga tagaaaacaa aatatagcgc gcaaactagg ataaattatc 240
gcgcgcggtg tcatctatgt tactagatcg ggaattc 277

<210> SEQ ID NO 108
<211> LENGTH: 3451
<212> TYPE: DNA
<213> ORGANISM: Artificial Sequence
<220> FEATURE:
<223> OTHER INFORMATION: HindIII Fragment containing the
beta-glucuronidase coding sequence, the rDNA intergenic spacer,
and the Mast1 sequence

<400> SEQUENCE: 108
aagcttgacc tggaatatcg cgagtaaact gaaaatcacg gaaaatgaga aatacacact 60
ttaggacgtg aaatatggcg aggaaaactg aaaaaggtgg aaaatttaga aatgtccact 120
gtaggacgtg gaatatggca agaaaactga aaatcatgga aaatgagaaa catccacttg 180
acgacttgaa aaatgacgaa atcactaaaa aacgtgaaaa atgagaaatg cacactgaag 240
gactccgcgg gaattcgatt gtgctagcca atgtttaaca agatgtcaag cacaatgaat 300
gttggtggtt ggtggtcgtg gctggcggtg gtggaaaatt gcggtggttc gagcggtagt 360
gatcggcgat ggttggtgtt tgcagcggtg tttgatatcg gaatcactta tggtggttgt 420
cacaatggag gtgcgtcatg gttattggtg gttggtcatc tatatatttt tataataata 480
ttaagtattt tacctatttt ttacatattt tttattaaat ttatgcattg tttgtatttt 540
taaatagttt ttatcgtact tgttttataa aatattttat tattttatgt gttatattat 600
tacttgatgt attggaaatt ttctccattg ttttttctat atttataata attttcttat 660

-continued

```
ttttttttgt tttattatgt atttttttcgt tttataataa atatttatta aaaaaaatat    720
tatttttgta aaatatatca tttacaatgt ttaaaagtca tttgtgaata tattagctaa    780
gttgtacttc tttttgtgca tttggtgttg tacatgtcta ttatgattct ctggccaaaa    840
catgtctact cctgtcactt gggttttttt ttttaagaca taatcactag tgattatatc    900
tagactgaag gcgggaaacg acaatctgat catgagcgga gaattaaggg agtcacgtta    960
tgacccccgc cgatgacgcg ggacaagccg ttttacgttt ggaactgaca gaaccgcaac   1020
gttgaaggag ccactcagcc gcgggtttct ggagtttaat gagctaagca catacgtcag   1080
aaaccattat tgcgcgttca aaagtcgcct aaggtcacta tcagctagca aatatttctt   1140
gtcaaaaatg ctccactgac gttccataaa ttcccctcgg tatccaatta gagtctcata   1200
ttcactctca atccaaataa tctgcaccgg atctcgagat cgaattcccg cggccgcgaa   1260
ttcactagtg gatccccggg tacggtcagt ccccttatgtt acgtcctgta gaaaccccaa   1320
cccgtgaaat caaaaaactc gacggcctgt gggcattcag tctggatcgc gaaaactgtg   1380
gaattgagca gcgttggtgg gaaagcgcgt tacaagaaag ccgggcaatt gctgtgccag   1440
gcagttttaa cgatcagttc gccgatgcag atattcgtaa ttatgtgggc aacgtctggt   1500
atcagcgcga agtctttata ccgaaaggtt gggcaggcca gcgtatcgtg ctgcgtttcg   1560
atgcggtcac tcattacggc aaagtgtggg tcaataatca ggaagtgatg gagcatcagg   1620
gcggctatac gccatttgaa gccgatgtca cgccgtatgt tattgccggg aaaagtgtac   1680
gtatcacagt ttgtgtgaac aacgaactga actggcagac tatcccgccg ggaatggtga   1740
ttaccgacga aaacggcaag aaaaagcagt cttacttcca tgatttcttt aactacgccg   1800
ggatccatcg cagcgtaatg ctctacacca cgccgaacac ctgggtggac gatatcaccg   1860
tggtgacgca tgtcgcgcaa gactgtaacc acgcgtctgt tgactggcag gtggtggcca   1920
atggtgatgt cagcgttgaa ctgcgtgatg cggatcaaca ggtggttgca actggacaag   1980
gcaccagcgg gactttgcaa gtggtgaatc cgcacctctg gcaaccgggt gaaggttatc   2040
tctatgaact gtacgtcaca gccaaaagcc agacagagtg tgatatctac ccgctgcgcg   2100
tcggcatccg gtcagtggca gtgaagggcg aacagttcct gatcaaccac aaaccgttct   2160
actttactgg ctttggccgt catgaagatg cggatttgcg cggcaaagga ttcgataacg   2220
tgctgatggt gcacgatcac gcattaatgg actggattgg ggccaactcc taccgtacct   2280
cgcattaccc ttacgctgaa gagatgctcg actgggcaga tgaacatggc atcgtggtga   2340
ttgatgaaac tgcagctgtc ggctttaacc tctctttagg cattggtttc gaagcgggca   2400
acaagccgaa agaactgtac agcgaagagg cagtcaacgg ggaaactcag caggcgcact   2460
tacaggcgat taaagagctg atagcgcgtg acaaaaacca cccaagcgtg gtgatgtgga   2520
gtattgccaa cgaaccggat acccgtccgc aaggtgcacg ggaatatttc gcgccactgg   2580
cggaagcaac gcgtaaactc gatccgacgc gtccgatcac ctgcgtcaat gtaatgttct   2640
gcgacgctca caccgatacc atcagcgatc tctttgatgt gctgtgcctg aaccgttatt   2700
acggttggta tgtccaaagc ggcgatttgg aaacggcaga gaaggtactg gaaaaagaac   2760
ttctggcctg gcaggagaaa ctgcatcagc cgattatcat caccgaatac ggcgtggata   2820
cgttagccgg gctgcactca atgtacaccg acatgtggag tgaagagtat cagtgtgcat   2880
ggctggatat gtatcaccgc gtctttgatc gcgtcagcgc cgtcgtcggt gaacaggtat   2940
ggaatttcgc cgattttgcg acctcgcaag gcatattgcg cgttggcggt aacaagaagg   3000
ggatcttcac ccgcgaccgc aaaccgaagt cggcggcttt tctgctgcaa aaacgctgga   3060
```

-continued ctggcatgaa cttcggtgaa aaaccgcagc agggaggcaa acaatgaatc aacaactctc 3120
ctggcgcacc atcgtcggct acagcctcgg gaattgcgta ccgagctcga atttccccga 3180
tcgttcaaac atttggcaat aaagtttctt aagattgaat cctgttgccg gtcttgcgat 3240
gattatcata taatttctgt tgaattacgt taagcatgta ataattaaca tgtaatgcat 3300
gacgttattt atgagatggg tttttatgat tagagtcccg caattataca tttaatacgc 3360
gatagaaaac aaaatatagc gcgcaaacta ggataaatta tcgcgcgcgg tgtcatctat 3420
gttactagat cgggaattcg atatcaagct t 3451

<210> SEQ ID NO 109
<211> LENGTH: 14627
<212> TYPE: DNA
<213> ORGANISM: Artificial Sequence
<220> FEATURE:
<223> OTHER INFORMATION: pAg11a Plasmid

<400> SEQUENCE: 109
catgccaacc acagggttcc cctcgggatc aaagtacttt gatccaaccc ctccgctgct 60
atagtgcagt cggcttctga cgttcagtgc agccgtcttc tgaaaacgac atgtcgcaca 120
agtcctaagt tacgcgacag gctgccgccc tgccctttc ctggcgtttt cttgtcgcgt 180
gttttagtcg cataaagtag aatacttgcg actagaaccg gagacattac gccatgaaca 240
agagcgccgc cgctggcctg ctgggctatg cccgcgtcag caccgacgac caggacttga 300
ccaaccaacg ggccgaactg cacgcggccg gctgcaccaa gctgttttcc gagaagatca 360
ccggcaccag gcgcgaccgc ccggagctgg ccaggatgct tgaccaccta cgccctggcg 420
acgttgtgac agtgaccagg ctagaccgcc tggcccgcag cacccgcgac ctactggaca 480
ttgccgagcg catccaggag gccggcgcgg gcctgcgtag cctggcagag ccgtgggccg 540
acaccaccac gccggccggc cgcatggtgt tgaccgtgtt cgccggcatt gccgagttcg 600
agcgttccct aatcatcgac cgcacccgga gcgggcgcga ggccgccaag gcccgaggcg 660
tgaagtttgg cccccgccct accctcaccc cggcacagat cgcgcacgcc cgcgagctga 720
tcgaccagga aggccgcacc gtgaaagagg cggctgcact gcttggcgtg catcgctcga 780
ccctgtaccg cgcacttgag cgcagcgagg aagtgacgcc caccgaggcc aggcggcgcg 840
gtgccttccg tgaggacgca ttgaccgagg ccgacgccct ggcggccgcc gagaatgaac 900
gccaagagga acaagcatga aaccgcacca ggacggccag gacgaaccgt ttttcattac 960
cgaagagatc gaggcggaga tgatcgcggc cgggtacgtg ttcgagccgc ccgcgcacgt 1020
ctcaaccgtg cggctgcatg aaatcctggc cggtttgtct gatgccaagc tggcggcctg 1080
gccggccagc ttggccgctg aagaaaccga gcgccgccgt ctaaaaaggt gatgtgtatt 1140
tgagtaaaac agcttgcgtc atgcggtcgc tgcgtatatg atgcgatgag taaataaaca 1200
aatacgcaag gggaacgcat gaaggttatc gctgtactta accagaaagg cgggtcaggc 1260
aagacgacca tcgcaaccca tctagcccgc gccctgcaac tcgccggggc cgatgttctg 1320
ttagtcgatt ccgatcccca gggcagtgcc cgcgattggg cggccgtgcg ggaagatcaa 1380
ccgctaaccg ttgtcggcat cgaccgcccg acgattgacc gcgacgtgaa ggccatcggc 1440
cggcgcgact tcgtagtgat cgacggagcg ccccaggcgg cggacttggc tgtgtccgcg 1500
atcaaggcag ccgacttcgt gctgattccg gtgcagccaa gcccttacga catatgggcc 1560
accgccgacc tggtggagct ggttaagcag cgcattgagg tcacggatgg aaggctacaa 1620

-continued

```
gcggcctttg tcgtgtcgcg ggcgatcaaa ggcacgcgca tcggcggtga ggttgccgag   1680
gcgctggccg ggtacgagct gcccattctt gagtcccgta tcacgcagcg cgtgagctac   1740
ccaggcactg ccgccgccgg cacaaccgtt cttgaatcag aacccgaggg cgacgctgcc   1800
cgcgaggtcc aggcgctggc cgctgaaatt aaatcaaaac tcatttgagt taatgaggta   1860
aagagaaaat gagcaaaagc acaaacacgc taagtgccgg ccgtccgagc gcacgcagca   1920
gcaaggctgc aacgttggcc agcctggcag acacgccagc catgaagcgg gtcaactttc   1980
agttgccggc ggaggatcac accaagctga agatgtacgc ggtacgccaa ggcaagacca   2040
ttaccgagct gctatctgaa tacatcgcgc agctaccaga gtaaatgagc aaatgaataa   2100
atgagtagat gaattttagc ggctaaagga ggcggcatgg aaaatcaaga acaaccaggc   2160
accgacgccg tggaatgccc catgtgtgga ggaacgggcg gttggccagg cgtaagcggc   2220
tgggttgtct gccggccctg caatggcact ggaaccccca agcccgagga atcggcgtga   2280
cggtcgcaaa ccatccggcc cggtacaaat cggcgcggcg ctgggtgatg acctggtgga   2340
gaagttgaag gccgcgcagg ccgcccagcg gcaacgcatc gaggcagaag cacgccccgg   2400
tgaatcgtgg caagcggccg ctgatcgaat ccgcaaagaa tcccggcaac cgccggcagc   2460
cggtgcgccg tcgattagga agccgcccaa gggcgacgag caaccagatt ttttcgttcc   2520
gatgctctat gacgtgggca cccgcgatag tcgcagcatc atggacgtgg ccgttttccg   2580
tctgtcgaag cgtgaccgac gagctggcga ggtgatccgc tacgagcttc cagacgggca   2640
cgtagaggtt tccgcagggc cggccggcat ggccagtgtg tgggattacg acctggtact   2700
gatggcggtt tcccatctaa ccgaatccat gaaccgatac cgggaaggga agggagacaa   2760
gcccggccgc gtgttccgtc cacacgttgc ggacgtactc aagttctgcc ggcgagccga   2820
tggcggaaag cagaaagacg acctggtaga aacctgcatt cggttaaaca ccacgcacgt   2880
tgccatgcag cgtacgaaga aggccaagaa cggccgcctg gtgacggtat ccgagggtga   2940
agccttgatt agccgctaca agatcgtaaa gagcgaaacc gggcggccgg agtacatcga   3000
gatcgagcta gctgattgga tgtaccgcga gatcacagaa ggcaagaacc cggacgtgct   3060
gacggttcac cccgattact ttttgatcga tcccggcatc ggccgttttc tctaccgcct   3120
ggcacgccgc gccgcaggca aggcagaagc cagatggttg ttcaagacga tctacgaacg   3180
cagtggcagc gccggagagt tcaagaagtt ctgtttcacc gtgcgcaagc tgatcgggtc   3240
aaatgacctg ccggagtacg atttgaagga ggaggcgggg caggctggcc cgatcctagt   3300
catgcgctac cgcaacctga tcgagggcga agcatccgcc ggttcctaat gtacggagca   3360
gatgctaggg caaattgccc tagcagggga aaaaggtcga aaaggtctct ttcctgtgga   3420
tagcacgtac attgggaacc caaagccgta cattgggaac cggaacccgt acattgggaa   3480
cccaaagccg tacattggga accggtcaca catgtaagtg actgatataa aagagaaaaa   3540
aggcgatttt tccgcctaaa actctttaaa acttattaaa actcttaaaa cccgcctggc   3600
ctgtgcataa ctgtctggcc agcgcacagc cgaagagctg caaaaagcgc ctacccttcg   3660
gtcgctgcgc tccctacgcc ccgccgcttc gcgtcggcct atcgcggccg ctggccgctc   3720
aaaaatggct ggcctacggc caggcaatct accagggcgc ggacaagccg cgccgtcgcc   3780
actcgaccgc cggcgcccac atcaaggcac cctgcctcgc gcgtttcggt gatgacggtg   3840
aaaacctctg acacatgcag ctcccggaga cggtcacagc ttgtctgtaa gcggatgccg   3900
ggagcagaca agcccgtcag ggcgcgtcag cgggtgttgg cgggtgtcgg ggcgcagcca   3960
tgacccagtc acgtagcgat agcggagtgt atactggctt aactatgcgg catcagagca   4020
```

-continued gattgtactg agagtgcacc atatgcggtg tgaaataccg cacagatgcg taaggagaaa 4080
ataccgcatc aggcgctctt ccgcttcctc gctcactgac tcgctgcgct cggtcgttcg 4140
gctgcggcga gcggtatcag ctcactcaaa ggcggtaata cggttatcca cagaatcagg 4200
ggataacgca ggaaagaaca tgtgagcaaa aggccagcaa aaggccagga accgtaaaaa 4260
ggccgcgttg ctggcgtttt tccataggct ccgcccccct gacgagcatc acaaaaatcg 4320
acgctcaagt cagaggtggc gaaacccgac aggactataa agataccagg cgtttccccc 4380
tggaagctcc ctcgtgcgct ctcctgttcc gaccctgccg cttaccggat acctgtccgc 4440
ctttctccct tcgggaagcg tggcgctttc tcatagctca cgctgtaggt atctcagttc 4500
ggtgtaggtc gttcgctcca agctgggctg tgtgcacgaa ccccccgttc agcccgaccg 4560
ctgcgcctta tccggtaact atcgtcttga gtccaacccg gtaagacacg acttatcgcc 4620
actggcagca gccactggta acaggattag cagagcgagg tatgtaggcg gtgctacaga 4680
gttcttgaag tggtggccta actacggcta cactagaagg acagtatttg gtatctgcgc 4740
tctgctgaag ccagttacct tcggaaaaag agttggtagc tcttgatccg gcaaacaaac 4800
caccgctggt agcggtggtt tttttgtttg caagcagcag attacgcgca gaaaaaaagg 4860
atctcaagaa gatcctttga tcttttctac ggggtctgac gctcagtgga acgaaaactc 4920
acgttaaggg attttggtca tgcattctag gtactaaaac aattcatcca gtaaaatata 4980
atattttatt ttctcccaat caggcttgat ccccagtaag tcaaaaaata gctcgacata 5040
ctgttcttcc ccgatatcct ccctgatcga ccggacgcag aaggcaatgt cataccactt 5100
gtccgccctg ccgcttctcc caagatcaat aaagccactt actttgccat ctttcacaaa 5160
gatgttgctg tctcccaggt cgccgtggga aaagacaagt tcctcttcgg gcttttccgt 5220
ctttaaaaaa tcatacagct cgcgcggatc tttaaatgga gtgtcttctt cccagttttc 5280
gcaatccaca tcggccagat cgttattcag taagtaatcc aattcggcta agcggctgtc 5340
taagctattc gtatagggac aatccgatat gtcgatggag tgaaagagcc tgatgcactc 5400
cgcatacagc tcgataatct tttcagggct ttgttcatct tcatactctt ccgagcaaag 5460
gacgccatcg gcctcactca tgagcagatt gctccagcca tcatgccgtt caaagtgcag 5520
gacctttgga acaggcagct ttccttccag ccatagcatc atgtcctttt cccgttccac 5580
atcataggtg gtccctttat accggctgtc cgtcattttt aaatataggt tttcattttc 5640
tcccaccagc ttatatacct tagcaggaga cattccttcc gtatctttta cgcagcggta 5700
tttttcgatc agtttttca attccggtga tattctcatt ttagccattt attatttcct 5760
tcctcttttc tacagtattt aaagataccc caagaagcta attataacaa gacgaactcc 5820
aattcactgt tccttgcatt ctaaaacctt aaataccaga aaacagcttt ttcaaagttg 5880
ttttcaaagt tggcgtataa catagtatcg acggagccga ttttgaaacc gcggtgatca 5940
caggcagcaa cgctctgtca tcgttacaat caacatgcta ccctccgcga gatcatccgt 6000
gtttcaaacc cggcagctta gttgccgttc ttccgaatag catcggtaac atgagcaaag 6060
tctgccgcct tacaacggct ctcccgctga cgccgtcccg gactgatggg ctgcctgtat 6120
cgagtggtga ttttgtgccg agctgccggt cggggagctg ttggctggct ggtggcagga 6180
tatattgtgg tgtaaacaaa ttgacgctta gacaacttaa taacacattg cggacgtttt 6240
taatgtactg aattaacgcc gaattaattc gggggatctg gattttagta ctggattttg 6300
gttttaggaa ttagaaattt tattgataga agtattttac aaatacaaat acatactaag 6360

-continued

```
ggtttcttat atgctcaaca catgagcgaa accctatagg aaccctaatt cccttatctg   6420
ggaactactc acacattatt atggagaaac tcgagtcaaa tctcggtgac gggcaggacc   6480
ggacggggcg gtaccggcag gctgaagtcc agctgccaga aacccacgtc atgccagttc   6540
ccgtgcttga agccggccgc ccgcagcatg ccgcgggggg catatccgag cgcctcgtgc   6600
atgcgcacgc tcgggtcgtt gggcagcccg atgacagcga ccacgctctt gaagccctgt   6660
gcctccaggg acttcagcag gtgggtgtag agcgtggagc ccagtcccgt ccgctggtgg   6720
cggggggaga cgtacacggt cgactcggcc gtccagtcgt aggcgttgcg tgccttccag   6780
gggcccgcgt aggcgatgcc ggcgacctcg ccgtccacct cggcgacgag ccagggatag   6840
cgctcccgca gacggacgag gtcgtccgtc cactcctgcg gttcctgcgg ctcggtacgg   6900
aagttgaccg tgcttgtctc gatgtagtgg ttgacgatgg tgcagaccgc cggcatgtcc   6960
gcctcggtgg cacggcggat gtcggccggg cgtcgttctg ggctcatggt agactcgaga   7020
gagatagatt tgtagagaga gactggtgat ttcagcgtgt cctctccaaa tgaaatgaac   7080
ttccttatat agaggaaggt cttgcgaagg atagtgggat tgtgcgtcat cccttacgtc   7140
agtggagata tcacatcaat ccacttgctt tgaagacgtg gttggaacgt cttcttttc    7200
cacgatgctc ctcgtgggtg ggggtccatc tttgggacca ctgtcggcag aggcatcttg   7260
aacgatagcc tttcctttat cgcaatgatg gcatttgtag gtgccacctt ccttttctac   7320
tgtccttttg atgaagtgac agatagctgg gcaatggaat ccgaggaggt ttcccgatat   7380
taccctttgt tgaaaagtct caatagccct ttggtcttct gagactgtat ctttgatatt   7440
cttggagtag acgagagtgt cgtgctccac catgttatca catcaatcca cttgctttga   7500
agacgtggtt ggaacgtctt ctttttccac gatgctcctc gtgggtgggg gtccatcttt   7560
gggaccactg tcggcagagg catcttgaac gatagccttt cctttatcgc aatgatggca   7620
tttgtaggtg ccaccttcct tttctactgt ccttttgatg aagtgacaga tagctgggca   7680
atggaatccg aggaggtttc ccgatattac cctttgttga aaagtctcaa tagccctttg   7740
gtcttctgag actgtatctt tgatattctt ggagtagacg agagtgtcgt gctccaccat   7800
gttggcaagc tgctctagcc aatacgcaaa ccgcctctcc ccgcgcgttg gccgattcat   7860
taatgcagct ggcacgacag gtttcccgac tggaaagcgg gcagtgagcg caacgcaatt   7920
aatgtgagtt agctcactca ttaggcaccc caggctttac actttatgct tccggctcgt   7980
atgttgtgtg gaattgtgag cggataacaa tttcacacag gaaacagcta tgaccatgat   8040
tacgaattcg agccttgact agagggtcga cggtatacag acatgataag atacattgat   8100
gagtttggac aaaccacaac tagaatgcag tgaaaaaaat gctttatttg tgaaatttgt   8160
gatgctattg ctttatttgt aaccattata agctgcaata aacaagttgg ggtgggcgaa   8220
gaactccagc atgagatccc cgcgctggag gatcatccag ccggcgtccc ggaaaacgat   8280
tccgaagccc aacctttcat agaaggcggc ggtggaatcg aaatctcgta gcacgtgtca   8340
gtcctgctcc tcggccacga agtgcacgca gttgccggcc gggtcgcgca gggcgaactc   8400
ccgcccccac ggctgctcgc cgatctcggt catggccggc ccggaggcgt cccggaagtt   8460
cgtggacacg acctccgacc actcggcgta cagctcgtcc aggccgcgca cccacaccca   8520
ggccagggtg ttgtccggca ccacctggtc ctggaccgcg ctgatgaaca gggtcacgtc   8580
gtcccggacc acaccggcga agtcgtcctc cacgaagtcc cgggagaacc cgagccggtc   8640
ggtccagaac tcgaccgctc cggcgacgtc gcgcgcggtg agcaccggaa cggcactggt   8700
caacttggcc atggatccag atttcgctca agttagtata aaaaagcagg cttcaatcct   8760
```

-continued

```
gcaggaattc gatcgacact ctcgtctact ccaagaatat caaagataca gtctcagaag   8820
accaaagggc tattgagact tttcaacaaa gggtaatatc gggaaacctc ctcggattcc   8880
attgcccagc tatctgtcac ttcatcaaaa ggacagtaga aaaggaaggt ggcacctaca   8940
aatgccatca ttgcgataaa ggaaaggcta tcgttcaaga tgcctctgcc gacagtggtc   9000
ccaaagatgg acccccaccc acgaggagca tcgtggaaaa agaagacgtt ccaaccacgt   9060
cttcaaagca agtggattga tgtgataaca tggtggagca cgacactctc gtctactcca   9120
agaatatcaa agatacagtc tcagaagacc aaagggctat tgagactttt caacaaaggg   9180
taatatcggg aaacctcctc ggattccatt gcccagctat ctgtcacttc atcaaaagga   9240
cagtagaaaa ggaaggtggc acctacaaat gccatcattg cgataaagga aaggctatcg   9300
ttcaagatgc ctctgccgac agtggtccca aagatggacc cccacccacg aggagcatcg   9360
tggaaaaaga agacgttcca accacgtctt caaagcaagt ggattgatgt gatatctcca   9420
ctgacgtaag ggatgacgca caatcccact atccttcgca agacccttcct ctatataagg  9480
aagttcattt catttggaga ggacacgctg aaatcaccag tctctctcta caaatctatc   9540
tctctcgagc tttcgcagat ccggggggc aatgagatat gaaaaagcct gaactcaccg    9600
cgacgtctgt cgagaagttt ctgatcgaaa agttcgacag cgtctccgac ctgatgcagc   9660
tctcggaggg cgaagaatct cgtgctttca gcttcgatgt aggagggcgt ggatatgtcc   9720
tgcgggtaaa tagctgcgcc gatggtttct acaaagatcg ttatgtttat cggcactttg   9780
catcggccgc gctcccgatt ccggaagtgc ttgacattgg ggagtttagc gagagcctga   9840
cctattgcat ctcccgccgt gcacagggtg tcacgttgca agacctgcct gaaaccgaac   9900
tgcccgctgt tctacaaccg gtcgcggagg ctatggatgc gatcgctgcg gccgatctta   9960
gccagacgag cgggttcggc ccattcggac cgcaaggaat cggtcaatac actacatggc  10020
gtgatttcat atgcgcgatt gctgatcccc atgtgtatca ctggcaaact gtgatggacg  10080
acaccgtcag tgcgtccgtc gcgcaggctc tcgatgagct gatgctttgg gccgaggact  10140
gccccgaagt ccggcacctc gtgcacgcgg atttcggctc caacaatgtc ctgacggaca  10200
atggccgcat aacagcggtc attgactgga gcgaggcgat gttcggggat tcccaatacg  10260
aggtcgccaa catcttcttc tggaggccgt ggttggcttg tatggagcag cagacgcgct  10320
acttcgagcg gaggcatccg gagcttgcag gatcgccacg actccgggcg tatatgctcc  10380
gcattggtct tgaccaactc tatcagagct tggttgacgg caatttcgat gatgcagctt  10440
gggcgcaggg tcgatgcgac gcaatcgtcc gatccggagc cgggactgtc gggcgtacac  10500
aaatcgcccg cagaagcgcg gccgtctgga ccgatggctg tgtagaagta ctcgccgata  10560
gtggaaaccg acgccccagc actcgtccga gggcaaagaa atagagtaga tgccgaccgg  10620
atctgtcgat cgacaagctc gagtttctcc ataataatgt gtgagtagtt cccagataag  10680
ggaattaggg ttcctatagg gtttcgctca tgtgttgagc atataagaaa cccttagtat  10740
gtatttgtat ttgtaaaata cttctatcaa taaaatttct aattcctaaa accaaaatcc  10800
agtactaaaa tccagatccc ccgaattaat tcggcgttaa ttcagatcaa gcttgacctg  10860
gaatatcgcg agtaaactga aaatcacgga aaatgagaaa tacacacttt aggacgtgaa  10920
atatggcgag gaaaactgaa aaaggtggaa aatttagaaa tgtccactgt aggacgtgga  10980
atatggcaag aaaactgaaa atcatggaaa atgagaaaca tccacttgac gacttgaaaa  11040
atgacgaaat cactaaaaaa cgtgaaaaat gagaaatgca cactgaagga ctccgcggga  11100
```

-continued

```
attcgattgt gctagccaat gtttaacaag atgtcaagca caatgaatgt tggtggttgg  11160
tggtcgtggc tggcggtggt ggaaaattgc ggtggttcga gcggtagtga tcggcgatgg  11220
ttggtgtttg cagcggtgtt tgatatcgga atcacttatg gtggttgtca caatggaggt  11280
gcgtcatggt tattggtggt tggtcatcta tatattttta taataatatt aagtatttta  11340
cctatttttt acatattttt tattaaattt atgcattgtt tgtattttta aatagttttt  11400
atcgtacttg ttttataaaa tattttatta ttttatgtgt tatattatta cttgatgtat  11460
tggaaatttt ctccattgtt ttttctatat ttataataat tttcttattt tttttgttt  11520
tattatgtat tttttcgttt tataataaat atttattaaa aaaaatatta tttttgtaaa  11580
atatatcatt tacaatgttt aaaagtcatt tgtgaatata ttagctaagt tgtacttctt  11640
tttgtgcatt tggtgttgta catgtctatt atgattctct ggccaaaaca tgtctactcc  11700
tgtcacttgg gttttttttt ttaagacata atcactagtg attatatcta gactgaaggc  11760
gggaaacgac aatctgatca tgagcggaga attaagggag tcacgttatg acccccgccg  11820
atgacgcggg acaagccgtt ttacgtttgg aactgacaga accgcaacgt tgaaggagcc  11880
actcagccgc gggtttctgg agtttaatga gctaagcaca tacgtcagaa accattattg  11940
cgcgttcaaa agtcgcctaa ggtcactatc agctagcaaa tatttcttgt caaaaatgct  12000
ccactgacgt tccataaatt cccctcggta tccaattaga gtctcatatt cactctcaat  12060
ccaaataatc tgcaccggat ctcgagatcg aattcccgcg gccgcgaatt cactagtgga  12120
tccccgggta cggtcagtcc cttatgttac gtcctgtaga aaccccaacc cgtgaaatca  12180
aaaaactcga cggcctgtgg gcattcagtc tggatcgcga aaactgtgga attgagcagc  12240
gttggtggga aagcgcgtta caagaaagcc gggcaattgc tgtgccaggc agttttaacg  12300
atcagttcgc cgatgcagat attcgtaatt atgtgggcaa cgtctggtat cagcgcgaag  12360
tctttatacc gaaaggttgg gcaggccagc gtatcgtgct gcgtttcgat gcggtcactc  12420
attacggcaa agtgtgggtc aataatcagg aagtgatgga gcatcagggc ggctatacgc  12480
catttgaagc cgatgtcacg ccgtatgtta ttgccgggaa aagtgtacgt atcacagttt  12540
gtgtgaacaa cgaactgaac tggcagacta tcccgccggg aatggtgatt accgacgaaa  12600
acggcaagaa aaagcagtct tacttccatg atttctttaa ctacgccggg atccatcgca  12660
gcgtaatgct ctacaccacg ccgaacacct gggtggacga tatcaccgtg gtgacgcatg  12720
tcgcgcaaga ctgtaaccac gcgtctgttg actggcaggt ggtggccaat ggtgatgtca  12780
gcgttgaact gcgtgatgcg gatcaacagg tggttgcaac tggacaaggc accagcggga  12840
ctttgcaagt ggtgaatccg cacctctggc aaccgggtga aggttatctc tatgaactgt  12900
acgtcacagc caaaagccag acagagtgtg atatctaccc gctgcgcgtc ggcatccggt  12960
cagtggcagt gaagggcgaa cagttcctga tcaaccacaa accgttctac tttactggct  13020
ttggccgtca tgaagatgcg gatttgcgcg gcaaaggatt cgataacgtg ctgatggtgc  13080
acgatcacgc attaatggac tggattgggg ccaactccta ccgtacctcg cattaccctt  13140
acgctgaaga gatgctcgac tgggcagatg aacatggcat cgtggtgatt gatgaaactg  13200
cagctgtcgg ctttaacctc tctttaggca ttggtttcga agcgggcaac aagccgaaag  13260
aactgtacag cgaagaggca gtcaacgggg aaactcagca ggcgcactta caggcgatta  13320
aagagctgat agcgcgtgac aaaaaccacc caagcgtggt gatgtggagt attgccaacg  13380
aaccggatac ccgtccgcaa ggtgcacggg aatatttcgc gccactggcg gaagcaacgc  13440
gtaaactcga tccgacgcgt ccgatcacct gcgtcaatgt aatgttctgc gacgctcaca  13500
```

-continued ccgataccat cagcgatctc tttgatgtgc tgtgcctgaa ccgttattac ggttggtatg 13560
tccaaagcgg cgatttggaa acggcagaga aggtactgga aaaagaactt ctggcctggc 13620
aggagaaact gcatcagccg attatcatca ccgaatacgg cgtggatacg ttagccgggc 13680
tgcactcaat gtacaccgac atgtggagtg aagagtatca gtgtgcatgg ctggatatgt 13740
atcaccgcgt ctttgatcgc gtcagcgccg tcgtcggtga acaggtatgg aatttcgccg 13800
attttgcgac ctcgcaaggc atattgcgcg ttggcggtaa caagaagggg atcttcaccc 13860
gcgaccgcaa accgaagtcg gcggcttttc tgctgcaaaa acgctggact ggcatgaact 13920
tcggtgaaaa accgcagcag ggaggcaaac aatgaatcaa caactctcct ggcgcaccat 13980
cgtcggctac agcctcggga attgcgtacc gagctcgaat ttccccgatc gttcaaacat 14040
ttggcaataa agtttcttaa gattgaatcc tgttgccggt cttgcgatga ttatcatata 14100
atttctgttg aattacgtta agcatgtaat aattaacatg taatgcatga cgttatttat 14160
gagatgggtt tttatgatta gagtcccgca attatacatt taatacgcga tagaaaacaa 14220
aatatagcgc gcaaactagg ataaattatc gcgcgcggtg tcatctatgt tactagatcg 14280
ggaattcgat atcaagcttg gcactggccg tcgttttaca acgtcgtgac tgggaaaacc 14340
ctggcgttac ccaacttaat cgccttgcag cacatccccc tttcgccagc tggcgtaata 14400
gcgaagaggc ccgcaccgat cgcccttccc aacagttgcg cagcctgaat ggcgaatgct 14460
agagcagctt gagcttggat cagattgtcg tttcccgcct tcagtttaaa ctatcagtgt 14520
ttgacaggat atattggcgg gtaaacctaa gagaaaagag cgtttattag aataacggat 14580
atttaaaagg gcgtgaaaag gtttatccgt tcgtccattt gtatgtg 14627

<210> SEQ ID NO 110
<211> LENGTH: 9080
<212> TYPE: DNA
<213> ORGANISM: Artificial Sequence
<220> FEATURE:
<223> OTHER INFORMATION: p18attBZeo(6XHS4)2eGFP Plasmid

<400> SEQUENCE: 110
cagttgccgg ccgggtcgcg cagggcgaac tcccgccccc acggctgctc gccgatctcg 60
gtcatggccg gcccggaggc gtcccggaag ttcgtggaca cgacctccga ccactcggcg 120
tacagctcgt ccaggccgcg cacccacacc caggccaggg tgttgtccgg caccacctgg 180
tcctggaccg cgctgatgaa cagggtcacg tcgtcccgga ccacaccggc gaagtcgtcc 240
tccacgaagt cccgggagaa cccgagccgg tcggtccaga actcgaccgc tccggcgacg 300
tcgcgcgcgg tgagcaccgg aacggcactg gtcaacttgg ccatggatcc agatttcgct 360
caagttagta taaaaaagca ggcttcaatc ctgcagagaa gcttgatatc gaattcctgc 420
agccccgcgg atccgctcac ggggacagcc ccccccaaa gcccccaggg atgtaattac 480
gtccctcccc cgctaggggg cagcagcgag ccgcccgggg ctccgctccg gtccggcgct 540
ccccccgcat ccccgagccg gcagcgtgcg gggacagccc gggcacgggg aaggtggcac 600
gggatcgctt tcctctgaac gcttctcgct gctctttgag cctgcagaca cctgggggat 660
acggggccgc ggatccgctc acggggacag cccccccca aagcccccag ggatgtaatt 720
acgtccctcc cccgctaggg ggcagcagcg agccgcccgg ggctccgctc cggtccggcg 780
ctccccccgc atccccgagc cggcagcgtg cggggacagc ccgggcacgg ggaaggtggc 840
acgggatcgc tttcctctga acgcttctcg ctgctctttg agcctgcaga cacctggggg 900

-continued

```
atacggggcc gcggatccgc tcacggggac agcccccccc caaagccccc agggatgtaa    960
ttacgtccct cccccgctag ggggcagcag cgagccgccc ggggctccgc tccggtccgg   1020
cgctcccccc gcatccccga gccggcagcg tgcggggaca gcccgggcac ggggaaggtg   1080
gcacgggatc gctttcctct gaacgcttct cgctgctctt tgagcctgca gacacctggg   1140
ggatacgggg ccgcggatcc gctcacgggg acagcccccc cccaaagccc ccagggatgt   1200
aattacgtcc ctcccccgct agggggcagc agcgagccgc ccggggctcc gctccggtcc   1260
ggcgctcccc ccgcatcccc gagccggcag cgtgcgggga cagcccgggc acggggaagg   1320
tggcacggga tcgctttcct ctgaacgctt ctcgctgctc tttgagcctg cagacacctg   1380
ggggatacgg ggccgcggat ccgctcacgg ggacagcccc cccccaaagc ccccagggat   1440
gtaattacgt ccctcccccg ctagggggca gcagcgagcc gcccggggct ccgctccggt   1500
ccggcgctcc ccccgcatcc ccgagccggc agcgtgcggg gacagcccgg gcacggggaa   1560
ggtggcacgg gatcgctttc ctctgaacgc ttctcgctgc tctttgagcc tgcagacacc   1620
tgggggatac ggggccgcgg atccgctcac ggggacagcc cccccccaaa gcccccaggg   1680
atgtaattac gtccctcccc cgctaggggg cagcagcgag ccgcccgggg ctccgctccg   1740
gtccggcgct ccccccgcat ccccgagccg gcagcgtgcg gggacagccc gggcacgggg   1800
aaggtggcac gggatcgctt tcctctgaac gcttctcgct gctctttgag cctgcagaca   1860
cctgggggat acggggcggg ggatccacta gttattaata gtaatcaatt acggggtcat   1920
tagttcatag cccatatatg gagttccgcg ttacataact tacggtaaat ggcccgcctg   1980
gctgaccgcc caacgacccc cgcccattga cgtcaataat gacgtatgtt cccatagtaa   2040
cgccaatagg gactttccat tgacgtcaat gggtggacta tttacggtaa actgcccact   2100
tggcagtaca tcaagtgtat catatgccaa gtacgccccc tattgacgtc aatgacggta   2160
aatggcccgc ctggcattat gcccagtaca tgaccttatg ggactttcct acttggcagt   2220
acatctacgt attagtcatc gctattacca tgggtcgagg tgagccccac gttctgcttc   2280
actctcccca tctccccccc ctccccaccc ccaattttgt atttatttat tttttaatta   2340
ttttgtgcag cgatgggggc gggggggggg ggggcgcgcg ccaggcgggg cggggcgggg   2400
cgaggggcgg ggcggggcga ggcggagagg tgcggcggca gccaatcaga gcggcgcgct   2460
ccgaaagttt ccttttatgg cgaggcggcg gcggcggcgg ccctataaaa agcgaagcgc   2520
gcggcgggcg ggagtcgctg cgttgccttc gccccgtgcc ccgctccgcg ccgcctcgcg   2580
ccgcccgccc cggctctgac tgaccgcgtt actcccacag gtgagcgggc gggacggccc   2640
ttctcctccg ggctgtaatt agcgcttggt ttaatgacgg ctcgtttctt ttctgtggct   2700
gcgtgaaagc cttaaagggc tccgggaggg ccctttgtgc ggggggggagc ggctcggggg   2760
gtgcgtgcgt gtgtgtgtgc gtggggagcg ccgcgtgcgg cccgcgctgc ccggcggctg   2820
tgagcgctgc gggcgcggcg cggggctttg tgcgctccgc gtgtgcgcga ggggagcgcg   2880
gccgggggcg gtgccccgcg gtgcgggggg gctgcgaggg gaacaaaggc tgcgtgcggg   2940
gtgtgtgcgt gggggggtga gcagggggtg tgggcgcggc ggtcgggctg taacccccc   3000
ctgcaccccc ctccccgagt tgctgagcac ggcccggctt cgggtgcggg gctccgtgcg   3060
gggcgtggcg cggggctcgc cgtgccgggc ggggggtggc ggcaggtggg ggtgccgggc   3120
ggggcggggc cgcctcgggc cggggagggc tcgggggagg ggcgcggcgg ccccggagcg   3180
ccggcggctg tcgaggcgcg gcgagccgca gccattgcct tttatggtaa tcgtgcgaga   3240
gggcgcaggg acttcctttg tcccaaatct ggcggagccg aaatctggga ggcgccgccg   3300
```

-continued

```
caccccctct agcgggcgcg ggcgaagcgg tgcggcgccg gcaggaagga aatgggcggg   3360
gagggccttc gtgcgtcgcc gcgccgccgt ccccttctcc atctccagcc tcggggctgc   3420
cgcaggggga cggctgcctt cgggggggac ggggcagggc ggggttcggc ttctggcgtg   3480
tgaccggcgg ctctagagcc tctgctaacc atgttcatgc cttcttcttt ttcctacagc   3540
tcctgggcaa cgtgctggtt gttgtgctgt ctcatcattt tggcaaagaa ttcgccacca   3600
tggtgagcaa gggcgaggag ctgttcaccg gggtggtgcc catcctggtc gagctggacg   3660
gcgacgtaaa cggccacaag ttcagcgtgt ccggcgaggg cgagggcgat gccacctacg   3720
gcaagctgac cctgaagttc atctgcacca ccggcaagct gcccgtgccc tggcccaccc   3780
tcgtgaccac cctgacctac ggcgtgcagt gcttcagccg ctaccccgac cacatgaagc   3840
agcacgactt cttcaagtcc gccatgcccg aaggctacgt ccaggagcgc accatcttct   3900
tcaaggacga cggcaactac aagacccgcg ccgaggtgaa gttcgagggc gacaccctgg   3960
tgaaccgcat cgagctgaag ggcatcgact tcaaggagga cggcaacatc ctggggcaca   4020
agctggagta caactacaac agccacaacg tctatatcat ggccgacaag cagaagaacg   4080
gcatcaaggt gaacttcaag atccgccaca acatcgagga cggcagcgtg cagctcgccg   4140
accactacca gcagaacacc cccatcggcg acggccccgt gctgctgccc gacaaccact   4200
acctgagcac ccagtccgcc ctgagcaaag accccaacga gaagcgcgat cacatggtcc   4260
tgctggagtt cgtgaccgcc gccgggatca ctctcggcat ggacgagctg tacaagtaag   4320
aattcactcc tcaggtgcag gctgcctatc agaaggtggt ggctggtgtg gccaatgccc   4380
tggctcacaa ataccactga gatctttttc cctctgccaa aaattatggg gacatcatga   4440
agccccttga gcatctgact tctggctaat aaaggaaatt tattttcatt gcaatagtgt   4500
gttggaattt tttgtgtctc tcactcggaa ggacatatgg gagggcaaat catttaaaac   4560
atcagaatga gtatttggtt tagagtttgg caacatatgc catatgctgg ctgccatgaa   4620
caaaggtggc tataaagagg tcatcagtat atgaaacagc cccctgctgt ccattcctta   4680
ttccatagaa aagccttgac ttgaggttag attttttttta tattttgttt tgtgttattt   4740
ttttctttaa catccctaaa attttcctta catgttttac tagccagatt tttcctcctc   4800
tcctgactac tcccagtcat agctgtccct cttctcttat gaagatccct cgacctgcag   4860
cccaagcttg catgcctgca ggtcgactct agtggatccc ccgccccgta tcccccaggt   4920
gtctgcaggc tcaaagagca gcgagaagcg ttcagaggaa agcgatcccg tgccaccttc   4980
cccgtgcccg ggctgtcccc gcacgctgcc ggctcgggga tgcgggggga gcgccggacc   5040
ggagcggagc cccgggcggc tcgctgctgc cccctagcgg gggagggacg taattacatc   5100
cctgggggct ttgggggggg gctgtccccg tgagcggatc cgcggccccg tatcccccag   5160
gtgtctgcag gctcaaagag cagcgagaag cgttcagagg aaagcgatcc cgtgccacct   5220
tccccgtgcc cgggctgtcc ccgcacgctg ccggctcggg gatgcggggg gagcgccgga   5280
ccggagcgga gccccgggcg gctcgctgct gccccctagc gggggaggga cgtaattaca   5340
tccctggggg ctttgggggg gggctgtccc cgtgagcgga tccgcggccc cgtatccccc   5400
aggtgtctgc aggctcaaag agcagcgaga agcgttcaga ggaaagcgat cccgtgccac   5460
cttccccgtg cccgggctgt ccccgcacgc tgccggctcg gggatgcggg gggagcgccg   5520
gaccggagcg gagccccggg cggctcgctg ctgcccccta gcgggggagg gacgtaatta   5580
catccctggg ggctttgggg gggggctgtc cccgtgagcg gatccgcggc cccgtatccc   5640
```

-continued

```
ccaggtgtct gcaggctcaa agagcagcga gaagcgttca gaggaaagcg atcccgtgcc   5700
accttccccg tgcccgggct gtccccgcac gctgccggct cggggatgcg gggggagcgc   5760
cggaccggag cggagccccg ggcggctcgc tgctgccccc tagcgggggga gggacgtaat   5820
tacatccctg gggctttgg gggggggctg tccccgtgag cggatccgcg gccccgtatc   5880
ccccaggtgt ctgcaggctc aaagagcagc gagaagcgtt cagaggaaag cgatcccgtg   5940
ccaccttccc cgtgcccggg ctgtccccgc acgctgccgg ctcggggatg cgggggggagc   6000
gccggaccgg agcggagccc cgggcggctc gctgctgccc cctagcgggg gagggacgta   6060
attacatccc tgggggcttt ggggggggggc tgtccccgtg agcggatccg cggccccgta   6120
tcccccaggt gtctgcaggc tcaaagagca gcgagaagcg ttcagaggaa agcgatcccg   6180
tgccaccttc cccgtgcccg ggctgtcccc gcacgctgcc ggctcgggga tgcgggggga   6240
gcgccggacc ggagcggagc cccgggcggc tcgctgctgc cccctagcgg gggagggacg   6300
taattacatc cctgggggct ttgggggggg gctgtccccg tgagcggatc cgcggggctg   6360
caggaattcg taatcatggt catagctgtt tcctgtgtga aattgttatc cgctcacaat   6420
tccacacaac atacgagccg gaagcataaa gtgtaaagcc tggggtgcct aatgagtgag   6480
ctaactcaca ttaattgcgt tgcgctcact gcccgctttc cagtcgggaa acctgtcgtg   6540
ccagctgcat taatgaatcg gccaacgcgc ggggagaggc ggtttgcgta ttgggcgctc   6600
ttccgcttcc tcgctcactg actcgctgcg ctcggtcgtt cggctgcggc gagcggtatc   6660
agctcactca aaggcggtaa tacggttatc cacagaatca ggggataacg caggaaagaa   6720
catgtgagca aaaggccagc aaaaggccag gaaccgtaaa aaggccgcgt tgctggcgtt   6780
tttccatagg ctccgccccc ctgacgagca tcacaaaaat cgacgctcaa gtcagaggtg   6840
gcgaaacccg acaggactat aaagatacca ggcgtttccc cctggaagct ccctcgtgcg   6900
ctctcctgtt ccgaccctgc cgcttaccgg atacctgtcc gcctttctcc cttcgggaag   6960
cgtggcgctt tctcatagct cacgctgtag gtatctcagt tcggtgtagg tcgttcgctc   7020
caagctgggc tgtgtgcacg aaccccccgt tcagcccgac cgctgcgcct tatccggtaa   7080
ctatcgtctt gagtccaacc cggtaagaca cgacttatcg ccactggcag cagccactgg   7140
taacaggatt agcagagcga ggtatgtagg cggtgctaca gagttcttga agtggtggcc   7200
taactacggc tacactagaa ggacagtatt tggtatctgc gctctgctga agccagttac   7260
cttcggaaaa agagttggta gctcttgatc cggcaaacaa accaccgctg gtagcggtgg   7320
tttttttgtt tgcaagcagc agattacgcg cagaaaaaaa ggatctcaag aagatccttt   7380
gatcttttct acggggtctg acgctcagtg gaacgaaaac tcacgttaag ggattttggt   7440
catgagatta tcaaaaagga tcttcaccta gatcctttta aattaaaaat gaagttttaa   7500
atcaatctaa agtatatatg agtaaacttg gtctgacagt taccaatgct taatcagtga   7560
ggcacctatc tcagcgatct gtctatttcg ttcatccata gttgcctgac tccccgtcgt   7620
gtagataact acgatacggg agggcttacc atctggcccc agtgctgcaa tgataccgcg   7680
agacccacgc tcaccggctc cagatttatc agcaataaac cagccagccg gaagggccga   7740
gcgcagaagt ggtcctgcaa ctttatccgc ctccatccag tctattaatt gttgccggga   7800
agctagagta agtagttcgc cagttaatag tttgcgcaac gttgttgcca ttgctacagg   7860
catcgtggtg tcacgctcgt cgtttggtat ggcttcattc agctccggtt cccaacgatc   7920
aaggcgagtt acatgatccc ccatgttgtg caaaaaagcg gttagctcct tcggtcctcc   7980
gatcgttgtc agaagtaagt tggccgcagt gttatcactc atggttatgg cagcactgca   8040
```

-continued

```
taattctctt actgtcatgc catccgtaag atgcttttct gtgactggtg agtactcaac   8100

caagtcattc tgagaatagt gtatgcggcg accgagttgc tcttgcccgg cgtcaatacg   8160

ggataatacc gcgccacata gcagaacttt aaaagtgctc atcattggaa aacgttcttc   8220

ggggcgaaaa ctctcaagga tcttaccgct gttgagatcc agttcgatgt aacccactcg   8280

tgcacccaac tgatcttcag catcttttac tttcaccagc gtttctgggt gagcaaaaac   8340

aggaaggcaa aatgccgcaa aaaagggaat aagggcgaca cggaaatgtt gaatactcat   8400

actcttcctt tttcaatatt attgaagcat ttatcagggt tattgtctca tgagcggata   8460

catatttgaa tgtatttaga aaaataaaca aataggggtt ccgcgcacat ttccccgaaa   8520

agtgccacct gacgtagtta acaaaaaaaa gcccgccgaa gcgggcttta ttaccaagcg   8580

aagcgccatt cgccattcag gctgcgcaac tgttgggaag ggcgatcggt gcgggcctct   8640

tcgctattac gccagctggc gaaaggggga tgtgctgcaa ggcgattaag ttgggtaacg   8700

ccagggtttt cccagtcacg acgttgtaaa acgacggcca gtccgtaata cgactcactt   8760

aaggccttga ctagagggtc gacggtatac agacatgata agatacattg atgagtttgg   8820

acaaaccaca actagaatgc agtgaaaaaa atgctttatt tgtgaaattt gtgatgctat   8880

tgctttattt gtaaccatta taagctgcaa taaacaagtt ggggtgggcg aagaactcca   8940

gcatgagatc cccgcgctgg aggatcatcc agccggcgtc ccggaaaacg attccgaagc   9000

ccaacctttc atagaaggcg gcggtggaat cgaaatctcg tagcacgtgt cagtcctgct   9060

cctcggccac gaagtgcacg                                               9080
```

```
<210> SEQ ID NO 111
<211> LENGTH: 4223
<212> TYPE: DNA
<213> ORGANISM: Artificial Sequence
<220> FEATURE:
<223> OTHER INFORMATION: pLIT38attBBSRpolyA10 Plasmid

<400> SEQUENCE: 111
```

```
gttaactacg tcaggtggca cttttcgggg aaatgtgcgc ggaaccccta tttgtttatt     60

tttctaaata cattcaaata tgtatccgct catgagacaa taaccctgat aaatgcttca    120

ataatattga aaaaggaaga gtatgagtat tcaacatttc cgtgtcgccc ttattccctt    180

ttttgcggca ttttgccttc ctgtttttgc tcacccagaa acgctggtga aagtaaaaga    240

tgctgaagat cagttgggtg cacgagtggg ttacatcgaa ctggatctca acagcggtaa    300

gatccttgag agttttcgcc ccgaagaacg ttctccaatg atgagcactt ttaaagttct    360

gctatgtggc gcggtattat cccgtgttga cgccgggcaa gagcaactcg gtcgccgcat    420

acactattct cagaatgact tggttgagta ctcaccagtc acagaaaagc atcttacgga    480

tggcatgaca gtaagagaat tatgcagtgc tgccataacc atgagtgata acactgcggc    540

caacttactt ctgacaacga tcggaggacc gaaggagcta accgcttttt tgcacaacat    600

gggggatcat gtaactcgcc ttgatcgttg ggaaccggag ctgaatgaag ccataccaaa    660

cgacgagcgt gacaccacga tgcctgtagc aatggcaaca acgttgcgca aactattaac    720

tggcgaacta cttactctag cttcccggca acaattaata gactggatgg aggcggataa    780

agttgcagga ccacttctgc gctcggccct tccggctggc tggtttattg ctgataaatc    840

tggagccggt gagcgtgggt ctcgcggtat cattgcagca ctggggccag atggtaagcc    900

ctcccgtatc gtagttatct acacgacggg gagtcaggca actatggatg aacgaaatag    960
```

-continued

```
acagatcgct gagataggtg cctcactgat taagcattgg taactgtcag accaagttta   1020
ctcatatata ctttagattg atttaccccg gttgataatc agaaaagccc caaaaacagg   1080
aagattgtat aagcaaatat ttaaattgta aacgttaata ttttgttaaa attcgcgtta   1140
aatttttgtt aaatcagctc atttttaac caataggccg aaatcggcaa aatcccttat   1200
aaatcaaaag aatagcccga gatagggttg agtgttgttc cagtttggaa caagagtcca   1260
ctattaaaga acgtggactc caacgtcaaa gggcgaaaaa ccgtctatca gggcgatggc   1320
ccactacgtg aaccatcacc caaatcaagt tttttggggt cgaggtgccg taaagcacta   1380
aatcggaacc ctaaagggag cccccgattt agagcttgac ggggaaagcg aacgtggcga   1440
gaaaggaagg gaagaaagcg aaaggagcgg gcgctagggc gctggcaagt gtagcggtca   1500
cgctgcgcgt aaccaccaca cccgccgcgc ttaatgcgcc gctacagggc gcgtaaaagg   1560
atctaggtga agatcctttt tgataatctc atgaccaaaa tcccttaacg tgagttttcg   1620
ttccactgag cgtcagaccc cgtagaaaag atcaaaggat cttcttgaga tcctttttt   1680
ctgcgcgtaa tctgctgctt gcaaacaaaa aaaccaccgc taccagcggt ggtttgtttg   1740
ccggatcaag agctaccaac tctttttccg aaggtaactg gcttcagcag agcgcagata   1800
ccaaatactg ttcttctagt gtagccgtag ttaggccacc acttcaagaa ctctgtagca   1860
ccgcctacat acctcgctct gctaatcctg ttaccagtgg ctgctgccag tggcgataag   1920
tcgtgtctta ccgggttgga ctcaagacga tagttaccgg ataaggcgca gcggtcgggc   1980
tgaacggggg gttcgtgcac acagcccagc ttggagcgaa cgacctacac cgaactgaga   2040
tacctacagc gtgagctatg agaaagcgcc acgcttcccg aagggagaaa ggcggacagg   2100
tatccggtaa gcggcagggt cggaacagga gagcgcacga gggagcttcc agggggaaac   2160
gcctggtatc tttatagtcc tgtcgggttt cgccacctct gacttgagcg tcgatttttg   2220
tgatgctcgt caggggggcg gagcctatgg aaaaacgcca gcaacgcggc ctttttacgg   2280
ttcctggcct tttgctggcc ttttgctcac atgtaatgtg agttagctca ctcattaggc   2340
accccaggct ttacacttta tgcttccggc tcgtatgttg tgtggaattg tgagcggata   2400
acaatttcac acaggaaaca gctatgacca tgattacgcc aagctacgta atacgactca   2460
ctagtggggc ccgtgcaatt gaagccggct ggcgccaagc ttctctgcag gattgaagcc   2520
tgctttttta tactaacttg agcgaaatct ggatcaccat gaaaacattt aacatttctc   2580
aacaagatct agaattagta gaagtagcga cagagaagat tacaatgctt tatgaggata   2640
ataaacatca tgtgggagcg gcaattcgta cgaaaacagg agaaatcatt tcggcagtac   2700
atattgaagc gtatatagga cgagtaactg tttgtgcaga agccattgcg attggtagtg   2760
cagtttcgaa tggacaaaag gattttgaca cgattgtagc tgttagacac ccttattctg   2820
acgaagtaga tagaagtatt cgagtggtaa gtccttgtgg tatgtgtagg gagttgattt   2880
cagactatgc accagattgt tttgtgttaa tagaaatgaa tggcaagtta gtcaaaacta   2940
cgattgaaga actcattcca ctcaaatata cccgaaatta aaagttttac cataccaagc   3000
ttggctgctg cctgaggctg gacgacctcg cggagttcta ccggcagtgc aaatccgtcg   3060
gcatccagga aaccagcagc ggctatccgc gcatccatgc cccgaactg caggagtggg   3120
gaggcacgat ggccgctttg gtccggatct ttgtgaagga accttacttc tgtggtgtga   3180
cataattgga caaactacct acagagattt aaagctctaa ggtaaatata aaatttttaa   3240
gtgtataatg tgttaaacta ctgattctaa ttgtttgtgt attttagatt ccaacctatg   3300
gaactgatga atgggagcag tggtggaatg cctttaatga ggaaaacctg ttttgctcag   3360
```

-continued

```
aagaaatgcc atctagtgat gatgaggcta ctgctgactc tcaacattct actcctccaa   3420

aaaagaagag aaaggtagaa gaccccaagg actttccttc agaattgcta agttttttga   3480

gtcatgctgt gtttagtaat agaactcttg cttgctttgc tatttacacc acaaaggaaa   3540

aagctgcact gctatacaag aaaattatgg aaaaatattc tgtaaccttt ataagtaggc   3600

ataacagtta taatcataac atactgtttt ttcttactcc acacaggcat agagtgtctg   3660

ctattaataa ctatgctcaa aaattgtgta cctttagctt tttaatttgt aaaggggtta   3720

ataaggaata tttgatgtat agtgccttga ctagagatca taatcagcca taccacattt   3780

gtagaggttt tacttgcttt aaaaaacctc ccacacctcc ccctgaacct gaaacataaa   3840

atgaatgcaa ttgttgttgt taacttgttt attgcagctt ataatggtta caaataaagc   3900

aatagcatca caaatttcac aaataaagat ccacgaattc gctagcttcg gccgtgacgc   3960

gtctccggat gtacaggcat gcgtcgaccc tctagtcaag gccttaagtg agtcgtatta   4020

cggactggcc gtcgttttac aacgtcgtga ctgggaaaac cctggcgtta cccaacttaa   4080

tcgccttgca gcacatcccc ctttcgccag ctggcgtaat agcgaagagg cccgcaccga   4140

tcgcccttcc caacagttgc gcagcctgaa tggcgaatgg cgcttcgctt ggtaataaag   4200

cccgcttcgg cgggcttttt ttt                                           4223
```

<210> SEQ ID NO 112
<211> LENGTH: 5855
<212> TYPE: DNA
<213> ORGANISM: Artificial Sequence
<220> FEATURE:
<223> OTHER INFORMATION: pCX-LamIntR Plasmid

<400> SEQUENCE: 112

```
gtcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggact atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atgggtcgag gtgagcccca cgttctgctt cactctcccc    420

atctcccccc cctccccacc cccaattttg tatttattta ttttttaatt attttgtgca    480

gcgatggggg cggggggggg gggggcgcgc gccaggcggg gcggggcggg gcgaggggcg    540

gggcggggcg aggcggagag gtgcggcggc agccaatcag agcggcgcgc tccgaaagtt    600

tccttttatg gcgaggcggc ggcggcggcg gccctataaa aagcgaagcg cgcggcgggc    660

gggagtcgct gcgttgcctt cgccccgtgc cccgctccgc gccgcctcgc gccgcccgcc    720

ccggctctga ctgaccgcgt tactcccaca ggtgagcggg cgggacggcc cttctcctcc    780

gggctgtaat tagcgcttgg tttaatgacg gctcgtttct tttctgtggc tgcgtgaaag    840

ccttaaaggg ctccgggagg gccctttgtg cggggggggag cggctcgggg ggtgcgtgcg    900

tgtgtgtgtg cgtggggagc gccgcgtgcg gcccgcgctg cccggcggct gtgagcgctg    960

cgggcgcggc gcggggcttt gtgcgctccg cgtgtgcgcg aggggagcgc ggccgggggc   1020

ggtgccccgc ggtgcggggg ggctgcgagg ggaacaaagg ctgcgtgcgg ggtgtgtgcg   1080

tggggggggtg agcagggggt gtgggcgcgg cggtcgggct gtaacccccc cctgcacccc   1140
```

-continued

```
cctccccgag ttgctgagca cggcccggct tcgggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcgggggag ggcgcggcg gccccggagc gccggcggct    1320
gtcgaggcgc ggcgagccgc agccattgcc ttttatggta atcgtgcgag agggcgcagg   1380
gacttccttt gtcccaaatc tggcggagcc gaaatctggg aggcgccgcc gcaccccctc   1440
tagcgggcgc gggcgaagcg gtgcggcgcc ggcaggaagg aaatgggcgg ggagggcctt   1500
cgtgcgtcgc cgcgccgccg tccccttctc catctccagc ctcggggctg ccgcaggggg   1560
acggctgcct tcggggggga cggggcaggg cggggttcgg cttctggcgt gtgaccggcg   1620
gctctagagc ctctgctaac catgttcatg ccttcttctt tttcctacag ctcctgggca   1680
acgtgctggt tgttgtgctg tctcatcatt ttggcaaaga attcatggga agaaggcgaa   1740
gtcatgagcg ccgggattta ccccctaacc tttatataag aaacaatgga tattactgct   1800
acagggaccc aaggacgggt aaagagtttg gattaggcag agacaggcga atcgcaatca   1860
ctgaagctat acaggccaac attgagttat tttcaggaca caaacacaag cctctgacag   1920
cgagaatcaa cagtgataat tccgttacgt tacattcatg gcttgatcgc tacgaaaaaa   1980
tcctggccag cagaggaatc aagcagaaga cactcataaa ttacatgagc aaaattaaag   2040
caataaggag ggtctgcct gatgctccac ttgaagacat caccacaaaa gaaattgcgg    2100
caatgctcaa tggatacata gacgagggca aggcggcgtc agccaagtta atcagatcaa   2160
cactgagcga tgcattccga gaggcaatag ctgaaggcca tataacaaca aaccatgtcg   2220
ctgccactcg cgcagcaaaa tctagagtaa ggagatcaag acttacggct gacgaatacc   2280
tgaaaattta tcaagcagca gaatcatcac catgttggct cagacttgca atggaactgg   2340
ctgttgttac cgggcaacga gttggtgatt tatgcgaaat gaagtggtct gatatcgtag   2400
atggatatct ttatgtcgag caaagcaaaa caggcgtaaa aattgccatc ccaacagcat   2460
tgcatattga tgctctcgga atatcaatga aggaaacact tgataaatgc aaagagattc   2520
ttggcggaga aaccataatt gcatctactc gtcgcgaacc gctttcatcc ggcacagtat   2580
caaggtattt tatgcgcgca cgaaaagcat caggtctttc cttcgaaggg gatccgccta   2640
cctttcacga gttgcgcagt ttgtctgcaa gactctatga gaagcagata agcgataagt   2700
ttgctcaaca tcttctcggg cataagtcgg acaccatggc atcacagtat cgtgatgaca   2760
gaggcaggga gtgggacaaa attgaaatca aataagaatt cactcctcag gtgcaggctg   2820
cctatcagaa ggtggtggct ggtgtggcca atgccctggc tcacaaatac cactgagatc   2880
tttttccctc tgccaaaaat tatggggaca tcatgaagcc ccttgagcat ctgacttctg   2940
gctaataaag gaaatttatt ttcattgcaa tagtgtgttg gaattttttg tgtctctcac   3000
tcggaaggac atatgggagg gcaaatcatt taaaacatca gaatgagtat ttggtttaga   3060
gtttggcaac atatgccata tgctggctgc catgaacaaa ggtggctata aagaggtcat   3120
cagtatatga aacagccccc tgctgtccat tccttattcc atagaaaagc cttgacttga   3180
ggttagattt tttttatatt ttgttttgtg ttattttttt ctttaacatc cctaaaattt   3240
tccttacatg ttttactagc cagatttttc ctcctctcct gactactccc agtcatagct   3300
gtccctcttc tcttatgaag atccctcgac ctgcagccca agcttggcgt aatcatggtc   3360
atagctgttt cctgtgtgaa attgttatcc gctcacaatt ccacacaaca tacgagccgg   3420
aagcataaag tgtaaagcct ggggtgccta atgagtgagc taactcacat taattgcgtt   3480
gcgctcactg cccgctttcc agtcgggaaa cctgtcgtgc cagcggatcc gcatctcaat   3540
```

-continued

```
tagtcagcaa ccatagtccc gcccctaact ccgcccatcc cgcccctaac tccgcccagt   3600
tccgcccatt ctccgcccca tggctgacta attttttta tttatgcaga ggccgaggcc   3660
gcctcggcct ctgagctatt ccagaagtag tgaggaggct tttttggagg cctaggcttt   3720
tgcaaaaagc taacttgttt attgcagctt ataatggtta caaataaagc aatagcatca   3780
caaatttcac aaataaagca ttttttcac tgcattctag ttgtggtttg tccaaactca   3840
tcaatgtatc ttatcatgtc tggatccgct gcattaatga atcggccaac gcgcggggag   3900
aggcggtttg cgtattgggc gctcttccgc ttcctcgctc actgactcgc tgcgctcggt   3960
cgttcggctg cggcgagcgg tatcagctca ctcaaaggcg gtaatacggt tatccacaga   4020
atcaggggat aacgcaggaa agaacatgtg agcaaaaggc cagcaaaagg ccaggaaccg   4080
taaaaaggcc gcgttgctgg cgtttttcca taggctccgc ccccctgacg agcatcacaa   4140
aaatcgacgc tcaagtcaga ggtggcgaaa cccgacagga ctataaagat accaggcgtt   4200
tccccctgga agctccctcg tgcgctctcc tgttccgacc ctgccgctta ccggatacct   4260
gtccgccttt ctcccttcgg gaagcgtggc gctttctcaa tgctcacgct gtaggtatct   4320
cagttcggtg taggtcgttc gctccaagct gggctgtgtg cacgaacccc ccgttcagcc   4380
cgaccgctgc gccttatccg gtaactatcg tcttgagtcc aacccggtaa gacacgactt   4440
atcgccactg gcagcagcca ctggtaacag gattagcaga gcgaggtatg taggcggtgc   4500
tacagagttc ttgaagtggt ggcctaacta cggctacact agaaggacag tatttggtat   4560
ctgcgctctg ctgaagccag ttaccttcgg aaaaagagtt ggtagctctt gatccggcaa   4620
acaaaccacc gctggtagcg gtggtttttt tgtttgcaag cagcagatta cgcgcagaaa   4680
aaaaggatct caagaagatc ctttgatctt ttctacgggg tctgacgctc agtggaacga   4740
aaactcacgt taagggattt tggtcatgag attatcaaaa aggatcttca cctagatcct   4800
tttaaattaa aaatgaagtt ttaaatcaat ctaaagtata tatgagtaaa cttggtctga   4860
cagttaccaa tgcttaatca gtgaggcacc tatctcagcg atctgtctat ttcgttcatc   4920
catagttgcc tgactccccg tcgtgtagat aactacgata cgggagggct taccatctgg   4980
ccccagtgct gcaatgatac cgcgagaccc acgctcaccg gctccagatt tatcagcaat   5040
aaaccagcca gccggaaggg ccgagcgcag aagtggtcct gcaactttat ccgcctccat   5100
ccagtctatt aattgttgcc gggaagctag agtaagtagt tcgccagtta atagtttgcg   5160
caacgttgtt gccattgcta caggcatcgt ggtgtcacgc tcgtcgtttg gtatggcttc   5220
attcagctcc ggttcccaac gatcaaggcg agttacatga tcccccatgt tgtgcaaaaa   5280
agcggttagc tccttcggtc ctccgatcgt tgtcagaagt aagttggccg cagtgttatc   5340
actcatggtt atggcagcac tgcataattc tcttactgtc atgccatccg taagatgctt   5400
ttctgtgact ggtgagtact caaccaagtc attctgagaa tagtgtatgc ggcgaccgag   5460
ttgctcttgc ccggcgtcaa tacgggataa taccgcgcca catagcagaa ctttaaaagt   5520
gctcatcatt ggaaaacgtt cttcggggcg aaaactctca aggatcttac cgctgttgag   5580
atccagttcg atgtaaccca ctcgtgcacc caactgatct tcagcatctt ttactttcac   5640
cagcgtttct gggtgagcaa aaacaggaag gcaaaatgcc gcaaaaaagg gaataagggc   5700
gacacggaaa tgttgaatac tcatactctt cctttttcaa tattattgaa gcatttatca   5760
gggttattgt ctcatgagcg gatacatatt tgaatgtatt tagaaaaata aacaaatagg   5820
ggttccgcgc acatttcccc gaaaagtgcc acctg                              5855
```

-continued

<210> SEQ ID NO 113
<211> LENGTH: 4346
<212> TYPE: DNA
<213> ORGANISM: Artificial Sequence
<220> FEATURE:
<223> OTHER INFORMATION: pSV40-193AttpsensePur Plasmid

<400> SEQUENCE: 113
ccggtgccgc caccatcccc tgacccacgc ccctgacccc tcacaaggag acgaccttcc 60
atgaccgagt acaagcccac ggtgcgcctc gccacccgcg acgacgtccc ccgggccgta 120
cgcaccctcg ccgccgcgtt cgccgactac cccgccacgc gccacaccgt cgacccggac 180
cgccacatcg agcgggtcac cgagctgcaa gaactcttcc tcacgcgcgt cgggctcgac 240
atcggcaagg tgtgggtcgc ggacgacggc gccgcggtgg cggtctggac cacgccggag 300
agcgtcgaag cgggggcggt gttcgccgag atcggcccgc gcatggccga gttgagcggt 360
tcccggctgg ccgcgcagca acagatggaa ggcctcctgg cgccgcaccg gcccaaggag 420
cccgcgtggt tcctggccac cgtcggcgtc tcgcccgacc accagggcaa gggtctgggc 480
agcgccgtcg tgctccccgg agtggaggcg gccgagcgcg ccggggtgcc cgccttcctg 540
gagacctccg cgccccgcaa cctccccttc tacgagcggc tcggcttcac cgtcaccgcc 600
gacgtcgagg tgcccgaagg accgcgcacc tggtgcatga cccgcaagcc cggtgcctga 660
cgcccgcccc acgacccgca gcgcccgacc gaaaggagcg cacgacccca tggctccgac 720
cgaagccgac ccgggcggcc ccgccgaccc cgcacccgcc cccgaggccc accgactcta 780
gaggatcata atcagccata ccacatttgt agaggtttta cttgctttaa aaaacctccc 840
acacctcccc ctgaacctga aacataaaat gaatgcaatt gttgttgtta acttgtttat 900
tgcagcttat aatggttaca aataaagcaa tagcatcaca aatttcacaa ataaagcatt 960
tttttcactg cattctagtt gtggtttgtc caaactcatc aatgtatctt atcatgtctg 1020
gatccgcgcc ggatccttaa ttaagtctag agtcgactgt ttaaacctgc aggcatgcaa 1080
gcttggcgta atcatggtca tagctgtttc ctgtgtgaaa ttgttatccg ctcacaattc 1140
cacacaacat acgagccgga agcataaagt gtaaagcctg gggtgcctaa tgagtgagct 1200
aactcacatt aattgcgttg cgctcactgc ccgctttcca gtcgggaaac ctgtcgtgcc 1260
agctgcatta atgaatcggc caacgcgcgg ggagaggcgg tttgcgtatt gggcgctctt 1320
ccgcttcctc gctcactgac tcgctgcgct cggtcgttcg gctgcggcga gcggtatcag 1380
ctcactcaaa ggcggtaata cggttatcca cagaatcagg ggataacgca ggaaagaaca 1440
tgtgagcaaa aggccagcaa aaggccagga accgtaaaaa ggccgcgttg ctggcgtttt 1500
tccataggct ccgcccccct gacgagcatc acaaaaatcg acgctcaagt cagaggtggc 1560
gaaacccgac aggactataa agataccagg cgtttccccc tggaagctcc ctcgtgcgct 1620
ctcctgttcc gaccctgccg cttaccggat acctgtccgc ctttctccct tcgggaagcg 1680
tggcgctttc tcatagctca cgctgtaggt atctcagttc ggtgtaggtc gttcgctcca 1740
agctgggctg tgtgcacgaa ccccccgttc agcccgaccg ctgcgcctta tccggtaact 1800
atcgtcttga gtccaacccg gtaagacacg acttatcgcc actggcagca gccactggta 1860
acaggattag cagagcgagg tatgtaggcg gtgctacaga gttcttgaag tggtggccta 1920
actacggcta cactagaagg acagtatttg gtatctgcgc tctgctgaag ccagttacct 1980
tcggaaaaag agttggtagc tcttgatccg gcaaacaaac caccgctggt agcggtggtt 2040
tttttgtttg caagcagcag attacgcgca gaaaaaaagg atctcaagaa gatcctttga 2100

-continued

```
tcttttctac ggggtctgac gctcagtgga acgaaaactc acgttaaggg attttggtca   2160
tgagattatc aaaaaggatc ttcacctaga tccttttaaa ttaaaaatga agttttaaat   2220
caatctaaag tatatatgag taaacttggt ctgacagtta ccaatgctta atcagtgagg   2280
cacctatctc agcgatctgt ctatttcgtt catccatagt tgcctgactc cccgtcgtgt   2340
agataactac gatacgggag ggcttaccat ctggccccag tgctgcaatg ataccgcgag   2400
acccacgctc accggctcca gatttatcag caataaacca gccagccgga agggccgagc   2460
gcagaagtgg tcctgcaact ttatccgcct ccatccagtc tattaattgt tgccgggaag   2520
ctagagtaag tagttcgcca gttaatagtt tgcgcaacgt tgttgccatt gctacaggca   2580
tcgtggtgtc acgctcgtcg tttggtatgg cttcattcag ctccggttcc caacgatcaa   2640
ggcgagttac atgatccccc atgttgtgca aaaaagcggt tagctccttc ggtcctccga   2700
tcgttgtcag aagtaagttg gccgcagtgt tatcactcat ggttatggca gcactgcata   2760
attctcttac tgtcatgcca tccgtaagat gcttttctgt gactggtgag tactcaacca   2820
agtcattctg agaatagtgt atgcggcgac cgagttgctc ttgcccggcg tcaatacggg   2880
ataataccgc gccacatagc agaactttaa aagtgctcat cattggaaaa cgttcttcgg   2940
ggcgaaaact ctcaaggatc ttaccgctgt tgagatccag ttcgatgtaa cccactcgtg   3000
cacccaactg atcttcagca tcttttactt tcaccagcgt ttctgggtga gcaaaaacag   3060
gaaggcaaaa tgccgcaaaa aagggaataa gggcgacacg gaaatgttga atactcatac   3120
tcttcctttt tcaatattat tgaagcattt atcagggtta ttgtctcatg agcggataca   3180
tatttgaatg tatttagaaa aataaacaaa taggggttcc gcgcacattt ccccgaaaag   3240
tgccacctga cgtctaagaa accattatta tcatgacatt aacctataaa aataggcgta   3300
tcacgaggcc ctttcgtctc gcgcgtttcg gtgatgacgg tgaaaacctc tgacacatgc   3360
agctcccgga gacggtcaca gcttgtctgt aagcggatgc cgggagcaga caagcccgtc   3420
agggcgcgtc agcgggtgtt ggcgggtgtc ggggctggct taactatgcg gcatcagagc   3480
agattgtact gagagtgcac catatgcggt gtgaaatacc gcacagatgc gtaaggagaa   3540
aataccgcat caggcgccat tcgccattca ggctgcgcaa ctgttgggaa gggcgatcgg   3600
tgcgggcctc ttcgctatta cgccagctgg cgaaaggggg atgtgctgca aggcgattaa   3660
gttgggtaac gccagggttt tcccagtcac gacgttgtaa aacgacggcc agtgaattcg   3720
agctgtggaa tgtgtgtcag ttagggtgtg gaaagtcccc aggctcccca gcaggcagaa   3780
gtatgcaaag catgcatctc aattagtcag caaccaggtg tggaaagtcc ccaggctccc   3840
cagcaggcag aagtatgcaa agcatgcatc tcaattagtc agcaaccata gtcccgcccc   3900
taactccgcc catcccgccc ctaactccgc ccagttccgc ccattctccg ccccatggct   3960
gactaatttt ttttatttat gcagaggccg aggccgcctc ggcctctgag ctattccaga   4020
agtagtgagg aggctttttt ggaggctcgg tacccccttg cgctaatgct ctgttacagg   4080
tcactaatac catctaagta gttgattcat agtgactgca tatgttgtgt tttacagtat   4140
tatgtagtct gtttttttatg caaaatctaa tttaatatat tgatatttat atcattttac   4200
gtttctcgtt cagctttttt atactaagtt ggcattataa aaaagcattg cttatcaatt   4260
tgttgcaacg aacaggtcac tatcagtcaa aataaaatca ttatttgatt tcaattttgt   4320
cccactccct gcctctgggg ggcgcg                                         4346
```

<210> SEQ ID NO 114

-continued

<211> LENGTH: 3166
<212> TYPE: DNA
<213> ORGANISM: Artificial Sequence
<220> FEATURE:
<223> OTHER INFORMATION: p18attBZeo Plasmid

<400> SEQUENCE: 114
cagttgccgg ccgggtcgcg cagggcgaac tcccgccccc acggctgctc gccgatctcg 60
gtcatggccg gcccggaggc gtcccggaag ttcgtggaca cgacctccga ccactcggcg 120
tacagctcgt ccaggccgcg cacccacacc caggccaggg tgttgtccgg caccacctgg 180
tcctggaccg cgctgatgaa cagggtcacg tcgtcccgga ccacaccggc gaagtcgtcc 240
tccacgaagt cccgggagaa cccgagccgg tcggtccaga actcgaccgc tccggcgacg 300
tcgcgcgcgg tgagcaccgg aacggcactg gtcaacttgg ccatggatcc agatttcgct 360
caagttagta taaaaaagca ggcttcaatc ctgcagagaa gcttgcatgc ctgcaggtcg 420
actctagagg atccccgggt accgagctcg aattcgtaat catggtcata gctgtttcct 480
gtgtgaaatt gttatccgct cacaattcca cacaacatac gagccggaag cataaagtgt 540
aaagcctggg gtgcctaatg agtgagctaa ctcacattaa ttgcgttgcg ctcactgccc 600
gctttccagt cgggaaacct gtcgtgccag ctgcattaat gaatcggcca acgcgcgggg 660
agaggcggtt tgcgtattgg gcgctcttcc gcttcctcgc tcactgactc gctgcgctcg 720
gtcgttcggc tgcggcgagc ggtatcagct cactcaaagg cggtaatacg gttatccaca 780
gaatcagggg ataacgcagg aaagaacatg tgagcaaaag gccagcaaaa ggccaggaac 840
cgtaaaaagg ccgcgttgct ggcgtttttc cataggctcc gcccccctga cgagcatcac 900
aaaaatcgac gctcaagtca gaggtggcga aacccgacag gactataaag ataccaggcg 960
tttccccctg gaagctccct cgtgcgctct cctgttccga ccctgccgct taccggatac 1020
ctgtccgcct ttctcccttc gggaagcgtg gcgctttctc atagctcacg ctgtaggtat 1080
ctcagttcgg tgtaggtcgt tcgctccaag ctgggctgtg tgcacgaacc ccccgttcag 1140
cccgaccgct gcgccttatc cggtaactat cgtcttgagt ccaacccggt aagacacgac 1200
ttatcgccac tggcagcagc cactggtaac aggattagca gagcgaggta tgtaggcggt 1260
gctacagagt tcttgaagtg gtggcctaac tacggctaca ctagaaggac agtatttggt 1320
atctgcgctc tgctgaagcc agttaccttc ggaaaaagag ttggtagctc ttgatccggc 1380
aaacaaacca ccgctggtag cggtggtttt tttgtttgca agcagcagat tacgcgcaga 1440
aaaaaaggat ctcaagaaga tcctttgatc ttttctacgg ggtctgacgc tcagtggaac 1500
gaaaactcac gttaagggat tttggtcatg agattatcaa aaaggatctt cacctagatc 1560
cttttaaatt aaaaatgaag ttttaaatca atctaaagta tatatgagta aacttggtct 1620
gacagttacc aatgcttaat cagtgaggca cctatctcag cgatctgtct atttcgttca 1680
tccatagttg cctgactccc cgtcgtgtag ataactacga tacgggaggg cttaccatct 1740
ggccccagtg ctgcaatgat accgcgagac ccacgctcac cggctccaga tttatcagca 1800
ataaaccagc cagccggaag ggccgagcgc agaagtggtc ctgcaacttt atccgcctcc 1860
atccagtcta ttaattgttg ccgggaagct agagtaagta gttcgccagt taatagtttg 1920
cgcaacgttg ttgccattgc tacaggcatc gtggtgtcac gctcgtcgtt tggtatggct 1980
tcattcagct ccggttccca acgatcaagg cgagttacat gatcccccat gttgtgcaaa 2040
aaagcggtta gctccttcgg tcctccgatc gttgtcagaa gtaagttggc cgcagtgtta 2100
tcactcatgg ttatggcagc actgcataat tctcttactg tcatgccatc cgtaagatgc 2160

-continued

```
ttttctgtga ctggtgagta ctcaaccaag tcattctgag aatagtgtat gcggcgaccg   2220

agttgctctt gcccggcgtc aatacgggat aataccgcgc cacatagcag aactttaaaa   2280

gtgctcatca ttggaaaacg ttcttcgggg cgaaaactct caaggatctt accgctgttg   2340

agatccagtt cgatgtaacc cactcgtgca cccaactgat cttcagcatc ttttactttc   2400

accagcgttt ctgggtgagc aaaaacagga aggcaaaatg ccgcaaaaaa gggaataagg   2460

gcgacacgga aatgttgaat actcatactc ttcctttttc aatattattg aagcatttat   2520

cagggttatt gtctcatgag cggatacata tttgaatgta tttagaaaaa taaacaaata   2580

ggggttccgc gcacatttcc ccgaaaagtg ccacctgacg tagttaacaa aaaaaagccc   2640

gccgaagcgg gctttattac caagcgaagc gccattcgcc attcaggctg cgcaactgtt   2700

gggaagggcg atcggtgcgg gcctcttcgc tattacgcca gctggcgaaa gggggatgtg   2760

ctgcaaggcg attaagttgg gtaacgccag ggttttccca gtcacgacgt tgtaaaacga   2820

cggccagtcc gtaatacgac tcacttaagg ccttgactag agggtcgacg gtatacagac   2880

atgataagat acattgatga gtttggacaa accacaacta gaatgcagtg aaaaaaatgc   2940

tttatttgtg aaatttgtga tgctattgct ttatttgtaa ccattataag ctgcaataaa   3000

caagttgggg tgggcgaaga actccagcat gagatccccg cgctggagga tcatccagcc   3060

ggcgtcccgg aaaacgattc cgaagcccaa cctttcatag aaggcggcgg tggaatcgaa   3120

atctcgtagc acgtgtcagt cctgctcctc ggccacgaag tgcacg                  3166
```

<210> SEQ ID NO 115
<211> LENGTH: 7600
<212> TYPE: DNA
<213> ORGANISM: Artificial Sequence
<220> FEATURE:
<223> OTHER INFORMATION: p18attBZeo3'6XHS4eGFP Plasmid

<400> SEQUENCE: 115

```
cagttgccgg ccgggtcgcg cagggcgaac tcccgccccc acggctgctc gccgatctcg     60

gtcatggccg gcccggaggc gtcccggaag ttcgtggaca cgacctccga ccactcggcg    120

tacagctcgt ccaggccgcg cacccacacc caggccaggg tgttgtccgg caccacctgg    180

tcctggaccg cgctgatgaa cagggtcacg tcgtcccgga ccacaccggc gaagtcgtcc    240

tccacgaagt cccgggagaa cccgagccgg tcggtccaga actcgaccgc tccggcgacg    300

tcgcgcgcgg tgagcaccgg aacggcactg gtcaacttgg ccatggatcc agatttcgct    360

caagttagta taaaaaagca ggcttcaatc ctgcagagaa gcttgatcta gttattaata    420

gtaatcaatt acggggtcat tagttcatag cccatatatg gagttccgcg ttacataact    480

tacggtaaat ggcccgcctg gctgaccgcc caacgacccc cgcccattga cgtcaataat    540

gacgtatgtt cccatagtaa cgccaatagg gactttccat tgacgtcaat gggtggacta    600

tttacggtaa actgcccact tggcagtaca tcaagtgtat catatgccaa gtacgccccc    660

tattgacgtc aatgacggta aatggcccgc ctggcattat gcccagtaca tgaccttatg    720

ggactttcct acttggcagt acatctacgt attagtcatc gctattacca tgggtcgagg    780

tgagccccac gttctgcttc actctcccca tctccccccc ctccccaccc ccaattttgt    840

atttatttat tttttaatta ttttgtgcag cgatgggggc gggggggggg ggggcgcgcg    900

ccaggcgggg cggggcgggg cgaggggcgg ggcggggcga ggcggagagg tgcggcggca    960

gccaatcaga gcggcgcgct ccgaaagttt ccttttatgg cgaggcggcg gcggcggcgg   1020
```

-continued

```
ccctataaaa agcgaagcgc gcggcgggcg ggagtcgctg cgttgccttc gccccgtgcc   1080
ccgctccgcg ccgcctcgcg ccgcccgccc cggctctgac tgaccgcgtt actcccacag   1140
gtgagcgggc gggacggccc ttctcctccg ggctgtaatt agcgcttggt ttaatgacgg   1200
ctcgtttctt ttctgtggct gcgtgaaagc cttaaagggc tccgggaggg ccctttgtgc   1260
ggggggggagc ggctcggggg gtgcgtgcgt gtgtgtgtgc gtggggagcg ccgcgtgcgg   1320
cccgcgctgc ccggcggctg tgagcgctgc gggcgcggcg cggggctttg tgcgctccgc   1380
gtgtgcgcga ggggagcgcg gccgggggcg gtgccccgcg gtgcgggggg gctgcgaggg   1440
gaacaaaggc tgcgtgcggg gtgtgtgcgt gggggggtga gcagggggtg tgggcgcggc   1500
ggtcgggctg taaccccccc ctgcaccccc ctccccgagt tgctgagcac ggcccggctt   1560
cgggtgcggg gctccgtgcg gggcgtggcg cggggctcgc cgtgccgggc ggggggtggc   1620
ggcaggtggg ggtgccgggc ggggcggggc cgcctcgggc cggggagggc tcgggggagg   1680
ggcgcggcgg ccccggagcg ccggcggctg tcgaggcgcg gcgagccgca gccattgcct   1740
tttatggtaa tcgtgcgaga gggcgcaggg acttcctttg tcccaaatct ggcggagccg   1800
aaatctggga ggcgccgccg cacccccctct agcgggcgcg ggcgaagcgg tgcggcgccg   1860
gcaggaagga aatgggcggg gagggccttc gtgcgtcgcc gcgccgccgt ccccttctcc   1920
atctccagcc tcggggctgc cgcagggggga cggctgcctt cgggggggac ggggcagggc   1980
ggggttcggc ttctggcgtg tgaccggcgg ctctagagcc tctgctaacc atgttcatgc   2040
cttcttcttt ttcctacagc tcctgggcaa cgtgctggtt gttgtgctgt ctcatcattt   2100
tggcaaagaa ttcgccacca tggtgagcaa gggcgaggag ctgttcaccg gggtggtgcc   2160
catcctggtc gagctggacg gcgacgtaaa cggccacaag ttcagcgtgt ccggcgaggg   2220
cgagggcgat gccacctacg gcaagctgac cctgaagttc atctgcacca ccggcaagct   2280
gcccgtgccc tggcccaccc tcgtgaccac cctgacctac ggcgtgcagt gcttcagccg   2340
ctaccccgac cacatgaagc agcacgactt cttcaagtcc gccatgcccg aaggctacgt   2400
ccaggagcgc accatcttct tcaaggacga cggcaactac aagacccgcg ccgaggtgaa   2460
gttcgagggc gacaccctgg tgaaccgcat cgagctgaag ggcatcgact tcaaggagga   2520
cggcaacatc ctggggcaca agctggagta caactacaac agccacaacg tctatatcat   2580
ggccgacaag cagaagaacg gcatcaaggt gaacttcaag atccgccaca acatcgagga   2640
cggcagcgtg cagctcgccg accactacca gcagaacacc cccatcggcg acggccccgt   2700
gctgctgccc gacaaccact acctgagcac ccagtccgcc ctgagcaaag accccaacga   2760
gaagcgcgat cacatggtcc tgctggagtt cgtgaccgcc gccgggatca ctctcggcat   2820
ggacgagctg tacaagtaag aattcactcc tcaggtgcag gctgcctatc agaaggtggt   2880
ggctggtgtg gccaatgccc tggctcacaa ataccactga gatctttttc cctctgccaa   2940
aaattatggg gacatcatga agccccttga gcatctgact tctggctaat aaaggaaatt   3000
tattttcatt gcaatagtgt gttggaattt tttgtgtctc tcactcggaa ggacatatgg   3060
gagggcaaat catttaaaac atcagaatga gtatttggtt tagagtttgg caacatatgc   3120
catatgctgg ctgccatgaa caaaggtggc tataaagagg tcatcagtat atgaaacagc   3180
cccctgctgt ccattcctta ttccatagaa aagccttgac ttgaggttag attttttttta   3240
tattttgttt tgtgttattt ttttctttaa catccctaaa attttcctta catgttttac   3300
tagccagatt tttcctcctc tcctgactac tcccagtcat agctgtccct cttctcttat   3360
gaagatccct cgacctgcag cccaagcttg catgcctgca ggtcgactct agtggatccc   3420
```

-continued

```
ccgccccgta tcccccaggt gtctgcaggc tcaaagagca gcgagaagcg ttcagaggaa   3480
agcgatcccg tgccaccttc cccgtgcccg ggctgtcccc gcacgctgcc ggctcgggga   3540
tgcgggggga gcgccggacc ggagcggagc cccgggcggc tcgctgctgc cccctagcgg   3600
gggagggacg taattacatc cctgggggct ttgggggggg gctgtccccg tgagcggatc   3660
cgcggccccg tatcccccag gtgtctgcag gctcaaagag cagcgagaag cgttcagagg   3720
aaagcgatcc cgtgccacct tccccgtgcc cgggctgtcc ccgcacgctg ccggctcggg   3780
gatgcggggg gagcgccgga ccggagcgga gccccgggcg gctcgctgct gccccctagc   3840
gggggaggga cgtaattaca tccctggggg ctttgggggg gggctgtccc cgtgagcgga   3900
tccgcggccc cgtatccccc aggtgtctgc aggctcaaag agcagcgaga agcgttcaga   3960
ggaaagcgat cccgtgccac cttccccgtg cccgggctgt ccccgcacgc tgccggctcg   4020
gggatgcggg gggagcgccg gaccggagcg gagccccggg cggctcgctg ctgcccccta   4080
gcgggggagg gacgtaatta catccctggg ggctttgggg gggggctgtc cccgtgagcg   4140
gatccgcggc cccgtatccc ccaggtgtct gcaggctcaa agagcagcga gaagcgttca   4200
gaggaaagcg atcccgtgcc accttccccg tgcccgggct gtccccgcac gctgccggct   4260
cggggatgcg gggggagcgc cggaccggag cggagccccg ggcggctcgc tgctgccccc   4320
tagcggggga gggacgtaat tacatccctg ggggctttgg gggggggctg tccccgtgag   4380
cggatccgcg gccccgtatc ccccaggtgt ctgcaggctc aaagagcagc gagaagcgtt   4440
cagaggaaag cgatcccgtg ccaccttccc cgtgcccggg ctgtccccgc acgctgccgg   4500
ctcggggatg cggggggagc gccggaccgg agcggagccc cgggcggctc gctgctgccc   4560
cctagcgggg gagggacgta attacatccc tgggggcttt gggggggggc tgtccccgtg   4620
agcggatccg cggccccgta tcccccaggt gtctgcaggc tcaaagagca gcgagaagcg   4680
ttcagaggaa agcgatcccg tgccaccttc cccgtgcccg ggctgtcccc gcacgctgcc   4740
ggctcgggga tgcgggggga gcgccggacc ggagcggagc cccgggcggc tcgctgctgc   4800
cccctagcgg gggagggacg taattacatc cctgggggct ttgggggggg gctgtccccg   4860
tgagcggatc cgcggggctg caggaattcg taatcatggt catagctgtt tcctgtgtga   4920
aattgttatc cgctcacaat tccacacaac atacgagccg gaagcataaa gtgtaaagcc   4980
tggggtgcct aatgagtgag ctaactcaca ttaattgcgt tgcgctcact gcccgctttc   5040
cagtcgggaa acctgtcgtg ccagctgcat taatgaatcg gccaacgcgc ggggagaggc   5100
ggtttgcgta ttgggcgctc ttccgcttcc tcgctcactg actcgctgcg ctcggtcgtt   5160
cggctgcggc gagcggtatc agctcactca aaggcggtaa tacggttatc cacagaatca   5220
ggggataacg caggaaagaa catgtgagca aaaggccagc aaaaggccag gaaccgtaaa   5280
aaggccgcgt tgctggcgtt tttccatagg ctccgccccc ctgacgagca tcacaaaaat   5340
cgacgctcaa gtcagaggtg gcgaaacccg acaggactat aaagatacca ggcgtttccc   5400
cctggaagct ccctcgtgcg ctctcctgtt ccgaccctgc cgcttaccgg atacctgtcc   5460
gcctttctcc cttcgggaag cgtggcgctt tctcatagct cacgctgtag gtatctcagt   5520
tcggtgtagg tcgttcgctc caagctgggc tgtgtgcacg aaccccccgt tcagcccgac   5580
cgctgcgcct tatccggtaa ctatcgtctt gagtccaacc cggtaagaca cgacttatcg   5640
ccactggcag cagccactgg taacaggatt agcagagcga ggtatgtagg cggtgctaca   5700
gagttcttga agtggtggcc taactacggc tacactagaa ggacagtatt tggtatctgc   5760
```

-continued

```
gctctgctga agccagttac cttcggaaaa agagttggta gctcttgatc cggcaaacaa   5820

accaccgctg gtagcggtgg tttttttgtt tgcaagcagc agattacgcg cagaaaaaaa   5880

ggatctcaag aagatccttt gatcttttct acggggtctg acgctcagtg gaacgaaaac   5940

tcacgttaag ggattttggt catgagatta tcaaaaagga tcttcaccta gatcctttta   6000

aattaaaaat gaagttttaa atcaatctaa agtatatatg agtaaacttg gtctgacagt   6060

taccaatgct taatcagtga ggcacctatc tcagcgatct gtctatttcg ttcatccata   6120

gttgcctgac tccccgtcgt gtagataact acgatacggg agggcttacc atctggcccc   6180

agtgctgcaa tgataccgcg agacccacgc tcaccggctc cagatttatc agcaataaac   6240

cagccagccg gaagggccga gcgcagaagt ggtcctgcaa ctttatccgc ctccatccag   6300

tctattaatt gttgccggga agctagagta agtagttcgc cagttaatag tttgcgcaac   6360

gttgttgcca ttgctacagg catcgtggtg tcacgctcgt cgtttggtat ggcttcattc   6420

agctccggtt cccaacgatc aaggcgagtt acatgatccc ccatgttgtg caaaaaagcg   6480

gttagctcct tcggtcctcc gatcgttgtc agaagtaagt tggccgcagt gttatcactc   6540

atggttatgg cagcactgca taattctctt actgtcatgc catccgtaag atgcttttct   6600

gtgactggtg agtactcaac caagtcattc tgagaatagt gtatgcggcg accgagttgc   6660

tcttgcccgg cgtcaatacg ggataatacc gcgccacata gcagaacttt aaaagtgctc   6720

atcattggaa aacgttcttc ggggcgaaaa ctctcaagga tcttaccgct gttgagatcc   6780

agttcgatgt aacccactcg tgcacccaac tgatcttcag catcttttac tttcaccagc   6840

gtttctgggt gagcaaaaac aggaaggcaa aatgccgcaa aaaagggaat aagggcgaca   6900

cggaaatgtt gaatactcat actcttcctt tttcaatatt attgaagcat ttatcagggt   6960

tattgtctca tgagcggata catatttgaa tgtatttaga aaaataaaca aataggggtt   7020

ccgcgcacat ttccccgaaa agtgccacct gacgtagtta acaaaaaaaa gcccgccgaa   7080

gcgggcttta ttaccaagcg aagcgccatt cgccattcag gctgcgcaac tgttgggaag   7140

ggcgatcggt gcgggcctct tcgctattac gccagctggc gaaaggggga tgtgctgcaa   7200

ggcgattaag ttgggtaacg ccagggtttt cccagtcacg acgttgtaaa acgacggcca   7260

gtccgtaata cgactcactt aaggccttga ctagagggtc gacggtatac agacatgata   7320

agatacattg atgagtttgg acaaaccaca actagaatgc agtgaaaaaa atgctttatt   7380

tgtgaaattt gtgatgctat tgctttattt gtaaccatta taagctgcaa taaacaagtt   7440

ggggtgggcg aagaactcca gcatgagatc cccgcgctgg aggatcatcc agccggcgtc   7500

ccggaaaacg attccgaagc ccaacctttc atagaaggcg gcggtggaat cgaaatctcg   7560

tagcacgtgt cagtcctgct cctcggccac gaagtgcacg                         7600
```

<210> SEQ ID NO 116
<211> LENGTH: 7631
<212> TYPE: DNA
<213> ORGANISM: Artificial Sequence
<220> FEATURE:
<223> OTHER INFORMATION: p18attBZeo5'6XHS4eGFP Plasmid

<400> SEQUENCE: 116

```
cagttgccgg ccgggtcgcg cagggcgaac tcccgccccc acggctgctc gccgatctcg     60

gtcatggccg gcccggaggc gtcccggaag ttcgtggaca cgacctccga ccactcggcg    120

tacagctcgt ccaggccgcg cacccacacc caggccaggg tgttgtccgg caccacctgg    180

tcctggaccg cgctgatgaa cagggtcacg tcgtcccgga ccacaccggc gaagtcgtcc    240
```

-continued

```
tccacgaagt cccgggagaa cccgagccgg tcggtccaga actcgaccgc tccggcgacg    300
tcgcgcgcgg tgagcaccgg aacggcactg gtcaacttgg ccatggatcc agatttcgct    360
caagttagta taaaaaagca ggcttcaatc ctgcagagaa gcttgatatc gaattcctgc    420
agccccgcgg atccgctcac ggggacagcc cccccccaaa gcccccaggg atgtaattac    480
gtccctcccc cgctaggggg cagcagcgag ccgcccgggg ctccgctccg gtccggcgct    540
ccccccgcat ccccgagccg gcagcgtgcg gggacagccc gggcacgggg aaggtggcac    600
gggatcgctt tcctctgaac gcttctcgct gctctttgag cctgcagaca cctgggggat    660
acggggccgc ggatccgctc acggggacag ccccccccca aagcccccag ggatgtaatt    720
acgtccctcc cccgctaggg ggcagcagcg agccgcccgg ggctccgctc cggtccggcg    780
ctcccccgc atccccgagc cggcagcgtg cggggacagc ccgggcacgg ggaaggtggc    840
acgggatcgc tttcctctga acgcttctcg ctgctctttg agcctgcaga cacctggggg    900
atacggggcc gcggatccgc tcacggggac agcccccccc caaagccccc agggatgtaa    960
ttacgtccct cccccgctag ggggcagcag cgagccgccc ggggctccgc tccggtccgg   1020
cgctcccccc gcatccccga gccggcagcg tgcggggaca gcccgggcac ggggaaggtg   1080
gcacgggatc gctttcctct gaacgcttct cgctgctctt tgagcctgca gacacctggg   1140
ggatacgggg ccgcggatcc gctcacgggg acagcccccc cccaaagccc ccagggatgt   1200
aattacgtcc ctcccccgct agggggcagc agcgagccgc ccggggctcc gctccggtcc   1260
ggcgctcccc ccgcatcccc gagccggcag cgtgcgggga cagcccgggc acggggaagg   1320
tggcacggga tcgctttcct ctgaacgctt ctcgctgctc tttgagcctg cagacacctg   1380
ggggatacgg ggccgcggat ccgctcacgg ggacagcccc cccccaaagc ccccagggat   1440
gtaattacgt ccctcccccg ctagggggca gcagcgagcc gcccggggct ccgctccggt   1500
ccggcgctcc ccccgcatcc ccgagccggc agcgtgcggg gacagcccgg gcacggggaa   1560
ggtggcacgg gatcgctttc ctctgaacgc ttctcgctgc tctttgagcc tgcagacacc   1620
tgggggatac ggggccgcgg atccgctcac ggggacagcc cccccccaaa gcccccaggg   1680
atgtaattac gtccctcccc cgctaggggg cagcagcgag ccgcccgggg ctccgctccg   1740
gtccggcgct ccccccgcat ccccgagccg gcagcgtgcg gggacagccc gggcacgggg   1800
aaggtggcac gggatcgctt tcctctgaac gcttctcgct gctctttgag cctgcagaca   1860
cctgggggat acggggcggg ggatccacta gttattaata gtaatcaatt acggggtcat   1920
tagttcatag cccatatatg gagttccgcg ttacataact tacggtaaat ggcccgcctg   1980
gctgaccgcc caacgacccc cgcccattga cgtcaataat gacgtatgtt cccatagtaa   2040
cgccaatagg gactttccat tgacgtcaat gggtggacta tttacggtaa actgcccact   2100
tggcagtaca tcaagtgtat catatgccaa gtacgccccc tattgacgtc aatgacggta   2160
aatggcccgc ctggcattat gcccagtaca tgaccttatg ggactttcct acttggcagt   2220
acatctacgt attagtcatc gctattacca tgggtcgagg tgagccccac gttctgcttc   2280
actctcccca tctccccccc ctccccaccc ccaattttgt atttatttat tttttaatta   2340
ttttgtgcag cgatgggggc gggggggggg ggggcgcgcg ccaggcgggg cggggcgggg   2400
cgaggggcgg ggcggggcga ggcggagagg tgcggcggca gccaatcaga gcggcgcgct   2460
ccgaaagttt ccttttatgg cgaggcggcg gcggcggcgg ccctataaaa agcgaagcgc   2520
gcggcgggcg ggagtcgctg cgttgccttc gccccgtgcc ccgctccgcg ccgcctcgcg   2580
```

-continued

```
ccgcccgccc cggctctgac tgaccgcgtt actcccacag gtgagcgggc gggacggccc   2640
ttctcctccg ggctgtaatt agcgcttggt ttaatgacgg ctcgtttctt ttctgtggct   2700
gcgtgaaagc cttaaagggc tccgggaggg ccctttgtgc ggggggggagc ggctcggggg   2760
gtgcgtgcgt gtgtgtgtgc gtggggagcg ccgcgtgcgg cccgcgctgc ccggcggctg   2820
tgagcgctgc gggcgcggcg cggggctttg tgcgctccgc gtgtgcgcga ggggagcgcg   2880
gccgggggcg gtgccccgcg gtgcgggggg gctgcgaggg gaacaaaggc tgcgtgcggg   2940
gtgtgtgcgt gggggggtga gcagggggtg tgggcgcggc ggtcgggctg taaccccccc   3000
ctgcaccccc ctccccgagt tgctgagcac ggcccggctt cgggtgcggg gctccgtgcg   3060
gggcgtggcg cggggctcgc cgtgccgggc ggggggtggc ggcaggtggg ggtgccgggc   3120
ggggcggggc cgcctcgggc cggggagggc tcgggggagg ggcgcggcgg ccccggagcg   3180
ccggcggctg tcgaggcgcg gcgagccgca gccattgcct tttatggtaa tcgtgcgaga   3240
gggcgcaggg acttcctttg tcccaaatct ggcggagccg aaatctggga ggcgccgccg   3300
cacccccctct agcgggcgcg ggcgaagcgg tgcggcgccg gcaggaagga aatgggcggg   3360
gagggccttc gtgcgtcgcc gcgccgccgt ccccttctcc atctccagcc tcggggctgc   3420
cgcagggggga cggctgcctt cgggggggac ggggcagggc ggggttcggc ttctggcgtg   3480
tgaccggcgg ctctagagcc tctgctaacc atgttcatgc cttcttcttt ttcctacagc   3540
tcctgggcaa cgtgctggtt gttgtgctgt ctcatcattt tggcaaagaa ttcgccacca   3600
tggtgagcaa gggcgaggag ctgttcaccg gggtggtgcc catcctggtc gagctggacg   3660
gcgacgtaaa cggccacaag ttcagcgtgt ccggcgaggg cgagggcgat gccacctacg   3720
gcaagctgac cctgaagttc atctgcacca ccggcaagct gcccgtgccc tggcccaccc   3780
tcgtgaccac cctgacctac ggcgtgcagt gcttcagccg ctaccccgac cacatgaagc   3840
agcacgactt cttcaagtcc gccatgcccg aaggctacgt ccaggagcgc accatcttct   3900
tcaaggacga cggcaactac aagacccgcg ccgaggtgaa gttcgagggc gacaccctgg   3960
tgaaccgcat cgagctgaag ggcatcgact tcaaggagga cggcaacatc ctggggcaca   4020
agctggagta caactacaac agccacaacg tctatatcat ggccgacaag cagaagaacg   4080
gcatcaaggt gaacttcaag atccgccaca acatcgagga cggcagcgtg cagctcgccg   4140
accactacca gcagaacacc cccatcggcg acggccccgt gctgctgccc gacaaccact   4200
acctgagcac ccagtccgcc ctgagcaaag accccaacga gaagcgcgat cacatggtcc   4260
tgctggagtt cgtgaccgcc gccgggatca ctctcggcat ggacgagctg tacaagtaag   4320
aattcactcc tcaggtgcag gctgcctatc agaaggtggt ggctggtgtg gccaatgccc   4380
tggctcacaa ataccactga gatctttttc cctctgccaa aaattatggg gacatcatga   4440
agccccttga gcatctgact tctggctaat aaaggaaatt tattttcatt gcaatagtgt   4500
gttggaattt tttgtgtctc tcactcggaa ggacatatgg gagggcaaat catttaaaac   4560
atcagaatga gtatttggtt tagagtttgg caacatatgc catatgctgg ctgccatgaa   4620
caaaggtggc tataaagagg tcatcagtat atgaaacagc cccctgctgt ccattcctta   4680
ttccatagaa aagccttgac ttgaggttag attttttttta tattttgttt tgtgttattt   4740
ttttctttaa catccctaaa atttccctta catgttttac tagccagatt tttcctcctc   4800
tcctgactac tcccagtcat agctgtccct cttctcttat gaagatccct cgacctgcag   4860
cccaagcttg catgcctgca ggtcgactct agaggatccc cgggtaccga gctcgaattc   4920
gtaatcatgg tcatagctgt ttcctgtgtg aaattgttat ccgctcacaa ttccacacaa   4980
```

-continued

```
catacgagcc ggaagcataa agtgtaaagc ctggggtgcc taatgagtga gctaactcac   5040
attaattgcg ttgcgctcac tgcccgcttt ccagtcggga aacctgtcgt gccagctgca   5100
ttaatgaatc ggccaacgcg cggggagagg cggtttgcgt attgggcgct cttccgcttc   5160
ctcgctcact gactcgctgc gctcggtcgt tcggctgcgg cgagcggtat cagctcactc   5220
aaaggcggta atacggttat ccacagaatc aggggataac gcaggaaaga acatgtgagc   5280
aaaaggccag caaaaggcca ggaaccgtaa aaaggccgcg ttgctggcgt ttttccatag   5340
gctccgcccc cctgacgagc atcacaaaaa tcgacgctca agtcagaggt ggcgaaaccc   5400
gacaggacta taaagatacc aggcgtttcc ccctggaagc tccctcgtgc gctctcctgt   5460
tccgaccctg ccgcttaccg gatacctgtc cgcctttctc ccttcgggaa gcgtggcgct   5520
ttctcatagc tcacgctgta ggtatctcag ttcggtgtag gtcgttcgct ccaagctggg   5580
ctgtgtgcac gaaccccccg ttcagcccga ccgctgcgcc ttatccggta actatcgtct   5640
tgagtccaac ccggtaagac acgacttatc gccactggca gcagccactg gtaacaggat   5700
tagcagagcg aggtatgtag gcggtgctac agagttcttg aagtggtggc ctaactacgg   5760
ctacactaga aggacagtat ttggtatctg cgctctgctg aagccagtta ccttcggaaa   5820
aagagttggt agctcttgat ccggcaaaca aaccaccgct ggtagcggtg gtttttttgt   5880
ttgcaagcag cagattacgc gcagaaaaaa aggatctcaa gaagatcctt tgatcttttc   5940
tacggggtct gacgctcagt ggaacgaaaa ctcacgttaa gggattttgg tcatgagatt   6000
atcaaaaagg atcttcacct agatcctttt aaattaaaaa tgaagtttta aatcaatcta   6060
aagtatatat gagtaaactt ggtctgacag ttaccaatgc ttaatcagtg aggcacctat   6120
ctcagcgatc tgtctatttc gttcatccat agttgcctga ctccccgtcg tgtagataac   6180
tacgatacgg gagggcttac catctggccc cagtgctgca atgataccgc gagacccacg   6240
ctcaccggct ccagatttat cagcaataaa ccagccagcc ggaagggccg agcgcagaag   6300
tggtcctgca actttatccg cctccatcca gtctattaat tgttgccggg aagctagagt   6360
aagtagttcg ccagttaata gtttgcgcaa cgttgttgcc attgctacag gcatcgtggt   6420
gtcacgctcg tcgtttggta tggcttcatt cagctccggt tcccaacgat caaggcgagt   6480
tacatgatcc cccatgttgt gcaaaaaagc ggttagctcc ttcggtcctc cgatcgttgt   6540
cagaagtaag ttggccgcag tgttatcact catggttatg gcagcactgc ataattctct   6600
tactgtcatg ccatccgtaa gatgcttttc tgtgactggt gagtactcaa ccaagtcatt   6660
ctgagaatag tgtatgcggc gaccgagttg ctcttgcccg gcgtcaatac gggataatac   6720
cgcgccacat agcagaactt taaaagtgct catcattgga aaacgttctt cggggcgaaa   6780
actctcaagg atcttaccgc tgttgagatc cagttcgatg taacccactc gtgcacccaa   6840
ctgatcttca gcatctttta ctttcaccag cgtttctggg tgagcaaaaa caggaaggca   6900
aaatgccgca aaaaagggaa taagggcgac acggaaatgt tgaatactca tactcttcct   6960
ttttcaatat tattgaagca tttatcaggg ttattgtctc atgagcggat acatatttga   7020
atgtatttag aaaaataaac aaataggggt tccgcgcaca tttccccgaa aagtgccacc   7080
tgacgtagtt aacaaaaaaa agcccgccga agcgggcttt attaccaagc gaagcgccat   7140
tcgccattca ggctgcgcaa ctgttgggaa gggcgatcgg tgcgggcctc ttcgctatta   7200
cgccagctgg cgaaaggggg atgtgctgca aggcgattaa gttgggtaac gccagggttt   7260
tcccagtcac gacgttgtaa aacgacggcc agtccgtaat acgactcact taaggccttg   7320
```

-continued actagagggt cgacggtata cagacatgat aagatacatt gatgagtttg gacaaaccac 7380
aactagaatg cagtgaaaaa aatgctttat ttgtgaaatt tgtgatgcta ttgctttatt 7440
tgtaaccatt ataagctgca ataaacaagt tggggtgggc gaagaactcc agcatgagat 7500
ccccgcgctg gaggatcatc cagccggcgt cccggaaaac gattccgaag cccaaccttt 7560
catagaaggc ggcggtggaa tcgaaatctc gtagcacgtg tcagtcctgc tcctcggcca 7620
cgaagtgcac g 7631

<210> SEQ ID NO 117
<211> LENGTH: 4615
<212> TYPE: DNA
<213> ORGANISM: Artificial Sequence
<220> FEATURE:
<223> OTHER INFORMATION: p18attBZeo6XHS4 Plasmid

<400> SEQUENCE: 117
cagttgccgg ccgggtcgcg cagggcgaac tcccgccccc acggctgctc gccgatctcg 60
gtcatggccg gcccggaggc gtcccggaag ttcgtggaca cgacctccga ccactcggcg 120
tacagctcgt ccaggccgcg cacccacacc caggccaggg tgttgtccgg caccacctgg 180
tcctggaccg cgctgatgaa cagggtcacg tcgtcccgga ccacaccggc gaagtcgtcc 240
tccacgaagt cccgggagaa cccgagccgg tcggtccaga actcgaccgc tccggcgacg 300
tcgcgcgcgg tgagcaccgg aacggcactg gtcaacttgg ccatggatcc agatttcgct 360
caagttagta taaaaaagca ggcttcaatc ctgcagagaa gcttgcatgc ctgcaggtcg 420
actctagtgg atcccccgcc ccgtatcccc caggtgtctg caggctcaaa gagcagcgag 480
aagcgttcag aggaaagcga tcccgtgcca ccttccccgt gcccgggctg tccccgcacg 540
ctgccggctc ggggatgcgg ggggagcgcc ggaccggagc ggagccccgg gcggctcgct 600
gctgccccct agcgggggag ggacgtaatt acatccctgg gggctttggg ggggggctgt 660
ccccgtgagc ggatccgcgg ccccgtatcc cccaggtgtc tgcaggctca aagagcagcg 720
agaagcgttc agaggaaagc gatcccgtgc caccttcccc gtgcccgggc tgtccccgca 780
cgctgccggc tcggggatgc ggggggagcg ccggaccgga gcggagcccc gggcggctcg 840
ctgctgcccc ctagcggggg agggacgtaa ttacatccct gggggctttg gggggggggct 900 gtccccgtga gcggatccgc ggccccgtat cccccaggtg tctgcaggct caaagagcag 960
cgagaagcgt tcagaggaaa gcgatcccgt gccaccttcc ccgtgcccgg gctgtccccg 1020
cacgctgccg gctcggggat gcggggggag cgccggaccg gagcggagcc ccgggcggct 1080
cgctgctgcc ccctagcggg ggagggacgt aattacatcc ctgggggctt tggggggggg 1140
ctgtccccgt gagcggatcc gcggccccgt atcccccagg tgtctgcagg ctcaaagagc 1200
agcgagaagc gttcagagga aagcgatccc gtgccacctt ccccgtgccc gggctgtccc 1260
cgcacgctgc cggctcgggg atgcgggggg agcgccggac cggagcggag ccccgggcgg 1320
ctcgctgctg ccccctagcg ggggagggac gtaattacat ccctgggggc tttggggggg 1380
ggctgtcccc gtgagcggat ccgcggcccc gtatccccca ggtgtctgca ggctcaaaga 1440
gcagcgagaa gcgttcagag gaaagcgatc ccgtgccacc ttccccgtgc ccgggctgtc 1500
cccgcacgct gccggctcgg ggatgcgggg ggagcgccgg accggagcgg agccccgggc 1560
ggctcgctgc tgccccctag cgggggaggg acgtaattac atccctgggg gctttggggg 1620
ggggctgtcc ccgtgagcgg atccgcggcc ccgtatcccc caggtgtctg caggctcaaa 1680
gagcagcgag aagcgttcag aggaaagcga tcccgtgcca ccttccccgt gcccgggctg 1740

-continued

```
tccccgcacg ctgccggctc ggggatgcgg ggggagcgcc ggaccggagc ggagccccgg   1800
gcggctcgct gctgcccct agcgggggag ggacgtaatt acatccctgg gggctttggg   1860
ggggggctgt ccccgtgagc ggatccgcgg ggctgcagga attcgtaatc atggtcatag   1920
ctgtttcctg tgtgaaattg ttatccgctc acaattccac acaacatacg agccggaagc   1980
ataaagtgta aagcctgggg tgcctaatga gtgagctaac tcacattaat tgcgttgcgc   2040
tcactgcccg ctttccagtc gggaaacctg tcgtgccagc tgcattaatg aatcggccaa   2100
cgcgcgggga gaggcggttt gcgtattggg cgctcttccg cttcctcgct cactgactcg   2160
ctgcgctcgg tcgttcggct gcggcgagcg gtatcagctc actcaaaggc ggtaatacgg   2220
ttatccacag aatcagggga taacgcagga aagaacatgt gagcaaaagg ccagcaaaag   2280
gccaggaacc gtaaaaaggc cgcgttgctg gcgtttttcc ataggctccg cccccctgac   2340
gagcatcaca aaaatcgacg ctcaagtcag aggtggcgaa acccgacagg actataaaga   2400
taccaggcgt ttccccctgg aagctccctc gtgcgctctc ctgttccgac cctgccgctt   2460
accggatacc tgtccgcctt tctcccttcg ggaagcgtgg cgctttctca tagctcacgc   2520
tgtaggtatc tcagttcggt gtaggtcgtt cgctccaagc tgggctgtgt gcacgaaccc   2580
cccgttcagc ccgaccgctg cgccttatcc ggtaactatc gtcttgagtc caacccggta   2640
agacacgact tatcgccact ggcagcagcc actggtaaca ggattagcag agcgaggtat   2700
gtaggcggtg ctacagagtt cttgaagtgg tggcctaact acggctacac tagaaggaca   2760
gtatttggta tctgcgctct gctgaagcca gttaccttcg gaaaaagagt tggtagctct   2820
tgatccggca aacaaaccac cgctggtagc ggtggttttt ttgtttgcaa gcagcagatt   2880
acgcgcagaa aaaaaggatc tcaagaagat cctttgatct tttctacggg gtctgacgct   2940
cagtggaacg aaaactcacg ttaagggatt ttggtcatga gattatcaaa aaggatcttc   3000
acctagatcc ttttaaatta aaaatgaagt tttaaatcaa tctaaagtat atatgagtaa   3060
acttggtctg acagttacca atgcttaatc agtgaggcac ctatctcagc gatctgtcta   3120
tttcgttcat ccatagttgc ctgactcccc gtcgtgtaga taactacgat acgggagggc   3180
ttaccatctg gccccagtgc tgcaatgata ccgcgagacc cacgctcacc ggctccagat   3240
ttatcagcaa taaaccagcc agccggaagg gccgagcgca gaagtggtcc tgcaacttta   3300
tccgcctcca tccagtctat taattgttgc cgggaagcta gagtaagtag ttcgccagtt   3360
aatagtttgc gcaacgttgt tgccattgct acaggcatcg tggtgtcacg ctcgtcgttt   3420
ggtatggctt cattcagctc cggttcccaa cgatcaaggc gagttacatg atcccccatg   3480
ttgtgcaaaa aagcggttag ctccttcggt cctccgatcg ttgtcagaag taagttggcc   3540
gcagtgttat cactcatggt tatggcagca ctgcataatt ctcttactgt catgccatcc   3600
gtaagatgct tttctgtgac tggtgagtac tcaaccaagt cattctgaga atagtgtatg   3660
cggcgaccga gttgctcttg cccggcgtca atacgggata ataccgcgcc acatagcaga   3720
actttaaaag tgctcatcat tggaaaacgt tcttcggggc gaaaactctc aaggatctta   3780
ccgctgttga gatccagttc gatgtaaccc actcgtgcac ccaactgatc ttcagcatct   3840
tttactttca ccagcgtttc tgggtgagca aaaacaggaa ggcaaaatgc cgcaaaaaag   3900
ggaataaggg cgacacggaa atgttgaata ctcatactct tcctttttca atattattga   3960
agcatttatc agggttattg tctcatgagc ggatacatat ttgaatgtat ttagaaaaat   4020
aaacaaatag gggttccgcg cacatttccc cgaaaagtgc cacctgacgt agttaacaaa   4080
```

-continued

```
aaaaagcccg ccgaagcggg ctttattacc aagcgaagcg ccattcgcca ttcaggctgc   4140

gcaactgttg ggaagggcga tcggtgcggg cctcttcgct attacgccag ctggcgaaag   4200

ggggatgtgc tgcaaggcga ttaagttggg taacgccagg gttttcccag tcacgacgtt   4260

gtaaaacgac ggccagtccg taatacgact cacttaaggc cttgactaga gggtcgacgg   4320

tatacagaca tgataagata cattgatgag tttggacaaa ccacaactag aatgcagtga   4380

aaaaaatgct ttatttgtga aatttgtgat gctattgctt tatttgtaac cattataagc   4440

tgcaataaac aagttggggt gggcgaagaa ctccagcatg agatccccgc gctggaggat   4500

catccagccg gcgtcccgga aaacgattcc gaagcccaac ctttcataga aggcggcggt   4560

ggaatcgaaa tctcgtagca cgtgtcagtc ctgctcctcg gccacgaagt gcacg        4615
```

<210> SEQ ID NO 118
<211> LENGTH: 17384
<212> TYPE: DNA
<213> ORGANISM: Artificial Sequence
<220> FEATURE:
<223> OTHER INFORMATION: pFK161 Plasmid

<400> SEQUENCE: 118

```
gcgcacgagg gagcttccag ggggaaacgc ctggtatctt tatagtcctg tcggggtttc     60

gccacctctg acttgagcgt cgatttttgt gatgctcgtc aggggggcgg agcctatgga    120

aaaacgccag caacgcggcc tttttacggt tcctggcctt ttgctggcct tttgctcaca    180

tgttctttcc tgcgttatcc cctgattctg tggataaccg tattaccgcc tttgagtgag    240

ctgataccgc tcgccgcagc cgaacgaccg agcgcagcga gtcagtgagc gaggaagcgg    300

aagagcgctg acttccgcgt ttccagactt tacgaaacac ggaaaccgaa gaccattcat    360

gttgttgctc aggtcgcaga cgttttgcag cagcagtcgc ttcacgttcg ctcgcgtatc    420

ggtgattcat tctgctaacc agtaaggcaa ccccgccagc ctagccgggt cctcaacgac    480

aggagcacga tcatgcgcac ccgtcagatc cagacatgat aagatacatt gatgagtttg    540

gacaaaccac aactagaatg cagtgaaaaa aatgctttat ttgtgaaatt tgtgatgcta    600

ttgctttatt tgtaaccatt ataagctgca ataaacaagt taacaacaac aattgcattc    660

attttatgtt tcaggttcag ggggaggtgt gggaggtttt ttaaagcaag taaaacctct    720

acaaatgtgg tatggctgat tatgatctct agtcaaggca ctatacatca aatattcctt    780

attaacccct ttacaaatta aaaagctaaa ggtacacaat ttttgagcat agttattaat    840

agcagacact ctatgcctgt gtggagtaag aaaaaacagt atgttatgat tataactgtt    900

atgcctactt ataaaggtta cagaatattt ttccataatt ttcttgtata gcagtgcagc    960

tttttccttt gtggtgtaaa tagcaaagca agcaagagtt ctattactaa acacagcatg   1020

actcaaaaaa cttagcaatt ctgaaggaaa gtccttgggg tcttctacct ttctcttctt   1080

ttttggagga gtagaatgtt gagagtcagc agtagcctca tcatcactag atggcatttc   1140

ttctgagcaa aacaggtttt cctcattaaa ggcattccac cactgctccc attcatcagt   1200

tccataggtt ggaatctaaa atacacaaac aattagaatc agtagtttaa cacattatac   1260

acttaaaaat tttatattta ccttagagct ttaaatctct gtaggtagtt tgtccaatta   1320

tgtcacacca cagaagtaag gttccttcac aaagatccgg accaaagcgg ccatcgtgcc   1380

tccccactcc tgcagttcgg gggcatggat gcgcggatag ccgctgctgg tttcctggat   1440

gccgacggat ttgcactgcc ggtagaactc gcgaggtcgt ccagcctcag gcagcagctg   1500

aaccaactcg cgaggggatc gagcccgggg tgggcgaaga actccagcat gagatccccg   1560
```

-continued

```
cgctggagga tcatccagcc ggcgtcccgg aaaacgattc cgaagcccaa cctttcatag   1620
aaggcggcgg tggaatcgaa atctcgtgat ggcaggttgg gcgtcgcttg gtcggtcatt   1680
tcgaacccca gagtcccgct cagaagaact cgtcaagaag gcgatagaag gcgatgcgct   1740
gcgaatcggg agcggcgata ccgtaaagca cgaggaagcg gtcagcccat tcgccgccaa   1800
gctcttcagc aatatcacgg gtagccaacg ctatgtcctg atagcggtcc gccacaccca   1860
gccggccaca gtcgatgaat ccagaaaagc ggccattttc caccatgata ttcggcaagc   1920
aggcatcgcc atgggtcacg acgagatcct cgccgtcggg atgcgcgcct tgagcctggc   1980
gaacagttcg gctggcgcga gcccctgatg ctcttcgtcc agatcatcct gatcgacaag   2040
accggcttcc atccgagtac gtgctcgctc gatgcgatgt ttcgcttggt ggtcgaatgg   2100
gcaggtagcc ggatcaagcg tatgcagccg ccgcattgca tcagccatga tggatacttt   2160
ctcggcagga gcaaggtgag atgacaggag atcctgcccc ggcacttcgc ccaatagcag   2220
ccagtccctt cccgcttcag tgacaacgtc gagcacagct gcgcaaggaa cgcccgtcgt   2280
ggccagccac gatagccgcg ctgcctcgtc ctgcagttca ttcagggcac cggacaggtc   2340
ggtcttgaca aaaagaaccg ggcgcccctg cgctgacagc cggaacacgg cggcatcaga   2400
gcagccgatt gtctgttgtg cccagtcata gccgaatagc ctctccaccc aagcggccgg   2460
agaacctgcg tgcaatccat cttgttcaat catgcgaaac gatcctcatc ctgtctcttg   2520
atcagatctt gatcccctgc gccatcagat ccttggcggc aagaaagcca tccagtttac   2580
tttgcagggc ttcccaacct taccagaggg cgccccagct ggcaattccg gttcgcttgc   2640
tgtccataaa accgcccagt ctagctatcg ccatgtaagc ccactgcaag ctacctgctt   2700
tctctttgcg cttgcgtttt cccttgtcca gatagcccag tagctgacat tcatccgggg   2760
tcagcaccgt ttctgcggac tggctttcta cgtgttccgc ttcctttagc agcccttgcg   2820
ccctgagtgc ttgcggcagc gtgaaagctt tttgcaaaag cctaggcctc caaaaaagcc   2880
tcctcactac ttctggaata gctcagaggc cgaggcggcc taaataaaaa aaattagtca   2940
gccatggggc ggagaatggg cggaactggg cggagttagg ggcgggatgg gcggagttag   3000
gggcgggact atggttgctg actaattgag atgcatgctt tgcatacttc tgcctgctgg   3060
ggagcctggg gactttccac acctggttgc tgactaattg agatgcatgc tttgcatact   3120
tctgcctgct ggggagcctg gggactttcc acaccctaac tgacacacat tccacagccg   3180
gatctgcagg acccaacgct gcccgagatg cgccgcgtgc ggctgctgga gatggcggac   3240
gcgatggata tgttctgcca agggttggtt tgcgcattca cagttctccg caagaattga   3300
ttggctccaa ttcttggagt ggtgaatccg ttagcgaggt gccgccggct tccattcagg   3360
tcgaggtggc ccggctccat gcaccgcgac gcaacgcggg gaggcagaca aggtataggg   3420
cggcgcctac aatccatgcc aacccgttcc atgtgctcgc cgaggcgcat aaatcgccgt   3480
gacgatcagc ggtccaatga tcgaagttag gctggtaaga gccgcgagcg atccttgaag   3540
ctgtccctga tggtcgtcat ctacctgcct ggacagcatg gcctgcaacg cggcatcccg   3600
atgccgccgg aagcgagaag aatcataatg gggaaggcca tccagcctcg cgtcgcgaac   3660
gccagcaaga cgtagcccag cgcgtcgggc cgccatgccg gcgataatgg cctgcttctc   3720
gccgaaacgt ttggtggcgg gaccagtgac gaaggcttga gcgagggcgt gcaagattcc   3780
gaataccgca agcgacaggc cgatcatcgt cgcgctccag cgaaagcggt cctcgccgaa   3840
aatgacccag agcgctgccg gcacctgtcc tacgagttgc atgataaaga agacagtcat   3900
```

-continued

```
aagtgcggcg acgatagtca tgccccgcgc ccaccggaag gagctgactg ggttgaaggc   3960
tctcaagggc atcggtcgac gctctccctt atgcgactcc tgcattagga agcagcccag   4020
tagtaggttg aggccgttga gcaccgccgc cgcaaggaat ggtgcatgca aggagatggc   4080
gcccaacagt cccccggcca cgggcctgcc accataccca cgccgaaaca agcgctcatg   4140
agcccgaagt ggcgagcccg atcttcccca tcggtgatgt cggcgatata ggcgccagca   4200
accgcacctg tggcgccggt gatgccggcc acgatgcgtc cggcgtagag gatcttggca   4260
gtcacagcat gcgcatatcc atgcttcgac catgcgctca caaagtaggt gaatgcgcaa   4320
tgtagtaccc acatcgtcat cgctttccac tgctctcgcg aataaagatg gaaaatcaat   4380
ctcatggtaa tagtccatga aaatccttgt attcataaat cctccaggta gctatatgca   4440
aattgaaaca aaagagatgg tgatctttct aagagatgat ggaatctccc ttcagtatcc   4500
cgatggtcaa tgcgctggat atgggataga tgggaatatg ctgattttta tgggacagag   4560
ttgcgaactg ttcccaacta aaatcatttt gcacgatcag cgcactacga actttaccca   4620
caaatagtca ggtaatgaat cctgatataa agacaggttg ataaatcagt cttctacgcg   4680
catcgcacgc gcacaccgta gaaagtcttt cagttgtgag cctgggcaaa ccgttaactt   4740
tcggcggctt tgctgtgcga caggctcacg tctaaaagga aataaatcat gggtcataaa   4800
attatcacgt tgtccggcgc ggcgacggat gttctgtatg cgctgttttt ccgtggcgcg   4860
ttgctgtctg gtgatctgcc ttctaaatct ggcacagccg aattgcgcga gcttggtttt   4920
gctgaaacca gacacacagc aactgaatac cagaaagaaa atcactttac ctttctgaca   4980
tcagaagggc agaaatttgc cgttgaacac ctggtcaata cgcgttttgg tgagcagcaa   5040
tattgcgctt cgatgacgct tggcgttgag attgatacct ctgctgcaca aaaggcaatc   5100
gacgagctgg accagcgcat tcgtgacacc gtctccttcg aacttattcg caatggagtg   5160
tcattcatca aggacgccgc tatcgcaaat ggtgctatcc acgcagcggc aatcgaaaca   5220
cctcagccgg tgaccaatat ctacaacatc agccttggta tccagcgtga tgagccagcg   5280
cagaacaagg taaccgtcag tgccgataag ttcaaagtta aacctggtgt tgataccaac   5340
attgaaacgt tgatcgaaaa cgcgctgaaa aacgctgctg aatgtgcggc gctggatgtc   5400
acaaagcaaa tggcagcaga caagaaagcg atggatgaac tggcttccta tgtccgcacg   5460
gccatcatga tggaatgttt ccccggtggt gttatctggc agcagtgccg tcgatagtat   5520
gcaattgata attattatca tttgcgggtc ctttccggcg atccgccttg ttacggggcg   5580
gcgacctcgc gggttttcgc tatttatgaa aattttccgg tttaaggcgt ttccgttctt   5640
cttcgtcata acttaatgtt tttatttaaa ataccctctg aaaagaaagg aaacgacagg   5700
tgctgaaagc gagctttttg gcctctgtcg tttcctttct ctgtttttgt ccgtggaatg   5760
aacaatggaa gtcaacaaaa agcagctggc tgacattttc ggtgcgagta tccgtaccat   5820
tcagaactgg caggaacagg gaatgcccgt tctgcgaggc ggtggcaagg gtaatgaggt   5880
gctttatgac tctgccgccg tcataaaatg gtatgccgaa agggatgctg aaattgagaa   5940
cgaaaagctg cgccgggagg ttgaagaact gcggcaggcc agcgaggcag atccacagga   6000
cgggtgtggt cgccatgatc gcgtagtcga tagtggctcc aagtagcgaa gcgagcagga   6060
ctgggcggcg gcaaagcggt cggacagtgc tccgagaacg ggtgcgcata gaaattgcat   6120
caacgcatat agcgctagca gcacgccata gtgactggcg atgctgtcgg aatggacgat   6180
atcccgcaag aggcccggca gtaccggcat aaccaagcct atgcctacag catccagggt   6240
gacggtgccg aggatgacga tgagcgcatt gttagatttc atacacggtg cctgactgcg   6300
```

-continued

```
ttagcaattt aactgtgata aactaccgca ttaaagctta tcgatgataa gcggtcaaac   6360
atgagaattc gcggccgctc ttctcgttct gccagcgggc cctcgtctct ccaccccatc   6420
cgtctgccgg tggtgtgtgg aaggcagggg tgcggctctc cggcccgacg ctgccccgcg   6480
cgcacttttc tcagtggttc gcgtggtcct tgtggatgtg tgaggcgccc ggttgtgccc   6540
tcacgtgttt cactttggtc gtgtctcgct tgaccatgtt cccagagtcg gtggatgtgg   6600
ccggtggcgt tgcataccct tcccgtctgg tgtgtgcacg cgctgtttct tgtaagcgtc   6660
gaggtgctcc tggagcgttc caggtttgtc tcctaggtgc ctgcttctga gctggtggtg   6720
gcgctcccca ttccctggtg tgcctccggt gctccgtctg gctgtgtgcc ttcccgtttg   6780
tgtctgagaa gcccgtgaga ggggggtcga ggagagaagg aggggcaaga ccccccttct   6840
tcgtcgggtg aggcgcccac cccgcgacta gtacgcctgt gcgtagggct ggtgctgagc   6900
ggtcgcggct ggggttggaa agtttctcga gagactcatt gctttcccgt ggggagcttt   6960
gagaggcctg gctttcgggg gggaccggtt gcagggtctc ccctgtccgc ggatgctcag   7020
aatgcccttg gaagagaacc ttcctgttgc cgcagacccc cccgcgcggt cgcccgcgtg   7080
ttggtcttct ggtttccctg tgtgctcgtc gcatgcatcc tctctcggtg gccggggctc   7140
gtcggggttt tgggtccgtc ccgccctcag tgagaaagtt tccttctcta gctatcttcc   7200
ggaaagggtg cgggcttctt acggtctcga ggggtctctc ccgaatggtc ccctggaggg   7260
ctcgcccccct gaccgcctcc cgcgcgcgca gcgtttgctc tctcgtctac cgcggcccgc   7320
ggcctccccg ctccgagttc ggggagggat cacgcggggc agagcctgtc tgtcgtcctg   7380
ccgttgctgc ggagcatgtg gctcggcttg tgtggttggt ggctggggag agggctccgt   7440
gcacaccccc gcgtgcgcgt actttcctcc cctcctgagg gccgccgtgc ggacggggtg   7500
tgggtaggcg acggtgggct cccgggtccc cacccgtctt cccgtgcctc acccgtgcct   7560
tccgtcgcgt gcgtccctct cgctcgcgtc cacgactttg gccgctcccg cgacggcggc   7620
ctgcgccgcg cgtggtgcgt gctgtgtgct tctcgggctg tgtggttgtg tcgcctcgcc   7680
ccccccttcc cgcggcagcg ttcccacggc tggcgaaatc gcgggagtcc tccttcccct   7740
cctcggggtc gagagggtcc gtgtctggcg ttgattgatc tcgctctcgg ggacgggacc   7800
gttctgtggg agaacggctg ttggccgcgt ccggcgcgac gtcggacgtg gggacccact   7860
gccgctcggg ggtcttcgtc ggtaggcatc ggtgtgtcgg catcggtctc tctctcgtgt   7920
cggtgtcgcc tcctcgggct cccgggggc cgtcgtgttt cgggtcggct cggcgctgca   7980
ggtgtggtgg gactgctcag gggagtggtg cagtgtgatt cccgccggtt ttgcctcgcg   8040
tgccctgacc ggtccgacgc ccgagcggtc tctcggtccc ttgtgaggac cccccttccgg   8100
gaggggcccg tttcggccgc ccttgccgtc gtcgccggcc ctcgttctgc tgtgtcgttc   8160
cccccctcccc gctcgccgca gccggtcttt tttcctctct cccccccctct cctctgactg   8220
acccgtggcc gtgctgtcgg accccccgca tgggggcggc cgggcacgta cgcgtccggg   8280
cggtcaccgg ggtcttgggg gggggccgag gggtaagaaa gtcggctcgg cgggcgggag   8340
gagctgtggt ttggagggcg tcccggcccc gcggccgtgg cggtgtcttg cgcggtcttg   8400
gagagggctg cgtgcgaggg gaaaaggttg ccccgcgagg gcaaagggaa agaggctagc   8460
agtggtcatt gtcccgacgg tgtggtggtc tgttggccga ggtgcgtctg gggggctcgt   8520
ccggccctgt cgtccgtcgg gaaggcgcgt gttggggcct gccggagtgc cgaggtgggt   8580
accctggcgg tgggattaac cccgcgcgcg tgtcccggtg tggcggtggg ggctccggtc   8640
```

-continued

```
gatgtctacc tccctctccc cgaggtctca ggccttctcc gcgcgggctc tcggccctcc   8700
cctcgttcct ccctctcgcg gggttcaagt cgctcgtcga cctcccctcc tccgtccttc   8760
catctctcgc gcaatggcgc cgcccgagtt cacggtgggt tcgtcctccg cctccgcttc   8820
tcgccggggg ctggccgctg tccggtctct cctgcccgac ccccgttggc gtggtcttct   8880
ctcgccggct tcgcggactc ctggcttcgc ccggagggtc agggggcttc ccggttcccc   8940
gacgttgcgc ctcgctgctg tgtgcttggg gggggcccgc tgcggcctcc gcccgcccgt   9000
gagcccctgc cgcacccgcc ggtgtgcggt ttcgcgccgc ggtcagttgg gccctggcgt   9060
tgtgtcgcgt cgggagcgtg tccgcctcgc ggcggctaga cgcgggtgtc gccgggctcc   9120
gacgggtggc ctatccaggg ctcgcccccg ccgacccccg cctgcccgtc ccggtggtgg   9180
tcgttggtgt ggggagtgaa tggtgctacc ggtcattccc tcccgcgtgg tttgactgtc   9240
tcgccggtgt cgcgcttctc tttccgccaa cccccacgcc aacccaccac cctgctctcc   9300
cggcccggtg cggtcgacgt tccggctctc ccgatgccga ggggttcggg atttgtgccg   9360
gggacggagg ggagagcggg taagagaggt gtcggagagc tgtcccgggg cgacgctcgg   9420
gttggctttg ccgcgtgcgt gtgctcgcgg acgggttttg tcggaccccg acggggtcgg   9480
tccggccgca tgcactctcc cgttccgcgc gagcgcccgc ccggctcacc cccggtttgt   9540
cctcccgcga ggctctccgc cgccgccgcc tcctcctcct ctctcgcgct ctctgtcccg   9600
cctggtcctg tcccaccccc gacgctccgc tcgcgcttcc ttacctggtt gatcctgcca   9660
ggtagcatat gcttgtctca aagattaagc catgcatgtc taagtacgca cggccggtac   9720
agtgaaactg cgaatggctc attaaatcag ttatggttcc tttggtcgct cgctcctctc   9780
ctacttggat aactgtggta attctagagc taatacatgc cgacgggcgc tgacccccct   9840
tcccgggggg ggatgcgtgc atttatcaga tcaaaaccaa cccggtgagc tccctcccgg   9900
ctccggccgg gggtcgggcg ccggcggctt ggtgactcta gataacctcg ggccgatcgc   9960
acgccccccg tggcggcgac gacccattcg aacgtctgcc ctatcaactt tcgatggtag  10020
tcgccgtgcc taccatggtg accacgggtg acggggaatc agggttcgat tccggagagg  10080
gagcctgaga aacggctacc acatccaagg aaggcagcag gcgcgcaaat tacccactcc  10140
cgacccgggg aggtagtgac gaaaaataac aatacaggac tctttcgagg ccctgtaatt  10200
ggaatgagtc cactttaaat cctttaacga ggatccattg gagggcaagt ctggtgccag  10260
cagccgcggt aattccagct ccaatagcgt atattaaagt tgctgcagtt aaaaagctcg  10320
tagttggatc ttgggagcgg gcgggcggtc cgccgcgagg cgagtcaccg cccgtccccg  10380
ccccttgcct ctcggcgccc cctcgatgct cttagctgag tgtcccgcgg ggcccgaagc  10440
gtttactttg aaaaaattag agtgttcaaa gcaggcccga gccgcctgga taccgcagct  10500
aggaataatg gaataggacc gcggttctat tttgttggtt ttcggaactg aggccatgat  10560
taagagggac ggccgggggc attcgtattg cgccgctaga ggtgaaattc ttggaccggc  10620
gcaagacgga ccagagcgaa agcatttgcc aagaatgttt tcattaatca agaacgaaag  10680
tcggaggttc gaagacgatc agataccgtc gtagttccga ccataaacga tgccgactgg  10740
cgatgcggcg gcgttattcc catgacccgc cgggcagctt ccgggaaacc aaagtctttg  10800
ggttccgggg ggagtatggt tgcaaagctg aaacttaaag gaattgacgg aagggcacca  10860
ccaggagtgg gcctgcggct taatttgact caacacggga aacctcaccc ggcccggaca  10920
cggacaggat tgacagattg atagctcttt ctcgattccg tgggtggtgg tgcatggccg  10980
ttcttagttg gtggagcgat ttgtctggtt aattccgata acgaacgaga ctctggcatg  11040
```

-continued

```
ctaactagtt acgcgacccc cgagcggtcg gcgtccccca acttcttaga gggacaagtg  11100
gcgttcagcc acccgagatt gagcaataac aggtctgtga tgcccttaga tgtccggggc  11160
tgcacgcgcg ctacactgac tggctcagcg tgtgcctacc ctgcgccggc aggcgcgggt  11220
aacccgttga accccattcg tgatggggat cggggattgc aattattccc catgaacgag  11280
gaattcccag taagtgcggg tcataagctt gcgttgatta agtccctgcc ctttgtacac  11340
accgcccgtc gctactaccg attggatggt ttagtgaggc cctcggatcg gccccgccgg  11400
ggtcggccca cggccctggc ggagcgctga gaagacggtc gaacttgact atctagagga  11460
agtaaaagtc gtaacaaggt ttccgtaggt gaacctgcgg aaggatcatt aaacgggaga  11520
ctgtggagga gcggcggcgt ggcccgctct ccccgtcttg tgtgtgtcct cgccgggagg  11580
cgcgtgcgtc ccgggtcccg tcgcccgcgt gtggagcgag gtgtctggag tgaggtgaga  11640
gaaggggtgg gtggggtcgg tctgggtccg tctgggaccg cctccgattt cccctccccc  11700
tcccctctcc ctcgtccggc tctgacctcg ccaccctacc gcggcggcgg ctgctcgcgg  11760
gcgtcttgcc tctttcccgt ccggctcttc cgtgtctacg aggggcggta cgtcgttacg  11820
ggtttttgac ccgtcccggg ggcgttcggt cgtcggggcg cgcgctttgc tctcccggca  11880
cccatccccg ccgcggctct ggcttttcta cgttggctgg ggcggttgtc gcgtgtgggg  11940
ggatgtgagt gtcgcgtgtg ggctcgcccg tcccgatgcc acgcttttct ggcctcgcgt  12000
gtcctccccg ctcctgtccc gggtacctag ctgtcgcgtt ccggcgcgga ggtttaagga  12060
ccccgggggg gtcgccctgc cgcccccagg gtcgggggc ggtggggccc gtagggaagt  12120
cggtcgttcg ggcggctctc cctcagactc catgaccctc ctccccccgc tgccgccgtt  12180
cccgaggcgg cggtcgtgtg gggggtgga tgtctggagc cccctcgggc gccgtggggg  12240
cccgacccgc gccgccggct tgcccgattt ccgcgggtcg gtcctgtcgg tgccggtcgt  12300
gggttcccgt gtcgttcccg tgtttttccg ctcccgaccc tttttttttc ctcccccca  12360
cacgtgtctc gtttcgttcc tgctggccgg cctgaggcta cccctcggtc catctgttct  12420
cctctctctc cggggagagg agggcggtgg tcgttggggg actgtgccgt cgtcagcacc  12480
cgtgagttcg ctcacacccg aaataccgat acgactctta gcggtggatc actcggctcg  12540
tgcgtcgatg aagaacgcag ctagctgcga gaattaatgt gaattgcagg acacattgat  12600
catcgacact tcgaacgcac ttgcggcccc gggttcctcc cggggctacg cctgtctgag  12660
cgtcggttga cgatcaatcg cgtcacccgc tgcggtgggt gctgcgcggc tgggagtttg  12720
ctcgcagggc caacccccca acccgggtcg ggccctccgt ctcccgaagt tcagacgtgt  12780
gggcggttgt cggtgtggcg cgcgcgcccg cgtcgcggag cctggtctcc cccgcgcatc  12840
cgcgctcgcg gcttcttccc gctccgccgt tcccgccctc gcccgtgcac cccggtcctg  12900
gcctcgcgtc ggcgcctccc ggaccgctgc ctcaccagtc tttctcggtc ccgtgccccg  12960
tgggaaccca ccgcgccccc gtggcgcccg ggggtgggcg cgtccgcatc tgctctggtc  13020
gaggttggcg gttgagggtg tgcgtgcgcc gaggtggtgg tcggtcccct gcggccgcgg  13080
ggttgtcggg gtggcggtcg acgagggccg gtcggtcgcc tgcggtggtt gtctgtgtgt  13140
gtttgggtct tgcgctgggg gaggcggggt cgaccgctcg cggggttggc gcggtcgccc  13200
ggcgccgcgc accctccggc ttgtgtggag ggagagcgag ggcgagaacg gagagaggtg  13260
gtatccccgg tggcgttgcg agggagggtt tggcgtcccg cgtccgtccg tccctccctc  13320
cctcggtggg cgccttcgcg ccgcacgcgg ccgctagggg cggtcggggc ccgtggcccc  13380
```

-continued

```
cgtggctctt cttcgtctcc gcttctcctt cacccgggcg gtacccgctc cggcgccggc  13440
ccgcgggacg ccgcggcgtc cgtgcgccga tgcgagtcac ccccgggtgt tgcgagttcg  13500
gggagggaga gggcctcgct gacccgttgc gtcccggctt ccctgggggg gacccggcgt  13560
ctgtgggctg tgcgtcccgg gggttgcgtg tgagtaagat cctccacccc cgccgccctc  13620
ccctcccgcc ggcctctcgg ggaccccctg agacggttcg ccggctcgtc ctcccgtgcc  13680
gccgggtgcc gtctctttcc cgcccgcctc ctcgctctct tcttcccgcg gctgggcgcg  13740
tgtccccccct ttctgaccgc gacctcagat cagacgtggc gacccgctga atttaagcat  13800
attagtcagc ggaggaaaag aaactaacca ggattccctc agtaacggcg agtgaacagg  13860
gaagagccca gcgccgaatc cccgccgcgc gtcgcggcgt gggaaatgtg gcgtacggaa  13920
gacccactcc ccggcgccgc tcgtgggggg cccaagtcct tctgatcgag gcccagcccg  13980
tggacggtgt gaggccggta gcggccccgg cgcgccgggc tcgggtcttc ccggagtcgg  14040
gttgcttggg aatgcagccc aaagcgggtg gtaaactcca tctaaggcta aataccggca  14100
cgagaccgat agtcaacaag taccgtaagg gaaagttgaa aagaactttg aagagagagt  14160
tcaagagggc gtgaaaccgt taagaggtaa acgggtgggg tccgcgcagt ccgcccggag  14220
gattcaaccc ggcggcgcgc gtccggccgt gcccggtggt cccggcggat ctttcccgct  14280
ccccgttcct cccgacccct ccacccgcgc gtcgttcccc tcttcctccc cgcgtccggc  14340
gcctccggcg gcgggcgcgg ggggtggtgt ggtggtggcg cgcgggcggg gccgggggtg  14400
gggtcggcgg gggaccgccc ccggccggcg accggccgcc gccgggcgca cttccaccgt  14460
ggcggtgcgc cgcgaccggc tccgggacgg ccgggaaggc ccggtgggga aggtggctcg  14520
ggggggcgg cgcgtctcag ggcgcgccga accacctcac cccgagtgtt acagccctcc  14580
ggccgcgctt tcgccgaatc ccggggccga ggaagccaga tacccgtcgc cgcgctctcc  14640
ctctcccccc gtccgcctcc cgggcgggcg tgggggtggg ggccgggccg cccctcccac  14700
ggcgcgaccg ctctcccacc cccctccgtc gcctctctcg gggcccggtg gggggcgggg  14760
cggactgtcc ccagtgcgcc ccgggcgtcg tcgcgccgtc gggtcccggg gggaccgtcg  14820
gtcacgcgtc tcccgacgaa gccgagcgca cggggtcggc ggcgatgtcg gctacccacc  14880
cgacccgtct tgaaacacgg accaaggagt ctaacgcgtg cgcgagtcag ggctcgtcc  14940
gaaagccgcc gtggcgcaat gaaggtgaag ggccccgccc gggggcccga ggtgggatcc  15000
cgaggcctct ccagtccgcc gagggcgcac caccggcccg tctcgcccgc cgcgccgggg  15060
aggtggagca cgagcgtacg cgttaggacc cgaaagatgg tgaactatgc ttgggcaggg  15120
cgaagccaga ggaaactctg gtggaggtcc gtagcggtcc tgacgtgcaa atcggtcgtc  15180
cgacctgggt ataggggcga aagactaatc gaaccatcta gtagctggtt ccctccgaag  15240
tttccctcag gatagctggc gctctcgctc ccgacgtacg cagttttatc cggtaaagcg  15300
aatgattaga ggtcttgggg ccgaaacgat ctcaacctat tctcaaactt taaatgggta  15360
agaagcccgg ctcgctggcg tggagccggg cgtggaatgc gagtgcctag tgggccactt  15420
ttggtaagca gaactggcgc tgcgggatga accgaacgcc gggttaaggc gcccgatgcc  15480
gacgctcatc agaccccaga aaaggtgttg gttgatatag acagcaggac ggtggccatg  15540
gaagtcggaa tccgctaagg agtgtgtaac aactcacctg ccgaatcaac tagccctgaa  15600
aatggatggc gctggagcgt cgggcccata cccggccgtc gccgcagtcg gaacggaacg  15660
ggacgggagc ggccgcgaat tcttgaagac gaaagggcct cgtgatacgc ctatttttat  15720
aggttaatgt catgataata atggtttctt agacgtcagg tggcactttt cggggaaatg  15780
```

-continued

```
tgcgcggaac ccctatttgt ttatttttct aaatacattc aaatatgtat ccgctcatga  15840

gacaataacc ctgataaatg cttcaataat attgaaaaag gaagagtatg agtattcaac  15900

atttccgtgt cgcccttatt ccctttttttg cggcattttg cttcctgttt ttgctcaccc  15960

agaaacgctg gtgaaagtaa aagatgctga agatcagttg ggtgcacgag tgggttacat  16020

cgaactggat ctcaacagcg gtaagatcct tgagagtttt cgccccgaag aacgttttcc  16080

aatgatgagc acttttaaag ttctgctatg tggcgcggta ttatcccgtg ttgacgccgg  16140

gcaagagcaa ctcggtcgcc gcatacacta ttctcagaat gacttggttg agtactcacc  16200

agtcacagaa aagcatctta cggatggcat gacagtaaga gaattatgca gtgctgccat  16260

aaccatgagt gataacactg cggccaactt acttctgaca acgatcggag gaccgaagga  16320

gctaaccgct tttttgcaca acatggggga tcatgtaact cgccttgatc gttgggaacc  16380

ggagctgaat gaagccatac caaacgacga gcgtgacacc acgatgcctg cagcaatggc  16440

aacaacgttg cgcaaactat taactggcga actacttact ctagcttccc ggcaacaatt  16500

aatagactgg atggaggcgg ataaagttgc aggaccactt ctgcgctcgg cccttccggc  16560

tggctggttt attgctgata aatctggagc cggtgagcgt gggtctcgcg gtatcattgc  16620

agcactgggg ccagatggta agccctcccg tatcgtagtt atctacacga cggggagtca  16680

ggcaactatg gatgaacgaa atagacagat cgctgagata ggtgcctcac tgattaagca  16740

ttggtaactg tcagaccaag tttactcata tatactttag attgatttaa aacttcattt  16800

ttaatttaaa aggatctagg tgaagatcct ttttgataat ctcatgacca aaatccctta  16860

acgtgagttt tcgttccact gagcgtcaga ccccgtagaa aagatcaaag gatcttcttg  16920

agatcctttt tttctgcgcg taatctgctg cttgcaaaca aaaaaaccac cgctaccagc  16980

ggtggtttgt ttgccggatc aagagctacc aactcttttt ccgaaggtaa ctggcttcag  17040

cagagcgcag ataccaaata ctgtccttct agtgtagccg tagttaggcc accacttcaa  17100

gaactctgta gcaccgccta catacctcgc tctgctaatc ctgttaccag tggctgctgc  17160

cagtggcgat aagtcgtgtc ttaccgggtt ggactcaaga cgatagttac cggataaggc  17220

gcagcggtcg ggctgaacgg ggggttcgtg cacacagccc agcttggagc gaacgaccta  17280

caccgaactg agatacctac agcgtgagct atgagaaagc gccacgcttc ccgaagggaga  17340

aaggcggaca ggtatccggt aagcggcagg gtcggaacag gaga                  17384
```

<210> SEQ ID NO 119
<211> LENGTH: 2814
<212> TYPE: DNA
<213> ORGANISM: Artificial Sequence
<220> FEATURE:
<223> OTHER INFORMATION: pLITMUS38 Plasmid

<400> SEQUENCE: 119

```
gttaactacg tcaggtggca cttttcgggg aaatgtgcgc ggaaccccta tttgtttatt     60

tttctaaata cattcaaata tgtatccgct catgagacaa taaccctgat aaatgcttca    120

ataatattga aaaaggaaga gtatgagtat tcaacatttc cgtgtcgccc ttattccctt    180

ttttgcggca ttttgccttc ctgtttttgc tcacccagaa acgctggtga aagtaaaaga    240

tgctgaagat cagttgggtg cacgagtggg ttacatcgaa ctggatctca acagcggtaa    300

gatccttgag agttttcgcc ccgaagaacg ttttccaatg atgagcactt ttaaagttct    360

gctatgtggc gcggtattat cccgtgttga cgccgggcaa gagcaactcg gtcgccgcat    420
```

-continued

```
acactattct cagaatgact tggttgagta ctcaccagtc acagaaaagc atcttacgga    480
tggcatgaca gtaagagaat tatgcagtgc tgccataacc atgagtgata acactgcggc    540
caacttactt ctgacaacga tcggaggacc gaaggagcta accgcttttt tgcacaacat    600
gggggatcat gtaactcgcc ttgatcgttg ggaaccggag ctgaatgaag ccataccaaa    660
cgacgagcgt gacaccacga tgcctgtagc aatggcaaca acgttgcgca aactattaac    720
tggcgaacta cttactctag cttcccggca acaattaata gactggatgg aggcggataa    780
agttgcagga ccacttctgc gctcggccct tccggctggc tggtttattg ctgataaatc    840
tggagccggt gagcgtgggt ctcgcggtat cattgcagca ctggggccag atggtaagcc    900
ctcccgtatc gtagttatct acacgacggg gagtcaggca actatggatg aacgaaatag    960
acagatcgct gagataggtg cctcactgat taagcattgg taactgtcag accaagttta   1020
ctcatatata ctttagattg atttaccccg gttgataatc agaaaagccc caaaaacagg   1080
aagattgtat aagcaaatat ttaaattgta aacgttaata ttttgttaaa attcgcgtta   1140
aatttttgtt aaatcagctc atttttaac caataggccg aaatcggcaa aatcccttat   1200
aaatcaaaag aatagcccga gatagggttg agtgttgttc cagtttggaa caagagtcca   1260
ctattaaaga acgtggactc caacgtcaaa gggcgaaaaa ccgtctatca gggcgatggc   1320
ccactacgtg aaccatcacc caaatcaagt tttttggggt cgaggtgccg taaagcacta   1380
aatcggaacc ctaaagggag cccccgattt agagcttgac ggggaaagcg aacgtggcga   1440
gaaaggaagg gaagaaagcg aaaggagcgg gcgctagggc gctggcaagt gtagcggtca   1500
cgctgcgcgt aaccaccaca cccgccgcgc ttaatgcgcc gctacagggc gcgtaaaagg   1560
atctaggtga agatcctttt tgataatctc atgaccaaaa tcccttaacg tgagttttcg   1620
ttccactgag cgtcagaccc cgtagaaaag atcaaaggat cttcttgaga tcctttttt   1680
ctgcgcgtaa tctgctgctt gcaaacaaaa aaaccaccgc taccagcggt ggtttgtttg   1740
ccggatcaag agctaccaac tctttttccg aaggtaactg gcttcagcag agcgcagata   1800
ccaaatactg ttcttctagt gtagccgtag ttaggccacc acttcaagaa ctctgtagca   1860
ccgcctacat acctcgctct gctaatcctg ttaccagtgg ctgctgccag tggcgataag   1920
tcgtgtctta ccgggttgga ctcaagacga tagttaccgg ataaggcgca gcggtcgggc   1980
tgaacggggg gttcgtgcac acagcccagc ttggagcgaa cgacctacac cgaactgaga   2040
tacctacagc gtgagctatg agaaagcgcc acgcttcccg aagggagaaa ggcggacagg   2100
tatccggtaa gcggcagggt cggaacagga gagcgcacga gggagcttcc agggggaaac   2160
gcctggtatc tttatagtcc tgtcgggttt cgccacctct gacttgagcg tcgatttttg   2220
tgatgctcgt caggggggcg gagcctatgg aaaaacgcca gcaacgcggc ctttttacgg   2280
ttcctggcct tttgctggcc ttttgctcac atgtaatgtg agttagctca ctcattaggc   2340
accccaggct ttacacttta tgcttccggc tcgtatgttg tgtggaattg tgagcggata   2400
acaatttcac acaggaaaca gctatgacca tgattacgcc aagctacgta atacgactca   2460
ctagtggggc ccgtgcaatt gaagccggct ggcgccaagc ttctctgcag gatatctgga   2520
tccacgaatt cgctagcttc ggccgtgacg cgtctccgga tgtacaggca tgcgtcgacc   2580
ctctagtcaa ggccttaagt gagtcgtatt acggactggc cgtcgtttta caacgtcgtg   2640
actgggaaaa ccctggcgtt acccaactta atcgccttgc agcacatccc cctttcgcca   2700
gctggcgtaa tagcgaagag gcccgcaccg atcgcccttc ccaacagttg cgcagcctga   2760
atggcgaatg gcgcttcgct tggtaataaa gcccgcttcg gcgggctttt tttt         2814
```

-continued

<210> SEQ ID NO 120
<211> LENGTH: 2847
<212> TYPE: DNA
<213> ORGANISM: Artificial Sequence
<220> FEATURE:
<223> OTHER INFORMATION: pLIT38attB Plasmid

<400> SEQUENCE: 120

```
gttaactacg tcaggtggca cttttcgggg aaatgtgcgc ggaaccccta tttgtttatt     60

tttctaaata cattcaaata tgtatccgct catgagacaa taaccctgat aaatgcttca    120

ataatattga aaaaggaaga gtatgagtat tcaacatttc cgtgtcgccc ttattccctt    180

ttttgcggca ttttgccttc ctgtttttgc tcacccagaa acgctggtga aagtaaaaga    240

tgctgaagat cagttgggtg cacgagtggg ttacatcgaa ctggatctca acagcggtaa    300

gatccttgag agttttcgcc ccgaagaacg ttctccaatg atgagcactt ttaaagttct    360

gctatgtggc gcggtattat cccgtgttga cgccgggcaa gagcaactcg gtcgccgcat    420

acactattct cagaatgact tggttgagta ctcaccagtc acagaaaagc atcttacgga    480

tggcatgaca gtaagagaat tatgcagtgc tgccataacc atgagtgata acactgcggc    540

caacttactt ctgacaacga tcggaggacc gaaggagcta accgcttttt tgcacaacat    600

gggggatcat gtaactcgcc ttgatcgttg ggaaccggag ctgaatgaag ccataccaaa    660

cgacgagcgt gacaccacga tgcctgtagc aatggcaaca acgttgcgca aactattaac    720

tggcgaacta cttactctag cttcccggca acaattaata gactggatgg aggcggataa    780

agttgcagga ccacttctgc gctcggccct tccggctggc tggtttattg ctgataaatc    840

tggagccggt gagcgtgggt ctcgcggtat cattgcagca ctggggccag atggtaagcc    900

ctcccgtatc gtagttatct acacgacggg gagtcaggca actatggatg aacgaaatag    960

acagatcgct gagataggtg cctcactgat taagcattgg taactgtcag accaagttta   1020

ctcatatata ctttagattg atttaccccg gttgataatc agaaaagccc caaaaacagg   1080

aagattgtat aagcaaatat ttaaattgta aacgttaata ttttgttaaa attcgcgtta   1140

aatttttgtt aaatcagctc attttttaac caataggccg aaatcggcaa aatcccttat   1200

aaatcaaaag aatagcccga gatagggttg agtgttgttc cagtttggaa caagagtcca   1260

ctattaaaga acgtggactc caacgtcaaa gggcgaaaaa ccgtctatca gggcgatggc   1320

ccactacgtg aaccatcacc caaatcaagt tttttggggt cgaggtgccg taaagcacta   1380

aatcggaacc ctaaagggag cccccgattt agagcttgac ggggaaagcg aacgtggcga   1440

gaaaggaagg gaagaaagcg aaaggagcgg gcgctagggc gctggcaagt gtagcggtca   1500

cgctgcgcgt aaccaccaca cccgccgcgc ttaatgcgcc gctacagggc gcgtaaaagg   1560

atctaggtga agatcctttt tgataatctc atgaccaaaa tcccttaacg tgagttttcg   1620

ttccactgag cgtcagaccc cgtagaaaag atcaaaggat cttcttgaga tccttttttt   1680

ctgcgcgtaa tctgctgctt gcaaacaaaa aaaccaccgc taccagcggt ggtttgtttg   1740

ccggatcaag agctaccaac tctttttccg aaggtaactg gcttcagcag agcgcagata   1800

ccaaatactg ttcttctagt gtagccgtag ttaggccacc acttcaagaa ctctgtagca   1860

ccgcctacat acctcgctct gctaatcctg ttaccagtgg ctgctgccag tggcgataag   1920

tcgtgtctta ccgggttgga ctcaagacga tagttaccgg ataaggcgca gcggtcgggc   1980

tgaacggggg gttcgtgcac acagcccagc ttggagcgaa cgacctacac cgaactgaga   2040
```

-continued

```
tacctacagc gtgagctatg agaaagcgcc acgcttcccg aagggagaaa ggcggacagg   2100

tatccggtaa gcggcagggt cggaacagga gagcgcacga gggagcttcc agggggaaac   2160

gcctggtatc tttatagtcc tgtcgggttt cgccacctct gacttgagcg tcgatttttg   2220

tgatgctcgt caggggggcg gagcctatgg aaaaacgcca gcaacgcggc ctttttacgg   2280

ttcctggcct tttgctggcc ttttgctcac atgtaatgtg agttagctca ctcattaggc   2340

accccaggct ttacacttta tgcttccggc tcgtatgttg tgtggaattg tgagcggata   2400

acaatttcac acaggaaaca gctatgacca tgattacgcc aagctacgta atacgactca   2460

ctagtggggc ccgtgcaatt gaagccggct ggcgccaagc ttctctgcag gattgaagcc   2520

tgctttttta tactaacttg agcgaaatct ggatccacga attcgctagc ttcggccgtg   2580

acgcgtctcc ggatgtacag gcatgcgtcg accctctagt caaggcctta agtgagtcgt   2640

attacggact ggccgtcgtt ttacaacgtc gtgactggga aaaccctggc gttacccaac   2700

ttaatcgcct tgcagcacat ccccctttcg ccagctggcg taatagcgaa gaggcccgca   2760

ccgatcgccc ttcccaacag ttgcgcagcc tgaatggcga atggcgcttc gcttggtaat   2820

aaagcccgct tcggcgggct ttttttt                                       2847
```

```
<210> SEQ ID NO 121
<211> LENGTH: 4223
<212> TYPE: DNA
<213> ORGANISM: Artificial Sequence
<220> FEATURE:
<223> OTHER INFORMATION: pLIT38attBBSRpolyA2 Plasmid

<400> SEQUENCE: 121

accatgaaaa catttaacat ttctcaacaa gatctagaat tagtagaagt agcgacagag     60

aagattacaa tgctttatga ggataataaa catcatgtgg gagcggcaat tcgtacgaaa    120

acaggagaaa tcatttcggc agtacatatt gaagcgtata taggacgagt aactgtttgt    180

gcagaagcca ttgcgattgg tagtgcagtt tcgaatggac aaaaggattt tgacacgatt    240

gtagctgtta gacaccctta ttctgacgaa gtagatagaa gtattcgagt ggtaagtcct    300

tgtggtatgt gtagggagtt gatttcagac tatgcaccag attgttttgt gttaatagaa    360

atgaatggca agttagtcaa aactacgatt gaagaactca ttccactcaa atatacccga    420

aattaaaagt tttaccatac caagcttggc tgctgcctga ggctggacga cctcgcggag    480

ttctaccggc agtgcaaatc cgtcggcatc caggaaacca gcagcggcta tccgcgcatc    540

catgcccccg aactgcagga gtggggaggc acgatggccg ctttggtccg gatctttgtg    600

aaggaacctt acttctgtgg tgtgacataa ttggacaaac tacctacaga gatttaaagc    660

tctaaggtaa atataaaatt tttaagtgta taatgtgtta aactactgat tctaattgtt    720

tgtgtatttt agattccaac ctatggaact gatgaatggg agcagtggtg gaatgccttt    780

aatgaggaaa acctgttttg ctcagaagaa atgccatcta gtgatgatga ggctactgct    840

gactctcaac attctactcc tccaaaaaag aagagaaagg tagaagaccc caaggacttt    900

ccttcagaat tgctaagttt tttgagtcat gctgtgttta gtaatagaac tcttgcttgc    960

tttgctattt acaccacaaa ggaaaaagct gcactgctat acaagaaaat tatggaaaaa   1020

tattctgtaa cctttataag taggcataac agttataatc ataacatact gtttttttctt   1080

actccacaca ggcatagagt gtctgctatt aataactatg ctcaaaaatt gtgtaccttt   1140

agctttttaa tttgtaaagg ggttaataag gaatatttga tgtatagtgc cttgactaga   1200

gatcataatc agccatacca catttgtaga ggttttactt gctttaaaaa acctcccaca   1260
```

-continued

```
cctcccccctg aacctgaaac ataaaatgaa tgcaattgtt gttgttaact tgtttattgc   1320
agcttataat ggttacaaat aaagcaatag catcacaaat ttcacaaata aagatccaga   1380
tttcgctcaa gttagtataa aaaagcaggc ttcaatcctg cagagaagct tggcgccagc   1440
cggcttcaat tgcacgggcc ccactagtga gtcgtattac gtagcttggc gtaatcatgg   1500
tcatagctgt ttcctgtgtg aaattgttat ccgctcacaa ttccacacaa catacgagcc   1560
ggaagcataa agtgtaaagc ctggggtgcc taatgagtga gctaactcac attacatgtg   1620
agcaaaaggc cagcaaaagg ccaggaaccg taaaaaggcc gcgttgctgg cgtttttcca   1680
taggctccgc ccccctgacg agcatcacaa aaatcgacgc tcaagtcaga ggtggcgaaa   1740
cccgacagga ctataaagat accaggcgtt tccccctgga agctccctcg tgcgctctcc   1800
tgttccgacc ctgccgctta ccggatacct gtccgccttt ctcccttcgg gaagcgtggc   1860
gctttctcat agctcacgct gtaggtatct cagttcggtg taggtcgttc gctccaagct   1920
gggctgtgtg cacgaacccc ccgttcagcc cgaccgctgc gccttatccg gtaactatcg   1980
tcttgagtcc aacccggtaa gacacgactt atcgccactg gcagcagcca ctggtaacag   2040
gattagcaga gcgaggtatg taggcggtgc tacagagttc ttgaagtggt ggcctaacta   2100
cggctacact agaagaacag tatttggtat ctgcgctctg ctgaagccag ttaccttcgg   2160
aaaaagagtt ggtagctctt gatccggcaa acaaaccacc gctggtagcg gtggtttttt   2220
tgtttgcaag cagcagatta cgcgcagaaa aaaaggatct caagaagatc ctttgatctt   2280
ttctacgggg tctgacgctc agtggaacga aaactcacgt taagggattt tggtcatgag   2340
attatcaaaa aggatcttca cctagatcct tttacgcgcc ctgtagcggc gcattaagcg   2400
cggcgggtgt ggtggttacg cgcagcgtga ccgctacact tgccagcgcc ctagcgcccg   2460
ctcctttcgc tttcttccct tcctttctcg ccacgttcgc tttccccgtc aagctctaaa   2520
tcgggggctc cctttagggt tccgatttag tgctttacgg cacctcgacc ccaaaaaact   2580
tgatttgggt gatggttcac gtagtgggcc atcgccctga tagacggttt ttcgcccttt   2640
gacgttggag tccacgttct ttaatagtgg actcttgttc caaactggaa caacactcaa   2700
ccctatctcg ggctattctt ttgatttata agggattttg ccgatttcgg cctattggtt   2760
aaaaaatgag ctgatttaac aaaaatttaa cgcgaatttt aacaaaatat taacgtttac   2820
aatttaaata tttgcttata caatcttcct gtttttgggg cttttctgat tatcaaccgg   2880
ggtaaatcaa tctaaagtat atatgagtaa acttggtctg acagttacca atgcttaatc   2940
agtgaggcac ctatctcagc gatctgtcta tttcgttcat ccatagttgc ctgactcccc   3000
gtcgtgtaga taactacgat acgggagggc ttaccatctg gccccagtgc tgcaatgata   3060
ccgcgagacc cacgctcacc ggctccagat ttatcagcaa taaaccagcc agccggaagg   3120
gccgagcgca gaagtggtcc tgcaacttta tccgcctcca tccagtctat taattgttgc   3180
cgggaagcta gagtaagtag ttcgccagtt aatagtttgc gcaacgttgt tgccattgct   3240
acaggcatcg tggtgtcacg ctcgtcgttt ggtatggctt cattcagctc cggttcccaa   3300
cgatcaaggc gagttacatg atcccccatg ttgtgcaaaa aagcggttag ctccttcggt   3360
cctccgatcg ttgtcagaag taagttggcc gcagtgttat cactcatggt tatggcagca   3420
ctgcataatt ctcttactgt catgccatcc gtaagatgct tttctgtgac tggtgagtac   3480
tcaaccaagt cattctgaga atagtgtatg cggcgaccga gttgctcttg cccggcgtca   3540
acacgggata ataccgcgcc acatagcaga actttaaaag tgctcatcat tggagaacgt   3600
```

-continued

```
tcttcggggc gaaaactctc aaggatctta ccgctgttga gatccagttc gatgtaaccc   3660

actcgtgcac ccaactgatc ttcagcatct tttactttca ccagcgtttc tgggtgagca   3720

aaaacaggaa ggcaaaatgc cgcaaaaaag ggaataaggg cgacacggaa atgttgaata   3780

ctcatactct tcctttttca atattattga agcatttatc agggttattg tctcatgagc   3840

ggatacatat ttgaatgtat ttagaaaaat aaacaaatag gggttccgcg cacatttccc   3900

cgaaaagtgc cacctgacgt agttaacaaa aaaaagcccg ccgaagcggg ctttattacc   3960

aagcgaagcg ccattcgcca ttcaggctgc gcaactgttg ggaagggcga tcggtgcggg   4020

cctcttcgct attacgccag ctggcgaaag ggggatgtgc tgcaaggcga ttaagttggg   4080

taacgccagg gttttcccag tcacgacgtt gtaaaacgac ggccagtccg taatacgact   4140

cacttaaggc cttgactaga gggtcgacgc atgcctgtac atccggagac gcgtcacggc   4200

cgaagctagc gaattcgtgg atc                                           4223
```

<210> SEQ ID NO 122
<211> LENGTH: 2686
<212> TYPE: DNA
<213> ORGANISM: Artificial Sequence
<220> FEATURE:
<223> OTHER INFORMATION: pUC18 Plasmid

<400> SEQUENCE: 122

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtgccaa gcttgcatgc ctgcaggtcg    420

actctagagg atccccgggt accgagctcg aattcgtaat catggtcata gctgtttcct    480

gtgtgaaatt gttatccgct cacaattcca cacaacatac gagccggaag cataaagtgt    540

aaagcctggg gtgcctaatg agtgagctaa ctcacattaa ttgcgttgcg ctcactgccc    600

gctttccagt cgggaaacct gtcgtgccag ctgcattaat gaatcggcca acgcgcgggg    660

agaggcggtt tgcgtattgg gcgctcttcc gcttcctcgc tcactgactc gctgcgctcg    720

gtcgttcggc tgcggcgagc ggtatcagct cactcaaagg cggtaatacg gttatccaca    780

gaatcagggg ataacgcagg aaagaacatg tgagcaaaag gccagcaaaa ggccaggaac    840

cgtaaaaagg ccgcgttgct ggcgtttttc cataggctcc gcccccctga cgagcatcac    900

aaaaatcgac gctcaagtca gaggtggcga aacccgacag gactataaag ataccaggcg    960

tttccccctg gaagctccct cgtgcgctct cctgttccga ccctgccgct taccggatac   1020

ctgtccgcct ttctcccttc gggaagcgtg gcgctttctc atagctcacg ctgtaggtat   1080

ctcagttcgg tgtaggtcgt tcgctccaag ctgggctgtg tgcacgaacc ccccgttcag   1140

cccgaccgct gcgccttatc cggtaactat cgtcttgagt ccaacccggt aagacacgac   1200

ttatcgccac tggcagcagc cactggtaac aggattagca gagcgaggta tgtaggcggt   1260

gctacagagt tcttgaagtg gtggcctaac tacggctaca ctagaaggac agtatttggt   1320

atctgcgctc tgctgaagcc agttaccttc ggaaaaagag ttggtagctc ttgatccggc   1380

aaacaaacca ccgctggtag cggtggtttt tttgtttgca agcagcagat tacgcgcaga   1440
```

-continued

```
aaaaaaggat ctcaagaaga tcctttgatc ttttctacgg ggtctgacgc tcagtggaac   1500
gaaaactcac gttaagggat tttggtcatg agattatcaa aaaggatctt cacctagatc   1560
cttttaaatt aaaaatgaag ttttaaatca atctaaagta tatatgagta aacttggtct   1620
gacagttacc aatgcttaat cagtgaggca cctatctcag cgatctgtct atttcgttca   1680
tccatagttg cctgactccc cgtcgtgtag ataactacga tacgggaggg cttaccatct   1740
ggccccagtg ctgcaatgat accgcgagac ccacgctcac cggctccaga tttatcagca   1800
ataaaccagc cagccggaag ggccgagcgc agaagtggtc ctgcaacttt atccgcctcc   1860
atccagtcta ttaattgttg ccgggaagct agagtaagta gttcgccagt taatagtttg   1920
cgcaacgttg ttgccattgc tacaggcatc gtggtgtcac gctcgtcgtt tggtatggct   1980
tcattcagct ccggttccca acgatcaagg cgagttacat gatcccccat gttgtgcaaa   2040
aaagcggtta gctccttcgg tcctccgatc gttgtcagaa gtaagttggc cgcagtgtta   2100
tcactcatgg ttatggcagc actgcataat tctcttactg tcatgccatc cgtaagatgc   2160
ttttctgtga ctggtgagta ctcaaccaag tcattctgag aatagtgtat gcggcgaccg   2220
agttgctctt gcccggcgtc aatacgggat aataccgcgc cacatagcag aactttaaaa   2280
gtgctcatca ttggaaaacg ttcttcgggg cgaaaactct caaggatctt accgctgttg   2340
agatccagtt cgatgtaacc cactcgtgca cccaactgat cttcagcatc ttttactttc   2400
accagcgttt ctgggtgagc aaaaacagga aggcaaaatg ccgcaaaaaa gggaataagg   2460
gcgacacgga aatgttgaat actcatactc ttcctttttc aatattattg aagcatttat   2520
cagggttatt gtctcatgag cggatacata tttgaatgta tttagaaaaa taaacaaata   2580
ggggttccgc gcacatttcc ccgaaaagtg ccacctgacg tctaagaaac cattattatc   2640
atgacattaa cctataaaaa taggcgtatc acgaggccct ttcgtc                  2686
```

<210> SEQ ID NO 123
<211> LENGTH: 8521
<212> TYPE: DNA
<213> ORGANISM: Artificial Sequence
<220> FEATURE:
<223> OTHER INFORMATION: pCXeGFPattB(6xHS4)2 Plasmid

<400> SEQUENCE: 123

```
tacggggcgg gggatccact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420
atctcccccc cctccccacc cccaattttg tatttattta ttttttaatt attttgtgca    480
gcgatggggg cggggggggg gggggcgcgc gccaggcggg gcggggcggg gcgaggggcg    540
gggcggggcg aggcggagag gtgcggcggc agccaatcag agcggcgcgc tccgaaagtt    600
tcctttttatg gcgaggcggc ggcggcggcg gccctataaa aagcgaagcg cgcggcgggc    660
gggagtcgct gcgttgcctt cgccccgtgc cccgctccgc gccgcctcgc gccgcccgcc    720
ccggctctga ctgaccgcgt tactcccaca ggtgagcggg cgggacggcc cttctcctcc    780
```

-continued gggctgtaat tagcgcttgg tttaatgacg gctcgtttct tttctgtggc tgcgtgaaag 840
ccttaaaggg ctccgggagg gccctttgtg cggggggag cggctcgggg ggtgcgtgcg 900
tgtgtgtgtg cgtggggagc gccgcgtgcg gcccgcgctg cccggcggct gtgagcgctg 960
cgggcgcggc gcggggcttt gtgcgctccg cgtgtgcgcg aggggagcgc ggccgggggc 1020
ggtgccccgc ggtgcggggg ggctgcgagg ggaacaaagg ctgcgtgcgg ggtgtgtgcg 1080
tgggggggtg agcagggggt gtgggcgcgg cggtcgggct gtaacccccc cctgcacccc 1140
cctccccgag ttgctgagca cggcccggct tcgggtgcgg ggctccgtgc ggggcgtggc 1200
gcggggctcg ccgtgccggg cgggggtgg cggcaggtgg gggtgccggg cggggcgggg 1260
ccgcctcggg ccggggaggg ctcgggggag ggcgcggcg gccccggagc gccggcggct 1320
gtcgaggcgc ggcgagccgc agccattgcc ttttatggta atcgtgcgag agggcgcagg 1380
gacttccttt gtcccaaatc tggcggagcc gaaatctggg aggcgccgcc gcaccccctc 1440
tagcgggcgc gggcgaagcg gtgcggcgcc ggcaggaagg aaatgggcgg ggagggcctt 1500
cgtgcgtcgc cgcgccgccg tccccttctc catctccagc ctcggggctg ccgcaggggg 1560
acggctgcct tcggggggga cggggcaggg cggggttcgg cttctggcgt gtgaccggcg 1620
gctctagagc ctctgctaac catgttcatg ccttcttctt tttcctacag ctcctgggca 1680
acgtgctggt tgttgtgctg tctcatcatt ttggcaaaga attcgccacc atggtgagca 1740
agggcgagga gctgttcacc ggggtggtgc ccatcctggt cgagctggac ggcgacgtaa 1800
acggccacaa gttcagcgtg tccggcgagg gcgagggcga tgccacctac ggcaagctga 1860
ccctgaagtt catctgcacc accggcaagc tgcccgtgcc ctggcccacc ctcgtgacca 1920
ccctgaccta cggcgtgcag tgcttcagcc gctaccccga ccacatgaag cagcacgact 1980
tcttcaagtc cgccatgccc gaaggctacg tccaggagcg caccatcttc ttcaaggacg 2040
acggcaacta caagacccgc gccgaggtga agttcgaggg cgacaccctg gtgaaccgca 2100
tcgagctgaa gggcatcgac ttcaaggagg acggcaacat cctggggcac aagctggagt 2160
acaactacaa cagccacaac gtctatatca tggccgacaa gcagaagaac ggcatcaagg 2220
tgaacttcaa gatccgccac aacatcgagg acggcagcgt gcagctcgcc gaccactacc 2280
agcagaacac ccccatcggc gacggccccg tgctgctgcc cgacaaccac tacctgagca 2340
cccagtccgc cctgagcaaa gaccccaacg agaagcgcga tcacatggtc ctgctggagt 2400
tcgtgaccgc cgccgggatc actctcggca tggacgagct gtacaagtaa gaattcactc 2460
ctcaggtgca ggctgcctat cagaaggtgg tggctggtgt ggccaatgcc ctggctcaca 2520
aataccactg agatcttttt ccctctgcca aaaattatgg ggacatcatg aagccccttg 2580
agcatctgac ttctggctaa taaaggaaat ttattttcat tgcaatagtg tgttggaatt 2640
ttttgtgtct ctcactcgga aggacatatg ggagggcaaa tcatttaaaa catcagaatg 2700
agtatttggt ttagagtttg gcaacatatg ccatatgctg gctgccatga acaaaggtgg 2760
ctataaagag gtcatcagta tatgaaacag ccccctgctg tccattcctt attccataga 2820
aaagccttga cttgaggtta gatttttttt atattttgtt ttgtgttatt tttttcttta 2880
acatccctaa aattttcctt acatgtttta ctagccagat ttttcctcct ctcctgacta 2940
ctcccagtca tagctgtccc tcttctctta tgaagatccc tcgacctgca gcccaagctt 3000
ggcgtaatca tggtcatagc tgtttcctgt gtgaaattgt tatccgctca caattccaca 3060
caacatacga gccggaagca taaagtgtaa agcctggggt gcctaatgag tgagctaact 3120
cacattaatt gcgttgcgct cactgcccgc tttccagtcg ggaaacctgt cgtgccagcg 3180

-continued

```
gatccgcatc tcaattagtc agcaaccata gtcccgcccc taactccgcc catcccgccc   3240
ctaactccgc ccagttccgc ccattctccg ccccatggct gactaatttt ttttatttat   3300
gcagaggccg aggccgcctc ggcctctgag ctattccaga agtagtgagg aggctttttt   3360
ggaggctagt ggatccccg  ccccgtatcc cccaggtgtc tgcaggctca aagagcagcg   3420
agaagcgttc agaggaaagc gatcccgtgc caccttcccc gtgcccgggc tgtccccgca   3480
cgctgccggc tcggggatgc ggggggagcg ccggaccgga gcggagcccc gggcggctcg   3540
ctgctgcccc ctagcggggg agggacgtaa ttacatccct gggggctttg gggggggggct  3600
gtccccgtga gcggatccgc ggccccgtat cccccaggtg tctgcaggct caaagagcag   3660
cgagaagcgt tcagaggaaa gcgatcccgt gccaccttcc ccgtgcccgg gctgtccccg   3720
cacgctgccg gctcggggat gcggggggag cgccggaccg gagcggagcc ccgggcggct   3780
cgctgctgcc ccctagcggg ggagggacgt aattacatcc ctgggggctt tggggggggg   3840
ctgtccccgt gagcggatcc gcggccccgt atcccccagg tgtctgcagg ctcaaagagc   3900
agcgagaagc gttcagagga aagcgatccc gtgccacctt ccccgtgccc gggctgtccc   3960
cgcacgctgc cggctcgggg atgcgggggg agcgccggac cggagcggag ccccgggcgg   4020
ctcgctgctg ccccctagcg ggggagggac gtaattacat ccctgggggc tttggggggg   4080
ggctgtcccc gtgagcggat ccgcggcccc gtatccccca ggtgtctgca ggctcaaaga   4140
gcagcgagaa gcgttcagag gaaagcgatc ccgtgccacc ttccccgtgc ccgggctgtc   4200
cccgcacgct gccggctcgg ggatgcgggg ggagcgccgg accggagcgg agccccgggc   4260
ggctcgctgc tgccccctag cgggggaggg acgtaattac atccctgggg gctttggggg   4320
ggggctgtcc ccgtgagcgg atccgcggcc ccgtatcccc caggtgtctg caggctcaaa   4380
gagcagcgag aagcgttcag aggaaagcga tcccgtgcca ccttccccgt gcccgggctg   4440
tccccgcacg ctgccggctc ggggatgcgg ggggagcgcc ggaccggagc ggagccccgg   4500
gcggctcgct gctgccccct agcgggggag ggacgtaatt acatccctgg gggctttggg   4560
ggggggctgt ccccgtgagc ggatccgcgg ccccgtatcc cccaggtgtc tgcaggctca   4620
aagagcagcg agaagcgttc agaggaaagc gatcccgtgc caccttcccc gtgcccgggc   4680
tgtccccgca cgctgccggc tcggggatgc ggggggagcg ccggaccgga gcggagcccc   4740
gggcggctcg ctgctgcccc ctagcggggg agggacgtaa ttacatccct gggggctttg   4800
ggggggggct gtccccgtga gcggatccgc ggggctgcag gaattcgatt gaagcctgct   4860
tttttatact aacttgagcg aaatcaagct cctaggcttt tgcaaaaagc taacttgttt   4920
attgcagctt ataatggtta caaataaagc aatagcatca caaatttcac aaataaagca   4980
tttttttcac tgcattctag ttgtggtttg tccaaactca tcaatgtatc ttatcatgtc   5040
tggatccgct gcattaatga atcggccaac gcgcggggag aggcggtttg cgtattgggc   5100
gctcttccgc ttcctcgctc actgactcgc tgcgctcggt cgttcggctg cggcgagcgg   5160
tatcagctca ctcaaaggcg gtaatacggt tatccacaga atcaggggat aacgcaggaa   5220
agaacatgtg agcaaaaggc cagcaaaagg ccaggaaccg taaaaaggcc gcgttgctgg   5280
cgtttttcca taggctccgc ccccctgacg agcatcacaa aaatcgacgc tcaagtcaga   5340
ggtggcgaaa cccgacagga ctataaagat accaggcgtt tccccctgga agctccctcg   5400
tgcgctctcc tgttccgacc ctgccgctta ccggatacct gtccgccttt ctcccttcgg   5460
gaagcgtggc gctttctcaa tgctcacgct gtaggtatct cagttcggtg taggtcgttc   5520
```

-continued

```
gctccaagct gggctgtgtg cacgaacccc ccgttcagcc cgaccgctgc gccttatccg   5580
gtaactatcg tcttgagtcc aacccggtaa gacacgactt atcgccactg gcagcagcca   5640
ctggtaacag gattagcaga gcgaggtatg taggcggtgc tacagagttc ttgaagtggt   5700
ggcctaacta cggctacact agaaggacag tatttggtat ctgcgctctg ctgaagccag   5760
ttaccttcgg aaaaagagtt ggtagctctt gatccggcaa acaaaccacc gctggtagcg   5820
gtggtttttt tgtttgcaag cagcagatta cgcgcagaaa aaaaggatct caagaagatc   5880
ctttgatctt ttctacgggg tctgacgctc agtggaacga aaactcacgt taagggattt   5940
tggtcatgag attatcaaaa aggatcttca cctagatcct tttaaattaa aaatgaagtt   6000
ttaaatcaat ctaaagtata tatgagtaaa cttggtctga cagttaccaa tgcttaatca   6060
gtgaggcacc tatctcagcg atctgtctat ttcgttcatc catagttgcc tgactccccg   6120
tcgtgtagat aactacgata cgggagggct taccatctgg ccccagtgct gcaatgatac   6180
cgcgagaccc acgctcaccg gctccagatt tatcagcaat aaaccagcca gccggaaggg   6240
ccgagcgcag aagtggtcct gcaactttat ccgcctccat ccagtctatt aattgttgcc   6300
gggaagctag agtaagtagt tcgccagtta atagtttgcg caacgttgtt gccattgcta   6360
caggcatcgt ggtgtcacgc tcgtcgtttg gtatggcttc attcagctcc ggttcccaac   6420
gatcaaggcg agttacatga tcccccatgt tgtgcaaaaa agcggttagc tccttcggtc   6480
ctccgatcgt tgtcagaagt aagttggccg cagtgttatc actcatggtt atggcagcac   6540
tgcataattc tcttactgtc atgccatccg taagatgctt ttctgtgact ggtgagtact   6600
caaccaagtc attctgagaa tagtgtatgc ggcgaccgag ttgctcttgc ccggcgtcaa   6660
tacgggataa taccgcgcca catagcagaa ctttaaaagt gctcatcatt ggaaaacgtt   6720
cttcggggcg aaaactctca aggatcttac cgctgttgag atccagttcg atgtaaccca   6780
ctcgtgcacc caactgatct tcagcatctt ttactttcac cagcgtttct gggtgagcaa   6840
aaacaggaag gcaaaatgcc gcaaaaaagg gaataagggc gacacggaaa tgttgaatac   6900
tcatactctt cctttttcaa tattattgaa gcatttatca gggttattgt ctcatgagcg   6960
gatacatatt tgaatgtatt tagaaaaata aacaaatagg ggttccgcgc acatttcccc   7020
gaaaagtgcc acctggtcga cggtatcgat aagcttgata tcgaattcct gcagcccccgc   7080
ggatccgctc acggggacag cccccccccca aagcccccag ggatgtaatt acgtccctcc   7140
cccgctaggg ggcagcagcg agccgcccgg ggctccgctc cggtccggcg ctcccccccgc   7200
atccccgagc cggcagcgtg cggggacagc ccgggcacgg ggaaggtggc acgggatcgc   7260
tttcctctga acgcttctcg ctgctctttg agcctgcaga cacctggggg atacggggcc   7320
gcggatccgc tcacggggac agcccccccc caaagccccc agggatgtaa ttacgtccct   7380
cccccgctag ggggcagcag cgagccgccc ggggctccgc tccggtccgg cgctcccccc   7440
gcatccccga gccggcagcg tgcggggaca gcccgggcac ggggaaggtg gcacgggatc   7500
gctttcctct gaacgcttct cgctgctctt tgagcctgca gacacctggg ggatacgggg   7560
ccgcggatcc gctcacgggg acagcccccc cccaaagccc ccagggatgt aattacgtcc   7620
ctcccccgct agggggcagc agcgagccgc ccggggctcc gctccggtcc ggcgctcccc   7680
ccgcatcccc gagccggcag cgtgcgggga cagcccgggc acggggaagg tggcacggga   7740
tcgctttcct ctgaacgctt ctcgctgctc tttgagcctg cagacacctg gggggatacgg   7800
ggccgcggat ccgctcacgg ggacagcccc cccccaaagc ccccagggat gtaattacgt   7860
ccctcccccg ctagggggca gcagcgagcc gcccggggct ccgctccggt ccggcgctcc   7920
```

-continued

```
cccgcatcc ccgagccggc agcgtgcggg gacagcccgg gcacggggaa ggtggcacgg   7980

gatcgctttc ctctgaacgc ttctcgctgc tctttgagcc tgcagacacc tgggggatac   8040

ggggccgcgg atccgctcac ggggacagcc ccccccaaa gcccccaggg atgtaattac   8100

gtccctcccc cgctaggggg cagcagcgag ccgcccgggg ctccgctccg gtccggcgct   8160

ccccccgcat ccccgagccg gcagcgtgcg gggacagccc gggcacgggg aaggtggcac   8220

gggatcgctt tcctctgaac gcttctcgct gctctttgag cctgcagaca cctgggggat   8280

acggggccgc ggatccgctc acggggacag ccccccccca aagcccccag ggatgtaatt   8340

acgtccctcc cccgctaggg ggcagcagcg agccgcccgg ggctccgctc cggtccggcg   8400

ctccccccgc atccccgagc cggcagcgtg cggggacagc ccgggcacgg ggaaggtggc   8460

acgggatcgc tttcctctga acgcttctcg ctgctctttg agcctgcaga cacctggggg   8520

a                                                                   8521
```

<210> SEQ ID NO 124
<211> LENGTH: 8851
<212> TYPE: DNA
<213> ORGANISM: Artificial Sequence
<220> FEATURE:
<223> OTHER INFORMATION: p18EPOcDNA Plasmid

<400> SEQUENCE: 124

```
cagttgccgg ccgggtcgcg cagggcgaac tcccgccccc acggctgctc gccgatctcg     60

gtcatggccg gcccggaggc gtcccggaag ttcgtggaca cgacctccga ccactcggcg    120

tacagctcgt ccaggccgcg cacccacacc caggccaggg tgttgtccgg caccacctgg    180

tcctggaccg cgctgatgaa cagggtcacg tcgtcccgga ccacaccggc gaagtcgtcc    240

tccacgaagt cccgggagaa cccgagccgg tcggtccaga actcgaccgc tccggcgacg    300

tcgcgcgcgg tgagcaccgg aacggcactg gtcaacttgg ccatggatcc agatttcgct    360

caagttagta taaaaaagca ggcttcaatc ctgcagagaa gcttgatatc gaattcctgc    420

agccccgcgg atccgctcac ggggacagcc ccccccaaa gcccccaggg atgtaattac    480

gtccctcccc cgctaggggg cagcagcgag ccgcccgggg ctccgctccg gtccggcgct    540

ccccccgcat ccccgagccg gcagcgtgcg gggacagccc gggcacgggg aaggtggcac    600

gggatcgctt tcctctgaac gcttctcgct gctctttgag cctgcagaca cctgggggat    660

acggggccgc ggatccgctc acggggacag ccccccccca aagcccccag ggatgtaatt    720

acgtccctcc cccgctaggg ggcagcagcg agccgcccgg ggctccgctc cggtccggcg    780

ctccccccgc atccccgagc cggcagcgtg cggggacagc ccgggcacgg ggaaggtggc    840

acgggatcgc tttcctctga acgcttctcg ctgctctttg agcctgcaga cacctggggg    900

atacggggcc gcggatccgc tcacggggac agcccccccc caaagccccc agggatgtaa    960

ttacgtccct cccccgctag ggggcagcag cgagccgccc ggggctccgc tccggtccgg   1020

cgctcccccc gcatccccga gccggcagcg tgcggggaca gcccgggcac ggggaaggtg   1080

gcacgggatc gctttcctct gaacgcttct cgctgctctt tgagcctgca gacacctggg   1140

ggatacgggg ccgcggatcc gctcacgggg acagcccccc cccaaagccc ccagggatgt   1200

aattacgtcc ctcccccgct agggggcagc agcgagccgc ccggggctcc gctccggtcc   1260

ggcgctcccc ccgcatcccc gagccggcag cgtgcgggga cagcccgggc acggggaagg   1320

tggcacggga tcgctttcct ctgaacgctt ctcgctgctc tttgagcctg cagacacctg   1380
```

-continued

```
ggggatacgg ggccgcggat ccgctcacgg ggacagcccc cccccaaagc ccccagggat   1440
gtaattacgt ccctcccccg ctagggggca gcagcgagcc gcccggggct ccgctccggt   1500
ccggcgctcc ccccgcatcc ccgagccggc agcgtgcggg gacagcccgg gcacggggaa   1560
ggtggcacgg gatcgctttc ctctgaacgc ttctcgctgc tctttgagcc tgcagacacc   1620
tgggggatac ggggccgcgg atccgctcac ggggacagcc cccccccaaa gcccccaggg   1680
atgtaattac gtccctcccc cgctaggggg cagcagcgag ccgcccgggg ctccgctccg   1740
gtccggcgct ccccccgcat ccccgagccg gcagcgtgcg gggacagccc gggcacgggg   1800
aaggtggcac gggatcgctt tcctctgaac gcttctcgct gctctttgag cctgcagaca   1860
cctgggggat acggggcggg ggatccacta gttattaata gtaatcaatt acggggtcat   1920
tagttcatag cccatatatg gagttccgcg ttacataact tacggtaaat ggcccgcctg   1980
gctgaccgcc caacgacccc cgcccattga cgtcaataat gacgtatgtt cccatagtaa   2040
cgccaatagg gactttccat tgacgtcaat gggtggacta tttacggtaa actgcccact   2100
tggcagtaca tcaagtgtat catatgccaa gtacgccccc tattgacgtc aatgacggta   2160
aatggcccgc ctggcattat gcccagtaca tgaccttatg ggactttcct acttggcagt   2220
acatctacgt attagtcatc gctattacca tgggtcgagg tgagccccac gttctgcttc   2280
actctcccca tctccccccc ctccccaccc ccaattttgt atttatttat tttttaatta   2340
ttttgtgcag cgatgggggc gggggggggg ggggcgcgcg ccaggcgggg cggggcgggg   2400
cgaggggcgg ggcggggcga ggcggagagg tgcggcggca gccaatcaga gcggcgcgct   2460
ccgaaagttt ccttttatgg cgaggcggcg gcggcggcgg ccctataaaa agcgaagcgc   2520
gcggcgggcg ggagtcgctg cgttgccttc gccccgtgcc ccgctccgcg ccgcctcgcg   2580
ccgcccgccc cggctctgac tgaccgcgtt actcccacag gtgagcgggc gggacggccc   2640
ttctcctccg ggctgtaatt agcgcttggt ttaatgacgg ctcgtttctt ttctgtggct   2700
gcgtgaaagc cttaaagggc tccgggaggg ccctttgtgc ggggggggagc ggctcggggg   2760
gtgcgtgcgt gtgtgtgtgc gtggggagcg ccgcgtgcgg cccgcgctgc ccggcggctg   2820
tgagcgctgc gggcgcggcg cggggctttg tgcgctccgc gtgtgcgcga ggggagcgcg   2880
gccgggggcg gtgccccgcg gtgcgggggg gctgcgaggg gaacaaaggc tgcgtgcggg   2940
gtgtgtgcgt gggggggtga gcagggggtg tgggcgcggc ggtcgggctg taaccccccc   3000
ctgcaccccc ctccccgagt tgctgagcac ggcccggctt cgggtgcggg gctccgtgcg   3060
gggcgtggcg cggggctcgc cgtgccgggc ggggggtggc ggcaggtggg ggtgccgggc   3120
ggggcggggc cgcctcgggc cggggagggc tcgggggagg ggcgcggcgg ccccggagcg   3180
ccggcggctg tcgaggcgcg gcgagccgca gccattgcct tttatggtaa tcgtgcgaga   3240
gggcgcaggg acttcctttg tcccaaatct ggcggagccg aaatctggga ggcgccgccg   3300
caccccctct agcgggcgcg ggcgaagcgg tgcggcgccg gcaggaagga aatgggcggg   3360
gagggccttc gtgcgtcgcc gcgccgccgt ccccttctcc atctccagcc tcggggctgc   3420
cgcaggggga cggctgcctt cgggggggac ggggcagggc ggggttcggc ttctggcgtg   3480
tgaccggcgg ctctagaatg ggggtgcacg aatgtcctgc ctggctgtgg cttctcctgt   3540
ccctgctgtc gctccctctg ggcctcccag tcctgggcgc ccccaccacgc ctcatctgtg   3600
acagccgagt cctggagagg tacctcttgg aggccaagga ggccgagaat atcacgacgg   3660
gctgtgctga acactgcagc ttgaatgaga atatcactgt cccagacacc aaagttaatt   3720
tctatgcctg gaagaggatg gaggtcgggc agcaggccgt agaagtctgg cagggcctgg   3780
```

-continued

```
ccctgctgtc ggaagctgtc ctgcggggcc aggccctgtt ggtcaactct tcccagccgt   3840
gggagcccct gcagctgcat gtggataaag ccgtcagtgg ccttcgcagc ctcaccactc   3900
tgcttcgggc tctgggagcc cagaaggaag ccatctcccc tccagatgcg gcctcagctg   3960
ctccactccg aacaatcact gctgacactt tccgcaaact cttccgagtc tactccaatt   4020
tcctccgggg aaagctgaag ctgtacacag gggaggcctg caggacaggg gacagatgac   4080
gtacaagtaa gaattcactc ctcaggtgca ggctgcctat cagaaggtgg tggctggtgt   4140
ggccaatgcc ctggctcaca aataccactg agatcttttt ccctctgcca aaaattatgg   4200
ggacatcatg aagccccttg agcatctgac ttctggctaa taaaggaaat ttattttcat   4260
tgcaatagtg tgttggaatt ttttgtgtct ctcactcgga aggacatatg ggagggcaaa   4320
tcatttaaaa catcagaatg agtatttggt ttagagtttg gcaacatatg ccatatgctg   4380
gctgccatga acaaaggtgg ctataaagag gtcatcagta tatgaaacag ccccctgctg   4440
tccattcctt attccataga aaagccttga cttgaggtta gattttttt atattttgtt   4500
ttgtgttatt tttttcttta acatccctaa aattttcctt acatgtttta ctagccagat   4560
ttttcctcct ctcctgacta ctcccagtca tagctgtccc tcttctctta tgaagatccc   4620
tcgacctgca gcccaagctt gcatgcctgc aggtcgactc tagtggatcc cccgccccgt   4680
atcccccagg tgtctgcagg ctcaaagagc agcgagaagc gttcagagga aagcgatccc   4740
gtgccacctt ccccgtgccc gggctgtccc cgcacgctgc cggctcgggg atgcgggggg   4800
agcgccggac cggagcggag ccccgggcgg ctcgctgctg ccccctagcg ggggagggac   4860
gtaattacat ccctgggggc tttggggggg ggctgtcccc gtgagcggat ccgcggcccc   4920
gtatccccca ggtgtctgca ggctcaaaga gcagcgagaa gcgttcagag gaaagcgatc   4980
ccgtgccacc ttccccgtgc ccgggctgtc cccgcacgct gccggctcgg ggatgcgggg   5040
ggagcgccgg accggagcgg agccccgggc ggctcgctgc tgccccctag cgggggaggg   5100
acgtaattac atccctgggg gctttggggg ggggctgtcc ccgtgagcgg atccgcggcc   5160
ccgtatcccc caggtgtctg caggctcaaa gagcagcgag aagcgttcag aggaaagcga   5220
tcccgtgcca ccttccccgt gcccgggctg tccccgcacg ctgccggctc ggggatgcgg   5280
ggggagcgcc ggaccggagc ggagccccgg gcggctcgct gctgccccct agcgggggag   5340
ggacgtaatt acatccctgg gggctttggg ggggggctgt ccccgtgagc ggatccgcgg   5400
ccccgtatcc cccaggtgtc tgcaggctca aagagcagcg agaagcgttc agaggaaagc   5460
gatcccgtgc caccttcccc gtgcccgggc tgtccccgca cgctgccggc tcggggatgc   5520
gggggggagcg ccggaccgga gcggagcccc gggcggctcg ctgctgcccc ctagcggggg   5580
agggacgtaa ttacatccct gggggctttg gggggggggct gtccccgtga gcggatccgc   5640
ggccccgtat cccccaggtg tctgcaggct caaagagcag cgagaagcgt tcagaggaaa   5700
gcgatcccgt gccaccttcc ccgtgcccgg gctgtccccg cacgctgccg gctcggggat   5760
gcggggggag cgccggaccg gagcggagcc ccgggcggct cgctgctgcc ccctagcggg   5820
ggagggacgt aattacatcc ctgggggctt tggggggggg ctgtccccgt gagcggatcc   5880
gcggccccgt atcccccagg tgtctgcagg ctcaaagagc agcgagaagc gttcagagga   5940
aagcgatccc gtgccacctt ccccgtgccc gggctgtccc cgcacgctgc cggctcgggg   6000
atgcgggggg agcgccggac cggagcggag ccccgggcgg ctcgctgctg ccccctagcg   6060
ggggagggac gtaattacat ccctgggggc tttggggggg ggctgtcccc gtgagcggat   6120
```

-continued

```
ccgcggggct gcaggaattc gtaatcatgg tcatagctgt ttcctgtgtg aaattgttat   6180
ccgctcacaa ttccacacaa catacgagcc ggaagcataa agtgtaaagc ctggggtgcc   6240
taatgagtga gctaactcac attaattgcg ttgcgctcac tgcccgcttt ccagtcggga   6300
aacctgtcgt gccagctgca ttaatgaatc ggccaacgcg cggggagagg cggtttgcgt   6360
attgggcgct cttccgcttc ctcgctcact gactcgctgc gctcggtcgt tcggctgcgg   6420
cgagcggtat cagctcactc aaaggcggta atacggttat ccacagaatc aggggataac   6480
gcaggaaaga acatgtgagc aaaaggccag caaaaggcca ggaaccgtaa aaaggccgcg   6540
ttgctggcgt ttttccatag gctccgcccc cctgacgagc atcacaaaaa tcgacgctca   6600
agtcagaggt ggcgaaaccc gacaggacta taaagatacc aggcgtttcc ccctggaagc   6660
tccctcgtgc gctctcctgt tccgaccctg ccgcttaccg gatacctgtc cgcctttctc   6720
ccttcgggaa gcgtggcgct ttctcatagc tcacgctgta ggtatctcag ttcggtgtag   6780
gtcgttcgct ccaagctggg ctgtgtgcac gaaccccccg ttcagcccga ccgctgcgcc   6840
ttatccggta actatcgtct tgagtccaac ccggtaagac acgacttatc gccactggca   6900
gcagccactg gtaacaggat tagcagagcg aggtatgtag gcggtgctac agagttcttg   6960
aagtggtggc ctaactacgg ctacactaga aggacagtat ttggtatctg cgctctgctg   7020
aagccagtta ccttcggaaa aagagttggt agctcttgat ccggcaaaca aaccaccgct   7080
ggtagcggtg gtttttttgt ttgcaagcag cagattacgc gcagaaaaaa aggatctcaa   7140
gaagatcctt tgatcttttc tacggggtct gacgctcagt ggaacgaaaa ctcacgttaa   7200
gggattttgg tcatgagatt atcaaaaagg atcttcacct agatcctttt aaattaaaaa   7260
tgaagtttta aatcaatcta aagtatatat gagtaaactt ggtctgacag ttaccaatgc   7320
ttaatcagtg aggcacctat ctcagcgatc tgtctatttc gttcatccat agttgcctga   7380
ctccccgtcg tgtagataac tacgatacgg gagggcttac catctggccc cagtgctgca   7440
atgataccgc gagacccacg ctcaccggct ccagatttat cagcaataaa ccagccagcc   7500
ggaagggccg agcgcagaag tggtcctgca actttatccg cctccatcca gtctattaat   7560
tgttgccggg aagctagagt aagtagttcg ccagttaata gtttgcgcaa cgttgttgcc   7620
attgctacag gcatcgtggt gtcacgctcg tcgtttggta tggcttcatt cagctccggt   7680
tcccaacgat caaggcgagt tacatgatcc cccatgttgt gcaaaaaagc ggttagctcc   7740
ttcggtcctc cgatcgttgt cagaagtaag ttggccgcag tgttatcact catggttatg   7800
gcagcactgc ataattctct tactgtcatg ccatccgtaa gatgcttttc tgtgactggt   7860
gagtactcaa ccaagtcatt ctgagaatag tgtatgcggc gaccgagttg ctcttgcccg   7920
gcgtcaatac gggataatac cgcgccacat agcagaactt taaaagtgct catcattgga   7980
aaacgttctt cggggcgaaa actctcaagg atcttaccgc tgttgagatc cagttcgatg   8040
taacccactc gtgcacccaa ctgatcttca gcatctttta ctttcaccag cgtttctggg   8100
tgagcaaaaa caggaaggca aaatgccgca aaaaagggaa taagggcgac acggaaatgt   8160
tgaatactca tactcttcct ttttcaatat tattgaagca tttatcaggg ttattgtctc   8220
atgagcggat acatatttga atgtatttag aaaaataaac aaataggggt tccgcgcaca   8280
tttccccgaa aagtgccacc tgacgtagtt aacaaaaaaa agcccgccga agcgggcttt   8340
attaccaagc gaagcgccat tcgccattca ggctgcgcaa ctgttgggaa gggcgatcgg   8400
tgcgggcctc ttcgctatta cgccagctgg cgaaaggggg atgtgctgca aggcgattaa   8460
gttgggtaac gccagggttt tcccagtcac gacgttgtaa aacgacggcc agtccgtaat   8520
```

-continued

```
acgactcact taaggccttg actagagggt cgacggtata cagacatgat aagatacatt   8580

gatgagtttg gacaaaccac aactagaatg cagtgaaaaa aatgctttat ttgtgaaatt   8640

tgtgatgcta ttgctttatt tgtaaccatt ataagctgca ataaacaagt tggggtgggc   8700

gaagaactcc agcatgagat ccccgcgctg gaggatcatc cagccggcgt cccggaaaac   8760

gattccgaag cccaaccttt catagaaggc ggcggtggaa tcgaaatctc gtagcacgtg   8820

tcagtcctgc tcctcggcca cgaagtgcac g                                  8851
```

```
<210> SEQ ID NO 125
<211> LENGTH: 10474
<212> TYPE: DNA
<213> ORGANISM: Artificial Sequence
<220> FEATURE:
<223> OTHER INFORMATION: p18genEPO Plasmid

<400> SEQUENCE: 125

cagttgccgg ccgggtcgcg cagggcgaac tcccgccccc acggctgctc gccgatctcg     60

gtcatggccg gcccggaggc gtcccggaag ttcgtggaca cgacctccga ccactcggcg    120

tacagctcgt ccaggccgcg cacccacacc caggccaggg tgttgtccgg caccacctgg    180

tcctggaccg cgctgatgaa cagggtcacg tcgtcccgga ccacaccggc gaagtcgtcc    240

tccacgaagt cccgggagaa cccgagccgg tcggtccaga actcgaccgc tccggcgacg    300

tcgcgcgcgg tgagcaccgg aacggcactg gtcaacttgg ccatggatcc agatttcgct    360

caagttagta taaaaaagca ggcttcaatc ctgcagagaa gcttgatatc gaattcctgc    420

agccccgcgg atccgctcac ggggacagcc cccccccaaa gcccccaggg atgtaattac    480

gtccctcccc cgctaggggg cagcagcgag ccgcccgggg ctccgctccg gtccggcgct    540

ccccccgcat ccccgagccg gcagcgtgcg gggacagccc gggcacgggg aaggtggcac    600

gggatcgctt tcctctgaac gcttctcgct gctctttgag cctgcagaca cctgggggat    660

acggggccgc ggatccgctc acggggacag cccccccccca aagcccccag ggatgtaatt    720

acgtccctcc cccgctaggg ggcagcagcg agccgcccgg ggctccgctc cggtccggcg    780

ctcccccccgc atccccgagc cggcagcgtg cggggacagc ccgggcacgg ggaaggtggc    840

acgggatcgc tttcctctga acgcttctcg ctgctctttg agcctgcaga cacctggggg    900

atacggggcc gcggatccgc tcacggggac agcccccccc caaagccccc agggatgtaa    960

ttacgtccct cccccgctag ggggcagcag cgagccgccc ggggctccgc tccggtccgg   1020

cgctcccccc gcatccccga gccggcagcg tgcggggaca gcccgggcac ggggaaggtg   1080

gcacgggatc gctttcctct gaacgcttct cgctgctctt tgagcctgca gacacctggg   1140

ggatacgggg ccgcggatcc gctcacgggg acagcccccc cccaaagccc ccagggatgt   1200

aattacgtcc ctcccccgct agggggcagc agcgagccgc ccggggctcc gctccggtcc   1260

ggcgctcccc ccgcatcccc gagccggcag cgtgcgggga cagcccgggc acggggaagg   1320

tggcacggga tcgctttcct ctgaacgctt ctcgctgctc tttgagcctg cagacacctg   1380

ggggatacgg ggccgcggat ccgctcacgg ggacagcccc cccccaaagc ccccagggat   1440

gtaattacgt ccctcccccg ctagggggca gcagcgagcc gcccggggct ccgctccggt   1500

ccggcgctcc ccccgcatcc ccgagccggc agcgtgcggg gacagcccgg gcacggggaa   1560

ggtggcacgg gatcgctttc ctctgaacgc ttctcgctgc tctttgagcc tgcagacacc   1620

tgggggatac ggggccgcgg atccgctcac ggggacagcc cccccccaaa gcccccaggg   1680
```

-continued

```
atgtaattac gtccctcccc cgctaggggg cagcagcgag ccgcccgggg ctccgctccg   1740
gtccggcgct ccccccgcat ccccgagccg gcagcgtgcg gggacagccc gggcacgggg   1800
aaggtggcac gggatcgctt tcctctgaac gcttctcgct gctctttgag cctgcagaca   1860
cctgggggat acggggcggg ggatccacta gttattaata gtaatcaatt acggggtcat   1920
tagttcatag cccatatatg gagttccgcg ttacataact tacggtaaat ggcccgcctg   1980
gctgaccgcc caacgacccc cgcccattga cgtcaataat gacgtatgtt cccatagtaa   2040
cgccaatagg gactttccat tgacgtcaat gggtggacta tttacggtaa actgcccact   2100
tggcagtaca tcaagtgtat catatgccaa gtacgccccc tattgacgtc aatgacggta   2160
aatggcccgc ctggcattat gcccagtaca tgaccttatg ggactttcct acttggcagt   2220
acatctacgt attagtcatc gctattacca tgggtcgagg tgagccccac gttctgcttc   2280
actctcccca tctccccccc ctccccaccc ccaattttgt atttatttat tttttaatta   2340
ttttgtgcag cgatgggggc gggggggggg ggggcgcgcg ccaggcgggg cggggcgggg   2400
cgaggggcgg ggcggggcga ggcggagagg tgcggcggca gccaatcaga gcggcgcgct   2460
ccgaaagttt ccttttatgg cgaggcggcg gcggcggcgg ccctataaaa agcgaagcgc   2520
gcggcgggcg ggagtcgctg cgttgccttc gccccgtgcc ccgctccgcg ccgcctcgcg   2580
ccgcccgccc cggctctgac tgaccgcgtt actcccacag gtgagcgggc gggacggccc   2640
ttctcctccg ggctgtaatt agcgcttggt ttaatgacgg ctcgtttctt ttctgtggct   2700
gcgtgaaagc cttaaagggc tccgggaggg ccctttgtgc ggggggggagc ggctcggggg   2760
gtgcgtgcgt gtgtgtgtgc gtggggagcg ccgcgtgcgg cccgcgctgc ccggcggctg   2820
tgagcgctgc gggcgcggcg cggggctttg tgcgctccgc gtgtgcgcga ggggagcgcg   2880
gccgggggcg gtgccccgcg gtgcgggggg gctgcgaggg gaacaaaggc tgcgtgcggg   2940
gtgtgtgcgt gggggggtga gcagggggtg tgggcgcggc ggtcgggctg taaccccccc   3000
ctgcaccccc ctccccgagt tgctgagcac ggcccggctt cgggtgcggg gctccgtgcg   3060
gggcgtggcg cggggctcgc cgtgccgggc ggggggtggc ggcaggtggg ggtgccgggc   3120
ggggcggggc cgcctcgggc cggggagggc tcgggggagg ggcgcggcgg ccccggagcg   3180
ccggcggctg tcgaggcgcg gcgagccgca gccattgcct tttatggtaa tcgtgcgaga   3240
gggcgcaggg acttcctttg tcccaaatct ggcggagccg aaatctggga ggcgccgccg   3300
caccccctct agcgggcgcg ggcgaagcgg tgcggcgccg gcaggaagga aatgggcggg   3360
gagggccttc gtgcgtcgcc gcgccgccgt ccccttctcc atctccagcc tcggggctgc   3420
cgcagggggga cggctgcctt cgggggggac ggggcagggc ggggttcggc ttctggcgtg   3480
tgaccggcgg ctctagatgc atgctcgagc ggccgccagt gtgatggata tctgcagaat   3540
tcgccctttc tagaatgggg gtgcacggtg agtactcgcg ggctgggcgc tcccgcccgc   3600
ccgggtccct gtttgagcgg ggatttagcg ccccggctat tggccaggag gtggctgggt   3660
tcaaggaccg gcgacttgtc aaggaccccg gaagggggag gggggtgggg tgcctccacg   3720
tgccagcggg gacttggggg agtccttggg gatggcaaaa acctgacctg tgaaggggac   3780
acagtttggg ggttgagggg aagaaggttt gggggttctg ctgtgccagt ggagaggaag   3840
ctgataagct gataacctgg gcgctggagc caccacttat ctgccagagg ggaagcctct   3900
gtcacaccag gattgaagtt tggccggaga agtggatgct ggtagctggg ggtggggtgt   3960
gcacacggca gcaggattga atgaaggcca gggaggcagc acctgagtgc ttgcatggtt   4020
ggggacagga aggacgagct ggggcagaga cgtggggatg aaggaagctg tccttccaca   4080
```

-continued

```
gccacccttc tccctccccg cctgactctc agcctggcta tctgttctag aatgtcctgc   4140

ctggctgtgg cttctcctgt ccctgctgtc gctccctctg ggcctcccag tcctgggcgc   4200

cccaccacgc ctcatctgtg acagccgagt cctggagagg tacctcttgg aggccaagga   4260

ggccgagaat atcacggtga gaccccttcc ccagcacatt ccacagaact cacgctcagg   4320

gcttcaggga actcctccca gatccaggaa cctggcactt ggtttggggt ggagttggga   4380

agctagacac tgccccccta cataagaata agtctggtgg ccccaaacca tacctggaaa   4440

ctaggcaagg agcaaagcca gcagatccta cggcctgtgg gccagggcca gagccttcag   4500

ggacccttga ctccccgggc tgtgtgcatt tcagacgggc tgtgctgaac actgcagctt   4560

gaatgagaat atcactgtcc cagacaccaa agttaatttc tatgcctgga agaggatgga   4620

ggtgagttcc tttttttttt tttttccttt cttttggaga atctcatttg cgagcctgat   4680

tttggatgaa agggagaatg atcgagggaa aggtaaaatg gagcagcaga gatgaggctg   4740

cctgggcgca gaggctcacg tctataatcc caggctgaga tggccgagat gggagaattg   4800

cttgagccct ggagtttcag accaacctag gcagcatagt gagatccccc atctctacaa   4860

acatttaaaa aaattagtca ggtgaagtgg tgcatggtgg tagtcccaga tatttggaag   4920

gctgaggcgg gaggatcgct tgagcccagg aatttgaggc tgcagtgagc tgtgatcaca   4980

ccactgcact ccagcctcag tgacagagtg aggccctgtc tcaaaaaaga aaagaaaaaa   5040

gaaaaataat gagggctgta tggaatacat tcattattca ttcactcact cactcactca   5100

ttcattcatt cattcattca acaagtctta ttgcatacct tctgtttgct cagcttggtg   5160

cttggggctg ctgaggggca ggagggagag ggtgacatgg gtcagctgac tcccagagtc   5220

cactccctgt aggtcgggca gcaggccgta gaagtctggc agggcctggc cctgctgtcg   5280

gaagctgtcc tgcggggcca ggccctgttg gtcaactctt cccagccgtg ggagcccctg   5340

cagctgcatg tggataaagc cgtcagtggc cttcgcagcc tcaccactct gcttcgggct   5400

ctgggagccc aggtgagtag gagcggacac ttctgcttgc cctttctgta agaaggggag   5460

aagggtcttg ctaaggagta caggaactgt ccgtattcct tccctttctg tggcactgca   5520

gcgacctcct gttttctcct tggcagaagg aagccatctc ccctccagat gcggcctcag   5580

ctgctccact ccgaacaatc actgctgaca ctttccgcaa actcttccga gtctactcca   5640

atttcctccg gggaaagctg aagctgtaca caggggaggc ctgcaggaca ggggacagat   5700

gacgtacaag taagaattca ctcctcaggt gcaggctgcc tatcagaagg tggtggctgg   5760

tgtggccaat gccctggctc acaaatacca ctgagatctt tttccctctg ccaaaaatta   5820

tggggacatc atgaagcccc ttgagcatct gacttctggc taataaagga aatttatttt   5880

cattgcaata gtgtgttgga atttttttgtg tctctcactc ggaaggacat atgggagggc   5940

aaatcattta aaacatcaga atgagtattt ggtttagagt ttggcaacat atgccatatg   6000

ctggctgcca tgaacaaagg tggctataaa gaggtcatca gtatatgaaa cagccccctg   6060

ctgtccattc cttattccat agaaaagcct tgacttgagg ttagattttt tttatatttt   6120

gttttgtgtt atttttttct ttaacatccc taaaattttc cttacatgtt ttactagcca   6180

gatttttcct cctctcctga ctactcccag tcatagctgt ccctcttctc ttatgaagat   6240

ccctcgacct gcagcccaag cttgcatgcc tgcaggtcga ctctagtgga tcccccgccc   6300

cgtatccccc aggtgtctgc aggctcaaag agcagcgaga agcgttcaga ggaaagcgat   6360

cccgtgccac cttccccgtg cccgggctgt ccccgcacgc tgccggctcg gggatgcggg   6420
```

-continued

```
gggagcgccg gaccggagcg gagccccggg cggctcgctg ctgcccccta gcgggggagg   6480
gacgtaatta catccctggg ggctttgggg gggggctgtc cccgtgagcg gatccgcggc   6540
cccgtatccc ccaggtgtct gcaggctcaa agagcagcga gaagcgttca gaggaaagcg   6600
atcccgtgcc accttccccg tgcccgggct gtccccgcac gctgccggct cggggatgcg   6660
gggggagcgc cggaccggag cggagccccg ggcggctcgc tgctgccccc tagcggggga   6720
gggacgtaat tacatccctg gggggctttgg ggggggctg tccccgtgag cggatccgcg   6780
gccccgtatc ccccaggtgt ctgcaggctc aaagagcagc gagaagcgtt cagaggaaag   6840
cgatcccgtg ccaccttccc cgtgcccggg ctgtccccgc acgctgccgg ctcggggatg   6900
cgggggggagc gccggaccgg agcggagccc cgggcggctc gctgctgccc cctagcgggg   6960
gagggacgta attacatccc tgggggcttt ggggggggggc tgtccccgtg agcggatccg   7020
cggccccgta tcccccaggt gtctgcaggc tcaaagagca gcgagaagcg ttcagaggaa   7080
agcgatcccg tgccaccttc cccgtgcccg ggctgtcccc gcacgctgcc ggctcgggga   7140
tgcgggggga gcgccggacc ggagcggagc cccgggcggc tcgctgctgc cccctagcgg   7200
gggagggacg taattacatc cctgggggct ttgggggggg gctgtccccg tgagcggatc   7260
cgcggccccg tatcccccag gtgtctgcag gctcaaagag cagcgagaag cgttcagagg   7320
aaagcgatcc cgtgccacct tccccgtgcc cgggctgtcc ccgcacgctg ccggctcggg   7380
gatgcggggg gagcgccgga ccggagcgga gccccgggcg gctcgctgct gccccctagc   7440
gggggaggga cgtaattaca tccctggggg ctttgggggg gggctgtccc cgtgagcgga   7500
tccgcggccc cgtatccccc aggtgtctgc aggctcaaag agcagcgaga agcgttcaga   7560
ggaaagcgat cccgtgccac cttccccgtg cccgggctgt ccccgcacgc tgccggctcg   7620
gggatgcggg gggagcgccg gaccggagcg gagccccggg cggctcgctg ctgcccccta   7680
gcgggggagg gacgtaatta catccctggg ggctttgggg gggggctgtc cccgtgagcg   7740
gatccgcggg gctgcaggaa ttcgtaatca tggtcatagc tgtttcctgt gtgaaattgt   7800
tatccgctca caattccaca caacatacga gccggaagca taaagtgtaa agcctggggt   7860
gcctaatgag tgagctaact cacattaatt gcgttgcgct cactgcccgc tttccagtcg   7920
ggaaacctgt cgtgccagct gcattaatga atcggccaac gcgcggggag aggcggtttg   7980
cgtattgggc gctcttccgc ttcctcgctc actgactcgc tgcgctcggt cgttcggctg   8040
cggcgagcgg tatcagctca ctcaaaggcg gtaatacggt tatccacaga atcaggggat   8100
aacgcaggaa agaacatgtg agcaaaaggc cagcaaaagg ccaggaaccg taaaaaggcc   8160
gcgttgctgg cgtttttcca taggctccgc ccccctgacg agcatcacaa aaatcgacgc   8220
tcaagtcaga ggtggcgaaa cccgacagga ctataaagat accaggcgtt tccccctgga   8280
agctccctcg tgcgctctcc tgttccgacc ctgccgctta ccggatacct gtccgccttt   8340
ctcccttcgg gaagcgtggc gctttctcat agctcacgct gtaggtatct cagttcggtg   8400
taggtcgttc gctccaagct gggctgtgtg cacgaacccc ccgttcagcc cgaccgctgc   8460
gccttatccg gtaactatcg tcttgagtcc aacccggtaa gacacgactt atcgccactg   8520
gcagcagcca ctggtaacag gattagcaga gcgaggtatg taggcggtgc tacagagttc   8580
ttgaagtggt ggcctaacta cggctacact agaaggacag tatttggtat ctgcgctctg   8640
ctgaagccag ttaccttcgg aaaaagagtt ggtagctctt gatccggcaa acaaaccacc   8700
gctggtagcg gtggtttttt tgtttgcaag cagcagatta cgcgcagaaa aaaggatctt   8760
caagaagatc ctttgatctt ttctacgggg tctgacgctc agtggaacga aaactcacgt   8820
```

-continued taagggattt tggtcatgag attatcaaaa aggatcttca cctagatcct tttaaattaa 8880
aaatgaagtt ttaaatcaat ctaaagtata tatgagtaaa cttggtctga cagttaccaa 8940
tgcttaatca gtgaggcacc tatctcagcg atctgtctat ttcgttcatc catagttgcc 9000
tgactccccg tcgtgtagat aactacgata cgggagggct taccatctgg ccccagtgct 9060
gcaatgatac cgcgagaccc acgctcaccg gctccagatt tatcagcaat aaaccagcca 9120
gccggaaggg ccgagcgcag aagtggtcct gcaactttat ccgcctccat ccagtctatt 9180
aattgttgcc gggaagctag agtaagtagt tcgccagtta atagtttgcg caacgttgtt 9240
gccattgcta caggcatcgt ggtgtcacgc tcgtcgtttg gtatggcttc attcagctcc 9300
ggttcccaac gatcaaggcg agttacatga tcccccatgt tgtgcaaaaa agcggttagc 9360
tccttcggtc ctccgatcgt tgtcagaagt aagttggccg cagtgttatc actcatggtt 9420
atggcagcac tgcataattc tcttactgtc atgccatccg taagatgctt ttctgtgact 9480
ggtgagtact caaccaagtc attctgagaa tagtgtatgc ggcgaccgag ttgctcttgc 9540
ccggcgtcaa tacgggataa taccgcgcca catagcagaa ctttaaaagt gctcatcatt 9600
ggaaaacgtt cttcggggcg aaaactctca aggatcttac cgctgttgag atccagttcg 9660
atgtaaccca ctcgtgcacc caactgatct tcagcatctt ttactttcac cagcgtttct 9720
gggtgagcaa aaacaggaag gcaaaatgcc gcaaaaaagg gaataagggc gacacggaaa 9780
tgttgaatac tcatactctt cctttttcaa tattattgaa gcatttatca gggttattgt 9840
ctcatgagcg gatacatatt tgaatgtatt tagaaaaata aacaaatagg ggttccgcgc 9900
acatttcccc gaaaagtgcc acctgacgta gttaacaaaa aaaagcccgc cgaagcgggc 9960
tttattacca agcgaagcgc cattcgccat tcaggctgcg caactgttgg gaagggcgat 10020
cggtgcgggc ctcttcgcta ttacgccagc tggcgaaagg gggatgtgct gcaaggcgat 10080
taagttgggt aacgccaggg ttttcccagt cacgacgttg taaaacgacg gccagtccgt 10140
aatacgactc acttaaggcc ttgactagag ggtcgacggt atacagacat gataagatac 10200
attgatgagt ttggacaaac cacaactaga atgcagtgaa aaaaatgctt tatttgtgaa 10260
atttgtgatg ctattgcttt atttgtaacc attataagct gcaataaaca agttggggtg 10320
ggcgaagaac tccagcatga gatccccgcg ctggaggatc atccagccgg cgtcccggaa 10380
aacgattccg aagcccaacc tttcatagaa ggcggcggtg gaatcgaaat ctcgtagcac 10440
gtgtcagtcc tgctcctcgg ccacgaagtg cacg 10474

<210> SEQ ID NO 126
<211> LENGTH: 6119
<212> TYPE: DNA
<213> ORGANISM: Artificial Sequence
<220> FEATURE:
<223> OTHER INFORMATION: p18attBZeoeGFP Plasmid

<400> SEQUENCE: 126
cagttgccgg ccgggtcgcg cagggcgaac tcccgccccc acggctgctc gccgatctcg 60
gtcatggccg gcccggaggc gtcccggaag ttcgtggaca cgacctccga ccactcggcg 120
tacagctcgt ccaggccgcg cacccacacc caggccaggg tgttgtccgg caccacctgg 180
tcctggaccg cgctgatgaa cagggtcacg tcgtcccgga ccacaccggc gaagtcgtcc 240
tccacgaagt cccgggagaa cccgagccgg tcggtccaga actcgaccgc tccggcgacg 300
tcgcgcgcgg tgagcaccgg aacggcactg gtcaacttgg ccatggatcc agatttcgct 360

-continued

```
caagttagta taaaaaagca ggcttcaatc ctgcagagaa gcttgggctg caggtcgagg    420
gatcttcata agagaagagg gacagctatg actgggagta gtcaggagag gaggaaaaat    480
ctggctagta aaacatgtaa ggaaaatttt agggatgtta aagaaaaaaa taacacaaaa    540
caaaatataa aaaaaatcta acctcaagtc aaggcttttc tatggaataa ggaatggaca    600
gcagggggct gtttcatata ctgatgacct ctttatagcc acctttgttc atggcagcca    660
gcatatggca tatgttgcca aactctaaac caaatactca ttctgatgtt ttaaatgatt    720
tgccctccca tatgtccttc cgagtgagag acacaaaaaa ttccaacaca ctattgcaat    780
gaaaataaat ttcctttatt agccagaagt cagatgctca aggggcttca tgatgtcccc    840
ataatttttg gcagagggaa aaagatctca gtggtatttg tgagccaggg cattggccac    900
accagccacc accttctgat aggcagcctg cacctgagga gtgaattctt acttgtacag    960
ctcgtccatg ccgagagtga tcccggcggc ggtcacgaac tccagcagga ccatgtgatc   1020
gcgcttctcg ttggggtctt tgctcagggc ggactgggtg ctcaggtagt ggttgtcggg   1080
cagcagcacg gggccgtcgc cgatgggggt gttctgctgg tagtggtcgg cgagctgcac   1140
gctgccgtcc tcgatgttgt ggcggatctt gaagttcacc ttgatgccgt tcttctgctt   1200
gtcggccatg atatagacgt tgtggctgtt gtagttgtac tccagcttgt gccccaggat   1260
gttgccgtcc tccttgaagt cgatgccctt cagctcgatg cggttcacca gggtgtcgcc   1320
ctcgaacttc acctcggcgc gggtcttgta gttgccgtcg tccttgaaga agatggtgcg   1380
ctcctggacg tagccttcgg gcatggcgga cttgaagaag tcgtgctgct tcatgtggtc   1440
ggggtagcgg ctgaagcact gcacgccgta ggtcagggtg gtcacgaggg tgggccaggg   1500
cacgggcagc ttgccggtgg tgcagatgaa cttcagggtc agcttgccgt aggtggcatc   1560
gccctcgccc tcgccggaca cgctgaactt gtggccgttt acgtcgccgt ccagctcgac   1620
caggatgggc accaccccgg tgaacagctc ctcgcccttg ctcaccatgg tggcgaattc   1680
tttgccaaaa tgatgagaca gcacaacaac cagcacgttg cccaggagct gtaggaaaaa   1740
gaagaaggca tgaacatggt tagcagaggc tctagagccg ccggtcacac gccagaagcc   1800
gaaccccgcc ctgccccgtc ccccccgaag gcagccgtcc ccctgcggca gccccgaggc   1860
tggagatgga gaaggggacg gcggcgcggc gacgcacgaa ggccctcccc gcccatttcc   1920
ttcctgccgg cgccgcaccg cttcgcccgc gcccgctaga gggggtgcgg cggcgcctcc   1980
cagatttcgg ctccgccaga tttgggacaa aggaagtccc tgcgccctct cgcacgatta   2040
ccataaaagg caatggctgc ggctcgccgc gcctcgacag ccgccggcgc tccggggccg   2100
ccgcgcccct cccccgagcc ctccccggcc cgaggcggcc ccgccccgcc cggcaccccc   2160
acctgccgcc accccccgcc cggcacggcg agccccgcgc cacgccccgc acggagcccc   2220
gcacccgaag ccgggccgtg ctcagcaact cggggagggg ggtgcagggg ggggttacag   2280
cccgaccgcc gcgcccacac cccctgctca cccccccacg cacacacccc gcacgcagcc   2340
tttgttcccc tcgcagcccc cccgcaccgc ggggcaccgc ccccggccgc gctcccctcg   2400
cgcacacgcg gagcgcacaa agccccgcgc cgcgcccgca gcgctcacag ccgccgggca   2460
gcgcgggccg cacgcggcgc tccccacgca cacacacacg cacgcacccc ccgagccgct   2520
cccccccgca caaagggccc tcccggagcc ctttaaggct ttcacgcagc cacagaaaag   2580
aaacgagccg tcattaaacc aagcgctaat tacagcccgg aggagaaggg ccgtcccgcc   2640
cgctcacctg tgggagtaac gcggtcagtc agagccgggg cgggcggcgc gaggcggcgc   2700
ggagcggggc acggggcgaa ggcaacgcag cgactcccgc ccgccgcgcg cttcgctttt   2760
```

-continued

```
tatagggccg ccgccgccgc cgcctcgcca taaaaggaaa ctttcggagc gcgccgctct   2820
gattggctgc cgccgcacct ctccgcctcg ccccgccccg cccctcgccc cgccccgccc   2880
cgcctggcgc gcgccccccc cccccccgcc cccatcgctg cacaaaataa ttaaaaaata   2940
aataaataca aaattggggg tggggagggg ggggagatgg ggagagtgaa gcagaacgtg   3000
gggctcacct cgacccatgg taatagcgat gactaatacg tagatgtact gccaagtagg   3060
aaagtcccat aaggtcatgt actgggcata atgccaggcg ggccatttac cgtcattgac   3120
gtcaataggg ggcgtacttg gcatatgata cacttgatgt actgccaagt gggcagttta   3180
ccgtaaatag tccacccatt gacgtcaatg gaaagtccct attggcgtta ctatgggaac   3240
atacgtcatt attgacgtca atgggcgggg gtcgttgggc ggtcagccag gcgggccatt   3300
taccgtaagt tatgtaacgc ggaactccat atatgggcta tgaactaatg accccgtaat   3360
tgattactat taataactag aggatccccg ggtaccgagc tcgaattcgt aatcatggtc   3420
atagctgttt cctgtgtgaa attgttatcc gctcacaatt ccacacaaca tacgagccgg   3480
aagcataaag tgtaaagcct ggggtgccta atgagtgagc taactcacat taattgcgtt   3540
gcgctcactg cccgctttcc agtcgggaaa cctgtcgtgc cagctgcatt aatgaatcgg   3600
ccaacgcgcg gggagaggcg gtttgcgtat tgggcgctct tccgcttcct cgctcactga   3660
ctcgctgcgc tcggtcgttc ggctgcggcg agcggtatca gctcactcaa aggcggtaat   3720
acggttatcc acagaatcag gggataacgc aggaaagaac atgtgagcaa aaggccagca   3780
aaaggccagg aaccgtaaaa aggccgcgtt gctggcgttt ttccataggc tccgcccccc   3840
tgacgagcat cacaaaaatc gacgctcaag tcagaggtgg cgaaacccga caggactata   3900
aagataccag gcgtttcccc ctggaagctc cctcgtgcgc tctcctgttc cgaccctgcc   3960
gcttaccgga tacctgtccg cctttctccc ttcgggaagc gtggcgcttt ctcatagctc   4020
acgctgtagg tatctcagtt cggtgtaggt cgttcgctcc aagctgggct gtgtgcacga   4080
accccccgtt cagcccgacc gctgcgcctt atccggtaac tatcgtcttg agtccaaccc   4140
ggtaagacac gacttatcgc cactggcagc agccactggt aacaggatta gcagagcgag   4200
gtatgtaggc ggtgctacag agttcttgaa gtggtggcct aactacggct acactagaag   4260
gacagtattt ggtatctgcg ctctgctgaa gccagttacc ttcggaaaaa gagttggtag   4320
ctcttgatcc ggcaaacaaa ccaccgctgg tagcggtggt ttttttgttt gcaagcagca   4380
gattacgcgc agaaaaaaag gatctcaaga agatcctttg atcttttcta cggggtctga   4440
cgctcagtgg aacgaaaact cacgttaagg gattttggtc atgagattat caaaaaggat   4500
cttcacctag atccttttaa attaaaaatg aagttttaaa tcaatctaaa gtatatatga   4560
gtaaacttgg tctgacagtt accaatgctt aatcagtgag gcacctatct cagcgatctg   4620
tctatttcgt tcatccatag ttgcctgact ccccgtcgtg tagataacta cgatacggga   4680
gggcttacca tctggcccca gtgctgcaat gataccgcga gacccacgct caccggctcc   4740
agatttatca gcaataaacc agccagccgg aagggccgag cgcagaagtg gtcctgcaac   4800
tttatccgcc tccatccagt ctattaattg ttgccgggaa gctagagtaa gtagttcgcc   4860
agttaatagt ttgcgcaacg ttgttgccat tgctacaggc atcgtggtgt cacgctcgtc   4920
gtttggtatg gcttcattca gctccggttc ccaacgatca aggcgagtta catgatcccc   4980
catgttgtgc aaaaaagcgg ttagctcctt cggtcctccg atcgttgtca gaagtaagtt   5040
ggccgcagtg ttatcactca tggttatggc agcactgcat aattctctta ctgtcatgcc   5100
```

-continued

```
atccgtaaga tgcttttctg tgactggtga gtactcaacc aagtcattct gagaatagtg   5160

tatgcggcga ccgagttgct cttgcccggc gtcaatacgg gataataccg cgccacatag   5220

cagaacttta aaagtgctca tcattggaaa acgttcttcg gggcgaaaac tctcaaggat   5280

cttaccgctg ttgagatcca gttcgatgta acccactcgt gcacccaact gatcttcagc   5340

atcttttact ttcaccagcg tttctgggtg agcaaaaaca ggaaggcaaa atgccgcaaa   5400

aaagggaata agggcgacac ggaaatgttg aatactcata ctcttccttt ttcaatatta   5460

ttgaagcatt tatcagggtt attgtctcat gagcggatac atatttgaat gtatttagaa   5520

aaataaacaa ataggggttc cgcgcacatt tccccgaaaa gtgccacctg acgtagttaa   5580

caaaaaaaag cccgccgaag cgggctttat taccaagcga agcgccattc gccattcagg   5640

ctgcgcaact gttgggaagg gcgatcggtg cgggcctctt cgctattacg ccagctggcg   5700

aaagggggat gtgctgcaag gcgattaagt tgggtaacgc cagggttttc ccagtcacga   5760

cgttgtaaaa cgacggccag tccgtaatac gactcactta aggccttgac tagagggtcg   5820

acggtataca gacatgataa gatacattga tgagtttgga caaaccacaa ctagaatgca   5880

gtgaaaaaaa tgctttattt gtgaaatttg tgatgctatt gctttatttg taaccattat   5940

aagctgcaat aaacaagttg ggtgggcga agaactccag catgagatcc ccgcgctgga   6000

ggatcatcca gccggcgtcc cggaaaacga ttccgaagcc caacctttca tagaaggcgg   6060

cggtggaatc gaaatctcgt agcacgtgtc agtcctgctc ctcggccacg aagtgcacg    6119
```

<210> SEQ ID NO 127
<211> LENGTH: 5855
<212> TYPE: DNA
<213> ORGANISM: Artificial Sequence
<220> FEATURE:
<223> OTHER INFORMATION: pCXLamInt Plasmid (Wildtype Integrase)

<400> SEQUENCE: 127

```
gtcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggact atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atgggtcgag gtgagcccca cgttctgctt cactctcccc    420

atctccccc cctccccacc cccaattttg tatttattta tttttaatt attttgtgca    480

gcgatggggg cggggggggg gggggcgcgc gccaggcggg gcggggcggg gcgaggggcg    540

gggcggggcg aggcggagag gtgcggcggc agccaatcag agcggcgcgc tccgaaagtt    600

tccttttatg gcgaggcggc ggcggcggcg gccctataaa aagcgaagcg cgcggcgggc    660

gggagtcgct gcgttgcctt cgccccgtgc cccgctccgc gccgcctcgc gccgcccgcc    720

ccggctctga ctgaccgcgt tactcccaca ggtgagcggg cgggacggcc cttctcctcc    780

gggctgtaat tagcgcttgg tttaatgacg gctcgtttct tttctgtggc tgcgtgaaag    840

ccttaaaggg ctccgggagg gccctttgtg cgggggggag cggctcgggg ggtgcgtgcg    900

tgtgtgtgtg cgtggggagc gccgcgtgcg gcccgcgctg cccggcggct gtgagcgctg    960

cgggcgcggc gcggggcttt gtgcgctccg cgtgtgcgcg aggggagcgc ggccgggggc   1020

ggtgccccgc ggtgcggggg ggctgcgagg ggaacaaagg ctgcgtgcgg ggtgtgtgcg   1080
```

-continued

```
tggggggggtg agcagggggt gtgggcgcgg cggtcgggct gtaacccccc cctgcacccc   1140
cctccccgag ttgctgagca cggcccggct tcgggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcgggggag gggcgcggcg gccccggagc gccggcggct   1320
gtcgaggcgc ggcgagccgc agccattgcc ttttatggta atcgtgcgag agggcgcagg   1380
gacttccttt gtcccaaatc tggcggagcc gaaatctggg aggcgccgcc gcaccccctc   1440
tagcgggcgc gggcgaagcg gtgcggcgcc ggcaggaagg aaatgggcgg ggagggcctt   1500
cgtgcgtcgc cgcgccgccg tccccttctc catctccagc ctcggggctg ccgcaggggg   1560
acggctgcct tcggggggga cggggcaggg cggggttcgg cttctggcgt gtgaccggcg   1620
gctctagagc ctctgctaac catgttcatg ccttcttctt tttcctacag ctcctgggca   1680
acgtgctggt tgttgtgctg tctcatcatt ttggcaaaga attcatggga agaaggcgaa   1740
gtcatgagcg ccgggattta ccccctaacc tttatataag aaacaatgga tattactgct   1800
acagggaccc aaggacgggt aaagagtttg gattaggcag agacaggcga atcgcaatca   1860
ctgaagctat acaggccaac attgagttat tttcaggaca caaacacaag cctctgacag   1920
cgagaatcaa cagtgataat tccgttacgt tacattcatg gcttgatcgc tacgaaaaaa   1980
tcctggccag cagaggaatc aagcagaaga cactcataaa ttacatgagc aaaattaaag   2040
caataaggag ggtctgcct gatgctccac ttgaagacat caccacaaaa gaaattgcgg   2100
caatgctcaa tggatacata gacgagggca aggcggcgtc agccaagtta atcagatcaa   2160
cactgagcga tgcattccga gaggcaatag ctgaaggcca tataacaaca aaccatgtcg   2220
ctgccactcg cgcagcaaaa tcagaggtaa ggagatcaag acttacggct gacgaatacc   2280
tgaaaattta tcaagcagca gaatcatcac catgttggct cagacttgca atggaactgg   2340
ctgttgttac cgggcaacga gttggtgatt tatgcgaaat gaagtggtct gatatcgtag   2400
atggatatct ttatgtcgag caaagcaaaa caggcgtaaa aattgccatc ccaacagcat   2460
tgcatattga tgctctcgga atatcaatga aggaaacact tgataaatgc aaagagattc   2520
ttggcggaga aaccataatt gcatctactc gtcgcgaacc gctttcatcc ggcacagtat   2580
caaggtattt tatgcgcgca cgaaaagcat caggtctttc cttcgaaggg gatccgccta   2640
cctttcacga gttgcgcagt ttgtctgcaa gactctatga gaagcagata agcgataagt   2700
ttgctcaaca tcttctcggg cataagtcgg acaccatggc atcacagtat cgtgatgaca   2760
gaggcaggga gtgggacaaa attgaaatca aataagaatt cactcctcag gtgcaggctg   2820
cctatcagaa ggtggtggct ggtgtggcca atgccctggc tcacaaatac cactgagatc   2880
tttttccctc tgccaaaaat tatggggaca tcatgaagcc ccttgagcat ctgacttctg   2940
gctaataaag gaaatttatt ttcattgcaa tagtgtgttg gaattttttg tgtctctcac   3000
tcggaaggac atatgggagg gcaaatcatt taaaacatca gaatgagtat ttggtttaga   3060
gtttggcaac atatgccata tgctggctgc catgaacaaa ggtggctata aagaggtcat   3120
cagtatatga aacagccccc tgctgtccat tccttattcc atagaaaagc cttgacttga   3180
ggttagattt tttttatatt ttgttttgtg ttattttttt ctttaacatc cctaaaattt   3240
tccttacatg ttttactagc cagatttttc ctcctctcct gactactccc agtcatagct   3300
gtccctcttc tcttatgaag atccctcgac ctgcagccca agcttggcgt aatcatggtc   3360
atagctgttt cctgtgtgaa attgttatcc gctcacaatt ccacacaaca tacgagccgg   3420
```

-continued

```
aagcataaag tgtaaagcct ggggtgccta atgagtgagc taactcacat taattgcgtt   3480
gcgctcactg cccgctttcc agtcgggaaa cctgtcgtgc cagcggatcc gcatctcaat   3540
tagtcagcaa ccatagtccc gcccctaact ccgcccatcc cgcccctaac tccgcccagt   3600
tccgcccatt ctccgcccca tggctgacta atttttttta tttatgcaga ggccgaggcc   3660
gcctcggcct ctgagctatt ccagaagtag tgaggaggct tttttggagg cctaggcttt   3720
tgcaaaaagc taacttgttt attgcagctt ataatggtta caaataaagc aatagcatca   3780
caaatttcac aaataaagca tttttttcac tgcattctag ttgtggtttg tccaaactca   3840
tcaatgtatc ttatcatgtc tggatccgct gcattaatga atcggccaac gcgcggggag   3900
aggcggtttg cgtattgggc gctcttccgc ttcctcgctc actgactcgc tgcgctcggt   3960
cgttcggctg cggcgagcgg tatcagctca ctcaaaggcg gtaatacggt tatccacaga   4020
atcaggggat aacgcaggaa agaacatgtg agcaaaaggc cagcaaaagg ccaggaaccg   4080
taaaaaggcc gcgttgctgg cgtttttcca taggctccgc ccccctgacg agcatcacaa   4140
aaatcgacgc tcaagtcaga ggtggcgaaa cccgacagga ctataaagat accaggcgtt   4200
tccccctgga agctccctcg tgcgctctcc tgttccgacc ctgccgctta ccggatacct   4260
gtccgccttt ctcccttcgg gaagcgtggc gctttctcaa tgctcacgct gtaggtatct   4320
cagttcggtg taggtcgttc gctccaagct gggctgtgtg cacgaacccc ccgttcagcc   4380
cgaccgctgc gccttatccg gtaactatcg tcttgagtcc aacccggtaa gacacgactt   4440
atcgccactg gcagcagcca ctggtaacag gattagcaga gcgaggtatg taggcggtgc   4500
tacagagttc ttgaagtggt ggcctaacta cggctacact agaaggacag tatttggtat   4560
ctgcgctctg ctgaagccag ttaccttcgg aaaaagagtt ggtagctctt gatccggcaa   4620
acaaaccacc gctggtagcg gtggtttttt tgtttgcaag cagcagatta cgcgcagaaa   4680
aaaaggatct caagaagatc ctttgatctt ttctacgggg tctgacgctc agtggaacga   4740
aaactcacgt taagggattt tggtcatgag attatcaaaa aggatcttca cctagatcct   4800
tttaaattaa aaatgaagtt ttaaatcaat ctaaagtata tatgagtaaa cttggtctga   4860
cagttaccaa tgcttaatca gtgaggcacc tatctcagcg atctgtctat ttcgttcatc   4920
catagttgcc tgactccccg tcgtgtagat aactacgata cgggagggct taccatctgg   4980
ccccagtgct gcaatgatac cgcgagaccc acgctcaccg gctccagatt tatcagcaat   5040
aaaccagcca gccggaaggg ccgagcgcag aagtggtcct gcaactttat ccgcctccat   5100
ccagtctatt aattgttgcc gggaagctag agtaagtagt tcgccagtta atagtttgcg   5160
caacgttgtt gccattgcta caggcatcgt ggtgtcacgc tcgtcgtttg gtatggcttc   5220
attcagctcc ggttcccaac gatcaaggcg agttacatga tcccccatgt tgtgcaaaaa   5280
agcggttagc tccttcggtc ctccgatcgt tgtcagaagt aagttggccg cagtgttatc   5340
actcatggtt atggcagcac tgcataattc tcttactgtc atgccatccg taagatgctt   5400
ttctgtgact ggtgagtact caaccaagtc attctgagaa tagtgtatgc ggcgaccgag   5460
ttgctcttgc ccggcgtcaa tacgggataa taccgcgcca catagcagaa ctttaaaagt   5520
gctcatcatt ggaaaacgtt cttcggggcg aaaactctca aggatcttac cgctgttgag   5580
atccagttcg atgtaaccca ctcgtgcacc caactgatct tcagcatctt ttactttcac   5640
cagcgtttct gggtgagcaa aaacaggaag gcaaaatgcc gcaaaaaagg gaataagggc   5700
gacacggaaa tgttgaatac tcatactctt cctttttcaa tattattgaa gcatttatca   5760
gggttattgt ctcatgagcg gatacatatt tgaatgtatt tagaaaaata aacaaatagg   5820
```

-continued ggttccgcgc acatttcccc gaaaagtgcc acctg 5855

<210> SEQ ID NO 128
<211> LENGTH: 303
<212> TYPE: DNA
<213> ORGANISM: Artificial Sequence
<220> FEATURE:
<223> OTHER INFORMATION: Human FER-1 Promoter

<400> SEQUENCE: 128
tccatgacaa agcacttttt gagcccaagc ccagcctagc tcgagctaaa cgggcacaga 60
gacgccaccg ctgtcccaga ggcagtcggc taccggtccc cgctcccgag ctccgccaga 120
gcgcgcgagg gcctccagcg gccgcccctc ccccacagca ggggcggggt cccgcgccca 180
ccggaaggag cgggctcggg gcgggcggcg ctgattggcc ggggcgggcc tgacgccgac 240
gcggctataa gagaccacaa gcgacccgca gggccagacg ttcttcgccg agagtcgggt 300
acc 303

<210> SEQ ID NO 129
<211> LENGTH: 6521
<212> TYPE: DNA
<213> ORGANISM: Artificial Sequence
<220> FEATURE:
<223> OTHER INFORMATION: pIRES-BSR Plasmid

<400> SEQUENCE: 129
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaacaactg 660
cgatcgcccg ccccgttgac gcaaatgggc ggtaggcgtg tacggtggga ggtctatata 720
agcagagctc gtttagtgaa ccgtcagatc actagaagct ttattgcggt agtttatcac 780
agttaaattg ctaacgcagt cagtgcttct gacacaacag tctcgaactt aagctgcagt 840
gactctctta aggtagcctt gcagaagttg gtcgtgaggc actgggcagg taagtatcaa 900
ggttacaaga caggtttaag gagaccaata gaaactgggc ttgtcgagac agagaagact 960
cttgcgtttc tgataggcac ctattggtct tactgacatc cactttgcct ttctctccac 1020
aggtgtccac tcccagttca attacagctc ttaaggctag agtacttaat acgactcact 1080
ataggctagc ctcgagaatt cacgcgtcga gcatgcatct agggcggcca attccgcccc 1140
tctccctccc ccccccctaa cgttactggc cgaagccgct tggaataagg ccggtgtgcg 1200
tttgtctata tgtgattttc caccatattg ccgtcttttg gcaatgtgag ggcccggaaa 1260
cctggccctg tcttcttgac gagcattcct aggggtcttt cccctctcgc caaaggaatg 1320

-continued

```
caaggtctgt tgaatgtcgt gaaggaagca gttcctctgg aagcttcttg aagacaaaca   1380
acgtctgtag cgaccctttg caggcagcgg aaccccccac ctggcgacag gtgcctctgc   1440
ggccaaaagc cacgtgtata agatacacct gcaaaggcgg cacaacccca gtgccacgtt   1500
gtgagttgga tagttgtgga aagagtcaaa tggctctcct caagcgtatt caacaagggg   1560
ctgaaggatg cccagaaggt accccattgt atgggatctg atctggggcc tcggtgcaca   1620
tgctttacat gtgtttagtc gaggttaaaa aaacgtctag gccccccgaa ccacggggac   1680
gtggttttcc tttgaaaaac acgatgataa gcttgccaca acccaccatg aaaacattta   1740
acatttctca acaagatcta gaattagtag aagtagcgac agagaagatt acaatgcttt   1800
atgaggataa taaacatcat gtgggagcgg caattcgtac gaaaacagga gaaatcattt   1860
cggcagtaca tattgaagcg tatataggac gagtaactgt ttgtgcagaa gccattgcga   1920
ttggtagtgc agtttcgaat ggacaaaagg attttgacac gattgtagct gttagacacc   1980
cttattctga cgaagtagat agaagtattc gagtggtaag tccttgtggt atgtgtaggg   2040
agttgatttc agactatgca ccagattgtt ttgtgttaat agaaatgaat ggcaagttag   2100
tcaaaactac gattgaagaa ctcattccac tcaaatatac ccgaaattaa aagttttacc   2160
ataccaagct tggcgggcgg ccgcttccct ttagtgaggg ttaatgcttc gagcagacat   2220
gataagatac attgatgagt ttggacaaac cacaactaga atgcagtgaa aaaaatgctt   2280
tatttgtgaa atttgtgatg ctattgcttt atttgtaacc attataagct gcaataaaca   2340
agttaacaac aacaattgca ttcattttat gtttcaggtt caggggggaga tgtgggaggt   2400
tttttaaagc aagtaaaacc tctacaaatg tggtaaaatc cgataaggat cgatccgggc   2460
tggcgtaata gcgaagaggc ccgcaccgat cgcccttccc aacagttgcg cagcctgaat   2520
ggcgaatgga cgcgccctgt agcggcgcat taagcgcggc gggtgtggtg gttacgcgca   2580
gcgtgaccgc tacacttgcc agcgccctag cgcccgctcc tttcgctttc ttcccttcct   2640
ttctcgccac gttcgccggc tttccccgtc aagctctaaa tcgggggctc cctttagggt   2700
tccgatttag agctttacgg cacctcgacc gcaaaaaact tgatttgggt gatggttcac   2760
gtagtgggcc atcgccctga tagacggttt ttcgcccttt gacgttggag tccacgttct   2820
ttaatagtgg actcttgttc caaactggaa caacactcaa ccctatctcg gtctattctt   2880
ttgatttata agggattttg ccgatttcgg cctattggtt aaaaaatgag ctgatttaac   2940
aaatatttaa cgcgaatttt aacaaaatat taacgtttac aatttcgcct gatgcggtat   3000
tttctcctta cgcatctgtg cggtatttca caccgcatac gcggatctgc gcagcaccat   3060
ggcctgaaat aacctctgaa agaggaactt ggttaggtac cttctgaggc ggaaagaacc   3120
agctgtggaa tgtgtgtcag ttagggtgtg gaaagtcccc aggctcccca gcaggcagaa   3180
gtatgcaaag catgcatctc aattagtcag caaccaggtg tggaaagtcc ccaggctccc   3240
cagcaggcag aagtatgcaa agcatgcatc tcaattagtc agcaaccata gtcccgcccc   3300
taactccgcc catcccgccc ctaactccgc ccagttccgc ccattctccg ccccatggct   3360
gactaatttt ttttatttat gcagaggccg aggccgcctc ggcctctgag ctattccaga   3420
agtagtgagg aggctttttt ggaggcctag gcttttgcaa aaagcttgat tcttctgaca   3480
caacagtctc gaacttaagg ctagagccac catgattgaa caagatggat tgcacgcagg   3540
ttctccggcc gcttgggtgg agaggctatt cggctatgac tgggcacaac agacaatcgg   3600
ctgctctgat gccgccgtgt tccggctgtc agcgcagggg cgcccggttc tttttgtcaa   3660
gaccgacctg tccggtgccc tgaatgaact gcaggacgag gcagcgcggc tatcgtggct   3720
```

-continued

```
ggccacgacg ggcgttcctt gcgcagctgt gctcgacgtt gtcactgaag cgggaaggga   3780
ctggctgcta ttgggcgaag tgccggggca ggatctcctg tcatctcacc ttgctcctgc   3840
cgagaaagta tccatcatgg ctgatgcaat gcggcggctg catacgcttg atccggctac   3900
ctgcccattc gaccaccaag cgaaacatcg catcgagcga gcacgtactc ggatggaagc   3960
cggtcttgtc gatcaggatg atctggacga agagcatcag gggctcgcgc cagccgaact   4020
gttcgccagg ctcaaggcgc gcatgcccga cggcgaggat ctcgtcgtga cccatggcga   4080
tgcctgcttg ccgaatatca tggtggaaaa tggccgcttt tctggattca tcgactgtgg   4140
ccggctgggt gtggcggacc gctatcagga catagcgttg gctacccgtg atattgctga   4200
agagcttggc ggcgaatggg ctgaccgctt cctcgtgctt tacggtatcg ccgctcccga   4260
ttcgcagcgc atcgccttct atcgccttct tgacgagttc ttctgagcgg gactctgggg   4320
ttcgaaatga ccgaccaagc gacgcccaac ctgccatcac gatggccgca ataaaatatc   4380
tttattttca ttacatctgt gtgttggttt tttgtgtgaa tcgatagcga taaggatccg   4440
cgtatggtgc actctcagta caatctgctc tgatgccgca tagttaagcc agccccgaca   4500
cccgccaaca cccgctgacg cgccctgacg ggcttgtctg ctcccggcat ccgcttacag   4560
acaagctgtg accgtctccg ggagctgcat gtgtcagagg ttttcaccgt catcaccgaa   4620
acgcgcgaga cgaaagggcc tcgtgatacg cctattttta taggttaatg tcatgataat   4680
aatggtttct tagacgtcag gtggcacttt tcggggaaat gtgcgcggaa cccctatttg   4740
tttatttttc taaatacatt caaatatgta tccgctcatg agacaataac cctgataaat   4800
gcttcaataa tattgaaaaa ggaagagtat gagtattcaa catttccgtg tcgcccttat   4860
tccctttttt gcggcatttt gccttcctgt ttttgctcac ccagaaacgc tggtgaaagt   4920
aaaagatgct gaagatcagt tgggtgcacg agtgggttac atcgaactgg atctcaacag   4980
cggtaagatc cttgagagtt ttcgccccga agaacgtttt ccaatgatga gcacttttaa   5040
agttctgcta tgtggcgcgg tattatcccg tattgacgcc gggcaagagc aactcggtcg   5100
ccgcatacac tattctcaga atgacttggt tgagtactca ccagtcacag aaaagcatct   5160
tacggatggc atgacagtaa gagaattatg cagtgctgcc ataaccatga gtgataacac   5220
tgcggccaac ttacttctga caacgatcgg aggaccgaag gagctaaccg cttttttgca   5280
caacatgggg gatcatgtaa ctcgccttga tcgttgggaa ccggagctga atgaagccat   5340
accaaacgac gagcgtgaca ccacgatgcc tgtagcaatg gcaacaacgt tgcgcaaact   5400
attaactggc gaactactta ctctagcttc ccggcaacaa ttaatagact ggatggaggc   5460
ggataaagtt gcaggaccac ttctgcgctc ggcccttccg gctggctggt ttattgctga   5520
taaatctgga gccggtgagc gtgggtctcg cggtatcatt gcagcactgg ggccagatgg   5580
taagccctcc cgtatcgtag ttatctacac gacggggagt caggcaacta tggatgaacg   5640
aaatagacag atcgctgaga taggtgcctc actgattaag cattggtaac tgtcagacca   5700
agtttactca tatatacttt agattgattt aaaacttcat ttttaattta aaaggatcta   5760
ggtgaagatc ctttttgata atctcatgac caaaatccct taacgtgagt tttcgttcca   5820
ctgagcgtca gaccccgtag aaaagatcaa aggatcttct tgagatcctt tttttctgcg   5880
cgtaatctgc tgcttgcaaa caaaaaaacc accgctacca gcggtggttt gtttgccgga   5940
tcaagagcta ccaactcttt ttccgaaggt aactggcttc agcagagcgc agataccaaa   6000
tactgtcctt ctagtgtagc cgtagttagg ccaccacttc aagaactctg tagcaccgcc   6060
```

-continued

| | |
|---|---|
| tacatacctc gctctgctaa tcctgttacc agtggctgct gccagtggcg ataagtcgtg | 6120 |
| tcttaccggg ttggactcaa gacgatagtt accggataag gcgcagcggt cgggctgaac | 6180 |
| ggggggttcg tgcacacagc ccagcttgga gcgaacgacc tacaccgaac tgagatacct | 6240 |
| acagcgtgag ctatgagaaa gcgccacgct tcccgaaggg agaaaggcgg acaggtatcc | 6300 |
| ggtaagcggc agggtcggaa caggagagcg cacgagggag cttccagggg gaaacgcctg | 6360 |
| gtatctttat agtcctgtcg ggtttcgcca cctctgactt gagcgtcgat ttttgtgatg | 6420 |
| ctcgtcaggg gggcggagcc tatggaaaaa cgccagcaac gcggcctttt tacggttcct | 6480 |
| ggccttttgc tggccttttg ctcacatggc tcgacagatc t | 6521 |